US011795169B2

(12) United States Patent
Schneider et al.

(10) Patent No.: US 11,795,169 B2
(45) Date of Patent: Oct. 24, 2023

(54) MAP4K4 INHIBITORS

(71) Applicant: IMPERIAL COLLEGE INNOVATIONS LIMITED, London (GB)

(72) Inventors: Michael Schneider, London (GB); Gary Newton, Saffron Walden (GB); Katie Chapman, Saffron Walden (GB); Trevor Perrior, Saffron Walden (GB); Ashley Jarvis, Abingdon (GB); Caroline Low, London (GB); Rehan Aqil, Saffron Walden (GB); Martin Fisher, Saffron Walden (GB); Melanie Bayford, Saffron Walden (GB); Nicholas Chapman, Saffron Walden (GB); Nicholas Martin, Saffron Walden (GB); Tifelle Reisinger, Saffron Walden (GB); Gabriel Negoita-Giras, Saffron Walden (GB); Lorna R. Fieldler, Reading (GB)

(73) Assignee: IMPERIAL COLLEGE INNOVATIONS LIMITED, London (GB)

( * ) Notice: Subject to any disclaimer, the term of this patent is extended or adjusted under 35 U.S.C. 154(b) by 27 days.

(21) Appl. No.: 16/754,496

(22) PCT Filed: Oct. 12, 2018

(86) PCT No.: PCT/GB2018/052936
§ 371 (c)(1),
(2) Date: Apr. 8, 2020

(87) PCT Pub. No.: WO2019/073253
PCT Pub. Date: Apr. 18, 2019

(65) Prior Publication Data

US 2020/0339583 A1 Oct. 29, 2020

(30) Foreign Application Priority Data

Oct. 13, 2017 (GB) .................................... 1716867
Aug. 14, 2018 (GB) .................................... 1813252

(51) Int. Cl.
*C07D 487/04* (2006.01)
*C07F 9/6561* (2006.01)

(52) U.S. Cl.
CPC .......... *C07D 487/04* (2013.01); *C07F 9/6561* (2013.01)

(58) Field of Classification Search
CPC ........................... C07D 487/04; C07F 9/6561
See application file for complete search history.

(56) References Cited

FOREIGN PATENT DOCUMENTS

| | | | |
|---|---|---|---|
| EP | 0482804 | | 4/1992 |
| WO | 1997/049706 | A1 | 12/1997 |
| WO | WO-2013/113669 | | 8/2013 |
| WO | 2013/180265 | A1 | 12/2013 |
| WO | 2019/073253 | A1 | 4/2019 |
| WO | 2020/115481 | A1 | 6/2020 |

OTHER PUBLICATIONS

Chemical Abstracts Registry No. 1348789-28-5, indexed in the Registry file on STN CAS Online Dec. 5, 2011. (Year: 2011).*
International Search Report and Written Opinion for International Patent Application No. PCT/GB2019/053429, dated Feb. 5, 2020, 8 pages.
U.S. Appl. No. 17/298,870, "MAP4K4 Inhibitors", filed Jun. 1, 2021, 208 pages.
Chow et al., "Human Induced Pluripotent Stem Cell-Derived Cardiomyocyte Encapsulating Bioactive Hydrogels Improve Rat Heart Function Post Myocardial Infarction," Stem Cell Reports, 9, pp. 1415-1422 (2017).
Dave and Desai, "Synthesis and Reactions of Fluoroaryl Substituted 2-Amino-3-cyanopyrroles and Pyrrolo[2,3-d]pyrimidines," J. Heterocyclic Chem., 36, pp. 729-733 (1999).
Dave and Patel, "Synthesis of 5,7-Disubstituted 7H-Pyrrolo[2,3-d]Pyrimidin-4(3H)-ones and Their N-Alkylation's under Phase Transfer Conditions," J. Heterocyclic Chem., 51, pp. 943-947 (2014).

(Continued)

*Primary Examiner* — Laura L Stockton
(74) *Attorney, Agent, or Firm* — Mintz, Levin, Cohn, Ferris, Glovsky and Popeo, P.C.

(57) ABSTRACT

This invention relates to pyrrolopyrimidine comprising compounds that may be useful as inhibitors of Mitogen-activated Protein Kinase Kinase Kinase Kinase-4 (MAP4K4). The invention also relates to the use of these pyrrolopyrimidine comprising compounds, for example in a method of treatment. There are also provided processes for producing compounds of the present invention and method of their use. In particular, the present invention relates to compounds of formula (I).

(I)

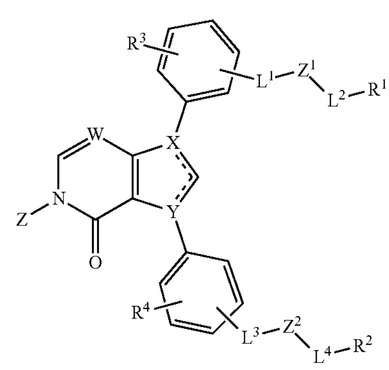

17 Claims, 21 Drawing Sheets

(56) References Cited

OTHER PUBLICATIONS

Desai, "Synthesis of Fused Tetrazolo[1,5-c] pyrrolo[3,2-e]pyrimidines and Their Reductive Conversion to New 4-Aminopyrrolo [2,3-d]pyrimidines," Synthetic Communications, 36, pp. 2169-2182 (2006).
El-Bayouki et al., "Pyrrolo[2,3-d]Pyrimidines. I: Synthesis of Novel Pyrrolo[2,3-d]pyrimidine Derivatives With Anti-microbial Activity," Journal of Chemical Research. Minipr, Scientific Reviews, 8(1) pp. 1901-1912 (1995).
El-Bayouki et al., "Synthesis of new pyrrole and pyrrolo[2,3-d]pyrimidine derivatives of potential antioxidant activity," Collect. Czech. Chem. Commun., 75(8), pp. 813-834 (2010).
Ghorab et al., "Computer-Based Ligand Design and Synthesis of Some New Sulfonamides Bearing Pyrrole or Pyrrolopyrimidine Moieties Having Potential Antitumor and Radioprotective Activities," Phosphorus, Sulfur, and Silicon and the Related Elements, 183(1), pp. 90-104 (2008).
Ghorab et al., "Novel Antitumor and Radioprotective Sulfonamides Containing Pyrrolo[2,3-d] pyrimidines," ArzneimForschDrugRes, 56(6), pp. 405-413 (2006).
Ghorab et al., "Synthesis and Molecular Docking of Some Novel Anticancer Sulfonamides Carrying a Biologically Active Pyrrole and Pyrrolopyrimidine Moieties," Acta Poloniae Pharmaceutica—Drug Research, 71(4), pp. 603-614 (2014).
Ghorab et al., "Synthesis of novel pyrrole and pyrrolo[2,3-d]pyrimidine derivatives bearing sulfonamide moiety for evaluation as anticancer and radiosensitizing agents," Bioorganic & Medicinal Chemistry Letters, 20, pp. 6316-6320 (2010).
Hassan et al., "Heteroaromatization with Sulfonamido Phenyl Ethanone, Part I: Synthesis of Novel Pyrrolo[2,3-D]Pyrimidine and Pyrrolo[3,2-E] [1,2,4]Triazolo[1,5-C]Pyrimidine Derivatives Containing Dimethylsulfonamide Moiety," Phosphorus, Sulfur, and Silicon, 184(2), pp. 291-308 (2009).
Hussein et al., "Synthesis and Kinetic Testing of Tetrahydropyrimidine-2-thione and Pyrrole Derivatives as Inhibitors of the Metallo-β-lactamase from *Klebsiella pneumonia* and *Pseudomonas aeruginosa*," Chem. Biol. Drug Des., 80, pp. 500-515 (2012).
International Search Report and Written Opinion for International Patent Application No. PCT/GB2018/052936, dated Dec. 19, 2018 (17 pages).
Mohamed et al., "Synthesis and kinetic testing of new inhibitors for a metallo-β-lactamase from *Klebsiella pneumonia* and *Pseudomonas aeruginosa*," European Journal of Medicinal Chemistry, 46, pp. 6075-6082 (2011).
Sarg et al., "Synthesis of Pyrroles and Condensed Pyrroles as Anti-Inflammatory Agents with Multiple Activities and Their Molecular Docking Study," Open Journal of Medicinal Chemistry, 5, pp. 49-96 (2015).
Tintori et al., "Docking, 3D-QSAR studies and in silico ADME prediction on c-Src tyrosine kinase inhibitors," European Journal of Medicinal Chemistry, 44, pp. 990-1000 (2009).
Virbasius and Czech, "Map4k4 Signaling Nodes in Metabolic and Cardiovascular Diseases," Trends in Endocrinology & Metabolism, 27(7), pp. 484-492 (2016).
Altmann et al., "N7-Substituted-5-aryl-pyrrolo[2,3-d]pyrimidines Represent a Versatile Class of Potent Inhibitors of the Tyrosine Kinase c-Src," Mini Reviews in Medicinal Chemistry, 2, pp. 201-208 (2002).
Augustine and Agrawal, "Syntheses of 1,3-disubstituted-5a-hydropyrrolo[2,3-d]quinazolino[3,2-e]pyrimidin-6(5H)-ones: A comparison of conventional and microwave technique," Indian Journal of Chemistry, 44B, pp. 1653-1658 (2005).
Chemistry Abstracts Registry No. 1348286-95-2, Indexed in the Registry file on STN CAS Online on Dec. 4, 2011.
Missbach Martin et al: "Substituted 5,7-diphenyl-pyrrolo[2,3d]pyrimidines: potent inhibitors of the tyrosine kinase c-Src" Bioorganic & Medicinal Chemistry Letters, vol. 10, No. 9, Jun. 5, 2017, pp. 945-949.
Ndubaku et al: "Structure-based design of GNE-495, a Potent and Selective MAP4K4 inhibitor with efficacy in retinal angiogenesis", ACS Med. Chem. Lett., 2015, 6, 913-918.
Wang et al: "Fragment-based identification and optimization of a class potent pyrrolo[2,1-f][1,2,4]triazine MAP4K4 inhibitors", Bioorganic & Medicinal Chemistry Letters, 2014, 24, 4546-4552.
St-Gallay, S. A., et al. "A high-throughput screening triage workflow to authenticate a novel series of PFKFB3 inhibitors," SLAS Discovery: Advancing Life Sciences R&D, 2018, 23(1), 11-22.

* cited by examiner

C

D

A

MAP4K4 INHIBITORS

CROSS-REFERENCE TO RELATED APPLICATIONS

This application is a U.S. National Phase Application of PCT International Application No. PCT/GB2018/052936, filed on Oct. 12, 2018, which is an International Application of and claims the benefit of priority to British Patent Application No. 1716867.5, filed on Oct. 13, 2017, and British Patent Application No. 1813252.2, filed on Aug. 14, 2018.

This invention relates to compounds that may be useful as inhibitors of Mitogen-activated Protein Kinase Kinase Kinase Kinase-4 (MAP4K4). The invention also relates to the use of these compounds, for example in a method of treatment. There are also provided processes for producing compounds of the present invention and method of their use. In particular, the present invention relates to compounds of formula (I).

BACKGROUND

Heart disease remains the single commonest cause of death and disability worldwide and is projected to increase as the population ages, its socio-economic burden consequently rising for the foreseeable future. Cardiac muscle cell death is an instrumental component of both acute ischemic injury and also chronic heart failure. In preclinical models, the molecular and genetic dissection of cardiac cell death suggests potential nodal control points _ENREF_8, among them, signaling pathways controlled by mitogen-activated protein kinases (MAPKs), especially Jun N-terminal Kinase (JNK) and p38 MAPK (Dorn, 2009; Fiedler et al., 2014; Rose et al., 2010; Whelan et al., 2010). Directly suppressing cardiomyocyte death is logical; however, no clinical counter-measures target the relevant intracellular pathways. Furthermore, to date few human trials for heart disease seek to enhance cardiomyocyte survival directly _ENREF_11, and several promising strategies have failed (Hausenloy and Yellon, 2015; Heusch, 2013; Newby et al., 2014a; Piot et al., 2008).

Human induced pluripotent stem cell-derived cardiomyocytes (hiPSC-CM) have already gained wide acceptance as predictive in the case of cardiotoxicity and patient-specific pathways, and provide a potentially transformative means to enhance target validation and improve cardiac drug discovery (Bellin et al., 2012; Blinova et al., 2017; Mathur et al., 2015; Matsa et al., 2014) _ENREF_14.

Because the "terminal" MAPKs p38 and JNK receive inputs from multiple signals, both protective and adverse, it is logical to consider targeting specific proximal kinases that might couple these MAPKs to cell death more selectively. MAP kinase kinase kinase kinases (MAP4Ks) are the most proximal protein kinases in the MAPK superfamily. MAP4K4 (HPK/GCK-like Kinase [HGK]; NCK-Interacting Kinase [NIK]) is a serine-threonine kinase related to Ste20 in *S. cerevisiae*. Like their yeast orthologue, the mammalian Ste20 kinases control cell motility, fate, proliferation and stress responses (Dan et al., 2001). With the cloning of human MAP4K4 came the first such evidence, namely, a key role coupling pro-inflammatory cytokines to JNK (Yao et al., 1999). MAP4K4 is now appreciated as a mediator of inflammation, cytoskeletal function, and, notably, cell death, with well-established contributions to cancer and diabetes (Chen et al., 2014; Lee et al., 2017a; Miled et al., 2005; Vitorino et al., 2015; Yang et al., 2013; Yue et al., 2014).

A pathobiological role for MAP4K4 has been suggested by its engagement of transforming growth factor-β-activated kinase-1 (TAK1/MAP3K7), JNK (Yao et al., 1999) and p38 MAPK (Zohn et al., 2006), these downstream MAPKs all having reported pro-death functions in cardiac muscle cells (Fiedler et al., 2014; Jacquet et al., 2008; Rose et al., 2010; Zhang et al., 2000). By contrast, the Raf-MEK-ERK pathway is cardioprotective (Fiedler et al., 2014; Lips et al., 2004; Rose et al., 2010).

Mitogen-activated Protein Kinase Kinase Kinase Kinase-4 (MAP4K4) is activated in failing human hearts and relevant rodent models. Using human induced pluripotent stem cell-derived cardiomyocytes (hiPSC-CM), we demonstrate that death induced by oxidative stress requires MAP4K4. Notably, gene silencing by means of MAP4K4 short hairpin RNA confers protection to hiPSC-CMs. Thus, we demonstrate MAP4K4 to be a relevant target in cardiac injury.

Certain embodiments of the present invention aim to provide pharmacological MAP4K4 inhibitors. An aim of the present invention is to rescue cell survival, mitochondrial function, and calcium cycling in cardiomyocytes. The present invention specifically aims to suppress human cardiac muscle cell death. The present invention further has the aim of reducing injury during "heart attacks" (ischemic injury or ischemia-reperfusion injury) for example in the adult human heart. Certain embodiments of the present invention provide selective modulation of MAP4K4 over other kinases and biological targets. In certain embodiments, the compounds of the present invention provide selectivity towards MAP4K4 over the kinases listed in Table 34, presented in the experimental section. Certain embodiments seek to achieve one or more of the aims discussed herein.

The present invention provides pharmacological inhibitors of MAP4K4, and demonstrates that inhibiting MAP4K4 effectively protects both the intact adult myocardium and, specifically, cardiomyocytes from injury. Further suggested functions of MAP4K4 in disease and, hence, therapeutic indications for a MAP4K4 inhibitor, include neurodegeneration and skeletal muscle disorders (Loh et al., 2008; Yang et al., 2013; Schroder et al., 2015; Wang et al., 2013).

BRIEF SUMMARY OF THE DISCLOSURE

In accordance with the present inventions there is provided a compound of formula (I) or a pharmaceutically acceptable salt thereof:

(I)

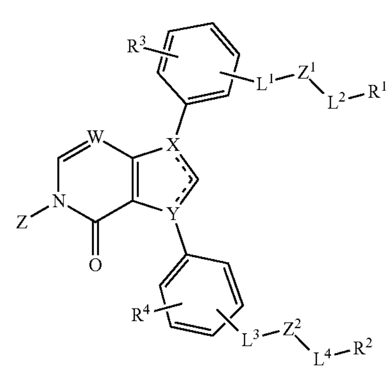

wherein

W is CH or N:

either X is N and Y is C, or Y is N and X is C;

Z is either H or —$CH_2OP(=O)(OH)_2$;

$L^1$ and $L^3$ are independently selected from a bond, —$(CR^aR^b)_m$—, —$O(CR^aR^b)_m$— or —$NH(CR^aR^b)_m$—, wherein m is at each occurrence independently selected from 1, 2, 3, or 4;

$Z^1$ is a bond, —$NR^{5a}$—, —O—, —C(O)—, —$SO_2$—, —$SO_2NR^{5a}$—, —$NR^{5a}SO_2$—, —$C(O)NR^{5a}$—, —$NR^{5a}C(O)$—, —C(O)O—, or —$NR^{5a}C(O)NR^{5a}$—;

$Z^2$ is a bond, —$NR^{5b}$—, —O—, —C(O)—, —$SO_2$—, —$SO_2NR^{5a}$—, —$NR^{5a}SO_2$—, —$C(O)NR^{5a}$—, —$NR^{5b}C(O)$—, or —C(O)O—;

$L^2$ and $L^4$ are independently either a bond or —$(CR^cR^d)_n$—, wherein n is at each occurrence independently selected from 1, 2, 3, or 4;

$R^1$ is selected from H, halo, $C_{1-6}$ alkyl, $C_{2-6}$ alkenyl, $C_{1-6}$ haloalkyl, —$NR^{6a}R^{6b}$, —$OR^{6a}$, —$OP(=O)(OH)_2$, —$C(O)R^{6a}$, 5 or 6 membered heteroaryl rings, or 3 to 8 membered heterocycloalkyl ring systems, wherein the heteroaryl and heterocycloalkyl rings are unsubstituted or substituted with 1 or 2 groups selected from: oxo, halo, $OR^{6a}$, $C_{1-6}$ alkyl, $C_{1-6}$ alkyl substituted with $NR^{6a}R^{6b}$, $C_{1-6}$ alkyl substituted with $OR^{6a}$, —$C(O)R^7$, and —$NR^8C(O)R^7$;

$R^2$ is selected from H, halo, $C_{1-6}$ alkyl, $C_{2-6}$ alkenyl, $C_{1-6}$ haloalkyl, —$NR^{6a}R^{6b}$, —$OR^{6a}$, —$OP(=O)(OH)_2$, —$C(O)R^{6a}$, —$NR^{5b}C(O)O$—$C_{1-6}$ alkyl, phenyl, 5 or 6 membered heteroaryl rings, or 3 to 8 membered heterocycloalkyl ring systems, wherein the phenyl, heteroaryl and heterocycloalkyl rings are unsubstituted or substituted with 1 or 2 groups selected from: oxo, halo, $OR^{6a}$, $C_{1-6}$ alkyl, $C_{1-6}$ alkyl substituted with $NR^{6a}R^{6b}$, $C_{1-6}$ alkyl substituted with $OR^{6a}$, —$C(O)OR^9$, and —$NR^8C(O)R^7$;

$R^3$ and $R^4$ are independently selected from H, halo, —CN and $C_{1-6}$ alkyl;

$R^{5a}$ and $R^{5b}$ are independently selected at each occurrence, from: H, $C_{1-6}$ alkyl, or $C_{3-6}$ cycloalkyl;

$R^6$ and $R^{6b}$ are, independently selected at each occurrence, from: H, $C_{1-6}$ alkyl, $C_{1-6}$ alkyl substituted with —$OR^e$, $C_{1-6}$ alkyl substituted with —$NR^eR^f$, and $C_{3-6}$ cycloalkyl;

$R^7$ is selected from H, —$OR^9$, $C_{1-6}$ alkyl and $C_{3-6}$ cycloalkyl;

$R^8$ is selected from H and $C_{1-6}$ alkyl;

$R^a$, $R^b$, $R^c$ and $R^d$ are, at each occurrence, independently selected from: H, halo, $C_{1-6}$ alkyl, and —$OR^h$, or $R^a$ and $R^b$ or $R^c$ and $R^d$ taken together with the atom to which they are attached form a 3 to 6 membered cycloalkyl ring or a 3 to 6 membered heterocycloalkyl ring containing 1 or 2 O, N or S atoms, wherein the cycloalkyl ring is unsubstituted or substituted with 1 or 2 halo groups; and $R^e$, $R^f$, $R^g$ and $R^h$ are each independently selected at each occurrence from H or $C_{1-6}$ alkyl, with the proviso that the compound of formula (I) is not a compound selected from:

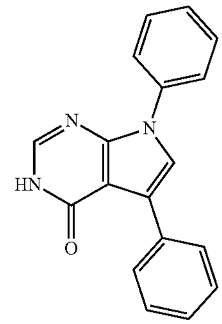
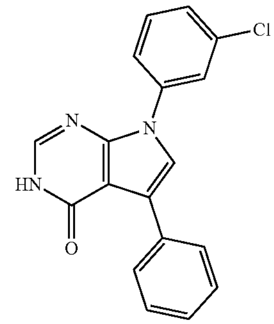
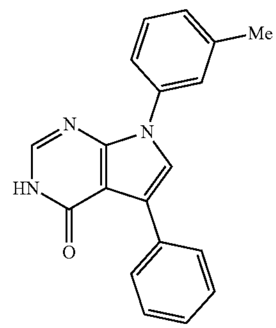
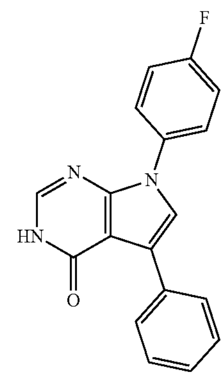
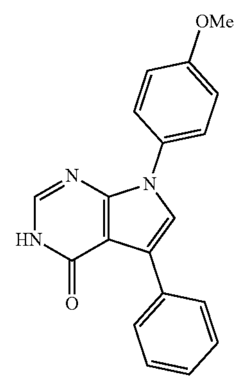
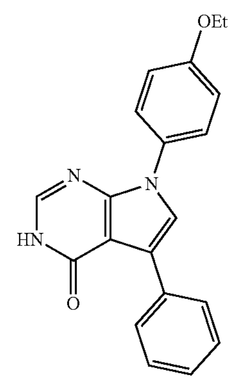
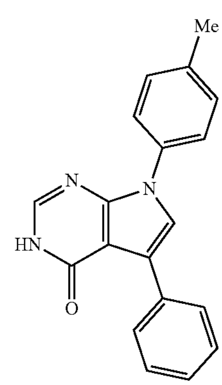
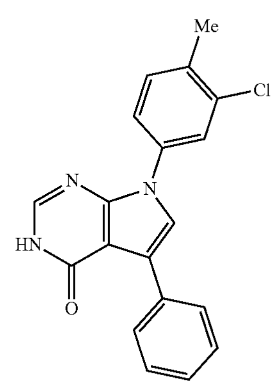

-continued
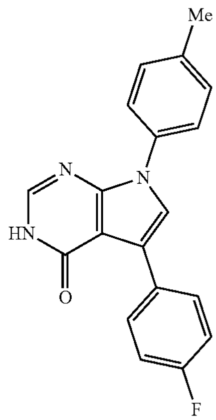
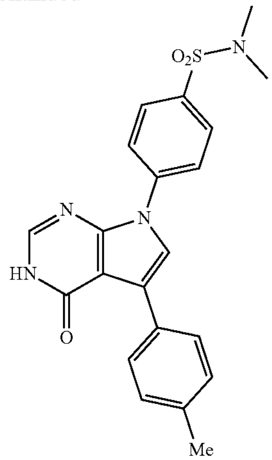
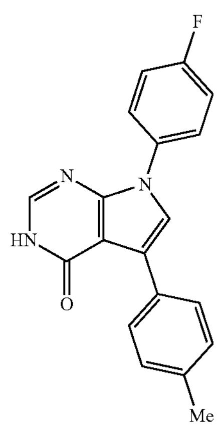
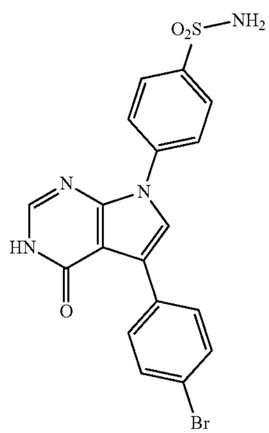
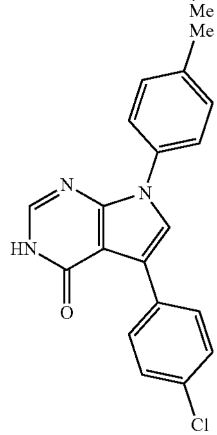
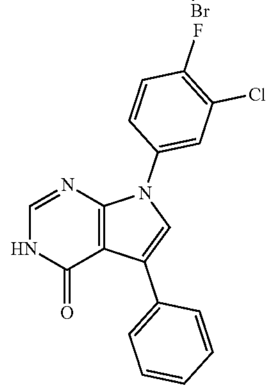
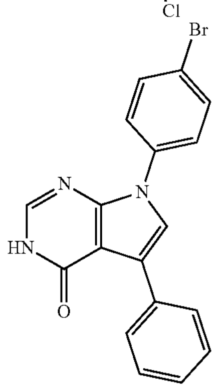
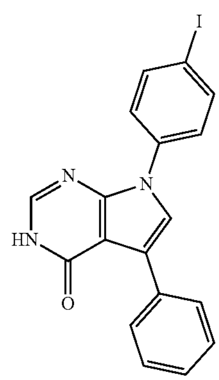
-continued
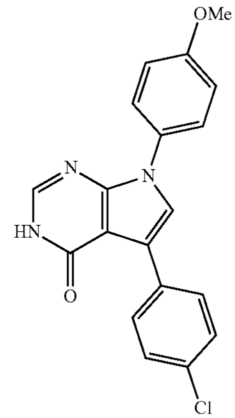
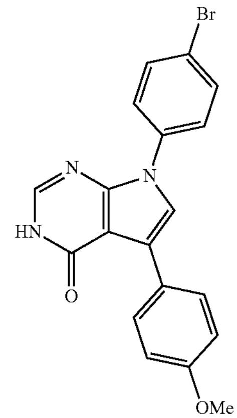
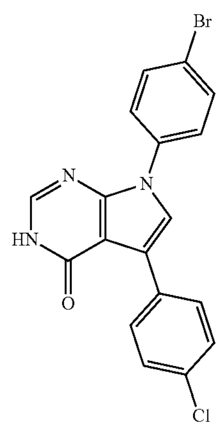
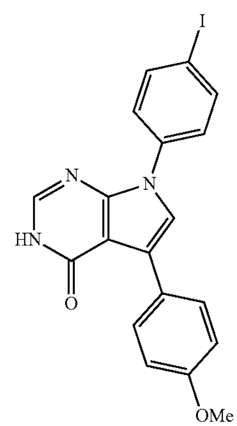
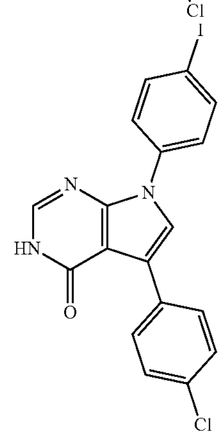
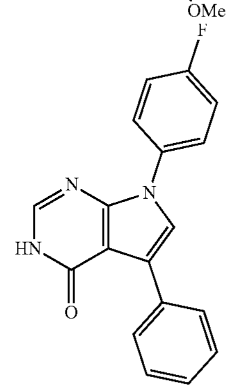
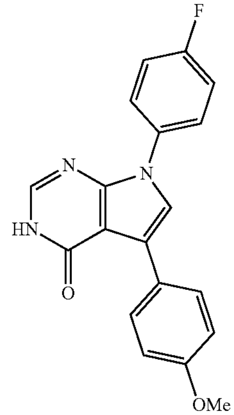
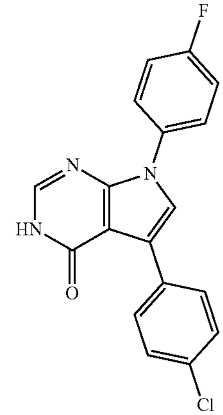

-continued
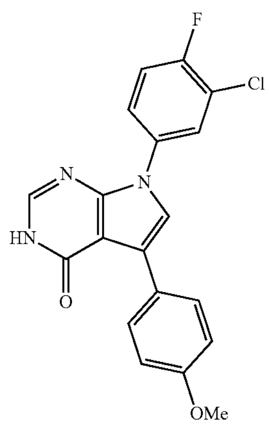
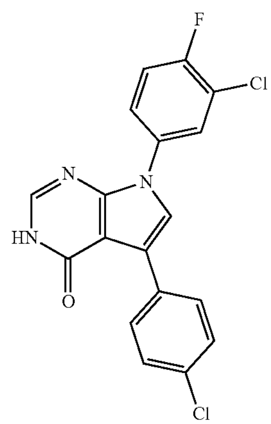
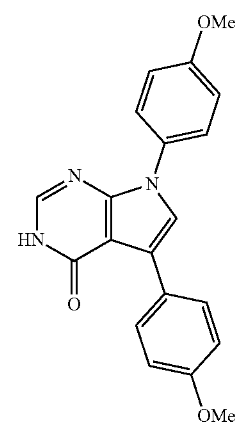
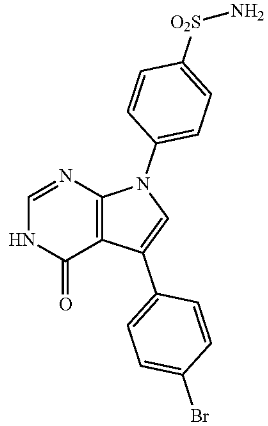
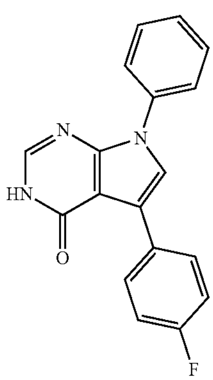
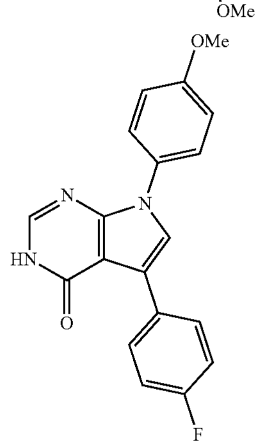
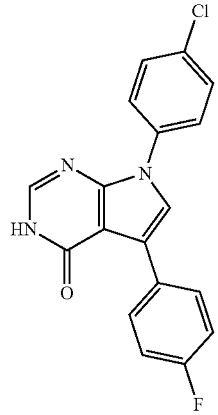
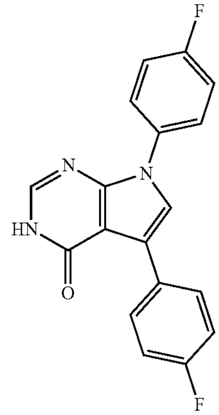
-continued
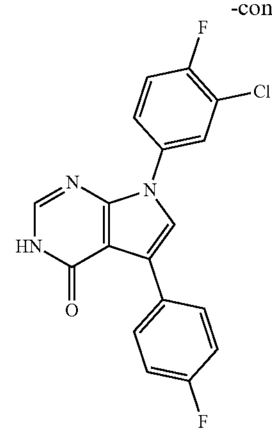
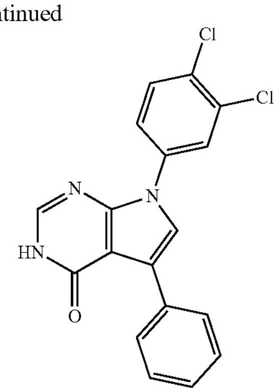
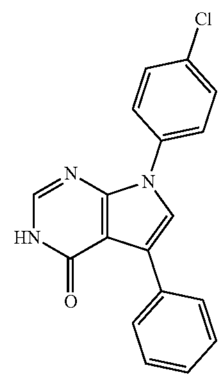
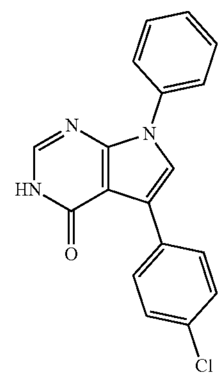
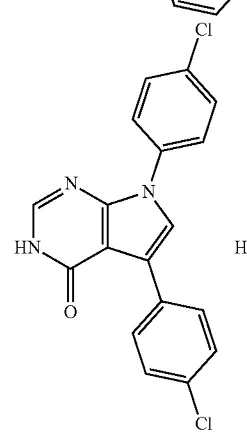
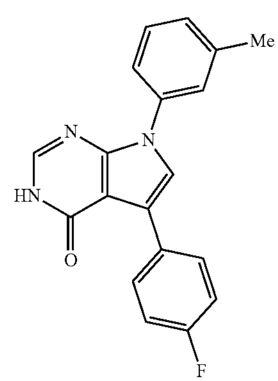
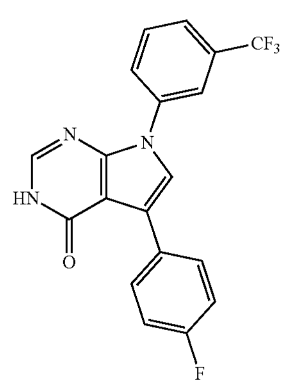
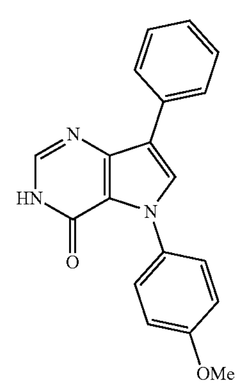

-continued

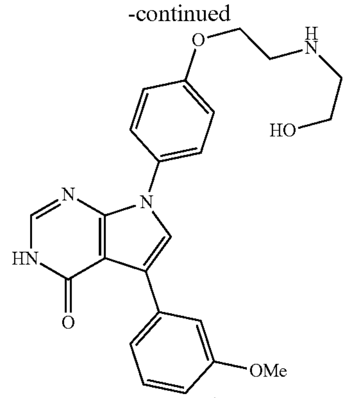

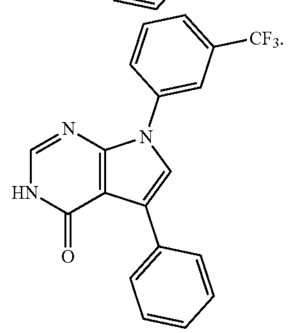

In an embodiment of the present invention the compound of formula (I) is a compound according to formula (I') or a pharmaceutically acceptable salt thereof:

(I')

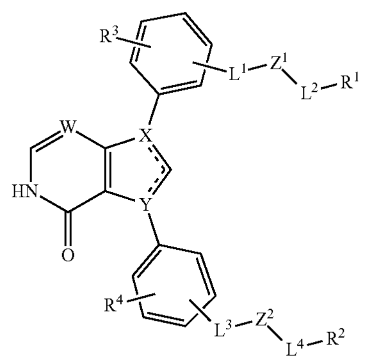

wherein either X is N and Y is C, or Y is N and X is C;

$L^1$ and $L^3$ are independently selected from a bond, —$(CR^aR^b)_m$—, —$O(CR^aR^b)_m$— or —$NH(CR^aR^b)_m$—, wherein m is at each occurrence independently selected from 1, 2, 3, or 4;

$Z^1$ is a bond, —$NR^{5a}$—, —O—, —C(O)—, —$SO_2$—, —$SO_2NR^{5a}$—, —$NR^{5a}SO_2$—, —$C(O)NR^{5a}$—, —$NR^{5a}C(O)$—, —C(O)O—, or —$NR^{5a}C(O)NR^{5a}$—;

$Z^2$ is a bond, —$NR^{5b}$—, —O—, —C(O)—, —$SO_2$—, —$SO_2NR^{5a}$—, —$NR^{5a}SO_2$—, —$C(O)NR^{5a}$—, —$NR^{5b}C(O)$—, or —C(O)O—;

$L^2$ and $L^4$ are independently either a bond or —$(CR^cR^d)_n$—, wherein n is at each occurrence independently selected from 1, 2, 3, or 4;

$R^1$ is selected from H, halo, $C_{1-6}$ alkyl, $C_{2-6}$ alkenyl, $C_{1-6}$ haloalkyl, —$NR^{6a}R^{6b}$, —$OR^{6a}$, —$C(O)R^{6a}$, 5 or 6 membered heteroaryl rings, or 3 to 8 membered heterocycloalkyl ring systems, wherein the heteroaryl and heterocycloalkyl rings are unsubstituted or substituted with 1 or 2 groups selected from: $C_{1-6}$ alkyl, oxo, halo, $OR^{6a}$, $C_{1-6}$ alkyl, $C_{1-6}$ alkyl substituted with $NR^{6a}R^{6b}$, $C_{1-6}$ alkyl substituted with $OR^{6a}$, —$C(O)R^7$, and —$NR^8C(O)R^7$;

$R^2$ is selected from H, halo, $C_{1-6}$ alkyl, $C_{2-6}$ alkenyl, $C_{1-6}$ haloalkyl, —$NR^{6a}R^{6b}$, —$OR^{6a}$, —$C(O)R^{6a}$, —$NR^{5b}C(O)O$—$C_{1-6}$ alkyl, phenyl, 5 or 6 membered heteroaryl rings, or 3 to 8 membered heterocycloalkyl ring systems, wherein the phenyl, heteroaryl and heterocycloalkyl rings are unsubstituted or substituted with 1 or 2 groups selected from: oxo, halo, $OR^{6a}$, $C_{1-6}$ alkyl, $C_{1-6}$ alkyl substituted with $NR^{6a}R^{6b}$, $C_{1-6}$ alkyl substituted with $OR^{6a}$, —$C(O)OR^9$, and —$NR^8C(O)R^7$;

$R^3$ and $R^4$ are independently selected from H, halo, —CN and $C_{1-6}$ alkyl;

$R^{5a}$ and $R^{5b}$ are independently selected at each occurrence, from: H, $C_{1-6}$ alkyl, or $C_{3-6}$ cycloalkyl;

$R^{6a}$ and $R^{6b}$ are, independently selected at each occurrence, from: H, $C_{1-6}$ alkyl, $C_{1-6}$ alkyl substituted with —$OR^e$, $C_{1-6}$ alkyl substituted with —$NR^eR^f$, and $C_{3-6}$ cycloalkyl;

$R^7$ is selected from H, —$OR^9$, $C_{1-6}$ alkyl and $C_{3-6}$ cycloalkyl;

$R^8$ is selected from H and $C_{1-6}$ alkyl;

$R^a$, $R^b$, $R^c$ and $R^d$ are, at each occurrence, independently selected from: H, halo, $C_{1-6}$ alkyl, and —$OR^h$, or $R^a$ and $R^b$ or $R^c$ and $R^d$ taken together with the atom to which they are attached form a 3 to 6 membered cycloalkyl ring or a 3 to 6 membered heterocycloalkyl ring containing 1 or 2 O, N or S atoms, wherein the cycloalkyl ring is unsubstituted or substituted with 1 or 2 halo groups; and $R^e$, $R^f$, $R^g$ and $R^h$ are each independently selected at each occurrence from H or $C_{1-6}$ alkyl, with the proviso that the compound of formula (I) is not a compound as defined above.

In embodiments the compounds of the invention have the proviso that when Y is N and X is C then -$L^3$-$Z^2$-$L^4$-$R^2$ cannot be OMe when -L-$Z^1$-$L^2$-$R^1$ is H and when X is N and Y is C then -$L^1$-$Z^1$-$L^2$-$R^1$ cannot be H, halo, methyl, trifluoromethyl, OMe, OEt, —$OCH_2CH_2NHCH_2CH_2OH$, —$SO_2NH_2$, or $SO_2NMe_2$ when -$L^3$-$Z^2$-$L^4$-$R^2$ is H, halo, methyl, or OMe.

In embodiments the compounds of the invention have the proviso that when Y is N, X is C, W is N, $R^3$ is H and $R^4$ is H then -$L^3$-$Z^2$-$L^4$-$R^2$ cannot be OMe when -$L^1$-$Z^1$-$L^2$-$R^1$ is H and when X is N, Y is C, W is N, $R^3$ is H and $R^4$ is H then -$L^1$-$Z^1$-$L^2$-$R^1$ cannot be H, halo, methyl, trifluoromethyl, OMe, OEt, —$OCH_2CH_2NHCH_2CH_2OH$, —$SO_2NH_2$, or $SO_2NMe_2$ when -$L^3$-$Z^2$-$L^4$-$R^2$ is H, halo, methyl, or OMe.

In embodiments the compounds of the invention have the proviso that (optionally if $R^3$ is H and $R^4$ is H then) -$L^1$-$Z^1$-$L^2$-$R^1$ and -$L^3$-$Z^2$-$L^4$-$R^2$ cannot be selected from the following definitions at the same time:

-$L^1$-Z-$L^2$-$R^1$ cannot be selected from: H, halo, $C_{1-6}$ alkyl, —$SO_2NR^{6a}R^{6b}$, or —O—$C_{1-6}$ alkyl; and -$L^3$-$Z^2$-$L^4$-$R^2$ cannot be selected from: H, halo, $C_{1-6}$ alkyl, —$SO_2NR^{6a}R^{6b}$, or —O—$C_{1-6}$ alkyl.

The dotted bonds in formula (I) represent the possibility for a double bond to be present. As the skilled person will appreciate both dotted bonds cannot represent a double bond at the same time; one dotted bond will be a double bond whilst the other bill be a single bond. The double bond will originate from X or Y when X or Y is C. For the avoidance of doubt, compounds of formula (I) may be compounds of formulae (Ia) or (Ib) which demonstrate the two possible configurations for the dotted bonds in formula (I):

(Ia)

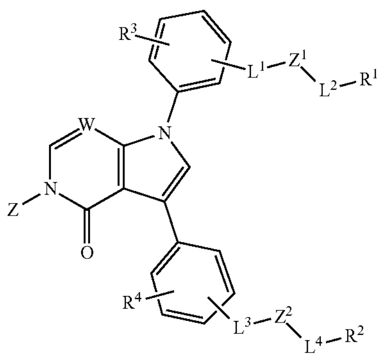

(Ib)

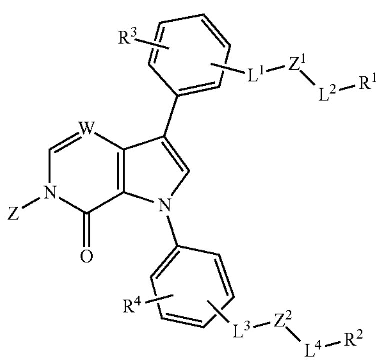

In embodiments $L^1$ is represented by a bond or —$CH_2$—.

In embodiments $Z^1$ is a bond, —O—, —C(O)—, —$SO_2$—, or —$NR^{5a}C(O)$—.

In embodiments $L^2$ is bond, —$CH_2$—, —$CH_2CH_2$—, —$(CH_2)_3$—, —$CH_2CH(OH)CH_2$— or

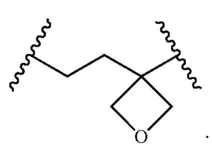 [SMILES: *CCC1(*)COC1]

.

In embodiments $R^1$ is selected from H, halo, $C_{1-6}$ alkyl, $C_{2-6}$ alkenyl, $C_{1-6}$ haloalkyl, —$NR^{6a}R^{6b}$, —$OR^{6a}$, 5 or 6 membered heteroaryl rings, or 3 to 8 membered heterocycloalkyl ring systems (optionally 4, 5 or 6 membered), wherein the heteroaryl and heterocycloalkyl rings are unsubstituted or substituted with 1 or 2 groups selected from: $C_{1-6}$ alkyl, —$OR^{6a}$ and oxo.

In embodiments $L^1$ is represented by a bond or —$CH_2$—; $Z^1$ is a bond, —O—, —C(O)—, —$SO_2$—, or —$NR^{5a}C(O)$—; $L^2$ is bond, —$CH_2$—, —$CH_2CH_2$—, —$(CH_2)_3$—, —$CH_2CH(OH)CH_2$— or

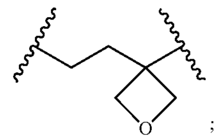 [SMILES: *CCC1(*)COC1]

;

and $R^1$ is selected from H, halo, $C_{1-6}$ alkyl, $C_{2-6}$ alkenyl, —$NR^{6a}R^{6b}$, —$OR^{6a}$, 5 or 6 membered heteroaryl rings, or 3 to 8 membered heterocycloalkyl ring systems (optionally 4, 5 or 6 membered), wherein the heteroaryl and heterocycloalkyl rings are unsubstituted or substituted with 1 or 2 groups selected from: $C_{1-6}$ alkyl, —$OR^{6a}$ and oxo.

In embodiments $L^1$ is represented by a bond.

In embodiments $Z^1$ is represented by a bond or —O—.

In embodiments $L^2$ is a bond, —$CH_2$—, —$CH_2CH_2$—, —$(CH_2)_3$—, or —$CH_2CH(OH)CH_2$—.

In embodiments $R^1$ is selected from H, halo, $C_{1-6}$ alkyl, —$NR^{6a}R^{6b}$ or —$OR^{6a}$. Optionally, $R^{6a}$ and $R^{6b}$ may be independently selected from: H or $C_{1-6}$ alkyl.

In embodiments $R^1$ is H, —$CF_3$, $CHF_2$, F, —OH, or —$NMe_2$.

In embodiments $L^1$ is represented by a bond; $Z^1$ is represented by a bond or —O—; $L^2$ is bond, —$CH_2$—, —$CH_2CH_2$—, —$(CH_2)_3$—, or —$CH_2CH(OH)CH_2$—; and $R^1$ is selected from H, halo, —$NR^{6a}R^{6b}$, or —$OR^6$. Optionally, $R^{6a}$ and $R^{6b}$ may be independently selected from: H or $C_{1-6}$ alkyl, optionally $R^1$ is H, —$CF_3$, $CHF_2$, F, —OH, or —$NMe_2$.

In embodiments $R^3$ is H, F, or CN.

In embodiments $L^3$ is represented by a bond or —$CH_2$—.

In embodiments $Z^2$ is a bond, —$NR^{5b}$—, —O—, —C(O)—, or —$NR^{5a}C(O)$—.

In embodiments $L^4$ is represented by a bond, —$CH_2$—, —$CH_2CH_2$—, —$CH_2C(Me)_2$-, —$CH(Me)CH_2$—, —$CH_2CH_2C(Me)_2$-, —$(CH_2)_3$—, —$CH_2CH(OH)CH_2$—, —$CH_2CH(OMe)CH_2$—, —$CH_2CH(Me)$-, —$CH_2CH(OH)CH(OH)$—, —$CH_2CH_2CH(OH)$—, —$CF_2CH_2$—, —$CH_2CH(CH_3)_2CH_2$—, —$CH_2CH(OH)C(Me)_2$-, or

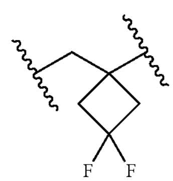

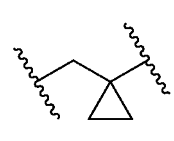

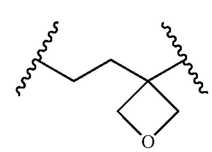

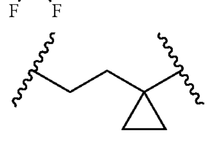

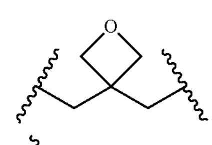

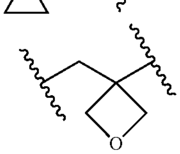

.

In embodiments $R^2$ is selected from: H, halo, $C_{1-6}$ alkyl, $C_{2-6}$ alkenyl, —$NR^{6a}R^{6b}$, —$OR^6$, —$C(O)R^{6a}$, —$NR^{5b}C(O)O$—$C_{1-6}$ alkyl, and 3 to 8 membered heterocycloalkyl ring systems, wherein the heterocycloalkyl rings are unsubstituted or substituted with 1 or 2 groups selected from: oxo, halo, $OR^{6a}$, $C_{1-6}$ alkyl, $C_{1-6}$ alkyl substituted with $NR^{6a}R^{6b}$, $C_{1-6}$ alkyl substituted with $OR^{6a}$, —$C(O)R^7$, and —$NR^8C(O)R^7$.

In embodiments $L^3$ is represented by a bond or —$CH_2$—; $Z^2$ is a bond, —$NR^{5b}$—, —O—, —C(O)—, or —$NR^{5a}$C(O)—; $L^4$ is represented by a bond, —$CH_2$—, —$CH_2CH_2$—, —$CH_2C(Me)_2$-, —$CH_2CH_2C(Me)_2$-, —$(CH_2)_3$—, —$CH_2CH(OH)CH_2$— or —$CH_2CH(OMe)CH_2$—; and $R^2$ is selected from: H, halo, $C_{1-6}$ alkyl, $C_{2-6}$ alkenyl, —$NR^{6a}R^{6b}$, —$OR^{6a}$, —C(O)$R^{6a}$, —$NR^{5b}$C(O)O—$C_{1-6}$ alkyl, and 3 to 8 membered heterocycloalkyl ring systems, wherein the heterocycloalkyl rings are unsubstituted or substituted with 1 or 2 groups selected from: oxo, halo, $OR^{6a}$, $C_{1-6}$ alkyl, $C_{1-6}$ alkyl substituted with $NR^{6a}R^{6b}$, $C_{1-6}$ alkyl substituted with ORS, —C(O)$R^7$, and —$NR^8$C(O)$R^7$.

In embodiments $L^3$ is represented by a bond.

In embodiments $Z^2$ is a bond or —O—.

In embodiments $L^4$ is represented by a bond, —$CH_2CH_2$—, —$CH_2CH(OH)CH_2$—, —$CH_2CH_2C(Me)_2$-, or —$(CH_2)_3$—.

In embodiments $R^2$ is selected from: —$OR^{6a}$, —OP(=O)$(OH)_2$, —$NR^{6a}R^{6b}$, and 3 to 8 membered heterocycloalkyl ring systems wherein the heterocycloalkyl rings are unsubstituted or substituted with 1 or 2 groups selected from: oxo, $OR^{6a}$, $C_{1-6}$ alkyl, $C_{1-6}$ alkyl substituted with $NR^{6a}R^{6b}$, and $C_{1-6}$ alkyl substituted with $OR^{6a}$. Optionally, $R^{6a}$ and $R^{6b}$ may be independently selected from: H or $C_{1-6}$ alkyl.

In embodiments $L^3$ is represented by a bond; $Z^2$ is a bond or —O—; $L^4$ is represented by a bond, —$CH_2CH_2$—, —$CH_2CH(OH)CH_2$—, —$CH_2CH_2C(Me)_2$-, or —$(CH_2)_3$—; and $R^2$ is selected from: —$OR^6$, —OP(=O)$(OH)_2$, —$NR^{6a}R^{6b}$, and 3 to 8 membered (optionally 5 or 6 membered) heterocycloalkyl ring systems wherein the heterocycloalkyl rings are unsubstituted or substituted with 1 or 2 groups selected from: oxo, $OR^{6a}$, $C_{1-6}$ alkyl, $C_{1-6}$ alkyl substituted with $NR^{6a}R^{6b}$, and $C_{1-6}$ alkyl substituted with $OR^{6a}$. Optionally, $R^{6a}$ and $R^{6b}$ may be independently selected from: H or $C_{1-6}$ alkyl.

In embodiments the 1 or 2 substituents on the heterocycloalkyl rings of $R^2$ is independently selected from: oxo, methyl, ethyl, OH, OMe, —$CH_2C(Me)_2OH$, -ethyl substituted with OH, and ethyl substituted with $NMe_2$.

In embodiments $R^2$ is selected from: H, Me, —OP(=O)$(OH)_2$, —OMe, —OH, —OEt, —$NH_2$, —NHMe, —$NMe_2$, —NHC(O)O-tert-butyl, imidazolyl, morphonlinyl, N-methyl-piperazinyl, pyrrolidinone, piperidinone, imidazolidinone, N-methyl imidazolidinone, azetidinyl, N-methyl azetidinyl, morphlinone, or

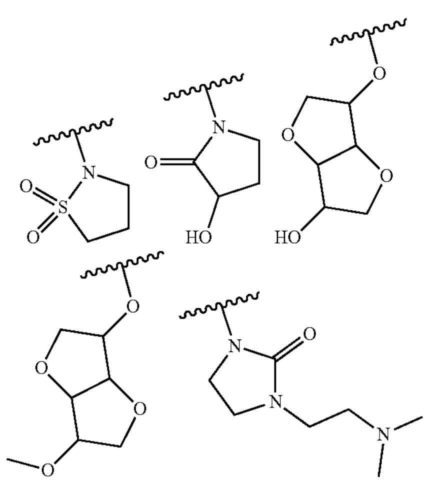

-continued

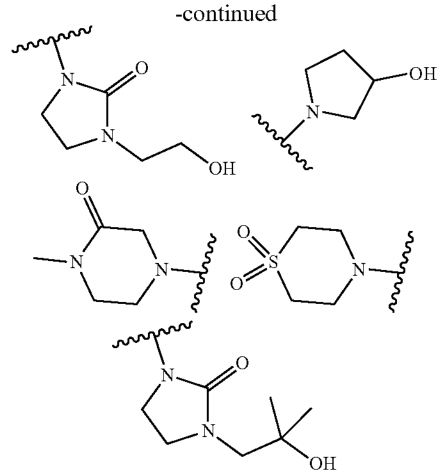

In embodiments $L^3$ is represented by a bond; $Z^2$ is a bond or —O—; $L^4$ is represented by a bond, —$CH_2CH_2$—, —$CH_2CH(OH)CH_2$—, —$CH_2CH_2C(Me)_2$-, or —$(CH_2)_3$—; and $R^2$ is selected from: H, Me, —OP(=O)$(OH)_2$, —OMe, —OH, —OEt, —$NH_2$, —NHMe, —$NMe_2$, —NHC(O)O-tert-butyl, imidazolyl, morphonlinyl, N-methyl-piperazinyl, pyrrolidinone, piperidinone, imidazolidinone, N-methyl imidazolidinone, azetidinyl, N-methyl azetidinyl, morphlinone, or

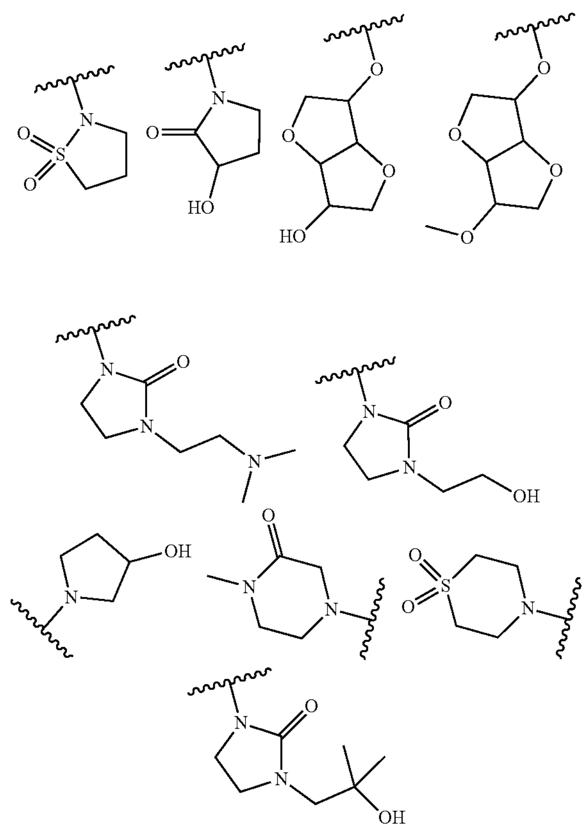

wherein the heterocycloalkyl rings are unsubstituted or substituted with 1 or 2 groups selected from: oxo, methyl, ethyl, OH, OMe, -ethyl substituted with OH, and ethyl substituted with $NMe_2$.

In embodiments compounds of formula (I) may be compounds of formulae (IIa) or (IIb):

(IIa)

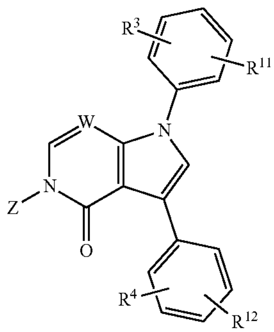

(IIb)

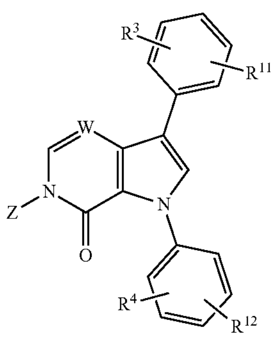

wherein $R^{11}$ is selected from: H, halo, $C_{1-6}$ alkyl, —O—$C_{1-6}$ haloalkyl, $C_{2-6}$ alkenyl, —$(CH_2)_oR^Y$, —$(CH_2)_oNR^ZR^{6a}$, —$(CH_2)_oOR^Z$, —$(CH_2)_oSO_2R^{6a}$, —$(CH_2)_oSO_2NR^{6a}R^{6b}$, —$(CH_2)_oC(O)NR^ZR^6$, —$(CR^aR^b)_pOP(=O)(OH)_2$ or —$(CH_2)_oC(O)OR^Z$, $R^Y$ is selected from 5 or 6 membered heteroaryl rings or 5 or 6 membered heterocycloalkyl rings, wherein the heteroaryl and heterocycloalkyl rings are unsubstituted or substituted with 1 or 2 groups selected from: oxo, halo, $OR^{6a}$, $C_{1-6}$ alkyl, $C_{1-6}$ alkyl substituted with $NR^{6a}R^{6b}$, $C_{1-6}$ alkyl substituted with $OR^6$, —$C(O)R^7$, and —$NR^8C(O)R^7$;

$R^Z$ is selected from H, $C_{1-6}$ alkyl, —$C(O)R^{6a}$, —$C(O)OR^{6a}$, —$C(O)(CR^aR^b)_pNR^{6a}R^{6b}$, $(CR^aR^b)_pOR^{6a}$, $(CR^aR^b)_pNR^{6a}R^{6b}$, $(CR^aR^b)_pR^V$; and $R^V$ is selected from 3 to 8 membered heterocycloalkyl ring systems, wherein the heterocycloalkyl ring is unsubstituted or substituted with 1 or 2 groups selected from: oxo, $C_{1-6}$ alkyl or halo, and $R^{12}$ is selected from: H, halo, $C_{1-6}$ alkyl, $C_{2-6}$ alkenyl, —$(CH_2)_oR^{Y2}$, —$(CH_2)_oNR^{Z2}R^{6a}$, —$(CH_2)_oOR^{Z2}$, —$(CH_2)_oC(O)NR^{Z2}R^{6a}$, —$(CR^aR^b)_pOP(=O)(OH)_2$ or —$(CH_2)_oC(O)OR^{Z2}$, $R^{Y2}$ is selected from 5 or 6 membered heteroaryl rings or 5 or 6 membered heterocycloalkyl rings, wherein the phenyl, heteroaryl and heterocycloalkyl rings are unsubstituted or substituted with 1 or 2 groups selected from: oxo, halo, $OR^{6a}$, $C_{1-6}$ alkyl, $C_{1-6}$ alkyl substituted with $NR^{6a}R^{6b}$, $C_{1-6}$ alkyl substituted with $OR^{6a}$, —$C(O)OR^9$, and —$NR^8C(O)R^7$;

$R^{Z2}$ is selected from H, $C_{1-6}$ alkyl, —$C(O)R^{6a}$, —$C(O)OR^{6a}$, —$C(O)(CR^aR^b)_nNR^{6a}R^{6b}$, $(CR^aR^b)_pOR^{6a}$, $(CR^aR^b)_pNR^{6a}R^{6b}$, $(CR^aR^b)_pR^{V2}$ or —$C(O)(CR^aR^b)_pR^{V2}$;

$R^{V2}$ is selected from 3 to 8 membered heterocycloalkyl ring systems, wherein the heterocycloalkyl ring is unsubstituted or substituted with 1 or 2 groups selected from: oxo, halo, $C_{1-6}$ alkyl, $C_{1-6}$ alkyl substituted with $NR^{6a}R^{6b}$, or $C_{1-6}$ alkyl substituted with $OR^{6a}$;

o is selected from 0, 1, 2 or 3; and p is selected from 0, 1, 2 or 3.

In embodiments $L^1$-$Z^1$-$L^2$-$R^1$ is $R^{11}$. Equally, $R^{11}$ may represent $L^1$-$Z^1$-$L^2$-$R^1$.

In embodiments $L^3$-$Z^2$-$L^4$-$R^2$ is $R^{12}$. Equally, $R^{12}$ may represent $L^3$-$Z^2$-$L^4$-$R^2$.

The skilled person will recognise that $L^1$-$Z^1$-$L^2$-$R^1$ or $R^{11}$ are substituted on to a phenyl ring. The phenyl ring is also substituted by the bicyclic ring that contains Y and X. Substitution of the -$L^1$-$Z^1$-$L^2$-$R^1$ or $R^{11}$ group on the phenyl ring is defined relative to the bicyclic ring containing Y and X. As such, $L^1$-$Z^1$-$L^2$-$R^1$ or $R^{11}$ may be substituted at the 2, 3 or 4 position of the phenyl ring (also referred to as the ortho, meta or para positions respectively).

Preferably, the -$L^1$-$Z^1$-$L^2$-$R^1$ or $R^{11}$ is substituted at the 3 or 4 position of the phenyl ring. Accordingly, compounds of formula (I) may be compounds of formulae (IIIa), where $R^{11}$ (or -$L^1$-$Z^1$-$L^2$-$R^1$ in place of $R^{11}$) is substituted at the 4 position, or (IIIb), where $R^{11}$ (or -$L^1$-$Z^1$-$L^2$-$R^1$ in place of $R^{11}$) is substituted at the 3 position:

(IIIa)

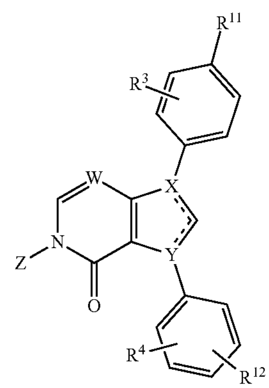

(IIIb)

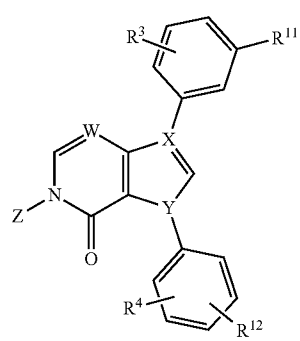

Equally, the skilled person will recognise that -$L^3$-$Z^2$-$L^4$-$R^2$ or $R^{12}$ are substituted on to a phenyl ring. The phenyl ring is also substituted by the bicyclic ring that contains Y and X. Substitution of the -$L^3$-$Z^2$-$L^4$-$R^2$ or $R^{12}$ group on the phenyl ring is defined relative to the bicyclic ring containing Y and X. As such, -$L^3$-$Z^2$-$L^4$-$R^2$ or $R^{12}$ may be substituted at the 2, 3 or 4 position of the phenyl ring (also referred to as the ortho, meta or para positions respectively).

Preferably, the -$L^3$-$Z^2$-$L^4$-$R^2$ or $R^{12}$ is substituted at the 3 or 4 position of the phenyl ring. Accordingly, compounds of formula (I) may be compounds of formulae (IVa), where $R^{12}$ (or -$L^3$-$Z^2$ $L^4$-$R^2$ in place of $R^{12}$) is substituted at the 4 position, or (IVb), where $R^{12}$ (or -$L^3$-$Z^2$-$L^4$-$R^2$ in place of $R^{12}$) is substituted at the 3 position:

(IVa)

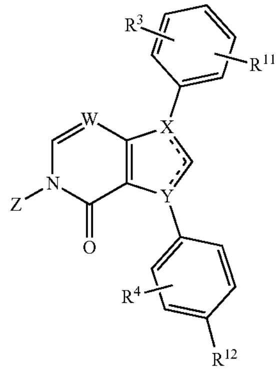

(IVb)

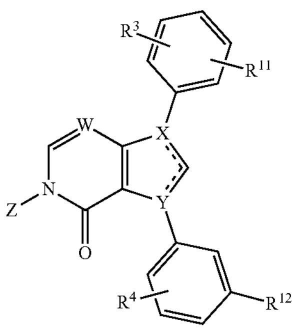

In embodiments $-L^1-Z^1-L^2-R^1$ or $R^{11}$ is selected from: H, halo, $—OR^{6a}$, $—(CR^aR^b)_m$-5 or 6 membered heteroaryl rings, $—SO_2—C_{1-6}$ alkyl, $—C(O)OR^{6a}$, $—C(O)NR^{6a}R^{6b}$, $—O(CR^aR^b)_n—NR^{6a}R^{6b}$, and $—O(CR^aR^b)_n$-3 to 8 membered heterocycloalkyl ring, wherein the heteroaryl and heterocycloalkyl rings are unsubstituted or substituted with 1 or 2 groups selected from: $C_{1-6}$ alkyl, oxo or halo. Optionally, $-L^3-Z^2-L^4-R^2$ or $R^{12}$ may also be H.

In embodiments $-L^1-Z^1-L^2-R^1$ or $R^{11}$ is selected from: H, halo, $—OR^{6a}$, $—O—C_{1-6}$ haloalkyl, $—(CR^aR^b)_o$-5 or 6 membered heteroaryl rings, $—(CR^aR^b)_o$-5 or 6 membered heteroaryl rings, $—SO_2—C_{1-6}$ alkyl, $—C(O)OR^{6a}$, $—C(O)NR^{6a}R^{6b}$, $—NR^{6a}C(O)R^{6a}$, $—(CH_2)_oSO_2NR^{6a}R^{6b}$, $—O(CR^aR^b)_n—NR^{6a}R^{6b}$, and $—O(CR^aR^b)_n$-3 to 8 membered heterocycloalkyl ring, —C(O)-3 to 8 membered heterocycloalkyl ring, wherein the heteroaryl and heterocycloalkyl rings are unsubstituted or substituted with 1 or 2 groups selected from: $C_{1-6}$ alkyl, oxo, $OR^{6a}$, or halo. Optionally, $-L^3-Z^2-L^4-R^2$ or $R^{12}$ may also be H.

Preferably, in embodiments $-L^1-Z^1-L^2-R^1$ or $R^{11}$ is selected from: H, halo, $—(CR^aR^b)_mOR^{6a}$, $—OR^{6a}$, and $—O(CR^aR^b)_m—NR^{6a}R^{6b}$.

Optionally, $-L^1-Z^1-L^2-R^1$ or $R^{11}$ is selected from: halo, $—(CR^aR^b)_mOR^{6a}$, $—OR^{6a}$, and $—O(CR^aR^b)_m—NR^{6a}R^{6b}$; and $-L^3-Z^2-L^4-R^2$ or $R^{12}$ are H.

In embodiments $-L^3-Z^2-L^4-R^2$ or $R^{12}$ is selected from: halo, $C_{1-6}$ alkyl, $C_{2-6}$ alkenyl, —CN, $—OR^6$, $—NR^{6a}R^{6b}$, $—(CR^aR^b)_m$-phenyl, $—(CR^aR^b)_m$-5 or 6 membered heteroaryl rings, $—(CR^aR^b)_mNR^{6a}R^{6b}$, $—(CR^aR^b)_mOR^{6a}$, $—(CR^aR^b)_mOC(O)R^{6a}$, $—(CR^aR^b)_mC(O)OR^{6a}$, $—(CR^aR^b)_m$ $C(O)NR^{6a}R^{6b}$, $(CR^aR^b)_mNR^{5a}C(O)—C_{1-6}$ alkyl, $—(CR^aR^b)_mNR^{5a}C(O)OR^{6a}$, $—O(CR^aR^b)_nOR^{6a}$, $—O(CR^aR^b)_nNR^{5b}C(O)OC_{1-6}$ alkyl, 3 to 8 membered heterocycloalkyl ring, $—O(CR^aR^b)_n$-3 to 8 membered heterocycloalkyl ring, $—O(CR^aR^b)_n—NR^{6a}R^{6b}$, $—NR^{5a}(CR^cR^d)_n OR^{6a}$, $—C(O)NR^{6a}R^{6b}$, $NR^{5b}C(O)—C_{1-6}$ alkyl, $—NR^{5b}C(O)(CR^cR^d)_nNR^{6a}R^{6b}$, $—NR^{5b}C(O)(CR^cR^d)_nOR^{6a}$, and $—NR^{5b}C(O)(CR^cR^d)_n$-3 to 8 membered heterocycloalkyl ring, wherein the phenyl, heteroaryl and heterocycloalkyl rings are unsubstituted or substituted with 1 or 2 groups selected from: oxo, halo, $OR^{6a}$, $C_{1-6}$ alkyl, $C_{1-6}$ alkyl substituted with $NR^{6a}R^{6b}$, $C_{1-6}$ alkyl substituted with $OR^{6a}$, $—C(O)R^7$, and $—NR^8C(O)R^7$. Optionally, $-L^1-Z^1-L^2-R^1$ or $R^{11}$ may be H.

Preferably, in embodiments $-L^3-Z^2-L^4-R^2$ or $R^{12}$ is selected from: $—O(CR^aR^b)_nOR^6$a; $—O(CR^aR^b)_n—NR^{6a}R^{6b}$; 3 to 8 membered heterocycloalkyl ring substituted with 1 or 2 groups selected from: oxo, $C_{1-6}$ alkyl, $C_{2-6}$ alkenyl, $C_{1-6}$ alkyl substituted with $NR^{6a}R^{6b}$, or $C_{1-6}$ alkyl substituted with $OR^{6a}$; $—O(CR^aR^b)_n$-3 to 8 membered heterocycloalkyl ring substituted with 1 or 2 groups selected from: oxo, or $C_{1-6}$ alkyl. Optionally, $-L^1-Z^1-L^2-R^1$ or $R^{11}$ may also be H.

In embodiments $L^1-Z^1-L^2-R^1$ or $R^{11}$ is selected from. H, F, —OMe, —C(O)OH, —C(O)OEt, —C(O)NHMe, $—C(O)NH_2$, $—SO_2Me$, $—CH_2$-imidazolyl $—O(CH_2)_3NMe_2$, $—OCH_2$-pyrolidinyl, $—OCH_2$—N-methylpyrolidinyl, $—O(CH_2)_3$-morpholinyl, or $—OCH_2CH(OH)CH_2$-morpholinyl.

In embodiments $L^1-Z^1-L^2-R^1$ or $R^{11}$ is selected from. H, Me, $C_1$, F, —OMe, $—CH_2OH$, —OH, $—OCF_3$, $—OCHF_2$, $—OCH_2C(Me)_2OP(=O)(OH)_2$, $—OCH_2CH_2C(Me)_2OP(=O)(OH)_2$, —C(O)OH, —C(O)OEt, —C(O)NHMe, $—C(O)NH_2$, $—SO_2Me$, $—SO_2NH_2$, $—C(O)NH_2$, —NHC(O)Me, $—C(O)NMe_2$, —C(O)—N-methyl piperazinyl, $—O(CH_2)_2OH$, $—CH_2$-imidazolyl $—O(CH_2)_3NMe_2$, $—OCH_2$-pyrolidinyl, $—OCH_2$—N-methylpyrolidinyl, $—O(CH_2)_3$-morpholinyl, $—OCH_2CH(OH)CH_2$-morpholinyl or

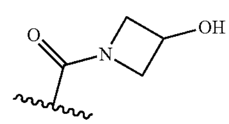

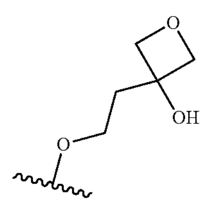

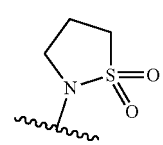

In embodiments $L^1-Z^1-L^2-R^1$ or $R^{11}$ is selected from H, —CN, —C(O)OH, —C(O)OEt, $—O(CH_2)_3NMe_2$, $—OCH_2$-pyrolidinyl, $—OCH_2$—N-methylpyrolidinyl, $—O(CH_2)_3$-morpholinyl, or $—OCH_2CH(OH)CH_2$-morpholinyl. Optionally, $L^1-Z-L^2-R^1$ or $R^{11}$ has the definition in the preceding sentence when X is C and Y is N.

In embodiments $L^1-Z^1-L^2-R^1$ or $R^{11}$ is selected from H, $—CH_2OH$, $—OCF_3$, $—OCHF_2$, $—SO_2NH_2$, —C(O)OH, —C(O)OEt, $—C(O)NH_2$, —NHC(O)Me, $—O(CH_2)_2OH$, $—O(CH_2)_3NMe_2$, $—OCH_2$-pyrolidinyl, $—OCH_2$—N-methylpyrolidinyl, $—O(CH_2)_3$-morpholinyl, or $—OCH_2CH(OH)CH_2$-morpholinyl or

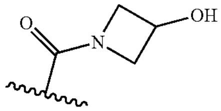
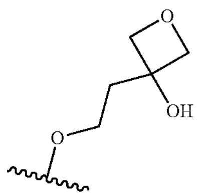

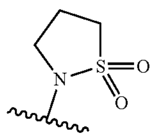

Optionally, $L^1$-Z-$L^2$-$R^1$ or $R^{11}$ has the definition in the preceding paragraph when X is C and Y is N. For example, in embodiments where the compounds are compounds of formula (Ib), $L^1$-$Z^1$-$L^2$-$R^1$ or $R^{11}$ is selected from the groups recited in this paragraph.

In embodiments -$L^1$-$Z^1$-$L^2$-$R^1$ or $R^{11}$ is selected from H, F, —OMe, —C(O)OH, —C(O)NHMe, —C(O)$NH_2$, —$SO_2$Me, or —$CH_2$-imidazolyl. Optionally, $L^1$-Z-$L^2$-$R^1$ or $R^{11}$ is selected from F, OMe, —C(O)OH, —C(O)NHMe, —C(O)$NH_2$, —$SO_2$Me, or —$CH_2$-imidazolyl, when X is N and Y is C.

In embodiments -$L^1$-$Z^1$-$L^2$-$R^1$ or $R^{11}$ is selected from H, F, —OMe, —C(O)OH, —C(O)NHMe, —C(O)$NH_2$, —C(O)$NMe_2$, —$SO_2$Me, —C(O)—N-methyl piperazinyl, or —$CH_2$-imidazolyl. Optionally, $L^1$-$Z^1$-$L^2$-$R^1$ or $R^{11}$ is selected from F, OMe, —C(O)OH, —C(O)NHMe, —C(O)$NH_2$, —$SO_2$Me, or —$CH_2$-imidazolyl, when X is N and Y is C. For example, in embodiments where the compounds are compounds of formula (Ia) $L^1$-Z-$L^2$-$R^1$ or $R^{11}$ is selected from the groups recited in this paragraph.

In embodiments -$L^3$-$Z^2$-$L^4$-$R^2$ or $R^{12}$ is selected from: H, F, $C_1$, —OMe, CN, methyl, $NH_2$, —$CH_2$-phenyl, —$CH_2$-imidazolyl, —$CH_2NH_2$, —$CH_2NMe_2$, —$CH_2$NHMe, —$CH_2$NHC(O)Me, —$CH_2$N(Me)C(O)Ot-Bu, —$CH_2$OH, —$CH_2CH_2$OH, —$CH_2CH_2$OMe, —$CH_2CH_2$NHMe, —$(CH_2)_3$OH, —$(CH_2)_3$OMe, —$CH_2$C($Me_2$)OH, —$CH_2CH_2$O C(O)Me, —$CH_2$C(O)OMe, —$CH_2$C(O)OH, —$CH_2$C(O)OEt, —$CH_2$C(O)$NH_2$, —OMe, —$OCH_2CH_2$OH, —$OCH_2CH_2$OMe, —$OCH_2C(Me)_2$OH, —$OCH_2CH_2C(Me)_2$OH, —$OCH_2$CH(OH)$CH_2$OH, —$OCH_2$C($Me_2$)OH, —$OCH_2CH_2NH_2$, —$OCH_2CH_2NMe_2$, —O$(CH_2)_3NMe_2$, —$OCH_2$CH(OH)$CH_2NMe_2$, —$OCH_2CH_2$NHC(O)$O^t$Bu, —$OCH_2$CH(OH)$CH_2$OMe, —$OCH_2$CH(OH)CH(OH)Me, —$OCH_2CH_2$CH(OH)Me, —$OCF_2CH_2$OH, —$OCH_2C(Me)_2$OP(═O)$(OH)_2$, —$OCH_2$CH(Me)$CH_2$OH, —$OCH_2CH_2C(Me)_2NH_2$, —$OCH_2C(Me)_2NH_2$, —$OCH_2$CH(OH)$C(Me)_2$OH, —$OCH_2C(Me)_2$OMe, —$OCH_2CH_2C(Me)_2$OP(═O)$(OH)_2$, —OCH(Me)$CH_2$OMe, —$OCH_2$CH(Me)OMe, —$OCH_2$-azetidinyl, —$OCH_2$—N-methylazetindinyl, —O—N-ethylpiperadinyl, —O$(CH_2)_3$-morpholinyl, —$OCH_2$CH(OH) $CH_2$-morpholinyl, —$OCH_2$CH(OMe)$CH_2$-morpholinyl, —O$(CH_2)_3$—N-methylpiperazinyl, —$OCH_2$CH(OH) $CH_2$—N-methylpiperazinyl, —$OCH_2$CH(OH)$CH_2$—N-methylpiperazinonyl, —O$(CH_2)_3$—N-methylpiperazinonyl, —$OCH_2$CH(OH)$CH_2$-morpholinonyl, —$OCH_2$CH(OH) $CH_2$-morpholinonyl, —$OCH_2$CH(OH)$CH_2$-thiomorpholindionyl, —$NHCH_2CH_2$OH, —N(Me)$CH_2CH_2$OH, —$NHCH_2CH_2$OMe, —C(O)$NHCH_2CH_2NMe_2$, —C(O) $NHCH_2CH_2$OH, —NHC(O)Me, —NHC(O)$CH_2$OH, —NHC(O)$CH_2NH_2$, —NHC(O)$CH_2$NHMe, —NHC(O) $CH_2NMe_2$, —NHC(O)$CH_2CH_2$NHMe, —NHC(O) $(CH_2)_3NMe_2$, —NHC(O)$CH_2$-morpholinyl, —NHC(O) $CH_2$—N— oxetanyl, azetidinyl, hydroxypyrolidinyl, methylpiperazinyl, pyrolidinonyl, imidazolidinonyl, N-methylimidazolidinonyl, piperidinonyl,

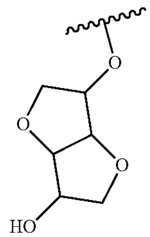
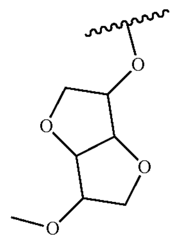

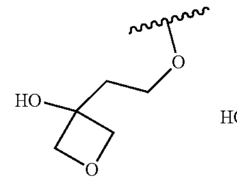
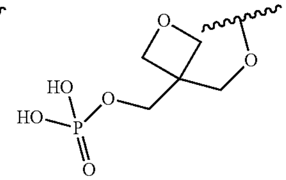

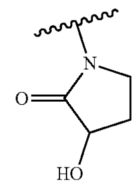
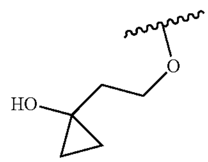
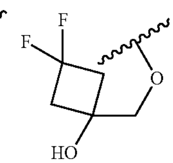

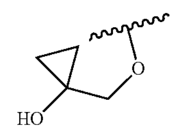
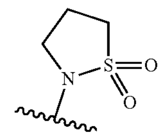
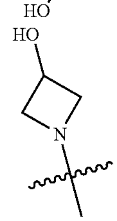

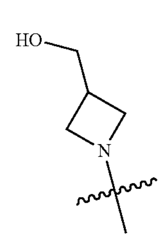
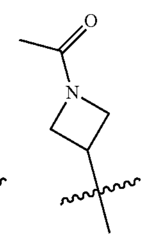
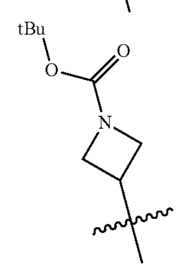

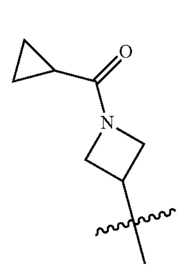
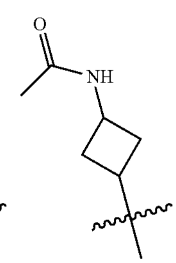
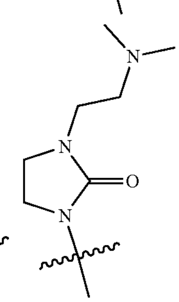

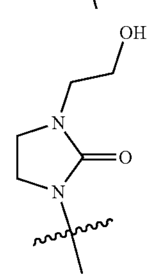
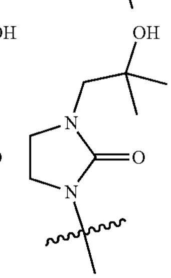
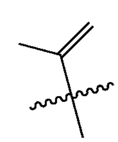

-continued

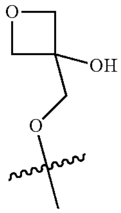

and

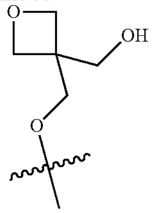

.

In embodiments -$L^3$-$Z^2$-$L^4$-$R^2$ or $R^{12}$ is selected from: H, F, Cl, —OMe, —$CH_2$-imidazolyl, —$CH_2OH$, —$CH_2NH_2$, —$CH_2NMe_2$, —$CH_2NHMe$, —$CH_2C(O)OH$, —$CH_2C(O)OEt$, —$CH_2C(O)NH_2$, —$CH_2NHC(O)Me$, —$CH_2N(Me)C(O)Ot$-Bu, —OMe, —$OCH_2CH_2OH$, —$OCH_2CH_2OMe$, —$OCH_2C(Me)_2OH$, —$OCH_2CH_2C(Me)_2OH$, —$OCH_2CH_2NH_2$, —$OCH_2CH_2NMe_2$, —$OCH_2CH(OH)CH_2NMe_2$, —$OCH_2CH(OH)CH_2OMe$, —$OCH_2CH(OH)CH(OH)Me$, —$OCH_2CH_2CH(OH)Me$, —$OCF_2CH_2OH$, —$OCH_2C(Me)_2OP({=}O)(OH)_2$, —$OCH_2CH(Me)_2CH_2OH$, —$OCH_2CH_2C(Me)_2NH_2$, —$OCH_2C(Me)_2NH_2$, —$OCH_2CH(OH)C(Me)_2OH$, —$OCH_2C(Me)_2OMe$, —$OCH_2CH_2C(Me)_2OP({=}O)(OH)_2$, —$OCH(Me)CH_2OMe$, —$OCH_2CH(Me)OMe$, —$OCH_2CH_2NHC(O)O^t$Bu, —$OCH_2$-azetidinyl, —$OCH_2$—N-methylazetindinyl, —O—N-ethylpiperadinyl, —$O(CH_2)_3$-morpholinyl, —$OCH_2CH(OH)CH_2$-morpholinyl, —$OCH_2CH(OMe)CH_2$-morpholinyl, —$O(CH_2)_3$—N-methylpiperazinyl, —$C(O)NHCH_2CH_2NMe_2$, —$C(O)NHCH_2CH_2OH$, —NHC(O)Me, —$NHC(O)CH_2OH$, —$NHC(O)CH_2NH_2$, —$NHC(O)CH_2NHMe$, —$NHC(O)CH_2NMe_2$, —$NHC(O)CH_2CH_2NHMe$, —$NHC(O)(CH_2)_3NMe_2$, —$NHC(O)CH_2$-morpholinyl, —$NHC(O)CH_2$—N-methylpiperazinyl, pyrolidinonyl, imidazolidinonyl, N-methylimidazolidinonyl, piperidinonyl,

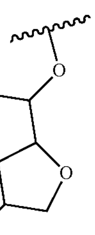
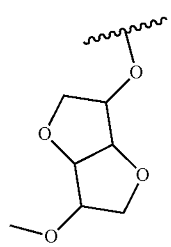
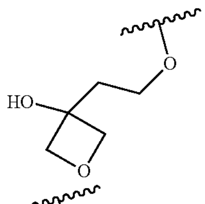
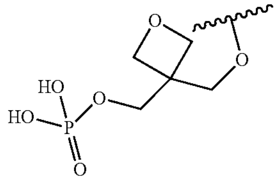
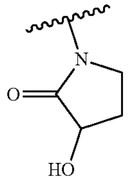
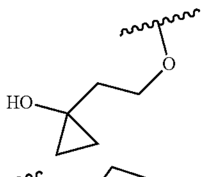
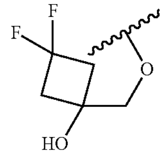
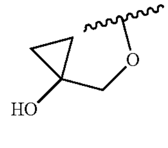
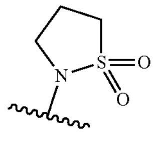
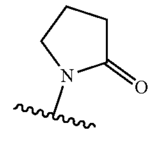

-continued

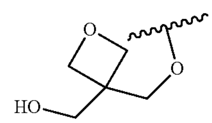
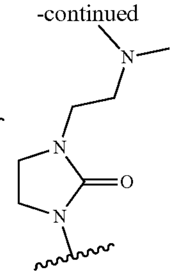

and

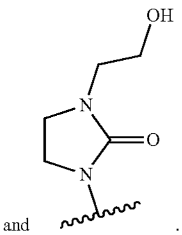

.

Optionally, $L^3$-$Z^2$-$L^4$-$R^2$ or $R^{12}$ has the definition in the preceding sentence when X is N and Y is C. For example, in embodiments where the compounds are compounds of formula (Ia) $L^3$-$Z^2$-$L^4$-$R^2$ or $R^{12}$ is selected from the groups recited in this paragraph.

In embodiments $L^3$-$Z^2$-$L^4$-$R^2$ or $R^{12}$ is H or OMe. Optionally, $L^3$-$Z^2$-$L^4$-$R^2$ or $R^{12}$ has the definition in the preceding sentence when X is C and Y is N. For example, in embodiments where the compounds are compounds of formula (Ib), $L^3$-$Z^2$-$L^4$-$R^2$ or $R^{12}$ is selected from the groups recited in this paragraph.

In embodiments $L^3$-$Z^2$-$L^4$-$R^2$ or $R^{12}$ is selected from: -Me, —F, —$NH_2$, —$CH_2$-phenyl, —$CH_2CH_2OH$, —$CH_2CH_2OMe$, —$CH_2CH_2NHMe$, —$(CH_2)_3OH$, —$(CH_2)_3OMe$, —$CH_2CH_2O$ C(O)Me, —$CH_2C(O)OMe$, —OMe, —$OCH_2CH_2OMe$, —$O(CH_2)_3NMe_2$, —$OCH_2C(Me)_2OH$, —$OCH_2CH_2C(Me)_2OH$, —$O(CH_2)_3$-morpholinyl, —$O(CH_2)_3$—N-methylpiperazinyl, —$OCH_2CH(OH)CH_2$-morpholinyl, —$OCH_2CH(OMe)CH_2$-morpholinyl, —$NHCH_2CH_2OH$, —$N(Me)CH_2CH_2OH$, —$NHCH_2CH_2OMe$, —NHC(O)Me, —$NHC(O)CH_2CH_2NHMe$, oxetanyl, azetidinyl, hydroxypyrolidinyl,

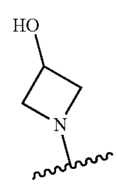
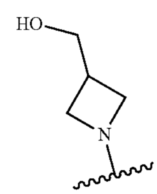
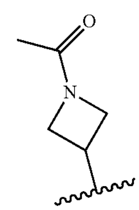
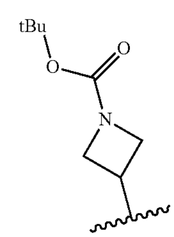
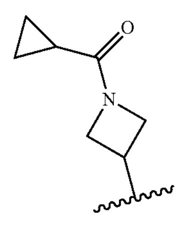

and

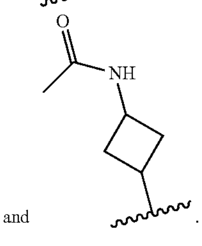

.

Optionally, $L^3$-$Z^2$-$L^4$-$R^2$ or $R^{12}$ has the definition in the preceding sentence when X is N and Y is C. For example, in embodiments where the compounds are compounds of formula (Ia) $L^3$-$Z^2$-$L^4$-$R^2$ or $R^{12}$ is selected from the groups recited in this paragraph.

In embodiments, -$L^3$-$Z^2$-$L^4$-$R^2$ or $R^{12}$ is —$OCH_2CH(OH)CH_2OH$, —$OCH_2C(Me_2)OH$, —$CH_2C(Me_2)OH$, —$OCH_2CH(OH)CH_2$—N-methylpiperazinyl, —$OCH_2CH(OH)CH_2$—N-methylpiperazinonyl, —$OCH_2CH(OH)CH_2$-morpholinonyl, —$OCH_2CH(OH)CH_2$-morpholinonyl, —$OCH_2CH(OH)CH_2$-thiomorpholin-dionyl or —$OCH_2CH(OH)CH_2$-morpholinyl.

In preferred embodiments $-L^1-Z^1-L^2-R^1$ or $R^{11}$ is H, F, $—CH_2OH$, $—OCH_2CH_2NMe_2$, $—O(CH_2)_3NMe_2$, $—OCH_2CH(OH)CH_2NMe_2$, or $—OCH_2CH_2OH$.

In preferred embodiments $-L^1-Z^1-L^2-R^1$ or $R^{11}$ is substituted at the 3 position of the phenyl ring (for example as demonstrated in formula (IIIb)) and is F or $—CH_2OH$.

In preferred embodiments $-L^1-Z^1-L^2-R^1$ or $R^{11}$ is substituted at the 4 position of the phenyl ring (for example as demonstrated in formula (IIIa)) and is selected from: $—OCH_2CH_2NMe_2$, $—O(CH_2)_3NMe_2$, $—OCH_2CH(OH)CH_2NMe_2$, and $—OCH_2CH_2OH$.

In preferred embodiments $-L^3-Z^2-L^4-R^2$ or $R^{12}$ is selected from: $—OCH_2CH_2OH$, $—OCH_2CH_2OMe$, $—OCH_2CH(OH)CH_2OH$, $—OCH_2CH_2C(Me)_2OH$, pyrolidinonyl, imidazolidinonyl, N-methylimidazolidinonyl, $—O(CH_2)_3$-morpholinyl, $—O(CH_2)_3$—N-methylpiperazinyl, $—O(CH_2)_3$—N-methylpiperazinonyl, $—OCH_2CH(OH)CH_2$-morpholinonyl, $—OCH_2CH(OH)CH_2$—N-methylpiperazinyl, $—OCH_2CH(OH)CH_2$—N-methylpiperazinonyl, $—O(CH_2)_3NMe_2$, $—OCH_2CH(OH)CH_2NMe_2$,

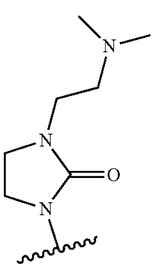

and

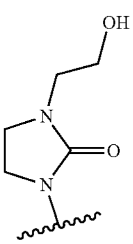

In preferred embodiments $R^4$ is substituted at the 3 position of the phenyl ring (for example this substitution pattern is exemplified by $R^{12}$ in formula (IVb)) and is —CN.

In embodiments $-L^3-Z^2-L^4-R^2$ or $R^{12}$ is substituted at the 4 position of the phenyl ring (for example as demonstrated in formula (IVa)) and is selected from: $—OCH_2CH_2OH$, $—OCH_2CH_2OMe$, $—OCH_2CH(OH)CH_2OH$, $—OCH_2CH_2C(Me)_2OH$, pyrolidinonyl, imidazolidinonyl, N-methylimidazolidinonyl, $—O(CH_2)_3$-morpholinyl, $—O(CH_2)_3$—N-methylpiperazinyl, $—O(CH_2)_3$—N-methylpiperazinonyl, $—OCH_2CH(OH)CH_2$-morpholinonyl, $—OCH_2CH(OH)CH_2$—N-methylpiperazinyl, $—OCH_2CH(OH)CH_2$—N-methylpiperazinonyl, $—O(CH_2)_3NMe_2$, $—OCH_2CH(OH)CH_2NMe_2$,

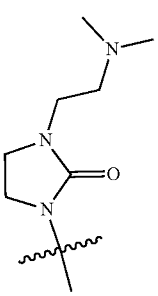

and

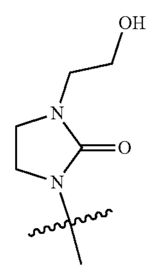

In embodiments $-L^3-Z^2-L^4-R^2$ or $R^{12}$ are a group other than H as defined above and $-L^1-Z^1-L^2-R^1$ or $R^{11}$ are H. In alternative embodiments $-L^1-Z^1-L^2-R^1$ or $R^{11}$ are a group other than H as defined above and $-L^3-Z^2-L^4-R^2$ or $R^{12}$ are H.

In an embodiment the compound of the present invention may be a compound according to formulae (Va) or (Vb):

(Va)

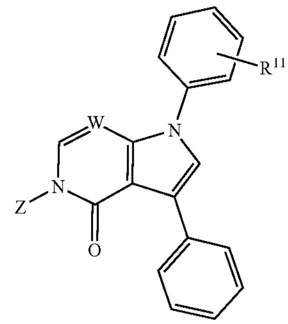

(Vb)

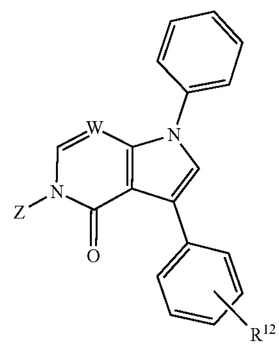

In an embodiment the compound of the present invention may be a compound according to formulae (VIa) or (VIb):

(VIa)

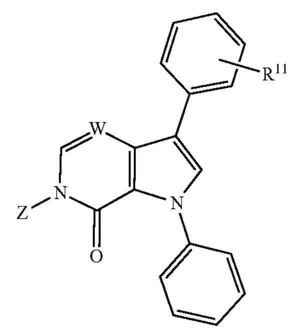

(VIb)

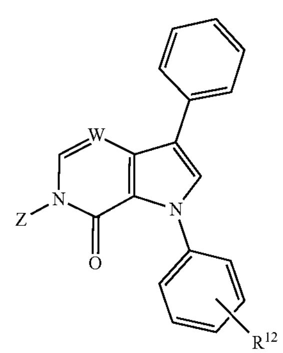

In preferred embodiments $-L^1-Z^1-L^2-R^1$ or $R^{11}$ is $—O(CR^aR^b)_{1-3}—R^1$.

In preferred embodiments $-L^3-Z^2-L^4-R^2$ or $R^{12}$ is $—O(CR^aR^b)_{1-3}—R^2$.

In embodiments W is N. In embodiments W is CH. In embodiments W is CH, X is N and Y is C.

In embodiment $-L^3-Z^2-L^4-R^2$ or $R^{12}$ is $—(CH_2)_oO(CR^aR^b)_pOR^{6a}$, $—(CH_2)_oO(CR^aR^b)_pNR^{6a}R^{6b}$, 5 or 6 membered heterocycloalkyl rings which is unsubstituted or substituted with 1 or 2 groups selected from: oxo, halo, ORS, and $C_{1-6}$ alkyl. In embodiments $-L^3-Z^2-L^4-R^2$ or $R^{12}$ is $—OCH_2CH_2OMe$, $—OCH_2CH_2C(Me)_2OH$, or pyrrolidinone.

In embodiments W is CH, X, is N, Y is C and $-L^3-Z^2-L^4-R^2$ or $R^{12}$ is $—OCH_2CH_2OMe$, $—OCH_2CH_2C(Me)_2OH$, or pyrrolidinone.

In certain embodiments where W is CH then $-L^1-Z^1-L^2-R^1$ or $R^{11}$ is H.

In an embodiment the compound of the present invention is a compound according to formula (XX) and pharmaceutically acceptable salts thereof:

(XX)

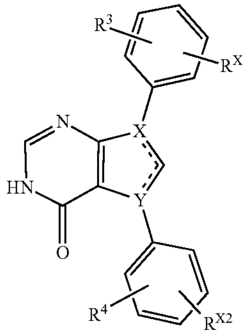

wherein either X is N and Y is C, or Y is N and X is C;

$R^X$ and $R^{X2}$ are either (A) or (B):

(A) $R^X$ is selected from: H, —CN, $—(CH_2)_mR^Y$, $—(CH_2)_mNR^ZR^{6a}$, $—(CH_2)_{1-3}OR^Z$, $—(CH_2)_mSO_2R^{6a}$, $—(CH_2)_mC(O)NR^ZR^{6a}$, $—(CH_2)_mC(O)OR^Z$, $R^Y$ is selected from 5 or 6 membered heteroaryl rings;

$R^Z$ is selected from H, $C_{1-6}$ alkyl, $—C(O)R^{6a}$, $—C(O)OR^{6a}$, $—C(O)(CR^aR^b)_nNR^{6a}R^{6b}$, $(CR^aR^b)_nOR^{6a}$, $(CR^aR^b)_nNR^{6a}R^{6b}$, $(CR^aR^b)_nR^V$; and $R^V$ is selected from 3 to 8 membered heterocycloalkyl ring systems, wherein the heterocycloalkyl ring is unsubstituted or substituted with 1 or 2 groups selected from: oxo, $C_{1-6}$ alkyl or halo; and $R^{X2}$ is selected from: H, halo, $C_{1-6}$ alkyl, —CN, $—(CH_2)_mR^{Y2}$, $—(CH_2)_mNR^{Z2}R^{6a}$, $—(CH_2)_mOR^{Z2}$, $—(CH_2)_mC(O)NR^{Z2}R^{6a}$, $—(CH_2)_mC(O)OR^{Z2}$, $R^{Y2}$ is selected from 5 or 6 membered heteroaryl rings;

$R^{Z2}$ is selected from H, $C_{1-6}$ alkyl, $—C(O)R^{6a}$, $—C(O)OR^{6a}$, $—C(O)(CR^aR^b)_nNR^{6a}R^{6b}$, $(CR^aR^b)_nOR^{6a}$, $(CR^aR^b)_nNR^{6a}R^{6b}$, $(CR^aR^b)_nR^2$ or $—C(O)(CR^aR^b)_nR^{V2}$; and $R^{V2}$ is selected from 3 to 8 membered heterocycloalkyl ring systems, wherein the heterocycloalkyl ring is unsubstituted or substituted with 1 or 2 groups selected from: oxo, halo, $C_{1-6}$ alkyl, $C_{1-6}$ alkyl substituted with $NR^{6a}R^{6b}$, or $C_{1-6}$ alkyl substituted with $OR^{6a}$; or (B) $R^X$ is selected from: H, halo, $C_{1-6}$ alkyl, —CN, $—(CH_2)_mR^Y$, $—(CH_2)_mNR^ZR^{6a}$, $—(CH_2)_mOR^Z$, $—(CH_2)_mSO_2R^{6a}$, $—(CH_2)_mC(O)NR^ZR^{6a}$, $—(CH_2)_mC(O)OR^Z$, $R^Y$ is selected from 5 or 6 membered heteroaryl rings;

$R^Z$ is selected from H, $C_{1-6}$ alkyl, $—C(O)R^{6a}$, $—C(O)OR^{6a}$, $—C(O)(CR^aR^b)_nNR^{6a}R^{6b}$, $(CR^aR^b)_nOR^{6a}$, $(CR^aR^b)_nNR^{6a}R^{6b}$, $(CR^aR^b)_nR^V$; and $R^V$ is selected from 3 to 8 membered heterocycloalkyl ring systems, wherein the heterocycloalkyl ring is unsubstituted or substituted with 1 or 2 groups selected from: oxo, $C_{1-6}$ alkyl or halo; and $R^{X2}$ is selected from: H, —CN, $—(CH_2)_mR^{Y2}$, $—(CH_2)_m NR^{Z2}R^{6a}$, $—(CH_2)_{1-3}OR^{Z2}$, $—(CH_2)_mC(O)NR^{Z2}R^{6a}$, $—(CH_2)_mC(O)OR^{Z2}$, $R^{Y2}$ is selected from 5 or 6 membered heteroaryl rings;

$R^{Z2}$ is selected from H, $C_{1-6}$ alkyl, $—C(O)R^{6a}$, $—C(O)OR^{6a}$, $—C(O)(CR^aR^b)_nNR^{6a}R^{6b}$, $(CR^aR^b)_nOR^{6a}$, $(CR^aR^b)_nNR^{6a}R^{6b}$, $(CR^aR^b)_nR^2$ or $—C(O)(CR^aR^b)_nR^{V2}$; and $R^{V2}$ is selected from 3 to 8 membered heterocycloalkyl ring systems, wherein the heterocycloalkyl ring is unsubstituted or substituted with 1 or 2 groups selected from: oxo, halo, $C_{1-6}$ alkyl, $C_{1-6}$ alkyl substituted with $NR^{6a}R^{6b}$, or $C_{1-6}$ alkyl substituted with $OR^{6a}$;

provided that $R^X$ and $R^{X2}$ are not both H and are not both halo;

m is selected from 1, 2, or 3;

n is selected from 1, 2, or 3;

$R^3$ and $R^4$ are independently selected from H, halo, —CN and $C_{1-6}$ alkyl;

$R^{6a}$ and $R^{6b}$ are, at each occurrence, independently selected from: H and $C_{1-6}$ alkyl;

$R^a$, $R^b$, $R^c$ and $R^d$ are, at each occurrence, independently selected from: H, halo, $C_{1-6}$ alkyl, and $—OR^e$; and $R^e$ is selected from H or $C_{1-6}$ alkyl.

In a preferred embodiment of the invention, the compound of formula (I) is a compound selected from:

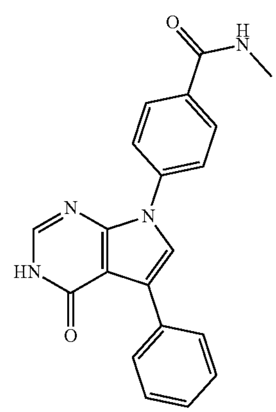

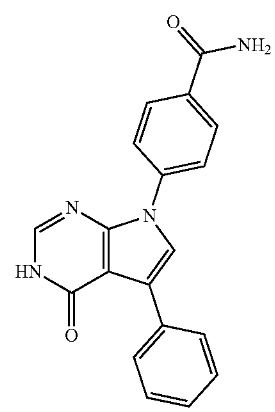

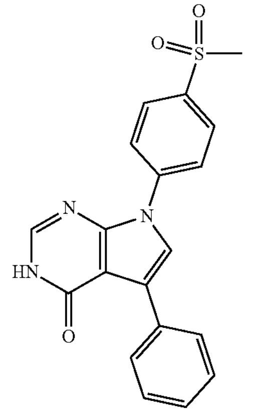

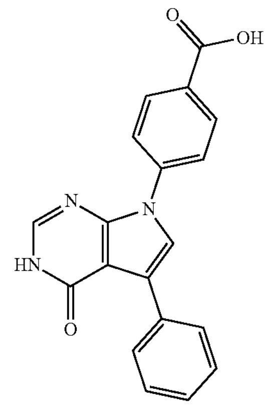

-continued
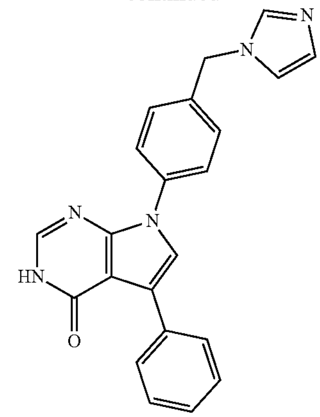
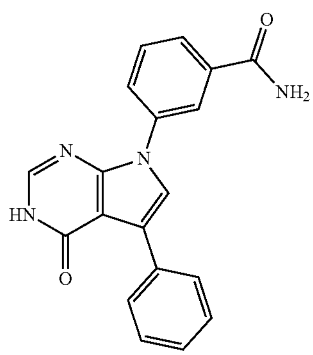
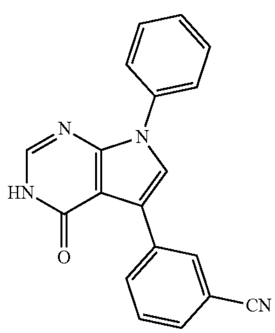
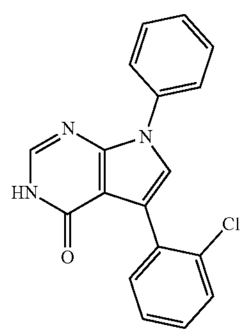
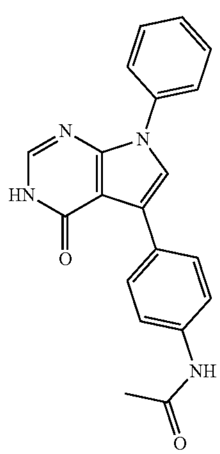
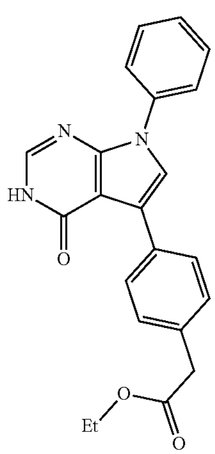
-continued
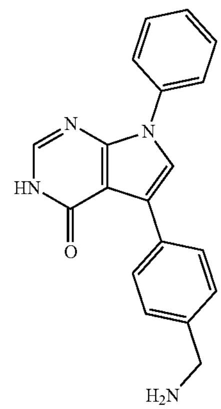
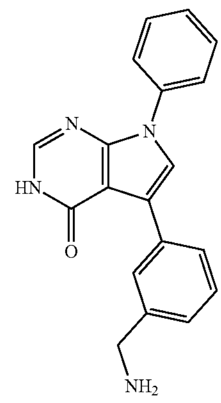
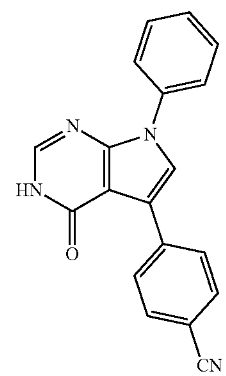
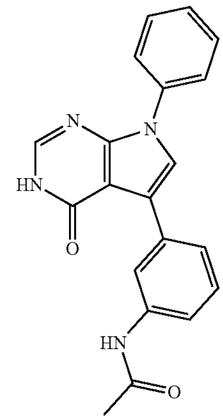
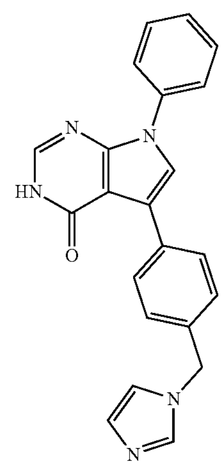
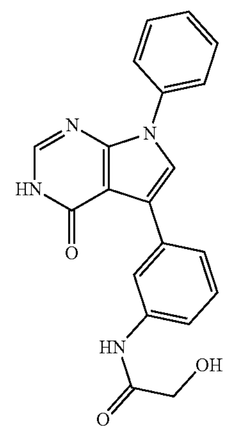
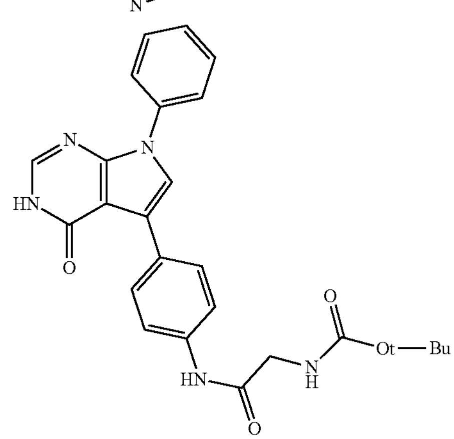

-continued
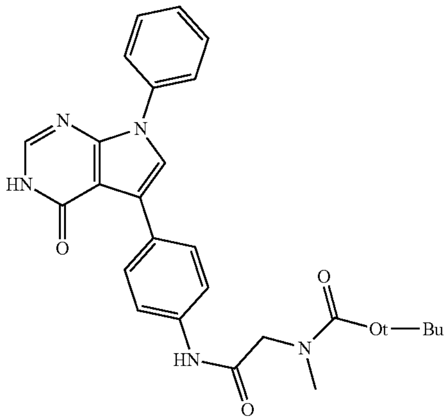
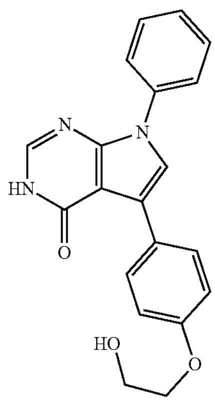
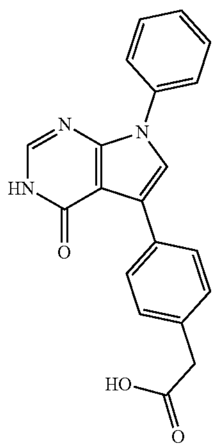
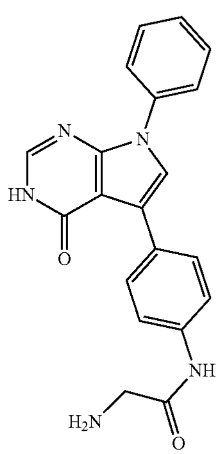
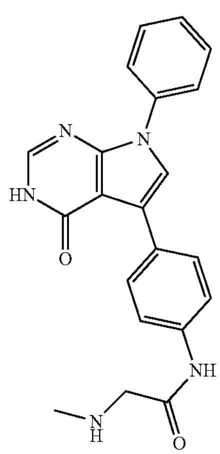
-continued
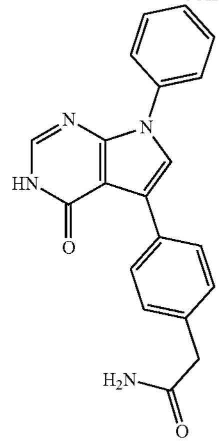
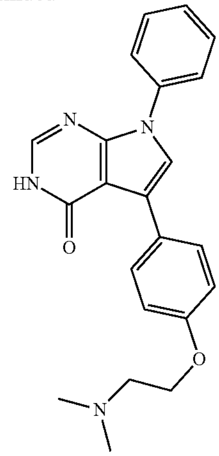
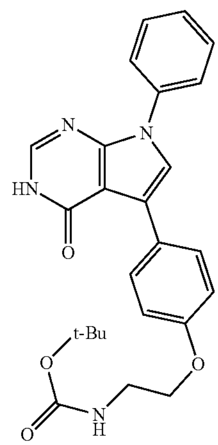
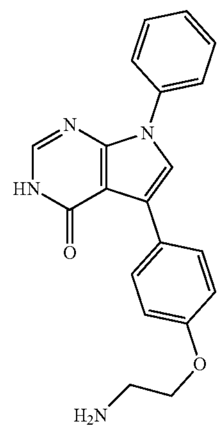
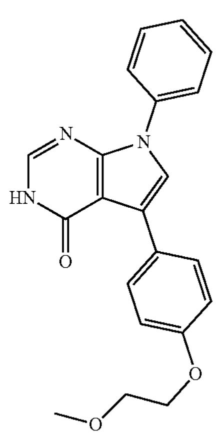
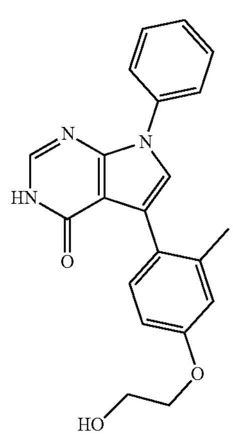

-continued
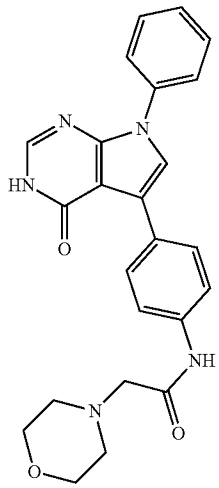
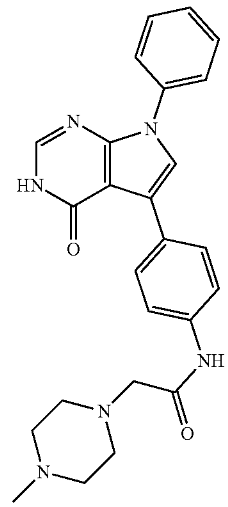
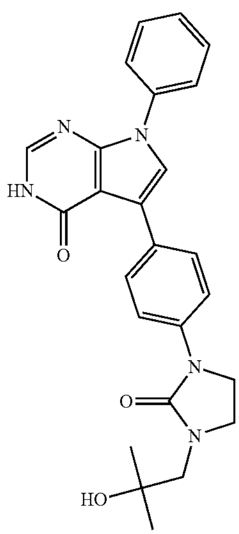
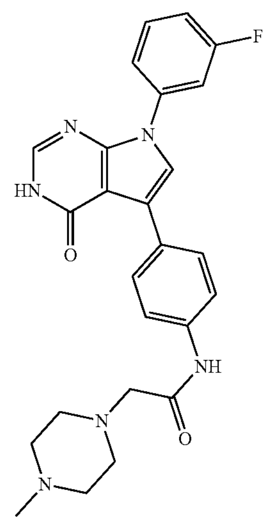
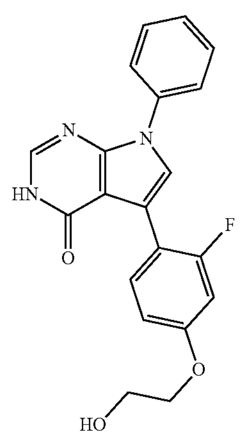
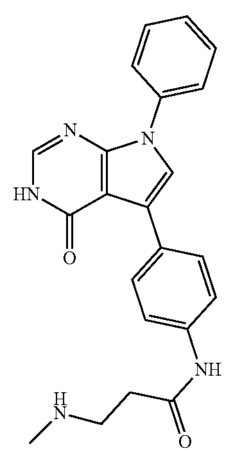
-continued
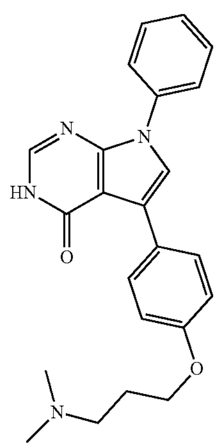
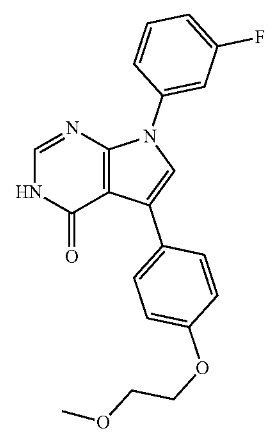
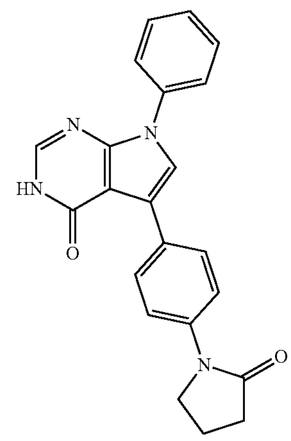
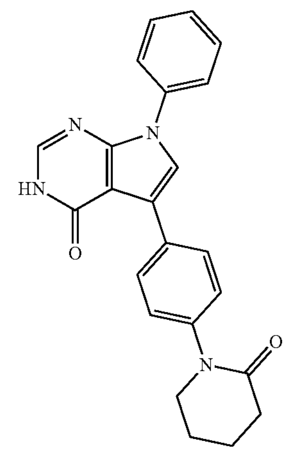
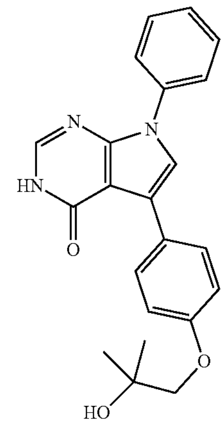
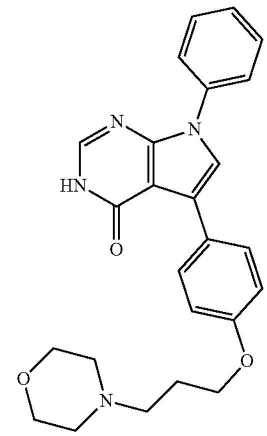
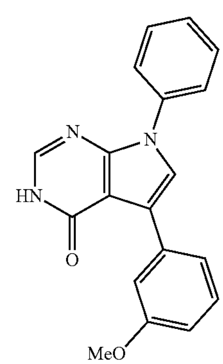
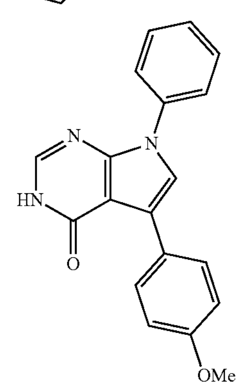

-continued
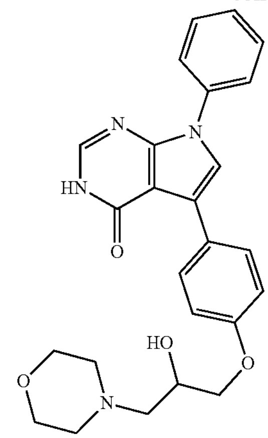
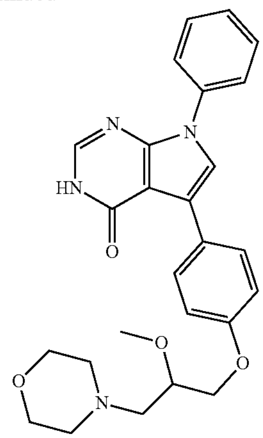
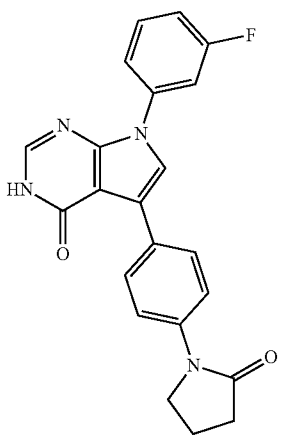
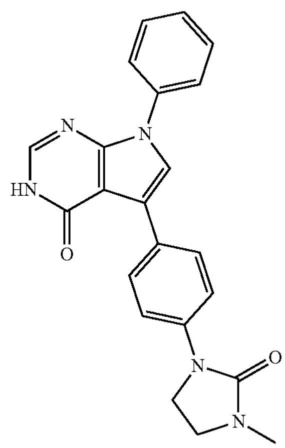
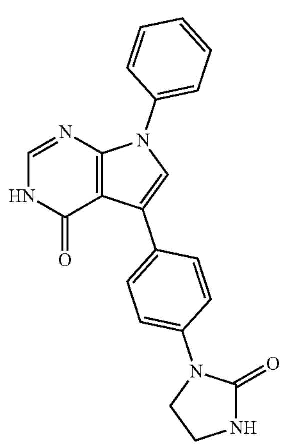
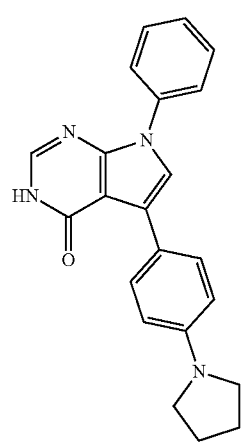
-continued
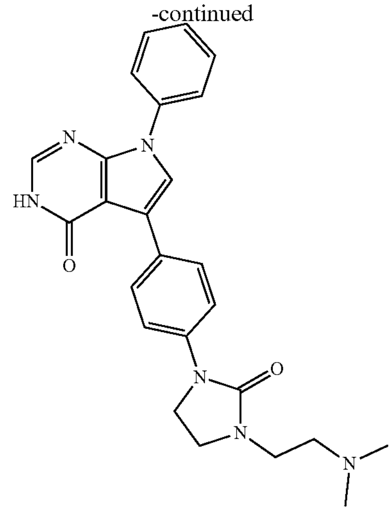
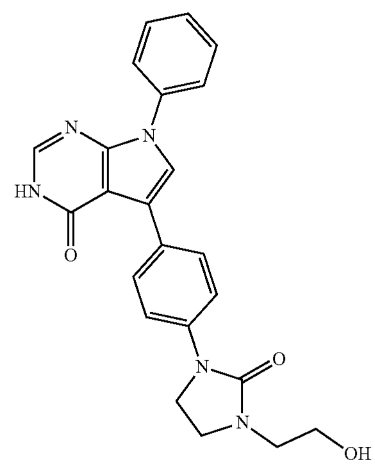
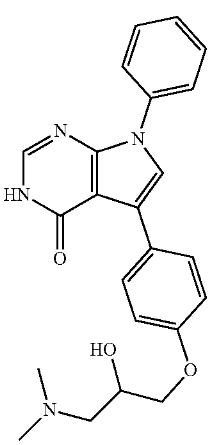
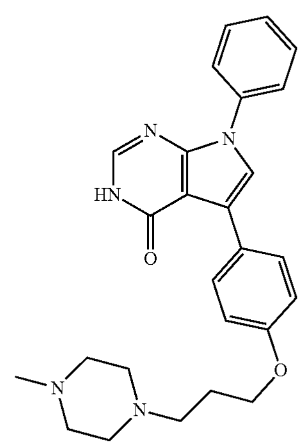

-continued
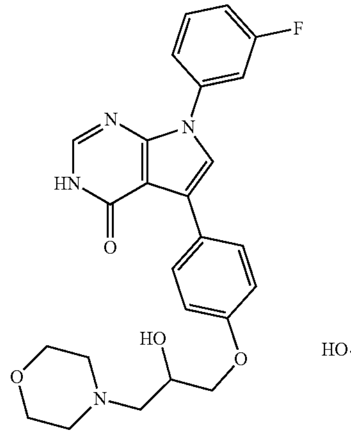
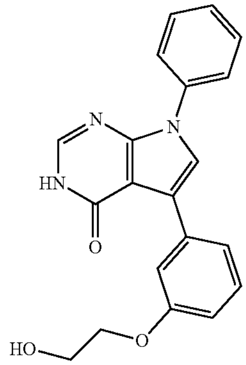
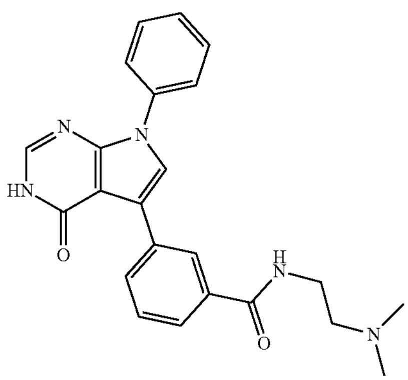
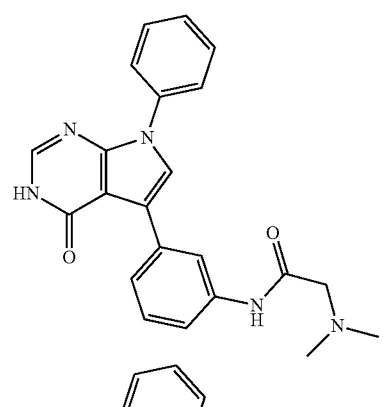
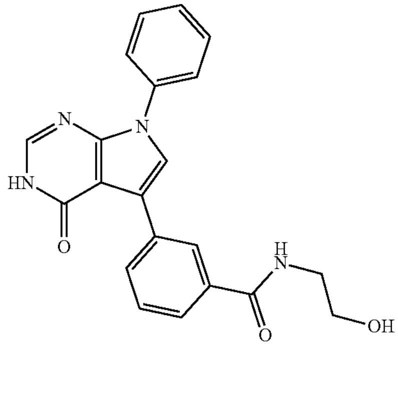
-continued
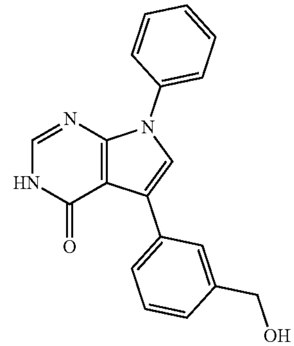
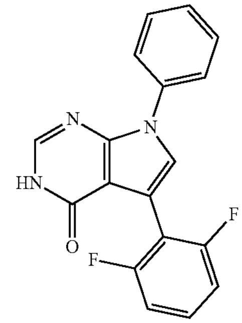
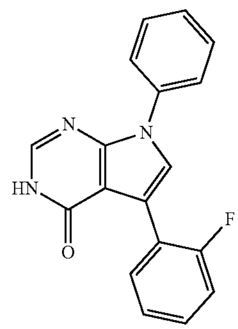
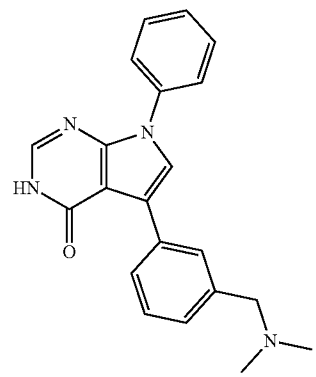
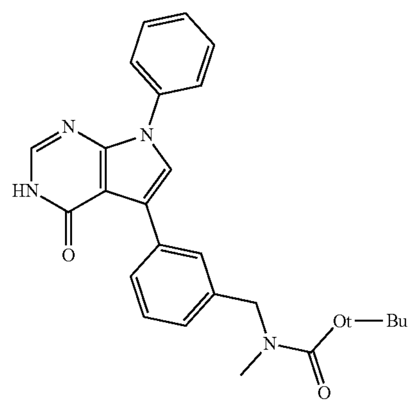
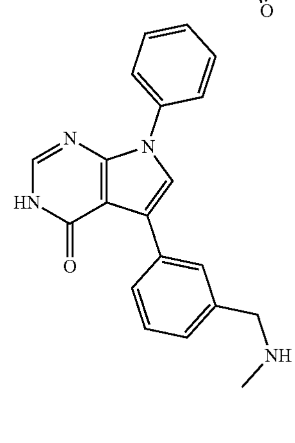

-continued
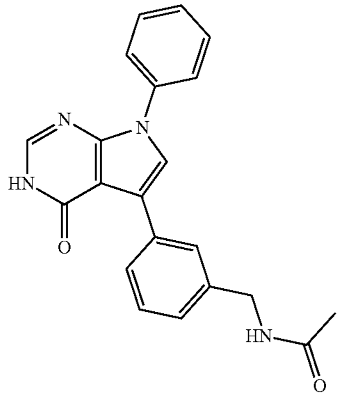
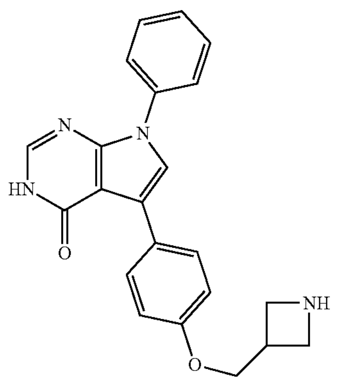
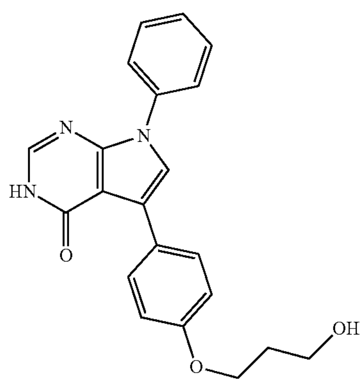
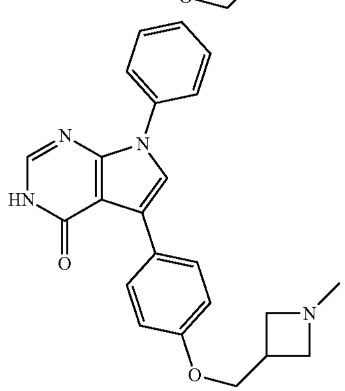
-continued
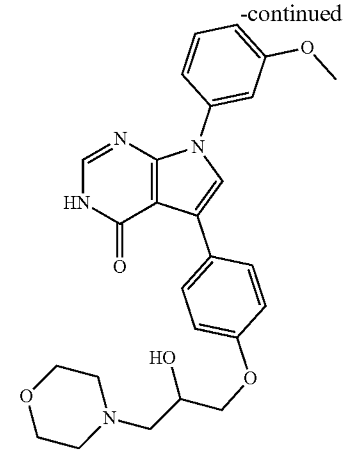
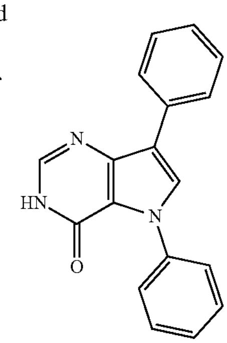
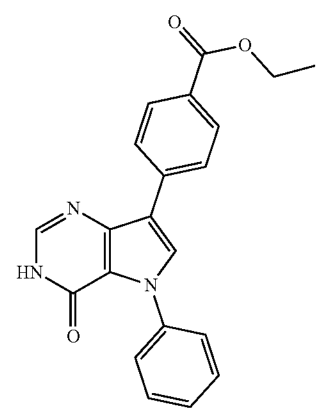
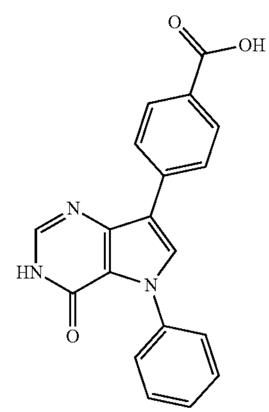
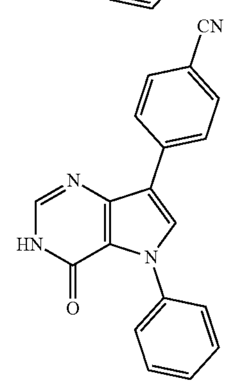
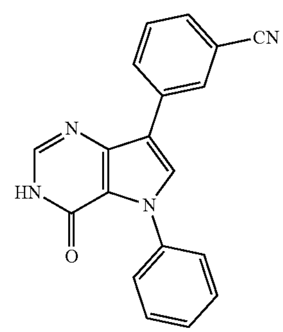
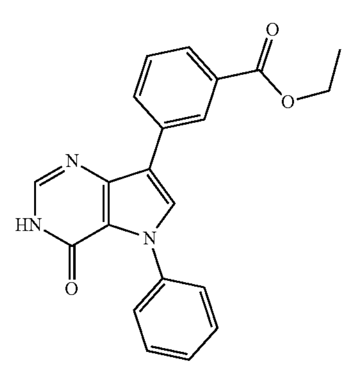

-continued
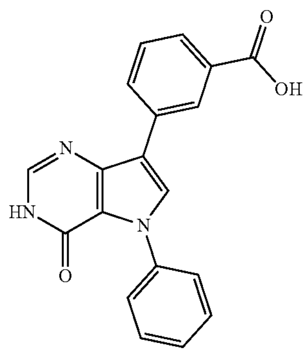
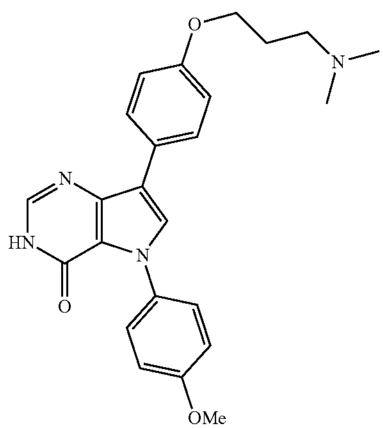
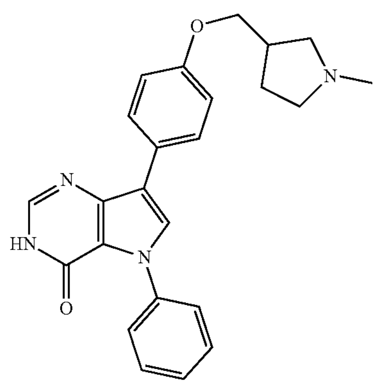
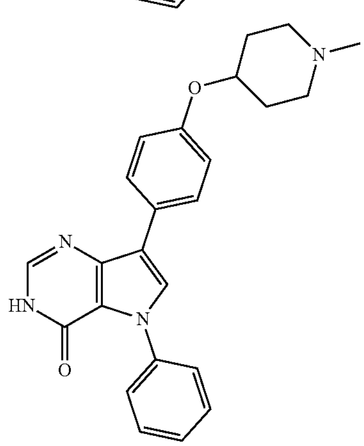
-continued
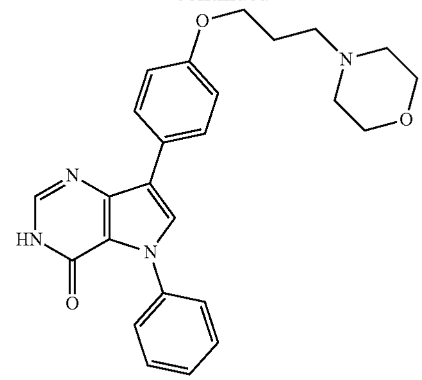
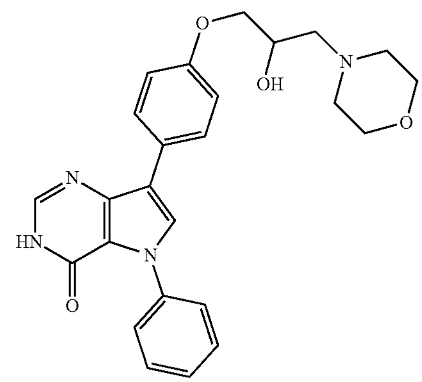
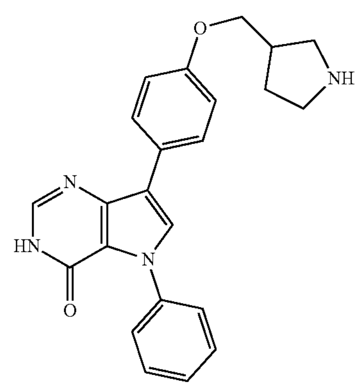
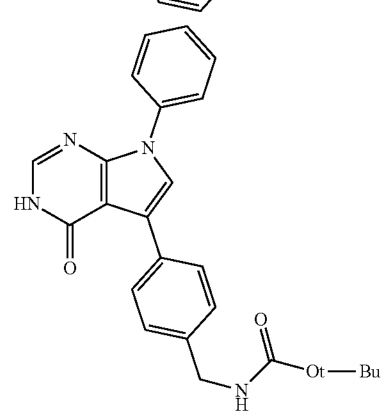

-continued
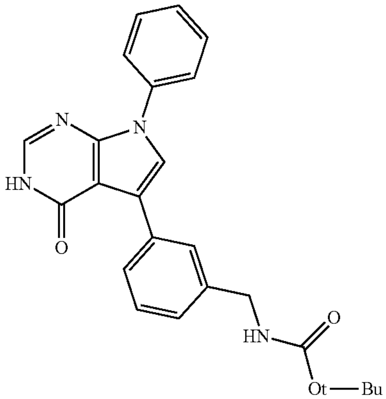
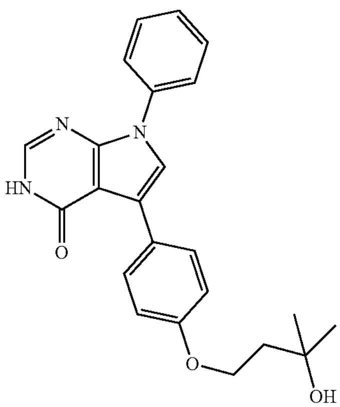
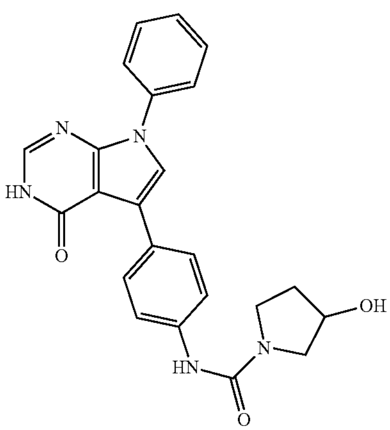
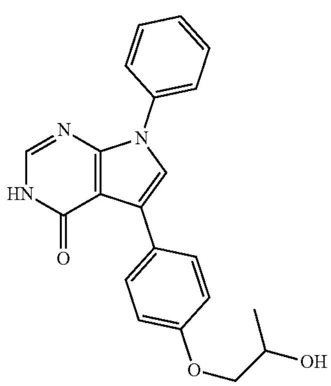
-continued
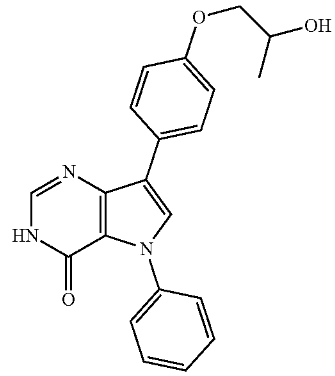
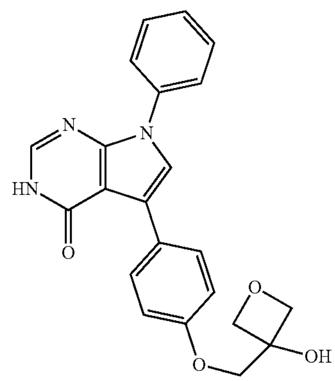
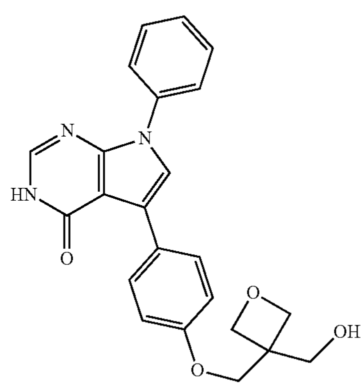
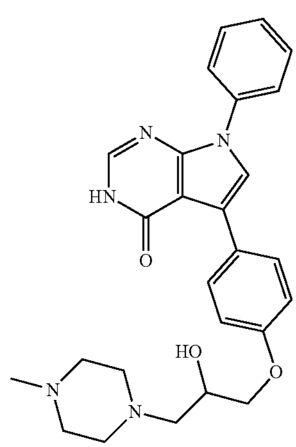
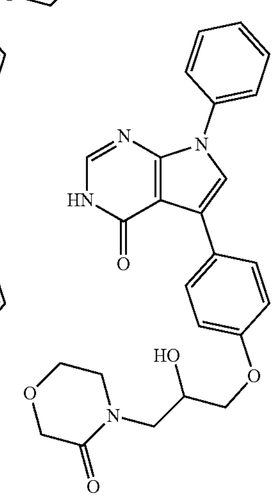

-continued
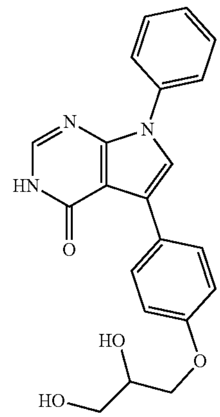
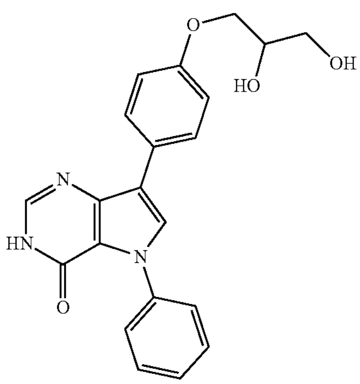
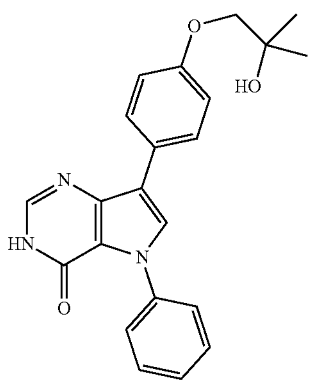
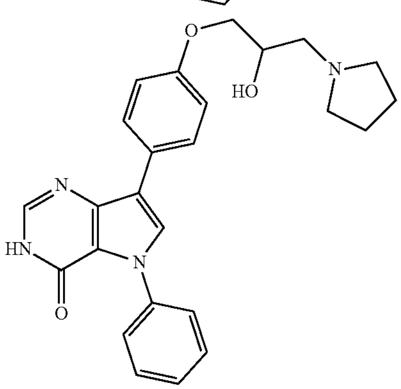
-continued
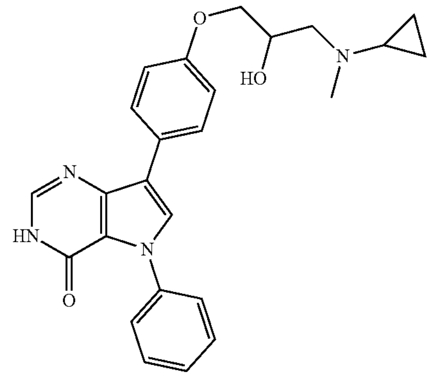
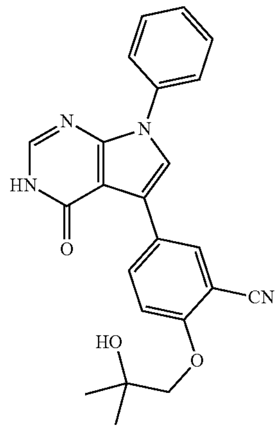
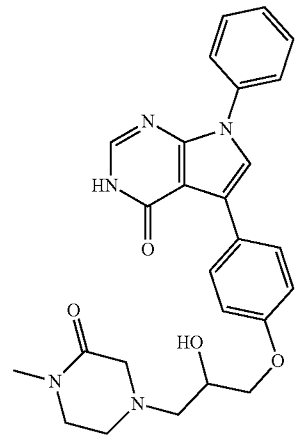
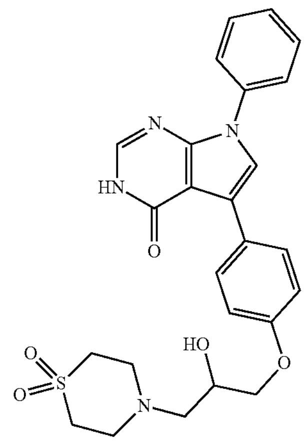
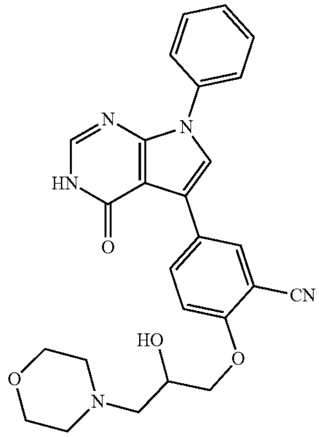
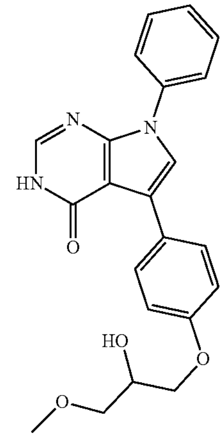

-continued
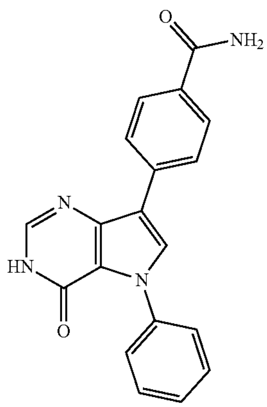
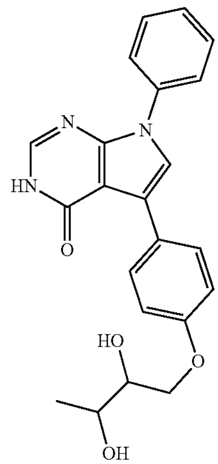
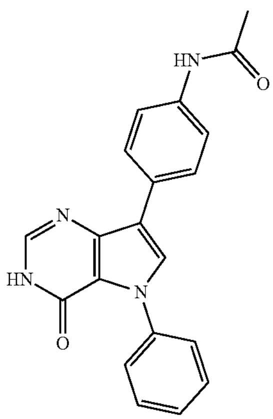
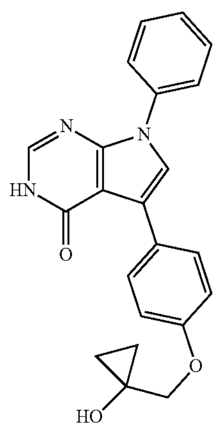
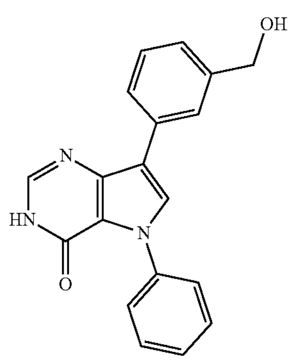
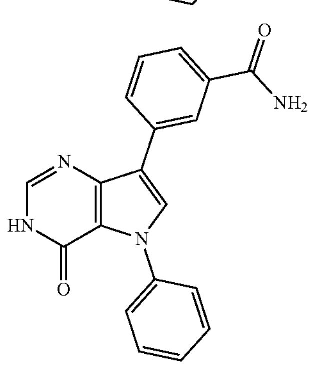
-continued
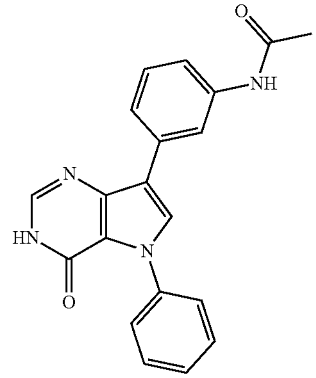
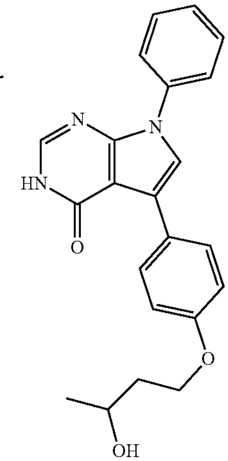
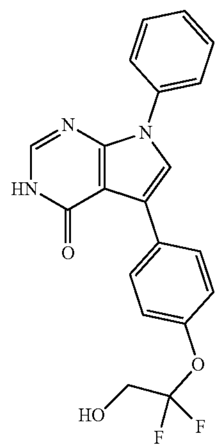
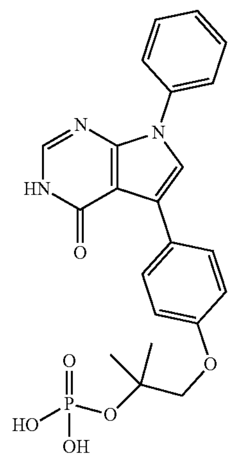
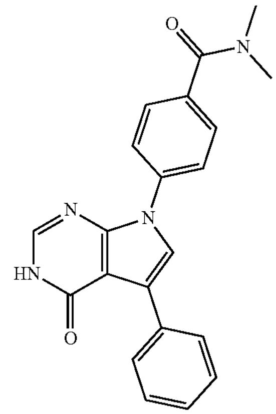

-continued
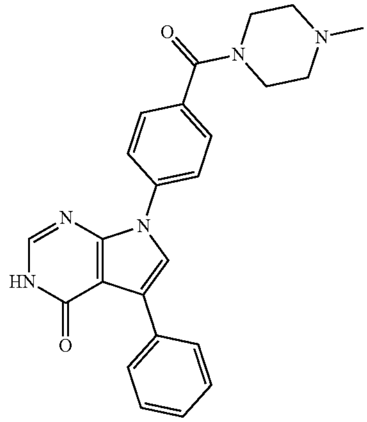
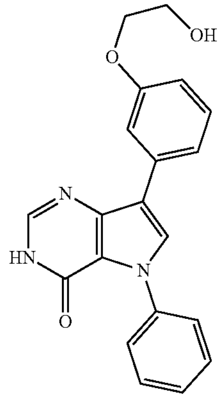
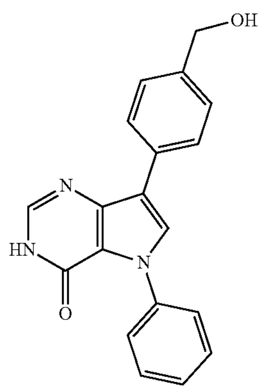
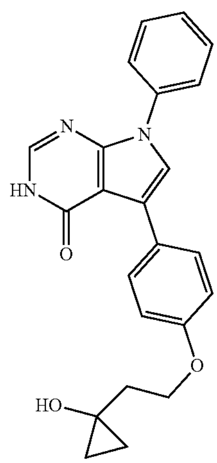
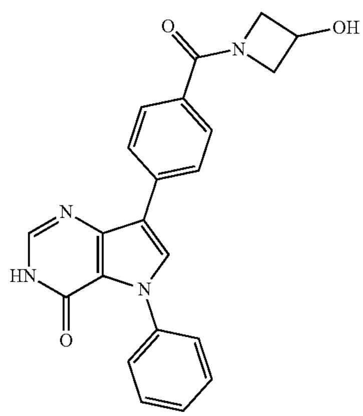
-continued
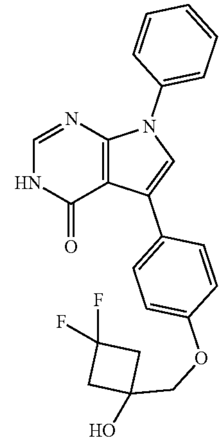
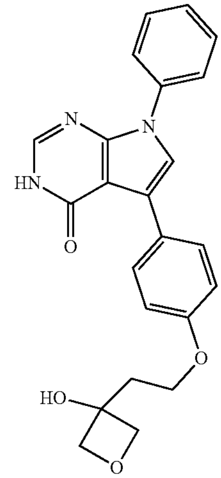
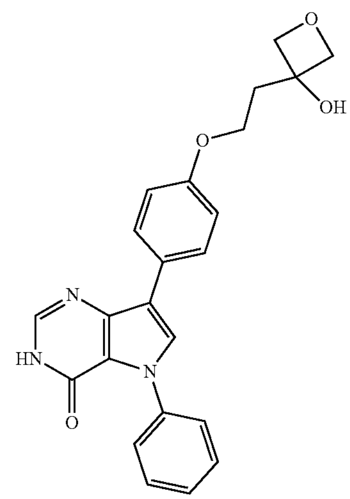
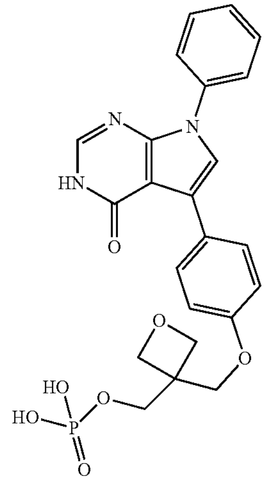
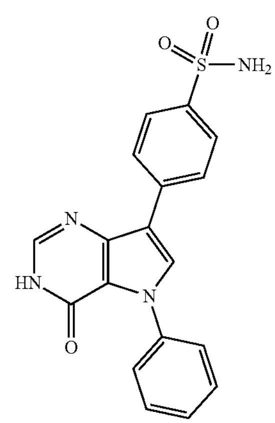

-continued
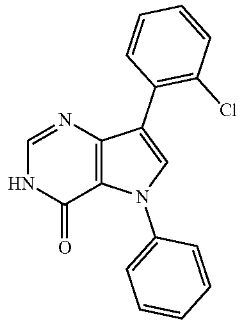
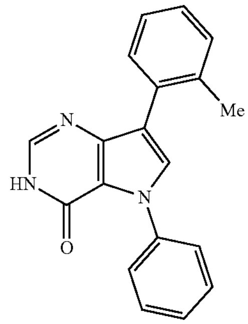
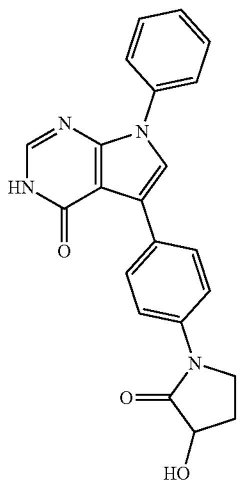
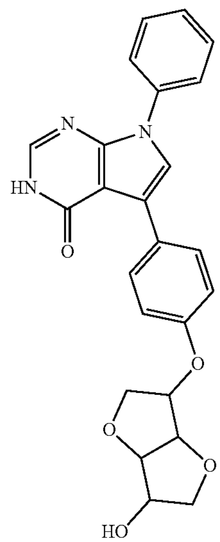
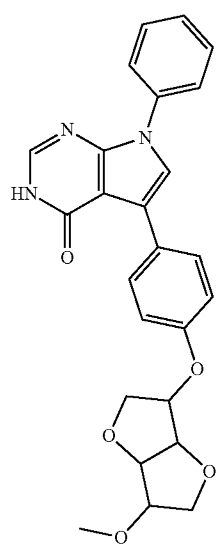
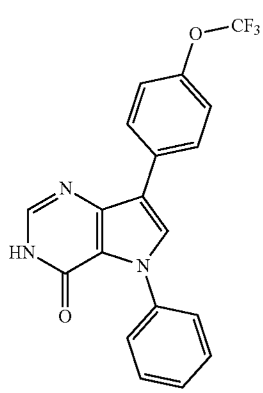
-continued
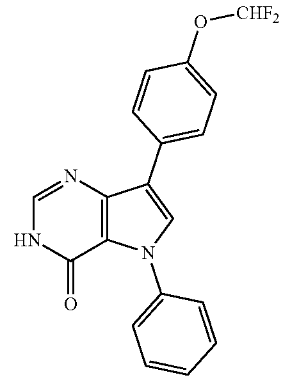
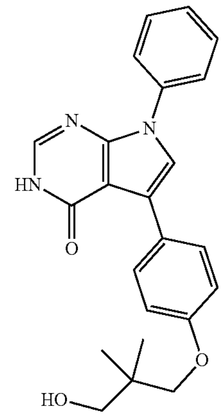
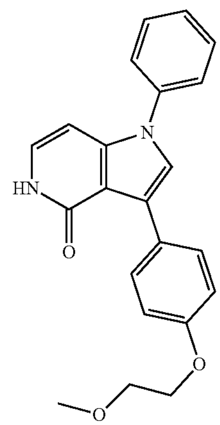
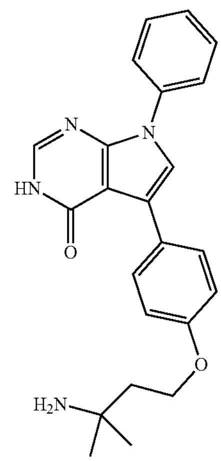
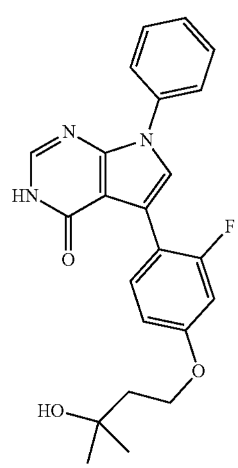
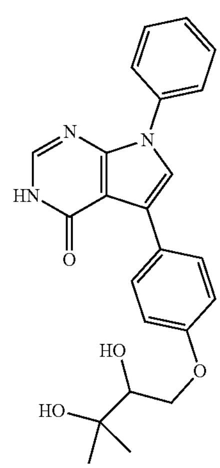

-continued
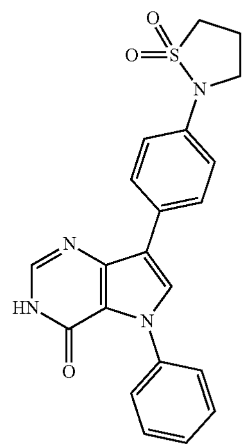
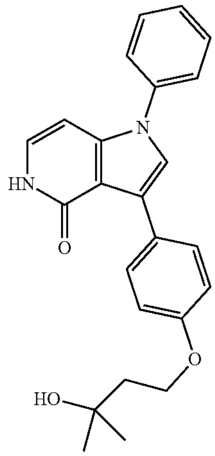
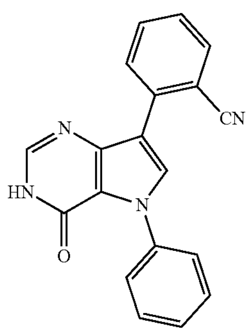
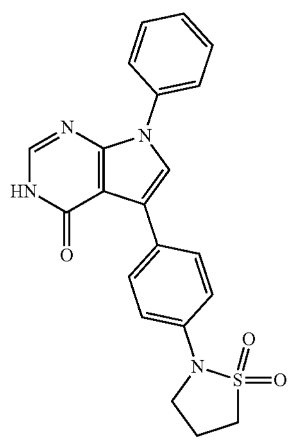
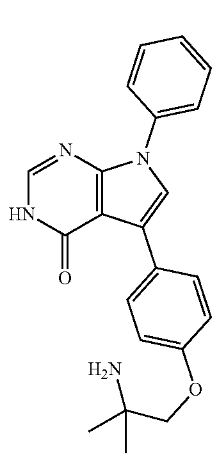
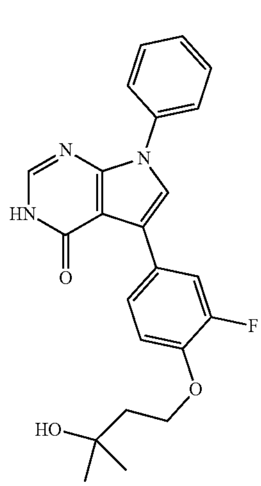
-continued
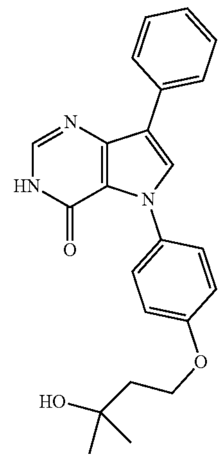
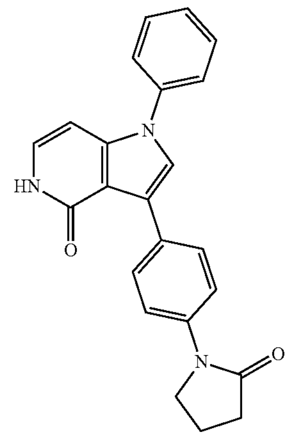
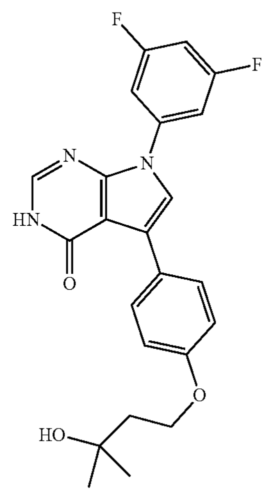
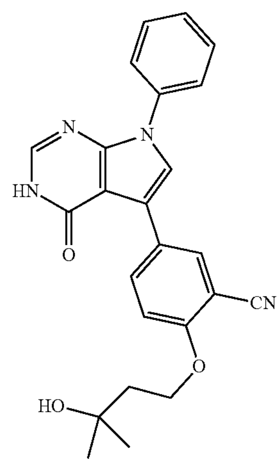
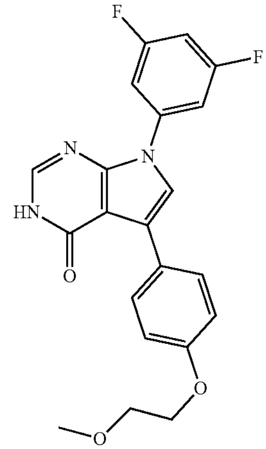
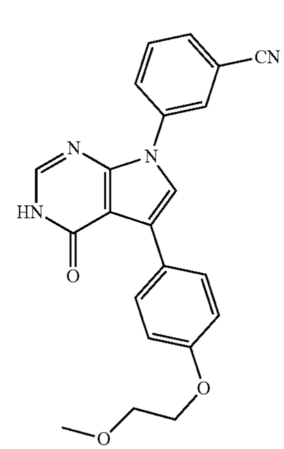

-continued
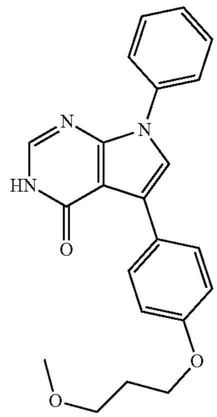
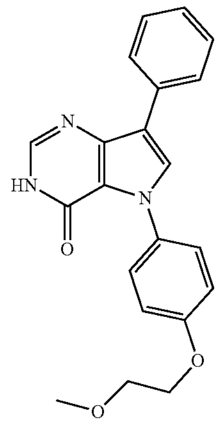
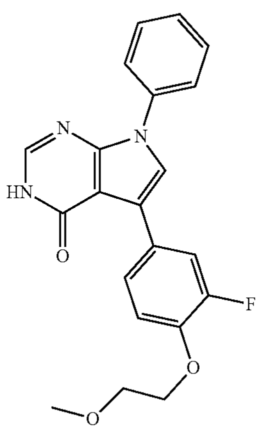
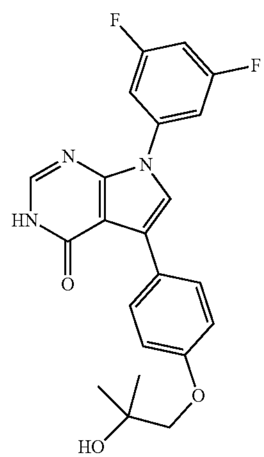
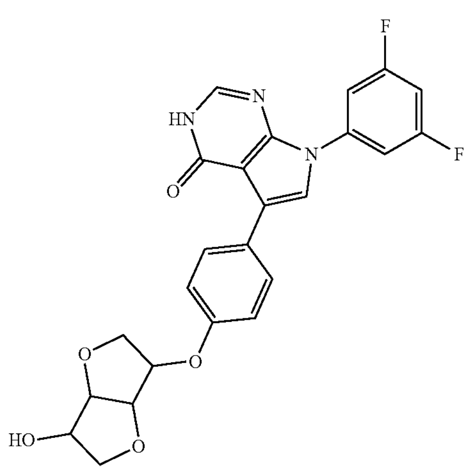
-continued
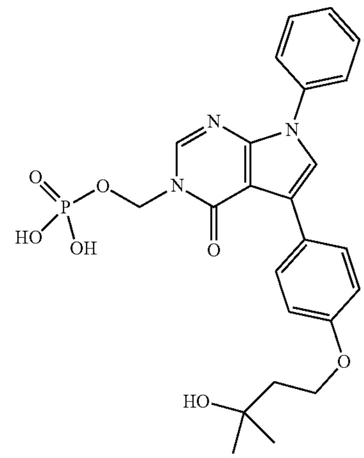
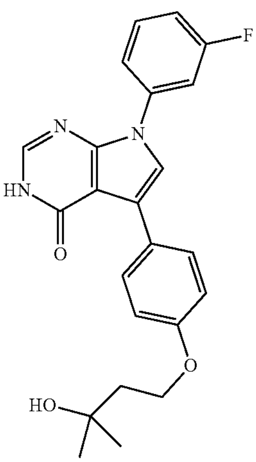
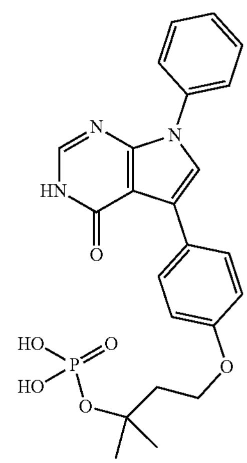
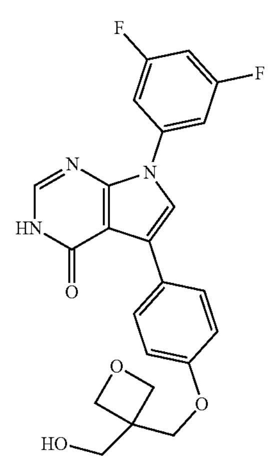
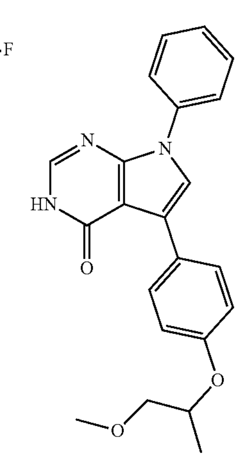

-continued

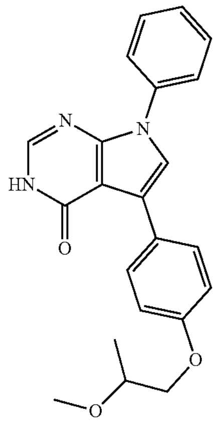

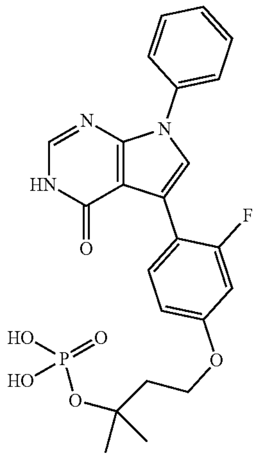

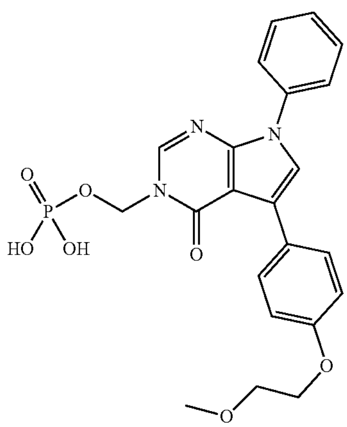

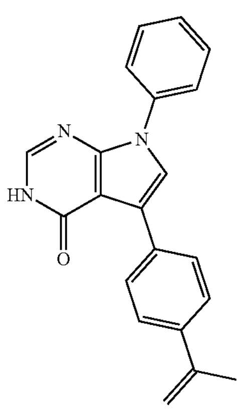

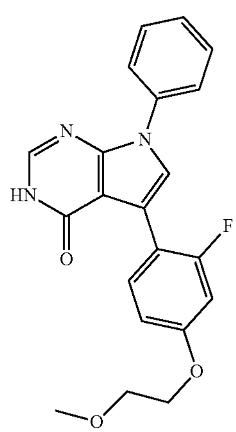

-continued

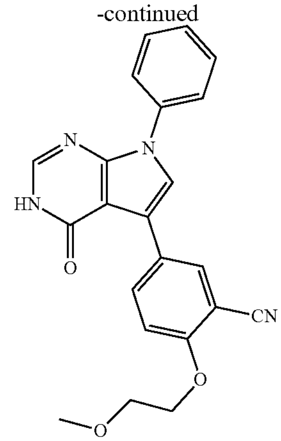

Any of the specific compounds in the preceding paragraph and the following paragraph may be a prodrug, wherein the prodrug is the compound with $—CH_2P(═O)(OH)_2$ substituted on the NH (replacing the H) of the bicyclic core of the compounds. Alternatively, where the compound comprises a free OH or a OMe, the H or the Me could be replaced by $—P(═O)(OH)_2$. An example of potential prodrugs of the invention are demonstrated below. The prodrugs may for part of the present invention. The compounds disclosed herein as prodrugs may also have activity against MAP4K4. Accordingly, those compounds disclosed herein as being prodrugs may also be compounds of the present invention.

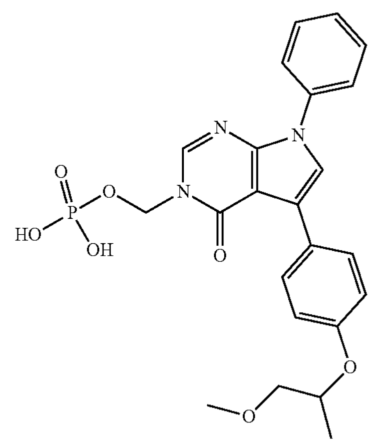

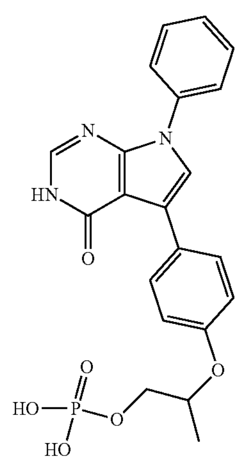

-continued
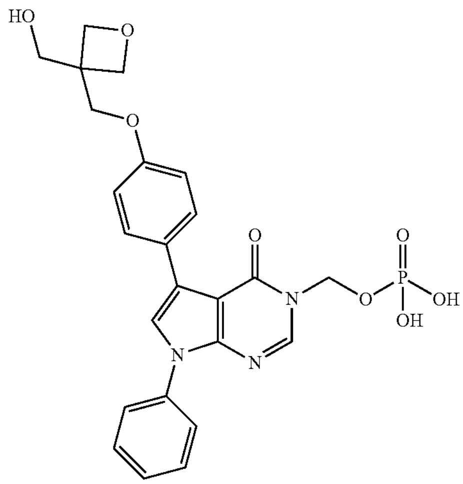
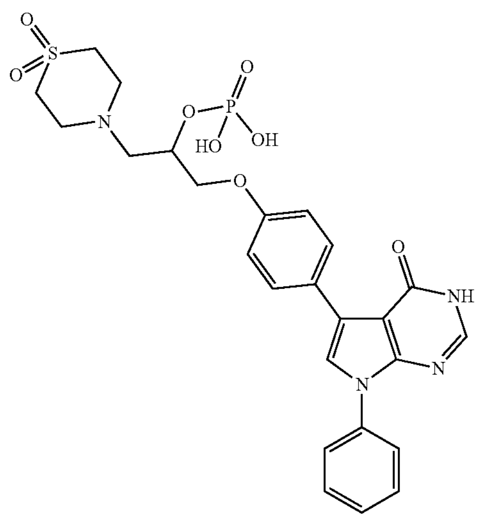
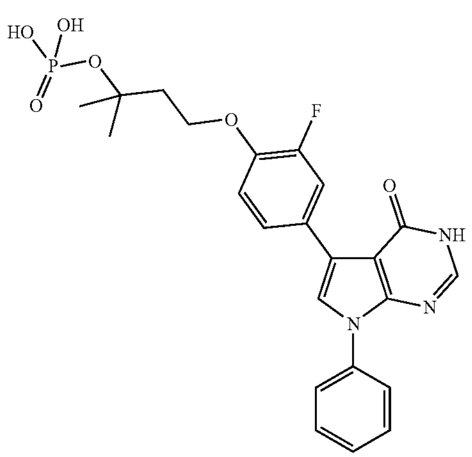
The present invention also contemplates that compounds according to formula (I) might be selected from:
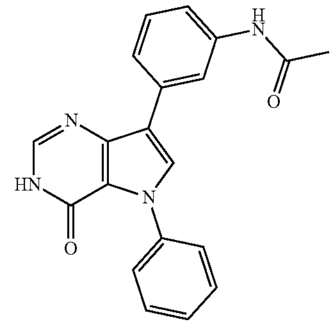
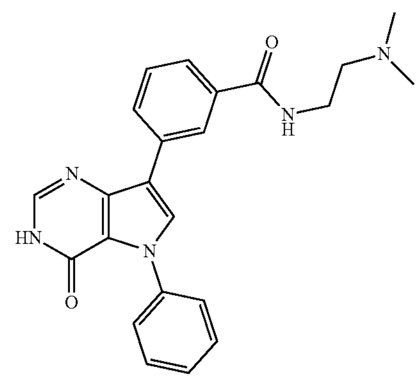
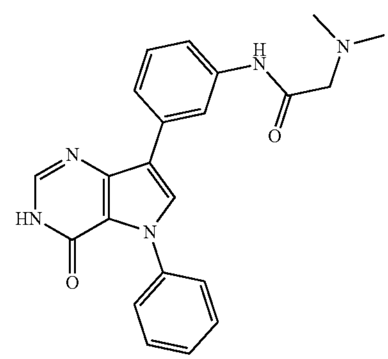
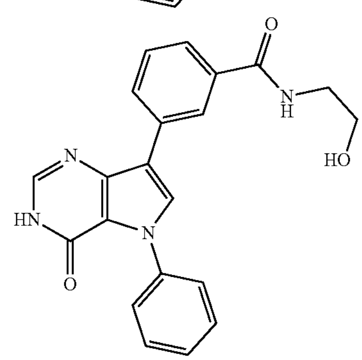

-continued
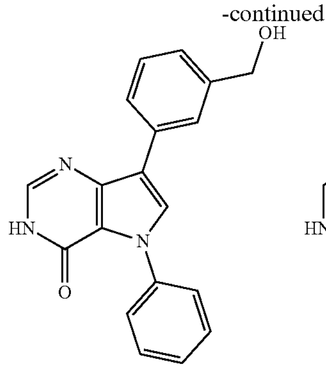
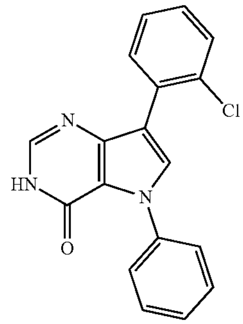
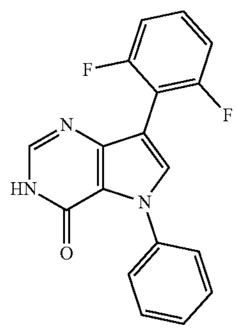
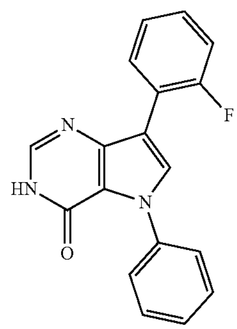
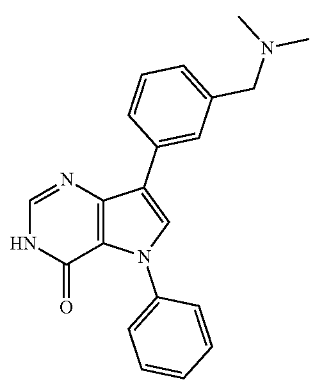
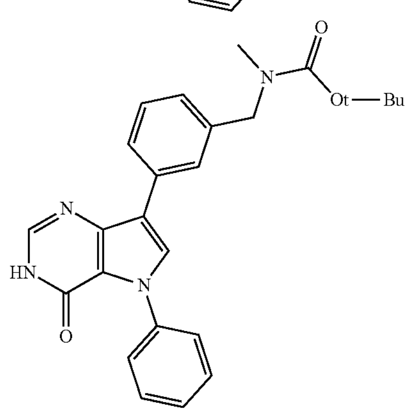
-continued
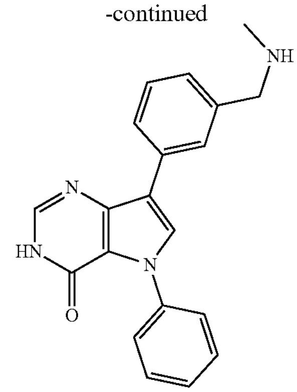
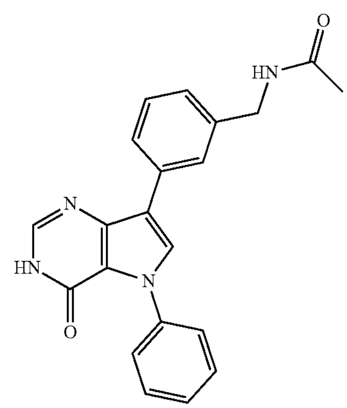
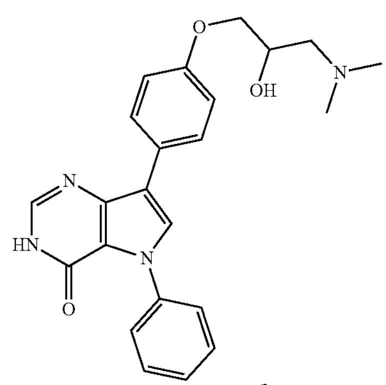
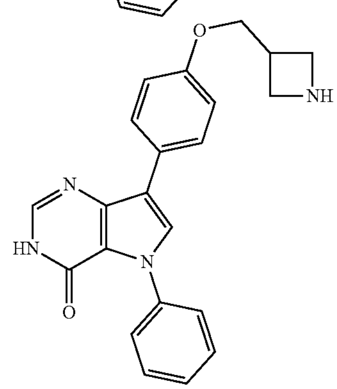

-continued

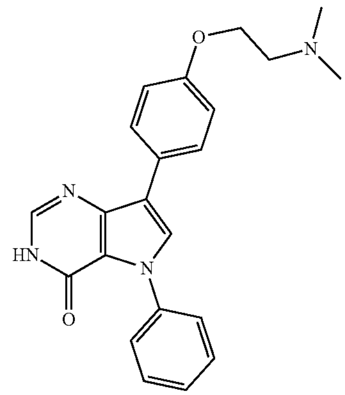

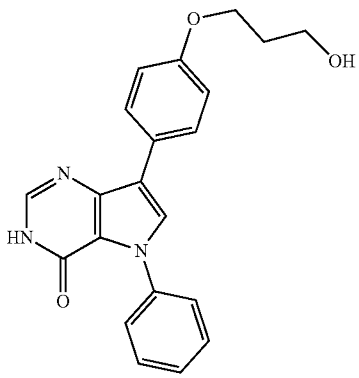

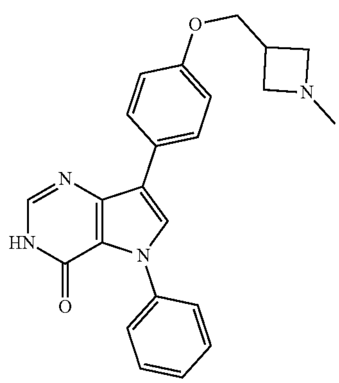

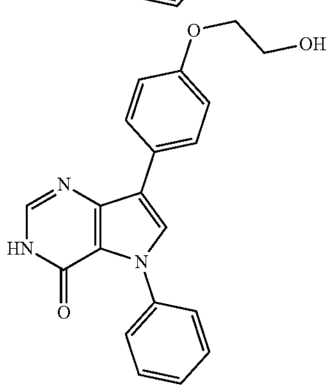

-continued

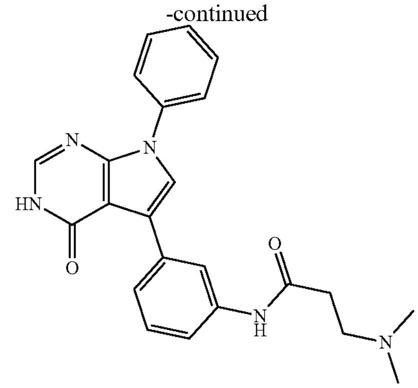

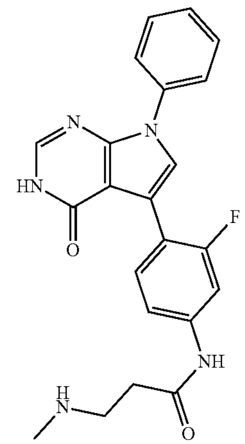 [SMILES: CNCCC(=O)Nc1ccc(-c2cn(-c3ccccc3)c3nc[nH]c(=O)c23)c(F)c1]

In accordance with the present invention there is provided a compound of formula (I) or a pharmaceutically acceptable salt thereof for use as a medicament:

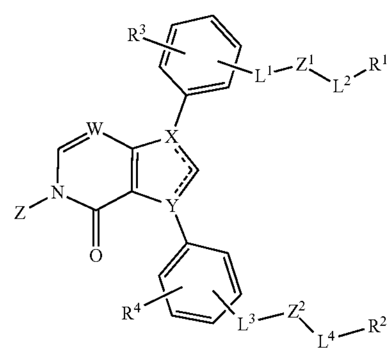

(I)

wherein

W is CH or N;

either X is N and Y is C, or Y is N and X is C;

Z is either H or $—CH_2OP(=O)(OH)_2$;

$L^1$ and $L^3$ are independently selected from a bond, $—(CR^aR^b)_m—$, $—O(CR^aR^b)_m—$ or $—NH(CR^aR^b)_m—$, wherein m is at each occurrence independently selected from 1, 2, 3, or 4;

$Z^1$ is a bond, $—NR^{5a}—$, $—O—$, $—C(O)—$, $—SO_2—$, $—SO_2NR^{5a}—$, $—NR^{5a}SO_2—$, $—C(O)NR^{5a}—$, $—NR^{5a}C(O)—$, $—C(O)O—$, or $—NR^{5a}C(O)NR^{5a}—$;

$Z^2$ is a bond, $—NR^{5b}—$, $—O—$, $—C(O)—$, $—SO_2—$, $—SO_2NR^{5a}—$, $—NR^{5a}SO_2—$, $—C(O)NR^{5a}—$, $—NR^{5b}C(O)—$, or $—C(O)O—$;

$L^2$ and $L^4$ are independently either a bond or $—(CR^cR^d)_n—$, wherein n is at each occurrence independently selected from 1, 2, 3, or 4;

$R^1$ is selected from H, halo, $C_{1-6}$ alkyl, $C_{2-6}$ alkenyl, $C_{1-6}$ haloalkyl, $—NR^{6a}R^{6b}$, $—OR^{6a}$, $—OP(═O)(OH)_2$, $—C(O)R^{6a}$, 5 or 6 membered heteroaryl rings, or 3 to 8 membered heterocycloalkyl ring systems, wherein the heteroaryl and heterocycloalkyl rings are unsubstituted or substituted with 1 or 2 groups selected from: oxo, halo, $OR^{6a}$, $C_{1-6}$ alkyl, $C_{1-6}$ alkyl substituted with $NR^{6a}R^{6b}$, $C_{1-6}$ alkyl substituted with $OR^{6a}$, $—C(O)R^7$, and $—NR^8C(O)R^7$;

$R^2$ is selected from H, halo, $C_{1-6}$ alkyl, $C_{2-6}$ alkenyl, $C_{1-6}$ haloalkyl, $—NR^{6a}R^{6b}$, $—OR^{6a}$, $—P(═O)(OH)_2$, $—C(O)R^{6a}$, $—NR^{5b}C(O)O—C_{1-6}$ alkyl, phenyl, 5 or 6 membered heteroaryl rings, or 3 to 8 membered heterocycloalkyl ring systems, wherein the phenyl, heteroaryl and heterocycloalkyl rings are unsubstituted or substituted with 1 or 2 groups selected from: oxo, halo, $OR^{6a}$, $C_{1-6}$ alkyl, $C_{1-6}$ alkyl substituted with $NR^{6a}R^{6b}$, $C_{1-6}$ alkyl substituted with $OR^{6a}$, $—C(O)OR^9$, and $—NR^8C(O)R^7$;

$R^3$ and $R^4$ are independently selected from H, halo, —CN and $C_{1-6}$ alkyl;

$R^{5a}$ and $R^{5b}$ are independently selected at each occurrence, from: H, $C_{1-6}$ alkyl, or $C_{3-6}$ cycloalkyl;

$R^6$ and $R^{6b}$ are, independently selected at each occurrence, from: H, $C_{1-6}$ alkyl, $C_{1-6}$ alkyl, $—P(═O)(OH)_2$, substituted with $—OR^e$, $C_{1-6}$ alkyl substituted with $—NR^eR^f$, and $C_{3-6}$ cycloalkyl;

$R^7$ is selected from H, $—OR^9$, $C_{1-6}$ alkyl and $C_{3-6}$ cycloalkyl;

$R^8$ is selected from H and $C_{1-6}$ alkyl;

$R^a$, $R^b$, $R^c$ and $R^d$ are, at each occurrence, independently selected from: H, halo, $C_{1-6}$ alkyl, and $—OR^h$, or $R^a$ and $R^b$ or $R^c$ and $R^d$ taken together with the atom to which they are attached form a 3 to 6 membered cycloalkyl ring or a 3 to 6 membered heterocycloalkyl ring containing 1 or 2 O, N or S atoms, wherein the cycloalkyl ring is unsubstituted or substituted with 1 or 2 halo groups; and $R^e$, $R^f$, $R^g$ and $R^h$ are each independently selected at each occurrence from H or $C_{1-6}$ alkyl.

In an embodiment of the present invention the compound of formula (I) for use as a medicament is a compound according to formula (I') or a pharmaceutically acceptable salt thereof:

(I')

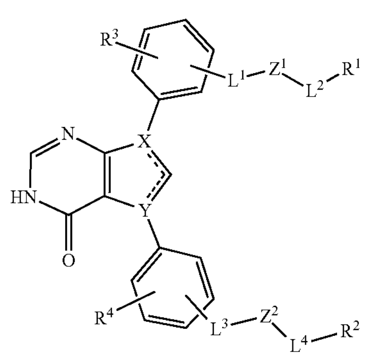

wherein either X is N and Y is C, or Y is N and X is C;

$L^1$ and $L^3$ are independently selected from a bond, $—(CR^aR^b)_m—$, $—O(CR^aR^b)_m—$ or $—NH(CR^aR^b)_m—$, wherein m is at each occurrence independently selected from 1, 2, 3, or 4;

$Z^1$ is a bond, $—NR^{5a}—$, —O—, $—C(O)_2—$, $SO_2NR^{5a}—$, $—NR^{5a}SO_2—$, $—C(O)NR^{5a}—$, $—NR^{5a}C(O)—$, —C(O)O—, or $—NR^{5a}C(O)NR^{5a}—$;

$Z^2$ is a bond, $—NR^{5b}—$, —O—, —C(O)—, $—SO_2—$, $—SO_2NR^{5a}—$, $—NR^{5a}SO_2—$, $—C(O)NR^{5a}—$, $—NR^{5b}C(O)—$, or $—C(O)O-L^2$ and $L^4$ are independently either a bond or $—(CR^cR^d)_n—$, wherein n is at each occurrence independently selected from 1, 2, 3, or 4;

$R^1$ is selected from H, halo, $C_{1-6}$ alkyl, $C_{2-6}$ alkenyl, $C_{1-6}$ haloalkyl, $—NR^{6a}R^{6b}$, $—OR^{6a}$, $—C(O)R^{6a}$, 5 or 6 membered heteroaryl rings, or 3 to 8 membered heterocycloalkyl ring systems, wherein the heteroaryl and heterocycloalkyl rings are unsubstituted or substituted with 1 or 2 groups selected from: $C_{1-6}$ alkyl, oxo, halo, $OR^{6a}$, $C_{1-6}$ alkyl, $C_{1-6}$ alkyl substituted with $NR^{6a}R^{6b}$, $C_{1-6}$ alkyl substituted with $OR^{6a}$, $—C(O)R^7$, and $—NR^8C(O)R^7$;

$R^2$ is selected from H, halo, $C_{1-6}$ alkyl, $C_{2-6}$ alkenyl, $C_{1-6}$ haloalkyl, $—NR^{6a}R^{6b}$, $—OR^{6a}$, $—C(O)R^{6a}$, $—NR^{5b}C(O)O—C_{1-6}$ alkyl, phenyl, 5 or 6 membered heteroaryl rings, or 3 to 8 membered heterocycloalkyl ring systems, wherein the phenyl, heteroaryl and heterocycloalkyl rings are unsubstituted or substituted with 1 or 2 groups selected from: oxo, halo, $OR^{6a}$, $C_{1-6}$ alkyl, $C_{1-6}$ alkyl substituted with $NR^{6a}R^{6b}$, $C_{1-6}$ alkyl substituted with $OR^{6a}$, $—C(O)OR^9$, and $—NR^8C(O)R^7$;

$R^3$ and $R^4$ are independently selected from H, halo, —CN and $C_{1-6}$ alkyl;

$R^{5a}$ and $R^{5b}$ are independently selected at each occurrence, from: H, $C_{1-6}$ alkyl, or $C_{3-6}$ cycloalkyl;

$R^{6a}$ and $R^{6b}$ are, independently selected at each occurrence, from: H, $C_{1-6}$ alkyl, $C_{1-6}$ alkyl substituted with $—OR^e$, $C_{1-6}$ alkyl substituted with $—NR^eR^f$, and $C_{3-6}$ cycloalkyl;

$R^7$ is selected from H, $—OR^9$, $C_{1-6}$ alkyl and $C_{3-6}$ cycloalkyl;

$R^8$ is selected from H and $C_{1-6}$ alkyl;

$R^a$, $R^b$, $R^c$ and $R^d$ are, at each occurrence, independently selected from: H, halo, $C_{1-6}$ alkyl, and $—OR^h$, or $R^a$ and $R^b$ or $R^c$ and $R^d$ taken together with the atom to which they are attached form a 3 to 6 membered cycloalkyl ring or a 3 to 6 membered heterocycloalkyl ring containing 1 or 2 O, N or S atoms, wherein the cycloalkyl ring is unsubstituted or substituted with 1 or 2 halo groups; and $R^e$, $R^f$, $R^g$ and $R^h$ are each independently selected at each occurrence from H or $C_{1-6}$ alkyl.

The compound of formula (I) or formula (I') above may be for use in a method of treatment. Equally a method of treatment may comprise the steps of administering a therapeutically effective amount of the compound of formula (I) or formula (I') to a patient in need thereof. The compound of formula (I) or formula (I') for use in the method is not subject to the proviso's provided above for the compound per se. However, in embodiments the compound of formula (I) or formula (I') for use in the method of treatment may be subject to the proviso's discussed above.

The compound of formula (I) or formula (I'), with or without the proviso's may be used in a method of treating any of the conditions discussed below.

Therapeutic Uses and Applications

In accordance with another aspect, the present invention provides a compound of the invention, or a pharmaceutically acceptable salt thereof, for use as a medicament.

The present invention also provides the compounds of the present invention for use in the treatment of a disease mediated by MAP4K4. Thus, the invention contemplates a method of treating a disease mediated by MAP4K4, wherein the method comprises administering to a patient in need thereof a therapeutically effective amount of a compound of the invention.

The present invention also provides a MAP4K4 inhibitor for use in the treatment of myocardial infarction (colloquially, "heart attacks" due to atherosclerosis, coronary thrombosis, coronary artery anomalies, or other interference with blood flow or oxygen and nutrient delivery to the heart). This aspect of the invention may be a method of treating infarcts, wherein the method comprises the administration of a therapeutically effective amount of a MAP4K4 inhibitor. This aspect may also provide a MAP4K4 inhibitor for use in a method of treating infarcts as an adjunct to standard therapies that restore coronary blood flow (angioplasty, stent placement, thrombolysis) but may, paradoxically, be offset by reperfusion injury. The treatment of an infarct may constitute the complete reversal of an infarct or the reduction in size of an infarct. Reduction of infarct size is known to lessen subsequent progression to heart failure (Selker et al. 2017. Am Heart J 188:18-25).

In an embodiment the MAP4K4 inhibitor is a compound of the present invention, for use in the prevention or treatment of other forms of heart muscle cell injury. These include but are not limited to drug-induced cardiomyopathies (Varga et al. 2015 Am J Physiol Heart Circ Physiol. 2015 November; 309(9):H1453-67), e.g widely used anticancer drugs [anthracyclines (Doxorubicin/Adriamycin), cisplatin, trastuzumab (Herceptin), arsenic trioxide (Trisenox), mitoxantrone (Novantrone), imatinib (Gleevec), bevacizumab (Avastin), sunitinib (Sutent), and sorafenib (Nevaxar)], antiviral compound azidothymidine (AZT, Zidovudine), several oral antidiabetics [e.g., rosiglitazone (Avandia)], and illicit drugs such as alcohol, cocaine, methamphetamine, ecstasy, and synthetic cannabinoids (spice, K2).

In an embodiment the MAP4K4 inhibitor is a compound of the present invention, for use in the prevention or treatment of other forms of heart muscle cell injury, optionally due to cardiopulmonary bypass.

In an embodiment the MAP4K4 inhibitor is a compound of the present invention, for use in the prevention or treatment of chronic forms of heart muscle cell injury, such as hypertrophic, dilated, or mitochondrial cardiomyopathies. These include cardiomyopathies due to: genetic conditions; high blood pressure; heart tissue damage from a previous heart attack; chronic rapid heart rate; heart valve problems; metabolic disorders, such as obesity, thyroid disease or diabetes; nutritional deficiencies of essential vitamins or minerals, such as thiamine (vitamin B1); pregnancy complications; alcohol consumption; use of cocaine, amphetamines or anabolic steroids; radiotherapy to treat cancer; certain infections, which may injure the heart and trigger cardiomyopathy; hemochromatosis; sarcoidosis; amyloidosis; and connective tissue disorders.

In an embodiment the MAP4K4 inhibitor is a compound of the present invention, for use in the prevention or treatment of other forms of ischemic injury or ischemia-reperfusion injury, including ischemia stroke, renal artery occlusion, and global ischemia-reperfusion injury (cardiac arrest).

In an embodiment the MAP4K4 inhibitor is a compound of the present invention, for use in the prevention or treatment of cardiac muscle cell necrosis or cardiac muscle cell apoptosis.

In embodiments there is provided a compound of the present invention for use in a method of treatment of heart muscle cell injury, heart muscle cell injury due to cardiopulmonary bypass, chronic forms of heart muscle cell injury, hypertrophic cardiomyopathies, dilated cardiomyopathies, mitochondrial cardiomyopathies, cardiomyopathies due to genetic conditions; cardiomyopathies due to high blood pressure; cardiomyopathies due to heart tissue damage from a previous heart attack; cardiomyopathies due to chronic rapid heart rate; cardiomyopathies due to heart valve problems; cardiomyopathies due to metabolic disorders; cardiomyopathies due to nutritional deficiencies of essential vitamins or minerals; cardiomyopathies due to alcohol consumption; cardiomyopathies due to use of cocaine, amphetamines or anabolic steroids; cardiomyopathies due to radiotherapy to treat cancer; cardiomyopathies due to certain infections which may injure the heart and trigger cardiomyopathy; cardiomyopathies due to hemochromatosis; cardiomyopathies due to sarcoidosis; cardiomyopathies due to amyloidosis; cardiomyopathies due to connective tissue disorders; drug- or radiation-induced cardiomyopathies; idiopathic or cryptogenic cardiomyopathies; other forms of ischemic injury, including but not limited to ischemia-reperfusion injury, ischemia stroke, renal artery occlusion, and global ischemia-reperfusion injury (cardiac arrest); cardiac muscle cell necrosis; or cardiac muscle cell apoptosis.

In an aspect there is provided a method of using stem cell-derived cardiomyocytes for the identification of therapies for myocardial infarction, wherein the method comprising contacting stem cell derived cardiomyocytes with compounds in a cell culture model of cardiac muscle cell death. For example, as indicated in the examples of the present application.

In embodiments the method is conducted ex vivo. Thus, in embodiments the method is not a method of treatment or diagnosis.

In an embodiment the method of using stem cell-derived cardiomyocytes for the identification of therapies for myocardial infarction uses human stem cell derived cardiomyocytes.

In embodiments there is provided a method of using human stem cell-derived cardiomyocytes for the identification of therapies for myocardial infarction wherein the method comprises subjecting human stem cell-derived cardiomyocytes with candidate test compounds in a cell culture model of cardiac muscle cell death. Examples of relevant stressors, by which compounds may be tested, include: $H_2O_2$, menadione, and other compounds that confer oxidative stress; hypoxia; hypoxia/reoxygenation; glucose deprivation or compounds that interfere with metabolism; cardiotoxic drugs; proteins or genes that promote cell death; interference with the expression or function of proteins or genes that antagonise cell death. Cell death is taken to encompass apoptosis, necrosis, necroptosis, or autophagy, singly or in combination.

BRIEF DESCRIPTION OF THE DRAWINGS

Embodiments of the invention are further described hereinafter with reference to the accompanying drawings, in which.

DETAILED DESCRIPTION

Figure 1:
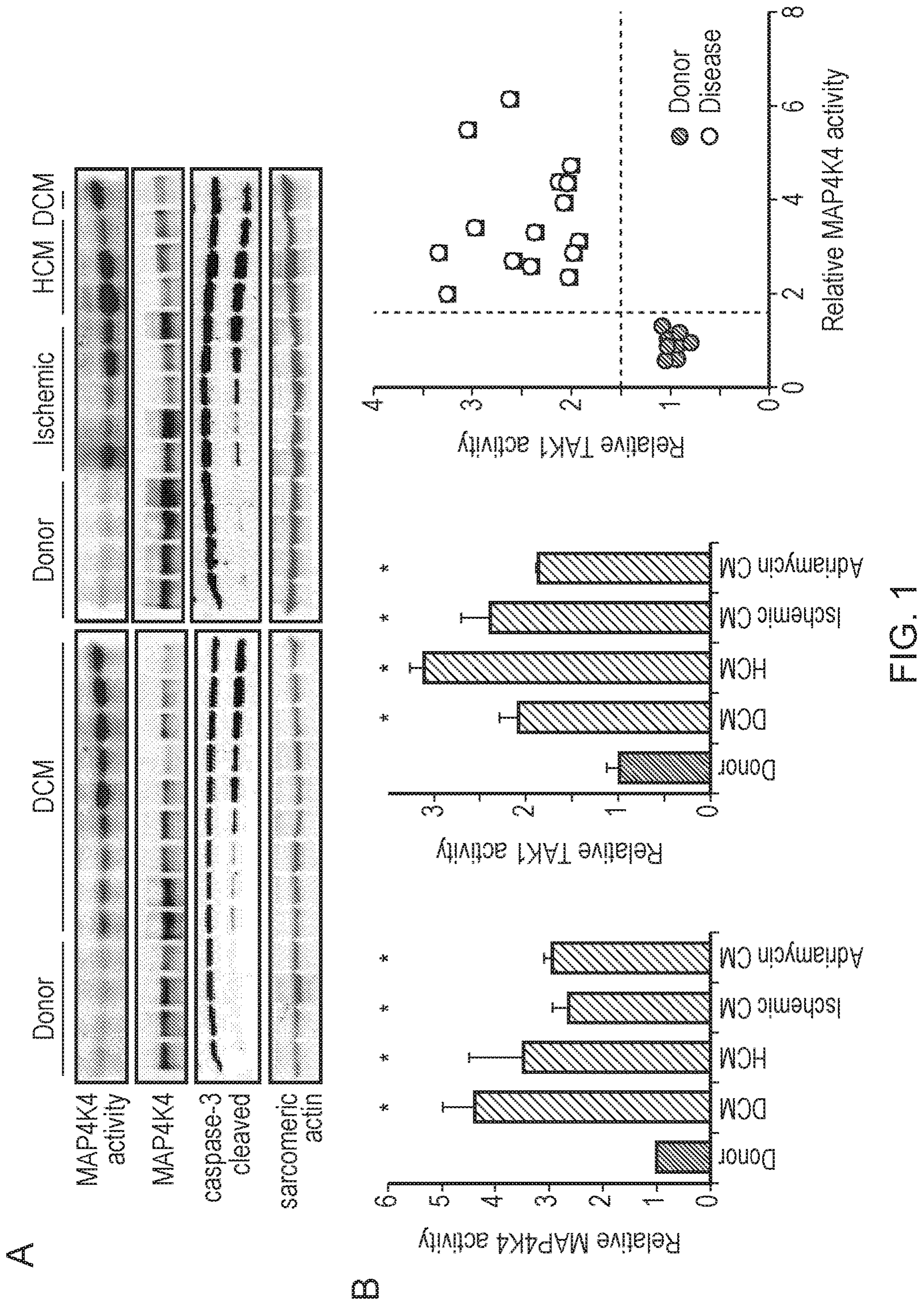
FIG. 1 provides data demonstrating the relationship between MAP4K4 and cardiac muscle cell death.
Figure 1:
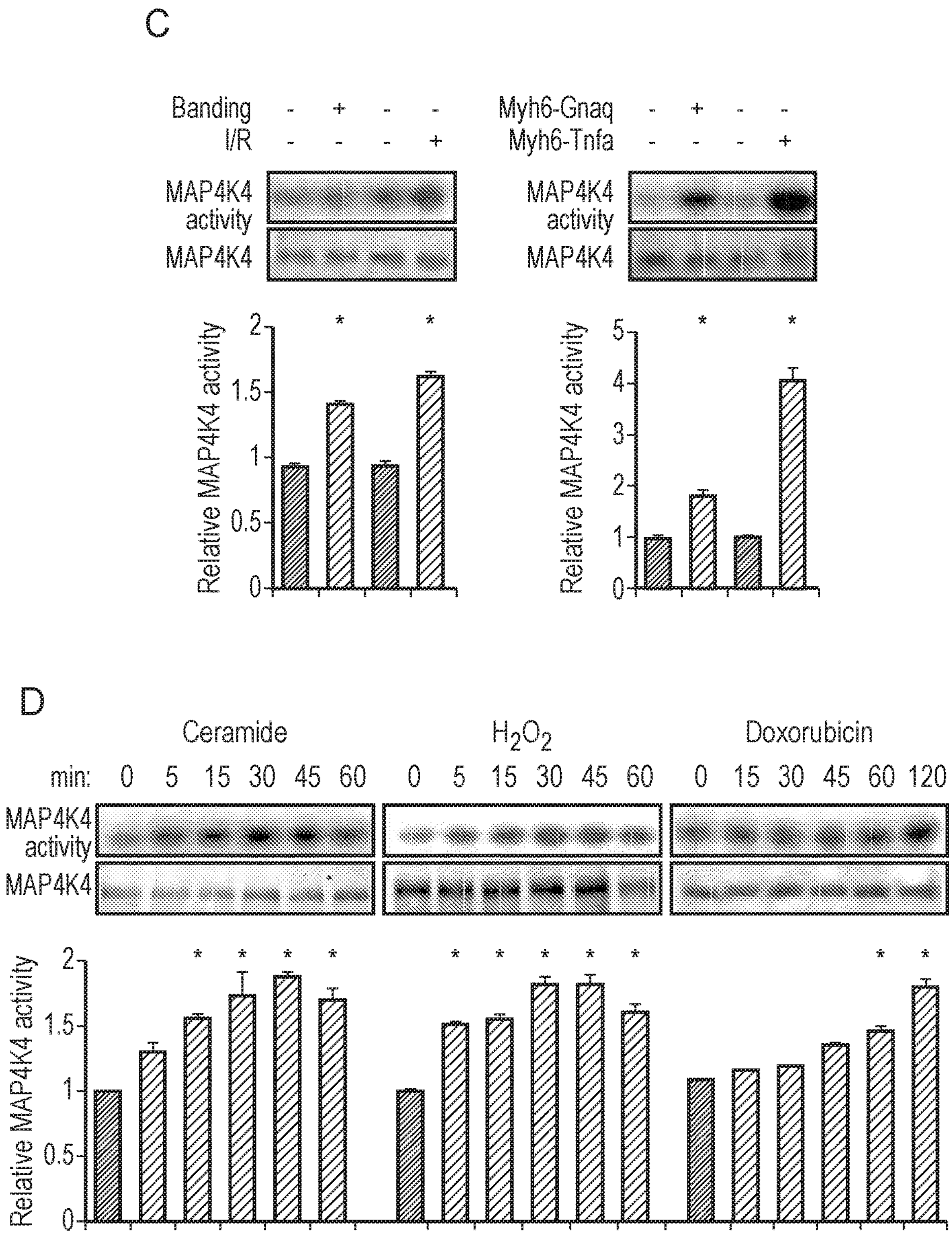
Figure 2:
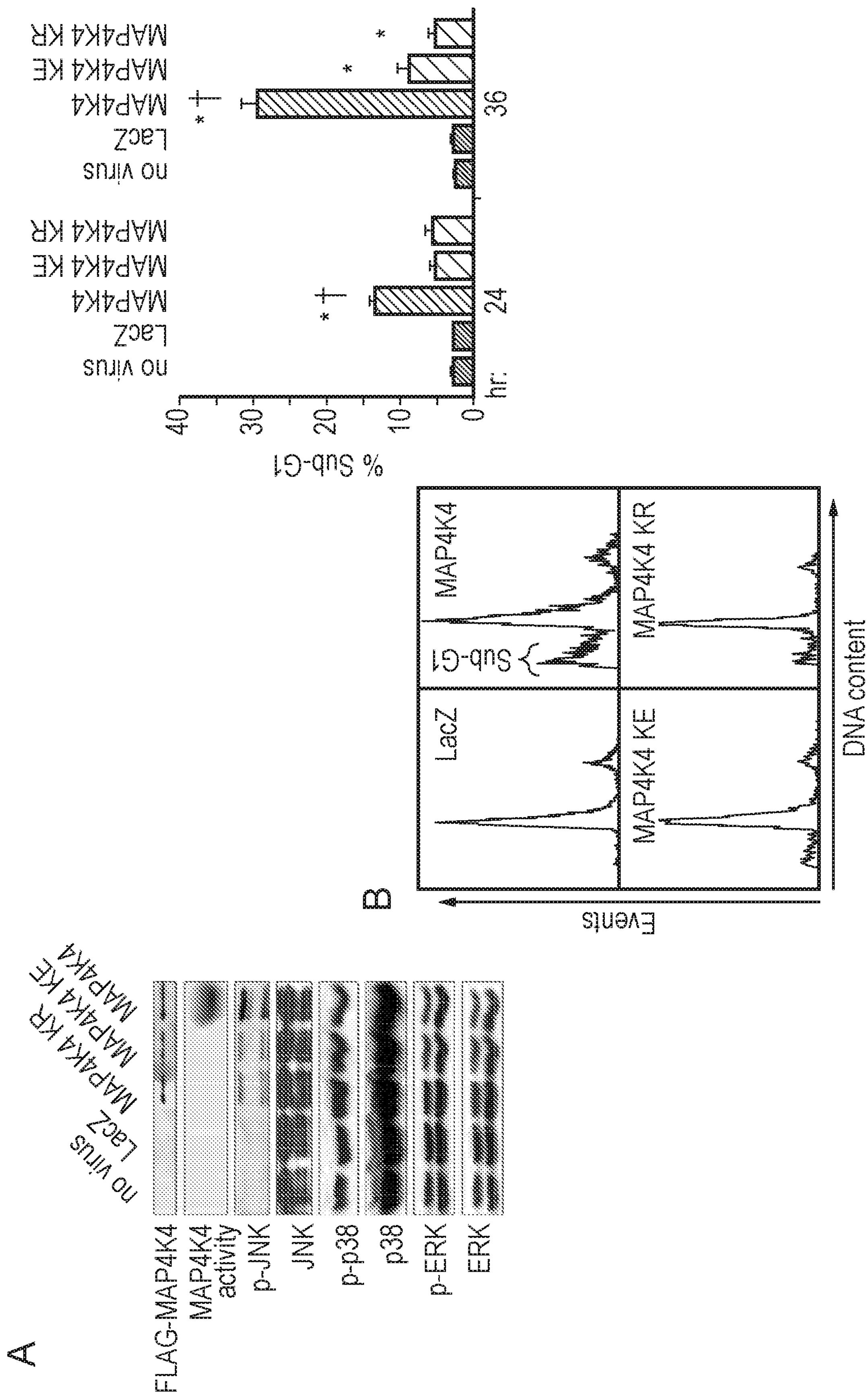
FIG. 2 provides data where a simulated increase in MAP4K4 activity was simulated and a pro-apoptotic effect of MAP4K4 was demonstrated.
Figure 2:
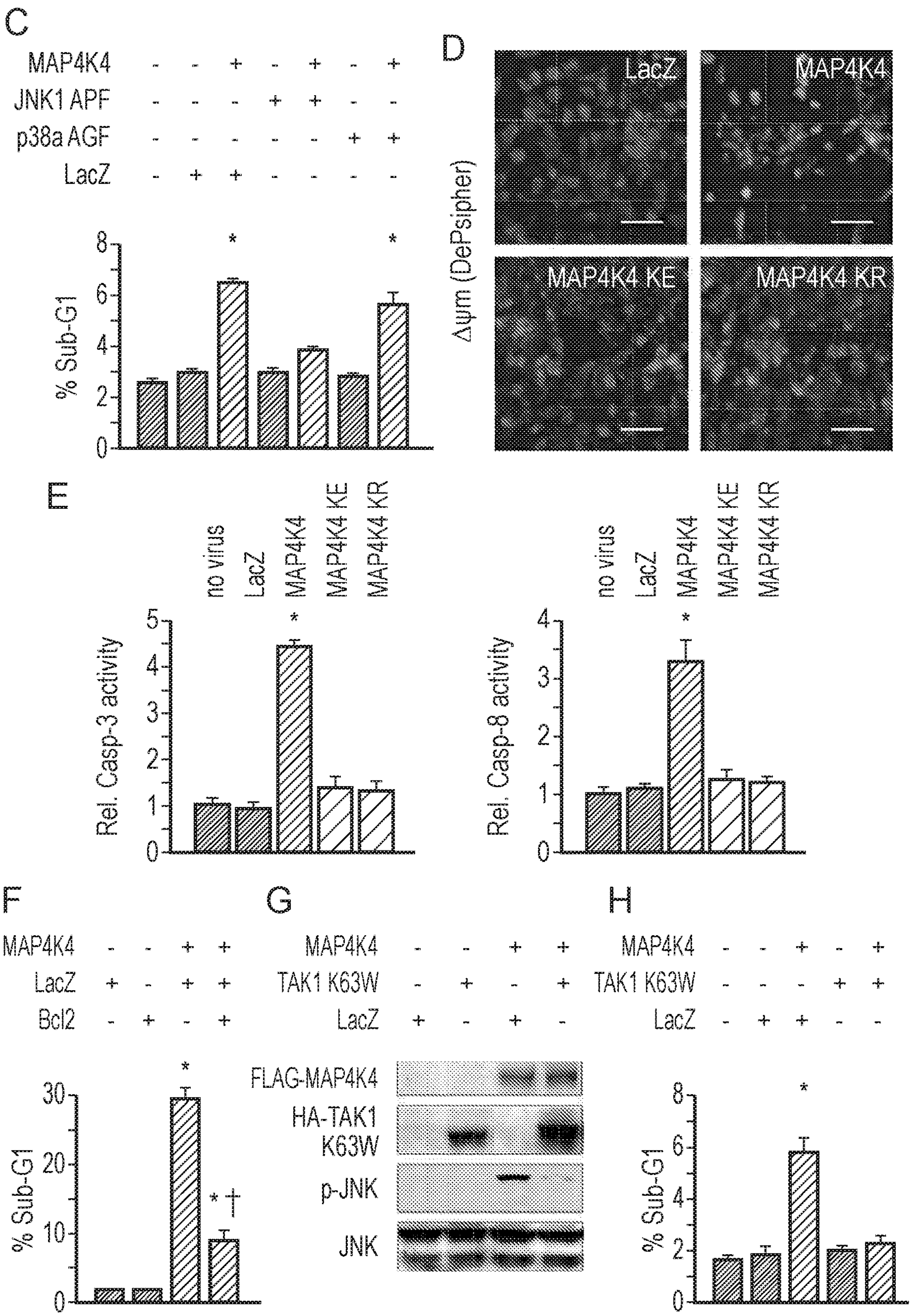

Unless otherwise stated, the following terms used in the specification and claims have the following meanings set out below.

It is to be appreciated that references to "treating" or "treatment" include prophylaxis as well as the alleviation of established symptoms or physical manifestations of a condition. "Treating" or "treatment" of a state, disorder or condition therefore includes: (1) preventing or delaying the appearance of clinical symptoms or physical manifestations of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the method of administration, the disease and its severity and the age, weight, etc., of the mammal to be treated.

The term "halo" or "halogen" refers to one of the halogens, group 17 of the periodic table. In particular the term refers to fluorine, chlorine, bromine and iodine. Preferably, the term refers to fluorine or chlorine.

The term $C_{m-n}$ refers to a group with m to n carbon atoms.

The term "$C_{1-6}$ alkyl" refers to a linear or branched hydrocarbon chain containing 1, 2, 3, 4, or 6 carbon atoms, for example methyl, ethyl, n-propyl, iso-propyl, n-butyl, sec-butyl, tert-butyl, n-pentyl and n-hexyl. "$C_{1-4}$ alkyl" similarly refers to such groups containing from 1 to 4 carbon atoms. Alkylene groups are divalent alkyl groups and may likewise be linear or branched and have two points of attachment to the remainder of the molecule. Furthermore, an alkylene group may, for example, correspond to one of those alkyl groups listed in this paragraph. The alkyl and alkylene groups may be unsubstituted or substituted by one or more substituents. Possible substituents are described in more detail below. Substituents for the alkyl group may be halogen, e.g. fluorine, chlorine, bromine and iodine, OH, $C_1$-$C_4$ alkoxy. Other substituents for the alkyl group may alternatively be used.

The term "haloalkyl", e.g. "$C_{1-6}$ haloalkyl", refers to a hydrocarbon chain substituted with at least one halogen atom independently chosen at each occurrence, for example from fluorine, chlorine, bromine and iodine. The halogen atom may be present at any position on the hydrocarbon chain. For example, $C_{1-6}$ haloalkyl may refer to chloromethyl, fluoromethyl, trifluoromethyl, chloroethyl e.g. 1-chloromethyl and 2-chloroethyl, trichloroethyl e.g. 1,2,2-trichloroethyl, 2,2,2-trichloroethyl, fluoroethyl e.g. 1-fluoromethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl.

The term "$C_{2-6}$ alkenyl" includes a branched or linear hydrocarbon chain containing at least one double bond and having 2, 3, 4, 5 or 6 carbon atoms. The double bond(s) may be present as the E or Z isomer. The double bond may be at any possible position of the hydrocarbon chain. For example, the "$C_{2-6}$ alkenyl" may be ethenyl, propenyl, butenyl, butadienyl, pentenyl, pentadienyl, hexenyl and hexadienyl.

The term "$C_{2-6}$ alkynyl" includes a branched or linear hydrocarbon chain containing at least one triple bond and having 2, 3, 4, 5 or 6 carbon atoms. The triple bond may be at any possible position of the hydrocarbon chain. For example, the "$C_{2-6}$ alkynyl" may be ethynyl, propynyl, butynyl, pentynyl and hexynyl.

The term "$C_{3-6}$ cycloalkyl" includes a saturated hydrocarbon ring system containing 3, 4, 5 or 6 carbon atoms. For example, the "$C_3$-$C_6$ cycloalkyl" may be cyclopropyl, cyclobutyl, cyclopentyl, cyclohexyl, bicyclo[2.1.1]hexane or bicyclo[1.1.1]pentane.

The term "heterocycloalkyl" includes a saturated monocyclic or fused, bridged, or spiro bicyclic heterocyclic ring system(s). The term "heterocycloalkyl" includes ring systems with from 1 to 5 (suitably 1, 2 or 3) heteroatoms selected from nitrogen, oxygen or sulfur in the ring. Unless otherwise indicated by a recital of the number of atoms within the heterocycloalkyl ring, monocyclic heterocycloalkyl rings may contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles may contain from 7 to 17 member atoms, suitably 7 to 12 member atoms, in the ring. Bicyclic heterocyclic(s) rings may be fused, spiro, or bridged ring systems. Examples of heterocycloalkyl groups include cyclic ethers such as oxiranyl, oxetanyl, tetrahydrofuranyl, dioxanyl, and substituted cyclic ethers. Heterocycloalkyl rings comprising at least one nitrogen in a ring position include, for example, azetidinyl, pyrrolidinyl, piperidinyl, piperazinyl, morpholinyl, thiomorpholinyl, tetrahydrotriazinyl, tetrahydropyrazolyl, tetrahydropyridinyl, homopiperidinyl, homopiperazinyl, 3,8-diaza-bicyclo[3.2.1]octanyl, 8-aza-bicyclo[3.2.1]octanyl, 2,5-Diaza-bicyclo[2.2.1]heptanyl and the like. Typical sulfur containing heterocycloalkyl rings include tetrahydrothienyl, dihydro-1,3-dithiol, tetrahydro-2H-thiopyran, and hexahydrothiepine.

Other heterocycloalkyl rings include dihydrooxathiolyl, tetrahydro oxazolyl, tetrahydro-oxadiazolyl, tetrahydrodioxazolyl, tetrahydrooxathiazolyl, hexahydrotriazinyl, tetrahydro oxazinyl, tetrahydropyrimidinyl, dioxolanyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (═O), for example, 2 oxopyrrolidinyl, 2-oxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. For example, the term "piperidino" or "morpholino" refers to a piperidin-1-yl or morpholin-4-yl ring that is linked via the ring nitrogen.

The term "bridged ring systems" includes ring systems in which two rings share more than two atoms, see for example Advanced Organic Chemistry, by Jerry March, 4th Edition, Wiley Interscience, pages 131-133, 1992.

The term "spiro bi-cyclic ring systems" includes ring systems in which two ring systems share one common spiro carbon atom, i.e. the heterocyclic ring is linked to a further carbocyclic or heterocyclic ring through a single common spiro carbon atom.

The term "aromatic" when applied to a substituent as a whole includes a single ring or polycyclic ring system with 4n+2 electrons in a conjugated π system within the ring or ring system where all atoms contributing to the conjugated π system are in the same plane.

The term "aryl" includes an aromatic hydrocarbon ring system. The ring system has 4n+2 electrons in a conjugated π system within a ring where all atoms contributing to the conjugated π system are in the same plane. For example, the "aryl" may be phenyl and naphthyl. The aryl system itself may be substituted with other groups.

The term "heteroaryl" includes an aromatic mono- or bicyclic ring incorporating one or more (for example 1-4, particularly 1, 2 or 3) heteroatoms selected from nitrogen, oxygen or sulfur. The ring or ring system has 4n+2 electrons in a conjugated π system where all atoms contributing to the conjugated π system are in the same plane.

Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl and imidazo[1,2-b][1,2,4]triazinyl. Examples of heteroaryl groups comprising at least one nitrogen in a ring position include pyrrolyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, indolyl, isoindolyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl and pteridinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

Particular examples of bicyclic heteroaryl groups containing a six membered ring fused to a five membered ring include but are not limited to benzofuranyl, benzothiophenyl, benzimidazolyl, benzoxazolyl, benzisoxazolyl, benzothiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl, pyrrolopyridine, and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

The term "optionally substituted" includes either groups, structures, or molecules that are substituted and those that are not substituted.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically. 

A bond terminating in a " 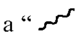 " represents that the bond is connected to another atom that is not shown in the structure. A bond terminating inside a cyclic structure and not terminating at an atom of the ring structure represents that the bond may be connected to any of the atoms in the ring structure where allowed by valency.

Where a moiety is substituted, it may be substituted at any point on the moiety where chemically possible and consistent with atomic valency requirements. The moiety may be substituted by one or more substituents, e.g. 1, 2, 3 or 4 substituents; optionally there are 1 or 2 substituents on a group. Where there are two or more substituents, the substituents may be the same or different.

Substituents are only present at positions where they are chemically possible, the person skilled in the art being able to decide (either experimentally or theoretically) without undue effort which substitutions are chemically possible and which are not.

Ortho, meta and para substitution are well understood terms in the art. For the absence of doubt, "ortho" substitution is a substitution pattern where adjacent carbons possess a substituent, whether a simple group, for example the fluoro group in the example below, or other portions of the molecule, as indicated by the bond ending in"  ".

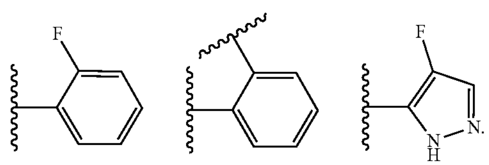

"Meta" substitution is a substitution pattern where two substituents are on carbons one carbon removed from each other, i.e. with a single carbon atom between the substituted carbons. In other words there is a substituent on the second atom away from the atom with another substituent. For example the groups below are meta substituted.

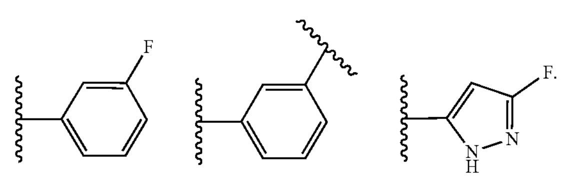

"Para" substitution is a substitution pattern where two substituents are on carbons two carbons removed from each other, i.e. with two carbon atoms between the substituted carbons. In other words there is a substituent on the third atom away from the atom with another substituent. For example the groups below are para substituted.

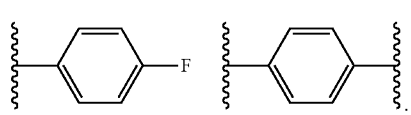

The term "acyl" includes an organic radical derived from, for example, an organic acid by the removal of the hydroxyl group, e.g. a radical having the formula R—C(O)—, where R may be selected from H, $C_{1-6}$ alkyl, $C_{3-8}$ cycloalkyl, phenyl, benzyl or phenethyl group, e.g. R is H or $C_{1-3}$ alkyl. In one embodiment acyl is alkyl-carbonyl. Examples of acyl groups include, but are not limited to, formyl, acetyl, propionyl and butyryl. A particular acyl group is acetyl (also represented as Ac).

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

Suitable or preferred features of any compounds of the present invention may also be suitable features of any other aspect.

The invention contemplates pharmaceutically acceptable salts of the compounds of the invention. These may include the acid addition and base salts of the compounds. These may be acid addition and base salts of the compounds.

Suitable acid addition salts are formed from acids which form non-toxic salts. Examples include the acetate, aspartate, benzoate, besylate, bicarbonate/carbonate, bisulfate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 1,5-naphthalenedisulfonate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulfate and hemicalcium salts. For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of the invention may be prepared by for example, one or more of the following methods:

(i) by reacting the compound of the invention with the desired acid or base;

(ii) by removing an acid- or base-labile protecting group from a suitable precursor of the compound of the invention or by ring-opening a suitable cyclic precursor, for example, a lactone or lactam, using the desired acid or base; or (iii) by converting one salt of the compound of the invention to another by reaction with an appropriate acid or base or by means of a suitable ion exchange column.

These methods are typically carried out in solution. The resulting salt may precipitate out and be collected by filtration or may be recovered by evaporation of the solvent. The degree of ionisation in the resulting salt may vary from completely ionised to almost non-ionised.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric centre, for example, it is bonded to four different groups, a pair of enantiomers is possible. An enantiomer can be characterized by the absolute configuration of its asymmetric centre and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Where a compound of the invention has two or more stereo centres any combination of (R) and (S) stereoisomers is contemplated. The combination of (R) and (S) stereoisomers may result in a diastereomeric mixture or a single diastereoisomer. The compounds of the invention may be present as a single stereoisomer or may be mixtures of stereoisomers, for example racemic mixtures and other enantiomeric mixtures, and diasteroemeric mixtures. Where the mixture is a mixture of enantiomers the enantiomeric excess may be any of those disclosed above. Where the compound is a single stereoisomer the compounds may still contain other diasteroisomers or enantiomers as impurities. Hence a single stereoisomer does not necessarily have an enantiomeric excess (e.e.) or diastereomeric excess (d.e.) of 100% but could have an e.e. or d.e. of about at least 85%.

The compounds of this invention may possess one or more asymmetric centres; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof.

Compounds and salts described in this specification may be isotopically-labelled (or "radio-labelled"). Accordingly, one or more atoms are replaced by an atom having an atomic mass or mass number different from the atomic mass or mass number typically found in nature. Examples of radionuclides that may be incorporated include $^{2}$H (also written as "D" for deuterium), $^{3}$H (also written as "T" for tritium), $^{11}$C, $^{13}$C, $^{14}$C, $^{15}$, $^{17}$, $^{18}$, $^{18}$F and the like. The radionuclide that is used will depend on the specific application of that radio-labelled derivative. For example, for in vitro competition assays, $^{3}$H or $^{14}$C are often useful. For radio-imaging applications, $^{11}$C or $^{18}$F are often useful. In some embodiments, the radionuclide is $^{3}$H. In some embodiments, the radionuclide is $^{14}$C. In some embodiments, the radionuclide is $^{11}$C. And in some embodiments, the radionuclide is $^{18}$F.

It is also to be understood that certain compounds of the invention may exist in solvated as well as unsolvated forms such as, for example, hydrated forms. It is to be understood that the invention encompasses all such solvated forms that possess MAP4K4 inhibitory activity.

It is also to be understood that certain compounds of the invention may exhibit polymorphism, and that the invention encompasses all such forms that possess MAP4K4 inhibitory activity.

Compounds of the invention may exist in a number of different tautomeric forms and references to compounds of the invention include all such forms. For the avoidance of doubt, where a compound can exist in one of several tautomeric forms, and only one is specifically described or shown, all others are nevertheless embraced by compounds of the invention. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol,andnitro/aci-nitro.

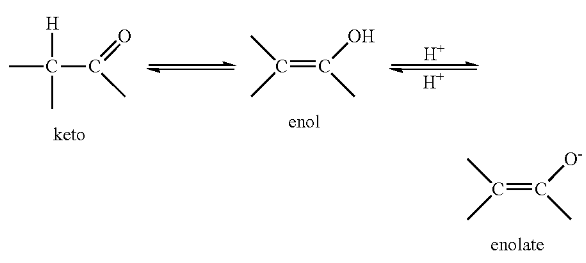

The in vivo effects of a compound of the invention may be exerted in part by one or more metabolites that are formed within the human or animal body after administration of a compound of the invention.

Equally a compound of the present invention may be responsible for in vivo effects but the compound may have been administered in a pro-drug form. Accordingly, the present invention contemplates pro-drugs of compounds of formula (I), whether with or without proviso.

Further information on the preparation of the compounds of the invention is provided in the Examples section. The general reaction schemes and specific methods described in the Examples form a further aspect of the invention.

The resultant compound of the invention from the processes defined above can be isolated and purified using techniques well known in the art.

Compounds of the invention may exist in a single crystal form or in a mixture of crystal forms or they may be amorphous. Thus, compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

The processes defined herein may further comprise the step of subjecting the compound of the invention to a salt exchange, particularly in situations where the compound of the invention is formed as a mixture of different salt forms. The salt exchange suitably comprises immobilising the compound of the invention on a suitable solid support or resin, and eluting the compounds with an appropriate acid to yield a single salt of the compound of the invention.

In a further aspect of the invention, there is provided a compound of the invention obtainable by any one of the processes defined herein.

Certain of the intermediates described in the reaction schemes above and in the Examples herein may be novel. Such novel intermediates, or a salt thereof, particularly a pharmaceutically acceptable salt thereof, form a further aspect of the invention.

Pharmaceutical Compositions

In accordance with another aspect, the present invention provides a pharmaceutical formulation comprising a compound of the invention, or a pharmaceutically acceptable salt thereof, and a pharmaceutically acceptable excipient.

Conventional procedures for the selection and preparation of suitable pharmaceutical formulations are described in, for example, "Pharmaceuticals—The Science of Dosage Form Designs", M. E. Aulton, Churchill Livingstone, 1988.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, intracoronary, subcutaneous, intramyocardial, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy of a condition is an amount sufficient to achieve symptomatic relief in a warm-blooded animal, particularly a human of the symptoms of the condition, to mitigate the physical manifestations of the condition, or to slow the progression of the condition.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the invention will naturally vary according to the nature and severity of the conditions, the concentration of the compound required for effectiveness in isolated cells, the concentration of the compound required for effectiveness in experimental animals, the age and sex of the animal or patient and the route of administration, according to well known principles of medicine.

In using a compound of the invention for therapeutic or prophylactic purposes it will generally be administered so that a daily dose in the range, for example, a daily dose selected from 0.1 mg/kg to 100 mg/kg, 1 mg/kg to 75 mg/kg, 1 mg/kg to 50 mg/kg, 1 mg/kg to 20 mg/kg or 5 mg/kg to 10 mg/kg body weight is received, given if required in divided doses. In general lower doses will be administered when a parenteral route is employed. Thus, for example, for intravenous or intraperitoneal administration, a dose in the range, for example, 0.1 mg/kg to 80 mg/kg body weight will generally be used. Similarly, for administration by inhalation, a dose in the range, for example, 0.05 mg/kg to 25 mg/kg body weight will be used. Suitably the compound of the invention is administered orally, for example in the form of a tablet, or capsule dosage form. The daily dose administered orally may be, for example a total daily dose selected from 1 mg to 2000 mg, 5 mg to 2000 mg, 5 mg to 1500 mg, 10 mg to 750 mg or 25 mg to 500 mg. Typically, unit dosage forms will contain about 0.5 mg to 0.5 g of a compound of this invention.

Experimental

General Chemical Synthesis

All reagents were either purchased from commercial sources or synthesised in accordance with known literature procedures unless otherwise stated. Commercial reagents were used without further purification unless otherwise stated. Microwave reactions were conducted using a CEM Discover (200 W). Flash column chromatography was conducted using pre-packed silica Biotage® SNAP (KP-Sil/KP-C18-HS) cartridges. Ion exchange chromatography was performed using Isolute® SCX-2 and Isolute NH2 cartridges. Palladium removal was conducted using SiliaPrep™ SPE Thiol cartridges referred to a Si-thiol in the experimental methods. On a number of occasions Biotage® phase separators were used to separate the organic from the aqueous layer during aqueous work up. These are referred to as phase separators.

Abbreviations Used

** apparent

AcOH acetic acid $Ac_2O$ acetic anhydride aq. aqueous br broad $(Bu_3P)_2Pd$ Bis(tri-tert-butylphosphine)palladium(0)

Cpd # Compound number $Cu(OAc)_2$ Copper(II) acetate monohydrate

CV column volume d doublet

DBU 1,8-Diazabicylo[5.4.0]undec-7-ene dd doublet of doublets

DCM dichloromethane

DIPEA N,N-diisopropylamine

DME dimethoxyethane
DMF N,N-dimethylformamide
DMSO dimethyl sulfoxide
DMSO-$d_6$ Dimethyl sulfoxide-$d_6$
EDC.HCl N-(3-Dimethylaminopropyl)-N'-ethylcarbodiimide hydrochloride
EDTA Ethylenediaminetetraacetic acid
ESI electrospray ionisation
$Et_2O$ diethyl ether
EtOAc ethyl acetate
EtOH ethanol
h hour(s)
HATU 2-(7-Aza-1H-benzotriazole-1-yl)-1,1,3,3-tetramethyluronium
hexafluorophosphate
HOAt 1-hydroxy-7-azabenzotriazole
HPLC high-performance liquid chromatography
HPLC-MS high-performance liquid chromatography-mass spectrometry
KOAc potassium acetate
LC-MS liquid chromatography-mass spectrometry
LiHMDS Lithium bis(trimethylsilyl)amide solution
m multiplet
MeCN acetonitrile
MeOH methanol
min minute(s)
m/z mass/charge ratio
NaOAc sodium acetate
$NEt_3$ triethylamine
NMR nuclear magnetic resonance
Pd(dppf)$Cl_2$.DCM [1,1'-bis(diphenylphosphino)ferrocene]dichloropalladium
Pd($d^t$BuPF)$Cl_2$ [1,1'-Bis(di-tert-butylphosphino)ferrocene]dichloropalladium(II)
Pd($PPh_3$)$_4$ Tetrakis(triphenylphosphine)palladium(0)
$PPh_3$ triphenyl phosphine
PS polymer supported
q quartet
quint quintet
quant quantitative
RT room temperature
Rt retention time
s singlet
satd. saturated
t triplet
tt triplet of triplets
TBAF tetra-n-butylammonium fluoride
TBTU O-(benzotriazol-1-yl)-N,N,N',N'tetramethyluronium tetrafluoroborate
TFA trifluoroacetic acid
THE tetrahydrofuran
WAX weak anion exchange Analytical Methods A number of compounds were purified by reversed phase preparative HPLC-MS: Mass-directed purification by preparative LC-MS using a preparative C-18 column (Phenomenex Luna C18 (2), 100×21.2 mm, 5 μm).

Analysis of products and intermediates has been carried out using reversed phase analytical HPLC-MS using the parameters set out below.

HPLC Analytical Methods:

AnalpH2_MeOH_4 min: Phenomenex Luna C18 (2) 3 μm, 50×4.6 mm; A=water+0.1% formic acid; B=MeOH; 45° C.; % B: 0 min 5%, 1 min 37.5%, 3 min 95%, 3.51 min 5%, 4.0 min 5%; 2.25 mL/min.

AnalpH2_MeOH_4 min(1): Phenomenex Luna C18 (2) 3 μm, 50×4.6 mm; A=water+0.1% formic acid; B=MeOH+0.1% formic acid; 45° C.; % B: 0 min 5%, 1 min 37.5%, 3 min 95%, 3.51 min 5%, 4.0 min 5%; 2.25 mL/min.

AnalpH2_MeCN_4 min: Phenomenex Luna C18 (2) 3 μm, 50×4.6 mm; A=water+0.1% formic acid; B=Acetonitrile; 45° C.; % B: 0 min 5%, 1 min 37.5%, 3 min 95%, 3.51 min 5%, 4.0 min 5%; 2.25 mL/min.

AnalpH2_MeCN_4 min(1): Acquity BEH C18 (2) 1.7 μm, 50×2.1 mm; A=water+0.1% formic acid; B=Acetonitrile+0.1% formic acid; 35° C.; % B: 0 min 3%, 0.4 min 3%, 2.5 min 98%, 3.4 min 98%, 3.5 min 3%, 4.0 min 3%; 0.6 mL/min.

AnalpH9_MeOH_4 min: Phenomenex Luna C18 (2) 3 μm, 50×4.6 mm; A=water pH9 (Ammonium Bicarbonate 10 mM); B=MeOH; 45° C.; % B: 0 min 5%, 1 min 37.5%, 3 min 95%, 3.51 min 5%, 4.0 min 5%; 2.25 mL/min.

AnalpH9_MeCN_4 min: Phenomenex Luna C18 (2) 3 μm, 50×4.6 mm; A=water pH9 (Ammonium Bicarbonate 10 mM); B=Acetonitrile; 45° C.; % B: 0 min 5%, 1 min 37.5%, 3 min 95%, 3.51 min 5%, 4.0 min 5%; 2.25 mL/min.

AnalpH9_MeCN_6 min: X Bridge BEH C18 2.5 μm, 50×4.6 mm; A=water pH9 (Ammonium Bicarbonate 10 mM); B=Acetonitrile; 35° C.; % B: 0 min 5%, 0.5 min 5%, 1 min 15%, 3.3 min 98%, 5.2 min 98%, 5.5 min 5%, 6.0 min 5%; 1.3 mL/min.

AnalpH2_MeOH_QC_V1: Phenomenex Gemini NX C18 5 μm, 150×4.6 mm; A=water+0.1% formic acid; B=MeOH; 40° C.; % B: 0 min 5%, 7.5 min 95%, 10 min 95%, 10.10 min 5%, 13.0 min 5%; 1.5 mL/min.

AnalpH2_MeOH_QC_V1(1): Phenomenex Gemini NX C18 (2) 5 μm, 150×4.6 mm; A=water+0.1% formic acid; B=MeOH+0.1% formic acid; 40° C.; % B: 0 min 5%, 7.5 min 95%, 10 min 95%, 10.10 min 5%, 13.0 min 5%; 1.5 mL/min.

AnalpH2_MeCN_QC_V1: Phenomenex Gemini NX C18 5 μm, 150×4.6 mm; A=water+0.1% formic acid; B=Acetonitrile; 40° C.; % B: 0 min 5%, 7.5 min 95%, 10 min 95%, 10.10 min 5%, 13.0 min 5%; 1.5 mL/min.

AnalpH9_MeOH_QC_V1: Phenomenex Gemini NX C18 5 μm, 150×4.6 mm; A=water+pH9 (Ammonium Bicarbonate 10 mM); B=MeOH; 45° C.; % B: 0 min 5%, 7.5 min 95%, 10 min 95%, 10.10 min 5%, 13.0 min 5%; 1.5 mL/min.

AnalpH9_MeOH_QC_V1(1): Phenomenex Gemini NX C18 5 μm, 150×4.6 mm; A=water+pH9 (Ammonium Bicarbonate 10 mM); B=MeOH; 40° C.; % B: 0 min 5%, 7.5 min 95%, 10 min 95%, 10.10 min 5%, 13.0 min 5%; 1.5 mL/min.

AnalpH9_MeCN_QC_V1: Phenomenex Gemini NX C18 5 μm, 150×4.6 mm; A=water+pH9 (Ammonium Bicarbonate 10 mM); B=Acetonitrile; 45° C.; % B: 0 min 5%, 7.5 min 95%, 10 min 95%, 10.10 min 5%, 13.0 min 5%; 1.5 mL/min.

Chemical Synthesis Examples

The synthesis of a number of the examples of formula (I) required the synthesis of boronic acid or esters that could not be readily purchased from commercial suppliers. A number of these boronic acids/esters were prepared from the corresponding bromo compounds.

1-(4-Bromo-phenyl)-3-methyl-imidazolidin-2-one (A1)

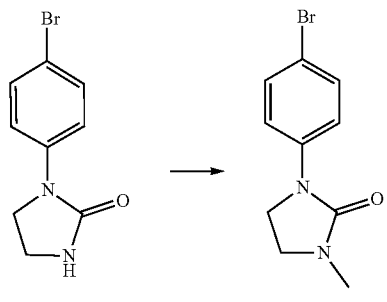

A1

To NaH, 60% dispersion in mineral oil, (120 mg, 2.99 mmol) at 000, under $N_2$, was added 1-(4-bromophenyl) tetrahydro-2H-imidazole-2-one (600 mg, 2.49 mmol) in anhydrous DMF (30 mL). After 15 min iodomethane (0.19 mL, 2.99 mmol) was added and the reaction mixture stirred at RT, under $N_2$, overnight. The reaction mixture was cooled with ice and quenched with 1 M HCl(aq). EtOAc was added and the organic layer separated. The organic layer was washed with $H_2O$, separated, passed through a phase separator and evaporated to dryness. The aqueous layer (also found to contain product) was extracted with DCM and the organic phase combined with the EtOAc layer and evaporated to dryness. The crude compound was purified by silica gel column chromatography eluting with 20-60% EtOAc/iso-hexane to afford 1-(4-bromo-phenyl)-3-methyl-imidazolidin-2-one (A1) as a white solid (413 mg, 65%); LC-MS. Rt 2.77 min, AnalpH2_MeOH_4 min(1); ($ESI^+$) m/z 255.2, 257.2 $[M+H]^+$.

The following bromo intermediates were prepared using analogous procedures to that used for the synthesis of compound A1:

TABLE 1

| Compound | Cpd # | Analytical Data | Mass, % Yield, Appearance |
|---|---|---|---|
| 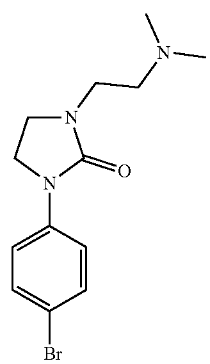 [SMILES: CN(C)CCN1CCN(c2ccc(Br)cc2)C1=O] | A2 | LC-MS. $R_t$ 1.54 min, AnalpH2_MeOH_4 min(1); ($ESI^+$) m/z 312.2 $[M + H]^+$ | 295 mg, 46%, white solid |
| 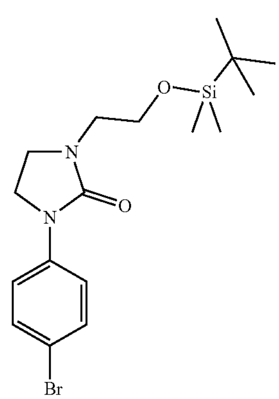 [SMILES: CC(C)(C)[Si](C)(C)OCCN1CCN(c2ccc(Br)cc2)C1=O] | A3 | LC-MS. $R_t$ 3.74 min, AnalpH2_MeOH_4 min(1); ($ESI^+$) m/z 399.1 $[M + H]^+$; $^1$H-NMR (400 MHz, $CDCl_3$): δ 7.47-7.40 (m, 4H), 3.81-3.75 (m, 4H), 3.67-3.62 (m, 2H), 3.40 (t, J = 5.3 Hz, 2H), 0.90 (s, 9H), 0.07 (s, 6H). | 1.16 g, 70%, white solid |

TABLE 1-continued

| Compound | Cpd # | Analytical Data | Mass, % Yield, Appearance |
|---|---|---|---|
| 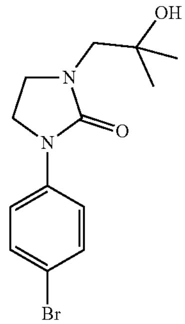 [SMILES: CC(C)(O)CN1CCN(c2ccc(Br)cc2)C1=O] | A4 | LC-MS. $R_t$ 2.95 min, AnalpH2_MeOH_4 min(1); ($ESI^+$) m/z 313.2, 315.2 $[M + H]^+$ | 260 mg, 40% |

A number of bromo intermediates were prepared via ring opening of the epoxide.

4-[3-(4-Bromo-phenoxy)-2-hydroxy-propyl]-morpholin-3-one (A5)

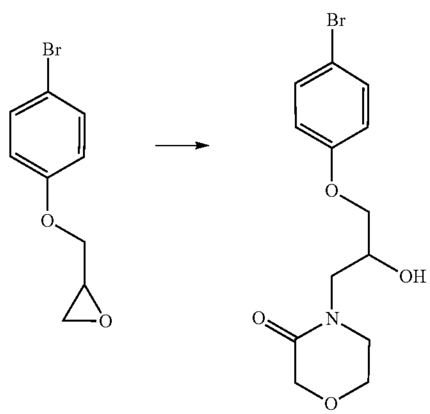

A5

To a suspension of NaH, 60% dispersion in mineral oil, (148 mg, 3.71 mmol) in anhydrous DMF (2 mL), under $N_2$ at 0° C., was added morpholin-3-one (250 mg, 2.47 mmol) in anhydrous DMF (3 mL) and the mixture stirred for 1 h at this temperature. After this time, the reaction mixture was allowed to warm to RT and 2-[(4-bromophenoxy)methyl] oxirane (850 mg, 3.71 mmol) in anhydrous DMF (5 mL) and the reaction stirred at RT, under $N_2$, overnight. The reaction mixture was added dropwise to ice-water (50 mL) and extracted with EtOAc (50 mL). The organic phase was separated (phase separator) and concentrated in vacuo. The crude compound was purified by silica gel column chromatography eluting with 0-3% MeOH/DCM. The compound was further purified by reversed phase preparative HPLC-MS to afford 4-[3-(4-Bromo-phenoxy)-2-hydroxy-propyl]-morpholin-3-one as a white solid (250 mg, 31%); LC-MS. Rt 1.72 min, AnalpH2_MeOH_4 min(1); ($ESI^+$) m/z 330.1, 332.1 $[M+H]^+$.

1-(4-Bromo-phenoxy)-3-morpholin-4-yl-propan-2-ol (A6)

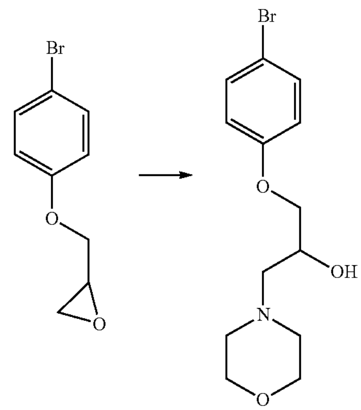

A6

A solution of 2-[(4-Bromophenoxy)methyl]oxirane (500 mg, 2.18 mmol) and morpholine (267 μL, 3.05 mmol) in isopropanol (10 mL) was heated at 100° C. for 30 min in a microwave reactor (200 W). The reaction was repeated once more. The 2 reaction mixtures were combined and concentrated in vacuo. The crude solid was pre-absorbed onto silica and purified by silica gel chromatography eluting with 0-20% MeOH/DCM to afford 1-(4-bromo-phenoxy)-3-morpholin-4-yl-propan-2-ol (A6) as a colourless oil (1.21 g, 88%). LC-MS. Rt 1.50 min, AnalpH2_MeOH_4 min(1); ($ESI^+$) m/z 316.2, 318.2 $[M+H]^+$.

1-(4-bromophenoxy)-3-methoxypropan-2-ol (A21)

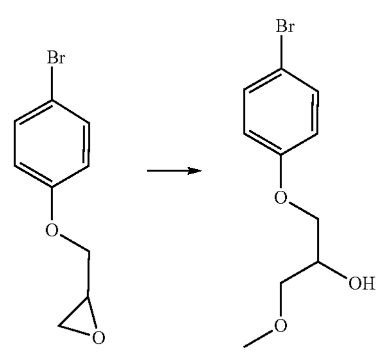

A21

To a solution of the 2-((4-bromophenoxy)methyl)oxirane (500 mg, 2.1 mmol) in anhydrous MeOH (10 mL) was added NaH (60% dispersion in oil) (167 mg, 4.3 mmol). Reaction was resealed and flushed with nitrogen and stirred for 66 h at RT. The reaction mixture was quenched with water and extracted with DCM. The organics were concentrated in vacuo. The crude solid was purified by silica gel chromatography eluting with 0-45% EtOAc/iso-hexane to afford the title compound A21 as a colourless oil (550 mg, 89%); LC-MS. Rt 2.87 min, AnalpH2_MeOH_4 min(1); (ESI$^+$) m/z 283.2, 285.3 $[M+Na]^+$.

The following methoxy compound was prepared via methylation of the corresponding alcohol:

4-[3-(4-Bromo-phenoxy)-2-methoxy-propyl]-morpholine (A7)

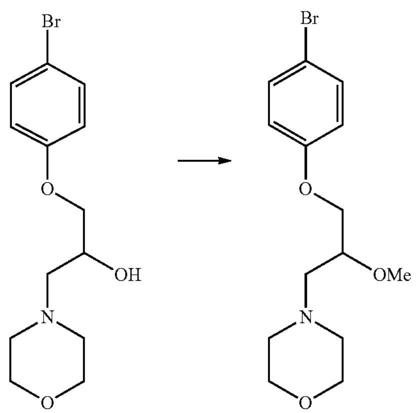

A6 A7

A solution of bromo compound (A6) (1.18 g, 3.7 mmol) was dissolved in THE (20 mL) and NaH (60% dispersion in oil, 448 mg, 11.2 mmol) was added. After 10 min, iodomethane (279 μL, 4.5 mmol) was added and the mixture stirred at RT for 4 h. The reaction mixture was quenched with water at 0° C. and reduced to a residue by rotary evaporator. The residue was partitioned between water (100 mL) and EtOAc (100 mL). The organic layer was washed with brine (100 mL), dried (anhydrous $Na_2SO_4$), filtered and concentrated in vacuo. The crude solid was pre-absorbed onto silica and purified by silica gel chromatography eluting with 0-100% EtOAc/iso-hexane to afford 4-[3-(4-bromo-phenoxy)-2-methoxy-propyl]-morpholine (A7) as a colourless oil (993 mg, 81%); LC-MS. Rt 1.72 min, AnalpH2_MeOH_4 min (1); (ESI$^+$) m/z 330.2, 332.2 $[M+H]^+$.

The following bromo intermediates were prepared via alkylation of the corresponding phenol:

4-(4-Bromo-phenoxy)-2-methyl-butan-2-ol (A8)

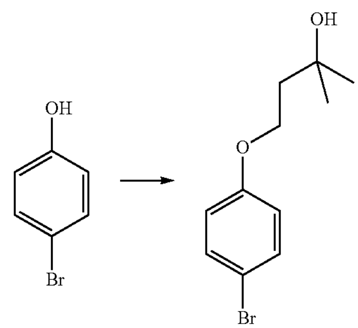

A8

4-Bromophenol (690 mg, 4.06 mmol) and $K_2CO_3$ (826 mg, 5.98 mmol) were dissolved in anhydrous DMF (20 mL) and 4-bromo-2-methyl butan-2-ol (800 mg, 4.79 mmol) was added. The mixture was stirred at 130° for 18 h before allowing to cool to RT. The reaction mixture was diluted with $H_2$ (30 mL) and extracted with DCM (3×20 mL). Combined organic fractions were dried by phase separator and evaporated to a residue using a Genevac. The crude solid was pre-absorbed onto silica and purified by silica gel chromatography eluting with 0-100% EtOAc/iso-hexane to afford 4-(4-bromo-phenoxy)-2-methyl-butan-2-ol (A8) as a yellow oil (483 mg, 47%); LC-MS. Rt 3.16 min, AnalpH2_MeOH_4 min(1); (ESI$^+$) m/z 243.2, 245.22 $[M-H_2O+H]^+$.

The following bromo compounds were prepared using analogous procedure to compound A8 with for 6-66 h heating at 80-140° C.

TABLE 2

| Compound | Cpd # | Analytical Data | Mass, % Yield, State |
|---|---|---|---|
| 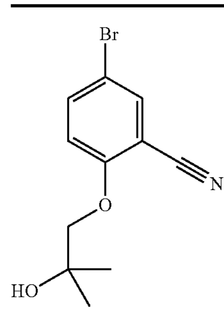 | A9[a] | LC-MS. $R_t$ 2.87 min, AnalpH2_MeOH_4 min(1); (ESI$^+$) m/z 292.2, 294.2 $[M + Na]^+$. | 1.44 g, 53%, yellow oil |

TABLE 2-continued

| Compound | Cpd # | Analytical Data | Mass, % Yield, State |
|---|---|---|---|
| 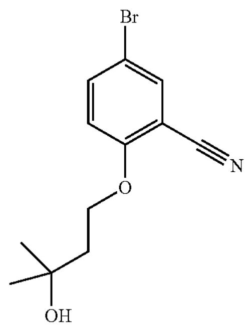 [SMILES: CC(C)(O)CCOc1ccc(Br)cc1C#N] | A22[b] | LC-MS. $R_t$ 2.94 min, AnalpH2_MeOH_4 min(1); ($ESI^+$) m/z 266.2, 268.2 $[M - H_2O + H]^+$. | 1.28 g, 60%, white solid |
| 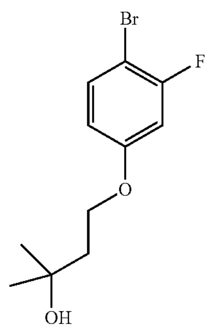 | A23[b,c] | LC-MS. $R_t$ 3.21 min, AnalpH2_MeOH_4 min(1); ($ESI^+$) m/z 299.2, 301.1 $[M + Na]^+$. | 1.45 g, quantitative, yellow oil |
| 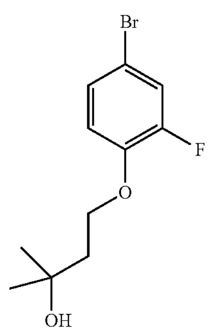 | A24[b,c] | LC-MS. $R_t$ 3.17 min, AnalpH2_MeOH_4 min(1); ($ESI^+$) m/z 299.1, 301.1 $[M + Na]^+$. | 1.70 g, 79%, orange oil |
| 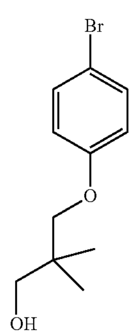 | A25[c,d] | LC-MS. $R_t$ 3.25 min, AnalpH2_MeOH_4 min(1); ($ESI^+$) m/z no ionization | 330 mg, 22%, light yellow oil |

TABLE 2-continued

| Compound | Cpd # | Analytical Data | Mass, % Yield, State |
|---|---|---|---|
| 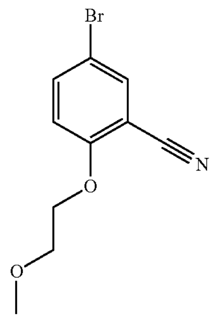 | A26[e] | LC-MS. $R_t$ 2.77 min, AnalpH2_MeOH_4 min(1); (ESI+) m/z 256.2, 258.1 [M + H]+. | 1.1 g, quant., white solid |
| 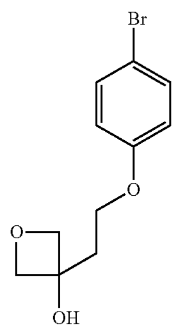 [SMILES: OC1(CCOc2ccc(Br)cc2)COC1] | A27[e,##] | LC-MS. $R_t$ 17 min, AnalpH2_MeCN_4 min(1); (ESI+) m/z 273.0, 275.0 [M + H]+. | 2.2 g, 63%, white solid |

[a]Chloride was used instead of the bromide.
[b]Tosylate reagent was used as the alkylating reagent.
[c]$Cs_2CO_3$ was used as the base.
[d]2 eq. of KI was also used.
[e]Acetonitrile was used instead of DMF.
[##]A27 required the synthesis from the corresponding mesylate rather than bromide. The mesylate A30 was synthesized in 3 steps by the following methods:

Step 1: Ethyl 2-(3-hydroxyoxetan-3-yl) acetate (A28)

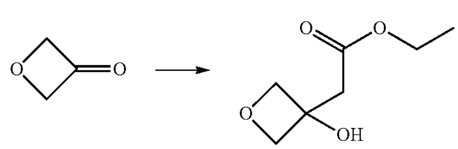

A28

To a solution of EtOAc (36.68 g, 416 mmol) in THE (400 mL) was added LiHMDS (229 mL, 458 mmol, 2 M in THF) dropwise at −70° C. for 20 min. After addition, the reaction mixture was stirred at the same temperature for a further 1 h, and then oxetan-3-one (30 g, 416 mmol) in THE (50 mL) was added dropwise to the reaction mixture and then stirred at −70° C. for 1 h. Reaction mixture was cooled to 0° C., quenched by adding satd. aq. $NH_4Cl$ (200 mL) and allowed to stir at RT for 30 min. The crude mixture was diluted with $H_2O$ (200 mL) and extracted with EtOAc (3×400 mL). The combined organic layer was washed with water (2×100 mL), brine (1×200 mL), dried with $Na_2SO_4$, filtered and concentrated under reduced pressure. The crude residue was purified by silica gel column chromatography eluting with 20% EtOAc/hexane to afford ethyl 2-(3-hydroxyoxetan-3-yl)acetate (A28) as a yellow liquid (25 g, 37%).

Step 2: 3-(2-hydroxyethyl) oxetan-3-ol (A29)

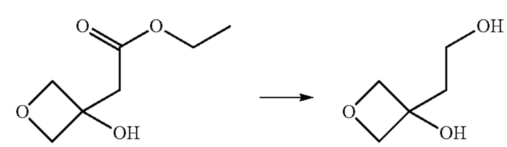

A28 A29

To a solution of ethyl 2-(3-hydroxyoxetan-3-yl) acetate (A28) (15 g, 93.8 mmol) in THE (400 mL) and EtOH (100 mL) was added sodium borohydride (7 g, 37.8 mmol) portionwise at 0° C. After addition, the reaction was stirred at ambient temperature for 16 h. The resulting suspension was acidified with Dowex 50WX8-100 ($H^+$ form) to pH 6 at 0° C. The reaction mixture was stirred for 15 mins and then the resin was filtered and washed with EtOAc (100 mL). The filtrate was concentrated under reduced pressure to afford 3-(2-hydroxyethyl) oxetan-3-ol (A29) as a white solid (8 g, 72%).

Step 3: Synthesis of 2-(3-hydroxyoxetan-3-yl) ethyl methanesulfonate (A30)

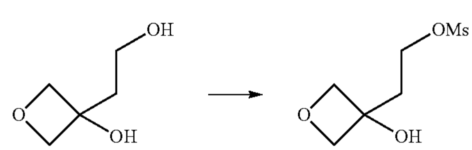

A29 A30

To a stirred solution of 3-(2-hydroxyethyl)oxetan-3-ol (A29) (8 g, 67.8 mmol) and $NEt_3$ (20.5 g, 203 mmol) in DCM (150 mL) was added mesyl chloride (11.59 g, 102 mmol) dropwise at 0° C. After addition, the reaction was stirred at 10° C. for 3 h. After completion, the reaction mixture was diluted with water (100 mL) and extracted with DCM (3×200 mL). The combined organic layer was washed with water (2×100 mL) and brine (1×200 mL), dried with $Na_2SO_4$, filtered and concentrated under reduced pressure to afford 2-(3-hydroxyoxetan-3-yl)ethyl methanesulfonate (A30) (5.5 g, 42%) as a yellow liquid.

[3-(4-Bromo-phenoxymethyl)-oxetan-3-yl]-methanol (A10)

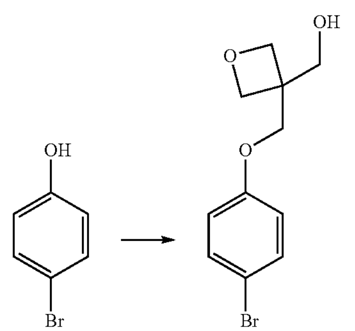

A10

4-Bromophenol (100 mg, 0.58 mmol) was dissolved in anhydrous DMF (8 mL) at 0° C. under $N_2$. NaH (60% dispersion in mineral oil, 25 mg, 0.64 mmol) was added portion wise and the solution stirred for 15 min. 3-(Bromomethyl)oxetan-3-ylmethanol (105 mg, 0.58 mmol) was added dropwise as a solution in DMF (2 mL). The solution was stirred at 0° C. and allowed to warm to RT over 4 h. Excess NaH was quenched with $H_2O$ (2 mL) and volatiles removed by rotary evaporator. The resulting residue was suspended in $H_2O$ (15 mL) and extracted with DCM (3×10 mL), combined organic fractions were dried by phase separator and residual DMF removed by high vacuum overnight. The product A10 was taken forward as a crude clear oil (155 mg, quant); LC-MS. Rt 2.92 min, AnalpH2_MeOH_4 min (1); ($ESI^+$) m/z 273.2, 275.2 $[M+H]^+$.

The following bromo compound A31 was prepared using analogous procedure to compound A10:

TABLE 3

| Compound | Cpd # | Analytical Data | Mass, % Yield, Appearance |
|---|---|---|---|
| 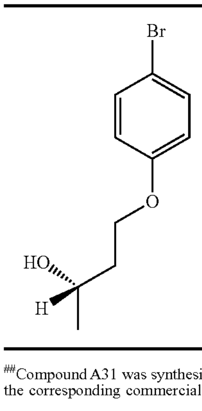 | A31[##] | LC-MS. $R_t$ 3.05 min, AnalpH2_MeOH_4 min(1); ($ESI^+$) m/z no mass detected | 141 mg, 98%, white solid |

[##]Compound A31 was synthesised from the corresponding tosylate rather than bromide. The tosylate was made from the corresponding commercially available alcohol:

(S)-3-hydroxybutyl 4-methylbenzenesulfonate (A32)

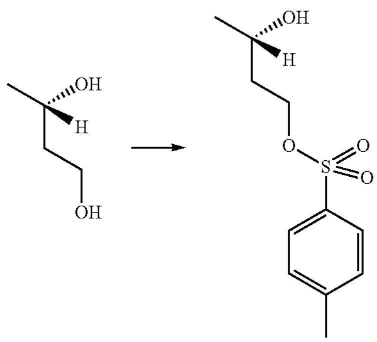

A32 p-Toluenesulfonyl chloride (381 mg, 1.68 mmol) was dissolved in anhydrous DCM (10 mL) at RT under $N_2$. (s)(+)-1,3-butandiol (300 μL, 3.33 mmol) was added followed by $NEt_3$ (450 μL, 3.33 mmol) and the solution stirred for 18 h. The solution was partitioned with $H_2O$ (15 mL) and extracted with DCM (3×10 mL), Combined organic fractions were dried by phase separator and the mixture loaded onto silica for purification by flash chromatography. The desired compound A32 was isolated as a clear oil (144 mg, 29%); $^1$H-NMR (400 MHz, DMSO-$d_6$): δ 7.78 (d, J=8.0 Hz, 2H), 7.48 (d, J=8.0 Hz, 2H), 4.56 (d, J=5.0 Hz, 1H), 4.12-4.00 (m, 2H), 3.65-3.57 (m, 1H). 2.43 (s, 3H), 1.69-1.54 (m, 2H), 1.00 (d, J=6.0 Hz, 3H).

The following bromo compound A33 was prepared via reduction of ethyl 2-(4-bromophenoxy)-2, 2-difluoroacetate (this ester was prepared in accordance to literature procedure as reported in *Org. Lett.,* 2016, 18, 18, 4570-4573):

2-(4-bromophenoxy)-2, 2-difluoroethanol (A33)

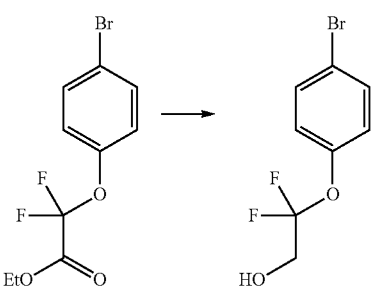

A33

To a solution of sodium borohydride (2.7 g, 71.4 mmol) in EtOH (40 mL) was added ethyl 2-(4-bromophenoxy)-2, 2-difluoroacetate (7 g, 23.8 mmol) portionwise at 0° C. The reaction mixture was slowly warmed to RT and stirred at this temperature for 2 h. After completion, the reaction was quenched with saturated ammonium chloride solution (30 mL), 1 M HCl solution (2 mL), and then extracted with EtOAc (2×300 mL). The combined organic layer dried over anhydrous $Na_2SO_4$, filtered and concentrated under reduced pressure to afford 2-(4-bromophenoxy)-2, 2-difluoroethanol (A33) as a white solid (5 g, 59%).

The following bromo-Isoglycosides were prepared from the corresponding triflate intermediates which were prepared in accordance to literature methods[a]:

(3R,3aS,6R,6aS)-6-(4-bromophenoxy)hexahydrofuro[3,2-b]furan-3-ol (A34)

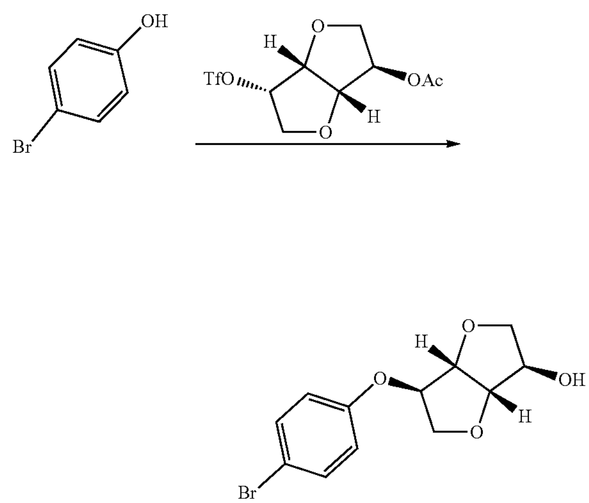

A34

Sodium hydride (73 mg, 2.16 mmol, 60% dispersion in oil) was added to a solution of 4-bromophenol in THE (10 mL) at 0° C. once bubbling had ceased the reaction was stirred for 30 mins at 0° C. Crude (3R,3aS,6S,6aR)-6-(((trifluoromethyl)sulfonyl)oxy)hexahydrofuro[3,2-b]furan-3-yl acetate (509 mg) as a solution in THE (6 mL) was then added dropwise. Once addition was complete the reaction was stirred at 0° C. for 2 h then 30 mins at RT. Analysis by TLC showed consumption of triflate; the reaction was concentrated under vacuum and redissolved in THE (12 mL). LiOH (890 mg, 15.9 mmol) in water (4 mL) was then added and the reaction stirred at 50° C. for 2 h. After which time a further amount of LiOH (800 mg) was added and the reaction stirred at RT for 16 h. The THF was removed under vacuum, EtOAc (50 mL) was added and the layers separated. The aqueous layer was extracted with EtOAc (3×50 mL), the organic layers combined then dried (phase separator). The crude material was purified by silica gel chromatography eluting with 5-65% EtOAc/iso-hexane to afford the title compound A34 as a white crystalline solid (352 mg, 73%). $^1$H NMR (400 MHz, $CDCl_3$): δ 7.38 (d, J=9.0 Hz, 2H), 6.81 (d, J=9.0 Hz, 2H), 4.76-4.70 (m, 2H), 4.59 (d, J=4.1 Hz, 1H), 4.38 (br s, 1H), 4.00 (ddd, J=4.1, 6.9, 10.5 Hz, 2H), 3.94-3.86 (m, 2H), 1.69 (br s, 1H).

(The anti isomer was prepared via an analogous procedure to compound A34.

TABLE 4

| Compound | Cpd # | Analytical Data | Mass, % Yield, Appearance |
|---|---|---|---|
| 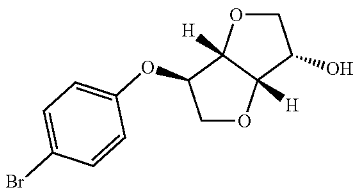 [SMILES: O[C@H]1CO[C@@H]2[C@H]1OC[C@H]2Oc1ccc(Br)cc1] | A35[a] | $^1H$ NMR (400 MHz, $CDCl_3$): δ 7.38 (d, J = 8.7 Hz, 2H), 6.80 (d, J = 8.7 Hz, 2H), 4.77 (d, J = 3.9 Hz, 1H), 4.68 (t, J = 4.8 Hz, 1H), 4.54 (d, J = 4.8 Hz, 1H), 4.31 (d, J = 6.9 Hz, 1H),4.19-4.14 (m, 1H), 4.09 (dd, J = 3.9, 10.5 Hz, 1H), 3.90 (dd, J = 6.0, 9.6 Hz, 1H), 3.63 (dd, J = 5.5, 9.6 Hz, 1H), 2.58 (d, J = 6.9 Hz, 1H). | 275 mg, 43%, white solid |

[a]Prepared in accordance to literature methods reported in *RSc Adv*., 2014, 4, 47937-47950.

The following cyclobutyl intermediate was prepared via ring opening of 5, 5-difluoro-1-oxaspiro [2.3]hexane, which was prepared in accordance to literature procedures as reported in J. Med. Chem., 2016, 59, 8848-8858.

1-((4-bromophenoxy)methyl)-3,3-difluorocyclobutan-1-ol (A36)

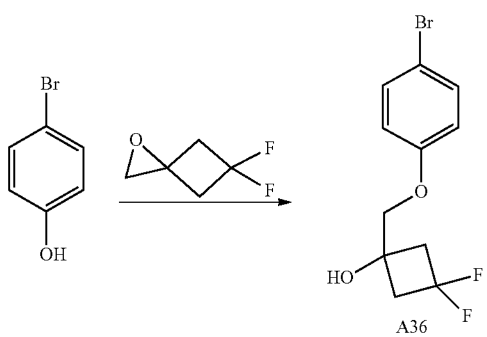

A36

Potassium carbonate (1.44 g, 10.4 mmol) was added to a stirred solution of 5, 5-difluoro-1-oxaspiro [2.3] hexane (500 mg, 4.17 mmol) and 4-bromophenol (788 mg, 4.58 m mol) in MeCN (5 mL) in a 30 mL sealed tube, and the resulting mixture was stirred at 120° C. for 2 h. Reaction mixture was cooled to RT, filtered and washed with EtOAc (10 mL). The filtrate was washed with water (10 mL) and brine (10 mL). Organic layer was dried over $Na_2SO_4$, filtered and concentrated to give crude product which was purified by silica gel column chromatography eluting with 0-10% of EtOAc/petroleum ether to afford the title compound A36 as a pale yellow gum (400 mg, 33%), LC-MS. Rt 3.59 min, AnalpH9_MeCN_4 min(1); ($ESI^-$) m/z 586.0 [2M−H]—.

Tert-butyl N-[3-(4-bromophenoxy)-1,1-dimethyl-propyl]carbamate (A37)

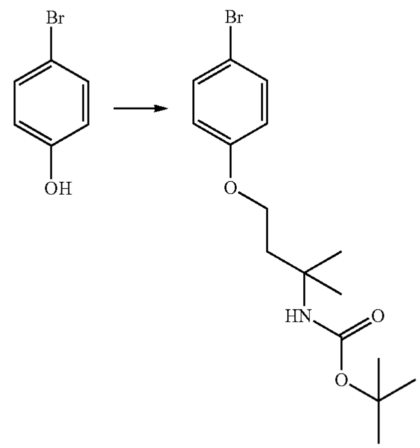

A37

To a solution of 4-bromophenol (471 mg, 2.72 mmol), tert-butyl (4-hydroxy-2-methylbutan-2-yl)carbamate (1.38 g, 6.81 mmol) and triphenylphosphine (1.78 g, 6.81 mmol) in dry THE (9 mL) at RT was added dropwise a solution of 1,1'-(azodicarbonyl)dipiperidine (1.73 g, 6.81 mmol) in dry THE (9 mL). The resulting mixture was stirred at RT for 2 days and the mixture was filtered to remove a white precipitate. The filtrate was diluted with DCM and washed with aq NaOH (2 M) to remove unreacted phenol starting material. The organic fraction was evaporated to dryness and was purified by silica gel chromatography eluting with 0-15% EtOAc/iso-hexane to afford the desired product A37 as a white solid (464 mg, 48%).

1-(4-Bromo-phenoxymethyl)-cyclopropanol (A38)

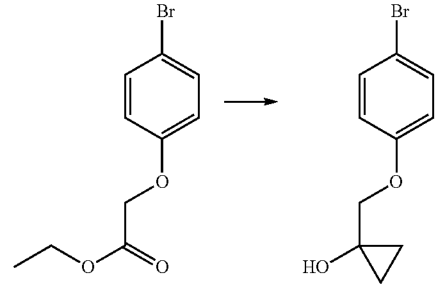

A38

To a solution of ethyl(4-bromophenyl)acetate (2 g, 7.7 mmol) in THE (20 mL), at 0° C., under $N_2$, was added titanium (IV) isopropoxide (2.3 mL, 7.7 mmol) followed by dropwise addition of ethylmagnesium bromide (3.0 M in $Et_2O$, 7 mL, 20.8 mmol). The reaction was allowed to warm to RT and stirred for 2.5 h. The reaction was added dropwise onto ice and the resultant mixture was extracted with EtOAc (200 mL), whereupon a solid precipitated which was collected by filtration. The organic layer was separated, passed through a phase separator and the solvent removed in vacuo. The crude material was purified by silica gel chromatography, eluting with 9-17% EtOAc/iso-hexane to afford 1-(4-bromo-phenoxymethyl)-cyclopropanol (A38) as a white solid (788 mg, 42%); LC-MS. Rt 2.90 min, AnalpH2_MeOH_4 min(1); ($ESI^-$) m/z 242.4 $(M-H)^-$; $^1$H-NMR (400 MHz, DMSO-$d_6$): δ 7.46-7.32 (m, 2H), 6.94-6.82 (m, 2H), 5.55 (s, 1H), 3.89 (s, 2H), 0.67-0.59 (m, 2H), 0.60-0.53 (m, 2H).

The following bromo intermediate was prepared using analogous procedure to that used for the synthesis of compound Ax:

TABLE 5

| Compound | Cpd # | Analytical Data | Mass, % Yield, State |
|---|---|---|---|
| 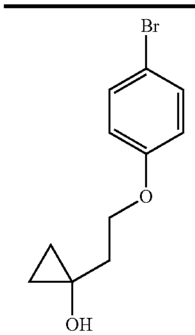 | A39[a] | LC-MS. $R_t$ 1.97 min, AnalpH2_MeOH_4 min(1); ($ESI^+$) m/z 257.0, 259.0 $[M + H]^+$. | 5.3 g, 75%, off-white solid |

[a]Compound A39 required the ester A40 which was prepared from the resulting acid:

Methyl 3-(4-bromophenoxy)propanoate (A40)

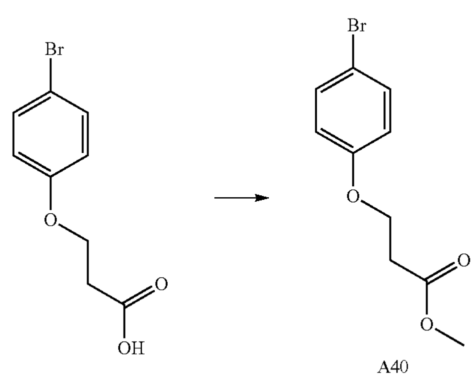

A40

To a stirred suspension of 3-(4-bromophenoxy)propanoic acid (4.90 g, 20 mmol) in methanol (16 mL) was carefully added fuming sulfuric acid (98%, 20-30% $SO_3$, 4 drops). The reaction mixture was heated at 140° C. for 5 mins in the microwave and repeated once more on the same scale. The combined reaction mixtures were concentrated in vacuo and the resulting residue was partitioned between EtOAc (100 mL) and aq. 10% sodium hydroxide (100 mL). The organic layer was separated, and the aq. layer was back-extracted with EtOAc (100 mL). The combined organic layer was then washed with brine (100 mL), dried over $MgSO_4$, filtered and concentrated in vacuo to afford the title compound A40 as pale yellow solid (9.86 g, 95%). LC-MS. Rt 3.10 min, AnalpH2_MeOH_4 min(1); ($ESI^+$) m/z 281.1, 283.1 $[M+Na]^+$.

5-Bromo-2-(oxiran-2-ylmethoxy)benzonitrile (A11)

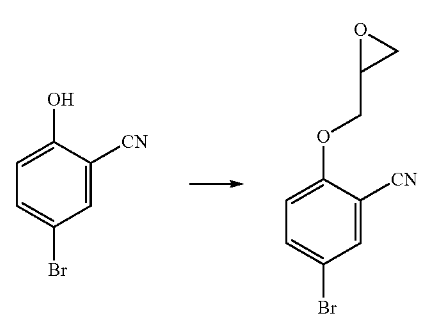

A11

5-Bromo-2-hydroxybenzonitrile (2 g, 10.1 mmol) and $Cs_2CO_3$ (3.9 g, 12.1 mmol) were dissolved in anhydrous THE (25 mL). 2-(Chloromethyl)oxirane (789 μL, 10.1 mmol) was added dropwise and the solution stirred at reflux for 18 h. The solution was allowed to cool to RT and diluted with EtOAc/iso-hexane solution (1:1, 150 mL). The resulting suspension was filtered and volatiles removed in vacuo. The crude solid was pre-absorbed onto silica and purified by silica gel chromatography eluting with 0-100% EtOAc/iso-hexane to afford 5-bromo-2-(oxiran-2-ylmethoxy)benzonitrile (A11) as a white solid (714 mg, 28%); LC-MS. Rt 2.77 min, AnalpH2_MeOH_4 min(1); (ESI+) m/z 254.3, 256.3 $[M+H]^+$.

(R)-1-(4-Bromo-phenoxy)-propan-2-ol (A12)

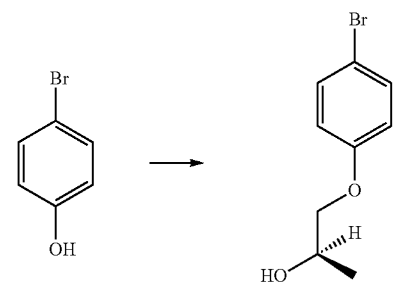

A12

R-(+)-Propylene oxide (1.22 mL, 17.3 mmol) was added to a reaction vessel containing a stirred suspension of 4-bromophenol (750 mg, 4.3 mmol) and $K_2CO_3$ (1.19 g, 8.7 mmol) in DMF. The reaction vessel was sealed and the suspension heated to 85° C. for 16 h overnight. Once complete the reaction was quenched by addition of 2 M NaOH (aq.) solution (10 mL) and allowed to stir for 1 h. $H_2O$ (80 mL) was then added and the resulting solution extracted with EtOAc (3×50 mL) the combined organics were combined and washed with brine (2×50 mL), then dried by filtration over $MgSO_4$ and concentrated in vacuo. The crude material was purified by silica gel chromatography, eluting with 0-40% EtOAc/iso-hexane to afford (R)-1-(4-bromo-phenoxy)-propan-2-ol (A12) as a colourless oil (744 mg, 75%); LC-MS. Rt 2.88 min, AnalpH2_MeOH_4 min(1), no mass ion detected. $^1$HNMR (400 MHz, DMSO-$d_6$): δ 7.37 (d, J=8.9 Hz, 2H), 6.78 (d, J=8.9 Hz, 2H), 4.22-4.14 (m, 1H), 3.89 (dd, J=9.2, 3.2 Hz, 1H), 3.75 (dd, J=9.2, 7.8 Hz, 1H). 2.32-2.21 (br s, 1H), 1.27 (d, J=6.4 Hz, 3H).

The S-enantiomer A13 was prepared via an analogous procedure to compound A12.

TABLE 6

| Compound | Cpd # | Analytical Data | Mass, % Yield, Appearance |
|---|---|---|---|
| 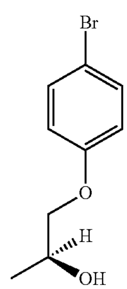 | A13 | LC-MS. $R_t$ 2.88 min, AnalpH2_MeOH_4 min(1); (ESI+) m/z no mass detected; 7.36 (d, J = 9.2 Hz, 2H), 6.78 (d, J = 9.2 Hz, 2H), 4.22-4.14 (m, 1H), 3.89 (dd, J = 9.2, 3.2 Hz, 1H), 3.75 (dd, J = 9.2, 7.8 Hz, 1H). 2.10-2.32 (br s, 1H), 1.27 (d, J = 6.4 Hz, 3H). | 791 mg, 80%, colourless oil |

The following bromo intermediates were synthesised in accordance with literature methods:

TABLE 7

| Bromo compound | Cpd # | Reference |
|---|---|---|
| 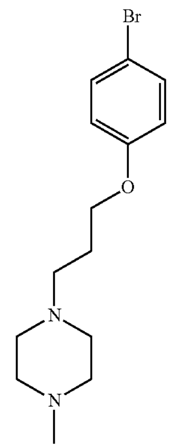 | A14 | WO2013/267493 |
| 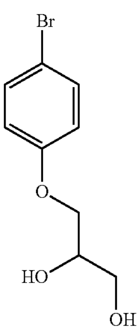 [SMILES: OCC(O)COc1ccc(Br)cc1] | A15 | WO2006/65659 |
| 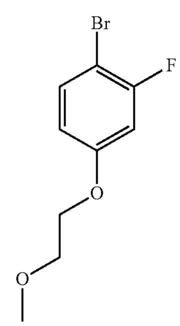 | A41 | *Bioorganic Med. Chem. Lett.*, 2007, 17, 6, 1659-1662 |
| 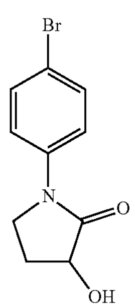 | A42 | WO2016/144936 |

1-(4-bromophenoxy)-2-methyl-propan-2-amine (A43)

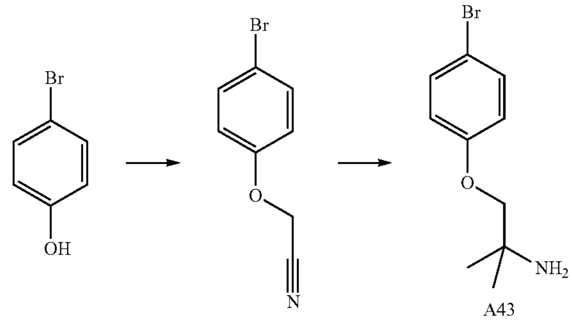

A43

Bromoacetonitrile (1.2 mL, 17.3 mmol) was added to a stirred suspension of 4-bromophenol (2.00 g, 11.6 mmol) and potassium carbonate in DMF (60 mL). Once addition was complete, the resulting mixture was heated at 50° C. overnight. The reaction mixture was cooled to RT, diluted with EtOAc (150 mL) and the organic layer was separated, washed with water (2×70 mL), brine (2×40 mL) then dried by passing through phase separator. The organics were concentrated in vacuo and the crude compound was purified by silica gel chromatography eluting with 0-50% EtOAc/iso-hexane to afford 2-(4-bromophenoxy)acetonitrile (2.40 g). A portion of this material (1.00 g, 4.72 mmol) was dissolved in dry THE (20 mL) under $N_2$ and methylmagnesium bromide (3 M in $Et_2O$, 5.5 mL, 16.5 mmol) was added dropwise. The reaction mixture was heated to 60° C. for 1 h, then titanium (IV) isopropoxide (1.4 mL, 4.72 mmol) was added dropwise. The reaction mixture was stirred at 50° C. for 16 h. The reaction mixture was partitioned between DCM and brine. The mixture was filtered through celite and the filter cake washed with DCM. The organic fraction was separated, washed with brine again, followed by washing with aq 10% NaOH (2×) to remove the phenol starting material, dried by passing through a phase separator and evaporated to dryness to afford the desired product A43 as a brown oil (712 mg, 62%); LC-MS. Rt 1.48 min, AnalpH2_MeCN_4 min(1); ($ESI^+$) m/z 244.0, 246.0 $(M+H)^+$.

Boc protection of the above bromo intermediate yielded A44:

Tert-butyl N-[2-(4-bromophenoxy)-1,1-dimethyl-ethyl]carbamate (A44)

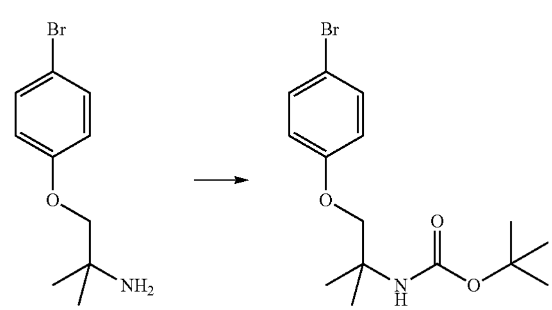

A43 A44

1-(4-bromophenoxy)-2-methylpropan-2-amine (A43) (712 mg, 2.92 mmol) was dissolved in DCM (5 mL). Di-tert-butyl dicarbonate (668 mg, 3.062 mmol) dissolved in DCM (4 mL) was added and the reaction mixture stirred at RT for 16 h. Water was added to the reaction mixture to quench unreacted di-tert-butyl dicarbonate and the mixture was stirred for a further 24 h. The reaction mixture was evaporated to dryness and purified by silica gel chromatography eluting with 0-15% EtOAc/iso-hexane to afford the product A44 as a pale yellow solid (516 mg, 51%); LC-MS. Rt 3.48 min, AnalpH2_MeCN_4 min(1); ($ESI^+$) m/z 365.9, 367.9 $(M+Na)^+$.

The following diol intermediate A45 was prepared in 2 steps from 4-bromophenol.

1-(4-bromophenoxy)-3-methylbutane-2,3-diol (A45)

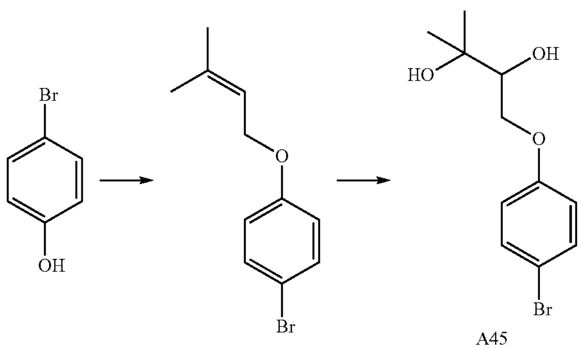

A45

A mixture of 4-bromophenol (1.00 g, 5.78 mmol) and NaH (388 mg, 11.56 mmol, 60% dispersion in oil) were suspended in anhydrous THE (80 mL) at 0° C. and stirred for 30 mins after which 1-bromo-3-methylbut-2-ene (1.29 g, 8.67 mmol) was added dropwise. Once addition was complete, the reaction was allowed to warm to RT and stirred overnight. The reaction mixture was diluted with water (70 mL), layers were separated and washed with EtOAc (2×75 mL). The combined organics were passed through a phase separator and concentrated in vacuo. The crude compound was purified by silica gel chromatography eluting with 0-50% EtOAc/iso-hexane to afford 1-bromo-4-((3-methylbut-2-en-1-yl)oxy)benzene (1.35 g) as a colourless oil, which was used for further derivatization. Admixα (2.00 g) was added to a stirred biphasic solution of 1-bromo-4-((3-methylbut-2-en-1-yl)oxy)benzene (1.35 g, 5.6 mmol) in tert-Butanol/water. A yellow biphasic solution formed and was allowed to stir for 16 h. A further portion of Admix-α (500 mg) was added and the reaction was allowed to stir for 18 h. A further potion of Admix-α (1.50 g) was added and reaction mixture was stirred for 18 h. The reaction mixture was quenched with sodium sulphite (5 g), and stirred for 1 h. The mixture was diluted with EtOAc (75 mL) and water (75 mL), layers were separated and the aqueous layer was extracted with EtOAc (3×50 mL), washed with brine (20 mL) and dried using a phase separator. The crude solid was purified by silica gel chromatography eluting with 0-75% EtOAc/iso-hexane to afford the title compound A45 as a yellow oil (1.13 g); LC-MS. Rt 2.81 min, AnalpH2_MeOH_4 min(1); ($ESI^+$) m/z 297.1, 299.1 $[M+Na]^+$. The enantiomeric excess was not determined.

The bromo intermediates were used to synthesise the corresponding boronic esters or acids using bis(pinacalato) diboron. These reactions could be carried out using either traditional heating methods or in a microwave reactor.

1-[4-(4,4,5,5-Tetramethyl-[1,3,2]dioxaborolan-2-yl)-phenyl]-imidazolidin-2-one (B1)

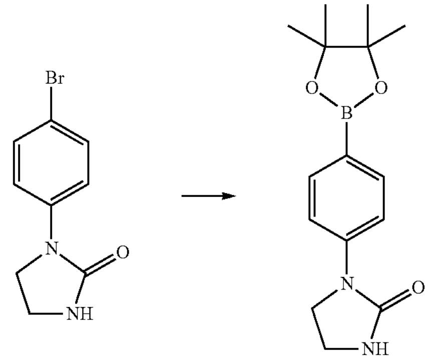

B1

KOAc (609 mg, 6.21 mmol) and bis(pinacolato)diboron (631 mg, 2.48 mmol) were added to a round bottom flask and placed under $N_2$. 1-(4-bromophenyl)tetrahydro-2H-imidazol-2-one (500 mg, 2.07 mmol) in DMSO (11 mL) was added followed by $Pd(dppf)Cl_2$.DCM (51 mg, 0.06 mmol). $N_2$ gas was bubbled through the reaction mixture for 10 min after which time the reaction was heated at 85° C. for 3.5 h. The reaction mixture was cooled to RT, EtOAc (50 mL) added, washed with saturated $NaHCO_3$ (aq, 50 mL) and brine (50 mL). The organic phase was separated, passed through a phase seperator and evaporated to dryness. The crude compound was purified by silica gel column chromatography eluting with 0%-2% MeOH/DCM to afford 1-[4-(4,4,5,5-tetramethyl-[1,3,2]dioxaborolan-2-yl)-phenyl]-imidazolidin-2-one (B1) as a white solid (377 mg, 63%); LC-MS. Rt 2.87 min, AnalpH2_MeOH_4 min(1); ($ESI^+$) m/z 289.3 $[M+H]^+$.

The following boronic ester was prepared using analogous procedures to compound B1 by heating at 85° C. for 3 h:

TABLE 8

| Compound | Cpd # | Analytical Data | Mass, % Yield, State |
| --- | --- | --- | --- |
| 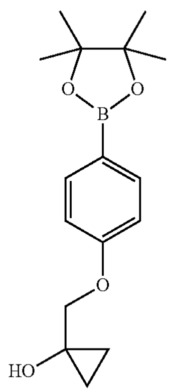 [SMILES: CC1(C)OB(c2ccc(OCC3(O)CC3)cc2)OC1(C)C] | B47 | LC-MS. $R_t$ 3.11 min, AnalpH2_MeOH_4 min(1); ($ESI^+$) m/z 313.3 $[M + Na]^+$; $^1$H-NMR (400 MHz, DMSO-$d_6$): δ 7.58-7.44 (m, 2H), 6.98-6.82 (m, 2H), 5.55 (s, 1H), 3.93 (s, 2H), 1.23 (s, 12H), 0.67-0.61 (m, 2H), 0.60-0.54 (m, 2H) | 272 mg, 29%, white solid |

1-[2-(tert-Butyl-dimethyl-silanyloxy)-ethyl]-3-[4-(4,4,5,5-tetramethyl-[1,3,2]dioxabolan-2-yl)-phenyl]-imidazolidin-2-one (B2)

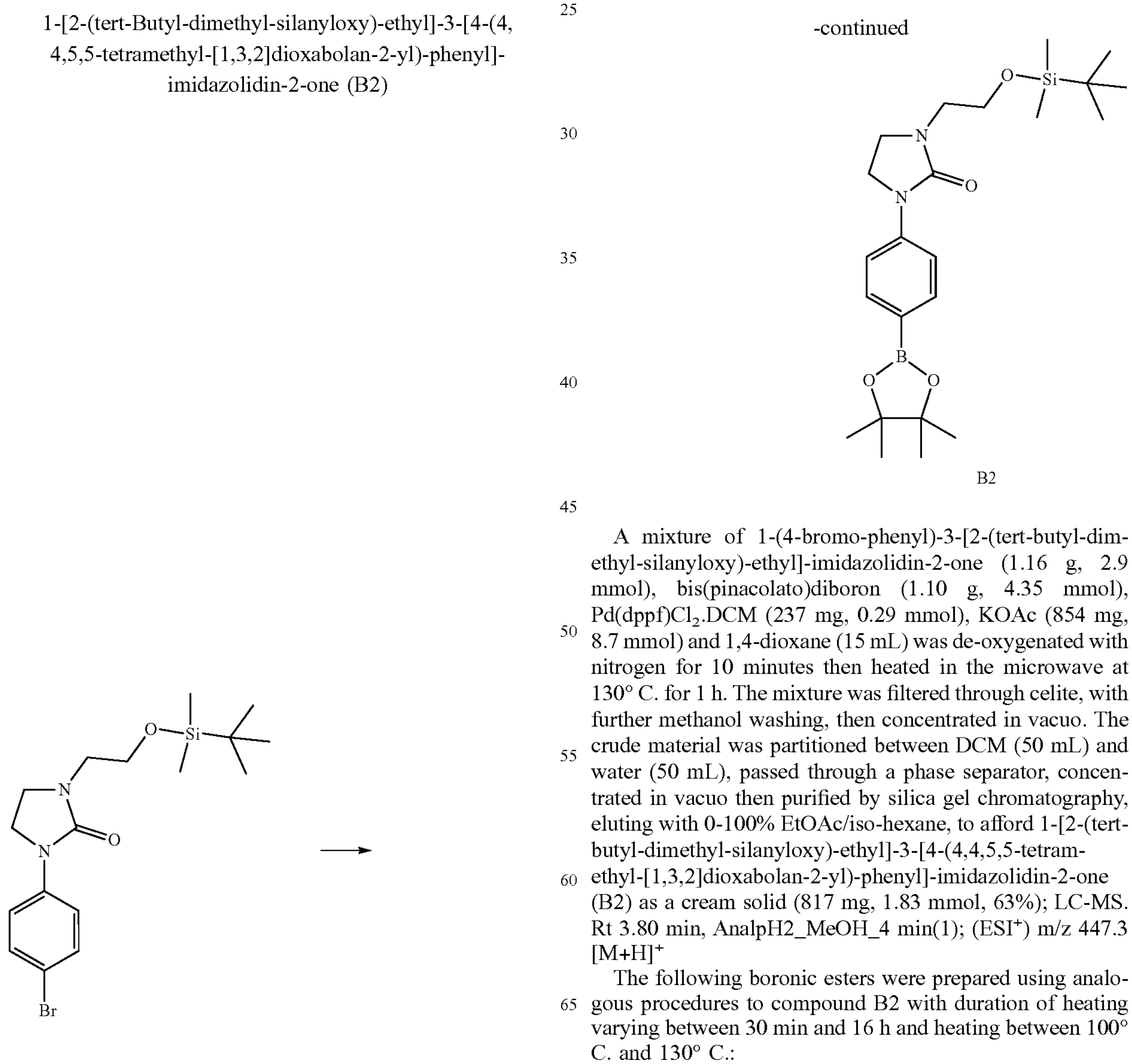

-continued

B2

A mixture of 1-(4-bromo-phenyl)-3-[2-(tert-butyl-dimethyl-silanyloxy)-ethyl]-imidazolidin-2-one (1.16 g, 2.9 mmol), bis(pinacolato)diboron (1.10 g, 4.35 mmol), $Pd(dppf)Cl_2$.DCM (237 mg, 0.29 mmol), KOAc (854 mg, 8.7 mmol) and 1,4-dioxane (15 mL) was de-oxygenated with nitrogen for 10 minutes then heated in the microwave at 130° C. for 1 h. The mixture was filtered through celite, with further methanol washing, then concentrated in vacuo. The crude material was partitioned between DCM (50 mL) and water (50 mL), passed through a phase separator, concentrated in vacuo then purified by silica gel chromatography, eluting with 0-100% EtOAc/iso-hexane, to afford 1-[2-(tert-butyl-dimethyl-silanyloxy)-ethyl]-3-[4-(4,4,5,5-tetramethyl-[1,3,2]dioxabolan-2-yl)-phenyl]-imidazolidin-2-one (B2) as a cream solid (817 mg, 1.83 mmol, 63%); LC-MS. Rt 3.80 min, AnalpH2_MeOH_4 min(1); ($ESI^+$) m/z 447.3 $[M+H]^+$ The following boronic esters were prepared using analogous procedures to compound B2 with duration of heating varying between 30 min and 16 h and heating between 100° C. and 130° C.:

TABLE 9
| Compound | Cpd # | Analytical Data | Mass, % Yield, State |
| --- | --- | --- | --- |
| 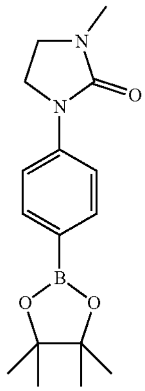 [SMILES: CN1CCN(c2ccc(B3OC(C)(C)C(C)(C)O3)cc2)C1=O] | B3 | LC-MS. $R_t$ 2.81 min, AnalpH2_MeOH_4 min(1); (ESI$^+$) m/z 303.2 $[M + H]^+$ | 90 mg, 38% |
| 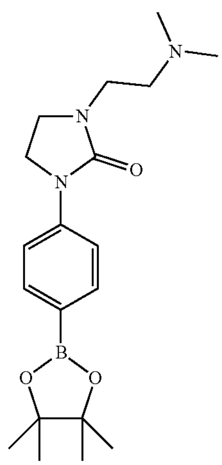 | B4 | LC-MS. $R_t$ 1.96 min, AnalpH2_MeOH_4 min(1); (ESI$^+$) m/z 360.4 $[M + H]^+$ | 98 mg, 29%, pale brown solid |
| 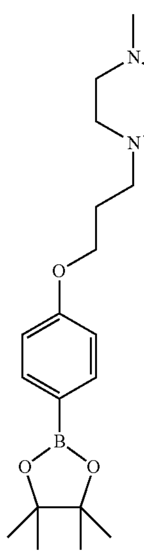 | B5 | LC-MS. $R_t$ 2.01 min, AnalpH2_MeOH_4 min(1); (ESI$^+$) m/z 361.3 $[M + H]^+$ | 195 mg, 95%, brown solid |

TABLE 9-continued
| Compound | Cpd # | Analytical Data | Mass, % Yield, State |
| --- | --- | --- | --- |
| 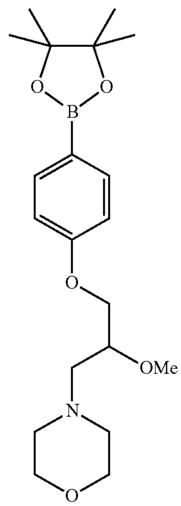 [SMILES: COC(COc1ccc(B2OC(C)(C)C(C)(C)O2)cc1)CN1CCOCC1] | B6 | LC-MS. $R_t$ 2.06 min, AnalpH2_MeOH_4 min(1); (ESI$^+$) m/z 378.3 $[M + H]^+$. | 168 mg, 73% yellow oil |
| 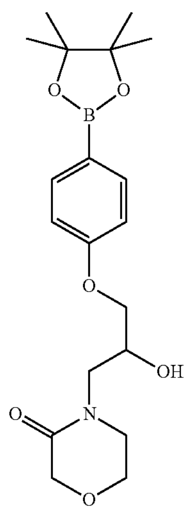 [SMILES: CC1(C)OB(c2ccc(OCC(O)CN3CCOCC3=O)cc2)OC1(C)C] | B7 | LC-MS. $R_t$ 2.87 min, AnalpH2_MeOH_4 min(1); (ESI$^+$) m/z 378.3 $[M + H]^+$. | 152 mg, 60% pale yellow solid |
| 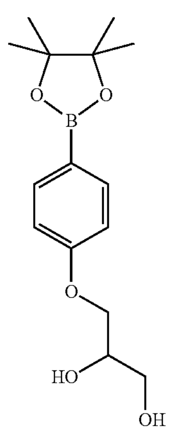 [SMILES: CC1(C)OB(c2ccc(OCC(O)CO)cc2)OC1(C)C] | B8 | LC-MS. $R_t$ 2.81 min, AnalpH2_MeOH_4 min(1); (ESI$^+$) m/z 317.4 $[M + Na]^+$. | 352 mg, 74%, off-white solid |

TABLE 9-continued
| Compound | Cpd # | Analytical Data | Mass, % Yield, State |
|---|---|---|---|
| 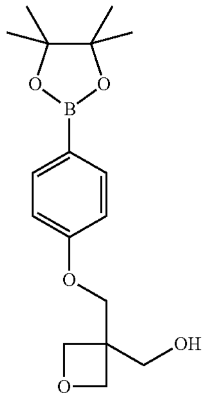 [SMILES: CC1(C)OB(c2ccc(OCC3(CO)COC3)cc2)OC1(C)C] | B9 | LC-MS. $R_t$ 3.13 min, AnalpH2_MeOH_4 min(1); ($ESI^+$) m/z 343.3 $[M + Na]^+$. | 174 mg, 99%, white solid |
| 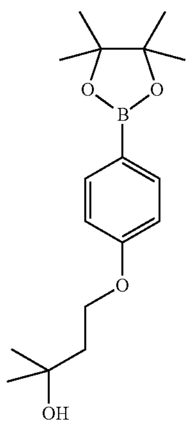 [SMILES: CC(C)(O)CCOc1ccc(B2OC(C)(C)C(C)(C)O2)cc1] | B10 | LC-MS. $R_t$ 3.31 min, AnalpH2_MeOH_4 min(1); ($ESI^+$) m/z 289.5 $[M - H_20 + H]^+$. | 325 mg, 57%, yellow solid |
| 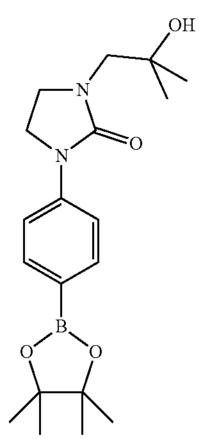 [SMILES: CC(C)(O)CN1CCN(c2ccc(B3OC(C)(C)C(C)(C)O3)cc2)C1=O] | B11 | LC-MS. $R_t$ 3.15 min, AnalpH2_MeOH_4 min(1); ($ESI^+$) m/z 361.4 $[M + H]^+$ | 154 mg, 52%, white solid |

TABLE 9-continued

| Compound | Cpd # | Analytical Data | Mass, % Yield, State |
|---|---|---|---|
| 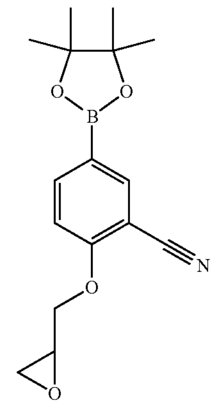 [SMILES: CC1(C)OB(c2ccc(OCC3CO3)c(C#N)c2)OC1(C)C] | B12 | LC-MS. $R_t$ 3.21 min, AnalpH2_MeOH_4 min(1); (ESI$^+$) m/z 302.3 $[M + H]^+$ | 158 mg, 38%, yellow oil |
| 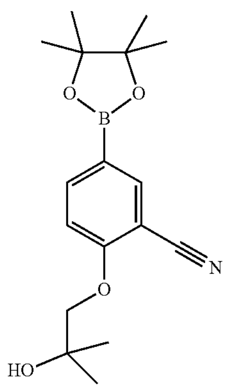 [SMILES: CC(C)(O)COc1ccc(B2OC(C)(C)C(C)(C)O2)cc1C#N] | B13 | LC-MS. $R_t$ 3.19 min, AnalpH2_MeOH_4 min(1); (ESI$^+$) m/z 340.3 $[M + Na]^+$. | 463 mg, 66%, pale yellow oil |
| 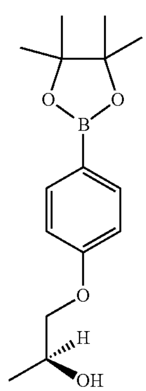 [SMILES: C[C@H](O)COc1ccc(B2OC(C)(C)C(C)(C)O2)cc1] | B14 | LC-MS. $R_t$ 3.10 min, analpH2_MeOH_4 min; (ESI$^+$) m/z 301.4 $[M + Na]^+$ $^1$HNMR (400 MHz, $CDCl_3$): 7.74 (d, J = 8.7 Hz, 2H), 6.89 (d J = 8.7 Hz, 2H), 4.23-4.15 (m, 1H), 3.96 (dd, J = 9.2, 3.2 Hz, 1H), 3.81 (dd, 9.2, 7.8 Hz, 1H), 1.32 (s, 12H), 1.27 (d, J = 6.4 Hz, 3H). | 481 mg, 54%, yellow oil |
| 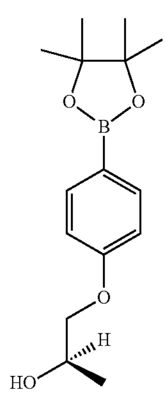 [SMILES: C[C@@H](O)COc1ccc(B2OC(C)(C)C(C)(C)O2)cc1] | B15 | LC-MS. $R_t$ 3.10 min, AnalpH2_MeOH_4 min; (ESI$^+$) m/z 301.4 $[M + Na]^+$ | 689 mg, 73%, yellow oil |

TABLE 9-continued
| Compound | Cpd # | Analytical Data | Mass, % Yield, State |
|---|---|---|---|
| 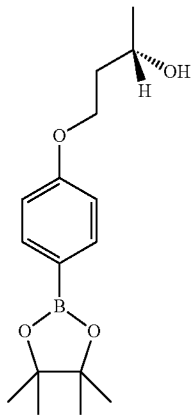 [SMILES: C[C@H](O)CCOc1ccc(B2OC(C)(C)C(C)(C)O2)cc1] | B48 | LC-MS. $R_t$ 3.20 min, AnalpH2_MeOH_4 min(1); (ESI$^+$) m/z 293.4 [M + H]$^+$ | 142 mg, 84%, white solid |
| 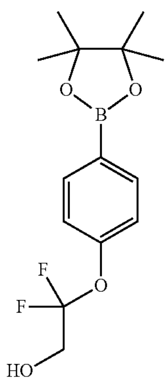 [SMILES: CC1(C)OB(c2ccc(OC(F)(F)CO)cc2)OC1(C)C] | B49 | LC-MS. $R_t$ 3.14 min, AnalpH2_MeOH_4 min (ESI$^+$); m/z 301.4 [M + H]$^+$ | 1.16 g 44%, white solid |
| 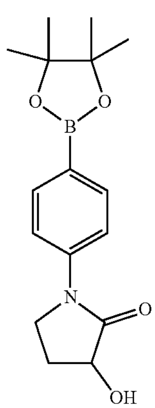 [SMILES: CC1(C)OB(c2ccc(N3CCC(O)C3=O)cc2)OC1(C)C] | B50 | LC-MS. $R_t$ 2.83 min, AnalpH2_MeOH_4 min(1); (ESI$^+$) m/z 304.2 [M + H]$^+$ | 267 mg, 36%, off-white solid |

TABLE 9-continued
| Compound | Cpd # | Analytical Data | Mass, % Yield, State |
|---|---|---|---|
| 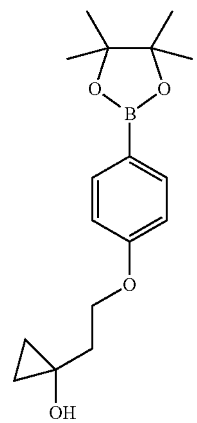 [SMILES: CC1(C)OB(c2ccc(OCCC3(O)CC3)cc2)OC1(C)C] | B51 | LC-MS. $R_t$ 3.27 min, AnalpH2_MeOH_4 min (ESI+); m/z 327.3 [M + Na]+ | 1.25 g, 20%, white solid |
| 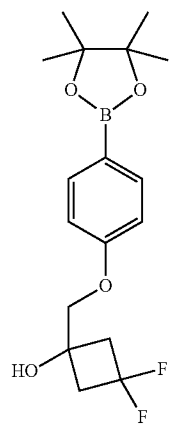 | B52 | LC-MS. $R_t$ 3.38 min, AnalpH2_MeOH_4 min (ESI+); m/z 363.2 [M + Na]+ | 150 mg, 31%, white solid |
| 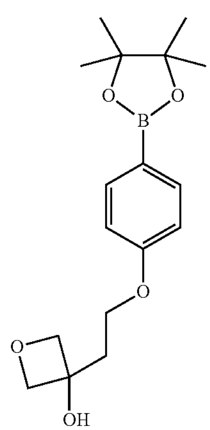 [SMILES: CC1(C)OB(c2ccc(OCCC3(O)COC3)cc2)OC1(C)C] | B53 | LC-MS. $R_t$ 3.04 min, AnalpH2_MeOH_4 min (ESI+); m/z 321.3 [M + H]+ | 1.20 g, 40%, white solid |

TABLE 9-continued
| Compound | Cpd # | Analytical Data | Mass, % Yield, State |
|---|---|---|---|
| 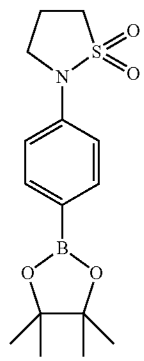 [SMILES: CC1(C)OB(c2ccc(N3CCCS3(=O)=O)cc2)OC1(C)C] | B54 | LC-MS. $R_t$ 2.88 min, AnalpH2_MeOH_4 min(1); (ESI$^+$) m/z 324.3 [M + H]$^+$ | 328 mg, 93%, yellow solid |
| 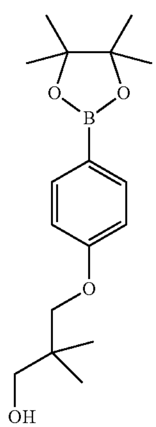 [SMILES: CC(C)(CO)COc1ccc(B2OC(C)(C)C(C)(C)O2)cc1] | B55 | LC-MS. $R_t$ 3.03 min, AnalpH2_MeOH_4 min(1); (ESI$^+$) m/z 307.2 [M + H]$^+$. | 361 mg, 93%, white solid |
| 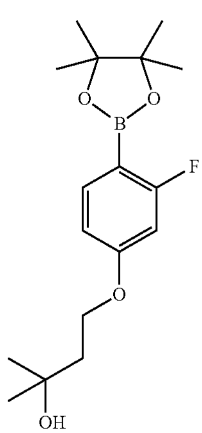 [SMILES: CC(C)(O)CCOc1ccc(B2OC(C)(C)C(C)(C)O2)c(F)c1] | B56 | LC-MS. $R_t$ 3.32 min, AnalpH2_MeOH_4 min (ESI$^+$); m/z 347.3 [M + Na]$^+$ | 454 mg, 65%, pale yellow solid |

TABLE 9-continued
| Compound | Cpd # | Analytical Data | Mass, % Yield, State |
|---|---|---|---|
| 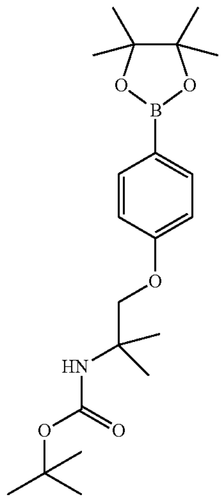 [SMILES: CC(C)(COc1ccc(B2OC(C)(C)C(C)(C)O2)cc1)NC(=O)OC(C)(C)C] | B57 | LC-MS. $R_t$ 3.55 min, AnalpH2_MeOH_4 min (ESI$^+$); m/z 392.3 [M + Na]$^+$ | 574 mg, 98%, pale yellow solid |
| 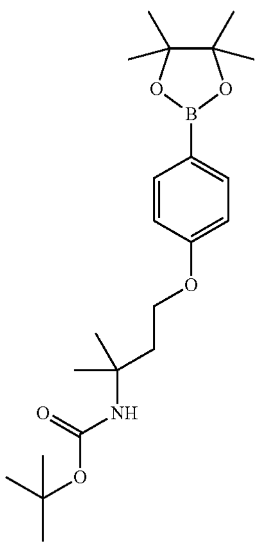 [SMILES: CC(C)(CCOc1ccc(B2OC(C)(C)C(C)(C)O2)cc1)NC(=O)OC(C)(C)C] | B58[a] | LC-MS. $R_t$ 3.52 min, AnalpH2_MeOH_4 min (ESI$^+$); m/z 306.1 [M − Boc + H]$^+$ | 305 mg, 58%, white solid |
| 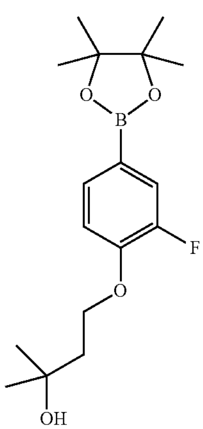 [SMILES: CC(C)(O)CCOc1ccc(B2OC(C)(C)C(C)(C)O2)cc1F] | B59 | LC-MS. $R_t$ 3.33 min, AnalpH2_MeOH_4 min (ESI$^+$); m/z 347.1 [M + Na]$^+$ | 1.64 g, 83%, pale orange solid |

TABLE 9-continued
| Compound | Cpd # | Analytical Data | Mass, % Yield, State |
|---|---|---|---|
| 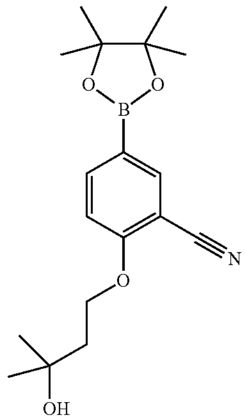 [SMILES: CC(C)(O)CCOc1ccc(B2OC(C)(C)C(C)(C)O2)cc1C#N] | B60 | LC-MS. $R_t$ 2.87 min, AnalpH2_MeOH_4 min(1); (ESI$^+$) m/z 332.2 [M + H]$^+$. | 1.52 g, Quantitative, pale yellow oil |
| 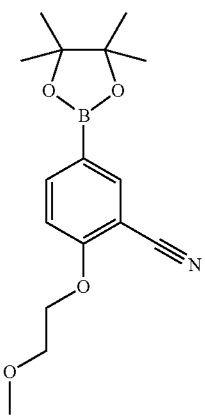 [SMILES: COCCOc1ccc(B2OC(C)(C)C(C)(C)O2)cc1C#N] | B61 | LC-MS. $R_t$ 3.02 min, AnalpH2_MeCN_4 min(1); (ESI$^+$) m/z 304.2 [M + H]$^+$. | 1.26 g, 97%, yellow oil |
| 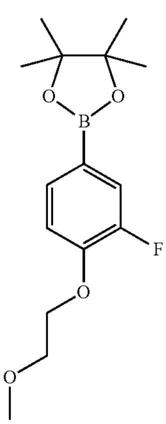 [SMILES: COCCOc1ccc(B2OC(C)(C)C(C)(C)O2)cc1F] | B62 | LC-MS. $R_t$ 3.02 min, AnalpH2_MeOH_4 min(1); (ESI$^+$) m/z 297.2 [M + H]$^+$. | 1.90 g, 80%, yellow oil |

TABLE 9-continued

| Compound | Cpd # | Analytical Data | Mass, % Yield, State |
|---|---|---|---|
| 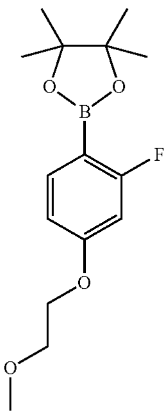 [SMILES: COCCOc1ccc(B2OC(C)(C)C(C)(C)O2)c(F)c1] | B63 | LC-MS. $R_t$ 2.95 min, AnalpH2_MeCN_4 min(1); (ESI$^+$) m/z 297.1 [M + H]$^+$. | 1.10 g, 47%, yellow oil |
| 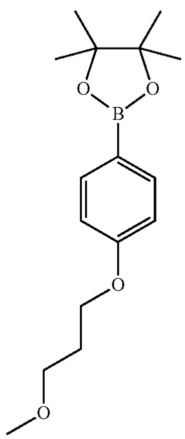 | B64 | LC-MS. $R_t$ 3.36 min, AnalpH2_MeOH_4 min (ESI$^+$); m/z 315.2 [M + Na]$^+$ | 1.72 g, 72%, pale yellow oil |
| 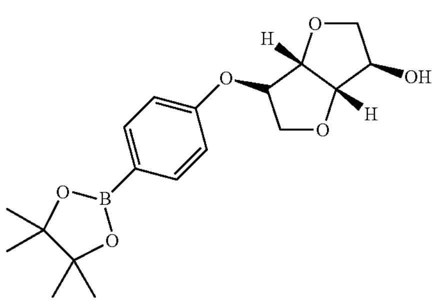 | B65 | LC-MS $R_t$ 3.06 AnalpH2_MeOH_4 min_(ESI$^+$); m/z no ionization; $^1$HNMR (400 MHz, $CDCl_3$): δ 7.74 (d, J = 8.7 Hz, 2H) 6.91 (d, J = 8.7 Hz, 2H), 4.80 (t, J = 3.2 Hz, 1H), 4.77 (d, J = 3.7 Hz, 1H), 4.60 (d, J = 4.1, 1H), 4.38 (br s, 1H), 4.03 (d, J = 3.2 Hz, 2H), 3.94-3.87 (m, 2H), 1.32 (s, 12H) | 320 mg, 79% colourless oil |
| 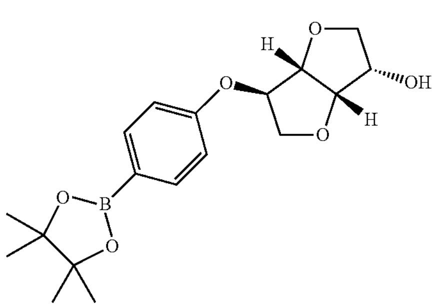 | B66 | LC-MS $R_t$ 3.06 min AnalpH2_MeOH_4 min_(ESI$^+$); m/z no ionization; $^1$HNMR (400 MHz, $CDCl_3$): δ 7.74 (d, J = 8.7 Hz, 2H), 6.89 (d, J = 8.7 Hz, 2H), 4.87 (d, J = 3.8 Hz, 1H), 4.69 (t, J = 4.6 Hz, 1H), 4.56 (d J = 4.6 Hz, 1H), 4.32 (q, J = 5.5 Hz, 1H), 4.19 (d, J = 10.3 Hz, 1H), 4.10 (dd, J = 3.8, 10.3 Hz, 1H), 3.89 (dd, J = 5.5, 9.4 Hz, 1H), 3.64 (dd, J = 5.5, 9.4 Hz, 1H), 1.25 (s, 12H). | 305 mg, 98%, colourless oil |

TABLE 9-continued

| Compound | Cpd # | Analytical Data | Mass, % Yield, State |
|---|---|---|---|
| 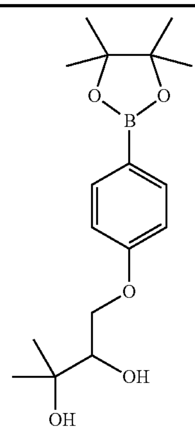 | B67 | LC-MS. $R_t$ 3.04 min, AnalpH2_MeOH_4 min(1); ($ESI^+$) m/z 345.3 $[M + Na]^+$. | 1.12 g, 99%, colourless oil |
| 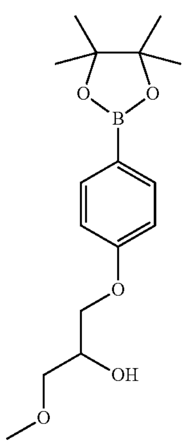 | B68 | LC-MS. $R_t$ 3.07 min, AnalpH2_MeOH_4 min(1); ($ESI^+$) m/z 331.4 $[M + Na]^+$. | 550 mg, 92%, yellow oil |

[a]THF was used as solvent instead of 1,4-dioxane

1-[4-(4,4,5,5-Tetramethyl-[1,3,2]dioxaborolan-2-yl)-phenyl]-pyrrolidin-2-one (B16)

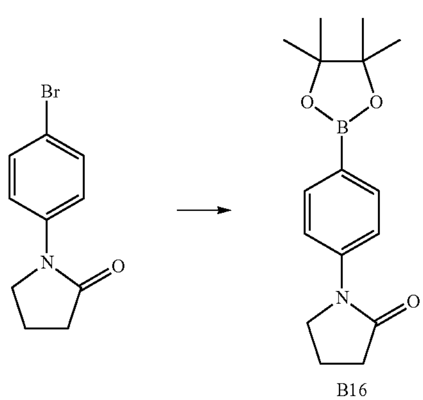 [SMILES: O=C1CCCN1c1ccc(Br)cc1 ; "B16" ; CC1(C)OB(c2ccc(N3CCCC3=O)cc2)OC1(C)C]

B16

To 1-(4-bromophenyl)pyrrolidin-2-one (1.51 g, 6.3 mmol) was added bis(pinacolato)diboron (1.92 g, 7.56 mmol), $Cs_2CO_3$ (2.46 g, 7.56 mmol), $Pd(dppf)Cl_2$.DCM (515 mg, 0.63 mmol) in a mixture of 1,4-dioxane:$H_2O$ (25 mL, 4:1) and the reaction mixture flushed with $N_2$ for 15 min. The reaction mixture was heated to reflux for 18 h. The reaction mixture was evaporated to dryness, suspended in EtOAc (100 mL) and washed with $H_2O$ (100 mL), whereupon a precipitate formed which was removed by filtration. The organic phase was separated, passed through a phase seperator and evaporated to dryness. The crude compound was purified by silica gel column chromatography eluting with 7-32% EtOAc/iso-hexane to obtain 1-[4-(4,4,5,5-tetramethyl-[1,3,2]dioxaborolan-2-yl)-phenyl]-pyrrolidin-2-one (B16) as a pale yellow solid (756 mg, 42%); LC-MS. Rt 3.00 min, AnalpH2_MeOH_4 min; ($ESI^+$) m/z 288.3 $[M+H]^+$.

The following boronic ester were prepared using analogous procedures to B16:

TABLE 10

| Compound | Cpd # | Analytical Data | Mass, % Yield, State |
|---|---|---|---|
| 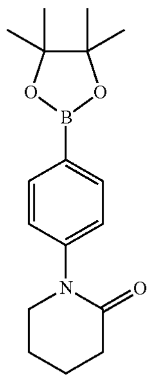 [SMILES: CC1(C)OB(c2ccc(N3CCCCC3=O)cc2)OC1(C)C] | B17 | LC-MS. $R_t$ 3.13 min, AnalpH2_MeOH_4 min(1); ($ESI^+$) m/z 302.5 $[M + H]^+$. | 59 mg, 9%, pale yellow solid |

Dimethyl-{2-[4-(4,4,5,5-tetramethyl-[1,3,2]dioxaborolan-2-yl)-phenoxy]-ethyl}-amine (B18)

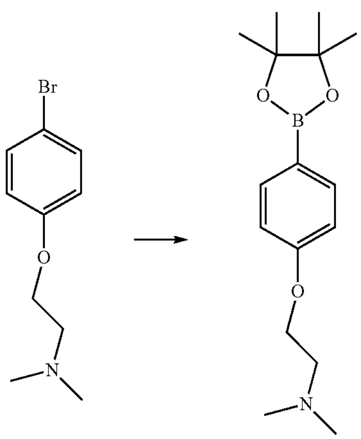

B18

To a suspension of N-[2-(4-bromophenoxy)ethyl]-N—N-dimethylamine (500 mg, 2.05 mmol), bis(pinacolato)diboron (625 mg, 2.46 mmol), K2CO3 (425 mg, 3.07 mmol) in DME (10 mL) was added Pd(dppf)$Cl_2$.DCM (84 mg, 0.1 mmol) and the reaction mixture de-oxygenated with $N_2$ for 10 min and the reaction mixture heated at 100° C. for 15 h. The reaction mixture was filtered through a celite cartridge (2.5 g), the column washed with MeOH (8×CV) and the filtrate evaporated in vacuo. The crude compound was purified by silica gel column chromatography eluting with 100% DCM—10% MeOH/DCM to obtain dimethyl-{2-[4-(4,4,5,5-tetramethyl-[1,3,2]dioxaborolan-2-yl)-phenoxy]-ethyl}-amine (B18) as a yellow oil (700 mg, quantitative); LC-MS. Rt 1.93 min, AnalpH2_MeOH_4 min(1); ($ESI^+$) m/z 292.4 $[M+H]^+$.

The following Isoglycoside boronic ester was prepared via methylation of the corresponding alcohol:

2-(4-(((3R,3aS,6S,6aS)-6-ethoxyhexahydrofuro[3,2-b]furan-3-yl)oxy)phenyl)-4,4,5,5-tetramethyl-1,3,2-dioxaborolane (B69)

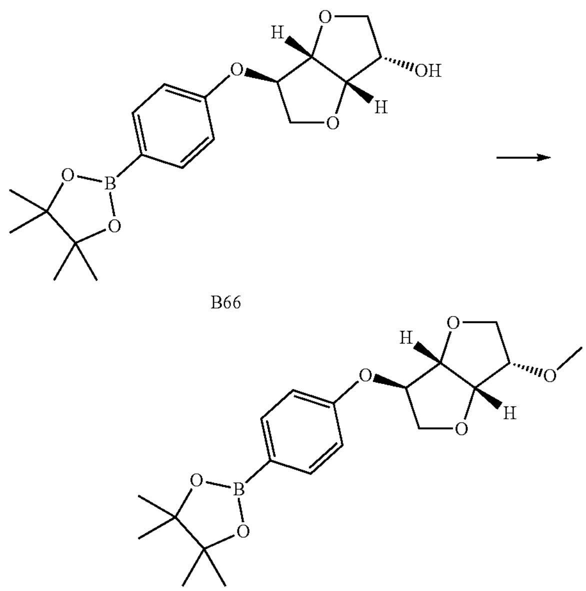

B66

B69

To a stirred suspension of sodium hydride (73 mg, 2.20 mmol, 60% dispersion in oil) in anhydrous THF (14 mL) at 0° C. was added (3S,3aS,6R,6aS)-6-(4-(4,4,5,5-tetramethyl-1,3,2-dioxaborolan-2-yl)phenoxy)hexahydrofuro[3,2-b]furan-3-ol (B66) (500 mg, 1.44 mmol) as a solution in anhydrous THF (5 mL). The reaction was stirred at 0° C. for 10 mins then methyl iodide (267 μL, 4.32 mmol) was added. The resulting reaction mixture was stirred for 30 mins at 0° C. then warmed to RT and concentrated in vacuo. The residue was re-dissolved in DCM, absorbed onto silica and purified by silica gel column chromatography eluting with 5-75% EtOAc/iso-hexane to obtain the title compound as a colourless oil (110 mg, 21%). $^1$HNMR (400 MHz, $CDCl_3$): δ 7.74 (d, J=8.7 Hz, 2H), 6.90 (d, J=8.7 Hz, 2H), 4.82 (d, J=3.2 Hz, 1H), 4.75 (d, J=4.4 Hz, 1H), 4.62 (d, J=4.6 Hz, 1H), 4.18 (dd, J=10.5, 4.1 Hz, 1H), 4.12 (d, J=8.7 Hz, 1H), 4.01-3.91 (m, 2H), 3.67 (t, J=7.3 Hz, 1H), 3.48 (s, 3H), 1.32 (s, 12H).

A number of boronic esters were synthesised from the corresponding anilino-substituted boronic ester using amide coupling reactions:

2-(4-Methyl-piperazin-1-yl)-N-[4-(4,4,5,5-tetramethyl-[1,3,2]dioxaborolan-2-yl) phenyl]acetamide (B19)

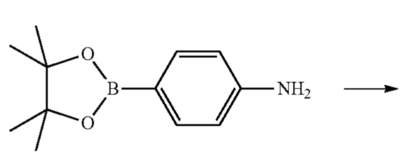

-continued

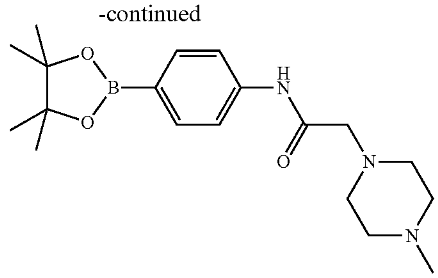

B19

To a mixture of 4-(4,4,5,5)tetramethyl-1,3,2-dioxaborolan-2-ylaniline (500 mg, 2.28 mmol). 2-(4-methylpiperazin- 1-yl) acetic acid (433 mg, 2.74 mmol) and HATU (1.04 g, 2.74 mmol) in DMF (11 mL) was added DIPEA (1.2 mL, 6.85 mmol) and the reaction stirred at RT for 2 h. The solvent was removed in vacuo, the residue dissolved in DCM (50 mL) and washed with saturated $NaHCO_3$ (aq) (50 mL). The layers were separated (phase seperator) and the organic phase evaporated to dryness. The crude compound was purified by silica gel column chromatography eluting with 100% DCM to 10% MeOH/DCM to afford 2-(4-methyl-piperazin-1-yl)-N-[4-(4,4,5,5-tetramethyl-[1,3,2]dioxaborolan-2-yl)-phenyl]acetamide (B19) as a white solid (565 mg, 69%); LC-MS. Rt 2.03 min, AnalpH2_MeOH_4 min(1); (ESI$^+$) m/z 360.4 $[M+H]^+$.

The following boronic acids/esters were prepared using analogous procedures to compound B19:

TABLE 11

| Compound | Cpd # | Analytical Data | Mass, % Yield, State |
|---|---|---|---|
| 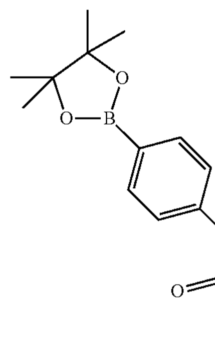 | B20[a] | LC-MS. $R_t$ 2.84 min, AnalpH2_MeOH_4 min; (ESI$^+$) m/z 278.3 $[M + H]^+$. | 379 mg, quant, dark orange oil |
| 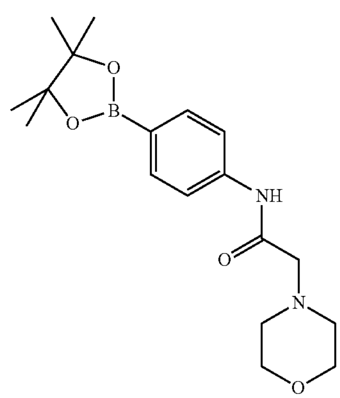 [SMILES: CC1(C)OB(c2ccc(NC(=O)CN3CCOCC3)cc2)OC1(C)C] | B21 | LC-MS. $R_t$ 2.22 min, AnalpH2_MeOH_4 min; (ESI$^+$) m/z 347.4 $[M + H]^+$. | 810 mg, quant, yellow solid |

TABLE 11-continued
| Compound | Cpd # | Analytical Data | Mass, % Yield, State |
|---|---|---|---|
| 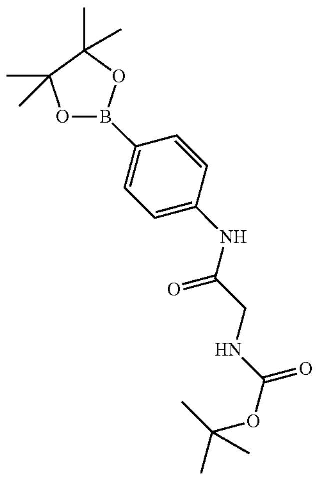 [SMILES: CC(C)(C)OC(=O)NCC(=O)Nc1ccc(B2OC(C)(C)C(C)(C)O2)cc1] | B22 | LC-MS. $R_t$ 3.26 min, AnalpH2_MeOH_4 min(1); (ESI$^+$) m/z 377.3 $[M + H]^+$. | 554 mg, 86%, off-white solid |
| 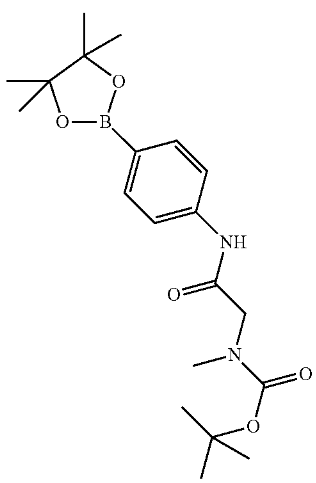 [SMILES: CN(CC(=O)Nc1ccc(B2OC(C)(C)C(C)(C)O2)cc1)C(=O)OC(C)(C)C] | B23 | LC-MS. $R_t$ 3.31 min, AnalpH2_MeOH_4 min(1); (ESI$^+$) m/z 391.4 $[M + H]^+$. | 610 mg, 98%, off-white solid |
| 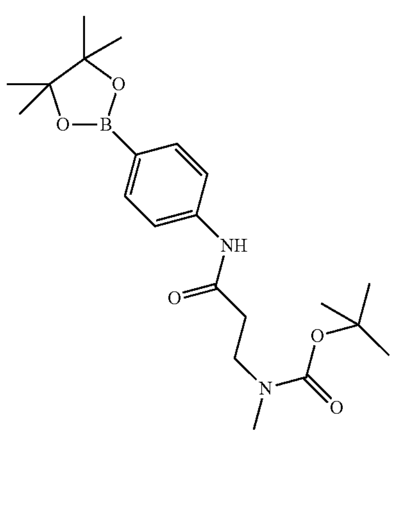 [SMILES: CN(CCC(=O)Nc1ccc(B2OC(C)(C)C(C)(C)O2)cc1)C(=O)OC(C)(C)C] | B24[b] | LC-MS. $R_t$ 3.24 min, AnalpH2_MeOH_4 min; (ESI$^+$) m/z 405.5 $[M + H]^+$. | 841 mg, 91%, pale orange solid |

TABLE 11-continued

| Compound | Cpd # | Analytical Data | Mass, % Yield, State |
|---|---|---|---|
| 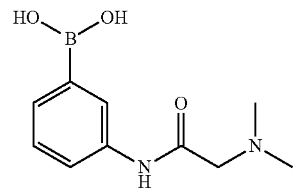 [SMILES: CN(C)CC(=O)Nc1cccc(B(O)O)c1] | B25[c] | LC-MS. $R_t$ 0.51 min, AnalpH2_MeOH_4 min(1); ($ESI^+$) m/z 223.3 $[M + H]^+$ | 604 mg, 83%, brown oil* |

[a]2.4 eq of HATU and acid species used, reaction time of 36 h;
[b]TBTU used in place of HATU;
[c]HOAt and EDC•HCl used in place of HATU, TEA used in place of DIPEA, DCM used in place of DMF, 24 h duration, purified SCX-2 cartridge.

The following amides were prepared from the corresponding benzoic acid using amide coupling conditions:

N-(2-Dimethylamino-ethyl)-3-(4,4,5,5-tetramethyl-[1,3,2]dioxaborolan-2-yl)-benzamide (B26)

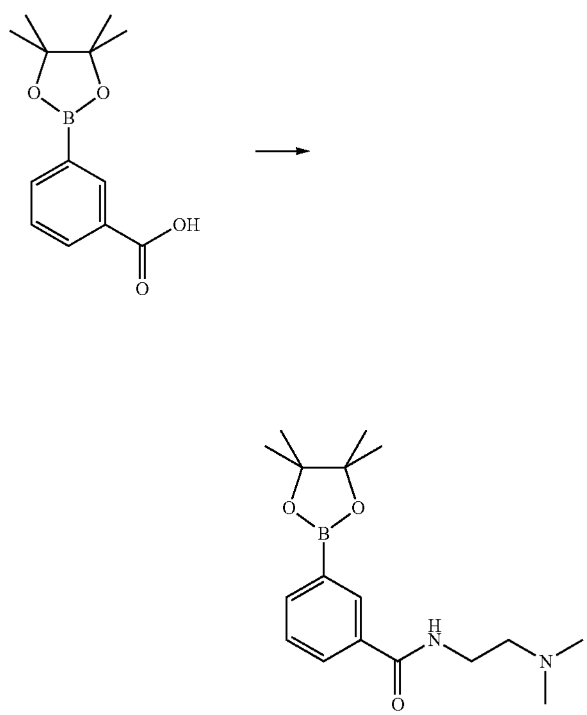

B26

To a solution of 3-carboxyphenyl boronic acid pinacol ester (500 mg, 2.02 mmol), HOAt (411 mg, 3.02 mmol) and EDC.HCl (579 mg, 3.02 mmol) in DMF (10 mL) was added N,N-dimethylethylene diamine (440 µL, 4.03 mmol). The mixture was stirred at RT for 1 h. The reaction mixture was diluted with saturated sodium bicarbonate solution (30 mL) then extracted in EtOAc (2×50 mL). The combined organics were washed with $H_2O$ (2×30 mL) then brine (30 mL), dried (anhydrous $MgSO_4$), filtered and concentrated in vacuo to afford N-(2-dimethylamino-ethyl)-3-(4,4,5,5-tetramethyl-[1,3,2]dioxaborolan-2-yl)-benzamide (B26) as a pale yellow oil (186 mg, 0.58 mmol, 29%); LC-MS. Rt 2.03 min, AnalpH2_MeOH_4 min(1); ($ESI^+$) m/z 319.3 $[M+H]^+$ A number of substituted boronic esters were synthesised via ring opening of the corresponding epoxide:

1-Morpholin-4-yl-3-[4-(4,4,5,5-tetramethyl-[1,3,2]dioxaborolan-2-yl)-phenoxy]-propan-2-ol-(B27)

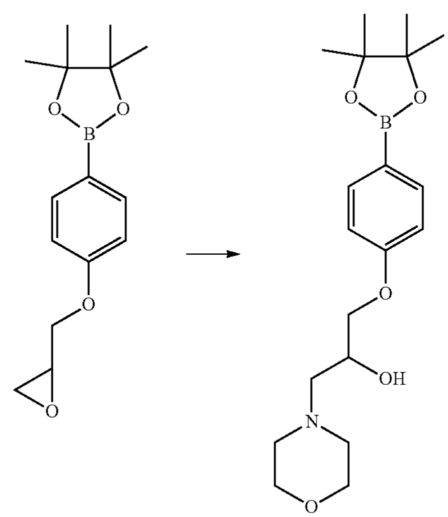

B27

A solution of 4-(oxiran-2-ylmethoxy)phenylboronic acid, pinacol ester (1.0 g, 3.62 mmol) and morpholine (443 µL, 5.07 mmol) in isopropanol (20 mL) was heated at 100° C. for 30 min in a microwave reactor (200 W). The reaction was repeated once more. The two reaction mixtures were combined and concentrated in vacuo. The crude solid was pre-absorbed onto silica and purified by silica gel chromatography eluting with 0-5% MeOH/DCM to afford 1-morpholin-4-yl-3-[4-(4,4,5,5-tetramethyl-[1,3,2]dioxaborolan-2-yl)-phenoxy]-propan-2-ol (B27) as a white solid (2.56 g, 97%); LC-MS. Rt 1.90 min, AnalpH2_MeOH_4 min(1); ($ESI^+$) m/z 364.4 $[M+H]^+$.

The following boronic esters were prepared using analogous procedures to compound B27:

TABLE 12

| Compound | Cpd # | Analytical Data | Mass, % Yield, State |
|---|---|---|---|
| 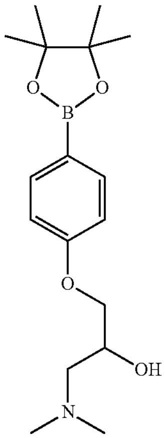 [SMILES: CN(C)CC(O)COc1ccc(B2OC(C)(C)C(C)(C)O2)cc1] | B28 | LC-MS. $R_t$ 1.82 min, AnalpH2_MeOH_4 min(1); (ESI$^+$) m/z 322.3 [M + H]$^+$ | 565 mg, 97%, orange oil |
| 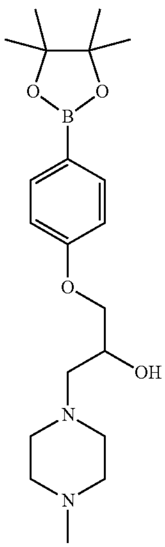 [SMILES: CN1CCN(CC(O)COc2ccc(B3OC(C)(C)C(C)(C)O3)cc2)CC1] | B29 | LC-MS. $R_t$ 2.04 min, AnalpH2_MeOH_4 min(1); (ESI$^+$) m/z 377.4 [M + H]$^+$. | 203 mg, 75%, pale yellow oil |
| 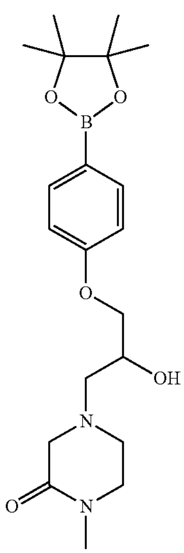 [SMILES: CN1CCN(CC(O)COc2ccc(B3OC(C)(C)C(C)(C)O3)cc2)CC1=O] | B30 | LC-MS. $R_t$ 2.48 min, AnalpH2_MeOH_4 min(1); (ESI$^+$) m/z 391.5 [M + H]$^+$. | 154 mg, 55%, pale yellow oil |
| 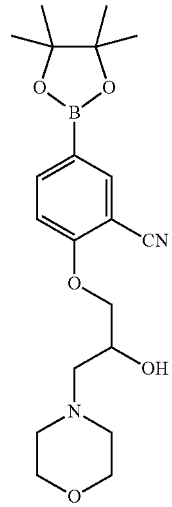 [SMILES: CC1(C)OB(c2ccc(OCC(O)CN3CCOCC3)c(C#N)c2)OC1(C)C] | B31[a] | LC-MS. $R_t$ 2.20 min, AnalpH2_MeOH_4 min(1); (ESI$^+$) m/z 389.3 [M + H]$^+$. | 117 mg, 58%, colourless oil |
| 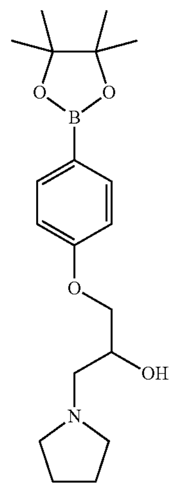 [SMILES: CC1(C)OB(c2ccc(OCC(O)CN3CCCC3)cc2)OC1(C)C] | B32 | LC-MS. $R_t$ 2.05 min, AnalpH2_MeOH_4 min(1); (ESI$^+$) m/z 348.3 [M + H]$^+$. | 248 mg, 99%, brown solid |
| 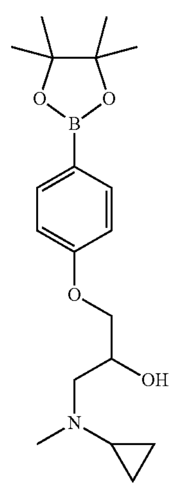 [SMILES: CN(CC(O)COc1ccc(B2OC(C)(C)C(C)(C)O2)cc1)C1CC1] | B33[b] | LC-MS. $R_t$ 2.15 min, AnalpH2_MeOH_4 min(1); (ESI$^+$) m/z 348.4 [M + H]$^+$. | 164 mg, 66%, Not given |

TABLE 12-continued

| Compound | Cpd # | Analytical Data | Mass, % Yield, State |
|---|---|---|---|
| 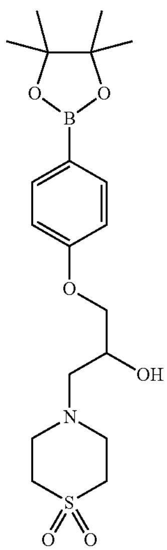 [SMILES: CC1(C)OB(c2ccc(OCC(O)CN3CCS(=O)(=O)CC3)cc2)OC1(C)C] | B34 | LC-MS. $R_t$ 2.81 min, AnalpH2_MeOH_4 min(1); (ESI) m/z 412.4 $[M + H]^+$. | 165 mg, 56%, pale yellow oil |

[a]Synthesized using 2-(oxiran-2-ylmethoxy)-5-(4,4,5,5-tetramethyl-1,3,2-dioxaborolan-2-yl)benzonitrile (B12);

[b]Amine species used as HCl salt therefore 1 eq of $Et_3N$ was also added.

The two enantiomers of the following urea-substituted boronic esters were prepared from the commercial available isocyanate.

(S)-3-Hydroxy-pyrrolidine-1-carboxylic acid [4-(4,4,5,5-tetramethyl-[1,3,2]dioxaborolan-2-yl)-phenyl]-amide (B35)

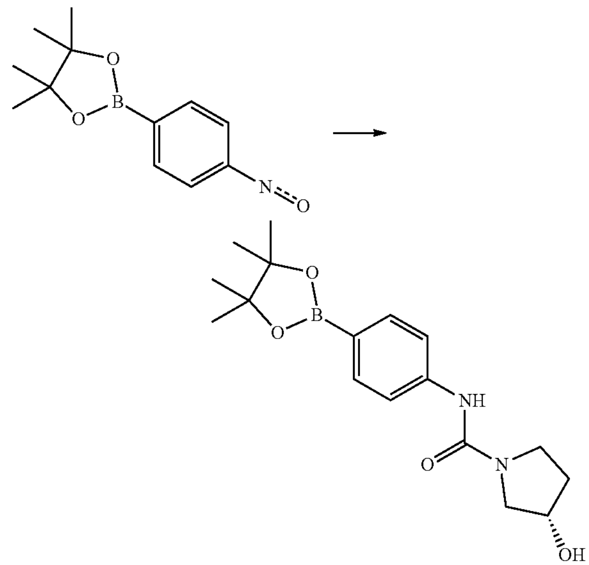

B35

To 4-(isocyanatophenyl)boronic acid, pinacol ester (100 mg, 0.41 mmol) and (S)-3-pyrridinol (53 mg, 0.61 mmol) was added DCM (1 mL) and the mixture stirred at RT, overnight. The reaction mixture was evaporated in vacuo, dissolved in MeOH (2 mL) and passed through a 5 g SCX-2 cartridge, eluting with MeOH (2×CV) and DCM (2×CV). The solvent was removed in vacuo to afford (S)-3-hydroxy-pyrrolidine-1-carboxylic acid [4-(4,4,5,5-tetramethyl-[1,3,2]dioxaborolan-2-yl)-phenyl]-amide (B35) as a purple oil (107 mg, 79%); LC-MS. Rt 2.72 min, AnalpH2_MeOH_4 min(1); (ESI+) m/z 333.4 $[M+H]^+$ The (R) enantiomer B36 was prepared using analogous procedures to compound B35.

TABLE 13

| Compound | Cpd # | Analytical Data | Mass, % Yield, Appearance |
|---|---|---|---|
| 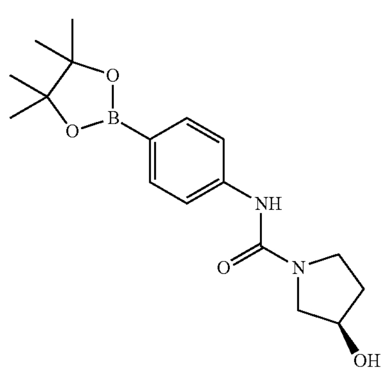 [SMILES: CC1(C)OB(c2ccc(NC(=O)N3CC[C@@H](O)C3)cc2)OC1(C)C] | B36 | LC-MS, $R_t$ 2.72 min, AnalpH2_MeOH_4 min(1); $(ESI^+)$ m/z 333.4 $[M + H]^+$. | 132 mg, 97%, pale yellow oil |

A number of boronic esters were prepared via Mitsunobu reactions of the corresponding phenol:

3-[4-(4,4,5,5-Tetramethyl-[1,3]dioxaborolan-2-yl)-phenoxymethyl]-azetidine-1-carboxylic acid tert-butyl ester (B37)

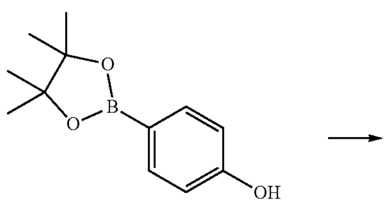

-continued

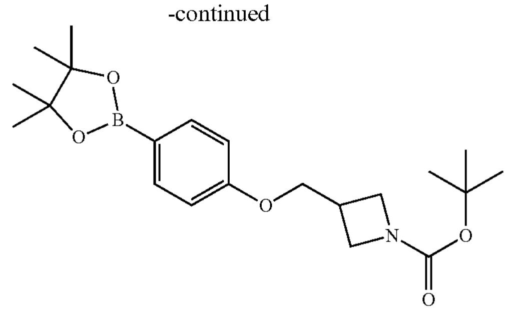

B37

4-(4,4,5,5-tetramethyl-[1,3]dioxaborolan-2-yl)-phenol (100 mg, 0.45 mmol), 1,1'-(azodicarbonyl)dipiperidine (230 mg, 0.91 mmol) and $PPh_3$ (238 mg, 0.91 mmol) were dissolved in THE (5 mL) under $N_2$ and 3-hydroxymethyl-azetidine-1-carboxylic acid tert-butyl ester (80 μL, 0.45 mmol) was added. The solution was stirred at RT for 18 h. The reaction was partitioned between $H_2O$ (10 mL) and DCM (3×15 mL) and the organic layer dried by phase separator. The final compound was obtained by flash chromatography (0-100% EtOAc in iso-hexane). The title compound was isolated as a clear gum (120 mg, 68%). LC-MS. Rt 3.53 min, AnalpH2_MeOH_4 min(1); (ESI+) m/z 390.3 $[M+H]^+$.

The following boronic esters were prepared using analogous procedures to compound B37.

TABLE 14

| Compound | Cpd # | Analytical Data | Mass, % Yield, State |
|---|---|---|---|
| 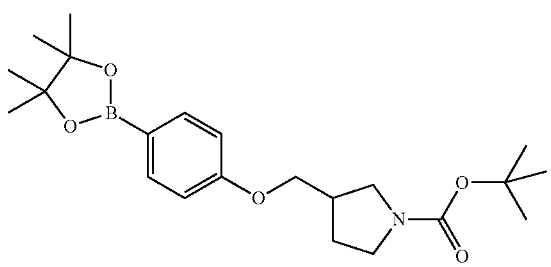 [SMILES: CC(C)(C)OC(=O)N1CCC(COc2ccc(B3OC(C)(C)C(C)(C)O3)cc2)C1] | B38[a] | LC-MS. $R_t$ 3.60 min, AnalpH2_MeOH_4 min(1); $(ESI^+)$ m/z 404.3 $[M + H]^+$. | 118 mg, 22%, yellow gum |
| 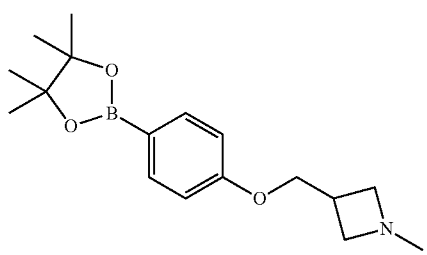 | B39 | LC-MS. $R_t$ 2.10 min, AnalpH2_MeOH_4 min(1); $(ESI^+)$ m/z 304.3 $[M + H]^+$. | 205 mg, 50%, orange oil |
| 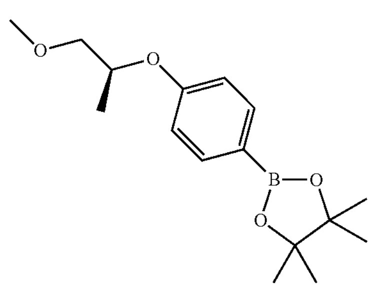 | B70[b] | LC-MS. $R_t$ 3.32 min, AnalpH2_MeOH_4 min(1); $(ESI^+)$ m/z 315.2 $[M + Na]^+$. | 878 mg, 66%, pale yellow oil |

TABLE 14-continued

| Compound | Cpd # | Analytical Data | Mass, % Yield, State |
|---|---|---|---|
| 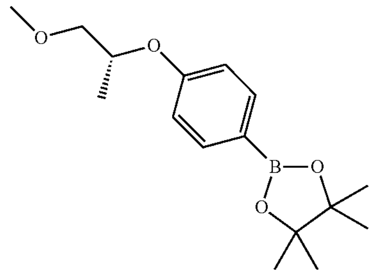 | B71[b] | LC-MS. $R_t$ 3.32 min, AnalpH2_MeOH_4 min(1); ($ESI^+$) m/z 315.3 $[M + Na]^+$. | 880 mg, 66%, pale yellow oil |
| 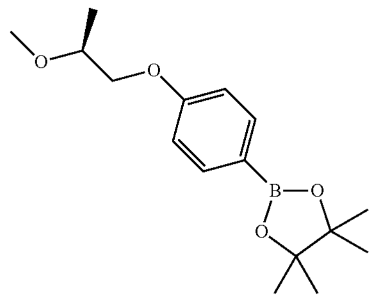 | B72[b] | LC-MS. $R_t$ 2.10 min, AnalpH2_MeOH_4 min(1); ($ESI^+$) m/z 315.3 $[M + Na]^+$. | 1.10 g, 83%, orange oil |
| 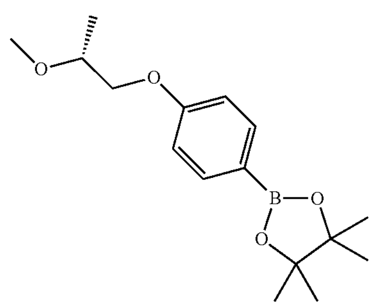 | B73[b] | LC-MS. $R_t$ 2.10 min, AnalpH2_MeOH_4 min(1); ($ESI^+$) m/z 315.3 $[M + Na]^+$. | 519 mg, 71%, pale yellow oil |

[a]Polymer supported triphenylphosphine was used.

[b]Diisopropyl azodicarboxylate was used instead of 1,1'-(azodicarbonyl)dipiperidine.

The following oxetane intermediate was prepared via displacement of the corresponding tosyl derivative:

Toluene-4-sulfonic acid 3-hydroxy-oxetan-3-ylmethyl ester (A46)

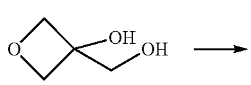

-continued

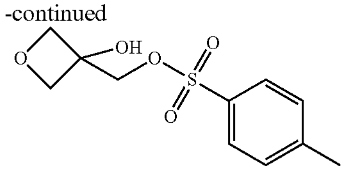

A46

To a stirred solution of 3-(hydroxymethyl)oxetan-3-ol (250 mg, 2.4 mmol) in anhydrous DCM (7 mL) and anhydrous pyridine (7 mL), under $N_2$ at 0° C. was added p-toluenesulfonyl chloride (595 mg, 3.12 mmol). The reaction was maintained at this temperature for 5.5 h. The reaction mixture was evaporated to dryness, partitioned between EtOAc (50 mL) and $H_2O$ (50 mL). The organic phase was separated, washed with 2M HCl (50 mL), satd. aq. $NaHCO_3$ (50 mL). The organic phase was separated (phase separator) and evaporated to dryness. The crude compound was purified by silica gel column chromatography eluting with 30-80% EtOAc/iso-hexane to afford toluene-4-sulfonic acid 3-hydroxy-oxetan-3-ylmethyl ester A46 as a white solid (411 mg, 66%); LC-MS. Rt 2.23 min, AnalpH2_MeOH_4 min(1); (ESI$^+$) m/z 259.3 [M+H]$^+$.

3-[4-(4,4,5,5-Tetramethyl-[1,3,2]dioxaborolan-2-yl)-phenoxymethyl]-oxetan-3-ol (B41)

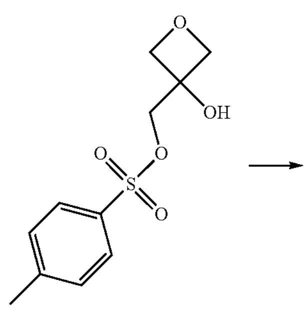

-continued

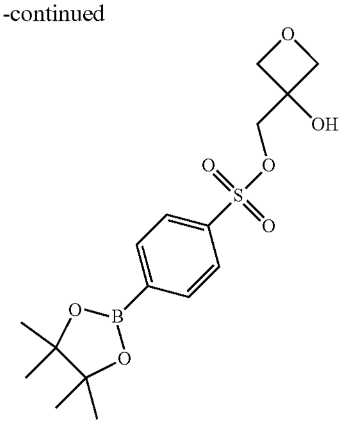

B41

Toluene-4-sulfonic acid 3-hydroxy-oxetan-3-ylmethyl ester (100 mg, 0.39 mmol), 4-hydroxybenzeneboronic ester (102 mg, 0.46 mmol), $K_2CO_3$ (80 mg, 0.58 mmol) and anhydrous DMF (1 mL) were added to a microwave vial and heated thermally at 80° C. for 4 h. The reaction mixture was evaporated to dryness, suspended in DCM (20 mL) and washed with $H_2O$ (20 mL). The organic phase was separated (phase seperator) and evaporated to dryness. The crude compound was purified by silica gel column chromatography eluting with 5-35% EtOAc/iso-hexane to afford 3-[4-(4,4,5,5-tetramethyl-[1,3,2]dioxaborolan-2-yl)-phenoxymethyl]-oxetan-3-ol as a white solid (71 mg, 60%); LC-MS. Rt 2.93 min, AnalpH2_MeOH_4 min(1); (ESI$^+$) m/z 329.3 [M+Na]$^+$; $^1$H NMR (400 MHz, DMSO-$d_6$): δ 7.58 (d, 2H, J=8.2 Hz), 6.94 (d, 2H, J=8.7 Hz), 5.99 (s, 1H), 4.47-4.43 (m, 4H), 4.09 (s, 2H), 1.24 (s, 12H).

The following boronic acids/esters were synthesised in accordance with literature methods:

TABLE 15

| Boronic ester | Cpd # | Reference |
|---|---|---|
| 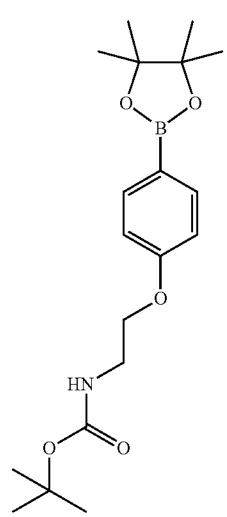 [SMILES: CC(C)(C)OC(=O)NCCOc1ccc(B2OC(C)(C)C(C)(C)O2)cc1] | B42 | WO2014/117090 |

TABLE 15-continued
| Boronic ester | Cpd # | Reference |
|---|---|---|
| 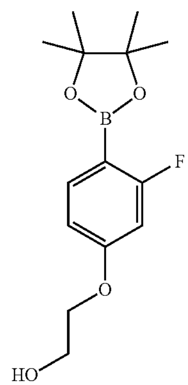 [SMILES: CC1(C)OB(c2ccc(OCCO)cc2F)OC1(C)C] | B43 | WO2015/132228 |
| 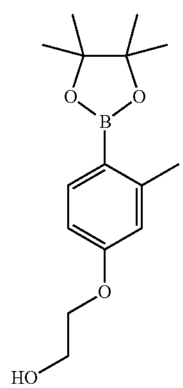 [SMILES: Cc1cc(OCCO)ccc1B1OC(C)(C)C(C)(C)O1] | B44 | EP1679304, 2006, A1 |
| 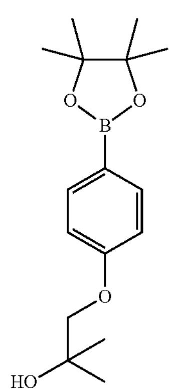 [SMILES: CC(C)(O)COc1ccc(B2OC(C)(C)C(C)(C)O2)cc1] | B45 | US2014/121200 |
| 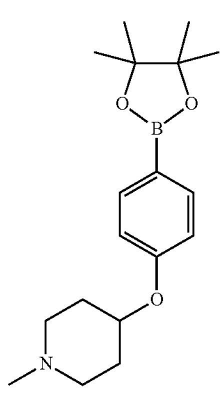 | B46 | Synthesis, 2016, 48, 8, 1226-1234 |

TABLE 15-continued
| Boronic ester | Cpd # | Reference |
|---|---|---|
| 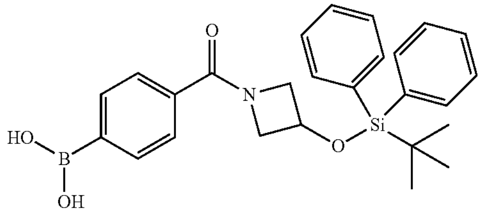 [SMILES: CC(C)(C)[Si](OC1CN(C(=O)c2ccc(B(O)O)cc2)C1)(c1ccccc1)c1ccccc1] | B40 | US2015/99732 |
A number of examples of formula (Ia) were synthesised according to the following route:
Route 1: Scheme 1
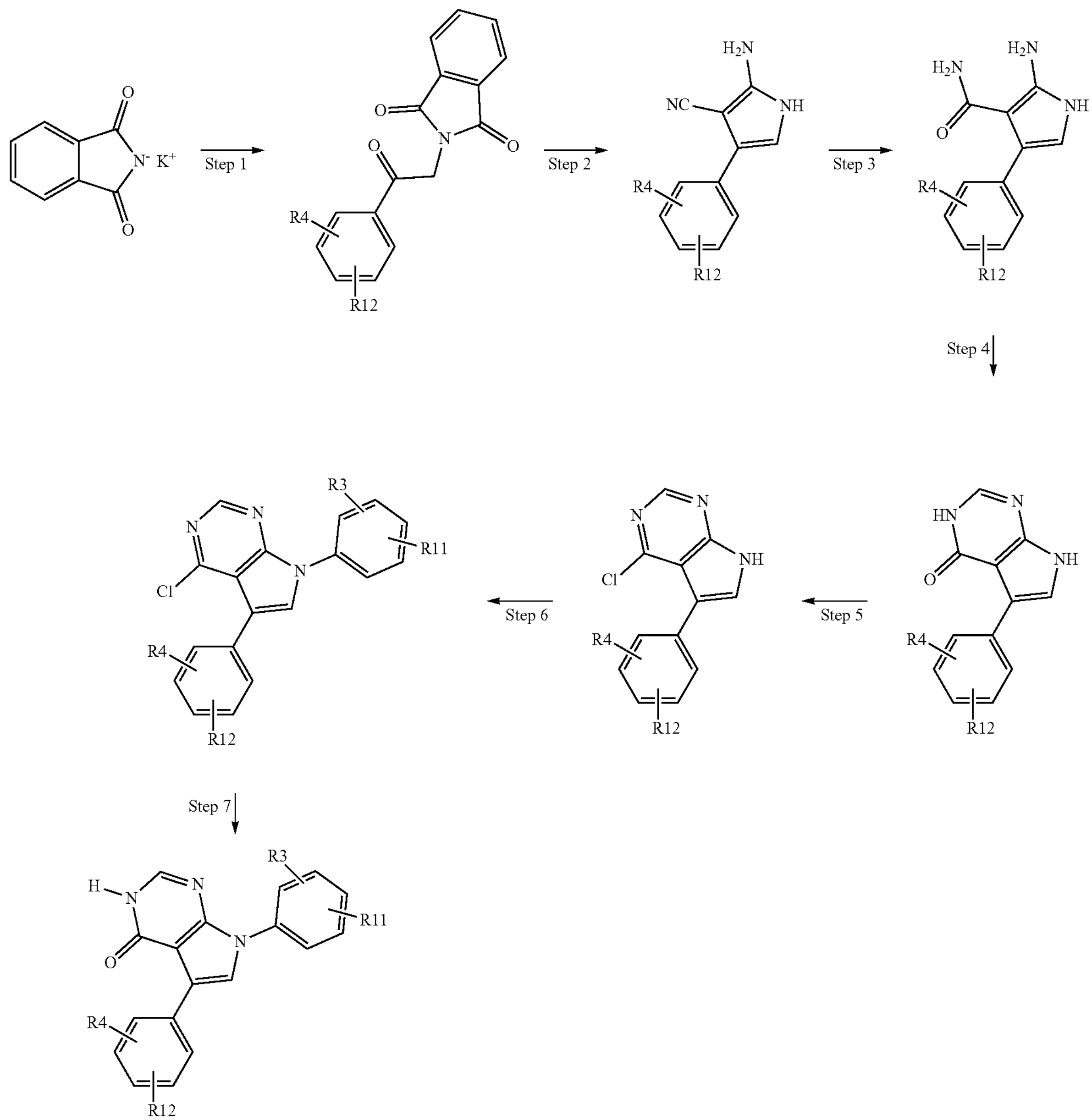

Example Ex-1: 4-(4-Oxo-5-phenyl-3,4-dihydro-pyrrolo[2,3-d]pyrimidin-7-yl)-benzoic acid 2-(2-Oxo-2-phenyl-ethyl)-isoindole-1,3-dione (A16)

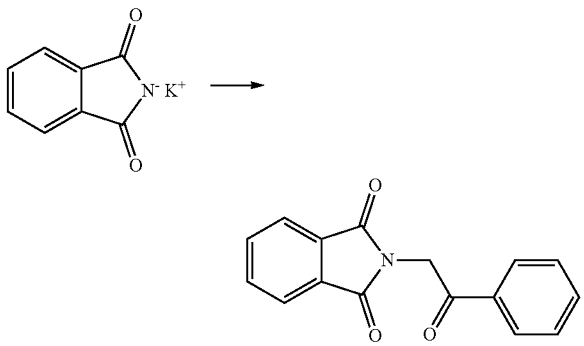

A16

Potassium phthalimide (6.00 g, 32 mmol) and 2-bromo-acetophenone (6.44 g, 32 mmol) in anhydrous DMF (64 mL) was stirred at RT gently until the exothermic reaction ceased. The reaction mixture was heated at 150° C. for 30 min. The reaction mixture was cooled to RT and the resulting solid filtered. The filtrate was poured into $H_2O$ and the resulting solid filtered, washed with $H_2O$ and dried, under vacuum, overnight to afford 2-(2-oxo-2-phenyl-ethyl)-isoindole-1,3-dione as a pale yellow solid (7.30 g, 85%); LC-MS. Rt 2.85 min, AnalpH2_MeOH_4 min; (ESI$^+$) m/z 266.2 $[M+H]^+$.

2-amino-4-phenyl-1H-pyrrole-3-carbonitrile (A17)

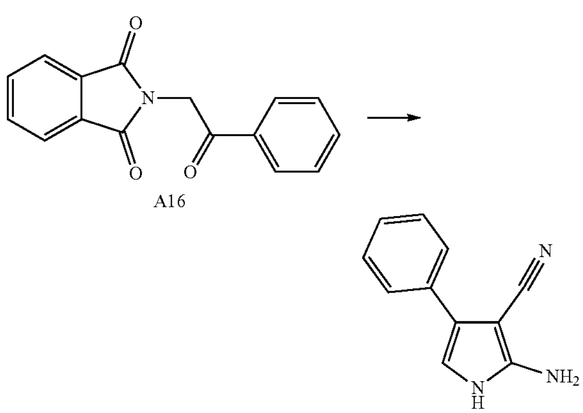

A16 A17

To 2-(2-oxo-2-phenyl-ethyl)-isoindole-1,3-dione (A16) (7.30 g, 27.0 mmol) and malononitrile (2.36 g, 35.6 mmol) in EtOH (55 mL) at 0° C. was added sodium ethoxide (3.75 g, 55.1 mmol) and the reaction was stirred at RT for 30 min and then at 60° C. for 1.5 h. The reaction mixture was cooled to RT and concentrated in vacuo. The residue was quenched with 1% AcOH (aq) (100 mL) to afford a brown precipitate which was filtered and washed with $H_2O$. The crude product was dissolved in MeOH (20 mL) and purified by SCX-2 (50 g) washing with MeOH (2×CV) and the compound eluted from the column with 0.5M $NH_3$/MeOH to afford 2-amino-4-phenyl-1H-pyrrole-3-carbonitrile (A17) as a dark red solid (3.30 g, 65%); LC-MS. Rt 2.47 min, AnalpH2_MeOH_4 min; (ESI$^+$) m/z 184.2 $[M+H]^+$.

2-Amino-4-phenyl-1H-pyrrole-3-carboxylic acid amide (A18)

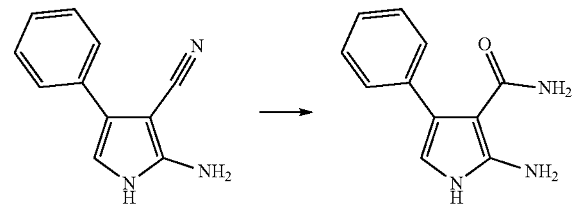

A17 A18

2-Amino-4-phenyl-1H-pyrrole-3-carbonitrile (A17) (670 mg, 3.65 mmol) was dissolved in conc. $H_2SO_4$ (6 mL) and the reaction mixture was heated at 100° C. for 45 min. The reaction mixture was cooled to 0° C. and quenched to pH 7-8 with 2M NaOH (100 mL). The compound was extracted with EtOAc (3×50 mL) and the combined organic layers washed with $H_2O$, dried over $Na_2SO_4$, filtered and the solvent removed in vacuo to afford 2-amino-4-phenyl-1H-pyrrole-3-carboxylic acid amide (A18) as a dark red solid (126 mg, 17%); LC-MS. Rt 2.19 min, AnalpH9_MeOH_4 min; (ESI$^+$) m/z 202.3 $[M+H]^+$.

5-Phenyl-3,7-dihydro-pyrrolo[2,3-d]pyrimidin-4-one (A19)

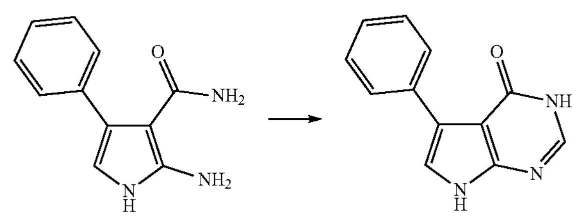

A18 A19

To a solution of 2-amino-4-phenyl-1H-pyrrole-3-carboxylic acid amide (A18) (1.46 g, 7.25 mmol) in DMF (18 mL) was added p-toluene sulfonic acid (41 mg, 0.22 mmol) and triethyl orthoformate (24 mL, 145 mmol) and the solution stirred at RT, under $N_2$ for 1 h. The reaction mixture was evaporated to dryness to afford 5-phenyl-3,7-dihydro-pyrrolo[2,3-d]pyrimidin-4-one (A19) as a dark red solid (1.8 g, quant) which was used in the next step without further purification; LC-MS. Rt 2.31 min, AnalpH2_MeOH_4 min (1); (ESI$^+$) m/z 212.3 $[M+H]^+$.

4-Chloro-5-phenyl-7H-pyrrolo[2,3-d]pyrimidine (A20)

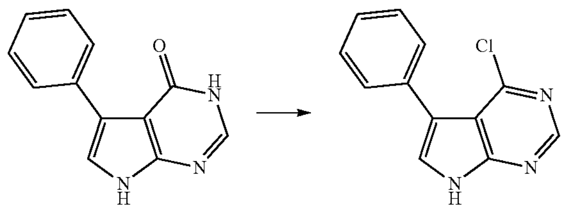

A19 A20

5-Phenyl-3,7-dihydro-pyrrolo[2,3-d]pyrimidin-4-one (A19) (1.53 g, 7.25 mmol) was dissolved in $POCl_3$ (36 mL, 7.2 mmol) and DMF (6.5 mL) and the reaction mixture was heated at 120° C. for 1 h. The reaction mixture was evaporated to obtain a viscous oil. Ice was added to the residue and the residue was placed in an ice-bath. $NH_4OH$ (aq, 30% $NH_3$) was added with continuous stirring and the residue basified to pH10 then extracted with DCM (3×200 mL). The organic layer was passed through a phase separator and evaporated to dryness. A precipitate was observed in both the aqueous layer and phase separation cartridge which was filtered and found to contain the desired product. This precipitate was combined with the evaporated filtrate. The crude compound was purified by silica gel column chromatography eluting with 15%-35% EtOAc/iso-hexane to obtain 4-chloro-5-phenyl-7H-pyrrolo[2,3-d]pyrimidine (A20) as an off-white solid (789 mg, 47%); LC-MS. Rt 3.01 min, AnalpH2_MeOH_4 min(1); ($ESI^+$) m/z 230.3, 232.3 $[M+H]^+$; $^1H$ NMR (400 MHz, DMSO-$d_6$): δ 12.83-12.79 (br s, 1H), 8.63 (s, 1H), 7.79 (s, 1H), 7.55 (m, 2H), 7.44 (m, 2H), 7.36 (m, 1H).

4-(4-Chloro-5-phenyl-pyrrolo[2,3-d]pyrimidin-7-yl)-benzoic acid (CP1)

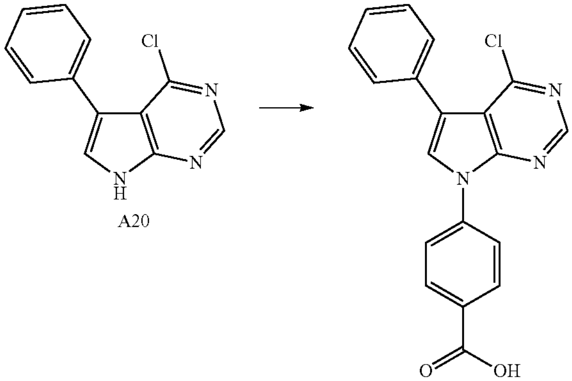

A20

CP1

To 4-chloro-5-phenyl-7H-pyrrolo[2,3-d]pyrimidine (A20) (100 mg, 0.44 mmol), $Cu(OAc)_2$ (198 mg, 1.09 mmol), 4-carboxybenzene boronic acid (181 mg, 1.09 mmol), $NEt_3$ (303 μL, 2.18 mmol) and molecular sieves (4 Å, 1×small spatula) was added to DMF (2.2 mL). The reaction vessel was capped and a needle inserted to allow $O_2$ (air) into the reaction mixture. The reaction mixture was heated at 60° C. for 2 h. Further amounts of $Cu(OAc)_2$ (79 mg, 0.44 mmol), 4-carboxybenzene boronic acid (72 mg, 0.44 mmol) and $NEt_3$ (121 μL, 0.88 mmol) were added and the reaction mixture heated at 60° for a further 1h. The reaction mixture was evaporated to dryness, suspended in DCM (50 mL) and washed with $H_2O$ (50 mL). The combined aqueous/organic layers was filtered and passed through a phase separator. The organic phase was evaporated to dryness, re-dissolved in DCM (2 mL) and passed through a Si-thiol cartridge (2 g), eluting with DCM (2CV), MeOH (2 CV) and the filtrate evaporated in vacuo. The crude compound was purified by reversed phase preparative HPLC-MS to afford 4-(4-chloro-5-phenyl-pyrrolo[2,3-d]pyrimidin-7-yl)-benzoic acid (CP1) as a white solid (21.6 mg, 14%); LC-MS. $R_t$ 3.42 min AnalpH2MeOH_4 min(1); ($ESI^+$) m/z 350.2, 352.23$[M+H]^+$.

The following substituted 4-chloro-5-phenyl pyrrolo[2,3-d]pyrimidine derivatives were prepared from (A20) using analogous procedures used for the synthesis of intermediate CP1 (duration of reactions between 1 and 3h) using commercially available boronic esters/acids:

TABLE 16

| Compound | Cpd # | Analytical Data | Mass, % Yield, State |
|---|---|---|---|
| 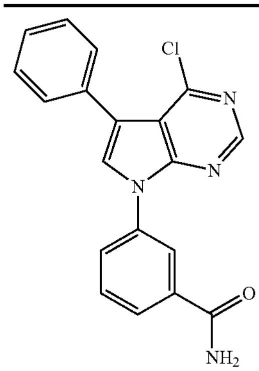 | CP2 | LC-MS. $R_t$ 3.16 min, AnalpH2_MeOH_4 min(1); ($ESI^+$) m/z 349.2, 351.2 $[M + H]^+$. | 19 mg, 12%, white solid |
| 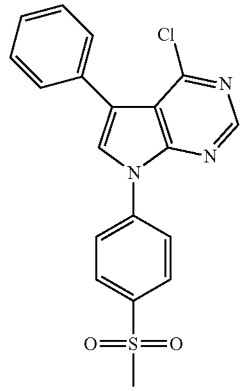 [SMILES: CS(=O)(=O)c1ccc(-n2cc(-c3ccccc3)c3c(Cl)ncnc32)cc1] | CP3 | LC-MS. $R_t$ 3.19 min, AnalpH2_MeOH_4 min(1); ($ESI^+$) m/z 384.1, 386.1 $[M + H]^+$. | 128 mg, 38%, white solid |

TABLE 16-continued

| Compound | Cpd # | Analytical Data | Mass, % Yield, State |
|---|---|---|---|
| 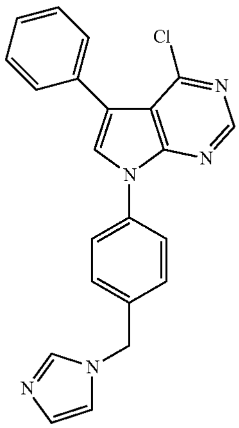 [SMILES: Clc1ncnc2c1c(-c1ccccc1)cn2-c1ccc(Cn2ccnc2)cc1] | CP4 | LC-MS. $R_t$ 2.36 min, AnalpH2_MeOH_4 min; ($ESI^+$) m/z 386.4, 388.4 $[M + H]^+$. | 126 mg, quantitative |

4-(4-Oxo-5-phenyl-3,4-dihydro-pyrrolo[2,3-d]pyrimidin-7-yl)-benzoic acid (Ex-1)

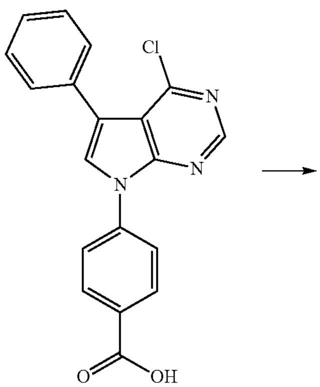

CP-1

-continued

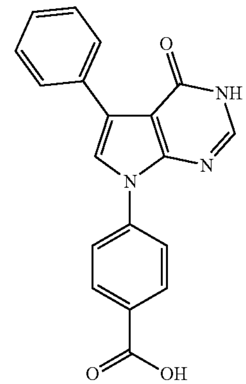

Ex-1

To 4-(4-chloro-5-phenyl-pyrrolo[2,3-d]pyrimidin-7-yl)-benzoic acid (CP1) (21.6 mg, 0.06 mmol) was added NaOAc (10.1 mg, 0.12 mmol) and glacial AcOH (0.12 mL, 0.06 mmol and the reaction mixture was heated at 100° C. overnight. The reaction mixture was diluted with DCM (5 mL) and $H_2O$ (5 mL) and a fine precipitate formed which was collected by filtration. The resulting filtrate was passed through a phase separator. The organic phase was combined with the filtered precipitate and evaporated to dryness. The product was lyophilised from 1:1 $MeCN/H_2O$ to obtain 4-(4-oxo-5-phenyl-3,4-dihydro-pyrrolo[2,3-d]pyrimidin-7-yl)-benzoic acid (Ex-1) as a white solid (20 mg, 100%); LC-MS. Rt 7.52 min, AnalpH2_MeOH_QC_V1(1); ($ESI^+$) m/z 332.2 $[M+H]^+$; $^1H$ NMR (400 MHz, DMSO-$d_6$): δ 13.13 (br s, 1H), 12.28 (br d, J=3.8 Hz, 1H), 8.11 (d, J=8.8 Hz, 2H), 8.04 (d, J=3.8 Hz, 1H), 8.02-7.97 (m, 4H), 7.93 (s, 1H), 7.40 (t, J=7.3 Hz, 2H), 7.28 (tt, J=7.3, 1.3 Hz, 1H).

The following examples were synthesised using analogous procedures to example Ex-1:

TABLE 17

| Compound | Ex. # (Intermediate | Analytical Data | Mass, & Yield, Appearance |
|---|---|---|---|
| 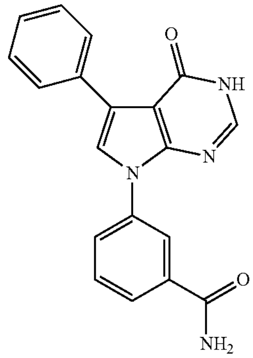 [SMILES: NC(=O)c1cccc(-n2cc(-c3ccccc3)c3c(=O)[nH]cnc32)c1] | Ex-2 (CP2) | LC-MS. $R_t$ 6.92 min, AnalpH2_MeOH_QC_V1(1); ($ESI^+$) m/z 331.2 $[M + H]^+$. | 10 mg, 57%, white solid |

TABLE 17-continued

| Compound | Ex. # (Intermediate | Analytical Data | Mass, & Yield, Appearance |
|---|---|---|---|
| 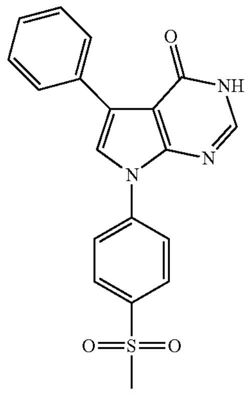 [SMILES: CS(=O)(=O)c1ccc(-n2cc(-c3ccccc3)c3c(=O)[nH]cnc32)cc1] | Ex-3 (CP3) | LC-MS. $R_t$ 6.98 min, AnalpH2_MeOH_QC_V1(1); (ESI$^+$) m/z 366.2 [M + H]$^+$; $^1$H NMR (400 MHz, DMSO-d$_6$): δ 12.39-12.26 (br s, 1H), 8.16 (d, J = 8.8 Hz, 2H), 8.12 (d, J = 8.8 Hz, 2H), 8.06 (s, 1H), 7.99 (dd, J = 8.3, 1.3 Hz, 2H), 7.96 (s, 1H), 7.41 (t, J = 7.3 Hz, 2H), 7.28 (tt, J = 7.3, 1.3 Hz, 1H), 3.31 (s, 3H). | 38 mg, 31%, off-white solid |
| 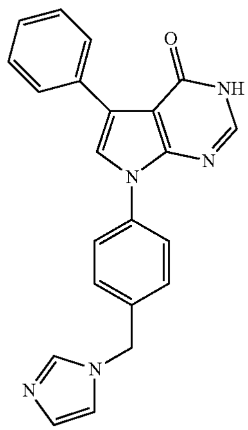 [SMILES: O=c1[nH]cnc2c1c(-c1ccccc1)cn2-c1ccc(Cn2ccnc2)cc1] | Ex-4[a,f] (CP4) | LC-MS. $R_t$ 5.02 min, AnalpH2_MeOH_QC_V1(1); (ESI$^+$) m/z 368.2 [M + H]$^+$; $^1$H NMR (400 MHz, DMSO-d$_6$): δ 12.20-12.13 (br s, 1H), 8.16-8.12 (br s, 1H), 7.98-7.97 (m, 1H), 7.96 (m, 2H), 785-7.80 (br s, 1H), 7.79 (s, 1H), 7.75 (d, J = 8.6 Hz, 2H), 7.44 (d, J = 8.6 Hz, 2H), 7.37 (**t, J = 7.3 Hz, 2H), 7.25 (tt, J = 7.3, 1.3 Hz, 2H), 6.98-6.91 (br s, 1H), 5.28 (s, 2H) | 44 mg, 36%[b], white solid |

[a]Yield calculated from substituted 4-chloro-5-phenyl pyrrolo[2,3-d]pyrimidine derivative.
[f]Isolated as a formate salt A number of amide examples were synthesised from Ex-1:

N-Methyl-4-(4-oxo-5-phenyl-3,4-dihydro-pyrrolo[2,3-d]pyrimidin-7-yl)-benzamide (Ex-5)

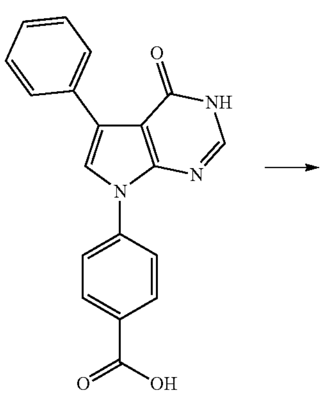

Ex-1

-continued

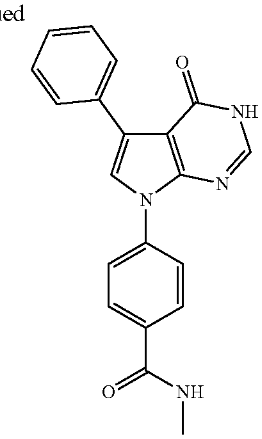

Ex-5

To 4-(4-oxo-5-phenyl-3,4-dihydro-pyrrolo[2,3-d]pyrimidin-7-yl)-benzoic acid (16 mg, 0.05 mmol) and TBTU (16 mg, 0.05 mmol) in dry DMF (0.55 mL) was added 1M DIPEA/DCM and the reaction mixture stirred at RT for 50 min (under $N_2$ balloon). Methylamine hydrochloride (7 mg, 0.1 mmol) in 1 M DIPEA/DCM was added and the reaction mixture stirred at RT overnight. The reaction mixture was passed through a 1 g Si—$NH_2$ cartridge (pre-conditioned with DMF+MeOH) and the column washed with DMF (2×CV) and MeOH (2×CV). The solvent was removed in vacuo. The crude compound was purified by reversed phase preparative HPLC-MS and the product was lyophilised from 1:1 MeCN/$H_2O$ to afford N-Methyl-4-(4-oxo-5-phenyl-3,4-dihydro-pyrrolo[2,3-d]pyrimidin-7-yl)-benz-amide (Ex-5) as an off-white solid (9 mg, 55%); LC-MS. Rt 7.10 min, AnalpH2_MeOH_QC(1); ($ESI^+$) m/z 345.2 $[M+H]^+$; $^1H$ NMR (400 MHz, DMSO-$d_6$): δ 12.27-12.08 (br s, 1H), 8.57 (q, J=4.5 Hz, 1H), 8.03-7.99 (m, 5H), 7.93 (d, J=8.8 Hz, 2H), 7.90 (s, 1H), 7.39 (t, J=7.3 Hz, 2H), 7.28 (tt, J=7.33, 1.3 Hz, 1H), 2.83 (d, J=4.5 Hz, 3H).

The following examples were synthesised using an analogous procedure to Ex-5:

TABLE 18

| Compound | Ex. # | Analytical Data | Mass, % Yield, Appearance |
|---|---|---|---|
| 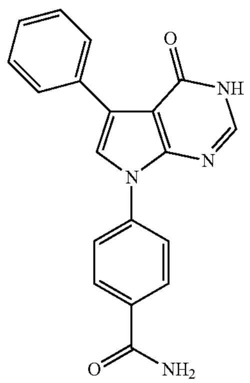 [SMILES: NC(=O)c1ccc(-n2cc(-c3ccccc3)c3c(=O)[nH]cnc32)cc1] | Ex-6 (Ex-1) | LC-MS. $R_t$ 6.86 min, AnalpH2_MeOH_QC_V1(1); ($ESI^+$) m/z 331.2 $[M + H]^+$; $^1H$ NMR (400 MHz, DMSO-$d_6$): δ12.22 (br s, 1H), 8.10 (br s, 1H), 8.05 (d, J = 8.8 Hz, 2H), 8.03 (s, 1H), 8.00 (dd, J = 8.3, 1.3 Hz, 2H), 7.93 (d, J = 8.8 Hz, 2H), 7.91 (s, 1H), 7.52-7.47 (br s, 1H), 7.39 (t, J = 7.3 Hz, 2H), 7.28 (tt, J = 7.3, 1.3 Hz, 1H) | 9 mg, 56%, off-white solid |

A number of examples of formula (Ia) were synthesised according to Route 2a or Route 2b:

Route 2: Scheme 2

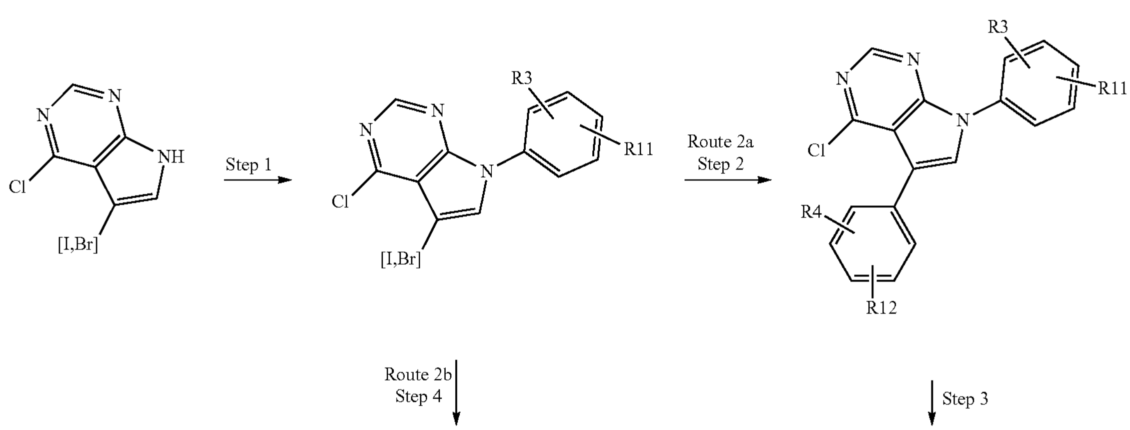

-continued

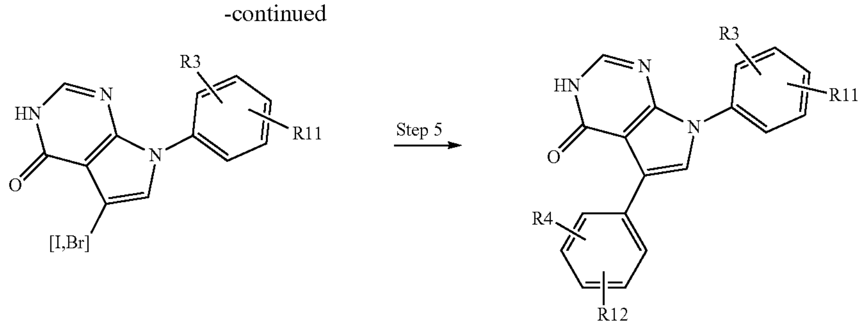

Synthesis of compounds using Route 2 required the synthesis of a number of 4-chloro-5-iodo-7-aryl-7H-pyrrolo[2,3-d]pyrimidine intermediates using Chan Lam chemistry.

4-Chloro-5-iodo-7-phenyl-7H-pyrrolo[2,3-d]pyrimidine (CH1)

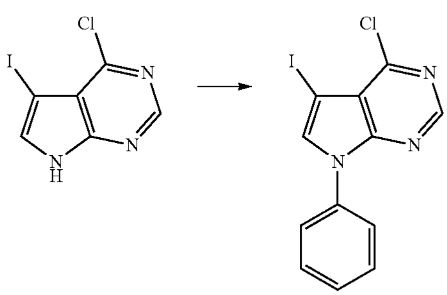

CH1

To a solution of 4-chloro-5-iodo-7H-pyrrolo[2,3-d]pyrimidine (15.0 g, 53.5 mmol) in DMF (100 mL) was added 2-phenyl-1,3,2-dioxoborinone (17.3 g, 107.0 mmol), copper (II) acetate monohydrate (21.35 g, 107.0 mmol) and activated molecular sieves (4 Å, 0.4 g), followed by addition of $NEt_3$ (22.3 mL, 160.4 mmol) and the resulting reaction mixture was stirred at 60° C. for 24 h. The reaction mixture was then cooled to RT and the solvent concentrated in vacuo. The crude residue was dissolved in DCM (300 mL) and quenched with saturated EDTA (aq) (100 mL). The separated aqueous layer was extracted with DCM (2×100 mL) and the combined organic layer was dried over anhydrous $Na_2SO_4$, filtered and concentrated in vacuo. The crude compound was purified by reversed phase preparative HPLC to afford 4-chloro-5-iodo-7-phenyl-7H-pyrrolo[2,3-d]pyrimidine as an off-white solid (6.2 g, 33%); LC-MS. Rt 3.37 min, AnalpH2_MeOH_4 min(1); ($ESI^+$) m/z 356.1, 358.0 $[M+H]^+$; $^1H$ NMR (400 MHz, DMSO-$d_6$): δ 8.70 (s, 1H), 8.39 (s, 1H), 7.81-7.77 (m, 2H), 7.61-7.56 (m, 2H), 7.47 (tt, J=7.8, 1.4 Hz, 1H).

The following intermediates were made using an analogous procedure to intermediate CH1 (reaction duration varied between 5-24 h):

TABLE 19

| Compound | Cpd # | Analytical Data | Mass, % Yield, State |
|---|---|---|---|
| 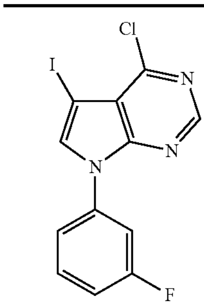 | CH2 | LC-MS. $R_t$ 3.47 min, AnalpH2_MeOH_4min; ($ESI^+$) m/z 374.0, 376.1 $[M + H]^+$. | 1.73 g, 65%, white solid |
| 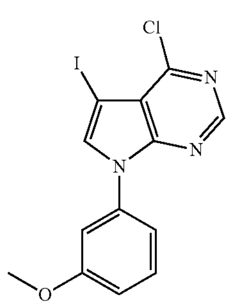 [SMILES: COc1cccc(-n2cc(I)c3c(Cl)ncnc32)c1] | CH3[a] | LC-MS. $R_t$ 3.41 min, AnalpH2_MeOH_4min(1); ($ESI^+$) m/z 386.0, 388.0 $[M + H]^+$; $^1H$ NMR (400 MHz, DMSO-$d_6$): δ 8.70 (s, 1H), 8.40 (s, 1H), 7.48 (**t, J = 7.3 Hz, 1H), 7.41-7.38 (m, 1H), 7.05-7.02 (m, 1H), 3.83 (s, 3H). | 569 mg, 41%, pale brown solid |

TABLE 19-continued

| Compound | Cpd # | Analytical Data | Mass, % Yield, State |
|---|---|---|---|
| 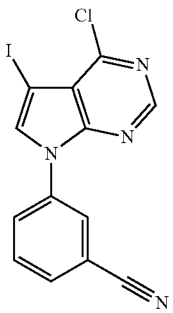 [SMILES: N#Cc1cccc(-n2cc(I)c3c(Cl)ncnc32)c1] | CH12[a,b] | LC-MS. $R_t$ 3.16 min, AnalpH2_MeCN_4min; ($ESI^+$) m/z 381.0 $[M + H]^+$. | 1.98 g, crude, white solid |
| 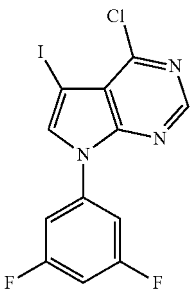 [SMILES: Fc1cc(F)cc(-n2cc(I)c3c(Cl)ncnc32)c1] | CH13[a,b] | LC-MS. $R_t$ 3.18 min, AnalpH2_MeCH_4min; ($ESI^+$) m/z 391.8 $[M + H]^+$. | 2.34 g, 62%, pink solid |

[a]Purified by silica gel chromatography.
[b]Work-up procedure involved passing the reaction mixture through a SCX-2 cartridge and eluting with MeOH, DMF, DCM and EtOAc.

Route 2a, Step 2, Suzuki-Miyaura Coupling 5-(4-Chloro-7-phenyl-7H-pyrrolo[2,3-d]pyrimidin-5-yl)-2-(2-hydroxy-2-methyl-propoxy)-benzonitrile (CP5)

-continued

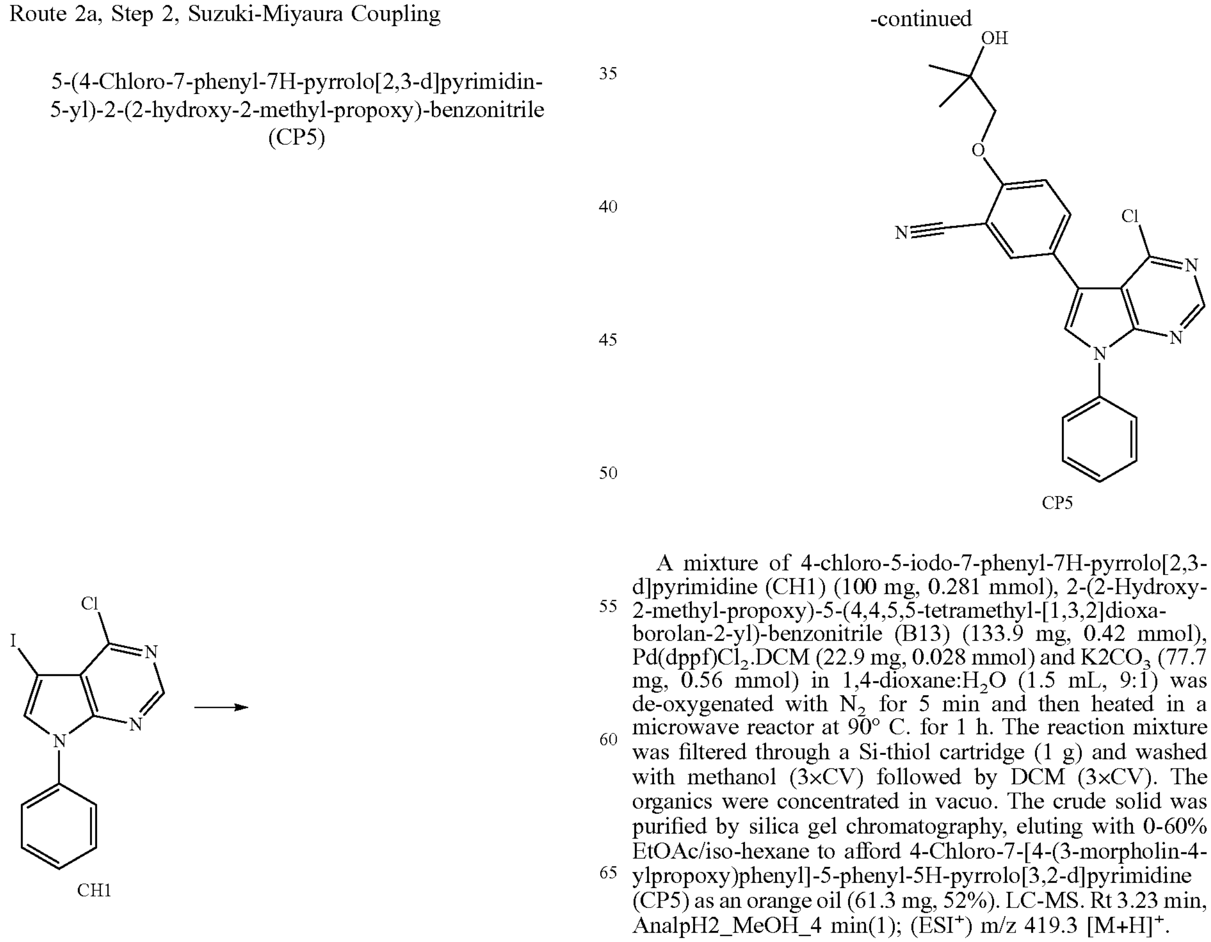

CH1

CP5

A mixture of 4-chloro-5-iodo-7-phenyl-7H-pyrrolo[2,3-d]pyrimidine (CH1) (100 mg, 0.281 mmol), 2-(2-Hydroxy-2-methyl-propoxy)-5-(4,4,5,5-tetramethyl-[1,3,2]dioxa-borolan-2-yl)-benzonitrile (B13) (133.9 mg, 0.42 mmol), Pd(dppf)$Cl_2$.DCM (22.9 mg, 0.028 mmol) and K2$CO_3$ (77.7 mg, 0.56 mmol) in 1,4-dioxane:$H_2O$ (1.5 mL, 9:1) was de-oxygenated with $N_2$ for 5 min and then heated in a microwave reactor at 90° C. for 1 h. The reaction mixture was filtered through a Si-thiol cartridge (1 g) and washed with methanol (3×CV) followed by DCM (3×CV). The organics were concentrated in vacuo. The crude solid was purified by silica gel chromatography, eluting with 0-60% EtOAc/iso-hexane to afford 4-Chloro-7-[4-(3-morpholin-4-ylpropoxy)phenyl]-5-phenyl-5H-pyrrolo[3,2-d]pyrimidine (CP5) as an orange oil (61.3 mg, 52%). LC-MS. Rt 3.23 min, AnalpH2_MeOH_4 min(1); ($ESI^+$) m/z 419.3 $[M+H]^+$.

The following compounds were made using analogous procedures to CP5 (duration of heating varied between 15-90 min: temperature varied between 90-95° C.):

TABLE 20

| Compound | Cpd # (Intermediate used^) | Analytical Data | Mass, % Yield, Appearance |
|---|---|---|---|
| 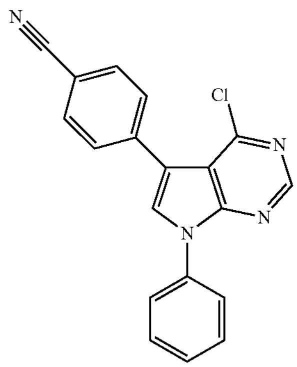 [SMILES: N#Cc1ccc(-c2cn(-c3ccccc3)c3ncnc(Cl)c23)cc1] | CP6 | LC-MS. $R_t$ 8.21 min, AnalpH2_MeOH_QC_V1(1); (ESI$^+$) m/z 331.0, 333.0 $[M + H]^+$. | 51 mg, 37%, off-white solid |
| 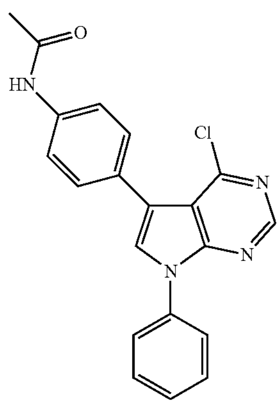 [SMILES: CC(=O)Nc1ccc(-c2cn(-c3ccccc3)c3ncnc(Cl)c23)cc1] | CP7 | LC-MS. $R_t$ 3.17 min, AnalpH2_MeOH_4 min; (ESI$^+$) m/z 363.4, 365.3 $[M + H]^+$. | 15 mg, 30%, orange solid |
| 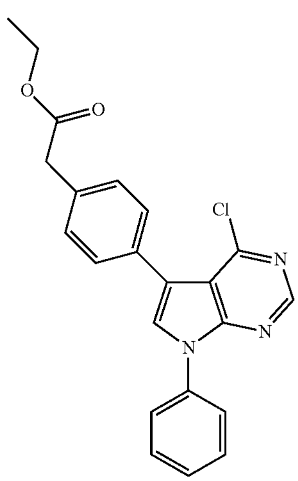 [SMILES: CCOC(=O)Cc1ccc(-c2cn(-c3ccccc3)c3ncnc(Cl)c23)cc1] | CP8 | LC-MS. $R_t$ 3.53 min, AnalpH2_MeOH_4 min(1); (ESI$^+$) m/z 392.2, 394.3 $[M + H]^+$. | 63 mg, 29%, brown oil |

TABLE 20-continued

| Compound | Cpd # (Intermediate used*) | Analytical Data | Mass, % Yield, Appearance |
|---|---|---|---|
| 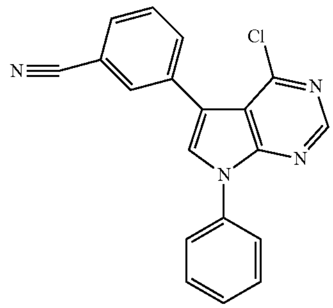 [SMILES: N#Cc1cccc(-c2cn(-c3ccccc3)c3ncnc(Cl)c23)c1] | CP9 | LC-MS. $R_t$ 3.32 min, AnalpH2_MeOH_4 min(1); ($ESI^+$) m/z 331.1, 333.1 $[M + H]^+$. | 93 mg, 67%, off-white solid |
| 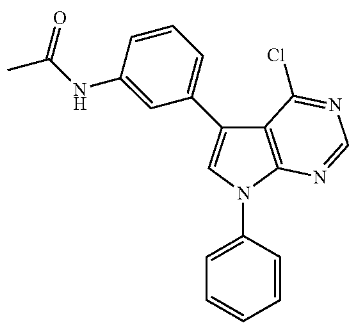 [SMILES: CC(=O)Nc1cccc(-c2cn(-c3ccccc3)c3ncnc(Cl)c23)c1] | CP10 | LC-MS. $R_t$ 3.16 min, AnalpH2_MeOH_4 min(1); ($ESI^+$) m/z 363.2, 365.2 $[M + H]^+$. | 24 mg, 47%, off-white solid |
| 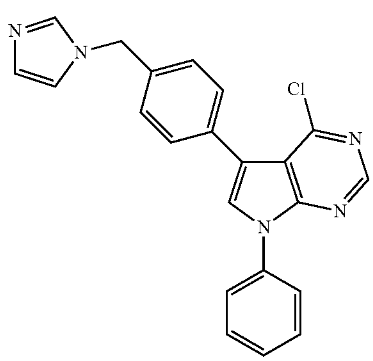 [SMILES: Clc1ncnc2c1c(-c1ccc(Cn3ccnc3)cc1)cn2-c1ccccc1] | CP11 | LC-MS. $R_t$ 2.19 min, AnalpH2_MeOH_4 min(1); ($ESI^+$) m/z 386.4, 388.4 $[M + H]^+$. | Used crude in next step |
| 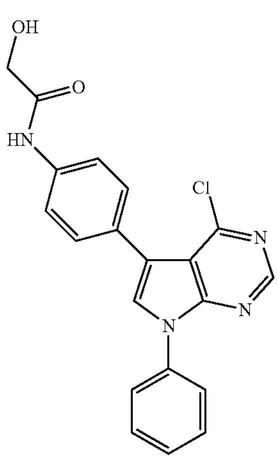 [SMILES: O=C(CO)Nc1ccc(-c2cn(-c3ccccc3)c3ncnc(Cl)c23)cc1] | CP12 (B20) | LC-MS. $R_t$ 3.05 min, AnalpH2_MeOH_4 min(1); ($ESI^+$) m/z 379.3, 381.2 $[M + H]^+$. | Used crude in next step |

TABLE 20-continued
| Compound | Cpd # (Intermediate used^a) | Analytical Data | Mass, % Yield, Appearance |
|---|---|---|---|
| 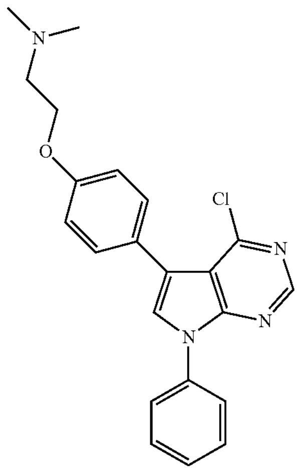 [SMILES: CN(C)CCOc1ccc(-c2cn(-c3ccccc3)c3ncnc(Cl)c23)cc1] | CP13^f (B18) | LC-MS. $R_t$ 2.21 min, AnalpH2_MeOH_4 min(1); ($ESI^+$) m/z 393.3, 395.3 $[M + H]^+$. | 45 mg, 68%, brown solid |
| 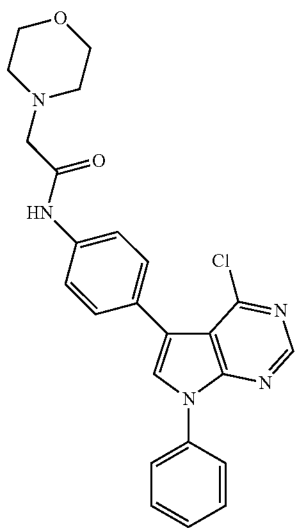 [SMILES: O=C(CN1CCOCC1)Nc1ccc(-c2cn(-c3ccccc3)c3ncnc(Cl)c23)cc1] | CP14 (B21) | LC-MS. $R_t$ 2.49 min, AnalpH2_MeOH_4 min(1); ($ESI^+$) m/z 448.3, 450.3 $[M + H]^+$. | 98 mg, 62%, brown oil |
| 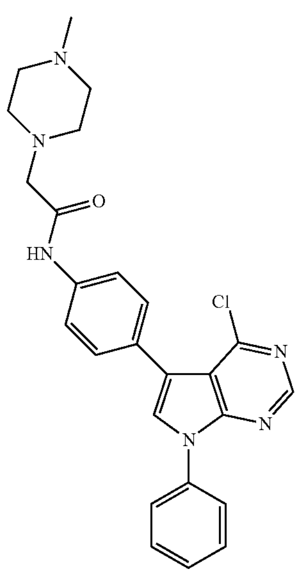 [SMILES: CN1CCN(CC(=O)Nc2ccc(-c3cn(-c4ccccc4)c4ncnc(Cl)c34)cc2)CC1] | CP15 (B19) | LC-MS. $R_t$ 2.29 min, AnalpH2_MeOH_4 min(1); ($ESI^+$) m/z 461.3, 462.2 $[M + H]^+$. | 26 mg, 20%, colourless oil |

TABLE 20-continued
| Compound | Cpd # (Intermediate used[a]) | Analytical Data | Mass, % Yield, Appearance |
|---|---|---|---|
| 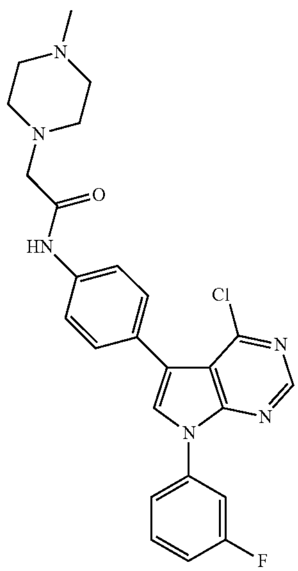 [SMILES: CN1CCN(CC(=O)Nc2ccc(-c3cn(-c4cccc(F)c4)c4ncnc(Cl)c34)cc2)CC1] | CP16 (CH2, B19) | LC-MS. $R_t$ 2.38 min, AnalpH2_MeOH_4 min(1); (ESI$^+$) m/z 479.3, 481.3 $[M + H]^+$. | 11 mg, 9%, yellow oil |
| 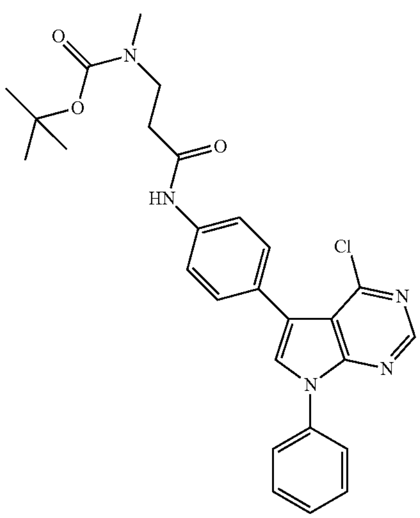 [SMILES: CN(CCC(=O)Nc1ccc(-c2cn(-c3ccccc3)c3ncnc(Cl)c23)cc1)C(=O)OC(C)(C)C] | CP17 (B24) | LC-MS. $R_t$ 2.38 min, AnalpH2_MeOH_4 min(1); (ESI$^+$) m/z 506.2, 508.3 $[M + H]^+$. | 45 mg, 28%, off-white solid |
| 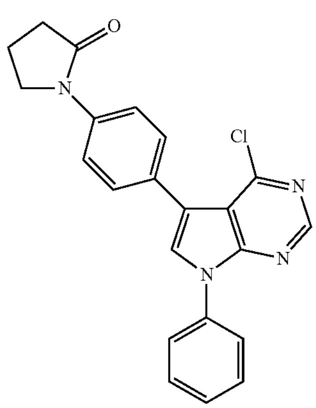 [SMILES: O=C1CCCN1c1ccc(-c2cn(-c3ccccc3)c3ncnc(Cl)c23)cc1] | CP18 (B16) | LC-MS. $R_t$ 3.28 min, AnalpH2_MeOH_4 min(1); (ESI$^+$) m/z 389.3, 391.2 $[M + H]^+$. | 45 mg, 25%, pale yellow solid |

TABLE 20-continued

| Compound | Cpd # (Intermediate used*) | Analytical Data | Mass, % Yield, Appearance |
| --- | --- | --- | --- |
| 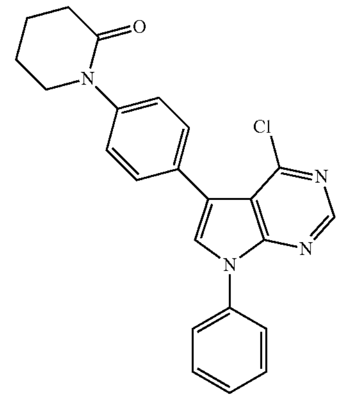 [SMILES: O=C1CCCCN1c1ccc(-c2cn(-c3ccccc3)c3ncnc(Cl)c23)cc1] | CP19 (B17) | LC-MS. $R_t$ 3.37 min, AnalpH2_MeOH_4 min(1); ($ESI^+$) m/z 403.2, 405.2 $[M + H]^+$. | 40 mg, 49%, orange oil |
| 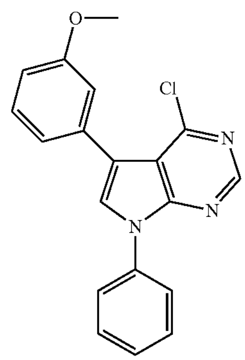 [SMILES: COc1cccc(-c2cn(-c3ccccc3)c3ncnc(Cl)c23)c1] | CP20 | LC-MS. $R_t$ 3.46 min, AnalpH2_MeOH_4 min(1); ($ESI^+$) m/z 336.2, 338.2 $[M + H]^+$. | 36 mg, 49%, off-white solid |
| 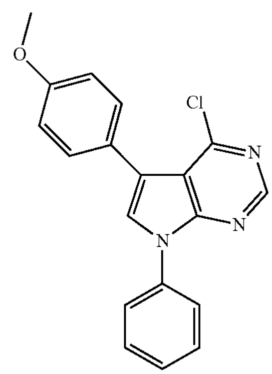 [SMILES: COc1ccc(-c2cn(-c3ccccc3)c3ncnc(Cl)c23)cc1] | CP21 | LC-MS. $R_t$ 3.46 min, AnalpH2_MeOH_4 min(1); ($ESI^+$) m/z 336.2, 338.2 | 11 mg, 15%, white solid |
| 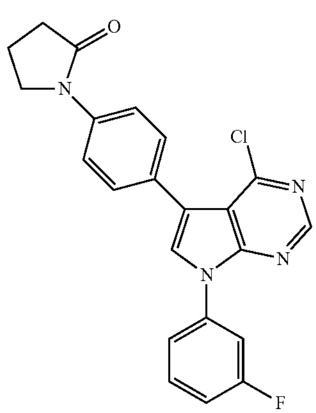 [SMILES: O=C1CCCN1c1ccc(-c2cn(-c3cccc(F)c3)c3ncnc(Cl)c23)cc1] | CP22 (CH2, B16) | LC-MS. $R_t$ 3.34 min, AnalpH2_MeOH_4 min(1); ($ESI^+$) m/z 407.2, 409.3 $[M + H]^+$. | 76 mg, 54%, pale yellow solid |

TABLE 20-continued
| Compound | Cpd # (Intermediate used*) | Analytical Data | Mass, % Yield, Appearance |
|---|---|---|---|
| 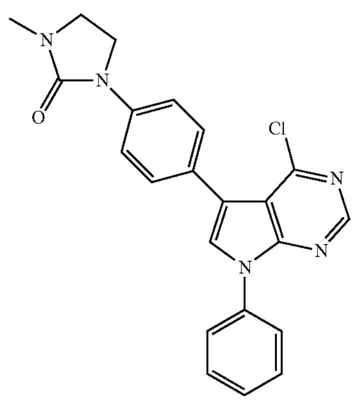 [SMILES: CN1CCN(c2ccc(-c3cn(-c4ccccc4)c4ncnc(Cl)c34)cc2)C1=O] | CP23 (B3) | LC-MS. $R_t$ 3.19 min, AnalpH2_MeOH_4 min(1); ($ESI^+$) m/z 404.3 $[M + H]^+$ | 21 mg, 17%, pale orange solid |
| 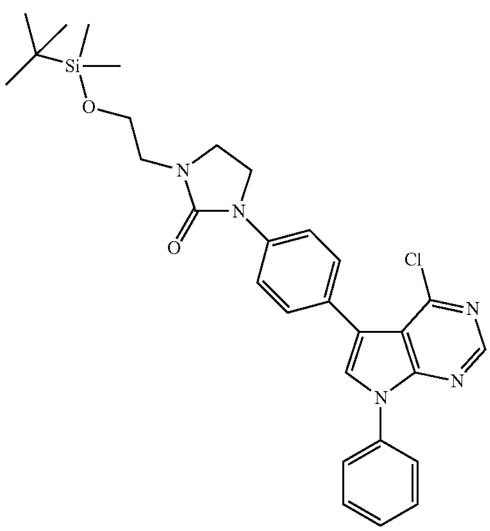 [SMILES: CC(C)(C)[Si](C)(C)OCCN1CCN(c2ccc(-c3cn(-c4ccccc4)c4ncnc(Cl)c34)cc2)C1=O] | CP24 (B2) | LC-MS, $R_t$ 3.87 min, AnalpH2_MeOH_4 min(1); ($ESI^+$) m/z 548.3 $[M + H]^+$ | 73 mg, 22%, white solid |
| 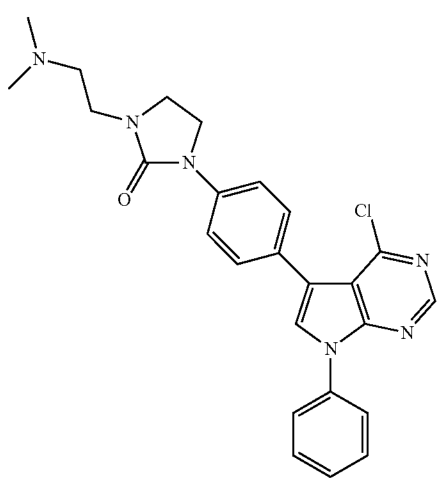 [SMILES: CN(C)CCN1CCN(c2ccc(-c3cn(-c4ccccc4)c4ncnc(Cl)c34)cc2)C1=O] | CP25 (B4) | LC-MS. $R_t$ 2.19 min, AnalpH2_MeOH_4 min(1); ($ESI^+$) m/z 461.3 $[M + H]^+$ | 75 mg, 60% |

TABLE 20-continued

| Compound | Cpd # (Intermediate used*) | Analytical Data | Mass, % Yield, Appearance |
|---|---|---|---|
| 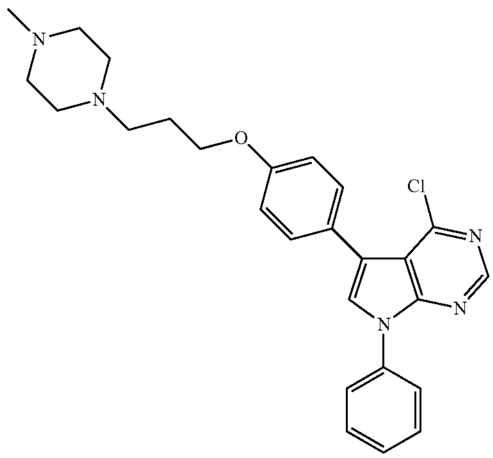 [SMILES: CN1CCN(CCCOc2ccc(-c3cn(-c4ccccc4)c4ncnc(Cl)c34)cc2)CC1] | CP26 (B5) | LC-MS. $R_t$ 2.19 min, AnalpH2_MeOH_4 min(1); ($ESI^+$) m/z 461.3 $[M + H]^+$ | 66 mg, 52%, brown solid |
| 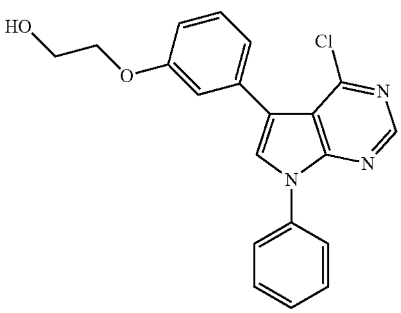 [SMILES: OCCOc1cccc(-c2cn(-c3ccccc3)c3ncnc(Cl)c23)c1] | CP27 | LC-MS. $R_t$ 3.16 min, AnalpH2_MeOH_4 min(1); ($ESI^+$) m/z 366.2 $[M + H]^+$. | 75 mg, 73%, off-white solid |
| 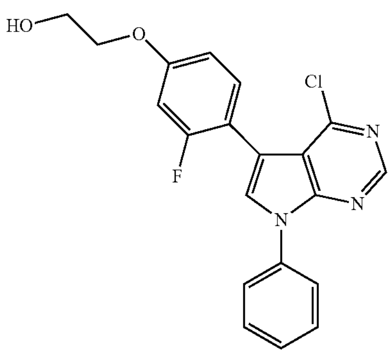 [SMILES: OCCOc1ccc(-c2cn(-c3ccccc3)c3ncnc(Cl)c23)c(F)c1] | CP28 (B43) | LC-MS. $R_t$ 3.20 min, AnalpH2_MeOH_4 min(1); ($ESI^+$) m/z 384.3 $[M + H]^+$. | 32 mg, 25%, orange oil |
| 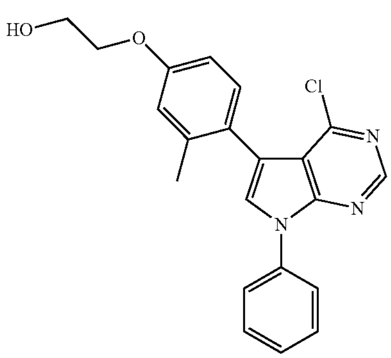 [SMILES: Cc1cc(OCCO)ccc1-c1cn(-c2ccccc2)c2ncnc(Cl)c12] | CP29 (B44) | LC-MS. $R_t$ 3.25 min, AnalpH2_MeOH_4 min(1); ($ESI^+$) m/z 380.3 $[M + H]^+$. | 22 mg, 17%, orange oil |

TABLE 20-continued
| Compound | Cpd # (Intermediate used*) | Analytical Data | Mass, % Yield, Appearance |
|---|---|---|---|
| 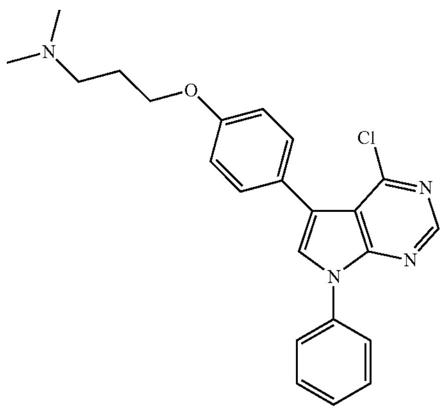 [SMILES: CN(C)CCCOc1ccc(-c2cn(-c3ccccc3)c3ncnc(Cl)c23)cc1] | CP30 | LC-MS. $R_t$ 2.36 min, AnalpH2_MeOH_4 min(1); ($ESI^+$) m/z 407.3 $[M + H]^+$. | 55 mg, 53%, yellow solid |
| 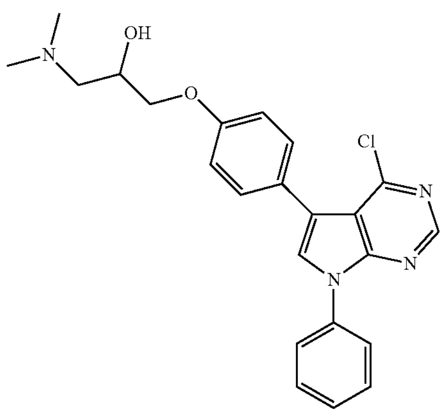 [SMILES: CN(C)CC(O)COc1ccc(-c2cn(-c3ccccc3)c3ncnc(Cl)c23)cc1] | CP31 (B28) | LC-MS. $R_t$ 2.17 min, AnalpH2_MeOH_4 min(1); ($ESI^+$) m/z 423.1 $[M + H]^+$. | 66 mg, 37% off-white solid |
| 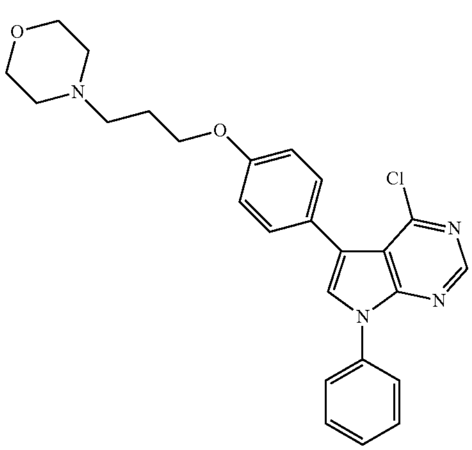 [SMILES: Clc1ncnc2c1c(-c1ccc(OCCCN3CCOCC3)cc1)cn2-c1ccccc1] | CP32 | LC-MS. $R_t$ 2.33 min, AnalpH2_MeOH_4 min(1); ($ESI^+$) m/z 449.3 $[M + H]^+$. | 42 mg, 33%, orange oil |

TABLE 20-continued
| Compound | Cpd # (Intermediate used[a]) | Analytical Data | Mass, % Yield, Appearance |
|---|---|---|---|
| 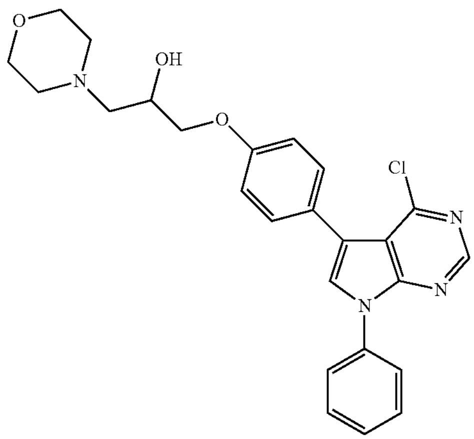 [SMILES: OC(COc1ccc(-c2cn(-c3ccccc3)c3ncnc(Cl)c23)cc1)CN1CCOCC1] | CP33[f] (B27) | LC-MS. $R_t$ 2.19 min, AnalpH2_MeOH_4 min(1); ($ESI^+$) m/z 465.3 $[M + H]^+$. | 573 mg, 20%, orange oil |
| 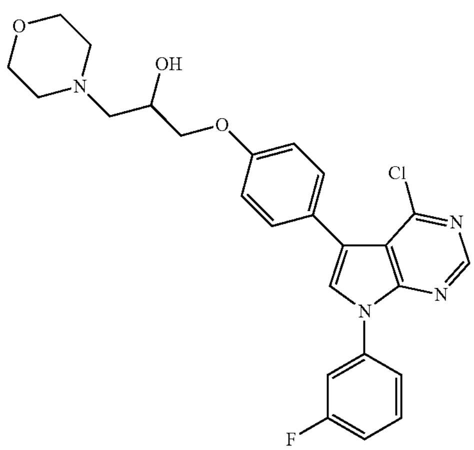 [SMILES: OC(COc1ccc(-c2cn(-c3cccc(F)c3)c3ncnc(Cl)c23)cc1)CN1CCOCC1] | CP34[f] (CH2, B27) | LC-MS. $R_t$ 2.31 min, AnalpH2_MeOH_4 min(1); ($ESI^+$) m/z 483.2 $[M + H]^+$. | 49 mg, 31%, orange oil |
| 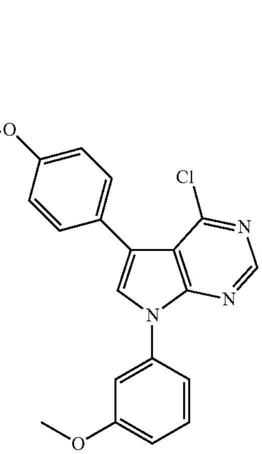 | CP35[f] (CH3, B27) | LC-MS. $R_t$ 2.28 min, AnalpH2_MeOH_4 min(1); ($ESI^+$) m/z 495.3 $[M + H]^+$. | 22 mg, 16%, orange oil |

TABLE 20-continued
| Compound | Cpd # (Intermediate used[a]) | Analytical Data | Mass, % Yield, Appearance |
|---|---|---|---|
| 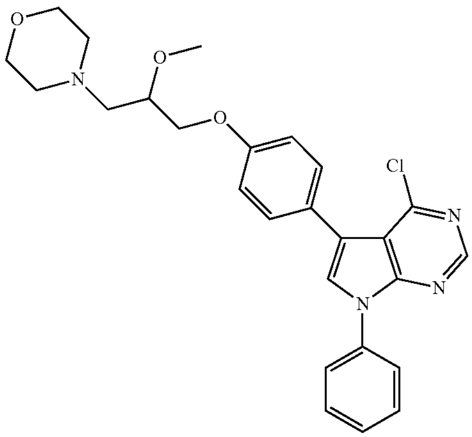 [SMILES: COC(COc1ccc(-c2cn(-c3ccccc3)c3ncnc(Cl)c23)cc1)CN1CCOCC1] | CP36[f] (B6) | LC-MS. $R_t$ 2.38 min, AnalpH2_MeOH_4 min(1); ($ESI^+$) m/z 479.3 $[M + H]^+$. | 29 mg, 20%, orange oil |
| 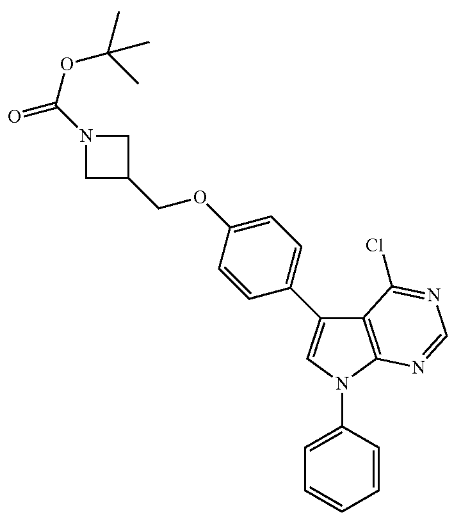 [SMILES: CC(C)(C)OC(=O)N1CC(COc2ccc(-c3cn(-c4ccccc4)c4ncnc(Cl)c34)cc2)C1] | CP37[a] (B37) | LC-MS. $R_t$ 3.70 min, AnalpH2_MeOH_4 min(1); ($ESI^+$) m/z 491.1 $[M + H]^+$. | 81 mg, 53%, yellow gum |
| 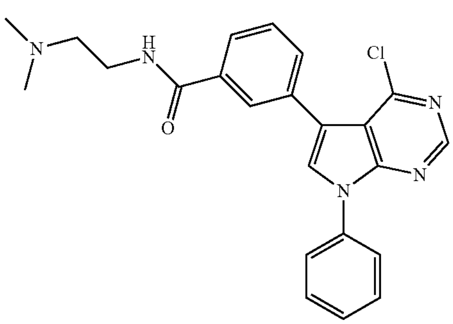 [SMILES: CN(C)CCNC(=O)c1cccc(-c2cn(-c3ccccc3)c3ncnc(Cl)c23)c1] | CP38 (B26) | LC-MS. $R_t$ 2.26 min, AnalpH2_MeOH_4 min(1); ($ESI^+$) m/z 420.2 $[M + H]^+$ | 35 mg, 40% |

TABLE 20-continued
| Compound | Cpd # (Intermediate used*) | Analytical Data | Mass, % Yield, Appearance |
|---|---|---|---|
| 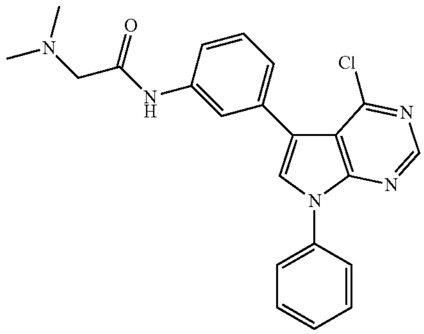 [SMILES: CN(C)CC(=O)Nc1cccc(-c2cn(-c3ccccc3)c3ncnc(Cl)c23)c1] | CP39 (B25) | LC-MS. $R_t$ 2.25 min, AnalpH2_MeOH_4 min(1); (ESI+) m/z 406.3 [M + H]+ | 46 mg, 40%, yellow wax |
| 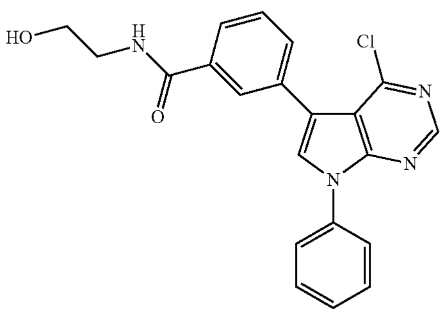 [SMILES: O=C(NCCO)c1cccc(-c2cn(-c3ccccc3)c3ncnc(Cl)c23)c1] | CP40 | LC-MS. $R_t$ 3.03 min, AnalpH2_MeOH_4 min(1); (ESI+) m/z 393.3 [M + H]+ | 87 mg, 79% |
| 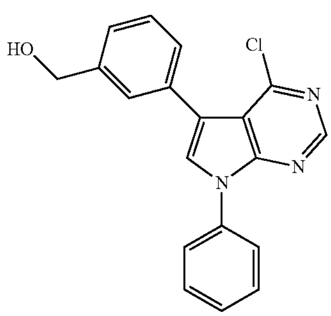 [SMILES: OCc1cccc(-c2cn(-c3ccccc3)c3ncnc(Cl)c23)c1] | CP41 | LC-MS. $R_t$ 3.54 min, AnalpH2_MeOH_4 min(1); (ESI+) m/z 336.3 [M + H]+ | 20 mg, 21%, yellow oil |
| 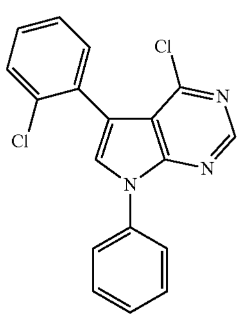 [SMILES: Clc1ccccc1-c1cn(-c2ccccc2)c2ncnc(Cl)c12] | CP42 | LC-MS. $R_t$ 3.46 min, AnalpH2_MeOH_4 min(1); (ESI+) m/z 340.1 [M + H]+. | 71 mg, 74%, off-white solid |

TABLE 20-continued
| Compound | Cpd # (Intermediate used^a) | Analytical Data | Mass, % Yield, Appearance |
| --- | --- | --- | --- |
| 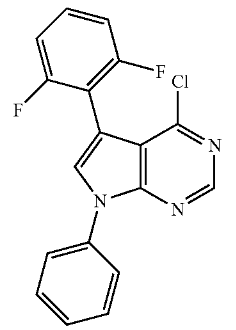 [SMILES: Fc1cccc(F)c1-c1cn(-c2ccccc2)c2ncnc(Cl)c12] | CP43[b] | LC-MS. $R_t$ 3.37 min, AnalpH2_MeOH_4 min(1); (ESI$^+$) m/z 342.1 $[M + H]^+$. | 71 mg, 75%, pale yellow solid |
| 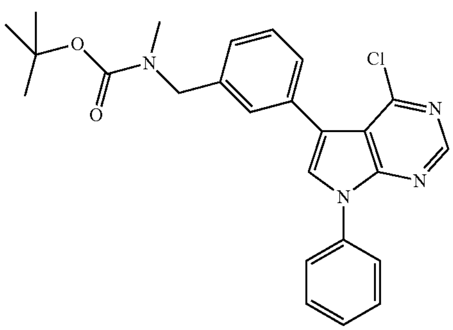 [SMILES: CN(Cc1cccc(-c2cn(-c3ccccc3)c3ncnc(Cl)c23)c1)C(=O)OC(C)(C)C] | CP44 | LC-MS. $R_t$ 3.58 min, AnalpH2_MeOH_4 min(1); (ESI$^+$) m/z 449.3 $[M + H]^+$. | 75 mg, 59%, off-white solid |
| 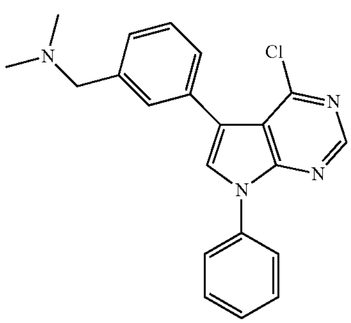 [SMILES: CN(C)Cc1cccc(-c2cn(-c3ccccc3)c3ncnc(Cl)c23)c1] | CP45[f] | LC-MS. $R_t$ 2.06 min, AnalpH2_MeOH_4 min(1); (ESI$^+$) m/z 363.2 $[M + H]^+$ | 30 mg, 29% |
| 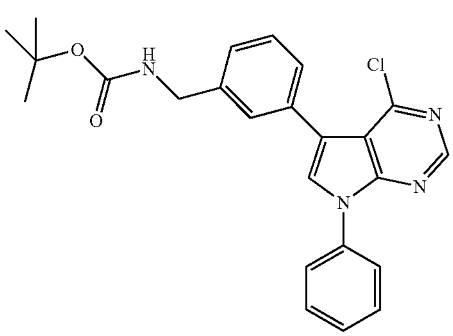 [SMILES: CC(C)(C)OC(=O)NCc1cccc(-c2cn(-c3ccccc3)c3ncnc(Cl)c23)c1] | CP46 | LC-MS. $R_t$ 3.44 min, AnalpH2_MeOH_4 min(1); (ESI$^+$) m/z 435.3 $[M + H]^+$ | 26 mg, 21% |

TABLE 20-continued
| Compound | Cpd # (Intermediate used[a]) | Analytical Data | Mass, % Yield, Appearance |
|---|---|---|---|
| 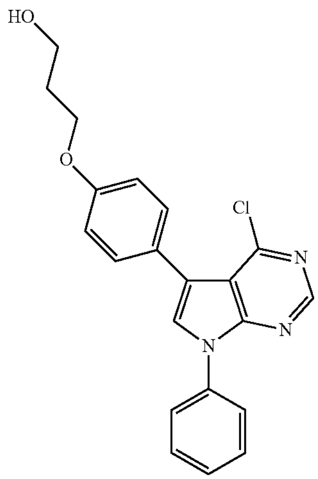 [SMILES: OCCCOc1ccc(-c2cn(-c3ccccc3)c3ncnc(Cl)c23)cc1] | CP47 | LC-MS. $R_t$ 3.24 min, AnalpH2_MeOH_4 min(1); ($ESI^+$) m/z 380.2 $[M + H]^+$. | 210 mg, quant, brown gum |
| 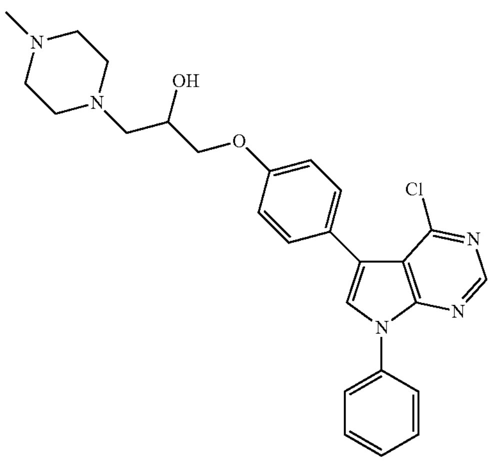 [SMILES: CN1CCN(CC(O)COc2ccc(-c3cn(-c4ccccc4)c4ncnc(Cl)c34)cc2)CC1] | CP48[f] (B29) | LC-MS. $R_t$ 2.24 min, AnalpH2_MeOH_4 min(1); ($ESI^+$) m/z 478.4 $[M + H]^+$. | 35 mg, 29%, pale yellow solid |
| 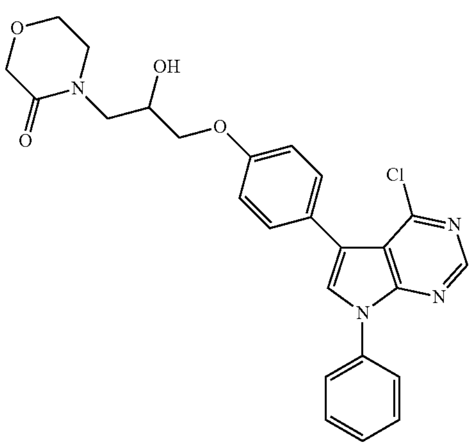 [SMILES: O=C1COCCN1CC(O)COc1ccc(-c2cn(-c3ccccc3)c3ncnc(Cl)c23)cc1] | CP49 (B7) | LC-MS. $R_t$ 3.16 min, AnalpH2_MeOH_4 min(1); ($ESI^+$) m/z 479.2 $[M + H]^+$. | 16 mg, 11% light brown oil |

TABLE 20-continued
| Compound | Cpd # (Intermediate used[a]) | Analytical Data | Mass, % Yield, Appearance |
| --- | --- | --- | --- |
| 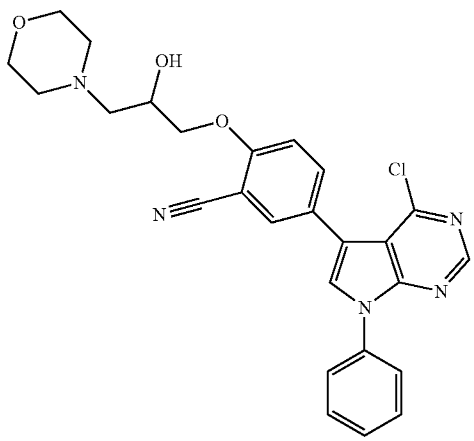 [SMILES: N#Cc1cc(-c2cn(-c3ccccc3)c3ncnc(Cl)c23)ccc1OCC(O)CN1CCOCC1] | CP50 (B31) | LC-MS. $R_t$ 2.41 min, AnalpH2_MeOH_4 min(1); $(ESI^+)$ m/z 490.3 $[M + H]^+$. | 77 mg, 59%, yellow oil |
| 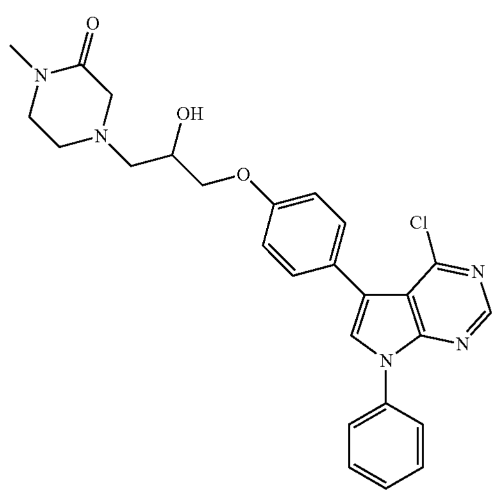 [SMILES: CN1CCN(CC(O)COc2ccc(-c3cn(-c4ccccc4)c4ncnc(Cl)c34)cc2)CC1=O] | CP51[f] (B30) | LC-MS. $R_t$ 2.88 min, AnalpH2_MeOH_4 min(1); $(ESI^+)$ m/z 492.3 $[M + H]^+$. | 38 mg, 21%, brown oil |
| 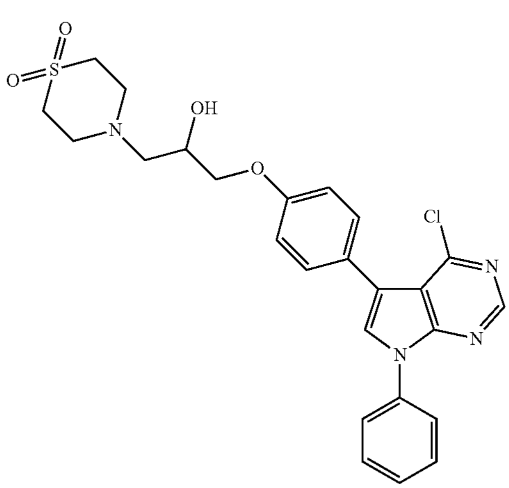 [SMILES: O=S1(=O)CCN(CC(O)COc2ccc(-c3cn(-c4ccccc4)c4ncnc(Cl)c34)cc2)CC1] | CP52[f] (B34) | LC-MS. $R_t$ 3.14 min, AnalpH2_MeOH_4 min(1); $(ESI^+)$ m/z 513.2 $[M + H]^+$. | 15 mg, 8%, brown oil |

TABLE 20-continued
| Compound | Cpd # (Intermediate used*) | Analytical Data | Mass, % Yield, Appearance |
| --- | --- | --- | --- |
| 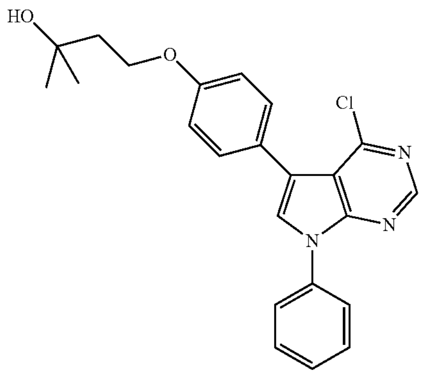 [SMILES: CC(C)(O)CCOc1ccc(-c2cn(-c3ccccc3)c3ncnc(Cl)c23)cc1] | CP53 (B10) | LC-MS. $R_t$ 3.43 min, AnalpH2_MeOH_4 min(1); ($ESI^+$) m/z 408.3 $[M + H]^+$. | 51 mg, 44%, yellow oil |
| 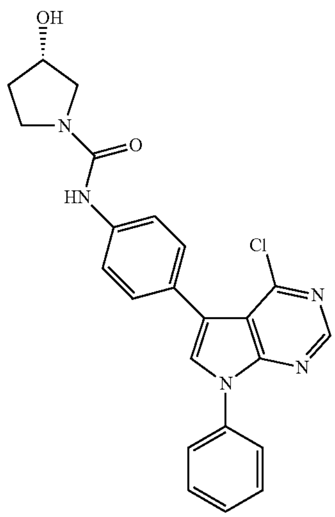 [SMILES: O=C(Nc1ccc(-c2cn(-c3ccccc3)c3ncnc(Cl)c23)cc1)N1CC[C@H](O)C1] | CP54 (B35) | LC-MS. $R_t$ 2.96 min, AnalpH2_MeOH_4 min(1); ($ESI^+$) m/z 434.3 $[M + H]^+$. | 20 mg, 17%, brown oil |
| 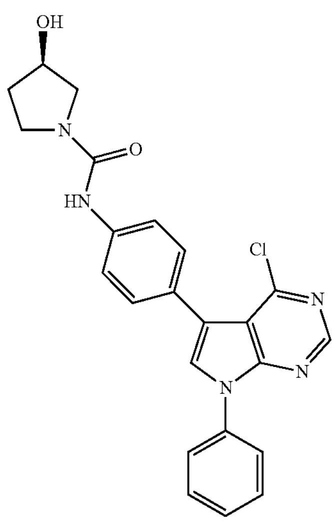 [SMILES: O=C(Nc1ccc(-c2cn(-c3ccccc3)c3ncnc(Cl)c23)cc1)N1CC[C@@H](O)C1] | CP55 (B36) | LC-MS. $R_t$ 2.96 min, AnalpH2_MeOH_4 min(1); ($ESI^+$) m/z 434.3 $[M + H]^+$. | 19 mg, 13%, light brown solid |

TABLE 20-continued
| Compound | Cpd # (Intermediate used*) | Analytical Data | Mass, % Yield, Appearance |
|---|---|---|---|
| 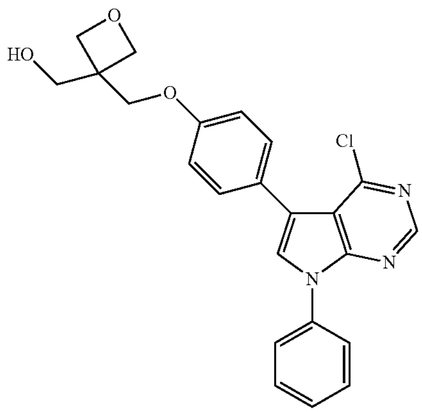 [SMILES: OCC1(COc2ccc(-c3cn(-c4ccccc4)c4ncnc(Cl)c34)cc2)COC1] | CP56 (B9) | LC-MS. $R_t$ 3.18 min, AnalpH2_MeOH_4 min(1); ($ESI^+$) m/z 422.2 $[M + H]^+$. | 61 mg, 52%, Yellow oil |
| 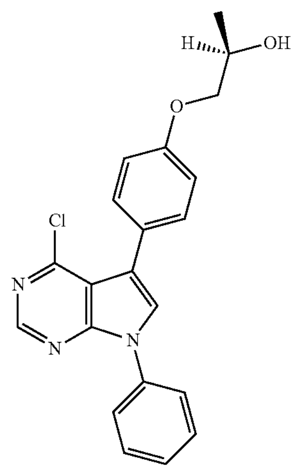 [SMILES: C[C@@H](O)COc1ccc(-c2cn(-c3ccccc3)c3ncnc(Cl)c23)cc1] | CP57 (B14) | LC-MS. $R_t$ 3.40 min, AnalpH2_MeOH_4 min(1); ($ESI^+$) m/z 380.3 $[M + H]^+$ | 55 mg, 45%, yellow oil |
| 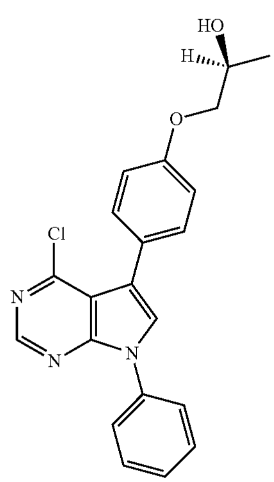 [SMILES: C[C@H](O)COc1ccc(-c2cn(-c3ccccc3)c3ncnc(Cl)c23)cc1] | CP58 (B15) | LC-MS. $R_t$ 3.26 min, AnalpH2_MeOH_4 min(1); ($ESI^+$) m/z 380.3 $[M + H]^+$ | 35.8 mg, 29% yellow oil |

TABLE 20-continued

| Compound | Cpd # (Intermediate used*) | Analytical Data | Mass, % Yield, Appearance |
|---|---|---|---|
| 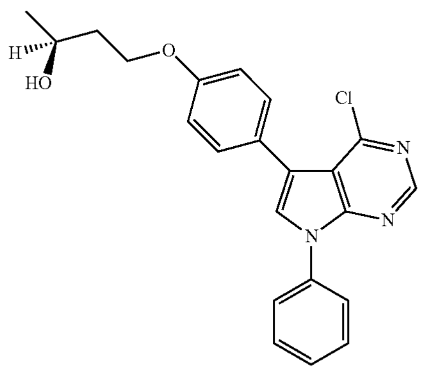 [SMILES: C[C@H](O)CCOc1ccc(-c2cn(-c3ccccc3)c3ncnc(Cl)c23)cc1] | CP72 (B48) | LC-MS. $R_t$ 3.36 min, AnalpH2_MeOH_4 min(1); ($ESI^+$) m/z 394.4 $[M + H]^+$ | 42 mg, 33%, yellow oil |
| 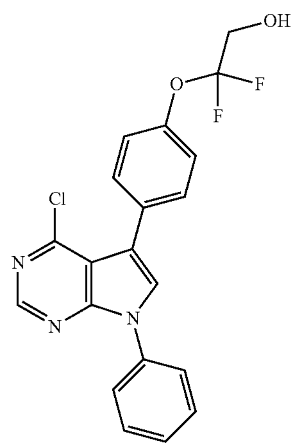 [SMILES: OCC(F)(F)Oc1ccc(-c2cn(-c3ccccc3)c3ncnc(Cl)c23)cc1] | CP73 (B49) | LC-MS. $R_t$ 3.24 min, AnalpH2_MeOH_4 min(1); ($ESI^+$) m/z 402.2 $[M + H]^+$ | 118 mg, 41% pale yellow oil |
| 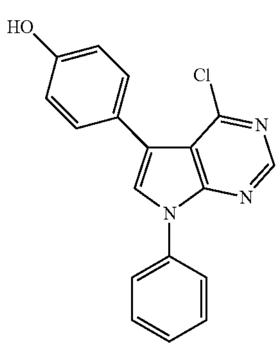 [SMILES: Oc1ccc(-c2cn(-c3ccccc3)c3ncnc(Cl)c23)cc1] | CP74 | LC-MS. $R_t$ 3.22 min, AnalpH2_MeOH_4 min(1); ($ESI^+$) m/z 322.0, 324.0 $[M + H]^+$ | 87 mg, 26%, pale yellow solid |

*Commercial starting material of CH1 used unless otherwise stated.

[a]Heated at 90° C. for 1 h then Pd($d^t$Bupf)$Cl_2$ added and heated for 230 mins;

[b]2,6-difluorophenylboronic acid (1.5 eq), $(tBu_3P)_2Pd$ (0.2 eq), DIPEA (2 eq), 1,4-dioxane:$H_2O$ (9:1).

[f]Isolated as a formate salt.

Route 2a, Step 2, Suzuki-Miyaura Coupling with Addition of $NEt_3$

1-[2-(tert-Butyl-dimethyl-silanyloxy)-ethyl]-3-[4-(4-chloro-7-phenyl-7H-pyrrolo[2,3-d]pyrimidin-5-yl)-phenyl]-imidazolidin-2-one (CP59)

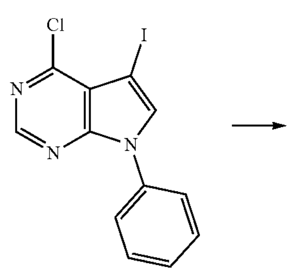

-continued

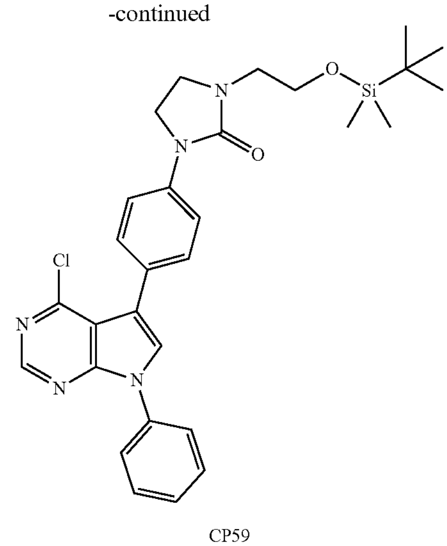

CP59

A mixture of 4-chloro-5-iodo-7-phenyl-7H-pyrrolo[2,3-d]pyrimidine (CH) (80 mg, 0.225 mmol), 1-[2-(tert-Butyl-dimethyl-silanyloxy)-ethyl]-3-[4-(4,4,5,5-tetramethyl-[1,3,2]dioxabolan-2-yl)-phenyl]-imidazolidin-2-one (B2) (151 mg, 0.338 mmol), Pd(dppf)$C_{12}$.DCM (9.2 mg, 0.011 mmol), K2$CO_3$ (62 mg, 0.450 mmol), $NEt_3$ (47 μL, 0.338 mmol) in 1,4-dioxane:$H_2O$ (2 mL, 4:1) was de-oxygenated with nitrogen for 10 min then heated in a microwave at 90° C. for 30 min. The mixture was filtered through celite, with further methanol washing, then concentrated in vacuo. The crude material was partitioned between DCM and water, passed through a phase separator, concentrated in vacuo then purified by silica gel chromatography, eluting with 0-100% EtOAc/iso-hexane. The material obtained was further purified by silica gel chromatography, eluting with 0-100% $Et_2O$/iso-hexane, to afford 1-[2-(tert-butyl-dimethyl-silanyloxy)-ethyl]-3-[4-(4-chloro-7-phenyl-7H-pyrrolo[2,3-d]pyrimidin-5-yl)-phenyl]-imidazolidin-2-one (CP5) (53 mg, 43%); LC-MS. Rt 3.86 min, AnalpH2_MeOH_4 min(1); ($ESI^+$) m/z 548.3 $[M+H]^+$.

The following compound were synthesised using an analogous procedure to CP59:

TABLE 21

| Compound | Cpd # (Intermediate used) | Analytical Data | Mass, % Yield, state |
|---|---|---|---|
| 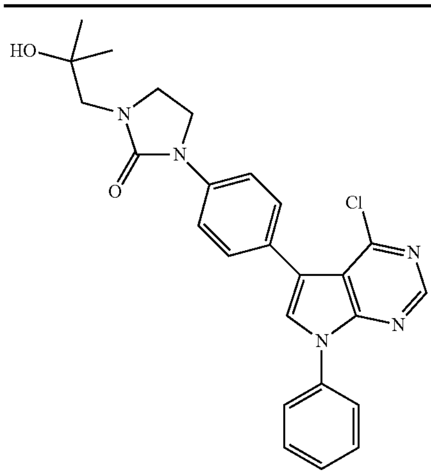 | CP60 (B11, CH1) | LC-MS. $R_t$ 3.31 min, AnalpH2_MeOH_4min(1); ($ESI^+$) m/z 462.3 $[M + H]^+$ | 41 mg, 32% |

The following chloro-pyrimidine compound was prepared via alkylation of the corresponding phenol:

5-(4-(but-2-en-1-yloxy)phenyl)-4-chloro-7-phenyl-7H-pyrrolo[2,3-d]pyrimidine (CP75)

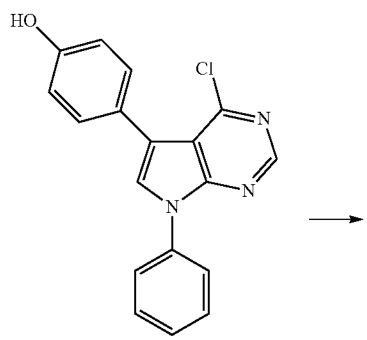

CP74

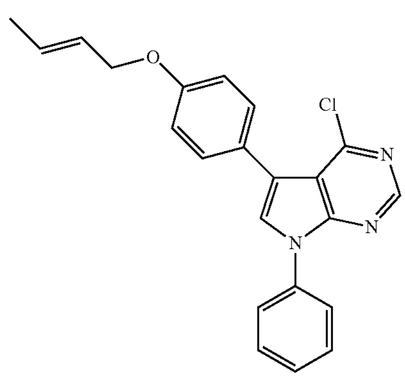

CP75

Potassium carbonate (75 mg, 0.54 mmol) was added to a solution of the 5-(4-hydroxyphenyl)-7-phenyl-3,7-dihydro-4H-pyrrolo[2,3-d]pyrimidin-4-one (CP74) (87 mg, 0.27 mmol) and trans-1-Bromo-2-butene (138 μL, 1.35 mmol) in acetone (6 mL) then heated to 60° C. for 18 h. The reaction mixture was filtered and the organics were concentrated in vacuo. The crude residue was then purified by silica gel chromatography eluting with 1-35% EtOAc/iso-hexane to afford (4-(but-2-en-1-yloxy)phenyl)-4-chloro-7-phenyl-7H-pyrrolo[2,3-d]pyrimidine (CP75) as a white solid (138 mg, 68%). LC-MS. Rt 3.65 min, AnalpH2_MeOH_4 min(1); ($ESI^+$) m/z 376.2 $[M+H]^+$.

Route 2a, Step 3: Final Compounds Via Acidic Hydrolysis 2-(2-Hydroxy-2-methylpropoxy)-5-(4-oxo-7-phenyl-4,7-dihydro-3H-pyrrolo[2,3-d]pyrimidin-5-yl)benzonitrile (Ex-7)

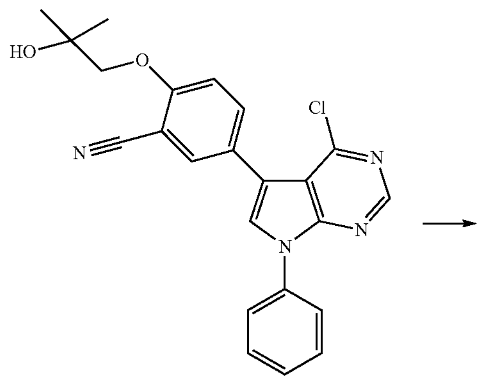

CP5

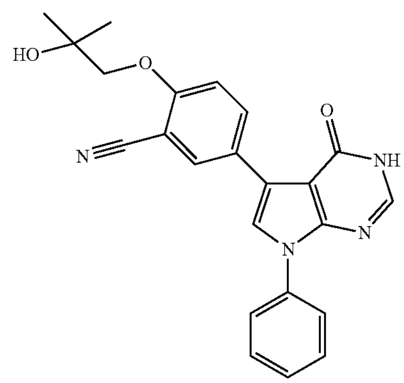

Ex-7

A mixture of 5-(4-Chloro-7-phenyl-7H-pyrrolo[2,3-d]pyrimidin-5-yl)-2-(2-hydroxy-2-methyl-propoxy)-benzonitrile (CP5) (74.8 mg, 0.179 mmol) and NaOAc (29.4 mg, 0.358 mmol) in AcOH (358 μL) was heated at 100° C. for 3 h. The reaction mixture was concentrated in vacuo. The crude residue was purified by reversed phase preparative HPLC-MS to afford 2-(2-Hydroxy-2-methylpropoxy)-5-(4-oxo-7-phenyl-4,7-dihydro-3H-pyrrolo[2,3-d]pyrimidin-5-yl)benzonitrile (Ex-7) as a white solid (48.6 mg, 68%). LC-MS. Rt 7.88 min, AnalpH2_MeOH_QC_V1(1); ($ESI^+$) m/z 401.3 $[M+H]^+$; $^1H$ NMR (400 MHz, DMSO-$d_6$): 12.23 (br s, 1H), 8.45 (d, J=2.5 Hz, 1H), 8.33 (dd, J=9.2, 2.3 Hz, 1H), 7.99 (s, 1H), 7.97 (s, 1H), 7.80-7.76 (m, 2H), 7.59-7.54 (m, 2H), 7.45-7.41 (m, 1H), 7.28 (d, J=8.7 Hz, 1H), 4.75 (s, 1H), 3.92 (s, 2H), 1.26 (s, 6H).

The following compounds were synthesised using an analogous procedure to Ex-7 (heating durations varied between 1.5-24 h):

TABLE 22
| Compound | Ex. # (Intermediate used) | Analytical Data | Mass, % Yield, Appearance |
|---|---|---|---|
| 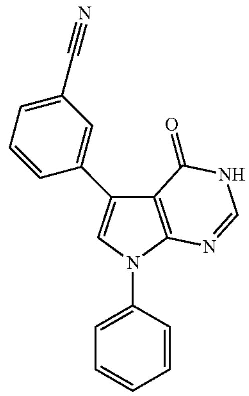 [SMILES: N#Cc1cccc(-c2cn(-c3ccccc3)c3nc[nH]c(=O)c23)c1] | Ex-8 (CP9) | LC-MS. $R_t$ 7.69 min, AnalpH2_MeOH_QC_V1(1); (ESI+) m/z 313.2 [M + H]+. | 8 mg, 13%, white solid |
| 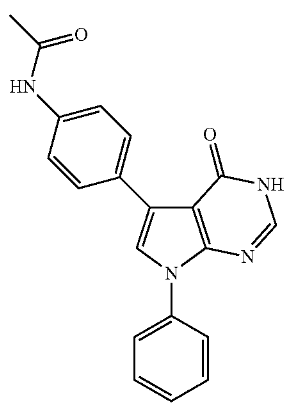 [SMILES: CC(=O)Nc1ccc(-c2cn(-c3ccccc3)c3nc[nH]c(=O)c23)cc1] | Ex-9 (CP7) | LC-MS. $R_t$ 7.21 min, AnalpH2_MeOH_QC_V1(1); (ESI+) m/z 345.3 [M + H]+. $^1$H NMR (400 MHz, DMSO-$d_6$): δ 12.33-11.94 (br s, 1H), 9.96 (s, 1H), 7.96 (s, 1H), 7.93 (**d, J = 8.8 Hz, 2H), 7.78-7.77 (m, 1H), 7.76-7.75 (m, 2H), 7.58-7.54 (m, 4H), 7.42 (tt, J = 7.3, 1.3 Hz, 1H), 2.06 (s, 3H). | 11 mg, 75%, white solid |
| 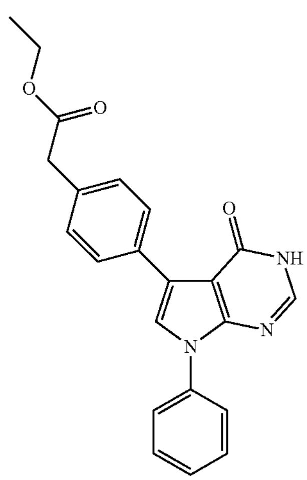 [SMILES: CCOC(=O)Cc1ccc(-c2cn(-c3ccccc3)c3nc[nH]c(=O)c23)cc1] | Ex-10 (CP8) | LC-MS. $R_t$ 8.06 min, AnalpH2_MeOH_QC_V1(1); (ESI+) m/z 374.3 [M + H]+. | 13 mg, 22%, off-white solid |

TABLE 22-continued

| Compound | Ex. # (Intermediate used) | Analytical Data | Mass, % Yield, Appearance |
|---|---|---|---|
| 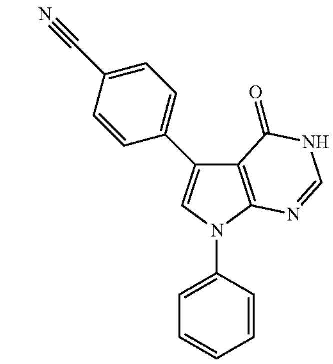 [SMILES: N#Cc1ccc(-c2cn(-c3ccccc3)c3nc[nH]c(=O)c23)cc1] | Ex-11 (CP6) | LC-MS. $R_t$ 7.62 min, AnalpH2_MeOH_QC_V1(1); (ESI$^+$) m/z 313.3 [M + H]$^+$. | 9 mg, 100% white solid |
| 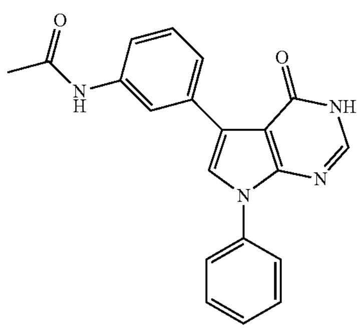 [SMILES: CC(=O)Nc1cccc(-c2cn(-c3ccccc3)c3nc[nH]c(=O)c23)c1] | Ex-12 (CP10) | LC-MS. $R_t$ 7.26 min, AnalpH2_MeOH_QC_V1(1); (ESI$^+$) m/z 345.3 [M + H]$^+$. $^1$H NMR (400 MHz, DMSO-$d_6$): δ 12.15 (br s, 1H), 9.97 (s, 1H), 7.98 (s, 1H), 7.94 (t, J = 2.0 Hz, 1H), 7.78-7.75 (m, 2H), 7.67 (s, 1H), 7.60-7.54 (m, 4H), 7.46 (tt, J = 7.3, 1.3 Hz, 1H), 7.29 (t, J = 8.1 Hz, 1H), 2.05 (s, 3H). | 15.2 mg, 69%, white solid |
| 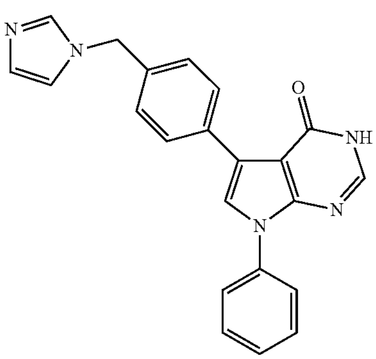 [SMILES: O=c1[nH]cnc2c1c(-c1ccc(Cn3ccnc3)cc1)cn2-c1ccccc1] | Ex-13 (CP11) | LC-MS. $R_t$ 5.23 min, AnalpH2_MeOH_QC_V1(1); (ESI$^+$) m/z 368.3 [M + H]$^+$. $^1$H NMR (400 MHz, DMSO-$d_6$): δ 12.17 (br d, J = 3.5 Hz, 1H), 7.96-7.95 (m, 3H), 7.81 (s, 1H), 7.79 (br s, 1H), 7.77-7.75 (m, 2H), 7.56 (**t, J = 7.6 Hz, 2H), 7.43 (tt, J = 7.3, 1.8 Hz, 1H), 7.27 (d, J = 8.6 Hz, 2H), 7.23 (t, J = 1.0 Hz, 1H), 6.91 (br s, 1H), 5.20 (s, 2H). | 16 mg, 31%, white solid |
| 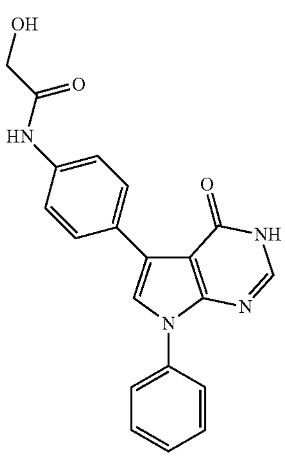 [SMILES: O=C(CO)Nc1ccc(-c2cn(-c3ccccc3)c3nc[nH]c(=O)c23)cc1] | Ex-14 (CP12) | LC-MS. $R_t$ 6.95 min, AnalpH2_MeOH_QC_V1(1); (ESI$^+$) m/z 361.2 [M + H]$^+$. | 8 mg, 15%, off-white solid |

TABLE 22-continued

| Compound | Ex. # (Intermediate used) | Analytical Data | Mass, % Yield, Appearance |
|---|---|---|---|
| 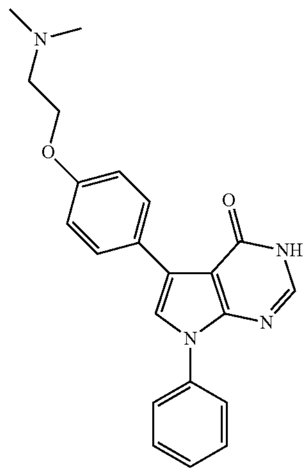 [SMILES: CN(C)CCOc1ccc(-c2cn(-c3ccccc3)c3nc[nH]c(=O)c23)cc1] | Ex-15 (CP13) | LC-MS, $R_t$ = 5.16 min, AnalpH2_MeOH_QC_V1(1); (ESI$^+$) m/z 375.3 [M + H]$^+$. | 5 mg, 11%, white solid |
| 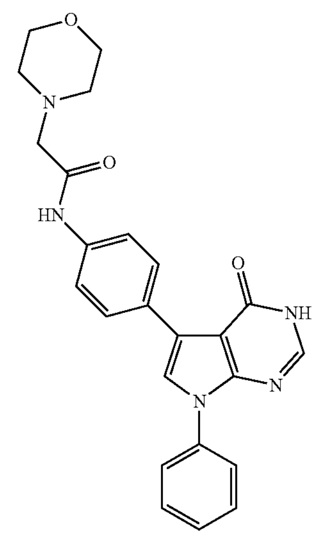 [SMILES: O=C(CN1CCOCC1)Nc1ccc(-c2cn(-c3ccccc3)c3nc[nH]c(=O)c23)cc1] | Ex-16 (CP14) | LC-MS. $R_t$ 5.37 min, AnalpH2_MeOH_QC_V1(1); (ESI$^+$) m/z 430.3 [M + H]$^+$. $^1$H NMR (400 MHz, DMSO-$d_6$): δ 12.15 (br s, 1H), 9.77 (s, 1H), 7.97 (s, 1H), 7.95 (d, J = 8.8 Hz, 2H), 7.79 (s, 1H), 7.77 (d, J = 8.6 Hz, 2H), 7.64 (d, J = 8.6 Hz, 2H), 7.57 (t, J = 7.6 Hz, 2H), 7.43 (t, J = 7.6 Hz, 1H), 3.67-3.64 (m, 4H), 3.15 (s, 2H), 2.54-2.53 (m, 4H). | 19 mg, 20%, white solid |
| 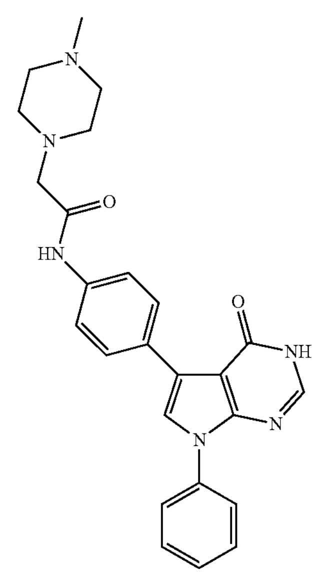 [SMILES: CN1CCN(CC(=O)Nc2ccc(-c3cn(-c4ccccc4)c4nc[nH]c(=O)c34)cc2)CC1] | Ex-17 (CP15) | LC-MS, $R_t$ 5.20 min, AnalpH2_MeOH_QC_V1(1); (ESI$^+$) m/z 443.4 [M + H]$^+$; $^1$H-NMR (400 MHz, DMSO-$d_6$): δ 12.13 (d, J = 3.7 Hz, 1H), 9.75 (s, 1H), 7.96-7.92 (m, 3H), 7.77-7.74 (m, 3H), 7.61 (d, J = 8.7 Hz, 2H), 7.75 (t, J = 7.8 Hz, 2H), 7.41 (t, J = 7.6 Hz, 1H), 3.32 (br s, 4H), 3.14 (s, 2H), 2.56 (br s, 4H), 2.25 (br s, 3H). | 18 mg, 76%, white solid |

TABLE 22-continued

| Compound | Ex. # (Intermediate used) | Analytical Data | Mass, % Yield, Appearance |
|---|---|---|---|
| 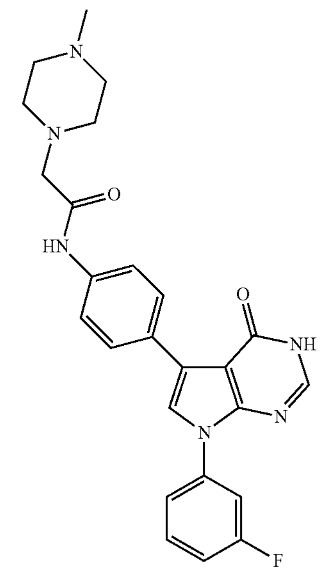 [SMILES: CN1CCN(CC(=O)Nc2ccc(-c3cn(-c4cccc(F)c4)c4nc[nH]c(=O)c34)cc2)CC1] | Ex-18 (CP16) | LC-MS, $R_t$ 5.33 min, AnalpH2_MeOH_QC_V1(1); (ESI$^+$) m/z 461.3 [M + H]$^+$. $^1$H NMR (400 MHz, DMSO-$d_6$): δ 12.21 (br s, 1H), 9.71 (s, 1H), 8.01 (s, 1H), 7.94 (**d, J = 8.6 Hz, 2H), 7.84 (s, 1H), 7.77 (dt, J = 10.6, 2.0 Hz, 1H), 7.73-7.67 (m, 1H), 7.63 (**d, J = 8.8 Hz, 2H), 7.61-7.57 (m, 1H), 7.30-7.23 (m, 1H), 3.12 (s, 2H), 2.17 (s, 3H), 2.38 (br s, 4H). Other piperazine protons masked by water peak @ δ 3.3 | 14 mg, 80%, white solid |
| 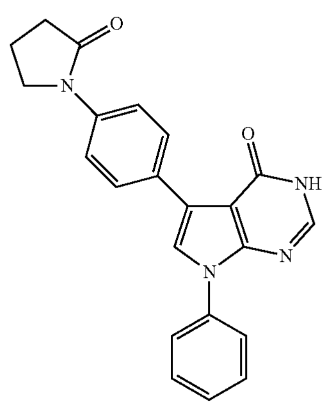 [SMILES: O=C1CCCN1c1ccc(-c2cn(-c3ccccc3)c3nc[nH]c(=O)c23)cc1] | Ex-19 (CP18) | LC-MS. $R_t$ 7.40 min, AnalpH2_MeOH_QC_V1(1); (ESI$^+$) m/z 371.4 [M + H]$^+$. $^1$H NMR (400 MHz, DMSO-$d_6$): δ 12.17 (br s, 1H), 8.03 (**d, J = 8.8 Hz, 2H), 7.98 (s, 1H), 7.82 (s, 1H), 7.73 (d, J = 7.6 Hz, 2H), 7.66 (**d, J = 8.6 Hz, 2H), 7.57 (t, J = 7.6 Hz, 2H), 7.43 (t, J = 7.3 Hz, 1H), 3.88 (t, J = 6.8 Hz, 2H), 2.53-2.50 (m, 2H), 2.12-2.07 (m, 2H). | 18 mg, 40%, off-white solid |
| 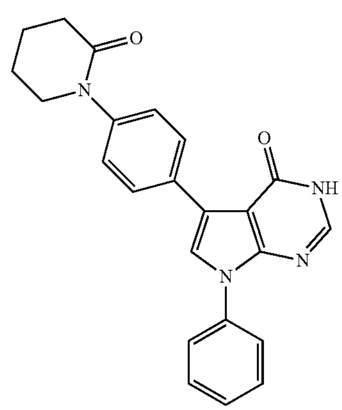 [SMILES: O=C1CCCCN1c1ccc(-c2cn(-c3ccccc3)c3nc[nH]c(=O)c23)cc1] | Ex-20 (CP19) | LC-MS. $R_t$ 7.36 min, AnalpH2_MeOH_QC_V1(1); (ESI$^+$) m/z 385.2 [M + H]$^+$. $^1$H NMR (400 MHz, DMSO-$d_6$): δ 12.13 (br s, 1H), 7.99-7.96 (m, 3H), 7.83 (s, 1H), 7.79-7.77 (m, 2H), 7.57 (t, J = 7.6 Hz, 2H), 7.43 (tt, J = 7.6, 1.0 Hz, 1H), 7.27 (d, J = 8.6 Hz, 2H), 3.64 (t, J = 5.1 Hz, 2H), 2.41 (t, J = 6.3 Hz, 2H), 1.90-1.85 (m, 4H). | 36 mg, 47%, white solid |

TABLE 22-continued

| Compound | Ex. # (Intermediate used) | Analytical Data | Mass, % Yield, Appearance |
|---|---|---|---|
| 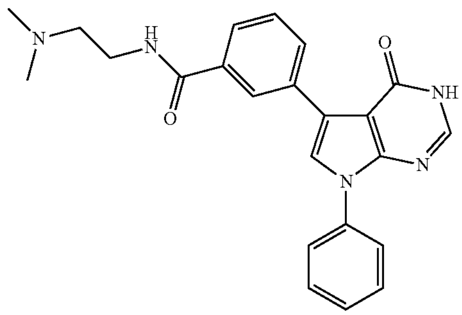 [SMILES: CN(C)CCNC(=O)c1cccc(-c2cn(-c3ccccc3)c3nc[nH]c(=O)c23)c1] | Ex-21 (CP38) | LC-MS. $R_t$ 5.21 min, AnalpH2_MeOH_QC_V1(1); (ESI$^+$) m/z 402.3 $[M + H]^+$ | 8 mg, 24%, white solid |
| 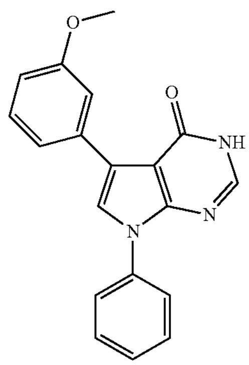 [SMILES: COc1cccc(-c2cn(-c3ccccc3)c3nc[nH]c(=O)c23)c1] | Ex-22 (CP20) | LC-MS. $R_t$ 7.78 min, AnalpH2_MeOH_QC_V1(1); (ESI$^+$) m/z 318.2 $[M + H]^+$. $^1$H NMR (400 MHz, DMSO-$d_6$): δ 12.19 (br s, 1H), 7.98 (s, 1H), 7.88 (s, 1H), 7.79-7.77 (m, 2H), 7.74-7.73 (m, 1H), 7.59-7.55 (m, 3H), 7.43 (tt, J = 7.3, 1.0 Hz, 1H), 7.28 (t, J = 7.8 Hz, 1H), 6.84-6.82 (m, 1H), 3.81 (s, 3H). | 21 mg, 59%, white solid |
| 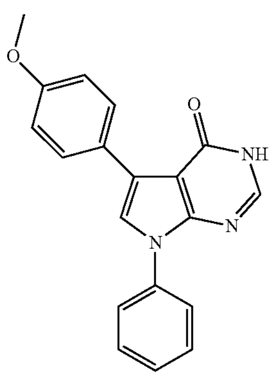 [SMILES: COc1ccc(-c2cn(-c3ccccc3)c3nc[nH]c(=O)c23)cc1] | Ex-23 (CP21) | LC-MS. $R_t$ 7.74 min, AnalpH2_MeOH_QC_V1(1); (ESI$^+$) m/z 318.2 $[M + H]^+$. | 8 mg, 77%, white solid |
| 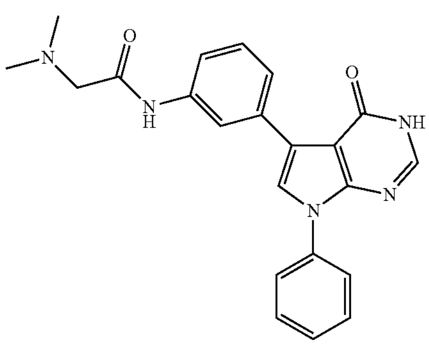 [SMILES: CN(C)CC(=O)Nc1cccc(-c2cn(-c3ccccc3)c3nc[nH]c(=O)c23)c1] | Ex-24 (CP39) | LC-MS. $R_t$ 5.19 min, AnalpH2_MeOH_QC_V1(1); (ESI$^+$) m/z 388.3 $[M + H]^+$; $^1$H-NMR (400 MHz, DMSO-$d_6$): δ 12.15 (br s, 1H), 9.65 (s, 1H), 8.01-7.98 (m, 2H), 7.79-7.75 (m, 2H), 7.73 (s, 1H), 7.71-7.68 (m, 2H), 7.58-7.54 (m, 2H), 7.43 (tt, J = 7.5, 1.3 Hz, 1H), 7.31 (t, J = 8.0 Hz, 1H), 3.09 (s, 2H), 2.30 (s, 6H); | 16 mg, 37%, white solid |

TABLE 22-continued

| Compound | Ex. # (Intermediate used) | Analytical Data | Mass, % Yield, Appearance |
|---|---|---|---|
| 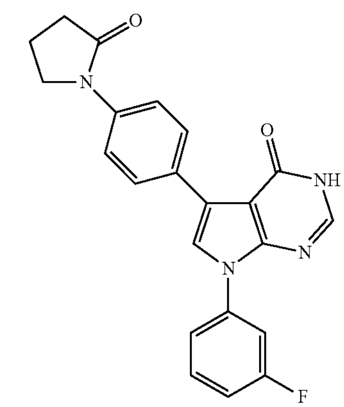 [SMILES: O=C1CCCN1c1ccc(-c2cn(-c3cccc(F)c3)c3nc[nH]c(=O)c23)cc1] | Ex-25 (CP22) | LC-MS. $R_t$ 7.53 min, AnalpH2_MeOH_QC_V1(1); (ESI$^+$) m/z 389.4 [M + H]$^+$. | 17 mg, 23%, white solid |
| 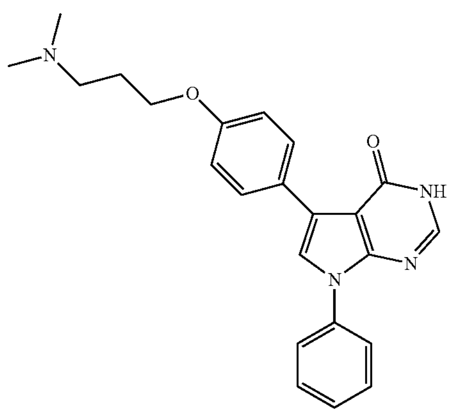 [SMILES: CN(C)CCCOc1ccc(-c2cn(-c3ccccc3)c3nc[nH]c(=O)c23)cc1] | Ex-26 (CP30) | LC-MS. $R_t$ 5.37 min, AnalpH2_MeOH_QC_V1(1); (ESI$^+$) m/z 389.2 [M + H]$^+$; $^1$H NMR (400 MHz, DMSO-$d_6$): 7.96-7.92 (m, 3H), 7.80-7.76 (m, 2H), 7.70 (s, 1H), 7.58-7.53 (m, 2H), 6.93 (d, J = 8.8 Hz, 2H), 4.03 (t, J = 6.3 Hz, 2H), 2.37 (t, J = 7.04 Hz, 2H), 2.15, (s, 6H), 1.89-1.83 (m, 2H). | 16 mg, 32%, white solid |
| 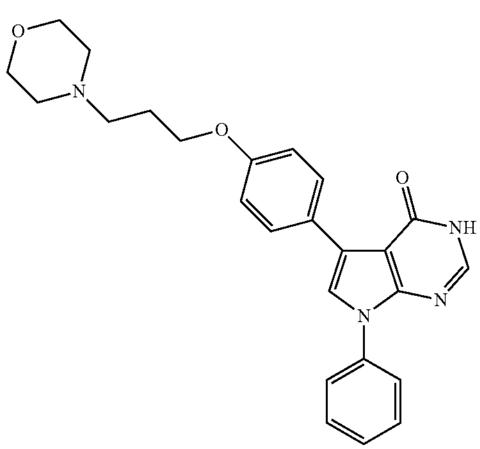 [SMILES: O=c1[nH]cnc2c1c(-c1ccc(OCCCN3CCOCC3)cc1)cn2-c1ccccc1] | Ex-27 (CP32) | LC-MS. $R_t$ 5.33 min, AnalpH2_MeOH_QC_V1(1); (ESI$^+$) m/z 431.2 [M + H]$^+$; $^1$H NMR (400 MHz, DMSO-$d_6$): 12.15-12.10 (br s, 1H), 7.97-7.90 (m, 3H), 7.80-7.75 (m, 2H), 7.72 (s, 1H), 7.59-7.53 (m, 2H), 7.45-7.39 (m, 1H), 6.97-6.92 (m, 2H), 4.04 (t, J = 6.3 Hz, 2H), 3.60-3.56 (m, 4H), 2.44 (t, J = 7.3 Hz, 2H), 2.40-2.35 (br s, 4H), 1.94-1.85 (m, 2H). | 24 mg, 59%, white solid |

TABLE 22-continued

| Compound | Ex. # (Intermediate used) | Analytical Data | Mass, % Yield, Appearance |
|---|---|---|---|
| 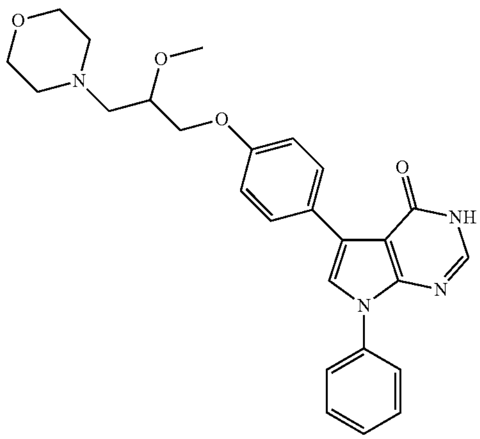 [SMILES: COC(COc1ccc(-c2cn(-c3ccccc3)c3nc[nH]c(=O)c23)cc1)CN1CCOCC1] | Ex-28 (CP36) | LC-MS. $R_t$ 5.47 min, AnalpH2_MeOH_QC_V1(1); ($ESI^+$) m/z 461.4 $[M + H]^+$; $^1H$ NMR (400 MHz, DMSO-$d_6$): 12.18-12.08 (br s, 1H), 7.97-7.92 (br s, 3H), 7.79-7.76 (m, 2H), 7.73 (s, 1H), 7.59-7.53 (m, 2H), 7.45-7.40 (m, 1H), 6.99-6.96 (m, 2H), 4.14 (dd, J = 10.6, 7.1 Hz, 1H), 4.02 (dd, J = 10.6, 5.1 Hz, 1H), 3.72-3.65 (m, 1H), 3.59-3.56 (m, 4H), 3.39 (s, 3H) 2.49-2.44 (m, 6H). | 19 mg, 77%, white solid |
| 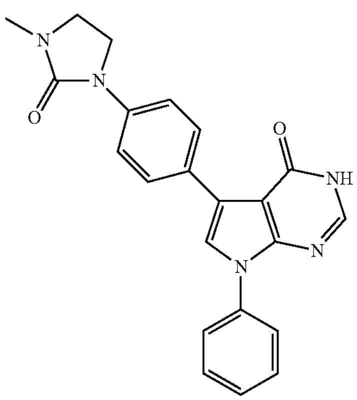 [SMILES: CN1CCN(c2ccc(-c3cn(-c4ccccc4)c4nc[nH]c(=O)c34)cc2)C1=O] | Ex-29 (CP23) | LC-MS. $R_t$ 7.30 min, AnalpH2_MeOH_QC_V1(1); ($ESI^+$) m/z 386.2 $[M + H]^+$ $^1H$-NMR (400 MHz, DMSO-$d_6$): δ 12.14 (br s, 1H), 7.98-7.95 (m, 3H), 7.79-7.75 (m, 3H), 7.58-7.53 (m, 4H), 7.42 (t, J = 7.3 Hz, 1H), 3.84-3.80 (m, 2H), 3.48-3.43 (m, 2H), 2.78 (s, 3H). | 6 mg, 30%, white solid |
| 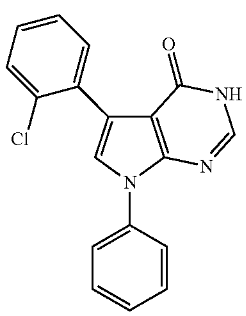 | Ex-30 (CP42) | LC-MS. $R_t$ 7.81 min, AnalpH2_MeOH_QC_V1(1); ($ESI^+$) m/z 322.2 $[M + H]^+$; $^1H$-NMR (400 MHz, DMSO-$d_6$): δ 12.12 (br-s, 1H), 7.98 (s, 1H), 7.77 (d, J = 8.7 Hz, 2H), 7.62 (s, 1H), 7.58-7.51 (m, 4H), 7.42 (t, J = 7.8 Hz, 1H), 7.37-7.35 (m, 2H). | 63 mg, 94%, off-white solid |
| 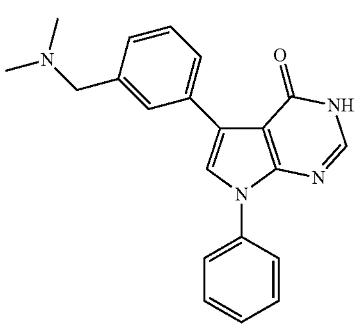 [SMILES: CN(C)Cc1cccc(-c2cn(-c3ccccc3)c3nc[nH]c(=O)c23)c1] | Ex-31 (CP45) | LC-MS. $R_t$ 5.00 min, AnalpH2_MeOH_QC_V1(1); ($ESI^+$) m/z 345.3 $[M + H]^+$; $^1H$-NMR (400 MHz, DMSO-$d_6$): δ 7.97 (s, 1H), 7.90-7.87 (m, 1H), 7.85-7.84 (m, 1H), 7.80-7.77 (m, 3H), 7.58-7.53 (m, 2H), 7.42 (tt, J = 7.3, 1.4 Hz, 1H), 7.32 (t, J = 7.7 Hz, 1H), 7.19-7.16 (m, 1H), 3.41 (s, 2H), 2.17 (s, 6H). | 15 mg, 54%, white solid |

TABLE 22-continued

| Compound | Ex. # (Intermediate used) | Analytical Data | Mass, % Yield, Appearance |
|---|---|---|---|
| 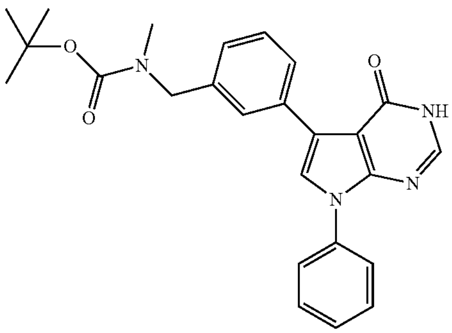 [SMILES: CN(Cc1cccc(-c2cn(-c3ccccc3)c3nc[nH]c(=O)c23)c1)C(=O)OC(C)(C)C] | Ex-32 (CP44) | LC-MS. $R_t$ 8.25 min, AnalpH2_MeOH_QC_V1(1); (ESI$^+$) m/z 431.3 [M + H]$^+$. | 27 mg, 37%, white solid |
| 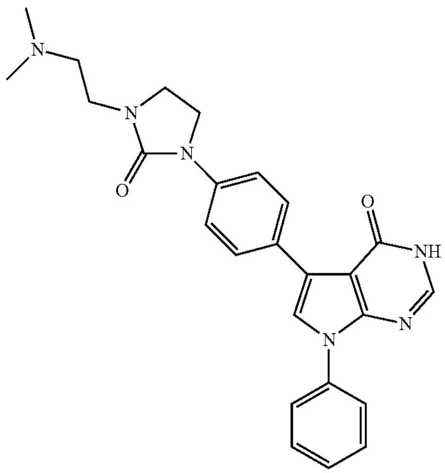 [SMILES: CN(C)CCN1CCN(c2ccc(-c3cn(-c4ccccc4)c4nc[nH]c(=O)c34)cc2)C1=O] | Ex-33 (CP25) | LC-MS. $R_t$ 5.21 min, AnalpH2_MeOH_QC_V1(1); (ESI$^+$) m/z 443.3 [M + H]$^+$ | 5 mg, 7%, white solid |
| 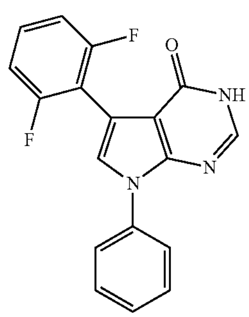 [SMILES: O=c1[nH]cnc2c1c(-c1c(F)cccc1F)cn2-c1ccccc1] | Ex-34 (CP43) | LC-MS. $R_t$ 7.60 min, AnalpH2_MeOH_QC_V1(1); (ESI$^+$) m/z 324.1 [M + H]$^+$; $^1$H NMR (400 MHz, DMSO-$d_6$): 12.15 (br s, 1H), 7.98 (s, 1H), 7.75 (d, J = 7.8 Hz, 2H), 7.68 (s, 1H), 7.57 (**t, J = 8.2 Hz, 2H), 7.48-7.41 (m, 2H), 7.16 (**t, J = 7.8 Hz, 2H). | 31 mg, 47%, pale yellow solid |
| 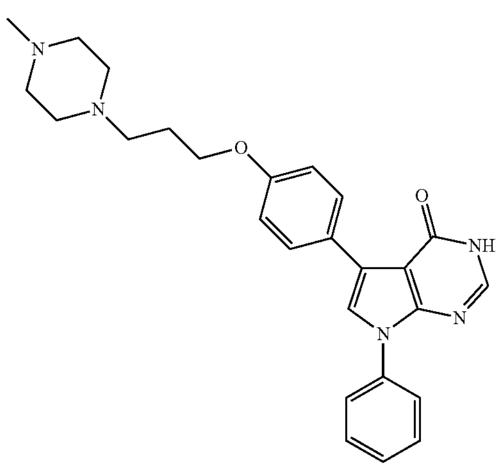 [SMILES: CN1CCN(CCCOc2ccc(-c3cn(-c4ccccc4)c4nc[nH]c(=O)c34)cc2)CC1] | Ex-35 (CP26) | LC-MS. $R_t$ 5.26 min, AnalpH2_MeOH_QC_V1(1); (ESI$^+$) m/z 444.3 [M + H]$^+$ | 15 mg, 24%, white solid |

TABLE 22-continued
| Compound | Ex. # (Intermediate used) | Analytical Data | Mass, % Yield, Appearance |
|---|---|---|---|
| 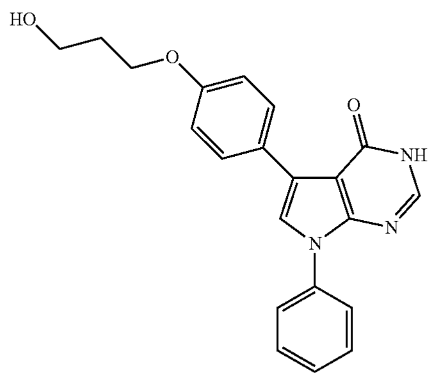 [SMILES: O=c1[nH]cnc2c1c(-c1ccc(OCCCO)cc1)cn2-c1ccccc1] | Ex-36 (CP47) | LC-MS. $R_t$ 7.71 min, AnalpH2_MeOH_QC_V1(1); (ESI$^+$) m/z 362.1 [M + H]$^+$. | 11 mg, 6%, white solid |
| 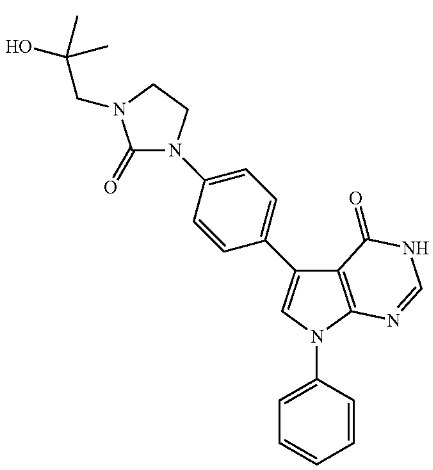 [SMILES: CC(C)(O)CN1CCN(c2ccc(-c3cn(-c4ccccc4)c4nc[nH]c(=O)c34)cc2)C1=O] | Ex-37 (CP60) | LC-MS. $R_t$ 7.67 min, AnalpH2_MeOH_QC_V1(1); (ESI$^+$) m/z 444.3 [M + H]$^+$ | 15 mg, 40%, white solid |
| 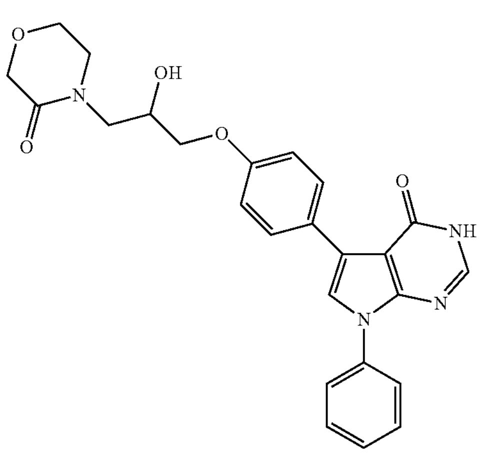 [SMILES: O=C1COCCN1CC(O)COc1ccc(-c2cn(-c3ccccc3)c3nc[nH]c(=O)c23)cc1] | Ex-38 (CP49) | LC-MS. $R_t$ 7.31 min, AnalpH2_MeOH_QC_V1(1); (ESI$^+$) m/z 461.3 [M + H]$^+$. | 5 mg, 12%, off-white solid |

TABLE 22-continued

| Compound | Ex. # (Intermediate used) | Analytical Data | Mass, % Yield, Appearance |
|---|---|---|---|
| 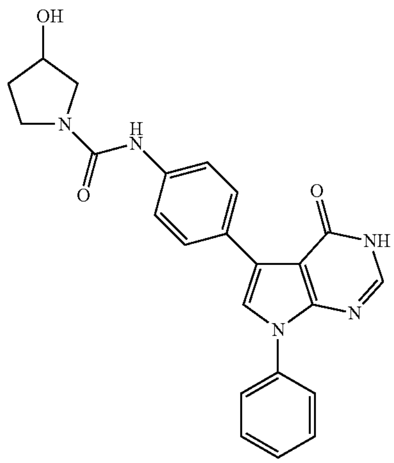 [SMILES: O=C(Nc1ccc(-c2cn(-c3ccccc3)c3nc[nH]c(=O)c23)cc1)N1CCC(O)C1] | Ex-39[a] (CP54, CP55) | LC-MS. $R_t$ 7.02 min, AnalpH2_MeOH_QC_V1(1); ($ESI^+$) m/z 416.3 $[M + H]^+$. | 5 mg, 12%, off-white solid |
| 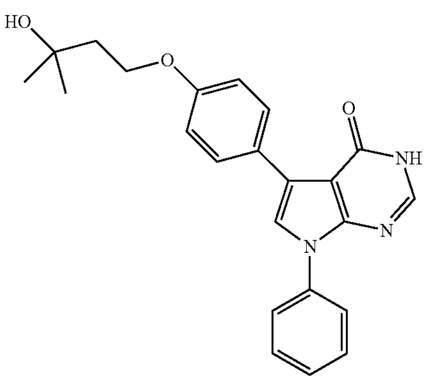 [SMILES: CC(C)(O)CCOc1ccc(-c2cn(-c3ccccc3)c3nc[nH]c(=O)c23)cc1] | Ex-40 (CP53) | LC-MS, $R_t$ 8.22 min, AnalpH2_MeOH_QC_V1(1); ($ESI^+$) m/z 390.3 $[M + H]^+$ $^1$H-NMR (400 MHz, DMSO-$d_6$): δ 12.06 (br s, 1H), 7.91 (s, 1H), 7.88 (d, J = 6.9 Hz, 2H), 7.73 (d, J = 7.3 Hz, 2H), 7.67 (s, 1H), 7.51 (**t, J = 7.3 Hz, 2H), 7.34 (t, J = 7.3 Hz, 1H), 6.90 (d, J = 9.2 Hz, 2H), 4.35 (s, 1H), 4.08 (t, J = 7.1 Hz, 2H), 1.82 (t, J = 7.1 Hz, 2H), 1.14 (s, 6H). | 15 mg, 32%, white solid |

[a]Mixture of enantiomers used.

Route 2a: Step 3, Final Compounds Via Acidic Followed by Basic Hydrolysis

5-[4-(2-Hydroxy-3-morpholin-4-yl-propoxy)-phenyl]-7-(3-methoxy-phenyl)-3,7-dihydro-pyrrolo[2,3-d]pyrimidin-4-one (Ex-41)

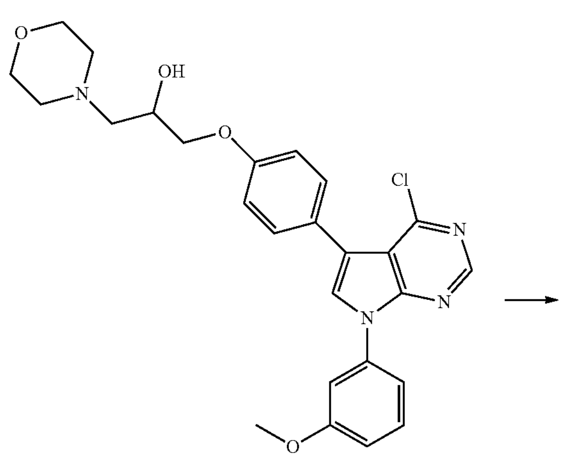

CP35

-continued

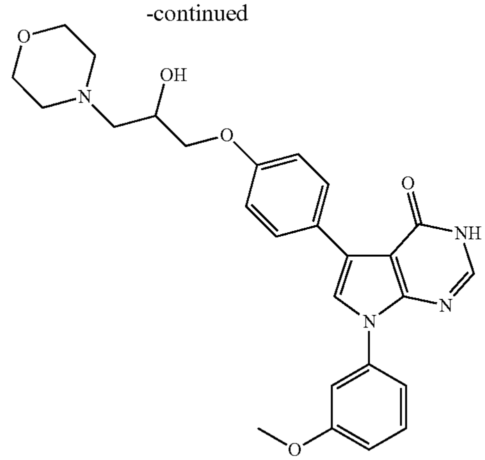

Ex-41

To a stirred solution of 1-{4-[4-chloro-7-(3-methoxy-phenyl)-7H-pyrrolo[2,3-d]pyrimidin-5-yl]-phenoxy}-3-morpholin-4-yl-propan-2-ol formic acid salt (CP35) (21.0 mg, 0.039 mmol) and NaOAc (6.40 mg, 0.078 mmol) in AcOH (50 μL) was heated at 100° C. for 3 h. The reaction mixture was then concentrated in vacuo and the resulting residue diluted with $H_2O$ and $LiOH \cdot H_2O$ (43.2 mg, 1.03 mmol) was added. The resulting mixture was heated at 40° C. for 2 h. Reaction mixture was concentrated in vacuo and the crude compound was purified by reversed phase preparative HPLC-MS to afford 5-[4-(2-Hydroxy-3-morpholin-4-yl-propoxy)-phenyl]-7-(3-methoxy-phenyl)-3,7-dihydro-pyrrolo[2,3-d]pyrimidin-4-one (Ex-41) as a white solid (15 mg, 83%); LC-MS. Rt 5.47 min, AnalpH2_MeOH_QC_V1 (1); ($ESI^+$) m/z 477.1 $[M+H]^+$; $^1H$ NMR (400 MHz, DMSO-$d_6$): 12.12-12.02 (br s, 1H), 7.93-7.86 (m, 3H), 7.68 (s, 1H), 7.43-7.38 (m, 1H), 7.34-7.30 (m, 2H), 6.96-6.89 (m, 3H), 4.84 (d, J=4.6 Hz, 1H), 4.00-3.93 (m, 3H), 3.79 (s, 3H), 3.56-3.50 (m, 4H), 2.44-2.38 (m, 6H).

The following examples were made using analogous procedures to Ex-41 with heating durations varying between 0.5-24 h for each hydrolysis:

TABLE 23

| Compound | Ex. # (Intermediate used) | Analytical Data | Mass, % Yield, Appearance |
|---|---|---|---|
| 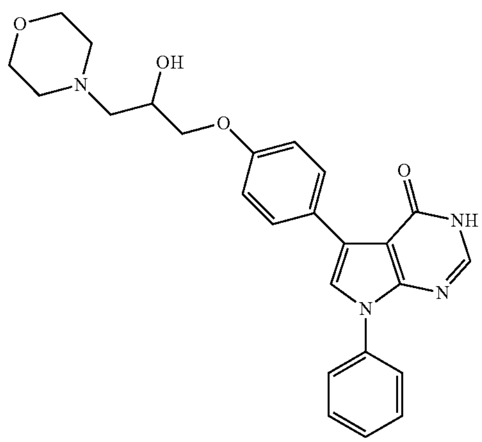 [SMILES: O=c1[nH]cnc2c1c(-c1ccc(OCC(O)CN3CCOCC3)cc1)cn2-c1ccccc1] | Ex-42 (CP33) | LC-MS. $R_t$ 5.07 min, AnalpH2_MeOH_QC_V1(1) ($ESI^+$) m/z 447.2 $[M + H]^+$; $^1H$ NMR (400 MHz, DMSO-$d_6$): δ 12.09-12.06 (br s, 1H), 7.93-7.86 (m, 3H), 7.75-7.71 (m, 2H), 7.69 (s, 1H), 7.54-7.49 (m, 2H), 7.40-7.36 (m, 1H), 6.91 (d, J = 9.2 Hz, 2H), 4.85 (d, J = 4.6 Hz, 1H), 4.00-3.84 (m, 3H), 3.57-3.51 (m, 4H), 2.48-2.32 (m, 6H). | 45 mg, 52%, white solid |
| 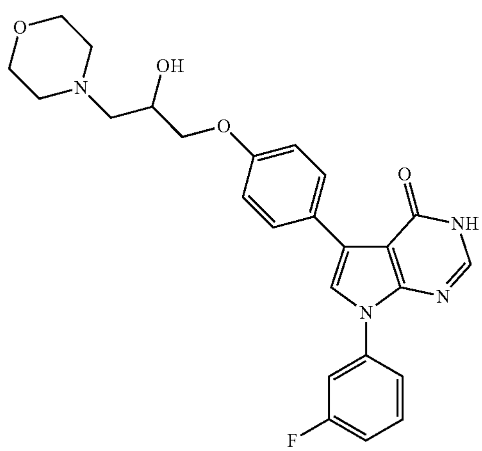 [SMILES: O=c1[nH]cnc2c1c(-c1ccc(OCC(O)CN3CCOCC3)cc1)cn2-c1cccc(F)c1] | Ex-43[a] (CP34) | LC-MS. $R_t$ 5.54 min, AnalpH2_MeOH_QC_V1(1) ($ESI^+$) m/z 465.2 $[M + H]^+$; $^1H$ NMR (400 MHz, DMSO-$d_6$): δ 12.15 (br s, 1H), 7.96 (s, 1H), 7.89 (d, J = 8.7 Hz, 2H), 7.76-7.71 (m, 2H), 7.69-7.59 (m, 1H), 7.59-7.52 (m, 1H), 7.22 (dt, J = 8.7, 2.3 Hz, 1H), 6.92 (d, J = 9.2 Hz, 2H), 4.85 (d, J = 4.6 Hz, 1H), 4.00-3.85 (m ,3H), 3.56-3.49 (m, 4H), 2.48-2.32 (m, 6H). | 28 mg, 61%, white solid |
| 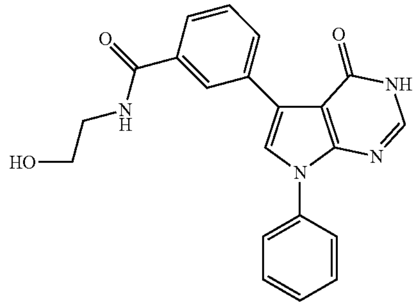 [SMILES: O=C(NCCO)c1cccc(-c2cn(-c3ccccc3)c3nc[nH]c(=O)c23)c1] | Ex-44 (CP40) | LC-MS. $R_t$ 6.82 min, AnalpH2_MeOH_QC_V1(1); ($ESI^+$) m/z 375.3 $[M + H]^+$ | 28 mg, 34%, white solid |

TABLE 23-continued

| Compound | Ex. # (Intermediate used) | Analytical Data | Mass, % Yield, Appearance |
|---|---|---|---|
| 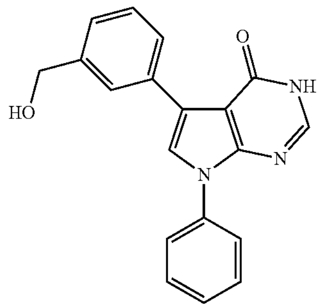 [SMILES: O=c1[nH]cnc2c1c(-c1cccc(CO)c1)cn2-c1ccccc1] | Ex-45 (CP41) | LC-MS. $R_t$ 6.97 min, AnalpH2_MeOH_QC_V1(1); ($ESI^+$) m/z 318.4 $[M + H]^+$; 12.12 (br s, 1H), 7.97 (s, 1H), 7.90-7.86 (m, 2H), 7.79-7.77 (m, 3H), 7.58-7.54 (m, 2H), 7.44-7.41 (m, 1H), 7.36-7.32 (m, 1H), 7.25-7.23 (m, 1H), 5.17 (t, J = 5.5 Hz, 1H), 4.53 (d, J = 5.5 Hz, 1H). | 6 mg, 33%, white solid |
| 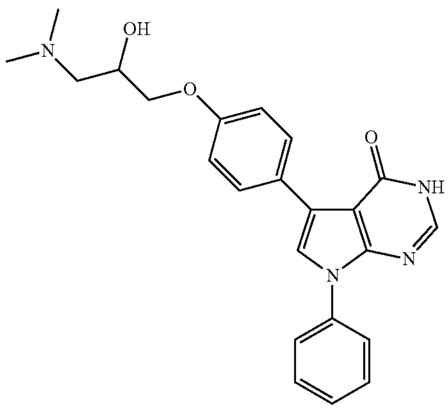 [SMILES: CN(C)CC(O)COc1ccc(-c2cn(-c3ccccc3)c3nc[nH]c(=O)c23)cc1] | Ex-46 (CP31) | LC-MS. $R_t$ 5.12 min, AnalpH2_MeOH_QC_V1(1); ($ESI^+$) m/z 405.3 $[M + H]^+$; $^1H$ NMR (400 MHz, DMSO-$d_6$): 12.08 (br s, 1H), 7.92-7.86 (m, 3H), 7.75-7.71 (m, 2H), 7.68 (s, 1H), 7.54-7.48 (m, 2H), 7.40-7.35 (m, 1H), 6.92-6.88 (m, 2H), 4.80 (d, J = 4.1 Hz, 1H), 3.96 (dd, J = 9.2, 3.2 Hz, 1H), 3.92-3.81 (m, 2H), 2.36 (dd, J = 12.4, 6.0 Hz, 1H), 2.25 (dd, ,J = 12.4, 6.4 Hz, 1H), 2.27 (s, 6H). | 17 mg, 26%, white solid |
| 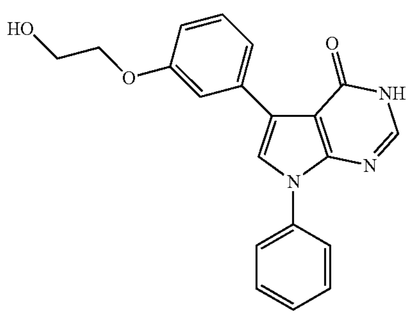 [SMILES: O=c1[nH]cnc2c1c(-c1cccc(OCCO)c1)cn2-c1ccccc1] | Ex-47 (CP27) | LC-MS. $R_t$ 7.57 min, AnalpH2_MeOH_QC_V1(1); ($ESI^+$) m/z 348.2 $[M + H]^+$; $^1H$ NMR (400 MHz, DMSO-$d_6$): 12.13-12.08 (br s, 1H), 7.94 (s, 1H), 7.83 (s, 1H), 7.76-7.71 (m, 2H), 7.70-7.68 (m, 1H), 7.55-7.49 (m, 3H), 7.42-7.37 (m, 1H), 7.22 (t, J = 7.8 Hz, 1H), 6.78 (dd, J = 8.2, 3.2 Hz, 1H), 4.90 (t, J = 5.5 Hz, 1H), 4.00 (t, J = 4.6 Hz, 2H), 3.71 (q, J = 5.1 Hz, 2H). | 13 mg, 18%, white solid |
| 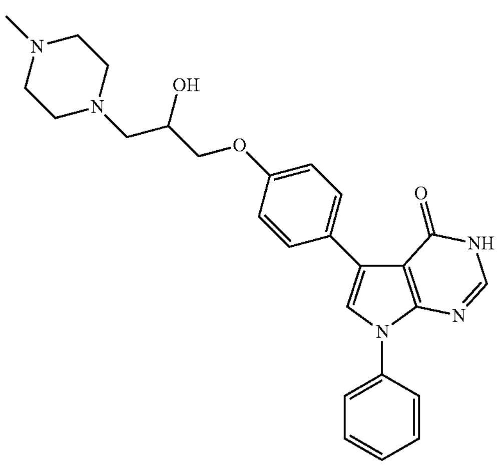 [SMILES: CN1CCN(CC(O)COc2ccc(-c3cn(-c4ccccc4)c4nc[nH]c(=O)c34)cc2)CC1] | Ex-48 (CP48) | LC-MS. $R_t$ 5.40 min, AnalpH2_MeOH_QC_V1(1); ($ESI^+$) m/z 460.4 $[M + H]^+$. | 27 mg, 84%, off-white solid |

TABLE 23-continued
| Compound | Ex. # (Intermediate used) | Analytical Data | Mass, % Yield, Appearance |
|---|---|---|---|
| 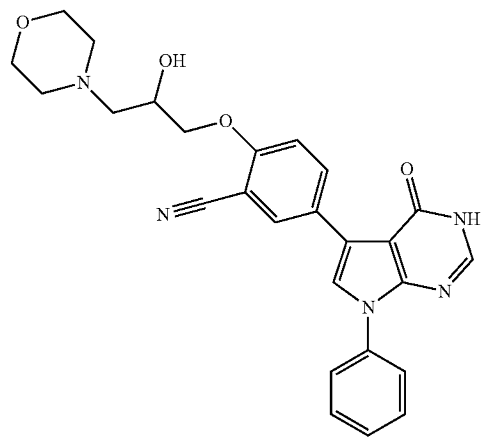 [SMILES: N#Cc1cc(-c2cn(-c3ccccc3)c3nc[nH]c(=O)c23)ccc1OCC(O)CN1CCOCC1] | Ex-49 (CP50) | LC-MS. $R_t$ 5.66 min, AnalpH2_MeOH_QC_V1(1) ($ESI^+$) m/z 472.3 $[M + H]^+$. | 23 mg, 31%, white solid |
| 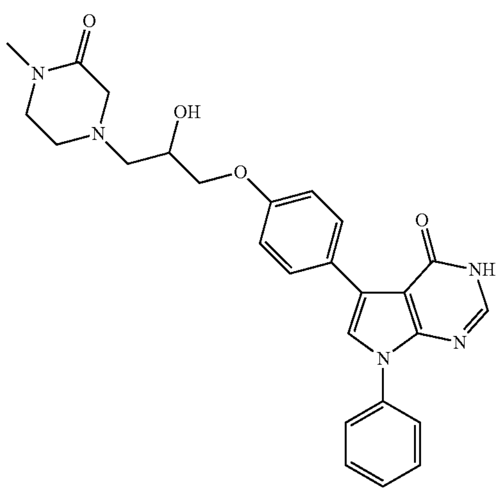 [SMILES: CN1CCN(CC(O)COc2ccc(-c3cn(-c4ccccc4)c4nc[nH]c(=O)c34)cc2)CC1=O] | Ex-50[f] (CP51) | LC-MS. $R_t$ 6.10 min, AnalpH2_MeOH_QC_V1(1); ($ESI^+$) m/z 474.4 $[M + H]^+$. | 4 mg, 5%, white solid |
| 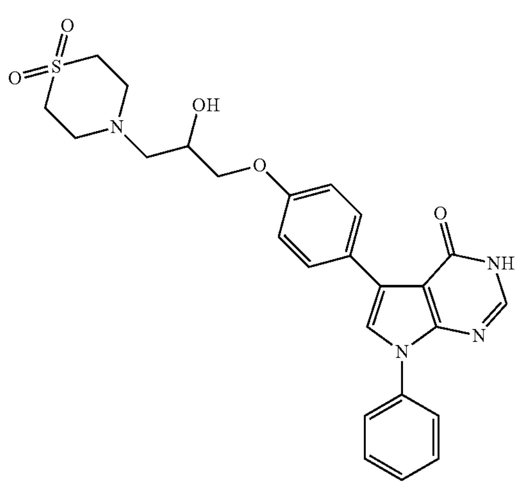 [SMILES: O=c1[nH]cnc2c1c(-c1ccc(OCC(O)CN3CCS(=O)(=O)CC3)cc1)cn2-c1ccccc1] | Ex-51 (CP52) | LC-MS. $R_t$ 7.01 min, AnalpH2_MeOH_QC_V1(1); ($ESI^+$) m/z 495.3 $[M + H]^+$. | 6 mg, 46%, off-white solid |

TABLE 23-continued

| Compound | Ex. # (Intermediate used) | Analytical Data | Mass, % Yield, Appearance |
|---|---|---|---|
| 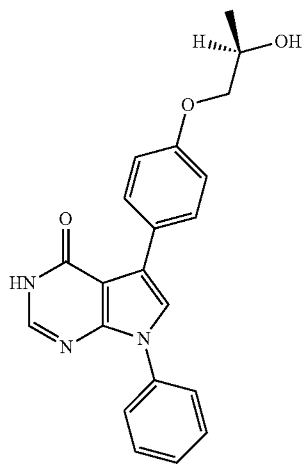 R isomer | Ex-52 (CP57) | LC-MS. $R_t$ 7.73 min, AnalpH2_MeOH_QC_V1(1); ($ESI^+$) m/z 362.2 $[M + H]^+$; $^1H$ NMR (400 MHz, DMSO-$d_6$): 12.09-12.06 (br s, 1H), 7.92-7.84 (m, 3H), 7.76-7.70 (m, 2H), 7.68 (s, 1H), 7.54-7.48 (m, 2H), 7.40-7.35 (m, 1H), 6.92-6.89 (m, 2H), 4.84 (d, J = 5.0, 1H), 3.97-3.89 (m, 1H), 3.85-3.74 (m, 2H), 1.13 (d, J = 6.4 Hz, 3H). | 12 mg, 25%, white solid. |
| 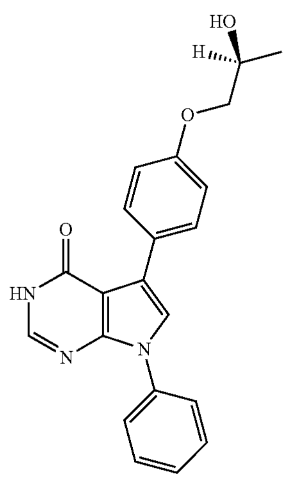 S isomer | Ex-53 (CP58) | LC-MS. $R_t$ 7.73 min, AnalpH2_MeOH_QC_V1(1); ($ESI^+$) m/z 362.2 $[M + H]^+$; $^1H$ NMR (400 MHz, DMSO-$d_6$): 12.10-12.07 (br s, 1H), 8.46-8.44 (br s, 1H), 7.92-7.86 (m, 3H), 7.71 (m, 2H), 7.51 (t, J = 7.3 Hz, 2H), 7.38 (t, J = 7.3 Hz, 1H), 6.90 (d, J = 9.2 Hz, 2H), 4.80 (d, J = 4.1 Hz, 1H), 3.97-3.89 (m, 1H), 3.85-3.75 (m, 2H), 1.13 (d, J = 6.0 Hz, 3H), | 6 mg, 16%, white solid |
| 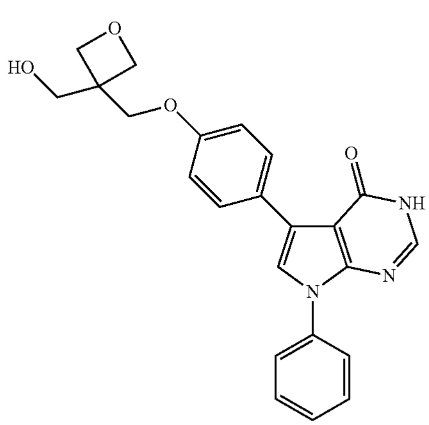 [SMILES: O=c1[nH]cnc2c1c(-c1ccc(OCC3(CO)COC3)cc1)cn2-c1ccccc1] | Ex-54 (CP56) | LC-MS. $R_t$ 7.54 min, AnalpH2_MeOH_QC_V1(1); ($ESI^+$) m/z 404.3 $[M + H]^+$ | 7 mg, 12%, white solid |

TABLE 23-continued

| Compound | Ex. # (Intermediate used) | Analytical Data | Mass, % Yield, Appearance |
|---|---|---|---|
| 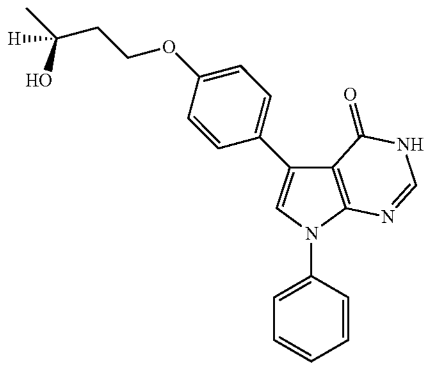 [SMILES: C[C@H](O)CCOc1ccc(-c2cn(-c3ccccc3)c3nc[nH]c(=O)c23)cc1] | Ex-103 (CP72) | LC-MS. $R_t$ 8.02 min, AnalpH2_MeOH_QC_V1(1); ($ESI^+$) m/z 376.3 $[M + H]^+$ | 2 mg, 5%, white solid |
| 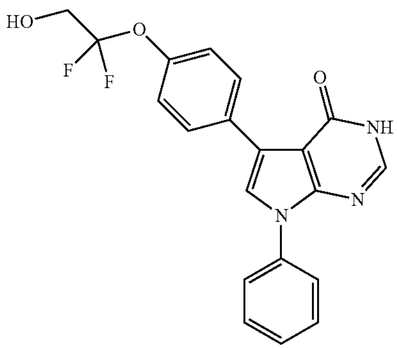 [SMILES: O=c1[nH]cnc2c1c(-c1ccc(OC(F)(F)CO)cc1)cn2-c1ccccc1] | Ex-104 (CP73) | LC-MS. $R_t$ 7.79 min, AnalpH2_MeOH_QC_V1(1); ($ESI^+$) m/z 384.3 $[M + H]^+$; $^1$H-NMR (400 MHz, DMSO-$d_6$): δ 12.16 (s, 1H), 7.99 (d, J = 8.7 Hz, 2H), 7.95 (s, 1H), 7.80 (s, 1H), 7.73 (d, J = 7.8 Hz, 2H), 7.53 (t, J = 7.8 Hz, 2H), 7.39 (t, J = 7.3 Hz, 1H), 7.17 (d, J = 8.2 Hz, 2H), 5.86 (t, J = 6.6 Hz, 1H), 3.90-3.76 (m, 2H) | 45 mg, 39%, white solid |

[e]Basic hydrolysis conducted at RT over 66 h.
[f]Isolated as a formic acid salt.

The following final compound was prepared directly from the silyl-protected chloro-pyrimidine.

5-{4-[3-(2-Hydroxy-ethyl)-2-oxo-imidazolidin-1-yl]-phenyl}-7-phenyl-3,7-dihydro-pyrrolo[2,3-d]pyrimidin-4-one (Ex-55)

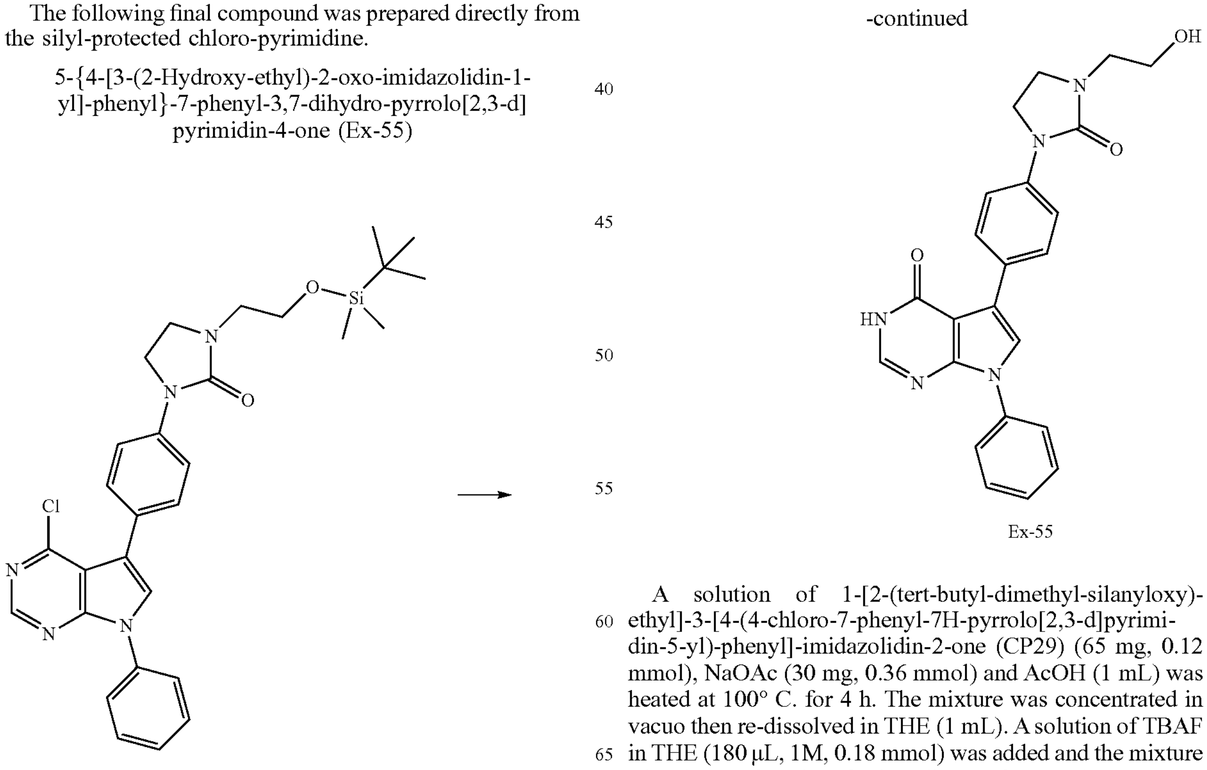

CP29

-continued

Ex-55

A solution of 1-[2-(tert-butyl-dimethyl-silanyloxy)-ethyl]-3-[4-(4-chloro-7-phenyl-7H-pyrrolo[2,3-d]pyrimidin-5-yl)-phenyl]-imidazolidin-2-one (CP29) (65 mg, 0.12 mmol), NaOAc (30 mg, 0.36 mmol) and AcOH (1 mL) was heated at 100° C. for 4 h. The mixture was concentrated in vacuo then re-dissolved in THE (1 mL). A solution of TBAF in THE (180 μL, 1M, 0.18 mmol) was added and the mixture stirred at RT for 3 h. A further aliquot of TBAF (180 μL, 1M, 0.18 mmol) was added and stirring continued at RT for 90 min. The mixture was concentrated in vacuo then re-dissolved in a mixture of THE (1 mL) and $H_2O$ (1 mL). $LiOH{\cdot}H_2O$ (25 mg, 0.6 mmol) was added and the mixture stirred at RT for 18 h. A further amount of $LiOH{\cdot}H_2O$ (15 mg, 0.36 mmol) was added and stirring continued at RT for a further 1 h. The mixture was purified by reversed phase preparative HPLC-MS. The material obtained was purified by silica gel chromatography, eluting with 0-20% MeOH/DCM. The material obtained was re-dissolved in MeCN: $H_2O$ (2 mL, 1:1) then lyophilised to afford 5-{4-[3-(2-hydroxy-ethyl)-2-oxo-imidazolidin-1-yl]-phenyl}-7-phenyl-3,7-dihydro-pyrrolo[2,3-d]pyrimidin-4-one as an off-white solid (24 mg, 48%); LC-MS. Rt 7.30 min. AnalpH2_MeOH_QC_V1(1); ($ESI^+$) m/z 416.1 $[M+H]^+$; $^1H$-NMR (400 MHz, DMSO-$d_6$): δ 12.11 (br s, 1H), 7.98-7.94 (m, 3H), 7.78-7.74 (m, 3H), 7.58-7.52 (m, 4H), 7.41 (t, J=7.6 Hz, 1H), 4.74 (br s, 1H), 3.84-3.80 (m, 2H), 3.57-3.52 (m, 4H), 3.25 (t, J=6.0 Hz, 2H).

Route 2a, Step 3: Final Compounds Via Basic Hydrolysis

5-[2-Fluoro-4-(2-hydroxy-ethoxy)-phenyl]-7-phenyl-3,7-dihydro-pyrrolo[2,3-d]pyrimidin-4-one (Ex-56)

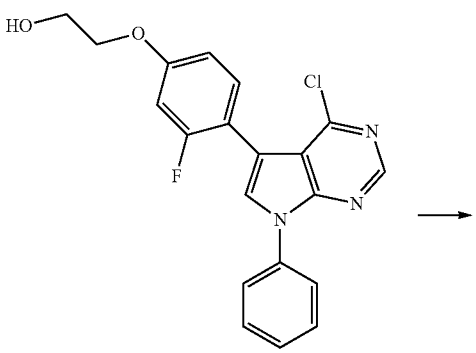

CP28

-continued

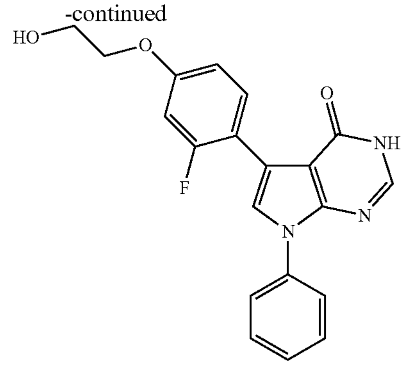

Ex-56

2M NaOH (415 μL, 0.83 mmol) was added to a stirred solution of 2-[4-(4-chloro-7-phenyl-7H-pyrrolo[2,3-d]pyrimidin-5-yl)-3-fluoro-phenoxy]-ethanol (CP28) (32.0 mg, 0.083 mmol) in 1,4-dioxane (500 μL). The resulting mixture was heated at reflux for 90 min. The reaction mixture was cooled to RT and acidified with formic acid to pH5. The resulting reaction mixture was concentrated in vacuo and the crude solid was then purified by reversed phase preparative HPLC-MS to afford 5-[2-fluoro-4-(2-hydroxy-ethoxy)-phenyl]-7-phenyl-3,7-dihydro-pyrrolo[2,3-d]pyrimidin-4-one (Ex-56) as a white solid (10 mg, 34%); LC-MS. Rt 7.36 min, AnalpH2_MeOH_QC_V1(1); ($ESI^+$) m/z 366.3 $[M+H]^+$; $^1H$ NMR (400 MHz, DMSO-$d_6$): 12.18-12.11 (br s, 1H), 7.98 (s, 1H), 7.80-7.72 (m, 3H), 7.60-7.53 (m, 3H), 7.46-7.41 (m, 1H), 6.88 (dd, J=12.6, 2.5 Hz, 1H), 6.84 (dd, J=8.6, 2.5 Hz, 1H), 4.86 (t, J=5.6 Hz, 1H), 4.03 (t, J=5.1 Hz, 2H), 3.74 (q, J=5.1 Hz, 2H).

The following examples were made using an analogous procedure to Ex-56:

TABLE 24

| Compound | Ex. # (Intermediate used) | Analytical Data | Mass, % Yield, Appearance |
|---|---|---|---|
| 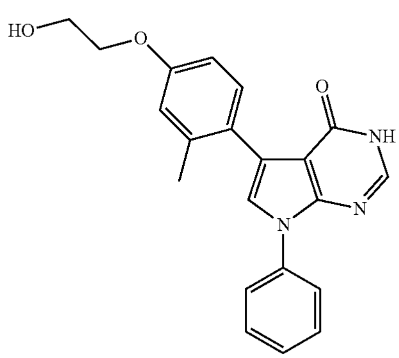 [SMILES: Cc1cc(OCCO)ccc1-c1cn(-c2ccccc2)c2nc[nH]c(=O)c12] | Ex-57 (CP29) | LC-MS. $R_t$ 7.33 min, AnalpH2_MeOH_QC_V1(1); ($ESI^+$) m/z 362.3 [M + H]$^+$. | 6 mg, 31%, off-white solid |

Route 2b, Step 4: Acidic Hydrolysis

5-Iodo-7-phenyl-3,7-dihydro-pyrrolo[2,3-d]pyrimidin-4-one (CH4)

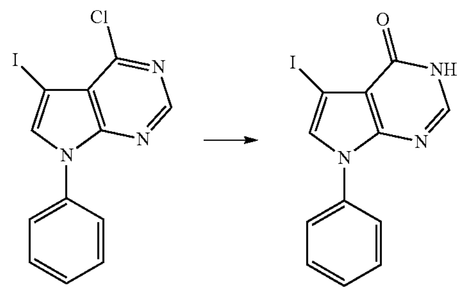

CH1 CH4

A suspension of 4-chloro-5-iodo-7-phenyl-7H-pyrrolo[2,3-d]pyrimidine (CH1) (4.00 g, 11.25 mmol) and NaOAc (1.85 g, 22.5 mmol) in AcOH (25 mL) was heated at 100° C. for 15 h. The reaction mixture was concentrated in vacuo. The crude solid was diluted with $H_2O$ and the resulting solid was filtered and dried under vacuum to afford 5-iodo-7-phenyl-3,7-dihydro-pyrrolo[2,3-d]pyrimidin-4-one (CH4) as a yellow solid (3.68 g, 97%); LC-MS. Rt 2.79 min, AnalpH2_MeOH_4 min(1); ($ESI^+$) m/z 338.1 $[M+H]^+$; $^1H$ NMR (400 MHz, DMSO-$d_6$): δ 12.16 (br s, 1H), 7.95 (s, 1H), 7.70-7.66 (m, 2H), 7.68 (s, 1H), 7.56-7.51 (m, 2H), 7.41 (tt, J=7.3 1.4 Hz, 1H).

The following intermediate was made using an analogous procedure to $CH_4$:

TABLE 25

| Compound | Cpd # (Intermediate Used) | Analytical Data | Mass, % Yield, Appearance |
|---|---|---|---|
| 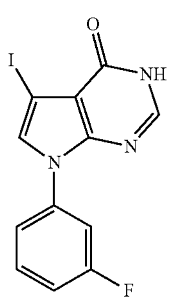 [SMILES: O=c1[nH]cnc2c1c(I)cn2-c1cccc(F)c1] | CH5 (CH2) | LC-MS, $R_t$ 2.94 min, AnalpH2_MeOH_4 min(1); ($ESI^+$) m/z 356.1 $[M + H]^+$. | 496 mg, 38%; white solid |

TABLE 25-continued

| Compound | Cpd # (Intermediate Used) | Analytical Data | Mass, % Yield, Appearance |
|---|---|---|---|
| 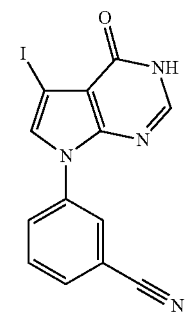 [SMILES: N#Cc1cccc(-n2cc(I)c3c(=O)[nH]cnc32)c1] | CH14[a] (CH12) | LC-MS. $R_t$ 2.58 min, AnalpH2_MeOH_4 min(1); ($ESI^+$) m/z 363.0 $[M + H]^+$. | 90 mg crude; white solid |
| 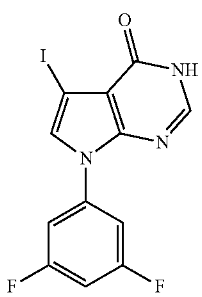 [SMILES: O=c1[nH]cnc2c1c(I)cn2-c1cc(F)cc(F)c1] | CH15 (CH13) | LC-MS. $R_t$ 2.99 min, AnalpH2_MeOH_4 min(1); ($ESI^+$) m/z 374.1 $[M + H]^+$. | 1.93 g, 85%; pink solid |

[a]Purified by silica gel chromatography.

Route 2b, Step 5: Final Compounds Via Suzuki-Miyaura Coupling

5-[4-(2-Methoxy-ethoxy)-phenyl]-7-phenyl-3,7-dihydro-pyrrolo[2,3-d]pyrimidin-4-one (Ex-58)

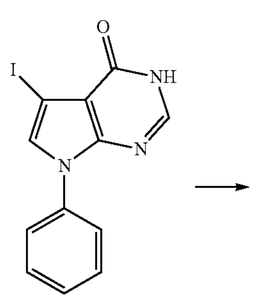

CH4

-continued

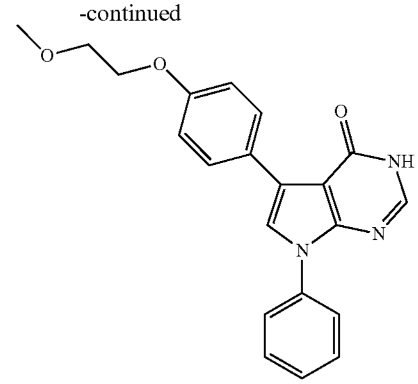

Ex-58

A mixture of 5-iodo-7-phenyl-3,7-dihydro-pyrrolo[2,3-d]pyrimidin-4-one (CH4) (180 mg, 0.534 mmol), 2-(4-(2-methoxyethoxy)phenyl-4,4,5,5-tetramethyl-1,3,2-dioxaborolane (186 mg, 0.667 mmol) (commercial source), Pd(dppf)$Cl_2$ (43.6 mg, 0.053 mmol) and $K_2CO_3$ (148 mg, 1.07 mmol) in 1,4-dioxane:$H_2O$ (3 mL, 9:1) was de-oxygenated for 5 min then heated in a microwave reactor at 120° C. for a total of 90 min. The reaction was repeated on the same scale with heating in a microwave reactor for 2 h. The reaction mixture were filtered through celite and washed with methanol. The combined organics were concentrated in vacuo. The crude solid was diluted with DCM (25 mL) and $H_2O$ (25 mL) and the layers separated via a phase separator. The combined organics were concentrated in vacuo. The crude solid was purified by silica gel chromatography eluting with 0-7.5% MeOH/DCM, followed by reversed phase preparative HPLC-MS. A final purification using silica gel chromatography was carried out by eluting with 0-5% MeOH/DCM to afford 5-[4-(2-methoxy-ethoxy)-phenyl]-7-phenyl-3,7-dihydro-pyrrolo[2,3-d]pyrimidin-4-one (Ex-58) as a white solid (70 mg, 18%); LC-MS. Rt 7.66 min, AnalpH2_MeOH_QC_V1(1); (ESI$^+$) m/z 362.2 [M+H]$^+$; $^1$H NMR (400 MHz, DMSO-$d_6$): 12.13 (br s, 1H), 7.95 (s, 1H), 7.93 (d, J=8.8 Hz, 2H), 7.78-7.75 (m, 2H), 7.73 (s, 1H), 7.58-7.55 (m, 2H), 7.42 (tt, J=7.6, 1.3 Hz, 1H), 6.95 (d, J=8.8 Hz, 2H), 4.13-4.11 (m, 2H), 3.69-3.66 (m, 2H), 3.32 (s, 3H).

The following examples were synthesised using analogous procedures to Ex-59 (duration of heating between 0.5-3 h)

TABLE 26

| Compound | Ex # (Intermediate used*) | Analytical Data | Mass, % Yield, Appearance |
|---|---|---|---|
| 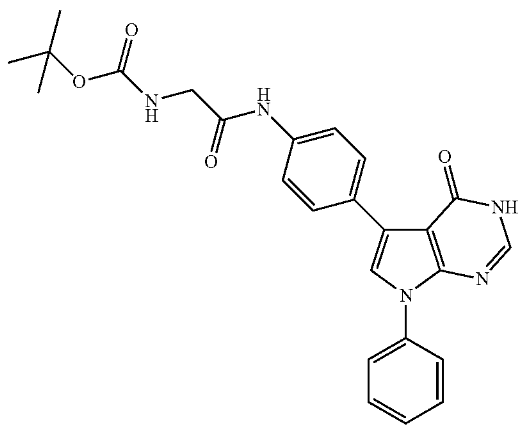 [SMILES: CC(C)(C)OC(=O)NCC(=O)Nc1ccc(-c2cn(-c3ccccc3)c3nc[nH]c(=O)c23)cc1] | Ex-59 (B22) | LC-MS. $R_t$ 3.14 min, AnalpH2_MeOH_4min; (ESI$^+$) m/z 460.4 [M + H]$^+$. | 30 mg, 44%, brown solid |
| 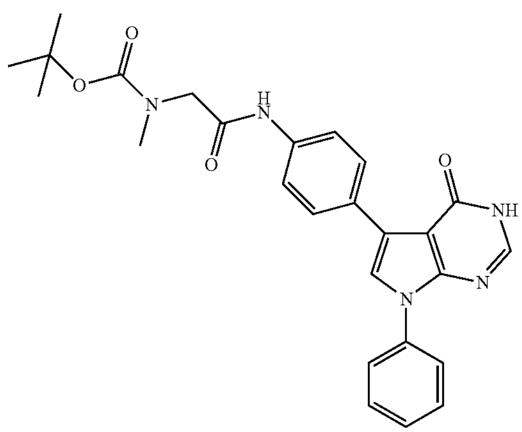 [SMILES: CN(CC(=O)Nc1ccc(-c2cn(-c3ccccc3)c3nc[nH]c(=O)c23)cc1)C(=O)OC(C)(C)C] | Ex-60 (B23) | LC-MS. $R_t$ 3.20 min, AnalpH2_MeOH_4min; (ESI$^+$) m/z 473.4 [M + H]$^+$. | 50 mg, 50%, brown oil |
| 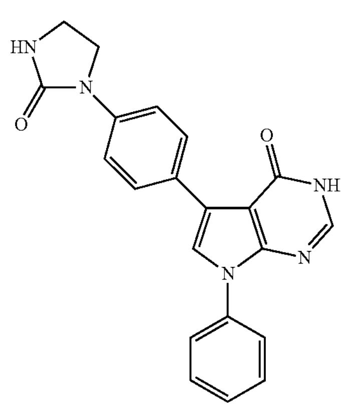 [SMILES: O=C1NCCN1c1ccc(-c2cn(-c3ccccc3)c3nc[nH]c(=O)c23)cc1] | Ex-61 (B1) | LC-MS. $R_t$ 7.10 min, AnalpH2_MeOH_QC_V1(1); (ESI$^+$) m/z 372.3 [M + H]$^+$ | 4 mg, 5%, pale brown solid |

TABLE 26-continued

| Compound | Ex # (Intermedi- ate used*) | Analytical Data | Mass, % Yield, Appearance |
| --- | --- | --- | --- |
| 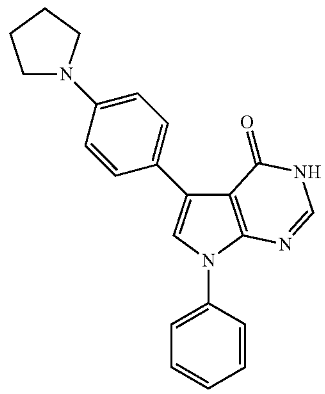 [SMILES: O=c1[nH]cnc2c1c(-c1ccc(N3CCCC3)cc1)cn2-c1ccccc1] | Ex-62 | LC-MS. $R_t$ 8.13 min, AnalpH2_MeOH_QC_V1(1); ($ESI^+$) m/z 357.3 $[M + H]^+$ | 5 mg, 5%, off-white solid |
| 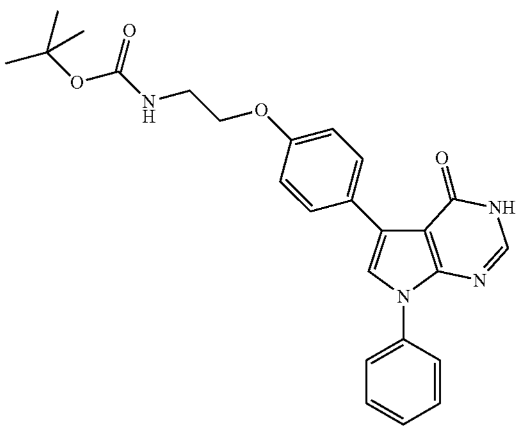 [SMILES: CC(C)(C)OC(=O)NCCOc1ccc(-c2cn(-c3ccccc3)c3nc[nH]c(=O)c23)cc1] | Ex-63 (B42) | LC-MS. $R_t$ 3.12 min, AnalpH2_MeOH_QC_V1(1); ($ESI^+$) m/z 447.3 $[M + H]^+$. | 25 mg, 25%, brown solid |
| 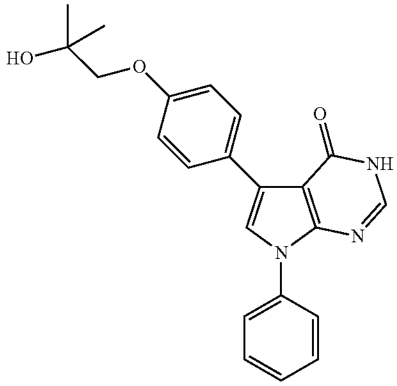 [SMILES: CC(C)(O)COc1ccc(-c2cn(-c3ccccc3)c3nc[nH]c(=O)c23)cc1] | Ex-64 (B45) | LC-MS. $R_t$ 8.02 min, AnalpH2_MeOH_QC_V1(1); ($ESI^+$) m/z 376.1 $[M + H]^+$; $^1H$ NMR (400 MHz, DMSO-$d_6$): 12.11 (br s, 1H), 7.95 (s, 1H), 7.92 (d, J = 8.7 Hz, 2H), 7.77 (d, J = 7.8 Hz, 2H), 7.72 (s, 1H), 7.55 (t, J = 8.0 Hz, 2H), 7.44-7.40 (m, 1H), 6.94 (d, J = 8.7 Hz, 2H), 4.64 (s, 1H), 3.74 (s, 2H), 1.22 (s, 6H). | 12 mg, 9%, white solid |

TABLE 26-continued

| Compound | Ex # (Intermediate used[a]) | Analytical Data | Mass, % Yield, Appearance |
|---|---|---|---|
| 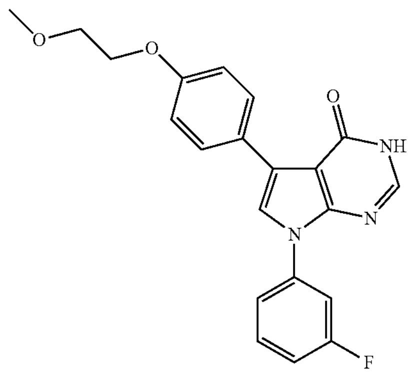 [SMILES: COCCOc1ccc(-c2cn(-c3cccc(F)c3)c3nc[nH]c(=O)c23)cc1] | Ex-65 (CH5) | LC-MS. $R_t$ 7.77 min, AnalpH2_MeOH_QC_V1(1); ($ESI^+$) m/z 380.2 $[M + H]^+$; | 8 mg, 3%, white solid |
| 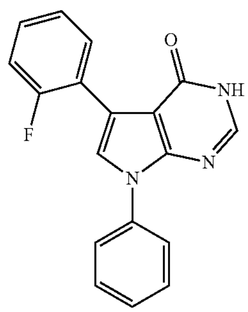 [SMILES: O=c1[nH]cnc2c1c(-c1ccccc1F)cn2-c1ccccc1] | Ex-66 | LC-MS. $R_t$ 7.87 min, AnalpH2_MeOH_QC_V1(1); ($ESI^+$) m/z 306.2 $[M + H]^+$. | 9 mg, 12%, off-white solid |
| 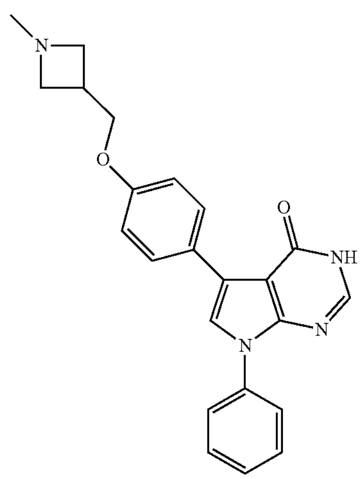 [SMILES: CN1CC(COc2ccc(-c3cn(-c4ccccc4)c4nc[nH]c(=O)c34)cc2)C1] | Ex-67[a,f] (B39) | LC-MS. $R_t$ 5.48 min, AnalpH2_MeOH_QC_V1(1); ($ESI^+$) m/z 387.2 $[M + H]^+$. | 2 mg, 2%, white solid |
| 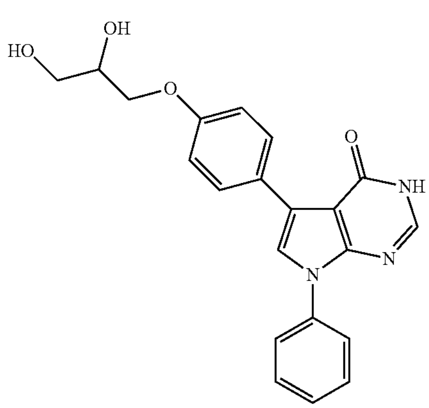 [SMILES: O=c1[nH]cnc2c1c(-c1ccc(OCC(O)CO)cc1)cn2-c1ccccc1] | Ex-68 (B8) | LC-MS. $R_t$ 7.14 min, AnalpH2_MeOH_QC_V1(1); ($ESI^+$) m/z 378.4 $[M + H]^+$. | 5.8 mg, 5%, white solid |

TABLE 26-continued

| Compound | Ex # (Intermediate used[a]) | Analytical Data | Mass, % Yield, Appearance |
|---|---|---|---|
| 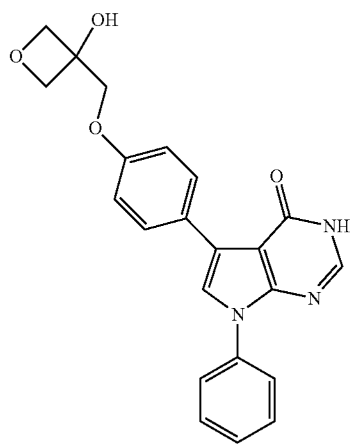 [SMILES: O=c1[nH]cnc2c1c(-c1ccc(OCC3(O)COC3)cc1)cn2-c1ccccc1] | Ex-69 (B41) | LC-MS. $R_t$ 7.41 min, AnalpH2_MeOH_QC_V1(1); ($ESI^+$) m/z 390.2 $[M + H]^+$. $^1H$ NMR (400 MHz, DMSO-$d_6$): 12.08 (br s, 1H), 7.92 (s, 1H), 7.92 (d, J = 8.7 Hz, 2H), 7.73 (d, J = 7.3 Hz, 2H), 7.70 (s, 1H), 7.52 (t, J = 7.8 Hz, 2H), 7.38 (t, J = 7.3 Hz, 1H), 6.97 (d, J = 8.7 Hz, 2H), 6.00 (s, 1H), 4.50 (d, J = 6.9 Hz, 2H), 4.46 (d, J = 6.4 Hz, 2H), 4.10 (s, 2H). | 31 mg, 9%, off-white solid |
| 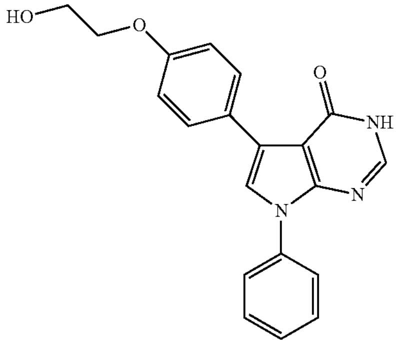 [SMILES: O=c1[nH]cnc2c1c(-c1ccc(OCCO)cc1)cn2-c1ccccc1] | Ex-70[b] | LC-MS. $R_t$ 7.32 min, AnalpH2_MeOH_QC_V1(1); ($ESI^+$) m/z 348.2 $[M + H]^+$; $^1H$ NMR (400 MHz, DMSO-$d_6$): 12.13 (br s, 1H), 7.96 (s, 1H), 7.93 (d, J = 8.8 Hz, 2H), 7.77 (dd, J = 8.8, 1.2 Hz, 2H), 7.73 (s, 1H), 7.57-7.53 (m, 2H), 7.44-7.40 (m, 1H), 6.95 (d, J = 8.8 Hz, 2H), 4.64 (t, J = 5.2 Hz, 1H), 4.02 (t, J = 4.8 Hz, 2H), 3.75-3.71 (m, 2H). | 14 mg, 27%, off-white solid |
| 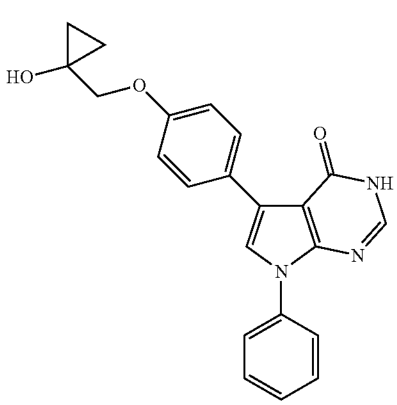 [SMILES: O=c1[nH]cnc2c1c(-c1ccc(OCC3(O)CC3)cc1)cn2-c1ccccc1] | Ex-105 (B47) | LC-MS. $R_t$ 7.77 min, AnalpH2_MeOH_QC_V1(1); ($ESI^+$) m/z 374.3 $[M + H]^+$; $^1H$-NMR (400 MHz, DMSO-$d_6$): δ 12.08 (s, 1H), 7.95-7.85 (m, 3H), 7.78-7.70 (m, 2H), 7.69 (s, 1H), 7.58-7.47 (m, 2H), 7.44-7.32 (m1H), 6.98-6.87 (m, 2H), 5.57 (s, 1H), 3.95 (s, 2H), 0.72-0.62 (m, 2H), 0.62-0.54 (m, 2H) | 17 mg, 12%, white solid |

TABLE 26-continued

| Compound | Ex # (Intermediate used[*]) | Analytical Data | Mass, % Yield, Appearance |
|---|---|---|---|
| 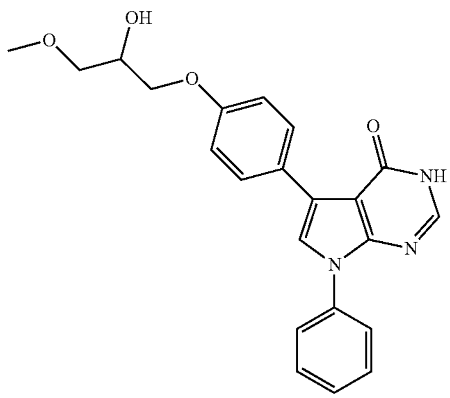 [SMILES: COCC(O)COc1ccc(-c2cn(-c3ccccc3)c3nc[nH]c(=O)c23)cc1] | Ex-106 (B68) | LCMS $R_t$ 7.65 min AnalpH2_MeOH_QC_V1(1), ($ESI^+$) m/z 391.4 $[M + H]^+$; | 10 mg, 18%, white solid |

[a] $Cs_2CO_3$ was used instead of $K_2CO_3$;
[b] $Pd(PPh_3)_4$ used instead of $Pd(dppf)Cl_2$•DCM;
[f] Isolated as a formic acid salt.
[*] If not stated commercial and/or CH4.

Route 2b, Step 5: Final Compounds Via Suzuki Coupling Using PdXPhosG3 with $K_3PO_4$ as base 5-(2-fluoro-4-(3-hydroxy-3-methyl butoxy)phenyl)-7-phenyl-3,7-dihydro-4H-pyrrolo[2,3-d]pyrimidin-4-one (Ex-107)

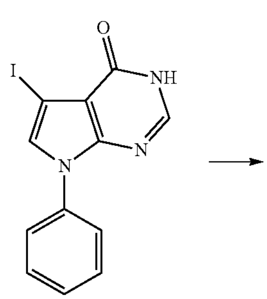

CH4

-continued

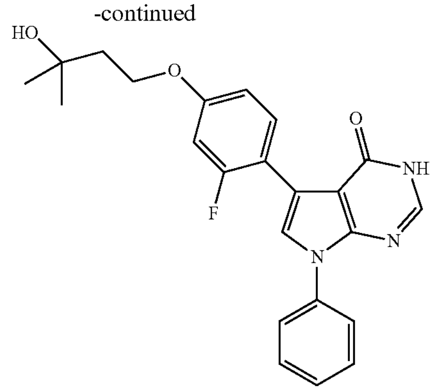

Ex-107

5-Iodo-7-phenyl-3,7-dihydro-4H-pyrrolo[2,3-d]pyrimidin-4-one (100 mg, 0.297 mmol), 4-(3-fluoro-4-(4,4,5,5-tetramethyl-1,3,2-dioxaborolan-2-yl)phenoxy)-2-methyl butan-2-ol (B56) (115 mg, 0.356 mmol), $K_3PO_4$ (126 mg, 0.594 mmol), PdXPhosG3 (12.7 mg, 0.015 mmol) in 1,4-dioxane:$H_2O$ (3 mL, 4:1) was de-oxygenated with $N_2$ for 5 min and then heated in a microwave reactor at 90° C. for 1 h. The reaction mixture was filtered through a Si-thiol cartridge (2 g) and washed with MeOH (3×CV) followed by DCM (3×CV). The filtrate was evaporated to dryness and the crude residue was purified by purified by silica gel column chromatography eluting with 0-10% MeOH/DCM followed by reversed phase preparative HPLC to afford 5-(2-fluoro-4-(3-hydroxy-3-methyl butoxy)phenyl)-7-phenyl-3,7-dihydro-4H-pyrrolo[2,3-d]pyrimidin-4-one as a white solid (47 mg, 39%); LC-MS. Rt 8.27 m, AnalpH2_MeOH_QC_V1(1); ($ESI^+$) m/z 408.3$[M+H]^+$; $^1$H-NMR (400 MHz, DMSO-$d_6$) δ 12.12 (s, 1H), 7.97 (m, 1H), 7.78-7.72 (m, 3H), 7.58-7.53 (3H), 7.45-7.40 (m, 1H), 6.90-6.80 (m, 2H), 4.41 (m, 1H), 4.14 (t, J 7.1 Hz, 2H), 1.86 (t, J, 2H), 1.18 (d, 6H).

The following compounds of formula (Ia) were made using analogous procedures to compound Ex-x with heating durations between hr-1.5 hrs:

TABLE 27
| Compound | Ex # (Intermediate used^a) | Analytical Data | Mass, % Yield, Appearance |
| --- | --- | --- | --- |
| 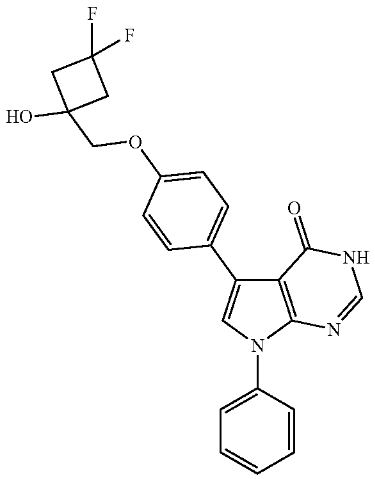 [SMILES: O=c1[nH]cnc2c1c(-c1ccc(OCC3(O)CC(F)(F)C3)cc1)cn2-c1ccccc1] | Ex-108 (B52) | LC-MS. $R_t$ 8.11 min, AnalpH2_MeOH_QC_V1(1); ($ESI^+$) m/z 424.2 $[M + H]^+$; $^1$H-NMR (400 MHz, DMSO-$d_6$): δ 12.12 (br s, 1H), 7.97-7.92 (m, 3H), 7.79-7.75 (m, 2H), 7.74 (s, 1H), 7.58-7.53 (m, 2H), 7.44-7.39 (m, 1H), 6.98 (d, J = 9.2 Hz, 2H), 5.85 (s, 1H), 3.99 (s, 2H), 2.91-2.80 (m, 2H), 2.68-2.56 (m, 2H). | 84 mg, 47%, white solid |
| 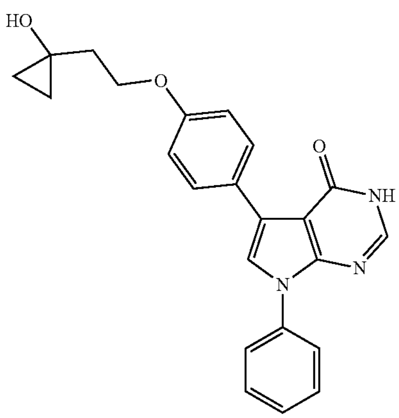 [SMILES: O=c1[nH]cnc2c1c(-c1ccc(OCCC3(O)CC3)cc1)cn2-c1ccccc1] | Ex-109 (B51) | LC-MS. $R_t$ 8.06 min, AnalpH2_MeOH_QC_V1(1); ($ESI^+$) m/z 388.2 $[M + H]^+$ | 58 mg, 17%, white solid |
| 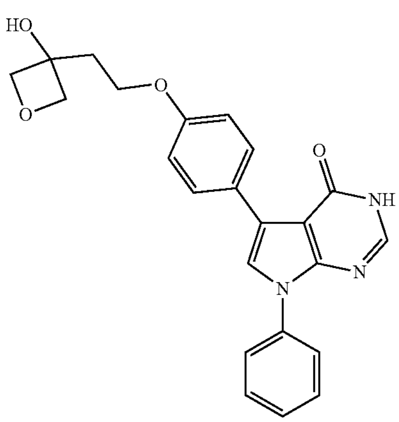 [SMILES: O=c1[nH]cnc2c1c(-c1ccc(OCCC3(O)COC3)cc1)cn2-c1ccccc1] | Ex-110 (B53) | LC-MS. $R_t$ 7.69 min, AnalpH2_MeOH_QC_V1(1); ($ESI^+$) m/z 404.3 $[M + H]^+$ | 85 mg, 47%, white solid |

TABLE 27-continued

| Compound | Ex # (Intermediate used[a]) | Analytical Data | Mass, % Yield, Appearance |
| --- | --- | --- | --- |
| 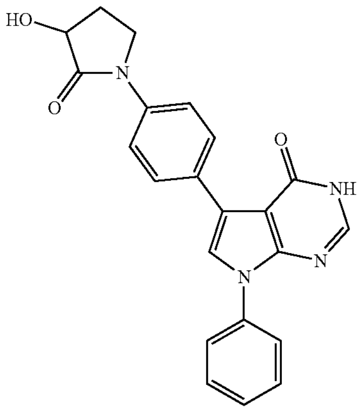 [SMILES: O=C1C(O)CCN1c1ccc(-c2cn(-c3ccccc3)c3nc[nH]c(=O)c23)cc1] | Ex-111 (B50) | LC-MS. $R_t$ 7.15 min, AnalpH2_MeOH_QC_V1(1); ($ESI^+$) m/z 387.2 $[M + H]^+$; $^1H$-NMR (400 MHz, DMSO-$d_6$): δ 12.14 (s, 1H), 8.05-7.97 (m, 2H), 7.94 (s, 1H), 7.79 (s, 1H), 7.76-7.70 (m, 2H), 7.69-7.62 (m, 2H), 7.57-7.49 (m, 2H), 7.43-7.35 (m, 1H), 5.83-5.60 (m, 1H), 4.36-4.18 (m, 1H), 3.85-3.62 (m, 2H), 2.44-2.32 (m, 1H), 1.92-1.65 (m, 1H) | 38 mg, 22%, white solid |
| 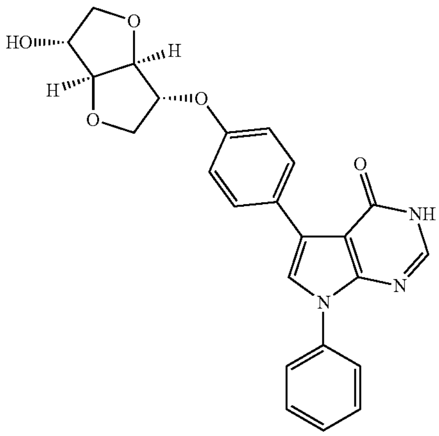 [SMILES: O=c1[nH]cnc2c1c(-c1ccc(O[C@@H]3CO[C@@H]4[C@H]3OC[C@H]4O)cc1)cn2-c1ccccc1] | Ex-112[a] (B65) | LCMS. $R_t$ 7.60 min AnalpH2_MeOH_QC_V1(1), ($ESI^+$) m/z 432.2 $[M + H]^+$; $^1H$-NMR (400 MHz, DMSO-$d_6$): δ 7.94-7.89 (m, 3H), 7.75-7.70 (m, 3H), 7.52 (t, J = 8.2 Hz, 2H), 7.41-7.35 (m, 1H), 6.95 (t, J = 8.7 Hz, 2H), 5.21 (d, J = 3.7 Hz, 1H), 4.86-4.82 (m, 1H), 4.56 (d, J = 4.1 Hz, 1H), 4.40 (d, J = 4.1 Hz, 1H), 4.08 (t, J = 3.4 Hz, 1H), 3.94 (dd, J = 4.1, 10.3 Hz, 1H), 3.83 (dd J = 1.4, 10.3 Hz, 1H), 3.75 (dd, J = 3.4, 9.6 Hz, 1H), 3.66 (d, J = 9.6 Hz, 1H). | 42 mg, 28% white solid |
| 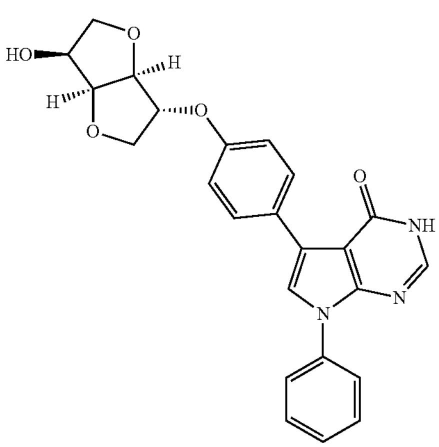 [SMILES: O=c1[nH]cnc2c1c(-c1ccc(O[C@@H]3CO[C@@H]4[C@H]3OC[C@@H]4O)cc1)cn2-c1ccccc1] | Ex-113[a] (B66) | LCMS $R_t$ 7.55 min AnalpH2_MeOH_QC_V1(1) ($ESI^+$) m/z, 432.2 $[M + H]^+$; $^1H$-NMR (400 MHz, DMSO-$d_6$): δ 12.10 (br s, 1H), 7.93-7.88 (m, 3H), 7.75-7.69 (m, 3H), 7.51 (t, J = 7.3 Hz, 2H), 7.40-7.35 (m, 1H), 6.93 (d, J = 8.7 Hz, 2H), 4.90 (d, J = 6.2 Hz, 1H), 4.80 (dd, J = 0.92, 3.8 Hz, 1H), 4.49-4.45 (m, 2H), 4.12-4.08 (m, 1H), 4.04 (dd, J = 3.8, 10.3 Hz, 1H), 3.92 (dd, J = 1.4, 10.3 Hz, 1H), 3.74 (dd, J = 6.2, 8.2 Hz, 1H) 3.40 (dd, J = 7.3, 8.2 Hz, 1H). | 140 mg, 74%, white solid |

TABLE 27-continued

| Compound | Ex # (Intermediate used[a]) | Analytical Data | Mass, % Yield, Appearance |
|---|---|---|---|
| 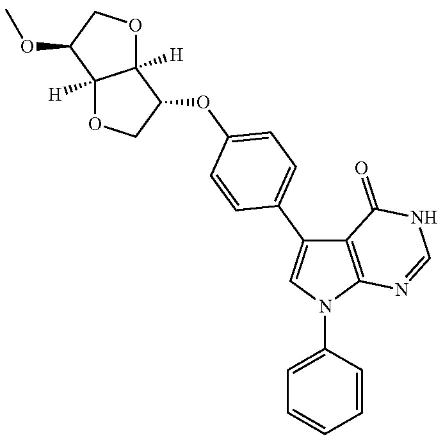 [SMILES: CO[C@H]1CO[C@@H]2[C@H]1OC[C@H]2Oc1ccc(-c2cn(-c3ccccc3)c3nc[nH]c(=O)c23)cc1] | Ex-114[a] (B69) | LCMS $R_t$ 7.89 min AnalpH2_MeOH_QC_V1(1), ($ESI^+$) m/z 446.2 $[M + H]^+$; $^1H$-NMR (400 MHz, DMSO-$d_6$): δ 12.05 (br s, 1H), 7.94-7.89 (m, 3H), 7.74-7.69 (m, 3H), 7.51 (t, J = 7.8 Hz, 2H), 7.40-7.35 (m, 1H), 6.93 (d, J = 8.7 Hz, 2H), 4.84 (d, J = 3.0 Hz, 1H), 4.69 (t, J = 5.0 Hz, 1H), 4.51 (d, J = 4.6 Hz, 1H), 4.00 (dd, J = 4.12, 10.5 Hz, 1H), 3.90-3.80 (m, 3H), 3.50 (dd, J = 7.33, 8.7 Hz, 1H), 3.31 (s, 3H) | 26 mg, 34%, white solid |
| 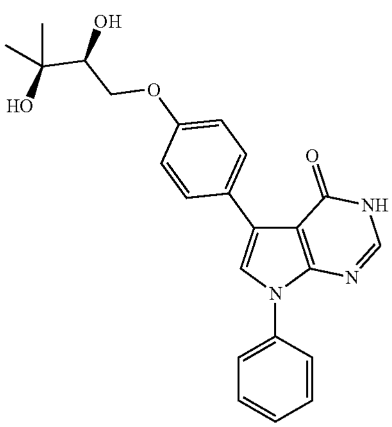 | Ex-115[a] (B67) | LCMS. $R_t$ 7.56 min AnalpH2_MeOH_QC_V1(1) ($ESI^+$); m/z 406.3 $[M + H]^+$; ; $^1H$-NMR (400 MHz, DMSO-$d_6$): δ 12.07 (br s, 1H), 7.93-7.85 (m, 3H), 7.72 (d, J = 8.0 Hz, 2H), 7.67 (s, 1H), 7.51 (t, J = 7.7 Hz, 2H), 7.73 (t, J = 7.3 Hz, 1H), 6.91 (d, J = 8.7 Hz, 2H), 4.96 (d, J = 5.5 Hz, 1H), 4.38 (br s, 1H), 4.22 (dd, J = 1.8, 10.1 Hz, 1H), 3.99 ( dd, J = 7.8, 9.6 Hz, 1H), 3.55-3.49 (m, 1H), 1.11 (s, 3H), 1.05 (s, 3H). | 10 mg, 7%, white solid |
| 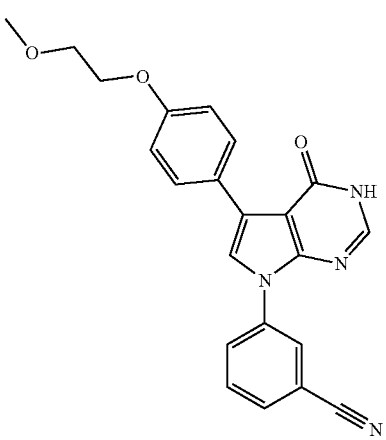 [SMILES: COCCOc1ccc(-c2cn(-c3cccc(C#N)c3)c3nc[nH]c(=O)c23)cc1] | Ex-116[a] (CH14) | LCMS. Rt 7.50 min AnalpH2_MeOH_4 min(1); ($ESI^+$) m/z 387.2 $[M + H]^+$; $^1H$-NMR (400 MHz, DMSO-$d_6$): δ 12.19 (s, 1H), 8.32 (t, J = 1.8 Hz, 1H), 8.21-8.16 (m, 1H), 7.99 (s, 1H), 7.90 (d, J = 8.7 Hz, 2H), 7.86-7.82 (m, 2H), 7.76-7.70 (m, 1H), 6.93 (d, J = 8.7 Hz, 2H), 4.11-4.07 (m, 2H), 3.67-3.61 (m, 2H), 3.25 (s, 3H) | 37 mg, 39%, white solid, |

TABLE 27-continued

| Compound | Ex # (Intermediate used^a) | Analytical Data | Mass, % Yield, Appearance |
|---|---|---|---|
| 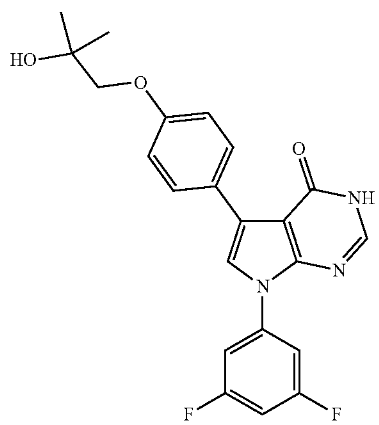 [SMILES: CC(C)(O)COc1ccc(-c2cn(-c3cc(F)cc(F)c3)c3nc[nH]c(=O)c23)cc1] | Ex-117[a] (B45, CH15) | LCMS. Rt 8.22 min AnalpH2_MeOH_4 min(1); ($ESI^+$) m/z 412.2 $[M + H]^+$; $^1$H-NMR (400 MHz, DMSO-$d_6$): δ 12.22 (bs, 1H), 8.01 (s, 1H), 7.88 (d, J = 8.7 Hz, 2H), 7.83 (s, 1H), 7.73 (dd, J = 8.9, 2.1 Hz, 2H), 7.31-7.24 (m, 1H), 6.92 (d, J = 8.7 Hz, 2H), 4.61 (s, 1H), 3.71 (s, 2H), 1.18 (s, 6H) | 20 mg, 12%, white solid |
| 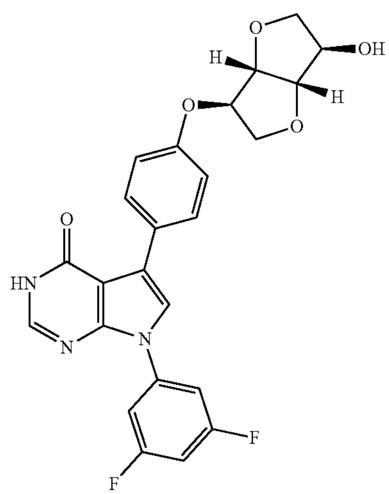 [SMILES: O=c1[nH]cnc2c1c(-c1ccc(O[C@@H]3CO[C@@H]4[C@H]3OC[C@H]4O)cc1)cn2-c1cc(F)cc(F)c1] | Ex-118[a] (B65, CH15) | LCMS. Rt 7.90 min AnalpH2_MeOH_4 min(1); ($ESI^+$) m/z 468.2 $[M + H]^+$. | 17 mg, 5%, white solid |
| 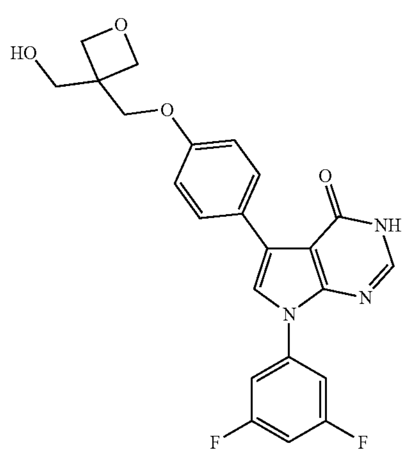 [SMILES: O=c1[nH]cnc2c1c(-c1ccc(OCC3(CO)COC3)cc1)cn2-c1cc(F)cc(F)c1] | Ex-119[a] (B9, CH15) | LCMS. Rt 7.85 min AnalpH2_MeOH_4 min(1); ($ESI^+$) m/z 440.2 $[M + H]^+$; $^1$H-NMR (400 MHz, DMSO-$d_6$): δ 12.23 (s, 1H), 8.03 (s, 1H), 7.92 (d, J = 8.7 Hz, 2H), 7.85 (s, 1H), 7.74 (dd, J = 8.5, 2.1 Hz, 2H), 7.29 (tt, J = 9.2, 2.2 Hz, 1H), 6.98 (d, J = 9.2 Hz, 2H), 4.99 (t, J = 5.3 Hz, 1H), 4.40 (q, J = 5.3 Hz, 4H), 4.16 (s, 2H), 3.70 (d, J = 5.5 Hz, 2H) | 81 mg, 46%, white solid |

TABLE 27-continued

| Compound | Ex # (Intermediate used^a) | Analytical Data | Mass, % Yield, Appearance |
| --- | --- | --- | --- |
| 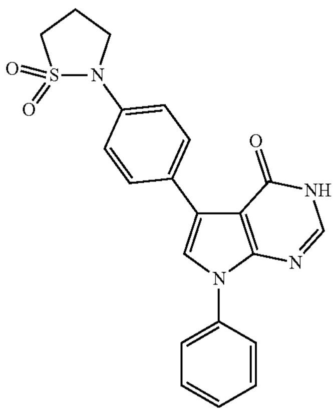 [SMILES: O=c1[nH]cnc2c1c(-c1ccc(N3CCCS3(=O)=O)cc1)cn2-c1ccccc1] | Ex-120[a] (B54) | LC-MS. $R_t$ 7.31 min, AnalpH2_MeOH_QC_V1(1); ($ESI^+$) m/z 407.2 $[M + H]^+$ | 48 mg, 27%, white solid |
| 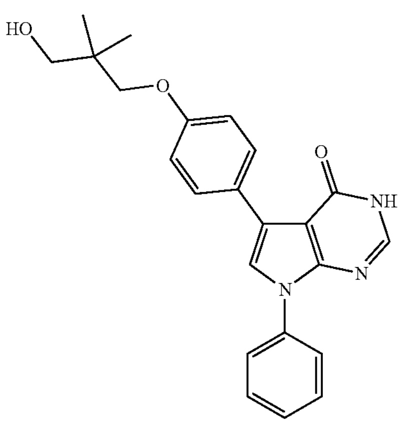 [SMILES: CC(C)(CO)COc1ccc(-c2cn(-c3ccccc3)c3nc[nH]c(=O)c23)cc1] | Ex-121[a] (B55) | LC-MS. $R_t$ 8.25 min, AnalpH2_MeOH_QC_V1(1); ($ESI^+$) m/z 390.3 $[M + H]^+$; $^1$H-NMR (400 MHz, DMSO-$d_6$): δ 12.10 (br s, 1H), 7.96 (s, 1H), 7.92 (** d, J = 9.2 Hz, 2H), 7.80-7.76 (m, 2H), 7.16 (s, 1H), 7.56 (t, J = 7.3 Hz, 2H), 7.42 (t, J = 7.3 Hz, 1H), 6.94 (** d, J = 9.2 Hz, 2H), 4.61 (t, J = 5.5 Hz, 1H), 3.74 (s, 2H), 3.31 (d, J = 5.5 Hz, 2H), 0.95 (s, 6H). | 53 mg, 46%, white solid |
| 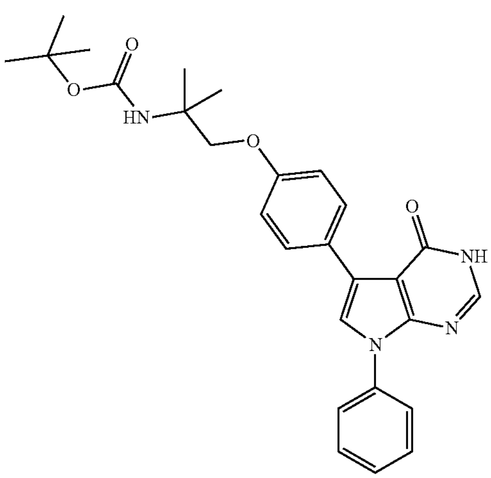 [SMILES: CC(C)(COc1ccc(-c2cn(-c3ccccc3)c3nc[nH]c(=O)c23)cc1)NC(=O)OC(C)(C)C] | Ex-122 (B57) | LC-MS. $R_t$ 3.44 min, AnalpH2_MeOH_4 min(1); ($ESI^+$) m/z 475.3 $[M + H]^+$. | 147 mg, 77%, pale brown solid |

TABLE 27-continued

| Compound | Ex # (Intermediate used*) | Analytical Data | Mass, % Yield, Appearance |
|---|---|---|---|
| 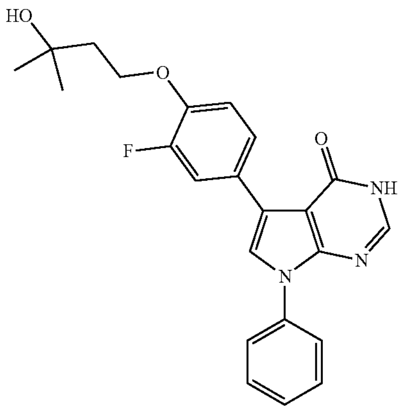 [SMILES: CC(C)(O)CCOc1ccc(-c2cn(-c3ccccc3)c3nc[nH]c(=O)c23)cc1F] | Ex-123 (B59) | LC-MS. $R_t$ 8.09 min, AnalpH2_MeOH_QC_V1(1); (ESI$^+$) m/z 408.2 [M + H]$^+$; $^1$H-NMR (400 MHz, DMSO-$d_6$): δ 12.18 (br s, 1H), 8.02 (dd, J = 13.7, 2.3 Hz, 1H), 7.97 (s, 1H), 7.86 (s, 1H), 7.84-7.80 (m, 1H), 7.79-7.75 (m, 2H), 7.59-7.53 (m, 2H), 7.45-7.40 (m, 1H), 7.18 (d, J = 9.0 Hz, 1H), 4.41 (s, 1H), 4.19 (t, J = 7.1 Hz, 2H), 1.88 (t, J = 7.1 Hz, 2H), 1.18 (s, 6H). | 63 mg, 35%, white solid |
| 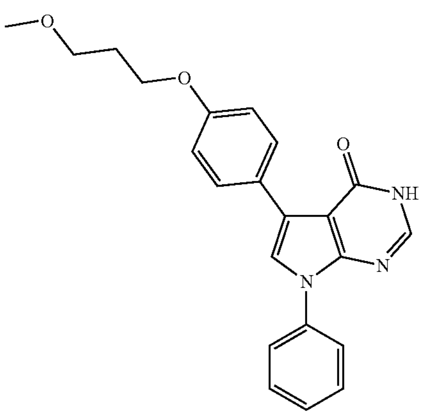 [SMILES: COCCCOc1ccc(-c2cn(-c3ccccc3)c3nc[nH]c(=O)c23)cc1] | Ex-124 (B64) | LC-MS. $R_t$ 8.19 min, AnalpH2_MeOH_QC_V1(1); (ESI$^+$) m/z 376.3 [M + H]$^+$; $^1$H-NMR (400 MHz, DMSO-$d_6$): δ 12.08 (br s, 1H), 7.95 (s, 1H), 7.92 (d, J = 8.7 Hz, 2H), 7.79-7.75 (m, 2H), 7.72 (s, 1H), 7.58-7.53 (m, 2H), 7.44-7.39 (m, 1H), 6.94 (d, J = 9.2 Hz, 2H), 4.05 (t, J = 6.4 Hz, 2H), 3.49 (t, J = 6.4 Hz, 2H), 2.91 (s, 3H), 1.96 (quint, J = 6.4 Hz, 2H). | 13 mg, 31%, white solid |
| 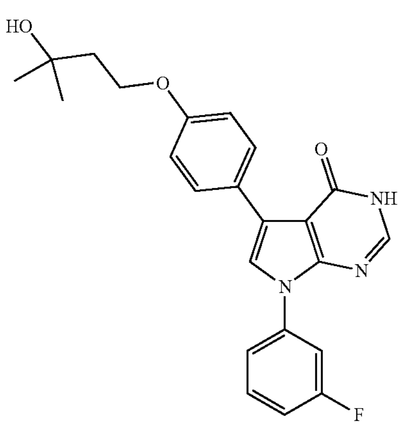 [SMILES: CC(C)(O)CCOc1ccc(-c2cn(-c3cccc(F)c3)c3nc[nH]c(=O)c23)cc1] | Ex-125 (B10, CH5) | LC-MS. $R_t$ 8.17 min, AnalpH2_MeOH_QC_V1(1); (ESI$^+$) m/z 408.2 [M + H]$^+$; | 51 mg, 44%, off-white solid |

TABLE 27-continued

| Compound | Ex # (Intermediate used^a) | Analytical Data | Mass, % Yield, Appearance |
|---|---|---|---|
| 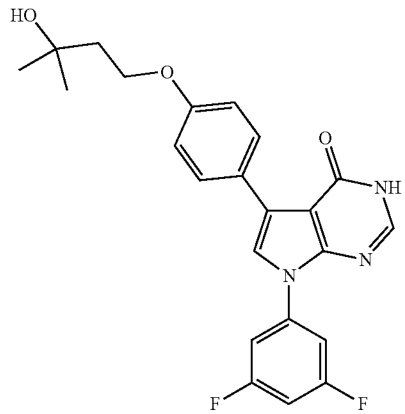 [SMILES: CC(C)(O)CCOc1ccc(-c2cn(-c3cc(F)cc(F)c3)c3nc[nH]c(=O)c23)cc1] | Ex-126[a] (B10, CH15) | LC-MS. $R_t$ 8.34 min, AnalpH2_MeOH_QC_V1(1); ($ESI^+$) m/z 426.2 $[M + H]^+$; $^1$H-NMR (400 MHz, DMSO-$d_6$): δ 12.28 (br s, 1H), 8.06 (s, 1H), 7.92 (** d, J = 9.2 Hz, 2H), 7.87 (s, 1H), 7.77 (dd, J = 8.7, 1.8 Hz, 2H), 7.32 (tt, J = 9.2, 2.3 Hz, 1H), 6.96 (** d, J = 9.2 Hz, 2H), 4.41 (s, 1H), 4.13 (t, J = 7.3 Hz, 2H), 1.87 (t, J = 7.3 Hz, 2H), 1.19 (s, 6H). | 60 mg, 35%, white solid |
| 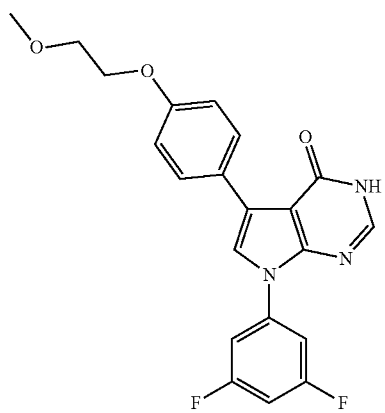 [SMILES: COCCOc1ccc(-c2cn(-c3cc(F)cc(F)c3)c3nc[nH]c(=O)c23)cc1] | Ex 127[a] (CH15) | LC-MS. $R_t$ 8.17 min, AnalpH2_MeOH_QC_V1(1); ($ESI^+$) m/z 398.2 $[M + H]^+$; $^1$H-NMR (400 MHz, DMSO-$d_6$): δ 12.28 (br s, 1H), 8.06 (s, 1H), 7.94 (app d, J = 8.7 Hz, 2H), 7.88 (s, 1H), 7.78 (dd, J = 8.2, 1.8 Hz, 2H), 7.32 (tt, J = 9.2, 2.3 Hz, 1H), 6.98 (** d, J = 8.7 Hz, 2H), 4.14 (t, J = 4.6 Hz, 2H), 3.69 (t, J = 4.6 Hz, 2H), 3.34 (s, 3H). | 25 mg, 16%, white solid |
| 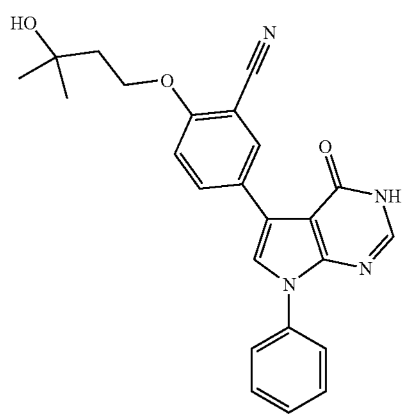 [SMILES: CC(C)(O)CCOc1ccc(-c2cn(-c3ccccc3)c3nc[nH]c(=O)c23)cc1C#N] | Ex-128[a] (B60) | LC-MS. $R_t$ 7.88 min, AnalpH2_MeOH_QC_V1(1); ($ESI^+$) m/z 415.3 $[M + H]^+$; $^1$H-NMR (400 MHz, DMSO-$d_6$): δ 12.24 (br s, 1H), 8.45 (d, J = 2.3 Hz, 1H), 8.36 (dd, J = 8.7, 2.3 Hz, 1H), 8.00 (s, 1H), 7.97 (s, 1H), 7.79 (d, J = 7.8 Hz, 2H), 7.58 (t, J = 7.8 Hz, 2H), 7.44 (t, J = 7.8 Hz, 1H), 7.32 (d, J = 8.7 Hz, 1H), 4.46 (s, 1H), 4.30 (t, J = 6.9 Hz, 2H), 1.91 (t, J = 6.9 Hz, 2H), 1.21 (s, 6H). | 64 mg, 35%, white solid |

TABLE 27-continued

| Compound | Ex # (Intermediate used[a]) | Analytical Data | Mass, % Yield, Appearance |
|---|---|---|---|
| 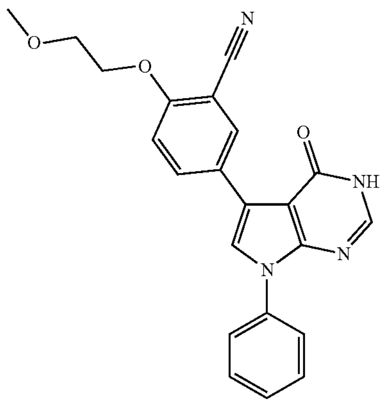 [SMILES: COCCOc1ccc(-c2cn(-c3ccccc3)c3nc[nH]c(=O)c23)cc1C#N] | Ex-129[a] (B61) | LC-MS. $R_t$ 7.69 min, AnalpH2_MeOH_QC_V1(1); ($ESI^+$) m/z 387.2 $[M + H]^+$ | 98 mg, 57%, white solid |
| 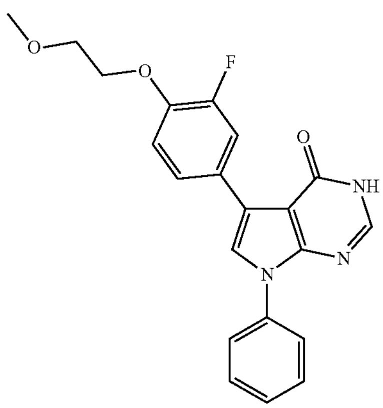 [SMILES: COCCOc1ccc(-c2cn(-c3ccccc3)c3nc[nH]c(=O)c23)cc1F] | Ex-130[a] (B62) | LC-MS. $R_t$ 7.88 min, AnalpH2_MeOH_QC_V1(1); ($ESI^+$) m/z 380.2 $[M + H]^+$; $^1$H-NMR (400 MHz, DMSO-$d_6$): δ 12.21 (br s, 1H), 8.05 (dd, J = 13.7, 2.3 Hz, 1H), 7.98 (s, 1H), 7.89 (s, 1H), 7.85 (br d, J = 8.7 Hz, 1H), 7.78 (d, J = 8.2 Hz, 2H), 7.57 (t, J = 8.2 Hz, 2H), 7.44 (t, J 8.2 Hz, 1H), 7.19 (t, J = 8.7 Hz, 2H), 4.24-4.19 (m, 1H), 3.73-3.67 (m, 2H), 3.34 (s, 3H-under water peak). | 77 mg, 46%, white solid |
| 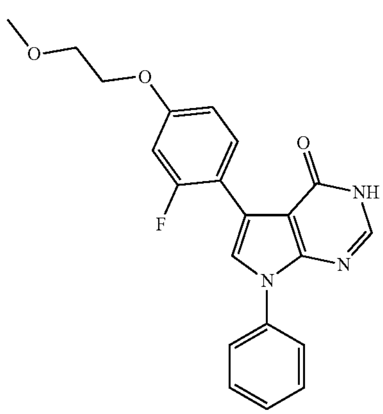 [SMILES: COCCOc1ccc(-c2cn(-c3ccccc3)c3nc[nH]c(=O)c23)c(F)c1] | Ex-131[a] (B63) | LC-MS. $R_t$ 7.97 min, AnalpH2_MeOH_QC_V1(1); ($ESI^+$) m/z 380.3 $[M + H]^+$ | 87 mg, 51%, white solid |

TABLE 27-continued
| Compound | Ex # (Intermediate used[a]) | Analytical Data | Mass, % Yield, Appearance |
|---|---|---|---|
| 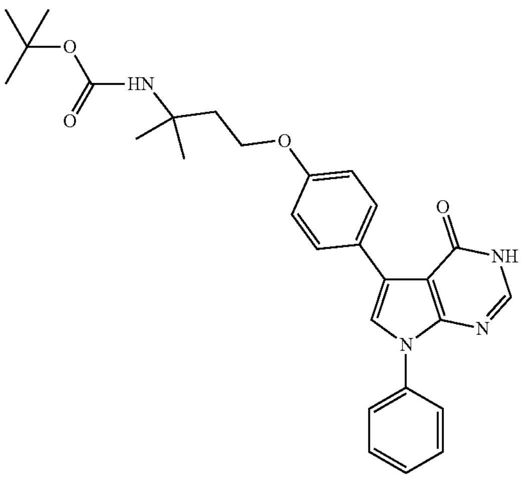 [SMILES: CC(C)(CCOc1ccc(-c2cn(-c3ccccc3)c3nc[nH]c(=O)c23)cc1)NC(=O)OC(C)(C)C] | Ex-132[a] (B58) | LC-MS. $R_t$ 3.09 min, AnalpH2_MeCN_4 min(1); ($ESI^+$) m/z 389.1 $[M - Boc + H]^+$. | 146 mg, brown solid, used crude for synthesis of Ex-138 |
| 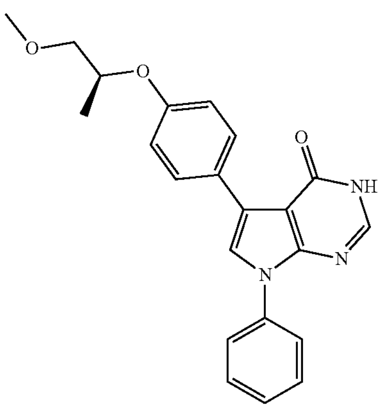 [SMILES: COC[C@H](C)Oc1ccc(-c2cn(-c3ccccc3)c3nc[nH]c(=O)c23)cc1] | Ex-133 (B70) | LC-MS. $R_t$ 8.13 min, AnalpH2_MeOH_QC_V1(1); ($ESI^+$) m/z 376.2 $[M + H]^+$. | 170 mg, 51%, white solid |
| 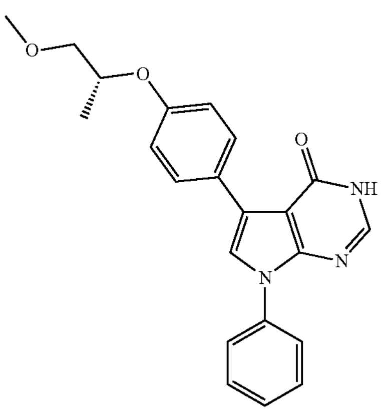 [SMILES: COC[C@@H](C)Oc1ccc(-c2cn(-c3ccccc3)c3nc[nH]c(=O)c23)cc1] | Ex-134 (B71) | LC-MS. $R_t$ 8.13 min, AnalpH2_MeOH_QC_V1(1); ($ESI^+$) m/z 376.3 $[M + H]^+$. | 176 mg, 53%, off-white solid |

TABLE 27-continued

| Compound | Ex # (Intermediate used*) | Analytical Data | Mass, % Yield, Appearance |
|---|---|---|---|
| 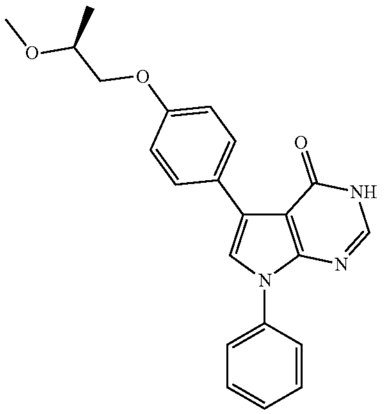 [SMILES: CO[C@@H](C)COc1ccc(-c2cn(-c3ccccc3)c3nc[nH]c(=O)c23)cc1] | Ex-135 (B72) | LC-MS. $R_t$ 8.14 min, AnalpH2_MeOH_QC_V1(1); ($ESI^+$) m/z 376.3 $[M + H]^+$. | 69 mg, 21%, off-white solid |
| 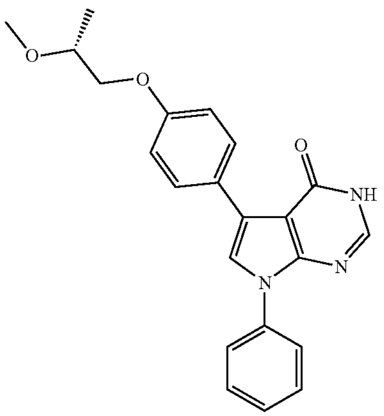 [SMILES: CO[C@H](C)COc1ccc(-c2cn(-c3ccccc3)c3nc[nH]c(=O)c23)cc1] | Ex-136 (B73) | LC-MS. $R_t$ 8.15 min, AnalpH2_MeOH_QC_V1(1); ($ESI^+$) m/z 376.3 $[M + H]^+$. | 31 mg, 9%, brown solid |

*If not stated commercial and/or CH4.

[a]$K_3PO_4$ added as a solution in water

Example Ex-71 was Prepared by Acidic Boc-Deprotection Followed by Acetylation of the Resulting amine N-[3-(4-Oxo-7-phenyl-4,7-dihydro-3H-pyrrolo[2,3-d]pyrimidin-5-yl)-benzyl]-acetamide (Ex-71)

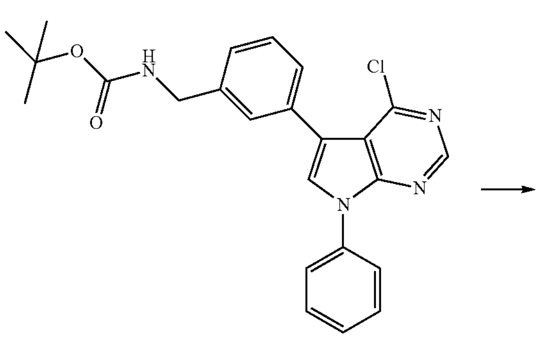

CP46

-continued

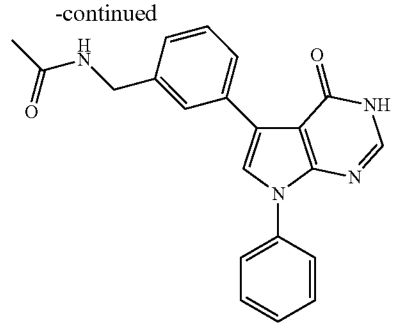

Ex-71

A mixture of [3-(4-chloro-5-phenyl-5H-pyrrolo[3,2-d]pyrimidin-7-yl)-benzyl]-carbamic acid tert-butyl ester (CP46) (26 mg, 0.06 mmol), NaOAc (15 mg, 0.18 mmol) and AcOH (1 mL) was heated at 100° C. for 18 h. The mixture was concentrated in vacuo then re-dissolved in DCM (5 mL). $Ac_2O$ (8.5 µl, 0.09 mmol) and pyridine (7.3 µl, 0.09 mmol) were added and the mixture stirred at RT for 5 min. The mixture was diluted with 1M HCl (aq), extracted into ethyl acetate (×2), washed with brine, dried (anhydrous $MgSO_4$), filtered, concentrated in vacuo, purified by reverse phase preparative HPLC-MS then lyophilised from a mixture of MeCN:$H_2O$ (2 mL, 1:1) to afford N-[3-(4-Oxo-5-phenyl-4,5-dihydro-3H-pyrrolo[3,2-d]pyrimidin-7-yl)-benzyl]-acetamide (Ex-71) as a white solid (9.8 mg, 0.027 mmol, 46%); LC-MS. Rt 7.02 min, AnalpH2_MeOH_QC_V1(1); (ESI$^+$) m/z 359.3 $[M+H]^+$.

Example Ex-72 was Synthesised from Ex-11

[4-(4-Oxo-7-phenyl-4,7-dihydro-3H-pyrrolo[2,3-d]pyrimidin-5-yl)-benzyl]-carbamic acid tert-butyl ester (Ex-72)

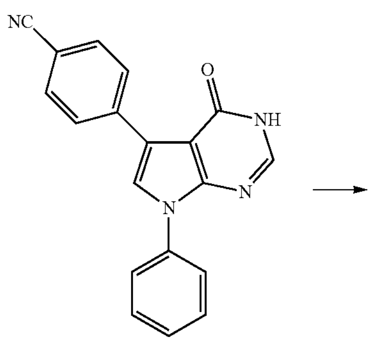

Ex-11

-continued

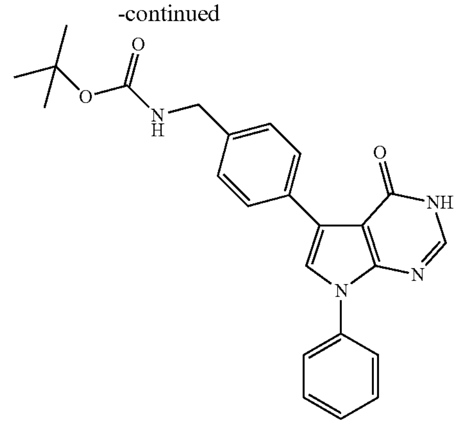

Ex-72

4-(4-oxo-7-phenyl-4,7-dihydro-3H-pyrrolo[2,3-d]pyrimidin-5-yl)-benzonitrile Ex-11 (30 mg, 0.1 mmol), $NiCl_2$ (12 mg, 0.1 mmol) and di-tert-butyl dicarbonate (42 mg, 0.2 mmol) were suspended in 1:1 THF:MeOH (0.8 mL) and cooled to 0° C. $NaBH_4$ (26 mg, 0.7 mmol) was added followed by further 1:1 THF:MeOH (0.2 mL) and the reaction was stirred at RT for 18 h. Further $NaBH_4$ (26 mg, 0.7 mmol) added and the reaction mixture stirred at RT for 1.5 h. Diethylenetriamine (11 μL, 0.1 mmol) in THE (0.1 mL) was added and the reaction mixture stirred for 30 min. The solvent was removed in vacuo and the residue suspended in DCM (20 mL) and washed with $NaHCO_3$ (aq., satd., 2×20 mL). The organic layer was separated (phase separator) and evaporated to dryness to afford [4-(4-oxo-7-phenyl-4,7-dihydro-3H-pyrrolo[2,3-d]pyrimidin-5-yl)-benzyl]-carbamic acid tert-butyl ester as a pale purple solid (22 mg, 52%) which was used in the next step without further purification; LC-MS. Rt 3.28 min, AnalpH2_MeOH_4 min (1); (ESI$^+$) m/z 361.2 $[M+H\text{-tert-Bu}]^+$., 833.2 $[2M+H]^+$.

The following examples were synthesised using an analogous procedure to Ex-72

TABLE 28

| Compound | Ex. # (Intermediate used) | Analytical Data | Mass, % Yield, Appearance |
|---|---|---|---|
| 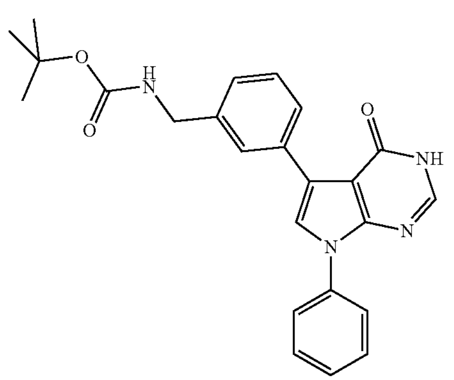 [SMILES: CC(C)(C)OC(=O)NCc1cccc(-c2cn(-c3ccccc3)c3nc[nH]c(=O)c23)c1] | Ex-73 (CP9) | LC-MS. $R_t$ 3.30 min, AnalpH2_MeOH_4 min(1); (ESI$^+$) m/z 417.3 $[M + H]^+$. | 95 mg, 97%, off-white solid |

Example Ex-74 was Synthesised from Ex-72

5-(4-Aminomethyl-phenyl)-7-phenyl-3,7-dihydro-pyrrolo[2,3-d]pyrimidin-4-one (Ex-74)

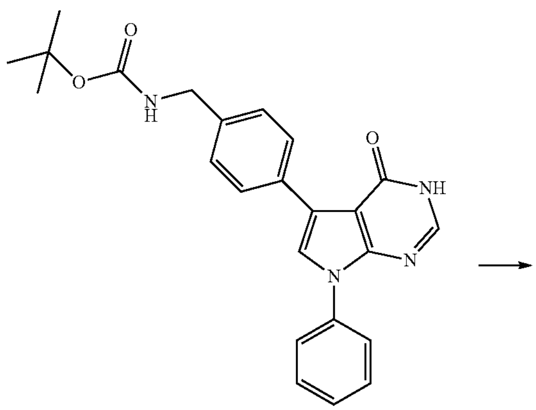

Ex-73

-continued

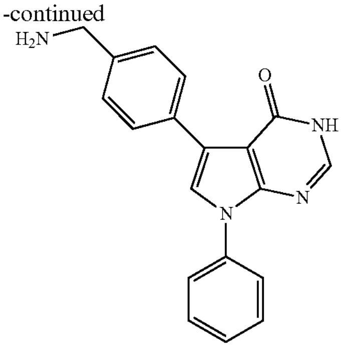

Ex-74

TFA/DCM 1:2 (0.45 mL) was added to [4-(4-oxo-7-phenyl-4,7-dihydro-3H-pyrrolo[2,3-d]pyrimidin-5-yl)-benzyl]-carbamic acid tert-butyl ester (Ex-72) (22 mg, 0.05 mmol) and the reaction mixture was stirred at RT for 1 h. The reaction mixture was evaporated to dryness, neutralised with 0.7 M $NH_3$/MeOH and evaporated to dryness. The residue was dissolved in DCM (2 mL) and passed through a SCX-2 cartridge (1 g), washing with MeOH (2×CV) and DCM (2×CV). The compound was eluted from the column with 0.7M $NH_3$/MeOH. The crude compound was purified by reverse phase preparative HPLC-MS and lyophilised from 1:1 MeCN/$H_2O$ to obtain 5-(4-aminomethyl-phenyl)-7-phenyl-3,7-dihydro-pyrrolo[2,3-d]pyrimidin-4-one as a white solid (5.4 mg, 34%); LC-MS. Rt 5.04 min, AnalpH2_MeOH_QC_V1(1); ($ESI^+$) m/z 317.3.

The following examples were synthesised using analogous procedures to example Ex-74 (reaction duration varied between 0.5-1.5 h):

TABLE 29

| Compound | Ex. #. (Intermediate used) | Analytical Data | Mass, % Yield, Appearance |
|---|---|---|---|
| 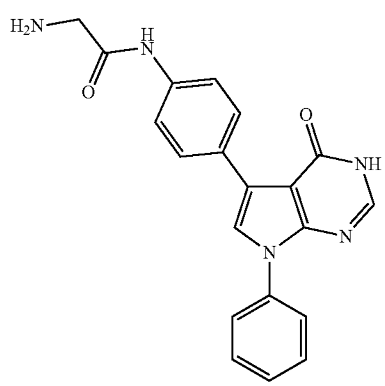 [SMILES: NCC(=O)Nc1ccc(-c2cn(-c3ccccc3)c3nc[nH]c(=O)c23)cc1] | Ex-76 (Ex-59) | LC-MS. $R_t$ 5.10 min, AnalpH2_MeOH_QC_V1(1); ($ESI^+$) m/z 360.3 | 2 mg, 7%, white solid |

TABLE 29-continued

| Compound | Ex. #. (Intermediate used) | Analytical Data | Mass, % Yield, Appearance |
|---|---|---|---|
| 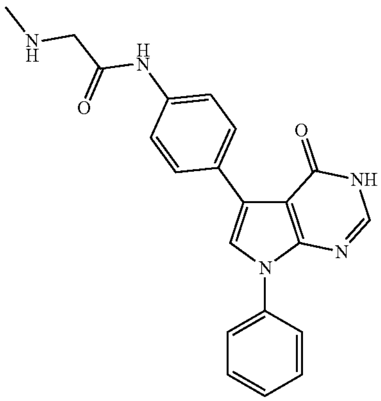 [SMILES: CNCC(=O)Nc1ccc(-c2cn(-c3ccccc3)c3nc[nH]c(=O)c23)cc1] | Ex-77 (Ex-60) | LC-MS. $R_t$ 5.14 min, AnalpH2_MeOH_QC_V1(1); ($ESI^+$) m/z 374.3 | 10 mg, 34%, white solid |
| 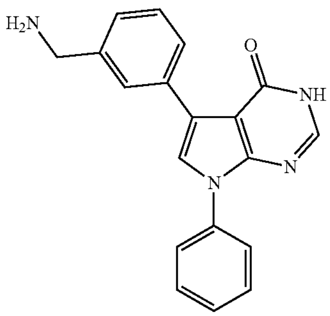 [SMILES: NCc1cccc(-c2cn(-c3ccccc3)c3nc[nH]c(=O)c23)c1] | Ex-75[f] (Ex-73) | LC-MS. $R_t$ 5.15 min, AnalpH2_MeOH_QC_V1(1); ($ESI^+$) m/z 317.3; $^1$H NMR (400 MHz, DMSO-$d_6$): δ 8.42 (s, 1H), 7.99 (s, 1H), 7.98-7.93 (m, 2H), 7.81 (s, 1H), 7.79-7.77 (m, 2H), 7.58 (t, J = 7.6 Hz, 2H), 7.44 (tt, J = 7.6, 1.3 Hz, 1H), 7.36 (t, J = 7.6 Hz, 1H), 7.28 (d, J = 7.8 Hz, 1H), 3.86 (s, 2H); | 23 mg, 32%, white solid |
| 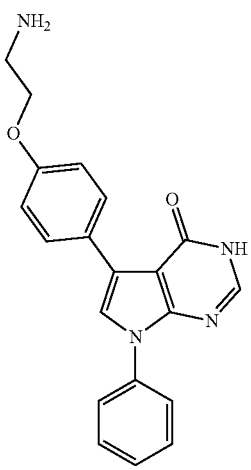 [SMILES: NCCOc1ccc(-c2cn(-c3ccccc3)c3nc[nH]c(=O)c23)cc1] | Ex-78 (Ex-63) | LC-MS. $R_t$ 5.10 min, AnalpH2_MeOH_QC_V1; ($ESI^+$) m/z 347.2 | 16 mg, quant, off-white solid |
| 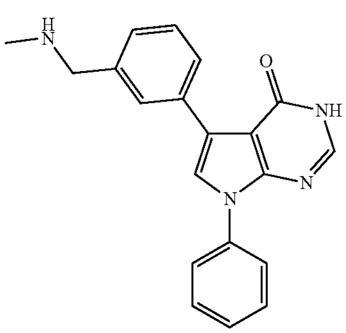 [SMILES: CNCc1cccc(-c2cn(-c3ccccc3)c3nc[nH]c(=O)c23)c1] | Ex-79 (Ex-32) | LC-MS. $R_t$ 4.98 min, AnalpH2_MeOH_QC_V1; ($ESI^+$) m/z 331.3 $[M + H]^+$ | 13.7 mg, 74%, white solid |

TABLE 29-continued

| Compound | Ex. #. (Intermediate used) | Analytical Data | Mass, % Yield, Appearance |
|---|---|---|---|
| 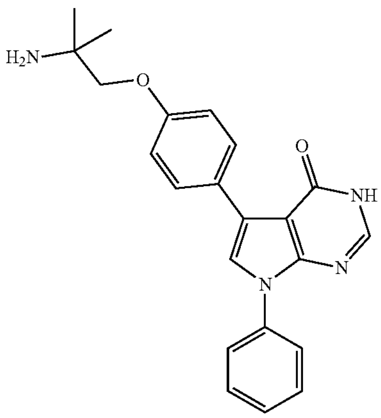 [SMILES: CC(C)(N)COc1ccc(-c2cn(-c3ccccc3)c3nc[nH]c(=O)c23)cc1] | Ex-137 (Ex-122) | LC-MS. $R_t$ 5.77 min, AnalpH2_MeOH_QC_V1(1); ($ESI^+$) m/z 375.3 $[M + H]^+$; $^1$H-NMR (400 MHz, DMSO-$d_6$): δ 7.95 (s, 1H), 7.94-7.91 (m, 2H), 7.78-7.75 (m, 2H), 7.72 (s, 1H), 7.58-7.53 (m, 2H), 7.44-7.40 (m, 1H), 6.97-6.93 (m, 2H), 3.71 (s, 2 h), 1.13 (s, 6H). | 39 mg, 34%, white solid |
| 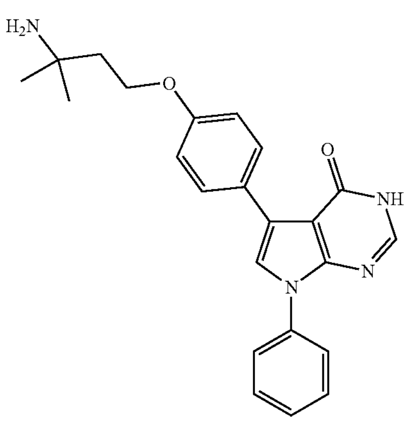 [SMILES: CC(C)(N)CCOc1ccc(-c2cn(-c3ccccc3)c3nc[nH]c(=O)c23)cc1] | Ex-138 (Ex-132) | LC-MS. $R_t$ 5.94 min, AnalpH2_MeOH_QC_V1(1); ($ESI^+$) m/z 389.2 $[M + H]^+$; $^1$H-NMR (400 MHz, DMSO-$d_6$): δ 7.96 (s, 1H), 7.93 (** d, J = 9.2 Hz, 2H), 7.78 (d, J = 8.2 Hz, 2H), 7.72 (s, 1H), 7.56 (t, J = 8.2 Hz, 2H), 7.42 (t, J = 8.2 Hz, 1H), 6.95 (app d, J = 9.2 Hz, 2H), 4.12 (t, J = 7.3 Hz, 2H), 1.78 (t, J = 7.3 Hz, 2H), 1.10 (s, 6H). | 44 mg, 30% over 2 steps (including Suzuki coupling), white solid |

[f]Isolated as formate salt.

The following final compounds were prepared directly from the Boc-protected chloro-pyrimidines:

Example Ex-80 was Synthesised from CP37

5-[4-(Azetidin-3-ylmethoxy)-phenyl]-7-phenyl-3,7-dihydro-pyrrolo[2,3-d]pyrimidin-4-one-formate salt (Ex-80)

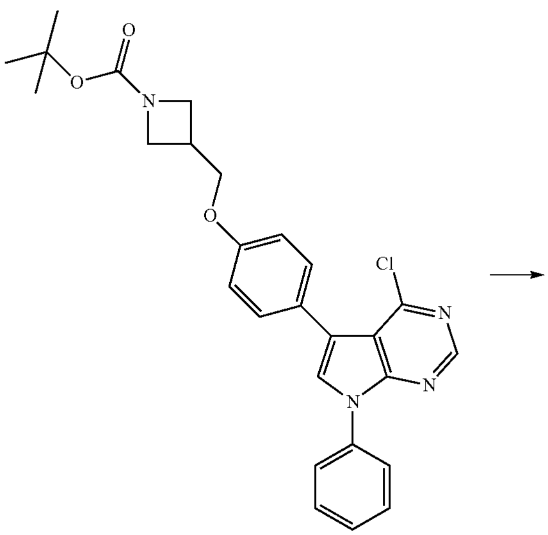

CP37

-continued

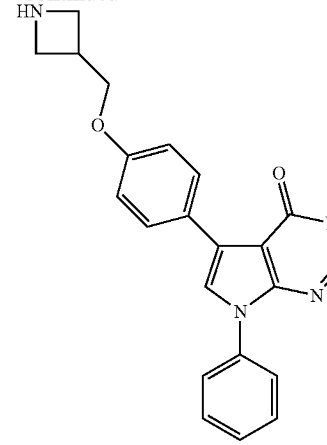

Ex-80

3-[4-(4-Chloro-5-phenyl-5H-pyrrolo[3,2-d]pyrimidin-7-yl)-phenoxymethyl]-azetidine-1-carboxylic acid tert-butyl ester CP37 (81 mg, 0.16 mmol) and NaOAc (41 mg, 0.49 mmol) were dissolved in AcOH (5 mL) and stirred at reflux for 18 h. The solution was neutralised with NaOH solution (50% in water) and the mixture partitioned between DCM and $H_2O$. The organic layer was dried by phase separator and volatiles removed in vacuo. The residue was dissolved in DMSO and purified by reversed phase preparative HPLC-MS. Ex-80 was obtained after freeze drying in 1:1 $H_2O$:MeCN as a white solid (5 mg, 8%); LC-MS. Rt 7.71 min, AnalpH2_MeOH_QC_V1(1); (ESI$^+$) m/z 373.2 [M+H]$^+$.

The following example was synthesised using an analogous procedure to Ex-80:

TABLE 30

| Compound | Ex. # (Intermediate used) | Analytical Data | Mass, % Yield, Appearance |
|---|---|---|---|
| 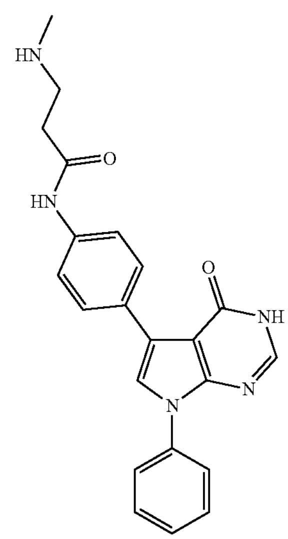 [SMILES: CNCCC(=O)Nc1ccc(-c2cn(-c3ccccc3)c3nc[nH]c(=O)c23)cc1] | Ex-81[f] (CP17) | LC-MS. $R_t$ 5.16 min, AnalpH2_MeOH_QC_V1(1); (ESI$^+$) m/z 388.4 [M + H]$^+$. | 5 mg, 16%, white solid |

[f]Isolated as a formic acid salt.

Example Ex-82 was Synthesised from Ex-10

[4-(4-Oxo-7-phenyl-4,7-dihydro-3H-pyrrolo[2,3-d]pyrimidin-5-yl)-phenyl]-acetic acid (Ex-82)

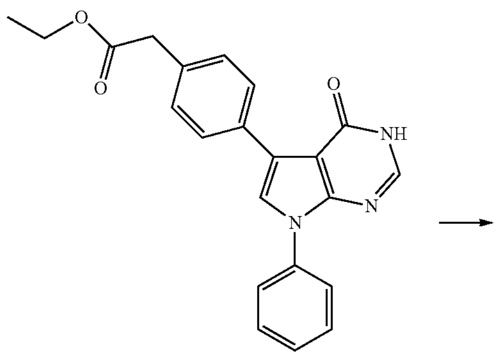

Ex-10

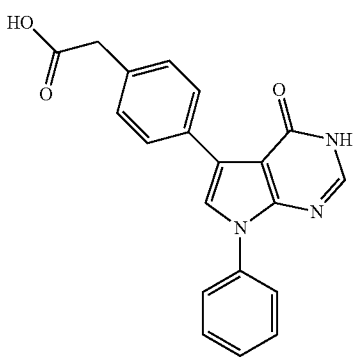

Ex-82

To [4-(4-oxo-7-phenyl-4,7-dihydro-3H-pyrrolo[2,3-d]pyrimidin-5-yl)-phenyl]-acetic acid ethyl ester (Ex-10) (40 mg, 0.11 mmol), LiOH·$H_2O$ (14 mg, 0.33 mmol) was added THF:MeOH 3:1 (2.2 mL) and the reaction mixture stirred at RT overnight. The reaction mixture was diluted with DCM (10 mL) and evaporated to dryness. The crude compound was purified by reversed phase preparative HPLC-MS and lyophilised from 1:1 MeCN/$H_2O$ to afford [4-(4-Oxo-7-phenyl-4,7-dihydro-3H-pyrrolo[2,3-d]pyrimidin-5-yl)-phenyl]-acetic acid (Ex-82) as a white solid (18.4 mg, 48%); LC-MS. Rt 7.40 min, AnalpH2_MeOH_QC_V1(1); (ESI$^+$) m/z 346.3.

Example Ex-83 was Synthesised from Ex-82

2-[4-(4-Oxo-7-phenyl-4,7-dihydro-3H-pyrrolo[2,3-d]pyrimidin-5-yl)-phenyl]-acetamide (Ex-83)

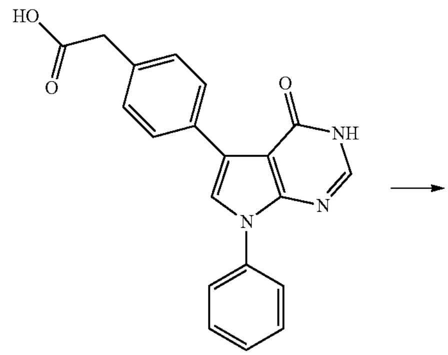

Ex-82

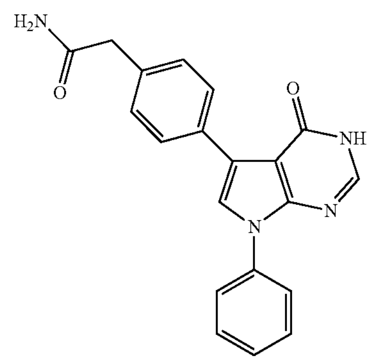

Ex-83

To [4-(4-oxo-7-phenyl-4,7-dihydro-3H-pyrrolo[2,3-d]pyrimidin-5-yl)-phenyl]-acetic acid (17 mg, 0.05 mmol) (Ex-82), TBTU (16 mg, 0.05 mmol) in anhydrous DMF (0.55 mL) was added a 1M solution of DIPEA/DCM (50 μL, 0.05 mmol) and the reaction mixture stirred for 50 min. Ammonium chloride (5.2 mg, 0.1 mmol) in a 1M solution of DIPEA/DCM (100 μL, 0.1 mmol) was added to the reaction mixture followed by anhydrous DMF (0.1 mL). The reaction vessel was sealed and stirred at RT for 18 h. The reaction mixture was passed through a 1 g Si—$NH_2$ cartridge (preconditioned with DMF+MeOH) and the column washed with DMF (2×CV) and MeOH (2×CV). The solvent was removed in vacuo. The crude compound was purified by reversed phase preparative HPLC-MS and the product was lyophilised from 1:1 MeCN/$H_2O$ to to afford 2-[4-(4-oxo-7-phenyl-4,7-dihydro-3H-pyrrolo[2,3-d]pyrimidin-5-yl)-phenyl]-acetamide as a white solid (13 mg, 77%); LC-MS. Rt 6.95 min, AnalpH2_MeOH_QC_V1(1); (ESI$^+$) m/z 345.3.

The following diol Ex-139 was prepared from CP75 in two steps.

5-(4-((2S,3S)-2,3-dihydroxybutoxy)phenyl)-7-phenyl-3,7-dihydro-4H-pyrrolo[2,3-d]pyrimidin-4-one (Ex-139)

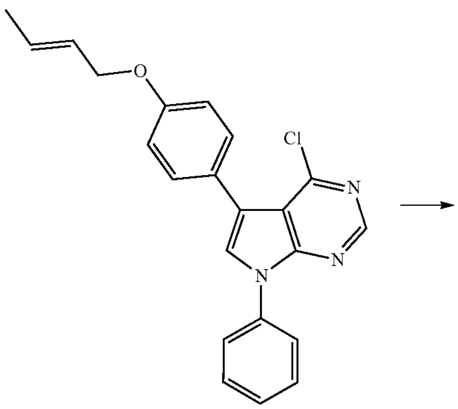

CP75

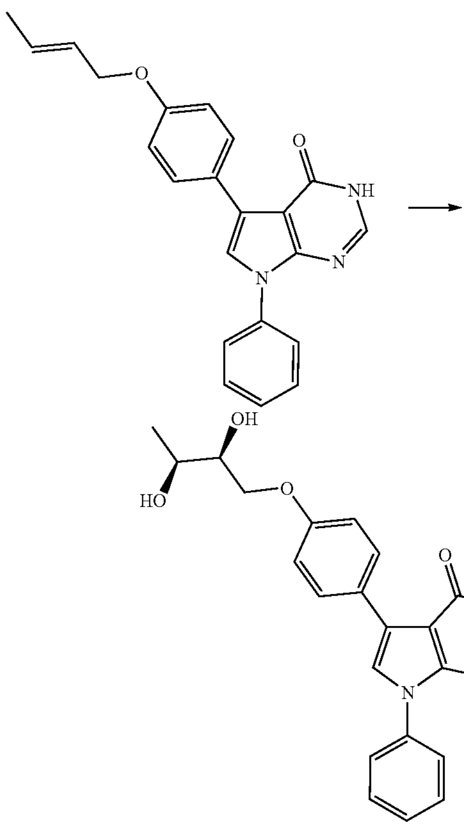

Ex-139

(4-(But-2-en-1-yloxy)phenyl)-4-chloro-7-phenyl-7H-pyrrolo[2,3-d]pyrimidine (CP75) (138 mg, 0.37 mmol) and NaOAc (60 mg, 0.74 mmol) in AcOH (2 mL) was heated at 100° C. for 2.5 h. The reaction mixture was concentrated in vacuo and the residue diluted with DCM and water. The organic layer was separated, washed with DCM (2×30 mL) followed by EtOAc (2×30 mL), dried with anhydrous $MgSO_4$, filtered and concentrated in vacuo to, afford 5-(4-(but-2-en-1-yloxy)phenyl)-7-phenyl-3,7-dihydro-4H-pyrrolo[2,3-d]pyrimidin-4-one (80 mg, 60%) as a white solid. LC-MS. $R_t$ 3.39 min, AnalpH2_MeOH_4 min(1); ($ESI^+$) m/z 358.3 $[M+H]^+$. A portion of this material was used in the next step without further purification. AD-mix a (120 mg) was added to a stirred solution of $^tBuOH/H_2O$ (1.5 mL, 1:1). The mixture was stirred until solids were dissolved, then cooled to 0° C. and a mixture of E and Z 5-(4-(but-2-en-1-yloxy)phenyl)-7-phenyl-3,7-dihydro-4H-pyrrolo[2,3-d]pyrimidin-4-one (40 mg, 0.11 mmol) was added. The resulting mixture was stirred for 4 h then allowed to warm to RT and stirred for a further 18 h. Methanesulfonamide (20 mg, 0.11 mmol), AD-mix a (100 mg) and $^tBuOH$ (750 μL) were added and the reaction mixture was heated at 40° C. for 3 h. The reaction was quenched by addition of sodium sulfite (675 mg), diluted with water (30 mL) and extracted EtOAc (3×30 mL). The crude residue was concentrated under vacuum. The crude residue was taken up in THE (800 μL) and added to a solution of AD-mix a in $^tBuOH$/water (50:50, 1 mL), then stirred overnight. AD-mix a (500 mg) was added and the reaction stirred overnight. Sodium sulfite (500 mg) was added and stirred until the reaction became colourless then diluted with water (30 mL) and extracted EtOAc (3×30 mL) and dried (anhydrous $MgSO_4$). The crude residue was purified by silica gel column chromatography eluting with 0-10% MeOH/DCM followed by reversed phase preparative HPLC to afford 5-(4-((2S,3S)-2,3-dihydroxybutoxy)phenyl)-7-phenyl-3,7-dihydro-4H-pyrrolo[2,3-d]pyrimidin-4-one (Ex-139) (10 mg, 23%) as a white solid. LCMS $R_t$ 7.53 min AnalpH2_MeOH_QC_V1(1), ($ESI^+$) m/z 392.3 $[M+H]^+$; $^1$H-NMR (400 MHz, DMSO-$d_6$): δ 12.09 (br s, 1H), 7.93-7.86 (m, 3H), 7.73 (d, J=7.3 Hz, 2H), 7.68 (s, 1H), 7.52 (t, J=7.8 Hz, 2H), 7.40-7.35 (m, 1H), 6.90 (d, J=8.7 Hz, 2H), 5.09 (d, J=5.0 Hz, 1H), 3.97-3.84 (m, 3H), 3.43-3.32 (m, 2H), 3.20 (s, 3H). Enantiomeric excess was not determined.

Synthesis of Phosphates

A number of examples of formula (Ia) were converted to phosphate analogues:

Phosphoric acid di-tert-butyl ester 5-[4-(2-methoxy-ethoxy)-phenyl]-4-oxo-7-phenyl-4,7-dihydro-pyrrolo[2,3-d]pyrimidin-3-ylmethyl ester (Ex-140)

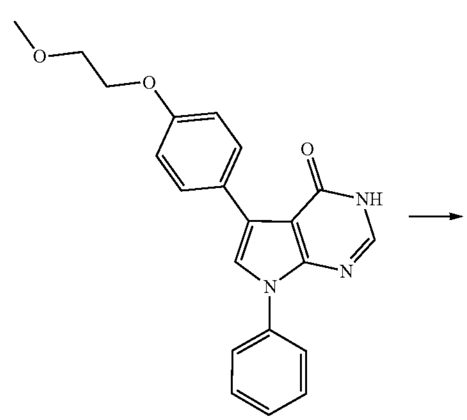

Ex-58

-continued

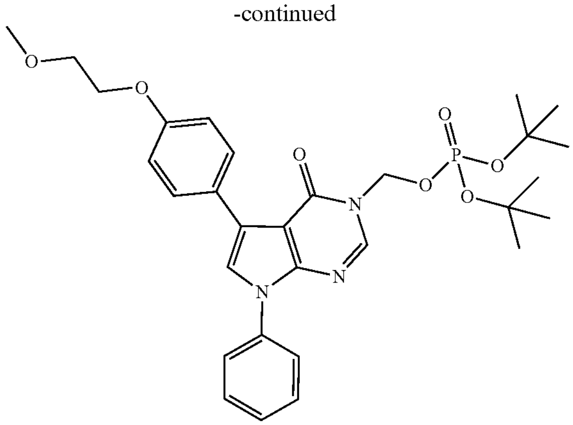

Ex-140

A mixture of 5-[4-(2-methoxy-ethoxy)-phenyl]-7-phenyl-3,7-dihydro-pyrrolo[2,3-d]pyrimidin-4-one (50 mg, 0.14 mmol), di-tert-butyl(chloromethyl)phosphate (Ex-58) (38 μL, 0.17 mmol), $Cs_2CO_3$ (50 mg, 0.15 mmol) and DMF (5 mL) were stirred at RT under $N_2$ for 18 h. The reaction mixture was diluted with $H_2O$ (20 mL), extracted with EtOAc (2×20 mL), washed with $H_2O$ (2×20 mL), brine (20 mL) and dried over $MgSO_4$. The organics were concentrated in vacuo and the crude compound was purified by silica gel column chromatography eluting with 20-100% EtOAc/iso-hexane to afford phosphoric acid di-tert-butyl ester 5-[4-(2-methoxy-ethoxy)-phenyl]-4-oxo-7-phenyl-4,7-dihydro-pyrrolo[2,3-d]pyrimidin-3-ylmethyl ester (Ex-140) as a colourless oil (30 mg, 37%); LC-MS. Rt 3.52 min, AnalpH2_MeOH_4 min(1); ($ESI^+$) m/z 584.3 $[M+H]^+$.

The following example was synthesised using an analogous procedure to Ex140:

TABLE 31

| Compound | Ex. # (Intermediate used) | Analytical Data | Mass, % Yield, Appearance |
|---|---|---|---|
| 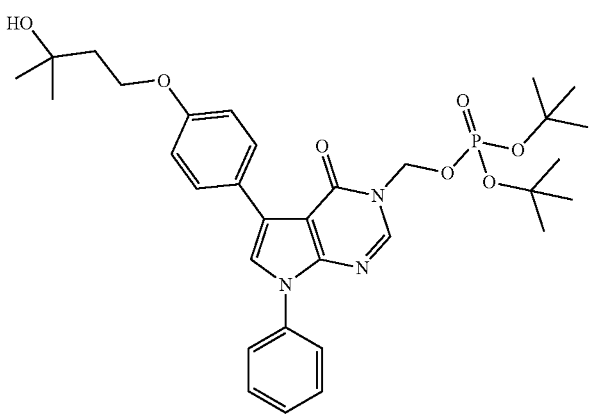 [SMILES: CC(C)(O)CCOc1ccc(-c2cn(-c3ccccc3)c3ncn(COP(=O)(OC(C)(C)C)OC(C)(C)C)c(=O)c23)cc1] | Ex-141 (Ex-40) | LC-MS. $R_t$ 3.57 min, AnalpH2_MeOH_4 min(1); ($ESI^+$) m/z 612.1 $[M + H]^+$ | 144 mg, 56%, yellow solid |

Phosphoric acid mono-{5-[4-(2-methoxy-ethoxy)-phenyl]-4-oxo-7-phenyl-4,7-dihydro pyrrolo[2,3-d]pyrimidin-3-ylmethyl} ester (Ex-142)

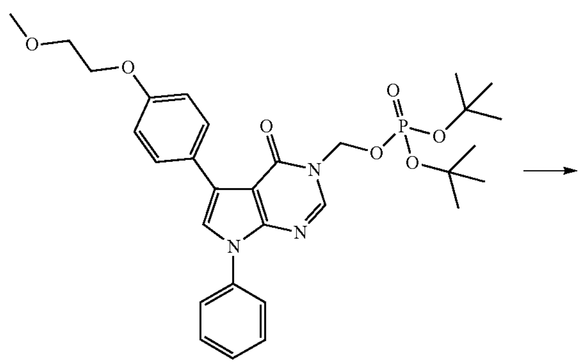

Ex-140

-continued

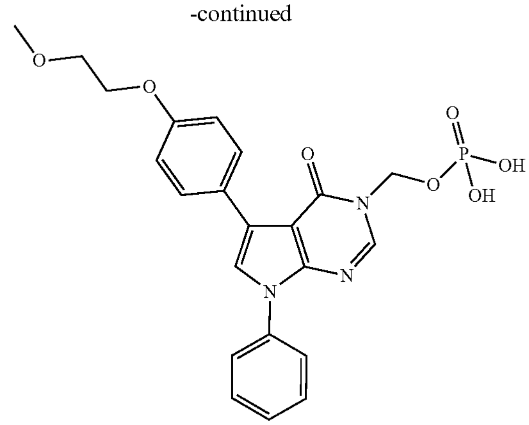

Ex-142

A mixture of phosphoric acid di-tert-butyl ester 5-[4-(2-methoxy-ethoxy)-phenyl]-4-oxo-7-phenyl-4,7-dihydro-pyrrolo[2,3-d]pyrimidin-3-ylmethyl ester (Ex-140) (30 mg, 0.05 mmol) and AcOH:$H_2O$ (4:1, 2 mL) was heated at 65° C. for 2 h. The reaction mixture was evaporated to dryness and the crude compound was purified by reversed phase preparative HPLC-MS to afford phosphoric acid mono-{5-[4-(2-methoxy-ethoxy)-phenyl]-4-oxo-7-phenyl-4,7-dihydro pyrrolo[2,3-d]pyrimidin-3-ylmethyl} ester (Ex-142) as the bis ammonium salt, white solid (16 mg, 68%); LC-MS. Rt 7.03 min, AnalpH9_MeOH_QC_V1(1); (ESI$^+$) m/z 472.2 $[M+H]^+$; $^1$H-NMR (400 MHz, DMSO-$d_6$): 8.43 (s, 1H), 7.87 (d, J=8.7 Hz, 2H), 7.77-7.75 (m, 2H), 7.69 (s, 1H), 7.55 (t, J=8.0 Hz, 2H), 7.43-7.39 (m, 1H), 6.94 (d, J=8.7 Hz, 2H), 5.55 (d, J=11.4 Hz, 2H), 4.13-4.10 (m, 2H), 3.69-3.66 (m, 2H), 3.32 (s, 3H).

The following example was synthesised using an analogous procedure to Ex-142:

TABLE 32

| Compound | Ex. # (Intermediate used) | Analytical Data | Mass, % Yield, Appearance |
|---|---|---|---|
| 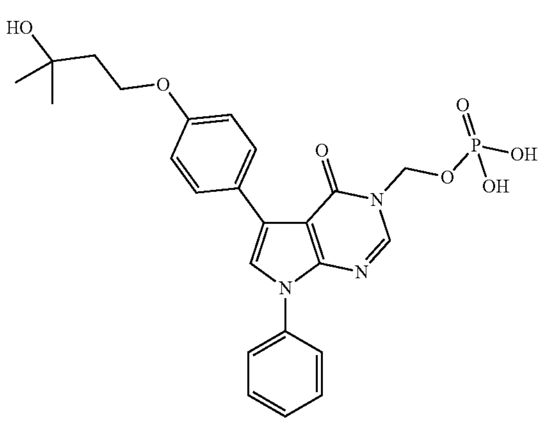 [SMILES: CC(C)(O)CCOc1ccc(-c2cn(-c3ccccc3)c3ncn(COP(=O)(O)O)c(=O)c23)cc1] | Ex-143 (Ex-141)[a] | LC-MS. $R_t$ 6.99 min, AnalpH9_MeOH_QC_V1(1); (ESI$^+$) m/z 500.2 $[M + H]^+$; $^1$H-NMR (400 MHz, DMSO-$d_6$): 8.42 (s, 1H), 7.86 (d, J = 8.7 Hz, 2H), 7.76 (d, J = 7.3 Hz, 2H), 7.71-7.62 (1H), 7.55 (t, J = 7.8 Hz, 2H), 7.41 (t, J = 7.6 Hz, 1H), 6.92 (d, J = 9.2 Hz, 2H), 5.55 (d, J = 11.6 Hz, 2H), 4.11 (t, J = 7.2 Hz, 2H), 1.86 (t, J = 7.2 Hz, 2H), 1.18 (s, 6H). | 27 mg, 18%, white solid |

[a]Isolated as a bis ammonium salt.

Dibenzyl-(2-methyl-4-(4-(4-oxo-7-phenyl-4,7-dihydro-3H-pyrrolo[2,3-d]pyrimidin-5-yl)phenoxy)butan-2-yl)phosphate (Ex-144)

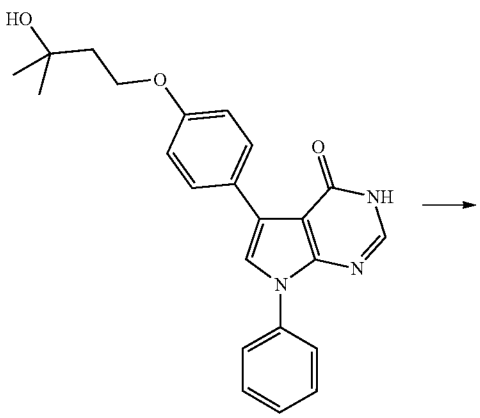

Ex-40

-continued

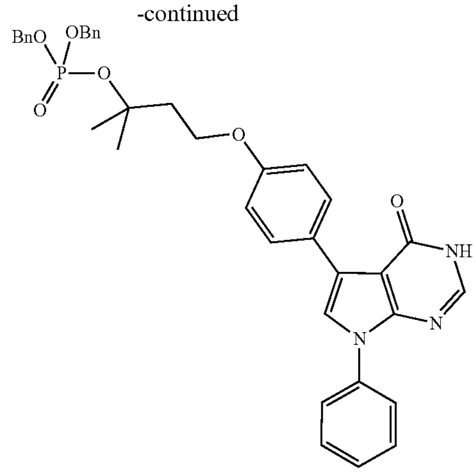

Ex-144

A mixture of 5-(4-(3-hydroxy-3-methylbutoxy)phenyl)-7-phenyl-3,7-dihydro-4H-pyrrolo[2,3-d]pyrimidin-4-one (Ex-40) (60 mg, 0.154 mmol), dibenzyl N,N-isopropylphosphoranidite (258 μL, 0.77 mmol) and 1,2,4-triazole (53.2 mg, 0.77 mmol) in 1,2-dichloroethane (3 mL) was heated at reflux for 90 min. After cooling to RT, 50% hydrogen peroxide (57 μL, 0.924 mmol) was slowly added dropwise. The resulting reaction mixture was stirred at RT for 30 mins, then diluted with DCM, washed sequentially with water and 5% aq. sodium thiosulfate. The organic layer was separated, dried (anhydrous $Na_2SO_4$), filtered and concentrated in vacuo. The crude residue was twice purified by silica gel column chromatography eluting with 0-5% MeOH/DCM and then 0-100% EtOAc/iso-hexane to afford Dibenzyl-(2-methyl-4-(4-(4-oxo-7-phenyl-4,7-dihydro-3H-pyrrolo[2,3-d]pyrimidin-5-yl)phenoxy)butan-2-yl)phosphate (Ex-144) as a gummy colourless oil (34 mg, 34%); LC-MS. Rt 3.56 min, AnalpH9_MeOH_4 min(1); (ESI$^+$) m/z 650.4 [M+H]$^+$; $^1$H-NMR (400 MHz, DMSO-$d_6$): 12.13 (s, 1H), 7.96 (s, 1H), 7.93 (d, J=8.7 Hz, 2H), 7.82-7.75 (m, 2H), 7.72 (s, 1H), 7.56 (t, J=7.8 Hz, 2H), 7.40-7.27 (m, 11H), 6.91 (d, J=8.7 Hz, 2H), 5.01 (dd, J=8.0, 1.6 Hz, 4H), 4.09 (t, J=6.6 Hz, 2H), 2.16 (t, J=6.6 Hz, 2H), 1.51 (s, 6H).

The following example was synthesised using an analogous procedure to Ex-144:

TABLE 33

| Compound | Ex. # (Intermediate used) | Analytical Data | Mass, % Yield, Appearance |
|---|---|---|---|
| 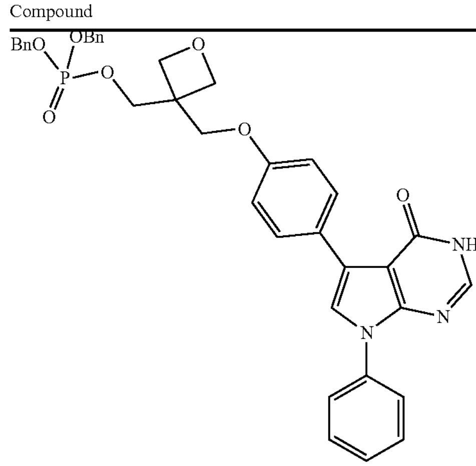 | Ex-145 (Ex-54) | LC-MS. $R_t$ 3.50 min, AnalpH9_MeOH_4 min(1); (ESI$^+$) m/z 664.3 [M + H]$^+$; $^1$H-NMR (400 MHz, DMSO-$d_6$): 12.13 (s, 1H), 7.96 (s, 1H), 7.96 (d, J = 9.2 Hz, 2H), 7.84-7.75 (m, 2H), 7.74 (s, 1H), 7.56 (t, J = 7.8 Hz, 2H), 7.43 (d, J = 7.3 Hz, 1H), 7.40-7.27 (m, 11H), 6.96 (d, J = 8.7 Hz, 2H), 5.04 (d, J = 8.0 Hz, 4H), 4.44 (d, J = 6.0 Hz, 4H), 4.31 (d, J = 5.5 Hz, 2H), 4.18 (s, 2H). | 362 mg, 73%, off-white solid |

TABLE 33-continued
| Compound | Ex. # (Inter-mediate used) | Analytical Data | Mass, % Yield, Appearance |
|---|---|---|---|
| 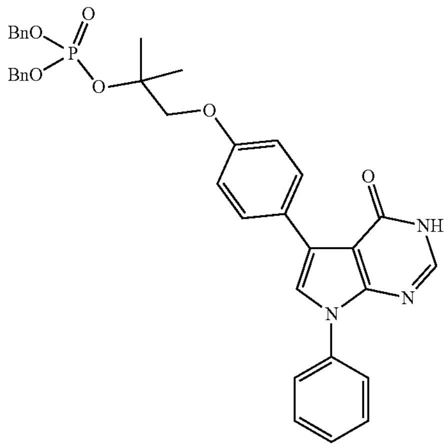 [SMILES: CC(C)(COc1ccc(-c2cn(-c3ccccc3)c3nc[nH]c(=O)c23)cc1)OP(=O)(OCc1ccccc1)OCc1ccccc1] | Ex-146 (Ex-64) | LC-MS. $R_t$ 3.53 min, AnalpH2_MeOH_4 min(1); (ESI$^+$) m/z 636.4 [M + H]$^+$; $^1$H-NMR (400 MHz, DMSO-$d_6$) δ 12.12 (s, 1H), 7.96 (s, 1H), 7.94 (d, J = 8.0 Hz, 2H), 7.78-7.75 (m, 2H), 7.72 (s, 1H), 7.58-7.53 (m, 2H), 7.44-7.31 (m, 11H), 6.95 (d, J = 9.2 Hz, 2H), 5.00 (d, J = 7.8 Hz, 4H), 4.09 (s, 2H), 1.55 (s, 6H). | 141 mg, 42%, white solid |
| 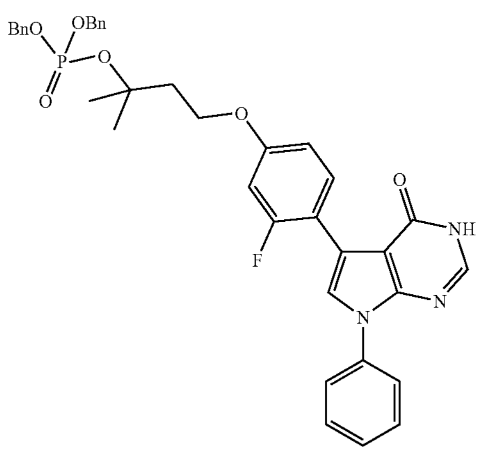 [SMILES: CC(C)(CCOc1ccc(-c2cn(-c3ccccc3)c3nc[nH]c(=O)c23)c(F)c1)OP(=O)(OCc1ccccc1)OCc1ccccc1] | Ex-147 (Ex-107) | LC-MS. $R_t$ 3.74 min, AnalpH9_MeOH_4 min(1); (ESI$^+$) m/z 668.3 [M + H]$^+$ | 192 mg, 47%, off-white solid |

2-methyl-4-(4-(4-oxo-7-phenyl-4,7-dihydro-3H-pyrrolo[2,3-d]pyrimidin-5-yl)phenoxy)butan-2-yl dihydrogen phosphate (Ex-148)

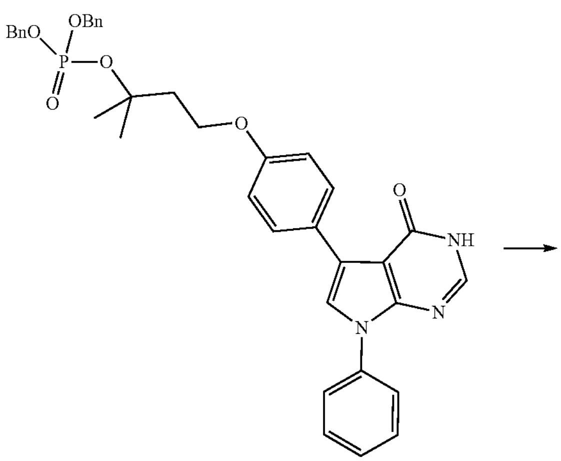

Ex-144

-continued

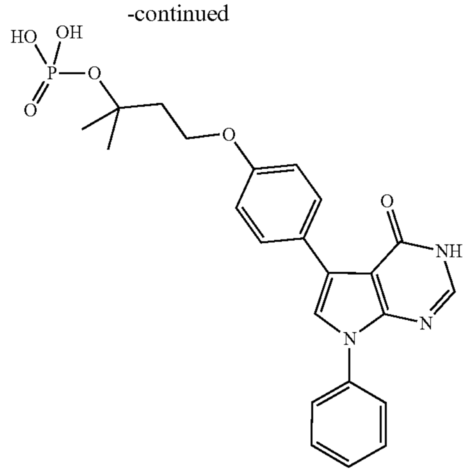

Ex-148

10% Palladium on carbon (3.2 mg) was added to a mixture of dibenzyl [1,1-dimethyl-2-[4-(4-oxo-7-phenyl-3H-pyrrolo[2,3-d]pyrimidin-5-yl)phenoxy]ethyl] phosphate (Ex-144) (32.0 mg, 0.049 mmol) in EtOH (3 mL) under nitrogen. Reaction mixture was stirred under a hydrogen atmosphere for 20 h, then filtered through a pad of celite, washed with EtOH (3×20 mL) and the organics were concentrated in vacuo. The crude compound was purified by reversed phase preparative HPLC-MS and the product was lyophilised from 1:1 MeCN/$H_2O$ to afford Dibenzyl-(2-methyl-4-(4-(4-oxo-7-phenyl-4,7-dihydro-3H-pyrrolo[2,3-d]pyrimidin-5-yl)phenoxy)butan-2-yl)phosphate (Ex-148) as the bis ammonium salt, white solid (15 mg, 61%). LC-MS. Rt 7.10 min, AnalpH9_MeOH_QC_V1(1); (ESI$^+$) m/z 470.3; $^1$H-NMR (400 MHz, DMSO-$d_6$): δ 7.94 (s, 1H), 7.90 (d, J=8.7 Hz, 2H), 7.78-7.74 (m, 2H), 7.69 (s, 1H), 7.57-7.51 (m, 2H), 7.43-7.38 (m, 1H), 6.93 (d, J=9.2 Hz, 2H), 4.14 (t, J=7.1 Hz, 2H), 2.08 (t, J=7.1 Hz, 2H), 1.40 (s, 6H).

The following example was synthesized using analogous procedures to example Ex-148:

TABLE 34

| Compound | Ex. # (Inter-mediate used) | Analytical Data | Mass, % Yield, Appearance |
|---|---|---|---|
| 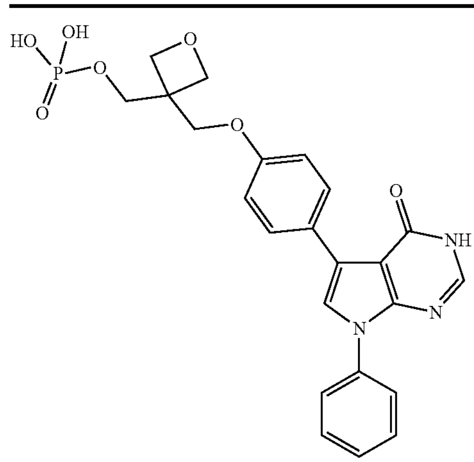 | Ex-149 (Ex-145)[a] | LC-MS. $R_t$ 6.47 min, AnalpH9_MeOH_QC_V1(1); (ESI$^+$) m/z 484.2 [M + H]$^+$; $^1$H-NMR (400 MHz, DMSO-$d_6$) δ 7.97-7.92 (m, 3H), 7.78-7.75 (m, 2H), 7.73 (s, 1H), 7.57-7.52 (m, 2H), 7.43-7.39 (m, 1H), 6.99 (d, J = 8.8 Hz, 2H), 4.45 (d, J = 6.0 Hz, 2H), 4.44 (d, J = 6.0 Hz, 2H), 4.16 (s, 2H), 3.95 (d, J = 6.0 Hz, 2H). | 102 mg, 64%, white solid |

TABLE 34-continued

| Compound | Ex. # (Intermediate used) | Analytical Data | Mass, % Yield, Appearance |
|---|---|---|---|
| 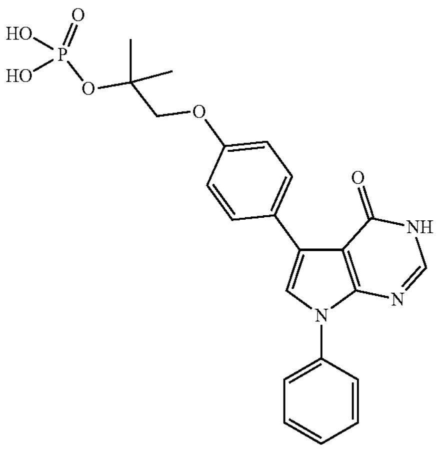 [SMILES: CC(C)(COc1ccc(-c2cn(-c3ccccc3)c3nc[nH]c(=O)c23)cc1)OP(=O)(O)O] | Ex-150 (Ex-146)[a,b] | LC-MS. $R_t$ 6.95 min, AnalpH9_MeOH_QC_V1(1); ($ESI^+$) m/z 456.3 $[M + H]^+$; $^1$H-NMR (400 MHz, DMSO-$d_6$): δ 7.95 (s, 1H), 7.91 (d, J = 9.2 Hz, 2H), 7.78-7.75 (m, 2H), 7.71 (s, 1H), 7.57-7.51 (m, 2H), 7.43-7.37 (m, 1H), 6.93 (d, J = 9.2 Hz, 2H), 3.98 (s, 2H), 1.44 (s, 6H). | 18 mg, 79%, white solid |
| 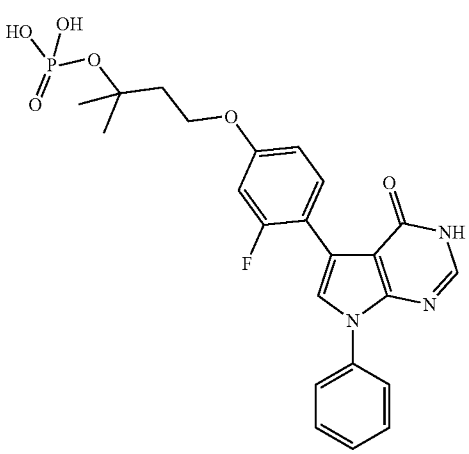 [SMILES: CC(C)(CCOc1ccc(-c2cn(-c3ccccc3)c3nc[nH]c(=O)c23)c(F)c1)OP(=O)(O)O] | Ex-151 (Ex-147)[a] | LC-MS. $R_t$ 7.32 min, AnalpH9_MeOH_QC_V1(1); ($ESI^+$) m/z 488.2 $[M + H]^+$; $^1$H-NMR (400 MHz, DMSO-$d_6$) δ 7.96 (s, 1H), 7.76-7.60 (m, 3H), 7.56-7.51 (m, 3H), 7.43-7.38 (m, 1H), 6.88-6.80 (m, 2H), 4.17 (t, J = 6.9 Hz, 2H), 2.09 (t, J = 6.9 Hz, 2H), 1.40 (s, 6H). | 68 mg, 48%, white solid |

[a]Isolated as a bis ammonium salt.

[b]EtOAc was used as the solvent.

A number of examples of formula (1b) were synthesised according to route 3a or route 3b:

Route 3: Scheme 3

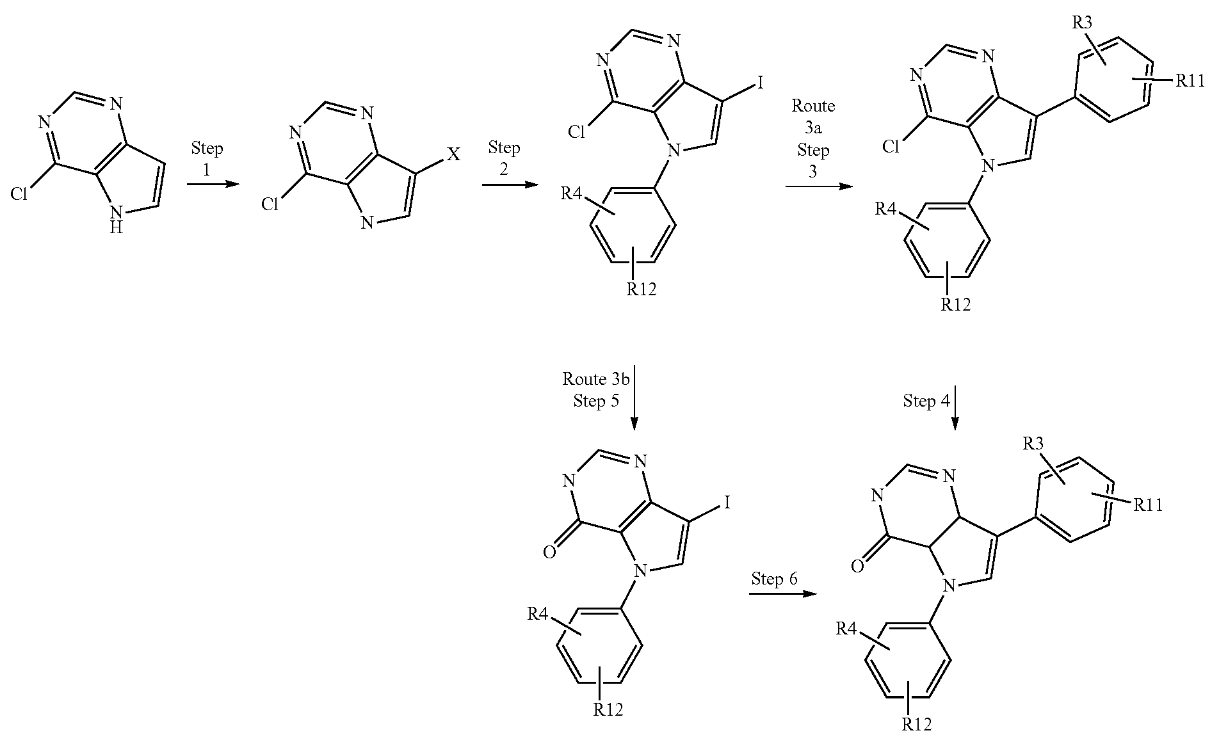

Route 3, Step 1: Iodination

4-Chloro-7-iodo-5H-pyrrolo[3,2-d]pyrimidine (CH6)

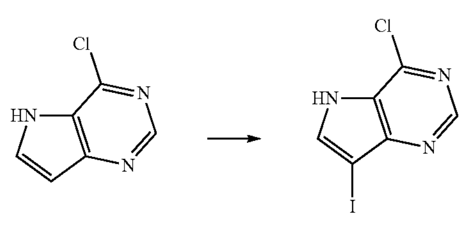

CH6

To a solution of 4-chloro-5H-pyrrolo[3,2-d]pyrimidine (25.0 g, 162.8 mmol) in THE (700 mL) was added N-iodo-succinamide (40.1 g, 179 mmol) at the resulting mixture was stirred for 4 h at RT and then was concentrated in vacuo. The residue triturated in $Et_2O$, the resulting solid was collected by filtration and washed with $Et_2O$. The crude compound was purified by silica gel column chromatography eluting with 20-30% EtOAc/petroleum ether to afford 4-chloro-7-iodo-5H-pyrrolo[3,2-d]pyrimidine (CH6) as a yellow solid (32.0 g, 70%); LC-MS. Rt 2.29 min, AnalpH2_MeOH_4 min(1); ($ESI^+$) m/z 280.0, 282.0 $[M+H]^+$.

Route 3, Step 2: Chan-Lam

4-Chloro-7-iodo-5-(4-methoxy-phenyl)-5H-pyrrolo[3,2-d]pyrimidine (CH7)

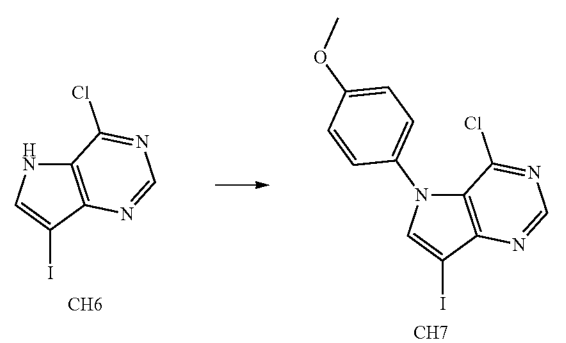

CH6 CH7

To 4-chloro-7-iodo-5H-pyrrolo[3,2-d]pyrimidine (150 mg, 0.54 mmol), 4-methoxyphenyl boronic acid (163 mg, 1.07 mmol), triethylamine (150 μL, 1.07 mmol), pyridine (87 μL, 1.07 mmol), copper (II) acetate monohydrate (195 mg, 1.07 mmol), molecular sieves (4 Å, ~320 mg) were added and suspended in DCM (3.6 mL). The reaction mixture was stirred, with a silica gel dehydrating guard, at RT overnight. The reaction mixture was evaporated to dryness, re-suspended in DCM and washed with aq. satd. EDTA. The precipitated solid was removed by filtration and the filtrate passed through a phase separation cartridge and the organic phase was evaporated evaporated in vacuo. The crude compound was purified by reversed phase preparative HPLC-MS to afford 4-chloro-7-iodo-5-(4-methoxy-phenyl)-5H-pyrrolo[3,2-d]pyrimidine (CH7) as an off-white solid (14.2 mg, 7%); LC-MS. Rt 3.10 min, AnalpH2_MeOH_4 min(1); ($ESI^+$) m/z 386.0, 388.0 $[M+H]^+$; $^1H$ NMR (400 MHz, DMSO-$d_6$): δ 8.77 (s, 1H), 8.30 (s, 1H), 7.50 (d, J=9.2 Hz, 2H), 7.07 (d, J=8.8 Hz, 2H), 3.84 (s, 3H).

4-Chloro-7-iodo-5-phenyl-5H-pyrrolo[3,2-d]pyrimidine (CH8)

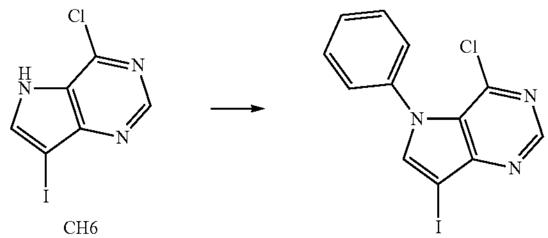

CH6 CH8

To a solution of 4-chloro-7-iodo-5H-pyrrolo[3,2-d]pyrimidine (CH6) (40.4 g, 249.55 mmol) in DMF (250 mL) was added copper (II) acetate monohydrate (49.8 g, 249.55 mmol) and activated molecular sieves (1.00 g) followed by addition of $NEt_3$ (52.07 mL, 374.31 mmol) and the resulting reaction mixture was heated at 60° C. for 24 h. The reaction mixture was cooled to RT and the solvent concentrated in vacuo. The crude solid was dissolved in DCM (600 mL) and quenched with saturated aqueous solution of EDTA (200 mL. The separated aqueous layer was dried (anhydrous $Na_2SO_4$), filtered and concentrated in vacuo to afford a crude solid. The crude compound was purified by silica gel column chromatography eluting with 0-5% EtOAc/petroleum ether to afford 4-chloro-7-iodo-5-phenyl-5H-pyrrolo[3,2-d]pyrimidine ($CH_8$) as an off-white solid (5.2 g, 12%); LC-MS. $R_t$ 3.08 min, AnalpH2_MeOH_4 min(1); ($ESI^+$) m/z 356.1, 358.1 $[M+H]^+$; $^1H$ NMR (400 MHz, DMSO-8.80 (m, 1H), 8.39 (1H), 7.64-7.54 (m, 5H).

The following intermediates were synthesised using an analogous procedure to CH8 from CH6 (reaction duration varied between 75 mins-10h:

TABLE 35

| Compound | Cpd # (Intermediate Used) | Analytical Data | Mass, % Yield, State |
| --- | --- | --- | --- |
| 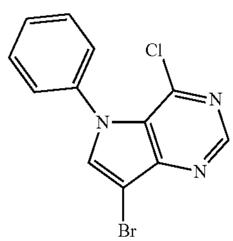 [SMILES: Clc1ncnc2c(Br)cn(-c3ccccc3)c12] | CH9[a] | LC-MS. $R_t$ 3.11 min, AnalpH2_MeOH_4 min; ($ESI^+$) m/z 308.2, 310.2 $[M + H]^+$ | 844 mg, 21%, off-white solid[p] |
| 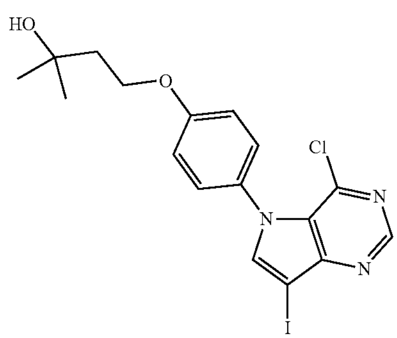 [SMILES: CC(C)(O)CCOc1ccc(-n2cc(I)c3ncnc(Cl)c32)cc1] | CH16 (B10) | LC-MS. $R_t$ 3.16 min, AnalpH2_MeOH_4 min; ($ESI^+$) m/z 457.9 $[M + H]^+$ | 792 mg, 17%, pale beige solid |
| 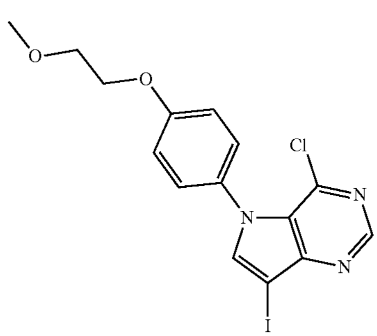 [SMILES: COCCOc1ccc(-n2cc(I)c3ncnc(Cl)c32)cc1] | CH17 | LC-MS. $R_t$ 3.02 min, AnalpH2_MeOH_4 min; ($ESI^+$) m/z 430.1 $[M + H]^+$ | 62 mg, 1%, yellow solid |

[a]Work-up carried out with 20% aq. $NH_4OH$.

Route 3a, Step 3: Suzuki-Miyaura Coupling

4-Chloro-7-[4-(3-morpholin-4-yl-propoxy)-phenyl]-5-phenyl-5H-pyrrolo[3,2-d]pyrimidine formic acid salt (CP61)

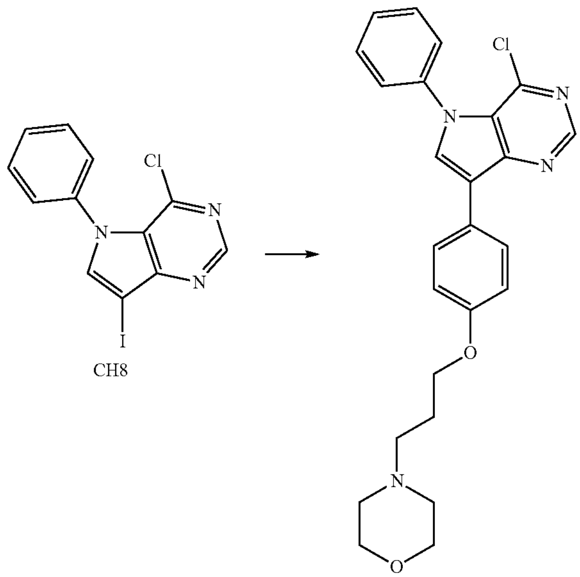

CH8

CP61

A mixture of 4-chloro-7-iodo-5-phenyl-5H-pyrrolo[3,2-d]pyrimidine (CH8) (100 mg, 0.161 mmol), 4-(3-morpholinopropoxy)phenyl boronic acid, pinacol ester (117.0 mg, 0.34 mmol), (commercial source), Pd(dppf)$Cl_2$.DCM (22.9 mg, 0.028 mmol) and K2$CO_3$ (77.7 mg, 0.56 mmol) in 1,4-dioxane:$H_2O$ (1.5 mL, 9:1) was de-oxygenated with $N_2$ for 5 mins and then heated in the microwave at 120° C. for 2 h. The reaction mixture was filtered through a celite cartridge (2.5 g) and washed with MeOH (3×CV) followed by DCM (3×CV). The organics were concentrated in vacuo. The crude solid was purified by reverse phase preparative HPLC-MS to afford 4-chloro-7-[4-(3-morpholin-4-yl-propoxy)-phenyl]-5-phenyl-5H-pyrrolo[3,2-d]pyrimidine formic acid salt (CP61) as an orange oil (63 mg, 45%). LC-MS. Rt 2.30 min, AnalpH2_MeOH_4 min(1); ($ESI^+$) m/z 449.3 $[M+H]^+$.

The following intermediates were synthesised using analogous procedures to CP61 from the chloropyrimidine $CH_8$ unless otherwise stated (total duration of heating varied between 0.5 and 5 h):

TABLE 36

| Compound | Cpd# (Intermediate used)[a] | Analytical Data | Mass, % Yield, Appearance |
|---|---|---|---|
| 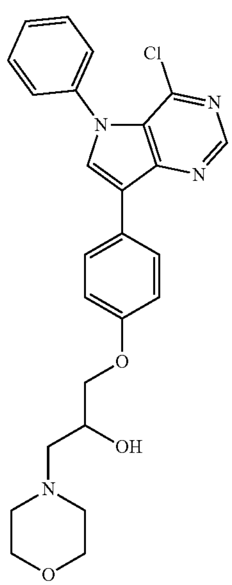 [SMILES: OC(COc1ccc(-c2cn(-c3ccccc3)c3c(Cl)ncnc23)cc1)CN1CCOCC1] | CP62[f] (B27) | LC-MS. $R_t$ 2.23 min, AnalpH2_MeOH_4 min(1); ($ESI^+$) m/z 465.3 $[M + H]^+$. | 61 mg, 43%, orange oil |

TABLE 36-continued
| Compound | Cpd# (Intermediate used)[a] | Analytical Data | Mass, % Yield, Appearance |
|---|---|---|---|
| 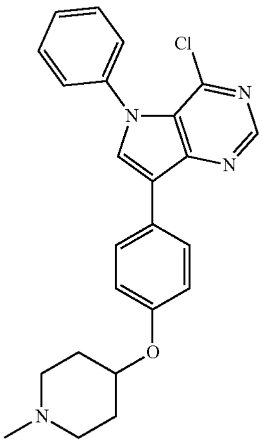 [SMILES: CN1CCC(Oc2ccc(-c3cn(-c4ccccc4)c4c(Cl)ncnc34)cc2)CC1] | CP63[f] (B46) | LC-MS. $R_t$ 2.31 min, AnalpH2_MeOH_4 min(1); ($ESI^+$) m/z 419.1 $[M + H]^+$. | 57 mg, 44%, pale brown solid |
| 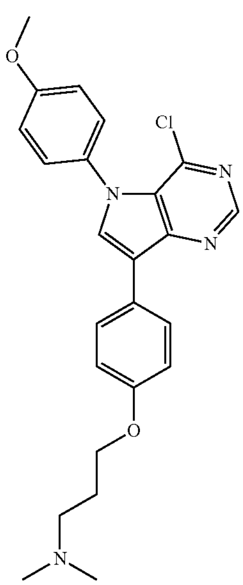 [SMILES: COc1ccc(-n2cc(-c3ccc(OCCCN(C)C)cc3)c3ncnc(Cl)c32)cc1] | CP64[f] (CH7) | LC-MS. $R_t$ 2.31 min, AnalpH2_MeOH_QC_V1(1); ($ESI^+$) m/z 437.3 $[M + H]^+$. | 34 mg, 47%, off-white solid[a] |

TABLE 36-continued
| Compound | Cpd# (Intermediate used)^a | Analytical Data | Mass, % Yield, Appearance |
|---|---|---|---|
| 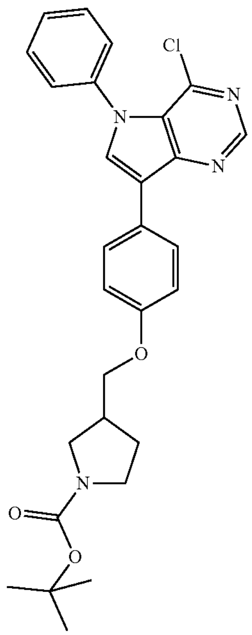 [SMILES: CC(C)(C)OC(=O)N1CCC(COc2ccc(-c3cn(-c4ccccc4)c4c(Cl)ncnc34)cc2)C1] | CP65 (B38) | LC-MS. $R_t$ 3.72 min, AnalpH2_MeOH_4 min(1); ($ESI^+$) m/z 505.1 $[M + H]^+$ | 132 mg, 97%, yellow solid |
| 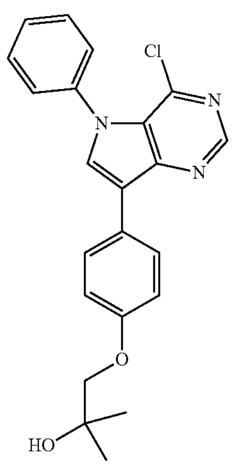 [SMILES: CC(C)(O)COc1ccc(-c2cn(-c3ccccc3)c3c(Cl)ncnc23)cc1] | CP66 (B45) | LC-MS. $R_t$ 3.34 min, AnalpH2_MeOH_4 min(1); ($ESI^+$) m/z 394.3 $[M + H]^+$ | 120 mg, 54%, pale yellow solid |
| 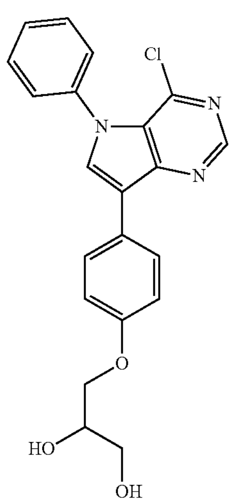 [SMILES: OCC(O)COc1ccc(-c2cn(-c3ccccc3)c3c(Cl)ncnc23)cc1] | CP67 (B8) | LC-MS. $R_t$ 3.03 min, AnalpH2_MeOH_4 min(1); ($ESI^+$) m/z 396.3 $[M + H]^+$ | 49 mg, 44%, pale orange oil |

TABLE 36-continued
| Compound | Cpd# (Intermediate used)* | Analytical Data | Mass, % Yield, Appearance |
|---|---|---|---|
| 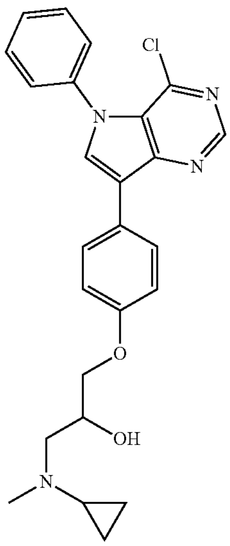 [SMILES: CN(CC(O)COc1ccc(-c2cn(-c3ccccc3)c3c(Cl)ncnc23)cc1)C1CC1] | CP68 (B33) | LC-MS. $R_t$ 2.38 min, AnalpH2_MeOH_4 min(1); ($ESI^+$) m/z 449.3 $[M + H]^+$ | 31 mg, 25% |
| 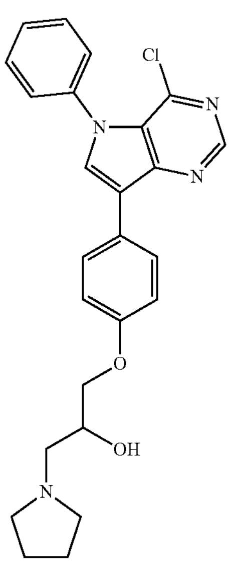 [SMILES: OC(COc1ccc(-c2cn(-c3ccccc3)c3c(Cl)ncnc23)cc1)CN1CCCC1] | CP69 (B32) | LC-MS. $R_t$ 2.34 min, AnalpH2_MeOH_4 min(1); ($ESI^+$) m/z 449.3 $[M + H]^+$ | 91 mg, 71%, yellow solid |

TABLE 36-continued
| Compound | Cpd# (Intermediate used)[a] | Analytical Data | Mass, % Yield, Appearance |
|---|---|---|---|
| 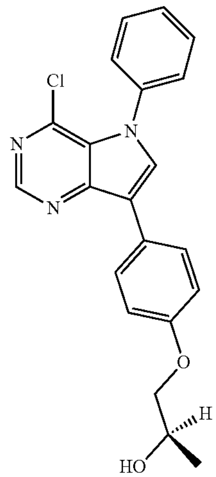 [SMILES: C[C@@H](O)COc1ccc(-c2cn(-c3ccccc3)c3c(Cl)ncnc23)cc1] | CP70 (B14) | LC-MS. $R_t$ 3.24 min, AnalpH2_MeOH_4 min(1); (ESI[+]) m/z 380.3 $[M + H]^+$ | 60 mg, 56%, pale yellow solid |
| 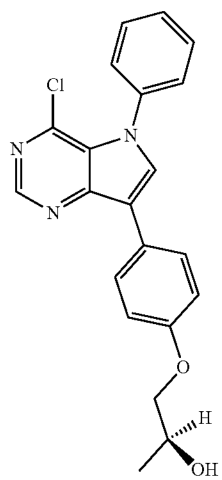 [SMILES: C[C@H](O)COc1ccc(-c2cn(-c3ccccc3)c3c(Cl)ncnc23)cc1] | CP71 (B15) | LC-MS. $R_t$ 3.23 min, AnalpH2_MeOH_4 min(1); (ESI[+]) m/z 380.3 $[M + H]^+$ | 60 mg, 56%, pale yellow solid |
| 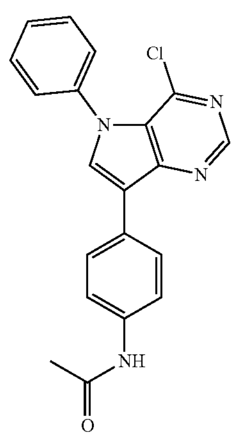 [SMILES: CC(=O)Nc1ccc(-c2cn(-c3ccccc3)c3c(Cl)ncnc23)cc1] | CP76 | LC-MS. $R_t$ 3.07 min, AnalpH2_MeOH_4 min(1); (ESI[+]) m/z 363.2 $[M + H]^+$ | 129 mg, quant, white solid |

TABLE 36-continued
| Compound | Cpd# (Intermediate used)^a | Analytical Data | Mass, % Yield, Appearance |
|---|---|---|---|
| 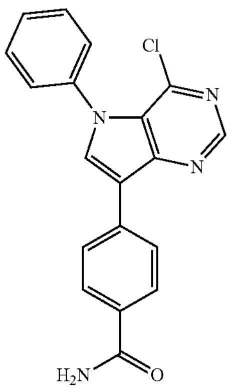 [SMILES: NC(=O)c1ccc(-c2cn(-c3ccccc3)c3c(Cl)ncnc23)cc1] | CP77 | LC-MS. $R_t$ 2.93 min, AnalpH2_MeOH_4 min(1); (ESI$^+$) m/z 349.2 [M + H]$^+$ | 90 mg, 83%, white solid |
| 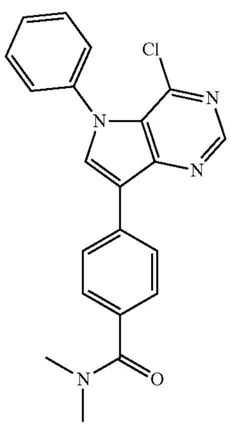 [SMILES: CN(C)C(=O)c1ccc(-c2cn(-c3ccccc3)c3c(Cl)ncnc23)cc1] | CP78 | LC-MS. $R_t$ 3.10 min, AnalpH2_MeOH_4 min(1); (ESI$^+$) m/z 377.2 [M + H]$^+$ | 52 mg, 62%, white solid |
| 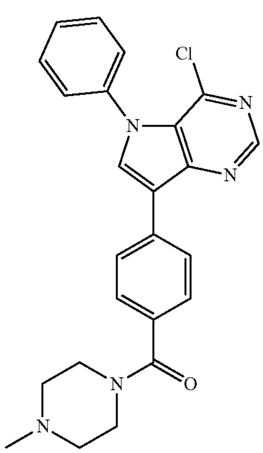 [SMILES: CN1CCN(C(=O)c2ccc(-c3cn(-c4ccccc4)c4c(Cl)ncnc34)cc2)CC1] | CP79 | LC-MS. $R_t$ 2.14 min, AnalpH2_MeOH_4 min(1); (ESI$^+$) m/z 432.3 [M + H]$^+$ | 79 mg, 81%, yellow solid |

TABLE 36-continued
| Compound | Cpd# (Intermediate used)[a] | Analytical Data | Mass, % Yield, Appearance |
|---|---|---|---|
| 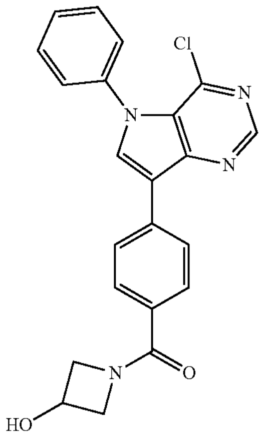 [SMILES: O=C(c1ccc(-c2cn(-c3ccccc3)c3c(Cl)ncnc23)cc1)N1CC(O)C1] | CP80 (B40)[a] | LC-MS. $R_t$ 2.95 min, AnalpH2_MeOH_4 min(1); (ESI$^+$) m/z 405.2 $[M + H]^+$ | 55 mg, 60%, brown gum |
| 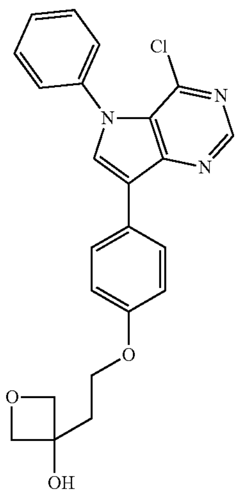 [SMILES: OC1(CCOc2ccc(-c3cn(-c4ccccc4)c4c(Cl)ncnc34)cc2)COC1] | CP81 (B53) | LC-MS. $R_t$ 3.21 min, AnalpH2_MeOH_4 min(1); (ESI$^+$) m/z 422.2 $[M + H]^+$ | 88 mg, 93%, brown gum |
| 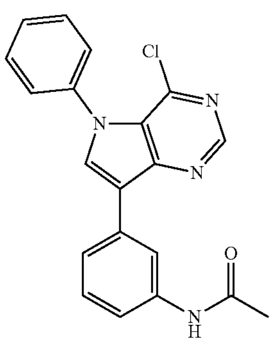 [SMILES: CC(=O)Nc1cccc(-c2cn(-c3ccccc3)c3c(Cl)ncnc23)c1] | CP82 | LCMS. Rt 3.09 AnalpH2_MeOH_4 min(1); (ESI$^+$) m/z 363.3 $[M + H]^+$ | 80 mg, 52%, white solid |

TABLE 36-continued
| Compound | Cpd# (Intermediate used)* | Analytical Data | Mass, % Yield, Appearance |
| --- | --- | --- | --- |
| 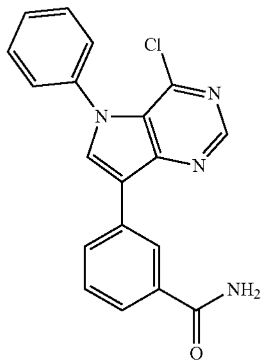 [SMILES: NC(=O)c1cccc(-c2cn(-c3ccccc3)c3c(Cl)ncnc23)c1] | CP83 | LCMS. Rt 2.98 AnalpH2_MeOH_4 min(1); ($ESI^+$) m/z 349.3 $[M + H]^+$ | 63 mg, 65%, white solid |
| 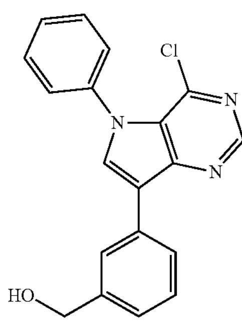 [SMILES: OCc1cccc(-c2cn(-c3ccccc3)c3c(Cl)ncnc23)c1] | CP84 | LCMS. Rt 3.09 AnalpH2_MeOH_4 min(1); ($ESI^+$) m/z 336.3 $[M + H]^+$ | 88 mg, 62%, brown oil |
| 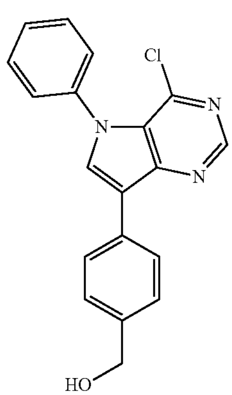 [SMILES: OCc1ccc(-c2cn(-c3ccccc3)c3c(Cl)ncnc23)cc1] | CP85 | LCMS. Rt 3.09 AnalpH2_MeOH_4 min(1); ($ESI^+$) m/z 336.3 $[M + H]^+$ | 36 mg, 38%, white solid |

TABLE 36-continued

| Compound | Cpd# (Intermediate used)[*] | Analytical Data | Mass, % Yield, Appearance |
|---|---|---|---|
| 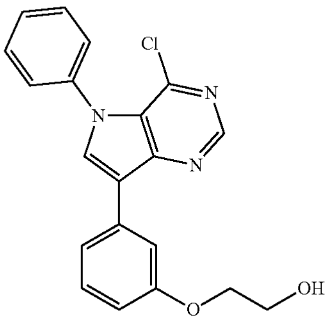 [SMILES: OCCOc1cccc(-c2cn(-c3ccccc3)c3c(Cl)ncnc23)c1] | CP86 | LCMS. Rt 3.14 AnalpH2_MeOH_4 min(1); ($ESI^+$) m/z 366.3 $[M + H]^+$ | 51 mg, 33%, colourless gum |

[*]If not stated commercial and/or CH4.

[a]Tert-butyldimethylsiyl protecting group was also removed under the Suzuki coupling conditions.

[f]Isolated as a formic acid salt.

Route 3a, Step 4: Final Compounds Via Acidic Hydrolysis

7-[4-(3-Morpholin-4-yl-propoxy)-phenyl]-5-phenyl-3,5-dihydro-pyrrolo[3,2-d]pyrimidin-4-one (Ex-84)

A mixture of 4-chloro-7-[4-(3-morpholin-4-yl-propoxy)-phenyl]-5-phenyl-5H-pyrrolo[3,2-d]pyrimidine formic acid salt CP61 (62.6 mg, 0.126 mmol) and NaOAc (20.7 mg, 0.252 mmol) in AcOH (256 μL) was heated at 100° C. for 4 h. The reaction mixture was concentrated in vacuo. The crude residue was purified by reversed phase preparative HPLC-MS to afford 7-[4-(3-Morpholin-4-yl-propoxy)-phenyl]-5-phenyl-3,5-dihydro-pyrrolo[3,2-d]pyrimidin-4-one (Ex-84) as an off-white solid (45.1 mg, 83%); LC-MS. $R_t$ 5.27 min, AnalpH2_MeOH_QC_V1(1); ($ESI^+$) m/z 431.2 $[M+H]^+$; $^1H$ NMR (400 MHz, DMSO-$d_6$): 12.14 (br s, 1H), 8.07-8.05 (m, 3H), 7.98 (s, 1H), 7.56 (d, J=8.7 Hz, 2H), 7.49 (**t, J=7.8 Hz, 2H), 7.40 (t, J=7.3 Hz, 1H), 6.97 (d, J=8.7 Hz, 2H), 4.03 (t, J=6.4 Hz, 2H), 3.58 (t, J=4.6 Hz, 4H), 2.43 (t, J=7.3 Hz, 2H), 2.40-2.35 (m, 4H), 1.88 (tt, J=6.4, 7.3 Hz, 2H).

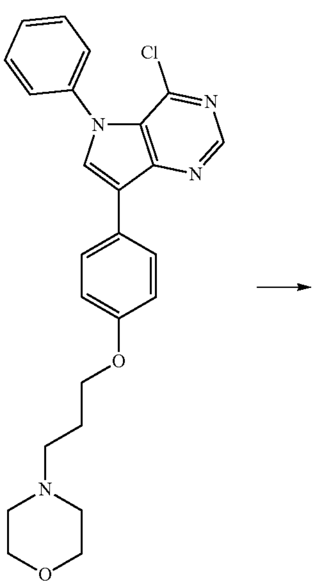

CP-61

-continued

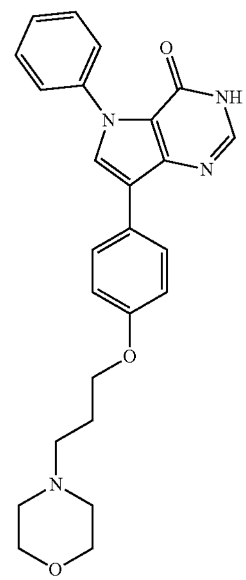

Ex-84

The following examples were synthesised using an analogous procedure to Ex-85 reaction duration of up to 24 h:

TABLE 37

| Compound | Ex. No. (Intermediate used) | Analytical Data | Mass, % Yield, Appearance |
| --- | --- | --- | --- |
| 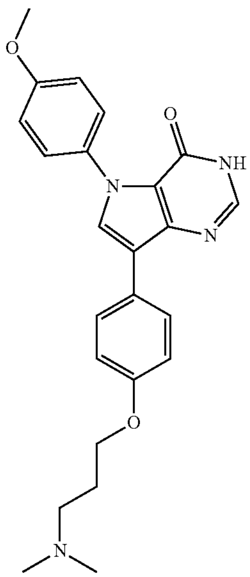 [SMILES: COc1ccc(-n2cc(-c3ccc(OCCCN(C)C)cc3)c3nc[nH]c(=O)c32)cc1] | Ex-85 (CP64) | LC-MS. $R_t$ 5.19 min, AnalpH2_MeOH_QC_V1(1); ($ESI^+$) m/z 419.3 $[M + H]^{+:}$ $^1H$ NMR (400 MHz, DMSO-$d_6$): 12.08 (br-s, 1H), 8.04 (d, J = 8.8 Hz, 2H), 7.97 (s, 1H), 7.95 (s, 1H), 7.46 (d, J = 8.8 Hz, 2H), 7.03 (d, J = 8.8 Hz, 2H), 6.96 (d, J = 8.8 Hz, 2H), 4.01 (t, J = 6.6 Hz, 2H), 3.83 (s, 3H), 2.36 (t, J = 7.0 Hz, 2H), 2.15 (s, 6H), 1.85 (tt, J = 7.0, 6.6 Hz, 2H). | 28 mg, 95%, off-white solid |
| 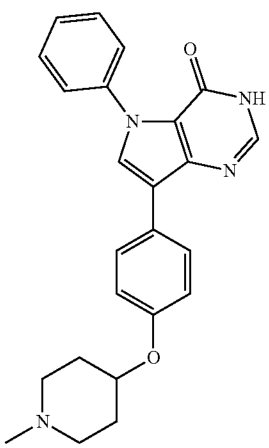 [SMILES: CN1CCC(Oc2ccc(-c3cn(-c4ccccc4)c4c(=O)[nH]cnc34)cc2)CC1] | Ex-86[f] (CP63) | LC-MS. $R_t$ 5.36 min, AnalpH2_MeOH_QC_V1(1); ($ESI^+$) m/z 401.2 $[M + H]^+$; $^1H$ NMR (400 MHz, DMSO-$d_6$): 12.14 (br s, 1H), 8.20 (s, 1H), 8.05 (s, 1H), 8.03 (d, J = 8.7 Hz, 2H), 7.98 (s, 1H), 7.56 (d, J = 8.2 Hz, 2H), 7.49 (**t, J = 7.8 Hz, 2H), 7.40 (t, J = 7.3 Hz, 1H), 6.99 (d, J = 8.7 Hz, 2H), 4.40 (m, 1H), 2.66-2.63 (m, 2H), 2.25-2.21 (m, 5H), 1.97-1.93 (m, 2H), 1.69-1.62 (m, 2H). | 33 mg, 60%, pale yellow solid |
| 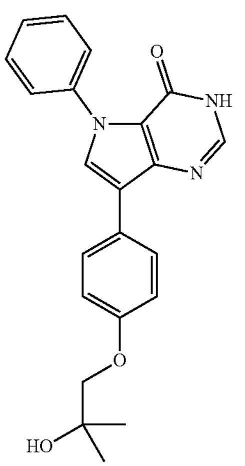 [SMILES: CC(C)(O)COc1ccc(-c2cn(-c3ccccc3)c3c(=O)[nH]cnc23)cc1] | Ex-87 (CP66) | LC-MS. $R_t$ 7.85 min, AnalpH2_MeOH_QC_V1(1); ($ESI^+$) m/z 376.4 $[M + H]^+$; $^1H$ NMR (400 MHz, DMSO-$d_6$): 12.15 (br s, 1H), 8.07 (d, J = 8.7 Hz, 2H), 8.07 (s, 1H), 7.99 (s, 1H), 7.58-7.55 (m, 2H), 7.51-7.47 (m, 2H), 7.43-7.38 (m, 1H), 6.98 (d, J = 8.6 Hz, 2H), 4.64 (s, 1H), 3.74 (s, 2H), 1.22 (s, 6H). | 50.0 mg, 44%, white solid |

TABLE 37-continued
| Compound | Ex. No. (Intermediate used) | Analytical Data | Mass, % Yield, Appearance |
|---|---|---|---|
| 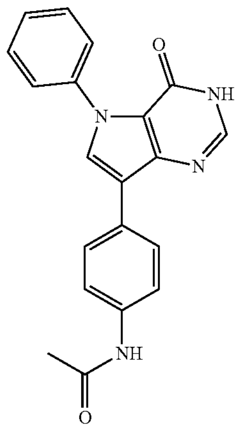 [SMILES: CC(=O)Nc1ccc(-c2cn(-c3ccccc3)c3c(=O)[nH]cnc23)cc1] | Ex-152 (CP76) | LC-MS. $R_t$ 7.10 min, AnalpH2_MeOH_QC_V1(1); ($ESI^+$) m/z 345.3 $[M + H]^+$ | 4 mg, 4%, white solid |
| 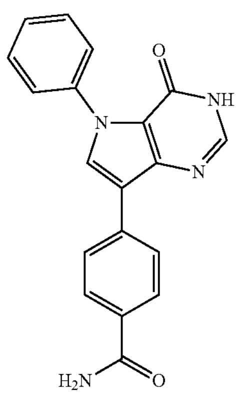 [SMILES: NC(=O)c1ccc(-c2cn(-c3ccccc3)c3c(=O)[nH]cnc23)cc1] | Ex-153 (CP77) | LC-MS. $R_t$ 6.71 min, AnalpH2_MeOH_QC_V1(1); ($ESI^+$) m/z 331.2 $[M + H]^+$ | 16 mg, 18%, white solid |
| 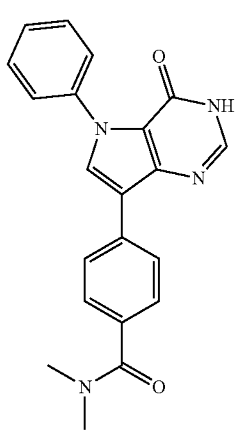 [SMILES: CN(C)C(=O)c1ccc(-c2cn(-c3ccccc3)c3c(=O)[nH]cnc23)cc1] | Ex-154 (CP78) | LC-MS. $R_t$ 7.22 min, AnalpH2_MeOH_QC_V1(1); ($ESI^+$) m/z 359.3 $[M + H]^+$ | 32 mg, 68%, white solid |

TABLE 37-continued
| Compound | Ex. No. (Intermediate used) | Analytical Data | Mass, % Yield, Appearance |
|---|---|---|---|
| 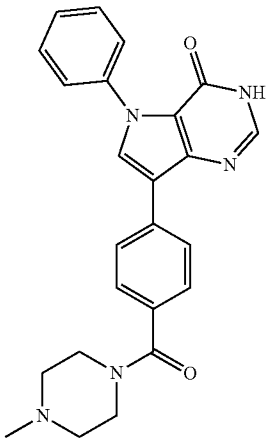 [SMILES: CN1CCN(C(=O)c2ccc(-c3cn(-c4ccccc4)c4c(=O)[nH]cnc34)cc2)CC1] | Ex-155 (CP79) | LC-MS. $R_t$ 4.83 min, AnalpH2_MeOH_QC_V1(1); ($ESI^+$) m/z 414.4 $[M + H]^+$ | 25 mg, 32%, white solid |
| 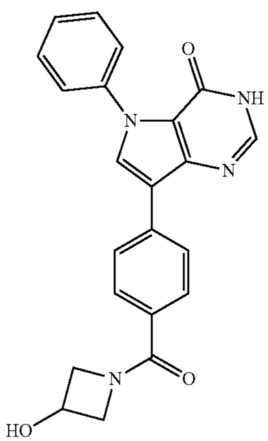 [SMILES: O=C(c1ccc(-c2cn(-c3ccccc3)c3c(=O)[nH]cnc23)cc1)N1CC(O)C1] | Ex-156 (CP80) | LC-MS. $R_t$ 6.82 min, AnalpH2_MeOH_QC_V1(1); ($ESI^+$) m/z 387.3 $[M + H]^+$ | 4 mg, 8%, off white solid |
| 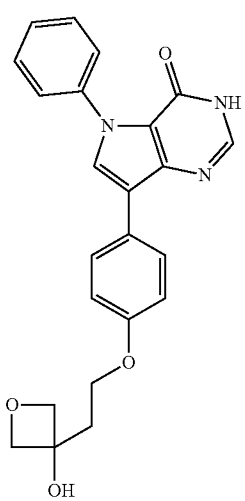 [SMILES: O=c1[nH]cnc2c(-c3ccc(OCCC4(O)COC4)cc3)cn(-c3ccccc3)c12] | Ex-157 (CP81) | LC-MS. $R_t$ 7.51 min, AnalpH2_MeOH_QC_V1(1); ($ESI^+$) m/z 404.3 $[M + H]^+$ | 13 mg, 15%, brown gum |

TABLE 37-continued

| Compound | Ex. No. (Intermediate used) | Analytical Data | Mass, % Yield, Appearance |
|---|---|---|---|
| 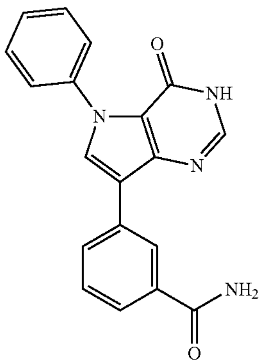 [SMILES: NC(=O)c1cccc(-c2cn(-c3ccccc3)c3c(=O)[nH]cnc23)c1] | Ex-158 (CP83) | LC-MS. $R_t$ 6.99 min, AnalpH2_MeOH_QC_V1(1); ($ESI^+$) m/z 331.2 $[M + H]^+$; $^1$H-NMR (400 MHz, DMSO-$d_6$): δ 8.49-8.51 (m, 1H), 8.31-8.35 (m, 1H), 8.18 (s, 1H), 7.99 (s, 1H), 7.90 (br s, 1H), 7.67-7.71 (m, 1H), 7.53-7.58 (m, 2H), 7.35-7.50 (m, 5H). | 13 mg, 21% white solid |
| 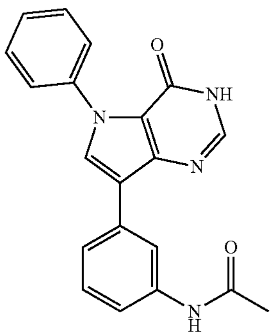 [SMILES: CC(=O)Nc1cccc(-c2cn(-c3ccccc3)c3c(=O)[nH]cnc23)c1] | Ex-159 (CP82)[a] | LC-MS. $R_t$ 7.30 min, AnalpH2_MeOH_QC_V1(1); ($ESI^+$) m/z 345.3 $[M + H]^+$ | 47 mg, 62%, white solid |

[f]Isolated as a formate salt.
[a]aq. work-up carried out with EtOAc and water.

Route 3a, Step 4: Final Compounds Via Acidic Hydrolysis Followed by Basic Hydroylsis 7-[4-(2,3-Dihydroxypropoxy)-phenyl]-5-phenyl-3,5-dihydropyrrolo[3,2-d]pyrimidin-4-one

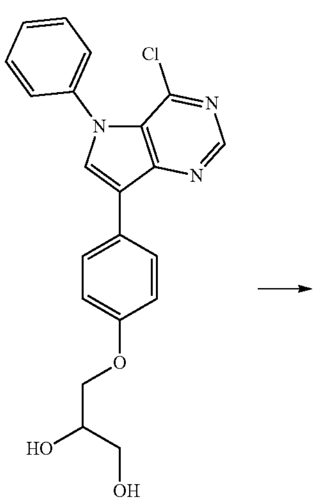

-continued

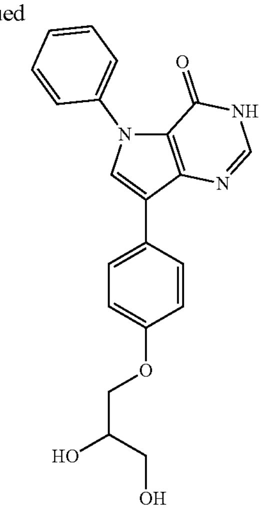

Ex-88

To a stirred solution of 3-[4-(4-chloro-5-phenyl-5H-pyrrolo[3,2-d]pyrimidin-7-yl)-phenoxy]-propane-1,2-diol (CP67) (48.7 mg, 0.123 mmol) and NaOAc (20.2 mg, 0.246 mmol) in AcOH (100 μL) was heated at 10000 for 3h. The reaction mixture was then concentrated in vacuo and the resulting residue diluted with water and $LiOH \cdot H_2O$ (51.6 mg, 1.23 mmol) was added. The resulting mixture was heated at 40° C. for 30 mins. Reaction mixture was concentrated in vacuo and the crude compound was purified by reversed phase preparative HPLC-MS to afford 7-[4-(2,3-dihydroxypropoxy)-phenyl]-5-phenyl-3,5-dihydropyrrolo[3,2-d]pyrimidin-4-one (Ex-88) as a white solid (29.2 mg, 63%); LC-MS. $R_t$ 6.92 min, AnalpH2_MeOH_QC_V1(1); ($ESI^+$) 378.3$[M+H]^+$; $^1H$ NMR (400 MHz, DMSO-$d_6$): 12.14 (br-s, 1H), 8.07-8.05 (m, 3H), 7.98 (s, 7.56 (d, J=7.3 Hz, 2H), 7.50 (**t, J=7.3 Hz, 2H), 7.40 (t, J=7.3 Hz, 1H), 6.98 (d, J=8.7 Hz, 2H), 4.95 (d, J=5.0 Hz, 1H), 4.68 (m, 1H), 4.02 (m, 1H), 3.88 (m, 1H), 3.80 (m, 1H), 3.46 (m, 2H).

A number of examples were made using an analogous procedure to Ex-88.

TABLE 38

| Compound | Ex. No. (Intermediate used) | Analytical Data | Mass, % Yield, Appearance |
| --- | --- | --- | --- |
| 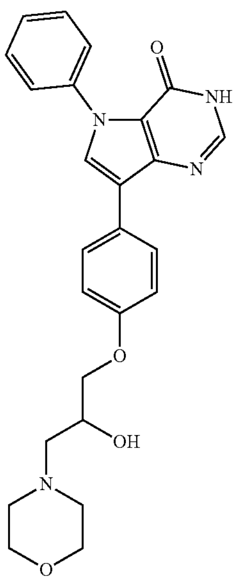 [SMILES: O=c1[nH]cnc2c(-c3ccc(OCC(O)CN4CCOCC4)cc3)cn(-c3ccccc3)c12] | Ex-89 (CP62) | LC-MS. $R_t$ 5.07 min, AnalpH2_MeOH_QC_V1(1); ($ESI^+$) m/z 447.2 $[M + H]^+$. | 32 mg, 59%, white solid |
| 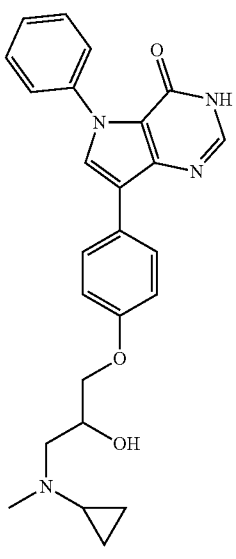 [SMILES: CN(CC(O)COc1ccc(-c2cn(-c3ccccc3)c3c(=O)[nH]cnc23)cc1)C1CC1] | Ex-90 (CP68) | LC-MS. $R_t$ 5.46 min, AnalpH2_MeOH_QC_V1(1); ($ESI^+$) m/z 431.3 $[M + H]^+$. | 9 mg, 29%, white solid |

TABLE 38-continued

| Compound | Ex. No. (Intermediate used) | Analytical Data | Mass, % Yield, Appearance |
|---|---|---|---|
| 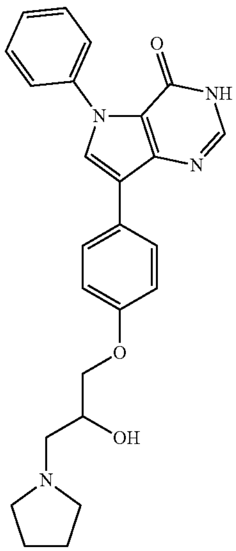 [SMILES: O=c1[nH]cnc2c(-c3ccc(OCC(O)CN4CCCC4)cc3)cn(-c3ccccc3)c12] | Ex-91 (CP69) | LC-MS. $R_t$ 5.23 min, AnalpH2_MeOH_QC_V1(1); ($ESI^+$) m/z 431.3 $[M + H]^+$; $^1H$ NMR (400 MHz, DMSO-$d_6$): 807-8.05 (m, 3H), 7.98 (s, 1H), 7.56 (d, J = 7.3 Hz, 2H), 7.49 (**t, J = 7.3 Hz, 2H), 7.40 (t, J = 7.3 Hz, 1H), 6.98 (d, J = 6.9 Hz, 2H), 4.87 (br s, 1H), 4.02-3.99 (m, 1H), 3.90-3.86 (m, 2H), 2.65-2.60 (m, 1H), 2.47-2.42 (m, 2H), 1.67 (s, 4H). | 37 mg, 43%, white solid |
| 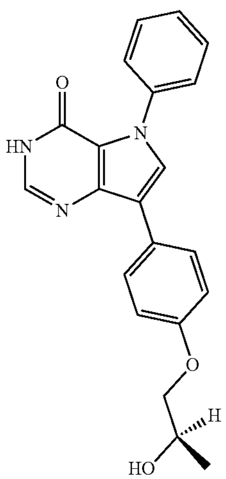 [SMILES: C[C@@H](O)COc1ccc(-c2cn(-c3ccccc3)c3c(=O)[nH]cnc23)cc1] | Ex-92 (CP70) | LC-MS. $R_t$ 7.57 min, AnalpH2_MeOH_QC_V1(1); ($ESI^+$) m/z 362.3 $[M + H]^+$. ; $^1H$ NMR (400 MHz, DMSO-$d_6$): 11.97-11.88 (br s, 0.6H), 7.89-7.85 (m, 3H), 7.79 (s, 1H), 7.39-7.35 (m, 2H), 7.33-7.28 (m, 2H), 7.24-7.19 (m, 1H), 6.79 (d, J = 9.2 Hz, 2H), 4.79 (d, J = 5.0 Hz, 1H) 3.81-3.74 (m, 1H), 3.69-3.59 (m, 2H), 0.98 (d, J = 6.41 Hz, 3H). | 12 mg, 21%, white solid |
| 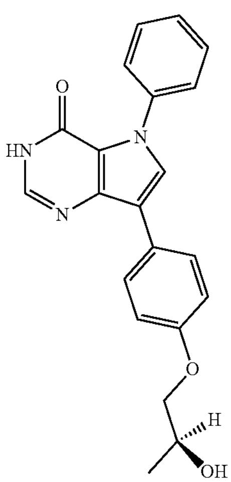 [SMILES: C[C@H](O)COc1ccc(-c2cn(-c3ccccc3)c3c(=O)[nH]cnc23)cc1] | Ex-93 (CP71) | LC-MS. $R_t$ 7.59 min, AnalpH2_MeOH_QC_V1(1); ($ESI^+$) m/z 362.3 $[M + H]^+$. ; $^1H$ NMR (400 MHz, DMSO-$d_6$): 11.99-11.95 (br s, 1H), 7.91-7.87 (m, 3H), 7.81 (s, 1H), 7.41-7.37 (m, 2H), 7.35-7.29 (m, 2H), 7.26-7.21 (m, 1H), 6.81 (d, J = 8.7 Hz, 2H), 4.71 (d, J = 4.8 Hz, 1H), 3.83-3.76 (m, 1H), 3.71-3.61 (m, 2H), 1.00 (d, J = 6.41 Hz, 3H). | 9 mg, 15%, white solid |

TABLE 38-continued

| Compound | Ex. No. (Intermediate used) | Analytical Data | Mass, % Yield, Appearance |
|---|---|---|---|
| 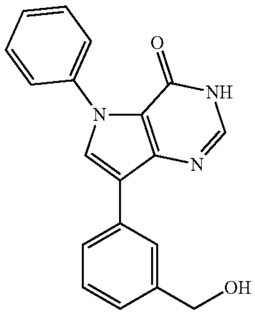 [SMILES: O=c1[nH]cnc2c(-c3cccc(CO)c3)cn(-c3ccccc3)c12] | Ex-160 (CP84) | LC-MS. $R_t$ 7.37 min, AnalpH2_MeOH_QC_V1(1); (ESI$^+$) m/z 318.3 [M + H]$^+$. | 12 mg, 15%, pale yellow solid. |
| 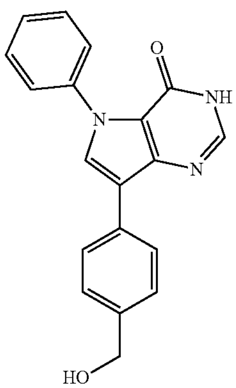 [SMILES: O=c1[nH]cnc2c(-c3ccc(CO)cc3)cn(-c3ccccc3)c12] | Ex-161 (CP85) | LC-MS. $R_t$ 7.21 min, AnalpH2_MeOH_QC_V1(1); (ESI$^+$) m/z 318.1 [M + H]$^+$; $^1$H-NMR (400 MHz, DMSO-$d_6$): δ 12.09 (br s, 1H), 8.11 (s, 1H), 8.07 (d, J = 8.2 Hz, 2H), 7.96 (s, 1H), 7.52-7.55 (m, 2H), 7.49-7.44 (m, 2H), 7.35-7.4 (m, 1H), 7.31 (d, J = 8.2 Hz, 2H), 5.13 (t, J = 5.7 Hz, 1H), 4.48 (d, J = 5.7 Hz, 2H) | 18 mg, 45%, white solid |
| 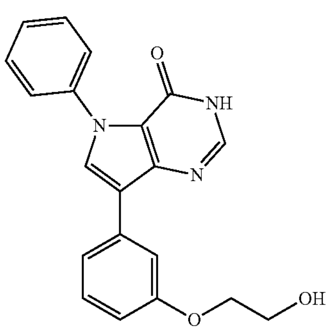 [SMILES: O=c1[nH]cnc2c(-c3cccc(OCCO)c3)cn(-c3ccccc3)c12] | Ex-162 (CP86) | LC-MS. $R_t$ 7.45 min, AnalpH2_MeOH_QC_V1(1); (ESI$^+$) m/z 348.3 [M + H]$^+$. | 28 mg, 58%, white solid |

Example Ex-94 was Made from CP65

5-Phenyl-7-[4-(pyrrolidin-3-ylmethoxy)-phenyl]-3,5-dihydro-pyrrolo[3,2-d]pyrimidin-4-one (Ex-94)

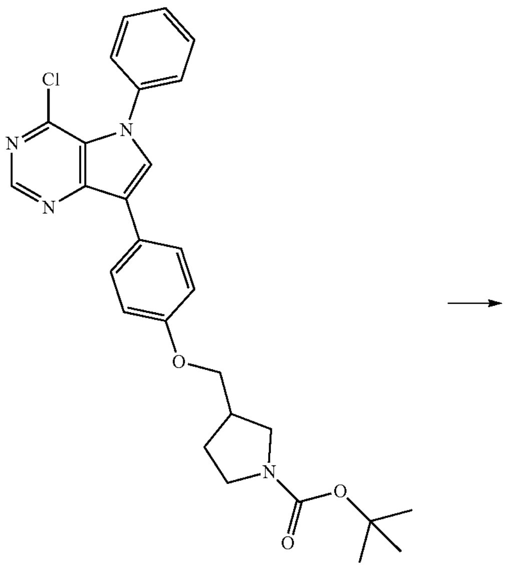

CP65

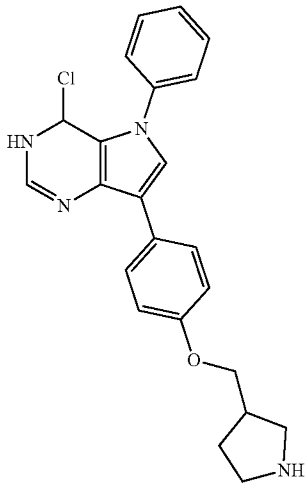

Ex-94

A mixture of 3-[4-(4-chloro-5-phenyl-5H-pyrrolo[3,2-d]pyrimidin-7-yl)-phenoxymethyl]-pyrrolidine-1-carboxylic acid tert-butyl ester (CP65) (132 mg, 0.26 mmol), 2M NaOH (aq) (2 mL) and 1,4-dioxane (2 mL) was heated at 100° C. for 18 h. The reaction mixture was allowed to cool to RT and two layers formed. The top layer was taken, concentrated in vacuo, re-dissolved in a mixture of MeOH (5 mL) and 4M HCl/dioxane (2 mL) then heated at 40° C. for 2.5 h. The mixture was concentrated in vacuo, purified by reversed phase preparative HPLC-MS then lyophilised from a mixture of MeCN:$H_2O$ (2 mL, 1:1) to afford 5-phenyl-7-[4-(pyrrolidin-3-ylmethoxy)-phenyl]-3,5-dihydro-pyrrolo[3,2-d]pyrimidin-4-one as a white solid (4 mg, 14%); LC-MS. Rt 5.48 min, AnalpH2_MeOH_QC_V1(1); ($ESI^+$) m/z 387.1 $[M+H]^+$ Example Ex-95 was Made from Ex-94

7-[4-(1-Methyl-pyrrolidin-3-ylmethoxy)-phenyl]-5-phenyl-3,5-dihydro-pyrrolo[3,2-d]pyrimidin-4-one (Ex-95)

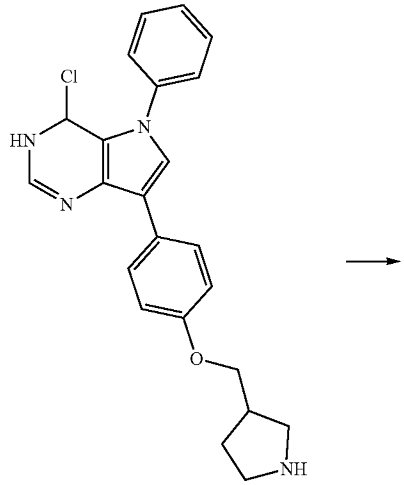

Ex-94

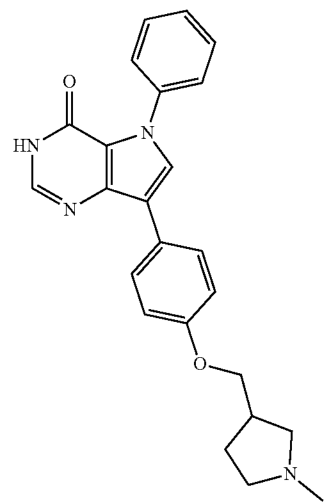

Ex-95

To a suspension of 5-phenyl-7-[4-(pyrrolidin-3-ylmethoxy)-phenyl]-3,5-dihydro-pyrrolo[3,2-d]pyrimidin-4-one Ex-94 (20 mg, 0.05 mmol) in DCM (5 mL) at RT was added 37 wt % formaldehyde solution in $H_2O$ (20 μl, 0.25 mmol) followed by sodium triacetoxyborohydride (16 mg, 0.08 mmol). The mixture was stirred at room temperature for 90 min. A further aliquot of formaldehyde (20 μl, 0.25 mmol) and sodium triacetoxyborohydride (11 mg, 0.05 mmol) were added and reaction mixture stirred for a further 45 min at RT. The mixture was diluted with DCM (10 mL), partitioned with $H_2O$ (10 mL), passed through a phase separator, concentrated in vacuo, purified by reversed phase preparative HPLC-MS then lyophilised from a mixture of MeCN:$H_2O$ (2 mL, 1:1) to afford 7-[4-(1-methyl-pyrrolidin-3-ylmethoxy)-phenyl]-5-phenyl-3,5-dihydro-pyrrolo[3,2-d]pyrimidin-4-one (Ex-95) as a white solid (1 mg, 4%); LC-MS. Rt 5.42 min, AnalpH2_MeOH_QC_V1(1); ($ESI^+$) m/z 401.2 $[M+H]^+$ A number of examples of formula (Ib) were made according to the Route 3b, Step 5—Acidic hydrolysis 7-Bromo-5-phenyl-3,5-dihydro-pyrrolo[3,2-d]pyrimidin-4-one (CH10)

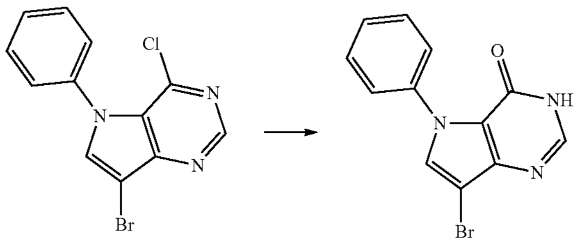

CH10

To a solution of 7-bromo-4-chloro-5-phenyl-5H-pyrrolo[3,2-d]pyrimidine (840 mg, 2.72 mmol) (commercial source) in AcOH (13.6 mL) was added NaOAc (447 mg, 5.44 mmol) and the reaction mixture heated at 100° C. for 18 h. The reaction mixture was cooled to RT, diluted with $H_2O$ and the layers separated (phase separator) and the organic phase evaporated in vacuo. The crude compound was purified by silica gel column chromatography eluting with 0-10% MeOH/DCM to obtain 7-bromo-5-phenyl-3,5-dihydro-pyrrolo[3,2-d]pyrimidin-4-one (CH10) as an off-white solid (341 mg, 43%); LC-MS. Rt 2.72 min, AnalpH2_MeOH_4 min(1); ($ESI^+$) m/z 290.2, 292.2 $[M+H]^+$.

The following intermediates were prepared from using an analogous procedure to CH10 reaction duration varied between 3-8 h:

TABLE 39

| Compound | Cpd # (Intermediate used) | Analytical Data | Mass, % Yield, Appearance |
|---|---|---|---|
| 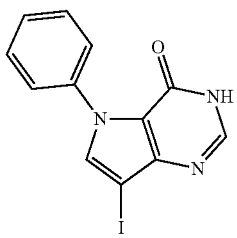 [SMILES: O=c1[nH]cnc2c(I)cn(-c3ccccc3)c12] | CH11 (CH8) | LC-MS. $R_t$ 2.81 min, AnalpH2_MeOH_4 min; ($ESI^+$) m/z 338.2 $[M + H]^+$. | 31 mg, 54%, off-white solid |
| 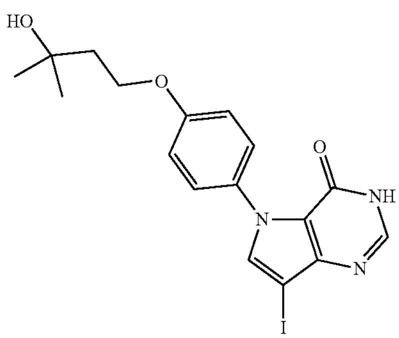 [SMILES: CC(C)(O)CCOc1ccc(-n2cc(I)c3nc[nH]c(=O)c32)cc1] | CH18 (CH16) | LC-MS. $R_t$ 2.93 min, AnalpH2_MeOH_4 min; ($ESI^+$) m/z 440.1 $[M + H]^+$. | 613 mg, 81%, pale brown solid |
| 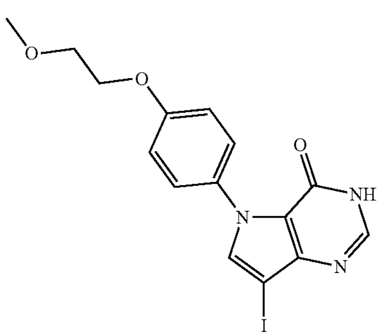 [SMILES: COCCOc1ccc(-n2cc(I)c3nc[nH]c(=O)c32)cc1] | CH19 (CH17) | LC-MS. $R_t$ 2.74 min, AnalpH2_MeOH_4 min; ($ESI^+$) m/z 412.1 $[M + H]^+$. | 49 mg, 84%, yellow solid |

Route 3b, Step 6—Suzuki Miyaura Coupling 3-(4-Oxo-5-phenyl-4,5-dihydro-3H-pyrrolo[3,2-d]pyrimidin-7-yl)-benzoic acid ethyl ester (Ex-96)

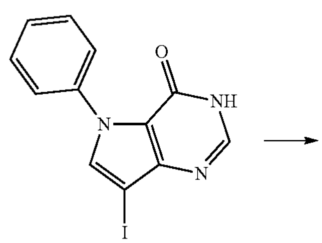

CH11

-continued

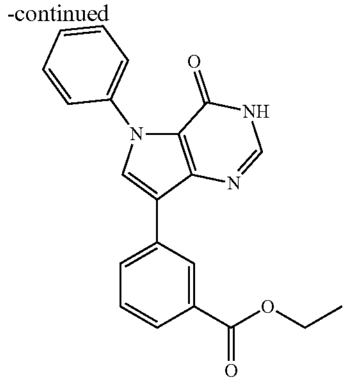

Ex-96

7-Iodo-5-phenyl-3,5-dihydro-pyrrolo[3,2-d]pyrimidin-4-one (CH11) (85 mg, 0.23 mmol), 3-(4,4,5,5-tetramethyl-[1,3,2]dioxaborolan-2-yl)-benzoic acid ethyl ester (75 mg, 0.27 mmol), $K_2CO_3$ (62 mg, 0.45 mmol), Pd(dppf)$Cl_2$.DCM (10 mg, 0.011 mmol) in 1,4-dioxane:$H_2O$ (4:1, 1.2 mL) was added to a microwave vial and de-oxygenated with $N_2$. The reaction mixture was heated at 120° C. for 1 h in a microwave reactor. The reaction mixture was passed through a 2 g Si-thiol cartridge, eluting with DCM (2×CV) and MeOH (2×CV) and the filtrate evaporated to dryness. The residue was suspended in DCM (10 mL) and washed with $H_2O$ (10 mL), the organic phase separated (phase separator) and evaporated to dryness. The crude compound was purified by reversed phase preparative HPLC-MS to afford 3-(4-oxo-5-phenyl-4,5-dihydro-3H-pyrrolo[3,2-d]pyrimidin-7-yl)-benzoic acid ethyl ester as an off-white solid (25 mg, 30%); LC-MS. Rt 8.21 min, AnalpH2_MeOH_QC_V1(1); ($ESI^+$) m/z 360.3 $[M+H]^+$.

The following examples were synthesised using an analogous procedure to Ex-96:

TABLE 40

| Compound | Ex. # (Intermediate used) | Analytical Data | Mass, % Yield, Appearance |
|---|---|---|---|
| 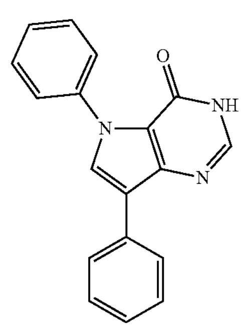 [SMILES: O=c1[nH]cnc2c(-c3ccccc3)cn(-c3ccccc3)c12] | Ex-97 (CH11) | LC-MS. $R_t$ 7.91 min, AnalpH2_MeOH_QC_V1(1); ($ESI^+$) m/z 288.2 $[M + H]^+$; $^1H$ NMR (400 MHz, DMSO-$d_6$): 12.20 (br s, 1H), 8.17 (s, 1H), 8.15 (dd, J = 8.3, 1.3 Hz, 2H), 8.01 (s, 1H), 7.60-7.56 (m, 2H), 7.53-7.48 (m, 2H), 7.45-7.40 (m, 3H), 7.28-7.24 (m, 1H). | 12 mg, 20%, white solid |

TABLE 40-continued

| Compound | Ex. # (Intermediate used) | Analytical Data | Mass, % Yield, Appearance |
|---|---|---|---|
| 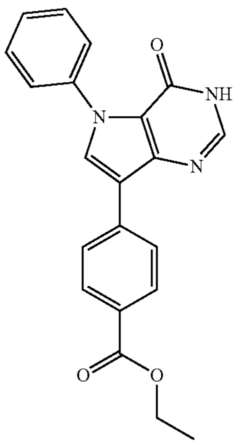 [SMILES: CCOC(=O)c1ccc(-c2cn(-c3ccccc3)c3c(=O)[nH]cnc23)cc1] | Ex-98 (CH11) | LC-MS. $R_t$ 8.18 min, AnalpH2_MeOH_QC_V1(1); ($ESI^+$) m/z 360.3 $[M + H]^+$. | 17 mg, 6%, off-white solid |
| 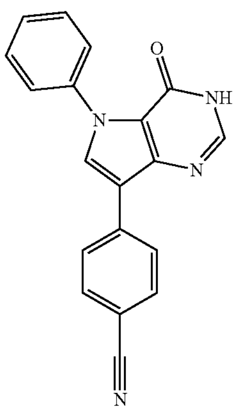 [SMILES: N#Cc1ccc(-c2cn(-c3ccccc3)c3c(=O)[nH]cnc23)cc1] | Ex-99 (CH11) | LC-MS. $R_t$ 7.55 min, AnalpH2_MeOH_QC_V1(1); ($ESI^+$) m/z 313.2 $[M + H]^+$; $^1H$ NMR (400 MHz, DMSO-$d_6$): 12.30 (br s, 1H), 8.43-8.41 (m, 3H), 8.06 (s, 1H), 7.87 (d, J = 8.7 Hz, 2H), 7.59 (d, J = 7.8 Hz, 2H), 7.52 (**t, J = 7.3 Hz, 2H), 7.44 (t, J = 7.3 Hz, 1H). | 6 mg, 8%, off-white solid |
| 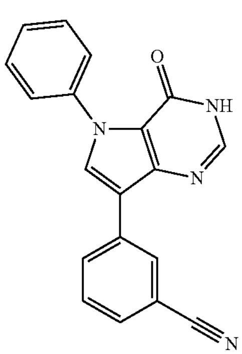 [SMILES: N#Cc1cccc(-c2cn(-c3ccccc3)c3c(=O)[nH]cnc23)c1] | Ex-100 (CH11) | LC-MS. $R_t$ 7.56 min, AnalpH2_MeOH_QC_V1(1); ($ESI^+$) m/z 313.2 $[M + H]^+$; $^1H$ NMR (400 MHz, DMSO-$d_6$): 12.31 (br s, 1H), 8.66 (s, 1H), 8.53 (d, J = 7.8 Hz, 1H), 8.39 (s, 1H), 8.07 (s, 1H), 7.70 (d, J = 7.8 Hz, 1H), 7.64 (**t, J = 7.8 Hz, 1H), 7.59 (d. J = 7.8 Hz, 2H), 7.52 (**t, J = 8.2 Hz, 2H), 7.44 (t, J = 7.3 Hz, 1H). | 7 mg, 9%, off-white solid |

Route 3b, Step 6: Final Compounds Via Suzuki Coupling Using PdXPhosG3 with $K_3PO_4$ as Base 5-(4-(3-hydroxy-3-methyl butoxy)phenyl)-7-phenyl-3,5-dihydro-4H-pyrrolo[3,2-d]pyrimidin-4-one (Ex-163)

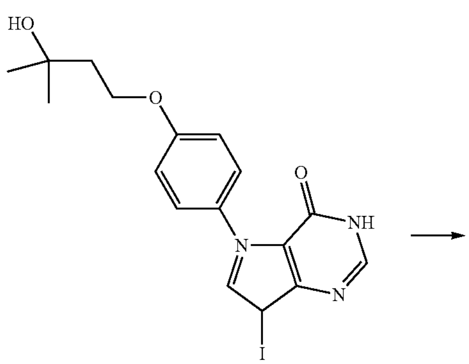

CH18

-continued

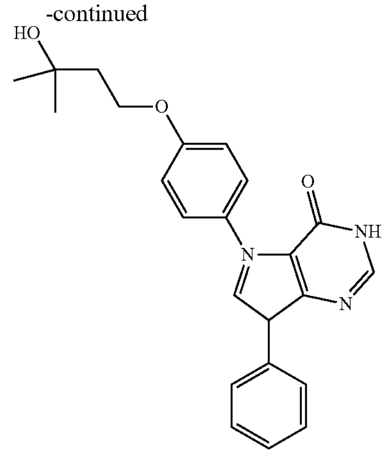

Ex-163

5-(4-(3-hydroxy-3-methyl butoxy)phenyl)-7-iodo-3,5-dihydro-4H-pyrrolo[3,2-d]pyrimidin-4-one (CH18) (150 mg, 0.341 mmol), phenylboronic acid (62.4 mg, 0.512 mmol), $K_3PO_4$ (145 mg, 0.682 mmol), PdXPhosG3 (14.4 mg, 0.017 mmol) in 1,4-dioxane:$H_2O$ (3 mL, 4:1) was de-oxygenated with $N_2$ for 5 min and then heated in a microwave reactor at 90° C. for h. There action mixture was filtered through a Si-thiol cartridge (1 g) and washed with MeOH (3×CV) followed by DCM (3×CV). The filtrate was evaporated to dryness and the crude residue was purified by purified by silica gel column chromatography eluting with 0-5% MeOH/DCM followed by reversed phase preparative HPLC to afford 5-(4-(3-hydroxy-3-methyl butoxy)phenyl)-7-phenyl-3,5-dihydro-4H-pyrrolo[3,2-d]pyrimidin-4-one (Ex-163) as a white solid (46 mg, 35%); LC-MS. Rt 8.20 min, AnalpH2_MeOH_QC_V1(1); ($ESI^+$) m/z 390.3$[M+H]^+$; $^1$HNMR (400 MHz, DMSO-$d_6$) δ 12.13 (br-s, 1H), 8.15-8.13 (2H), 8.07, (s, 1H), 7.97 (m, 1H), 7.46 (d, J=8.7 Hz, 2H), 7.42-7.37 (m, 2H), 7.25-7.22 (m, 1H), 7.02 (d, =8.7 Hz, 2H), 4.43 (m, 1H), 4.15 (t, J=7.1 Hz, 2H), 1.88 (t, J=7.1 Hz, 2H), 1.19 (s, 16H).

The following compounds of formula ( ) were made using analogous procedures to compound Ex-163 reaction duration varied between 1-2.5 h:

TABLE 41

| Compound | Ex. # (Intermediate used) | Analytical Data | Mass, % Yield, Appearance |
|---|---|---|---|
| 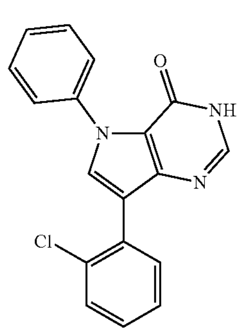 [SMILES: O=c1[nH]cnc2c(-c3ccccc3Cl)cn(-c3ccccc3)c12] | Ex-164 (CH11) | LC-MS. $R_t$ 8.17 min, AnalpH2_MeOH_QC_V1(1); ($ESI^+$) m/z 322.1 $[M + H]^+$; $^1$H-NMR (400 MHz, DMSO-$d_6$): δ 12.17 (br s, 1H), 7.93 (d, J = 4.6 Hz, 2H), 7.81 (dd, J = 7.3, 1.8 Hz, 1H), 7.60-7.53 (m, , 3H), 7.49 (t, J = 7.6 Hz, 2H), 7.41 (td, J = 7.4, 1.5 Hz, 2H), 7.35 (td, J = 7.7, 1.7 Hz, 1H). | 28 mg, 30%, white solid |

TABLE 41-continued

| Compound | Ex. # (Intermediate used) | Analytical Data | Mass, % Yield, Appearance |
|---|---|---|---|
| 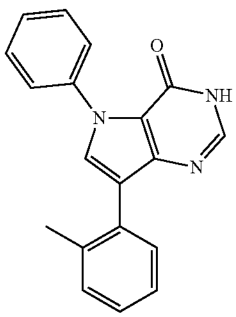 [SMILES: Cc1ccccc1-c1cn(-c2ccccc2)c2c(=O)[nH]cnc12] | Ex-165 (CH11) | LC-MS. $R_t$ 8.10 min, AnalpH2_MeOH_QC_V1(1); ($ESI^+$) m/z 302.2 $[M + H]^+$; $^1H$-NMR (400 MHz, DMSO-$d_6$): δ 12.10 (br s, 1H), 7.89 (s, 1H), 7.78 (s, 1H), 7.61-7.53 (m, 2H), 7.52-7.44 (m, 3H), 7.43-7.36 (m, 1H), 7.33-7.17 (m, 3H), 2.36 (s, 3H). | 16 mg, 18%, white solid |
| 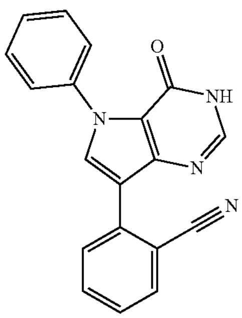 [SMILES: N#Cc1ccccc1-c1cn(-c2ccccc2)c2c(=O)[nH]cnc12] | Ex-166 (CH11) | LC-MS. $R_t$ 7.49 min, AnalpH2_MeOH_QC_V1(1); ($ESI^+$) m/z 313.3 $[M + H]^+$. | 15 mg, 18%, white solid |
| 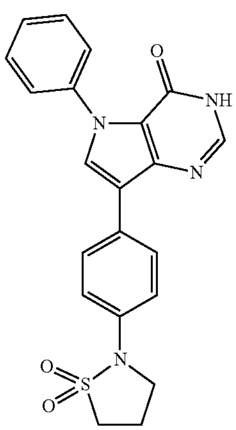 [SMILES: O=c1[nH]cnc2c(-c3ccc(N4CCCS4(=O)=O)cc3)cn(-c3ccccc3)c12] | Ex-167[a] (CH11, B54) | LC-MS. $R_t$ 7.12 min, AnalpH2_MeOH_QC_V1(1); ($ESI^+$) m/z 407.2 $[M + H]^+$; | 11 mg, 9%, white solid |
| 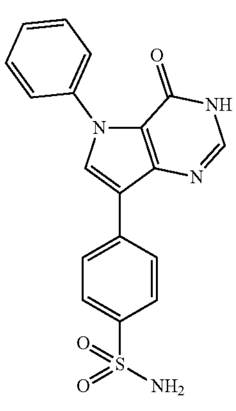 [SMILES: NS(=O)(=O)c1ccc(-c2cn(-c3ccccc3)c3c(=O)[nH]cnc23)cc1] | Ex-168[a] (CH11) | LC-MS. $R_t$ 6.51 min, AnalpH2_MeOH_QC_V1(1); ($ESI^+$) m/z 367.1 $[M + H]^+$; | 4 mg, 4%. White solid |

TABLE 41-continued

| Compound | Ex. # (Intermediate used) | Analytical Data | Mass, % Yield, Appearance |
|---|---|---|---|
| 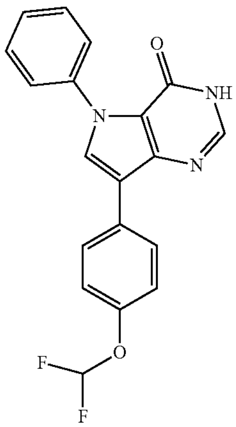 [SMILES: O=c1[nH]cnc2c(-c3ccc(OC(F)F)cc3)cn(-c3ccccc3)c12] | Ex-169[a] (CH11) | LC-MS. $R_t$ 8.02 min, AnalpH2_MeOH_QC_V1(1); ($ESI^+$) m/z 354.2 $[M + H]^+$; $^1H$-NMR (400 MHz, DMSO-$d_6$): δ 12.16 (br s, 1H), 8.19-8.13 (m, 3H), 7.97 (s, 1H), 7.53 (d, J = 8.3, 2H), 7.46 (t, J = 7.3, 2H), 7.42-4.35 (m, 1H), 7.17-7.22 (m, 3H) | 12 mg, 11%, white solid |
| 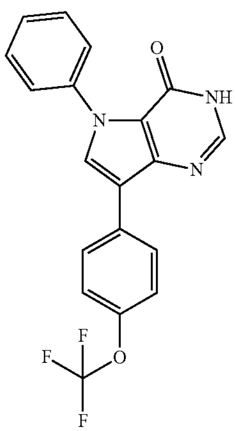 [SMILES: O=c1[nH]cnc2c(-c3ccc(OC(F)(F)F)cc3)cn(-c3ccccc3)c12] | Ex-170[a] (CH11) | LC-MS. $R_t$ 8.53 min, AnalpH2_MeOH_QC_V1(1); ($ESI^+$) m/z 372.1 $[M + H]^+$; $^1H$-NMR (400 MHz, DMSO-$d_6$): δ 12.16 (br s, 1H), 8.19-8.13 (m, 3H), 7.97 (s, 1H), 7.53 (d, J = 8.3, 2H), 7.46 (t, J = 7.3, 2H), 7.42-4.35 (m, 3H). | 24 mg, 23%, off white solid |
| 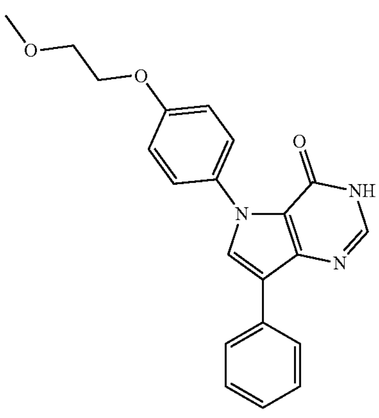 [SMILES: COCCOc1ccc(-n2cc(-c3ccccc3)c3nc[nH]c(=O)c32)cc1] | Ex-171 (CH11) | LC-MS. $R_t$ 7.90 min, AnalpH2_MeOH_QC_V1(1); ($ESI^+$) m/z 362.3 $[M + H]^+$; $^1H$-NMR (400 MHz, DMSO-$d_6$): δ 12.13 (br s, 1H), 8.15-8.13 (m, 2H), 8.08 (s, 1H), 7.97 (s, 1H), 7.47 (d, J = 8.7 Hz, 2H), 7.42-7.38 (m, 2H), 7.25-7.22 (m, 1H), 7.04 (d, J = 8.7 Hz, 2H), 4.24-4.12 (m, 2H), 3.77-3.67 (m, 2H), 3.33 (s, 3H, masked by water peak). | 13 mg, 31%, white solid |

[a]$K_3PO_4$ added as a solution in waterEx-101 was synthesised from Ex-96.

3-(4-Oxo-5-phenyl-4,5-dihydro-3H-pyrrolo[3,2-d]pyrimidin-7-yl)-benzoic acid (Ex-101)

-continued

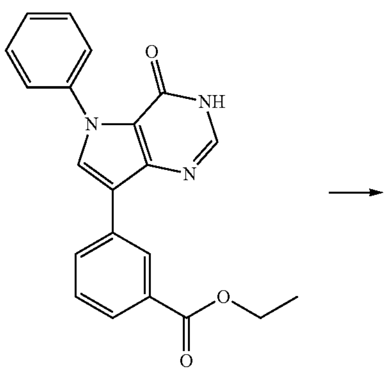

Ex-96

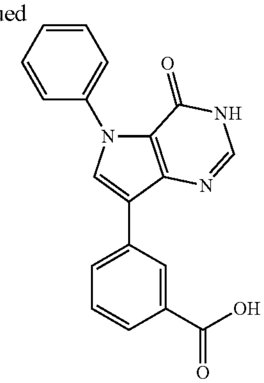

Ex-101

To 3-(4-oxo-5-phenyl-4,5-dihydro-3H-pyrrolo[3,2-d]pyrimidin-7-yl)-benzoic acid ethyl ester (Ex-96) (24 mg, 0.07 mmol), $LiOH{\cdot}H_2O$ (8.4 mg, 0.2 mmol) was added in a mixture of THF:MeOH 3:1 (1.4 mL) and the mixture was stirred at RT overnight. The reaction mixture was diluted with DCM (2 mL) and evaporated to dryness. DMSO (1 mL) was added to the crude compound whereupon a solid precipitated out of solution. The solid was collected by filtration and the filtrate was concentrated in vacuo then purified by reversed phase preparative HPLC-MS. The product, along with the precipitated solid which was found to be clean desired product, was lyophilised from a mixture of $MeCN/H_2O$ (1:1) to afford 3-(4-oxo-5-phenyl-4,5-dihydro-3H-pyrrolo[3,2-d]pyrimidin-7-yl)-benzoic acid as a white solid (10 mg, 42%); LC-MS. Rt 7.40 min, AnalpH2_MeOH_QC_V1(1); ($ESI^+$) m/z 332.3 $[M+H]^+$.

The following examples were synthesised in an analogous procedure to Ex-101:

TABLE 42

| Compound | Ex. # (Intermediate used) | Analytical Data | Mass, % Yield, Appearance |
|---|---|---|---|
| 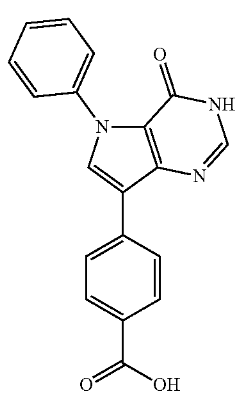 [SMILES: O=C(O)c1ccc(-c2cn(-c3ccccc3)c3c(=O)[nH]cnc23)cc1] | Ex-102 (Ex-98) | LC-MS. $R_t$ 7.32 min, AnalpH2_MeOH_QC_V1(1); ($ESI^+$) m/z 332.2 $[M + H]^+$. | 6 mg, 47%, white solid |

A number of examples of formula (Ia) were synthesised according to Route 4

Route 4: Scheme 4

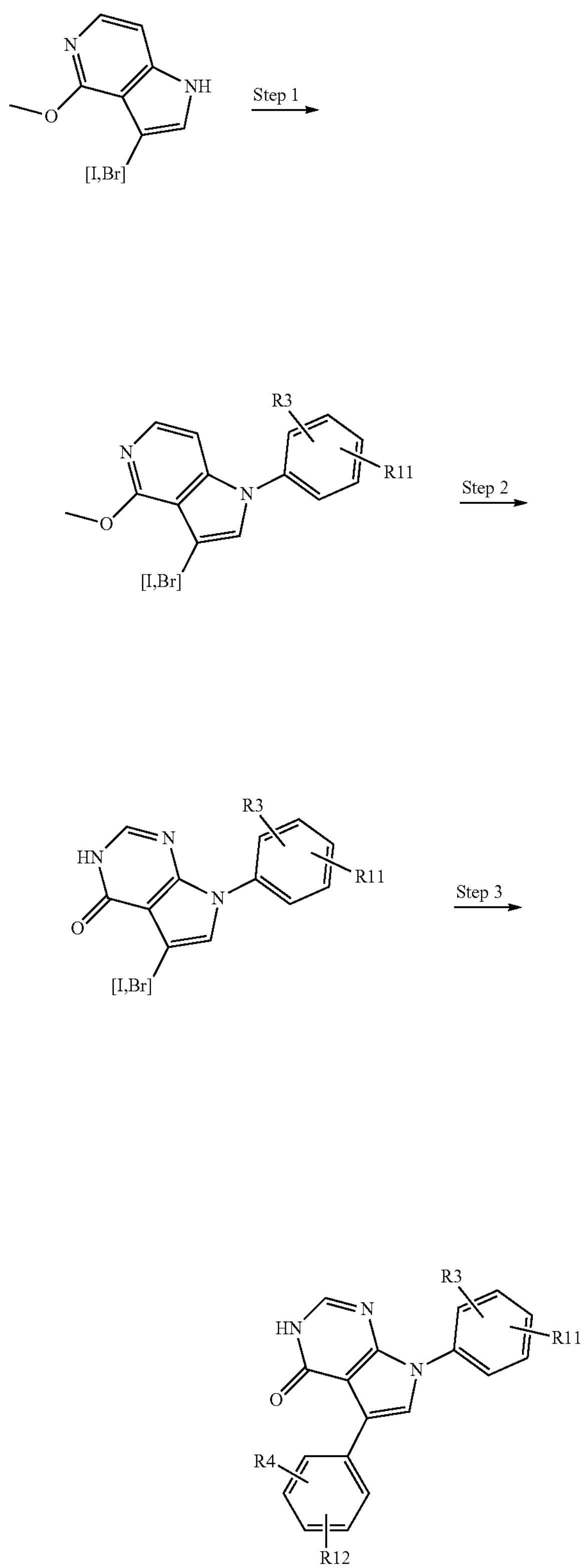

3-Iodo-4-methoxy-1-phenyl-1H-pyrrolo[3,2-c]pyridine (CH20)

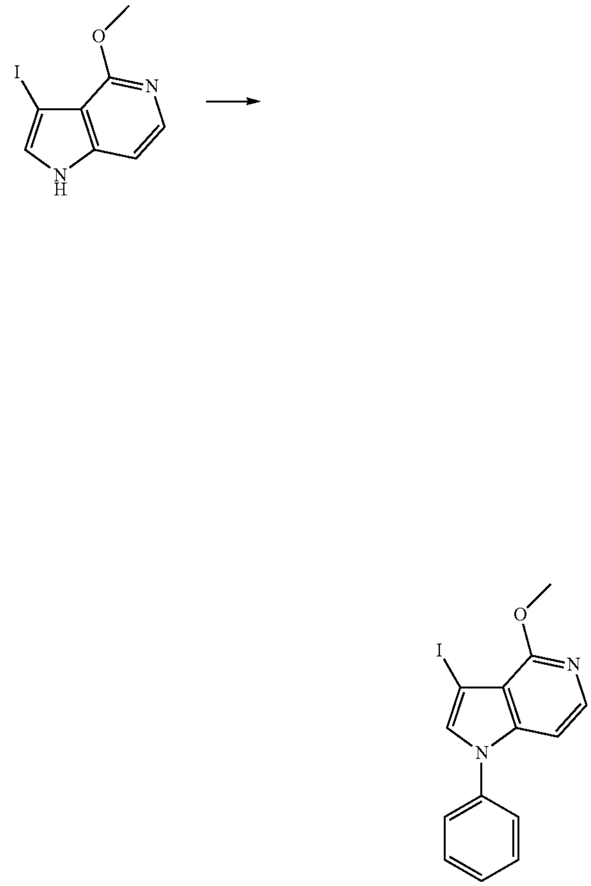

CH20

To 3-Iodo-4-methoxy-1H-pyrrolo[3,2-c]pyridine (1.01 g, 3.68 mmol), phenyl boronic acid (719 mg, 5.9 mmol), 2,2'-bipyridyl (1.15 g, 7.4 mmol), triethylamine (7.7 mL, 55.2 mmol) and molecular sieves (4 Å, 1 g) in DCM (18 mL) was added $Cu(OAc)_2$ (1.34 g, 7.4 mmol). The flask was evacuated and flushed with air (×2). The flask was sealed and a $P_2O_5$ filled syringe was placed in the suba seal and the reaction was stirred at RT overnight. The reaction mixture was passed through a celite cartridge (10 g) and the cartridge washed with MeOH (2×CV) and DCM (2×CV) and the filtrate evaporated to dryness. The residue was dissolved in MeOH and passed through a SCX-2 cartridge (25 g), washing with MeOH (2×CV) and DCM (2×CV). The compound was eluted from the column with 0.7 M $NH_3$/MeOH and the solvent removed in vacuo. The crude compound was purified by silica gel column chromatography eluting with 6-10% EtOAc/iso-hexane to obtain 3-Iodo-4-methoxy-1-phenyl-1H-pyrrolo[3,2-c]pyridine (CH20) as an yellow oil which crystallised on standing (688 mg, 53%); LC-MS. Rt 3.40 min, AnalpH2_MeOH_4 min(1); ($ESI^+$) m/z 351.1 $[M+H]^+$. $^1$H-NMR (400 MHz, DMSO-$d_6$): δ 7.79 (s, 1H), 7.78 (s, 1H), 7.59-7.49 (m, 4H), 7.46-7.39 (m, 1H), 7.10 (d, J=6.0 Hz, 1H), 3.96 (s, 3H)

3-Iodo-1-phenyl-1,5-dihydro-pyrrolo[3,2-c]pyridin-4-one (CH21)

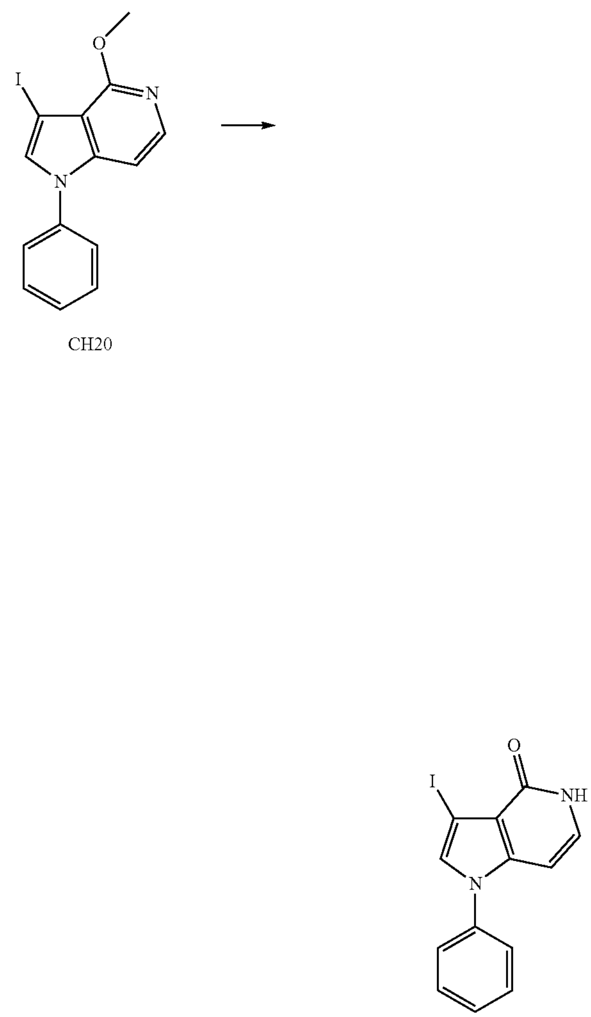

CH20

CH21

To 3-Iodo-4-methoxy-1-phenyl-1H-pyrrolo[3,2-c]pyridine (CH20) (451 mg, 1.29 mmol) and sodium iodide (502 mg, 3.35 mmol) in MeCN (10.5 mL) was added chlorotrimethylsilane (1.63 mL, 12.9 mmol) dropwise and the reaction mixture heated at 50° C. for 5 h. The reaction mixture was added to $NaHCO_3$ (50 mL, aq., satd) and the mixture extracted with EtOAc (2×50 mL). The organic layer was separated, washed with brine (100 mL) and passed through a phase separator and the solvent was removed in vacuo. The crude compound was purified by silica gel column chromatography eluting with DCM 0-5% MeOH/DCM to obtain 3-Iodo-1-phenyl-1,5-dihydro-pyrrolo[3,2-c]pyridin-4-one (CH21) as a pale yellow solid (337 mg, 78%); LC-MS. Rt 2.84 min, AnalpH2_MeOH_4 min(1); ($ESI^+$) m/z 337.1 $[M+H]^+$; $^1$H-NMR (400 MHz, DMSO-$d_6$): δ 11.00 (d, br, J=5.0 Hz, 1H), 7.60-7.39 (m, 6H), 7.08-6.99 (m, 1H), 6.31 (d, J=7.3 Hz, 1H).

3-[4-(2-Methoxy-ethoxy)-phenyl]-1-phenyl-1,5-dihydro-pyrrolo[3,2-c]pyridin-4-one (Ex-172)

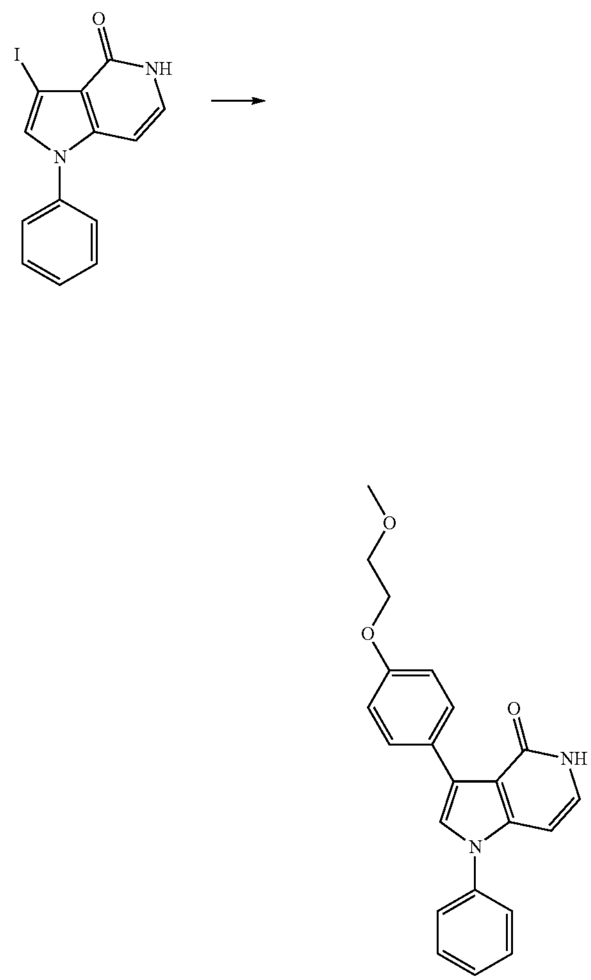

Ex-172

3-Iodo-1-phenyl-1,5-dihydro-pyrrolo[3,2-c]pyridin-4-one (58 mg, 0.17 mmol), 2-(4-(2-methoxyethoxy)phenyl-4,4,5,5-tetramethyl-1,3,2-dioxaborolane (72 mg, 0.26 mmol), $K_3PO_4$ (74 mg, 0.35 mmol), PdXPhosG3 (17 mg, 0.02 mmol) in 1,4-dioxane:$H_2O$ (0.9 mL, 4:1) was de-oxygenated with $N_2$ for 5 min and then heated in a microwave reactor at 90° C. for 1 h. The reaction mixture was filtered through a Si-thiol cartridge (1 g) and washed with DCM (2×CV) followed by MeOH (2×CV). The crude solid was purified by silica gel chromatography, eluting with 5%-95% DCM/iso-hexane, then DCM—65% EtOAc/DCM with 0.2% AcOH. The fractions were combined, evaporated in vacuo and lyophilised from MeCN:$H_2O$ (1:1) to afford 3-[4-(2-methoxy-ethoxy)-phenyl]-1-phenyl-1,5-dihydro-pyrrolo[3,2-c]pyridin-4-one (Ex-172) as a pale yellow solid (44 mg, 72%); LC-MS. Rt 7.95 min. AnalpH2_MeOH_QC_V1(1); ($ESI^+$) m/z 361.2 [M+H]1; $^1$H-NMR (400 MHz, DMSO-$d_6$): δ 10.93 (br d, J=6.0 Hz, 1H), 7.79 (d, J=8.7 Hz, 2H), 7.62-7.52 (m, 4H), 7.50 (s, 1H), 7.47-7.38 (n, 1H), 7.05 (t, J=6.4 Hz, 1H), 6.94-6.75 (m, 2H), 6.35 (d, J=7.3 Hz, 1H), 4.14-3.88 (m, 2H), 3.76-3.42 (m, 2H), 3.29 (s, 3H).

The following examples were synthesised in an analogous procedure to Ex-172:

TABLE 43

| Compound | Ex. # (Intermediate used) | Analytical Data | Mass, % Yield, Appearance |
|---|---|---|---|
| 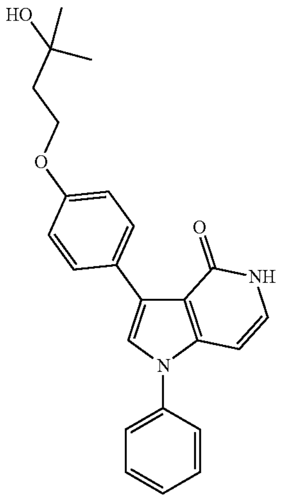 [SMILES: CC(C)(O)CCOc1ccc(-c2cn(-c3ccccc3)c3cc[nH]c(=O)c23)cc1] | Ex-173 | LC-MS. $R_t$ 8.16 min, AnalpH2_MeOH_QC_V1(1); (ESI$^+$) m/z 389.3 [M + H]$^+$. $^1$H-NMR (400 MHz, DMSO-$d_6$): δ 10.91 (d, J = 6.0 Hz, 1H), 7.84-7.73 (m, 2H), 7.59-7.51 (m, 4H), 7.48 (s, 1H), 7.46-7.39 (m, 1H), 7.05 (t, J = 6.6 Hz, 1H), 6.92-6.80 (m, 2H), 6.35 (d, J = 7.3 Hz, 1H), 4.35 (s, 1H), 4.07 (t, J = 7.1 Hz, 2H), 1.82 (t, J = 7.1 Hz, 2H), 1.14 (s, 6H) | 31 mg, 31%, white solid |
| 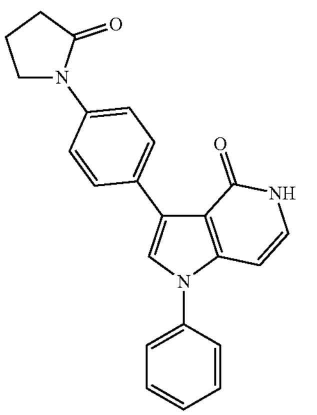 [SMILES: O=C1CCCN1c1ccc(-c2cn(-c3ccccc3)c3cc[nH]c(=O)c23)cc1] | Ex-174 | LC-MS. $R_t$ 7.64 min, AnalpH2_MeOH_QC_V1(1); (ESI$^+$) m/z 370.3 [M + H]$^+$. | 60 mg, 43%, pale yellow solid |

MAP4K4 is Activated by Cardiac Death Signals and Promotes Cardiac Muscle Cell Death To ascertain the scientific case for inhibiting MAP4K4 in cardiac cell death, three biological settings first were explored: diseased human heart tissue, mouse models, and rat cardiomyocytes (FIGS. 1-4). Activation of human cardiac MAP4K4 was prevalent in chronic heart failure from diverse etiologies (N=26), relative to healthy donor hearts (N=10; FIG. 1). MAP4K4 activation was associated uniformly with active (cleaved) caspase-3, a mediator of apoptosis (FIG. 1A), and activation of its MAP3K intermediary, TAK1 (FIG. 1B), which itself can drive cardiac cell death (Zhang et al., 2000). In adult mouse myocardium, MAP4K4 was activated by ischemia/reperfusion injury, biomechanical load (transverse aortic constriction, TAO), and cardiomyocyte-restricted expression of tumour necrosis factor-α or the G-protein Gαq all of which promote cardiac muscle cell death, FIG. 10. Likewise, in cultured rat cardiomyocytes, MAP4K4 was activated by defined death signals: the cardiotoxic drug, doxorubicin; ceramide, a mediator of apoptotic signals including ischemia/reperfusion and TNFα (Suematsu et al., 2003); and $H_2O_2$, a surrogate for oxidative stress (Brown and Griendling, 2015) (FIG. 1D). Thus, it was shown that MAP4K4 activation accompanies cardiac muscle cell death, both in vitro and in vivo.

Figure 3:
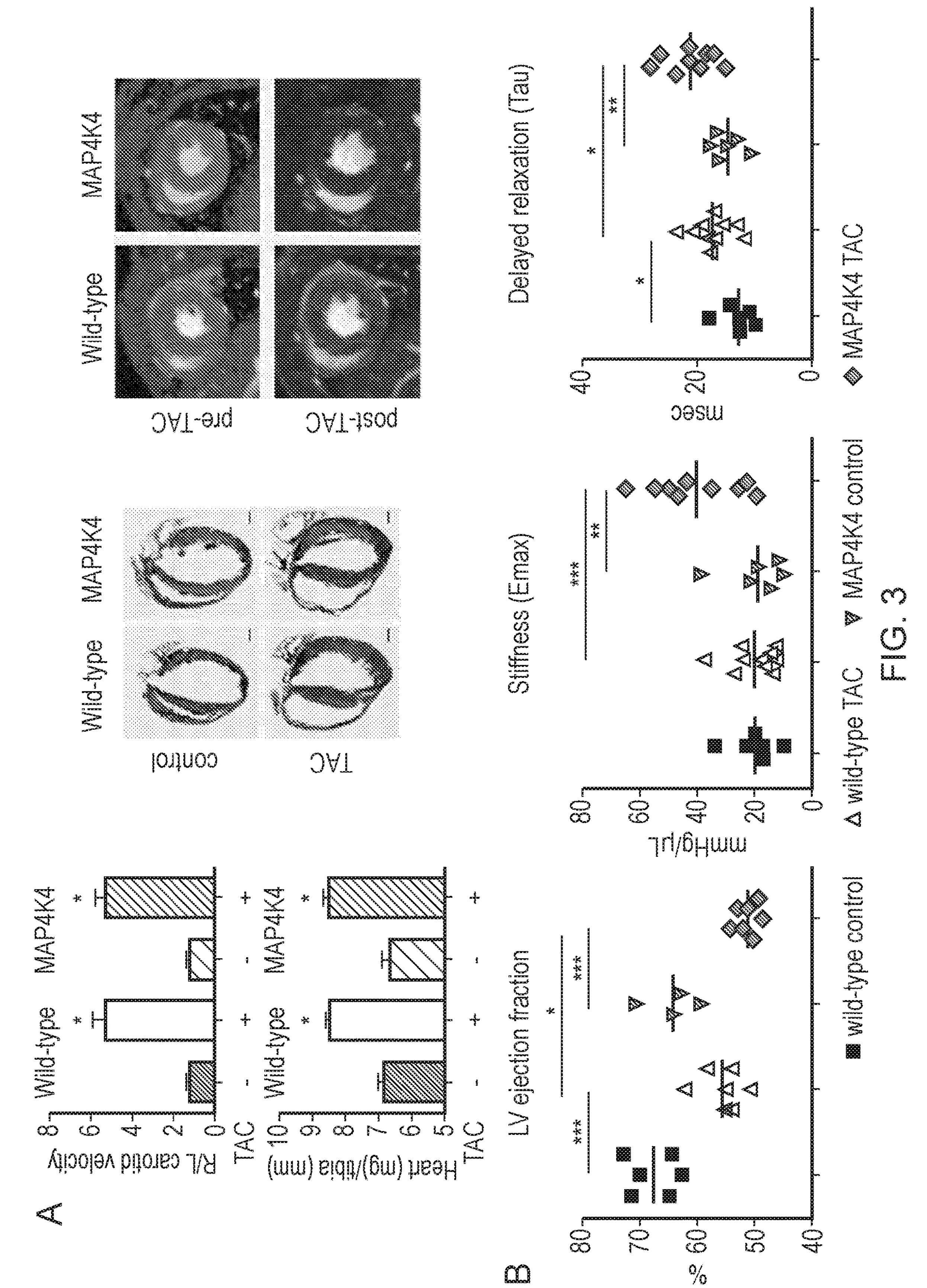
FIG. 3 provides demonstrating that cardiomyocyte-restricted MAP4K4 sensitized the myocardium to otherwise sub-lethal death signals potentiating myocyte loss, fibrosis, and dysfunction.
Figure 3:
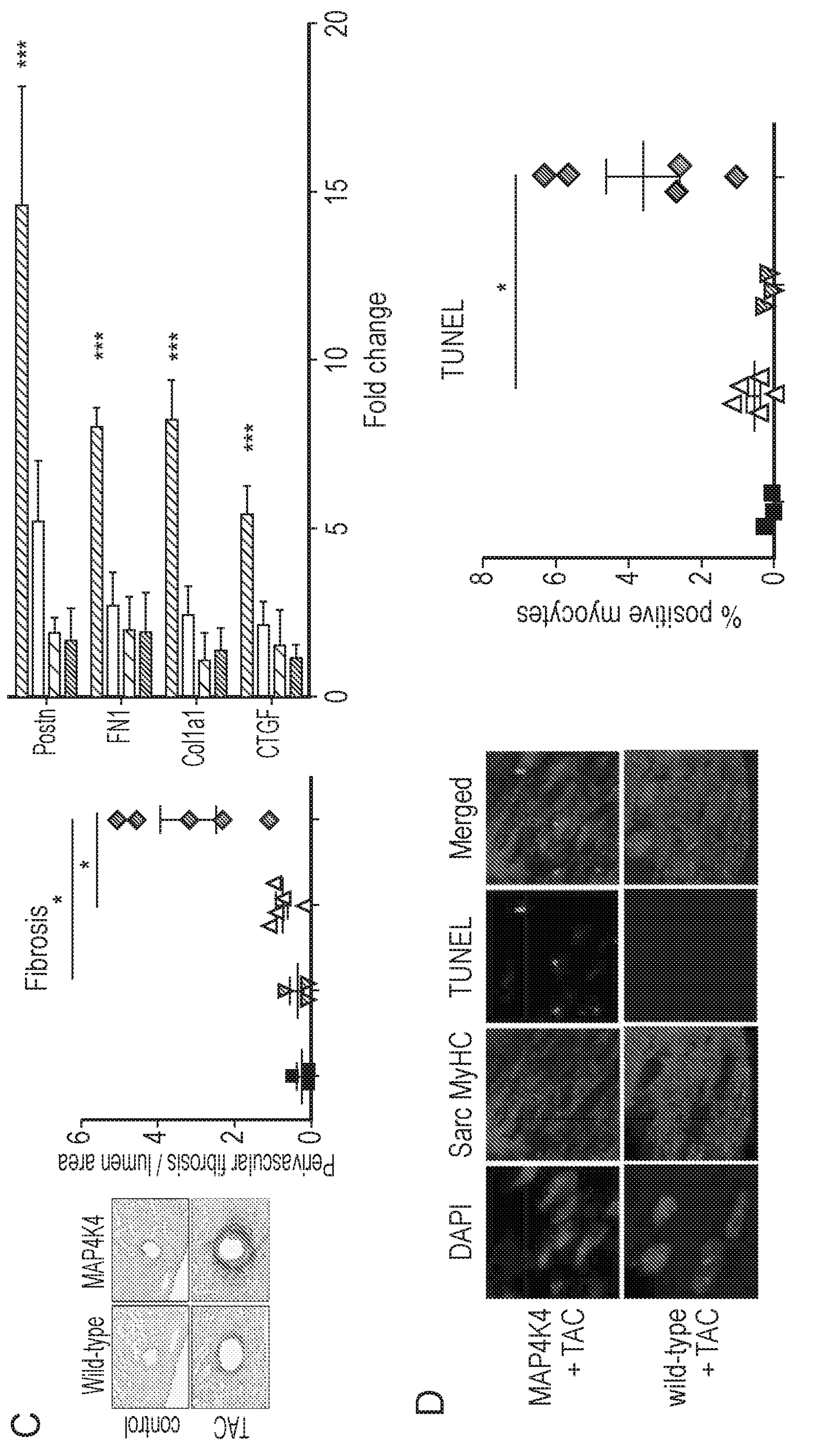
Figure 3:
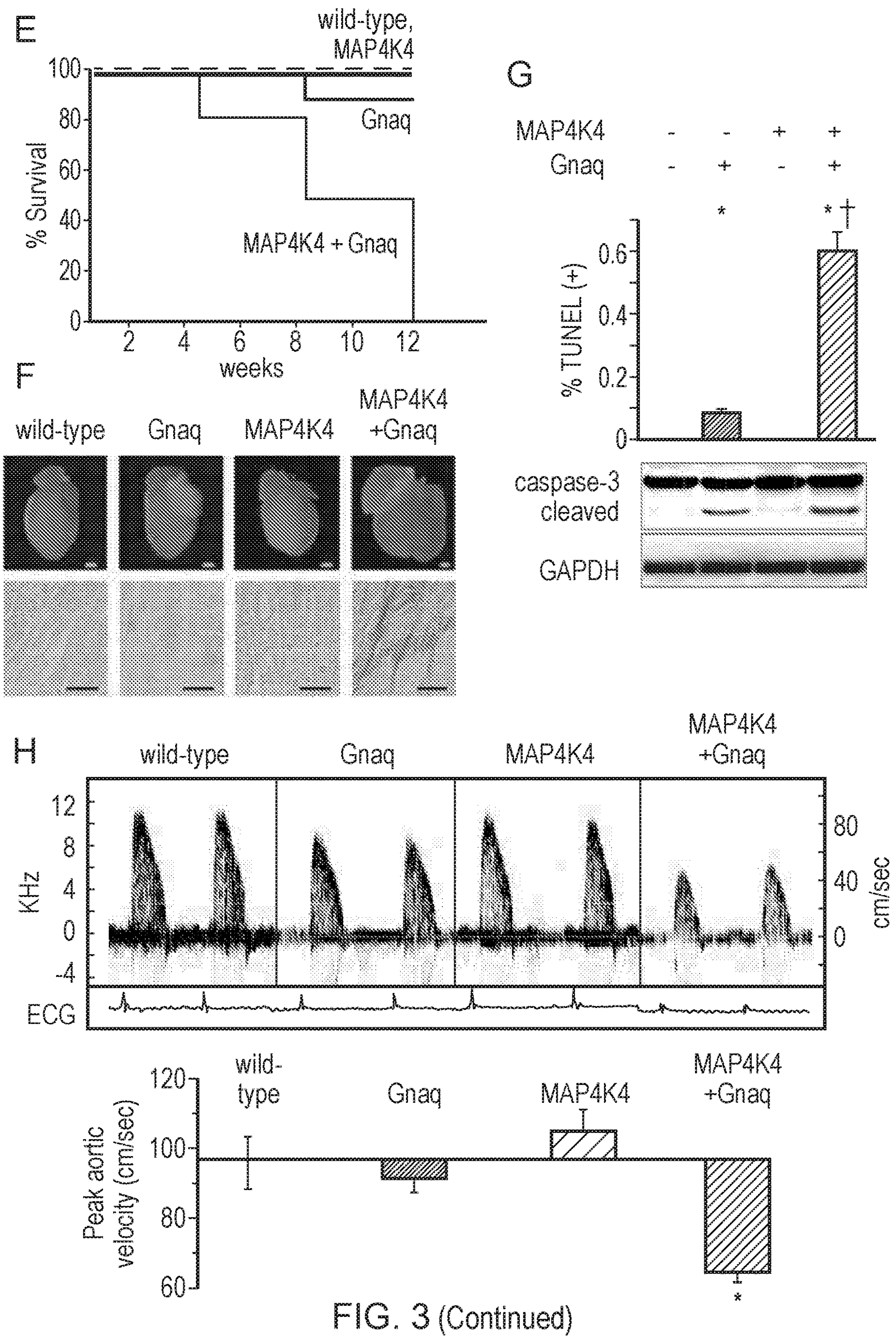
Figure 4:
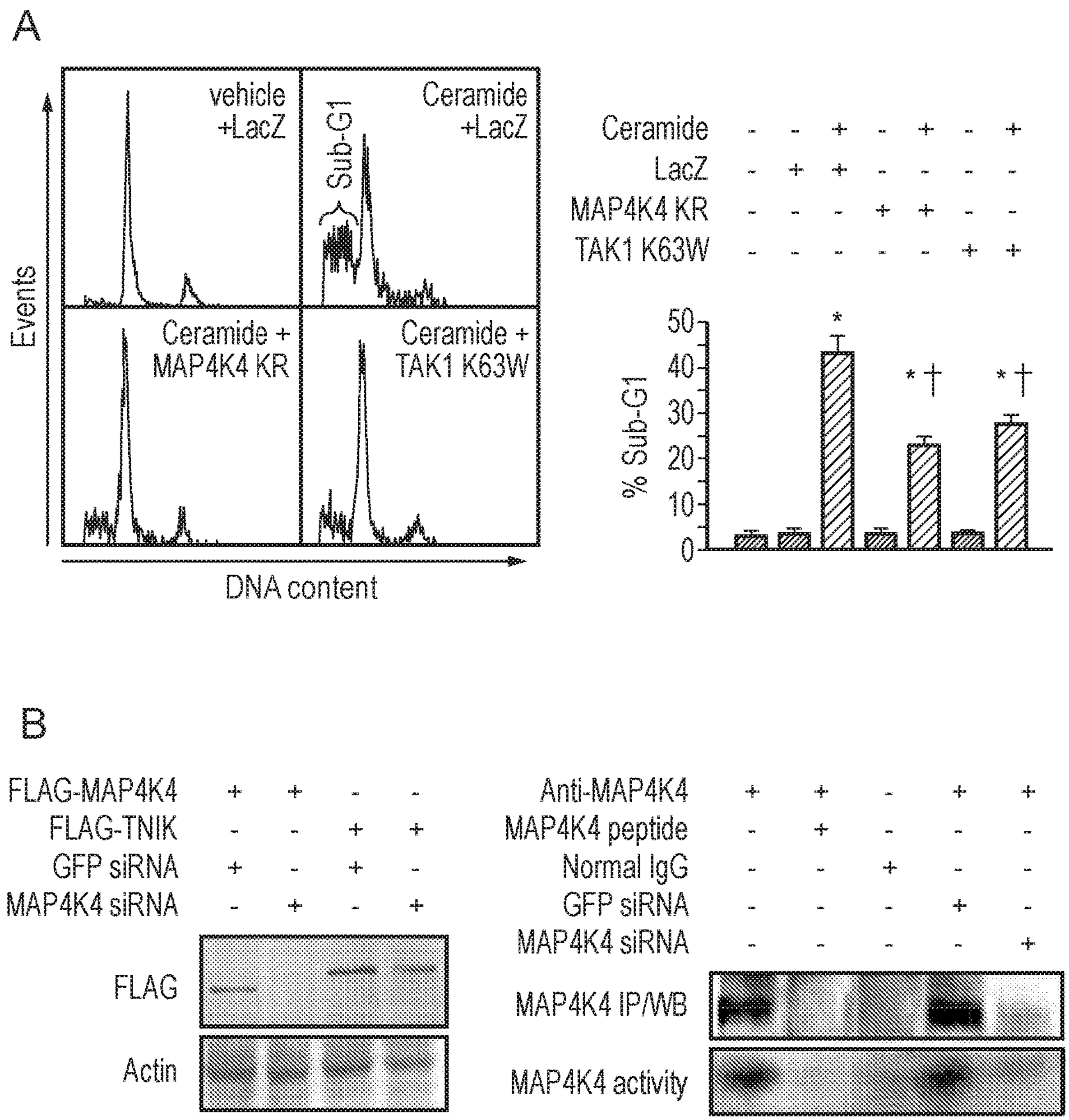
FIG. 4 provides data suggest a pivotal role for MAP4K4 in cardiac muscle cell death.
Figure 4:
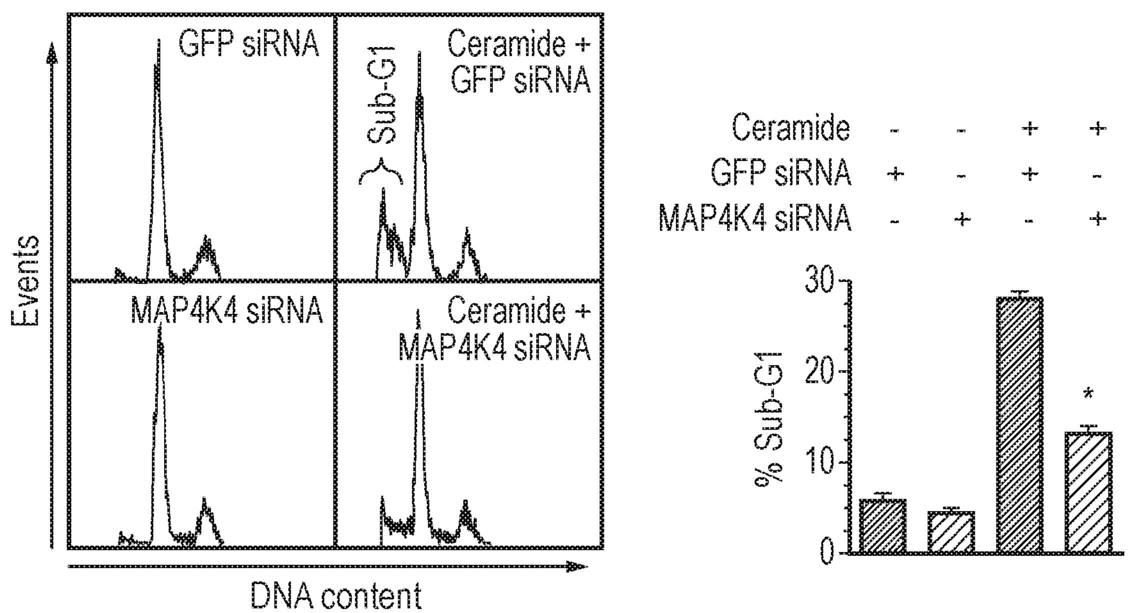
Figure 4:
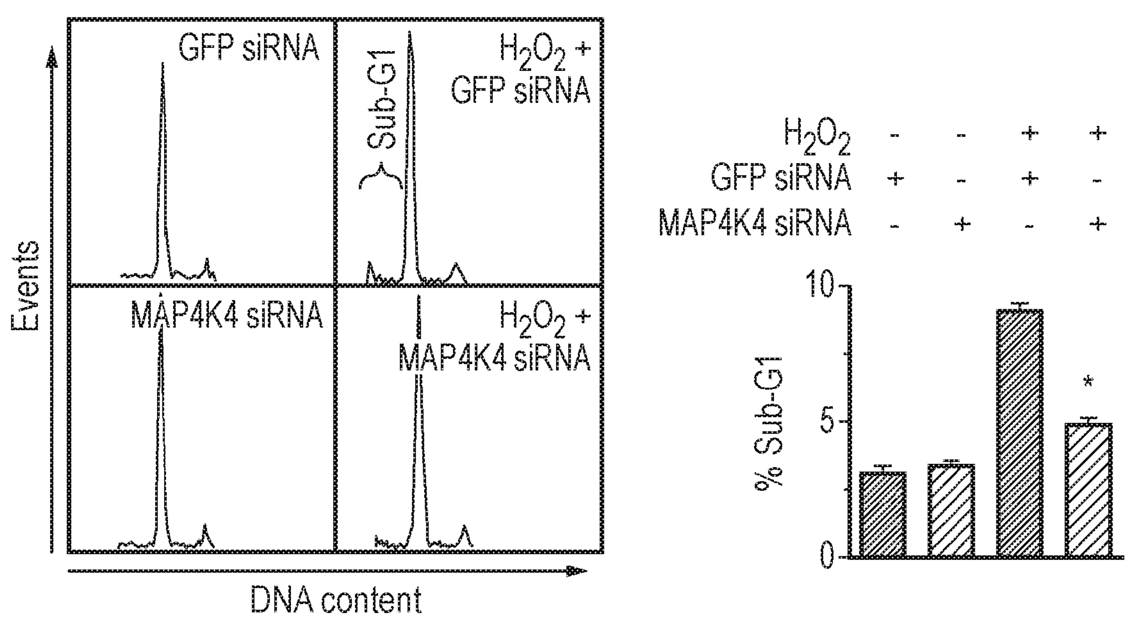
Figure 4:
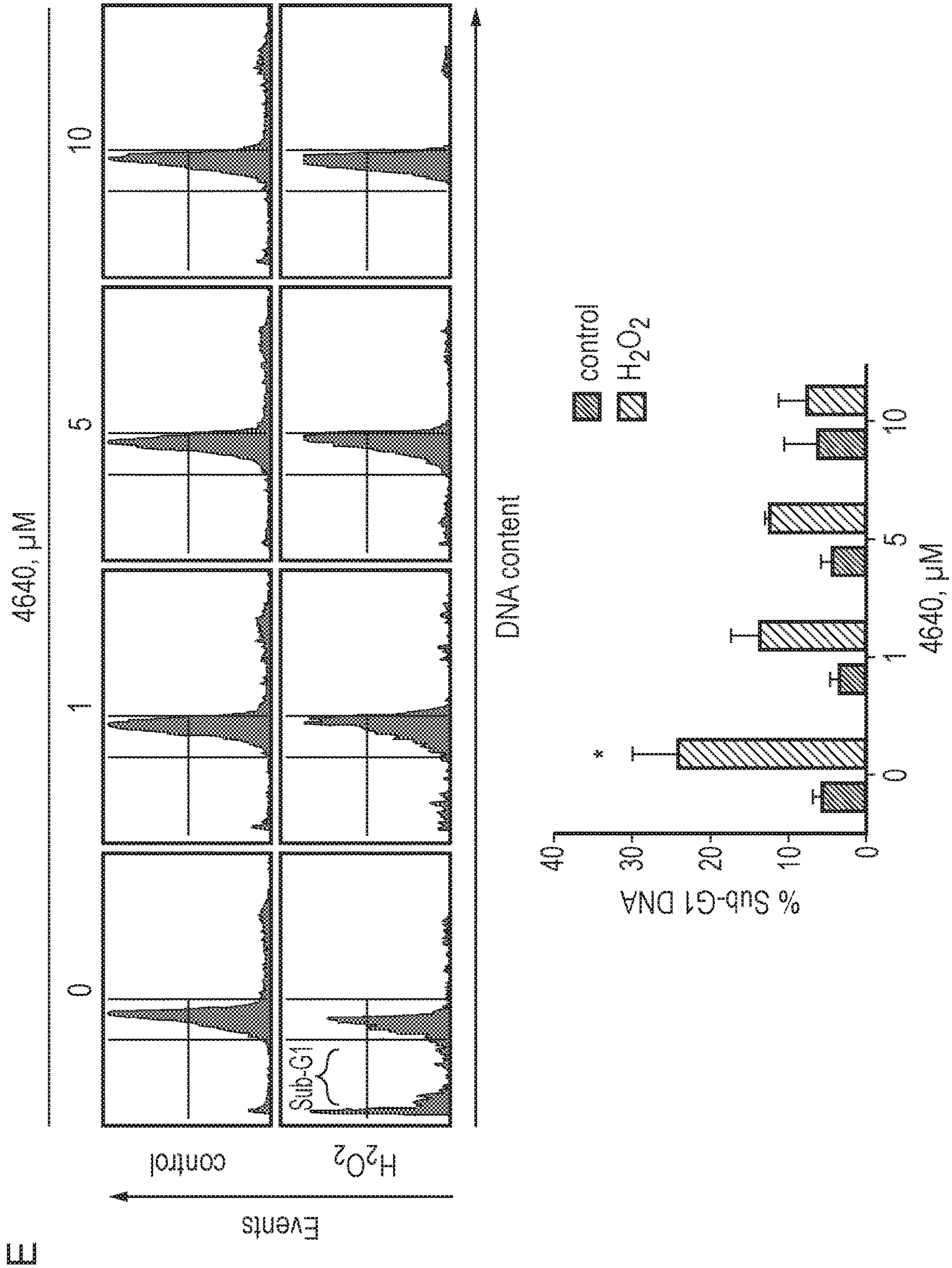

Next, an increase in MAP4K4 activity was simulated by viral gene transfer in rat cardiomyocytes (FIG. 2A), with the caveat that kinase activity, not expression, increases in the settings above. A pro-apoptotic effect of exogenous MAP4K4 was confirmed (FIG. 2B), potentially involving TAK1 (FIG. 2C), JNK (FIG. 2D, E), and the mitochondrial death pathway (FIG. 2E, F). In adult mice, cardiomyocyte-restricted MAP4K4 sensitized the myocardium to otherwise sub-lethal death signals—TAC and low copy number Myh6-Gnaq—potentiating myocyte loss, fibrosis, and dysfunction (FIG. 3). In clear contrast to the pro-apoptotic effect of wild-type MAP4K4, cultured rat cardiomyocytes were protected at least 50% not only by dominant-interfering mutations (FIG. 4A), but also by MAP4K4 shRNA (FIG. 4B-D). Together, these gain-of-function, dominant-negative, and loss-of-function studies suggest a pivotal role for MAP4K4 in cardiac muscle cell death, albeit with the limitations inherent to non-human models.

MAP4K4 Target Validation in Human Stem Cell-Derived Cardiomyocytes

To establish whether an equivalent requirement for MAP4K4 also exists in human cardiac muscle cells, the role of MAP4K4 in cardiomyocytes derived from human induced pluripotent stem cells was investigated. Human stem cell-derived cardiomyocytes (hiPSC-CMs) are envisioned as a highly auspicious tool for cardiac drug discovery. MAP4K4 function was tested in well-characterized, purified, commercially available hiPSC-CMs that have already gained acceptance by industry and regulatory authorities as a human platform (Blinova et al., 2017; Rana et al., 2012; Sirenko et al., 2013), and initiated our studies using iCell cardiomyocytes (Ma et al., 2011).

Figure 5:
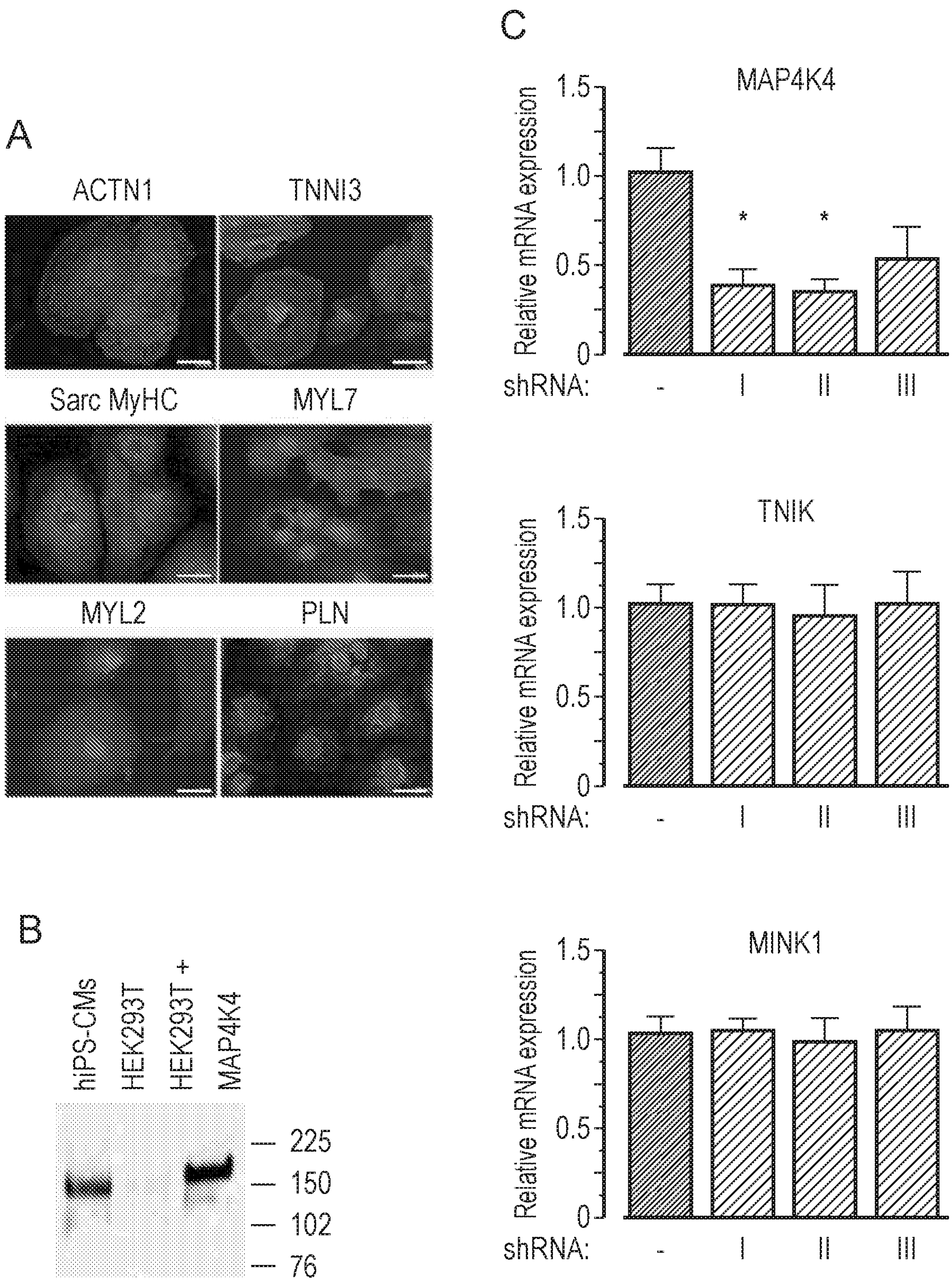
FIG. 5 provides data for the role of MAP4K4 in cardiomyocytes derived from human induced pluripotent stem cells.
Figure 5:
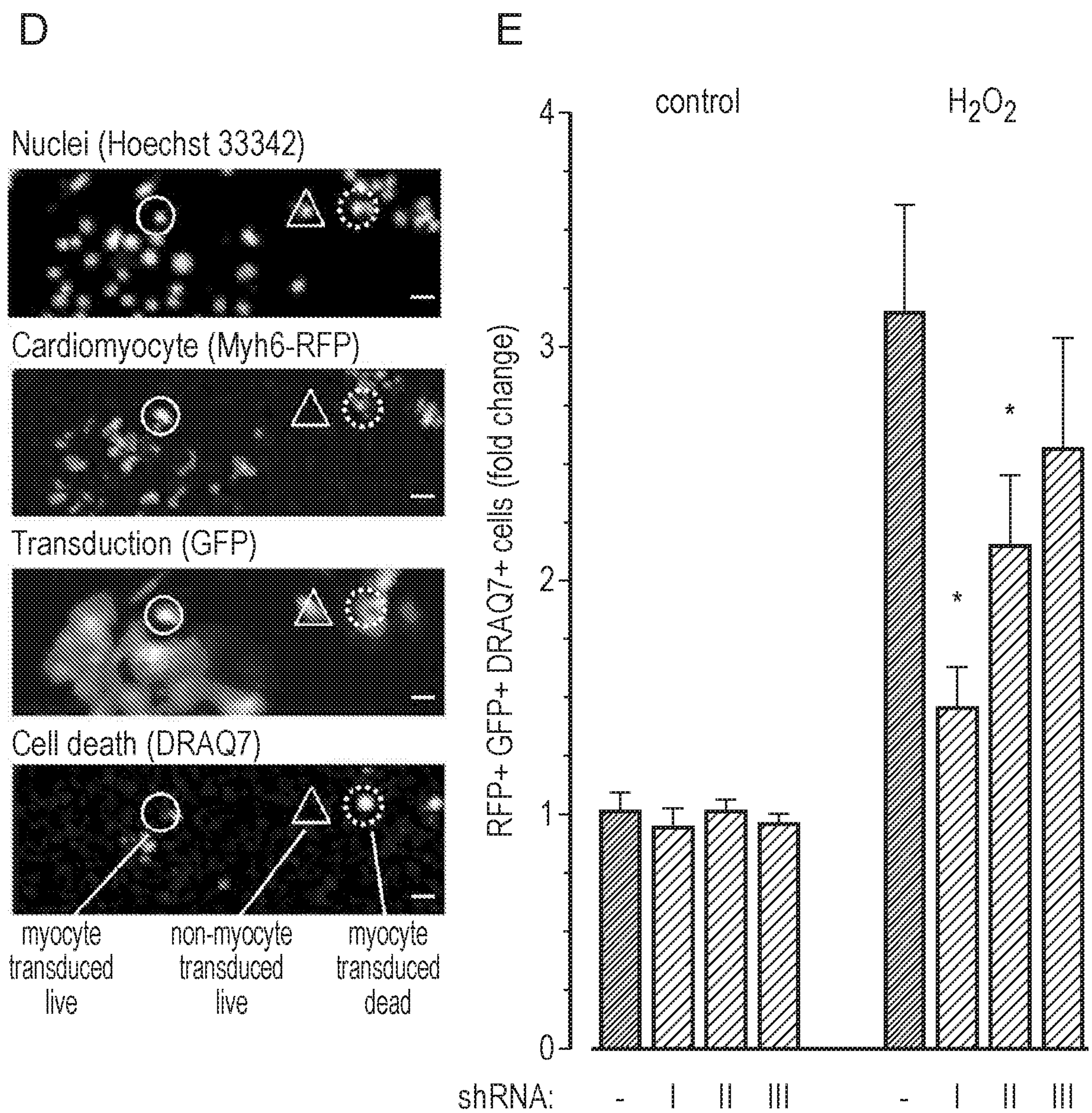

First, the expression of cardiomyocyte-specific markers and of MAP4K4 protein was validated (FIG. 5A, B). Two of three shRNAs directed against human MAP4K4 reduced expression >60%, with no extraneous effect on M/NK/MAP4K6 and TN/K/MAP4K7, the most closely related genes (FIG. 5C). Cell death was quantified by high-content analysis (FIG. 5D) as the loss of membrane integrity (DRAQ7 uptake) in successfully transduced ($GFP^+$) hiPSC-CMs (Myh6-$RFP^+$). Each of the two potent shRNAs conferred protection against $H_2O_2$: myocyte loss was reduced up to 50% (FIG. 5E). By contrast, shRNA with little effect on MAP4K4 did not confer protection. Thus, the results of gene silencing strongly suggest a requirement for endogenous MAP4K4 in human cardiac muscle cell death.

Novel Inhibitors of MAP4K4

Small molecule inhibitors of MAP4K4 were identified with sufficient potency and selectivity. One such compound was the known compound F1386-0303 (5,7-diphenyl-7H-pyrrolo[2,3-d]pyrimidin-4-ol).

Compounds of the present invention were screened for their inhibitory activity against MAP4K4, versus selected off-target hits found with early members of this chemical series. MAP4K4 kinase activity was monitored using the CisBio HTRF Transcreener ADP assay, acompetitive immunoassay with a reproducible Z'>0.6. In the detection step, endogenous ADP and d2-labeled ADP compete for binding an anti-ADP monoclonal antibody labelled with $Eu^{3+}$ cryptate. A ratiometric fluorescent read-out is used at 665 and 620 nm. Reactions were performed in the presence of 1% DMSO with ATP added at $K_m$(10 μM), 0.5 nM human MAP4K4 kinase domain (Invitrogen), 1 M biotin-myelin basic protein as substrate (Invitrogen), and extension of reaction time to 2h. Assays were run in Greiner low volume plates with a final reaction volume of 10 μl. The MAP4K4 inhibition data are provided in Table 33 below for selected compounds of the present invention. The data has been categorised based on the $IC_{50}$ value of the compound as "A", "B" or "C". $IC_{50}$: A≤100 nM; 100 nM<B≤1 μM; 1 μM<C; nd=not determined.

TABLE 33

| Ex. No. | MAP4K4 (nM) |
|---|---|
| 1 | B |
| 2 | A |
| 3 | C |
| 4 | C |
| 5 | C |
| 6 | B |
| 7 | A |
| 8 | A |
| 9 | A |
| 10 | A |

TABLE 33-continued

| Ex. No. | MAP4K4 (nM) |
|---|---|
| 11 | A |
| 12 | B |
| 13 | A |
| 14 | A |
| 15 | A |
| 16 | A |
| 17 | A |
| 18 | A |
| 19 | A |
| 20 | B |
| 21 | C |
| 22 | B |
| 23 | A |
| 24 | C |
| 25 | A |
| 26 | A |
| 27 | A |
| 28 | A |
| 29 | A |
| 30 | B |
| 31 | C |
| 32 | B |
| 33 | A |
| 34 | B |
| 35 | A |
| 36 | A |
| 37 | A |
| 38 | A |
| 39 | A |
| 40 | A |
| 41 | A |
| 42 | A |
| 43 | A |
| 44 | C |
| 45 | A |
| 46 | A |
| 47 | B |
| 48 | A |
| 49 | A |
| 50 | A |
| 51 | A |
| 52 | A |
| 53 | A |
| 54 | nd |
| 55 | A |
| 56 | A |
| 57 | A |
| 58 | A |
| 59 | nd |
| 60 | nd |
| 61 | A |
| 62 | A |
| 63 | B |
| 64 | A |
| 65 | A |
| 66 | B |
| 67 | B |
| 68 | A |
| 69 | A |
| 70 | A |
| 71 | B |
| 72 | nd |
| 73 | nd |
| 74 | B |
| 75 | B |
| 76 | A |
| 77 | A |
| 78 | A |
| 79 | C |
| 80 | A |
| 81 | A |
| 82 | A |
| 83 | A |
| 84 | B |
| 85 | A |
| 86 | A |
| 87 | C |
| 88 | B |

TABLE 33-continued

| Ex. No. | MAP4K4 (nM) |
|---|---|
| 89 | B |
| 90 | B |
| 91 | B |
| 92 | B |
| 93 | C |
| 94 | C |
| 95 | C |
| 96 | C |
| 97 | A |
| 98 | C |
| 99 | B |
| 100 | B |
| 101 | C |
| 102 | B |

MAP4K4 inhibitory data and comparative data for 13 other protein kinases are provided in Table 34. The data in Table 34 also provides the fold selectivity of the two compounds in favour of MAP4K4 over the tested kinase. The fold selectivity is indicated in parenthesis. Ex-58 represents a highly selective inhibitor of MAP4K4 compared to the known compound F1386-303.

TABLE 34

| Target | F1386-303 pIC50 (fold selectivity) | Ex-58 pIC50 (fold selectivity) | Ex-56 pIC50 (fold selectivity) | Ex-27 pIC50 (fold selectivity) |
|---|---|---|---|---|
| MAP4K4 | 7.46 | 8.55 | 8.3 | 8.2 |
| MINK1/ MAP4K6 | 7.42 | 8.18 | 8.1 | 8.2 |
| TNIK/ MAP4K7 | 7.03 | 7.96 | 7.7 | 8 |
| GCK/ MAP4K2 | 5.91 (35) | 6.50 (112) | 6.4 (79) | 6.7 (31) |
| GLK/ MAP4K3 | 4.52 (871) | 4.95 (3981) | 4.5 (6309) | 5.8 (251) |
| KHS/ MAP4K5 | 5.22 (174) | 6.36 (153) | 6 (199) | 7.4 (6) |
| ABL1 | 4.52 (865) | 5.80 (560) | 5.7 (398) | 5.5 (501) |
| Aurora B | 4.88 (380) | 5.49 (560) | 5.2 (1258) | 5 (1584) |
| FLT3 | 5.66 (63) | 5.31 (1148) | 4.8 (3162) | 5.1 (1258) |
| GSK3β | 4.57 (776) | 4.66 (7762) | | 4.5 (5011) |
| MLK1/ MAP3K9 | 6.28 (15) | 7.19 (23) | 6.7 (39) | 7.1 (13) |
| MLK3/ MAP3K11 | 6.09 (23) | 6.99 (36) | 6.7 (39) | |
| NUAK | 6.16 (20) | 6.88 (47) | 5.6 (501) | |
| VEGFR | 5.72 (55) | 5.72 (675) | 4.5 (6309) | 6.1 (125) |

| Target | | Ex-22 pIC50 (fold selectivity) | Ex-61 pIC50 (fold selectivity) |
|---|---|---|---|
| MAP4K4 | 6.8 | 8.8 | |
| MINK1/ MAP4K6 | 8.18 | 8.1 | |
| TNIK/ MAP4K7 | 6.7 | 8.3 | |
| GCK/ MAP4K2 | | 5.1 (50) | 6.5 (316) |
| GLK/ MAP4K3 | | 4.5 (199) | 4.5 (31622) |
| KHS/ MAP4K5 | | 6.36 (199) | 6 (316) |
| ABL1 | | 4.5 (199) | 6.1 (794) |
| Aurora B | | 4.5 (199) | 4.5 (31622) |
| FLT3 | | 4.5 (199) | 4.5 (31622) |
| GSK3β | | 4.5 (199) | 4.5 (31622) |
| MLK1/ MAP3K9 | | 5.4 (25) | 7.2 (63) |
| MLK3/ MAP3K11 | | 4.5 (199) | 7.2 (63) |
| NUAK | | | 7.2 (63) |
| VEGFR | | 4.9 (79) | 6.3 (501) |

Pharmacological Inhibition of MAP4K4 Suppresses Human Cardiac Muscle Cell Death

Figure 7:
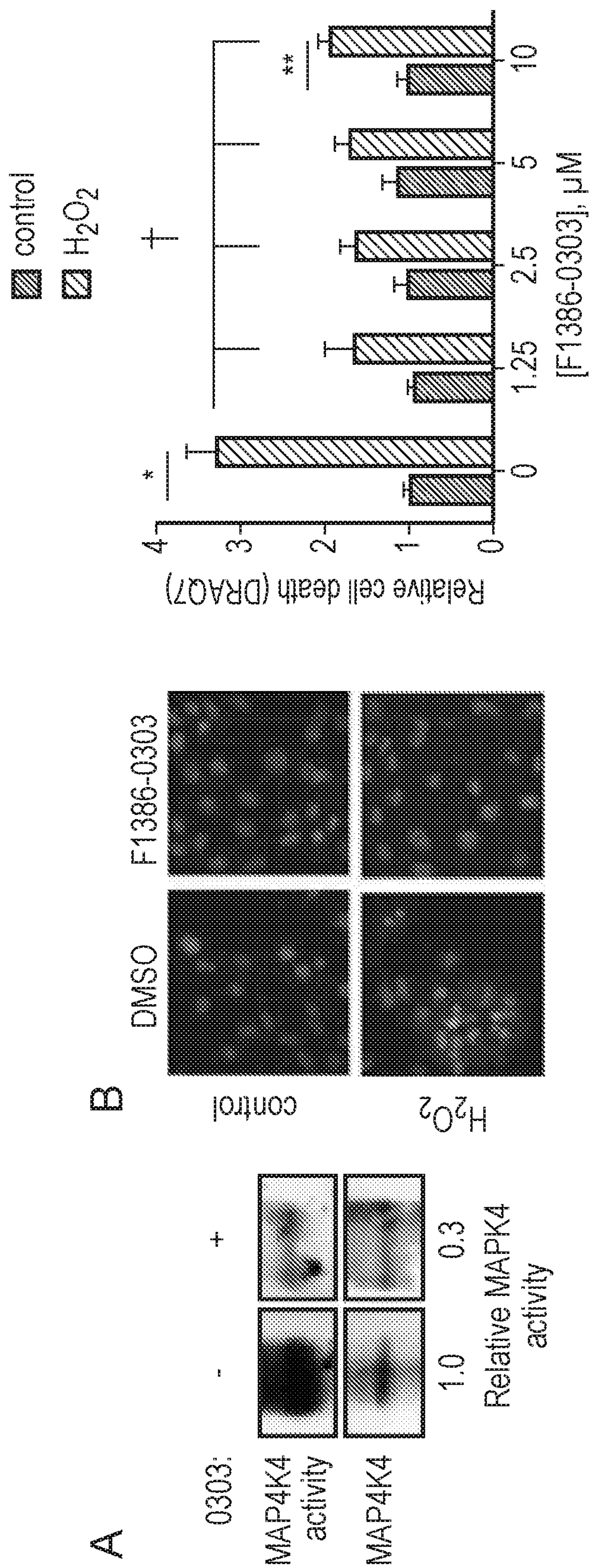
FIG. 7 provides data demonstrating that inhibition of MAP4K4 suppresses human cardiac muscle cell death.
Figure 7:
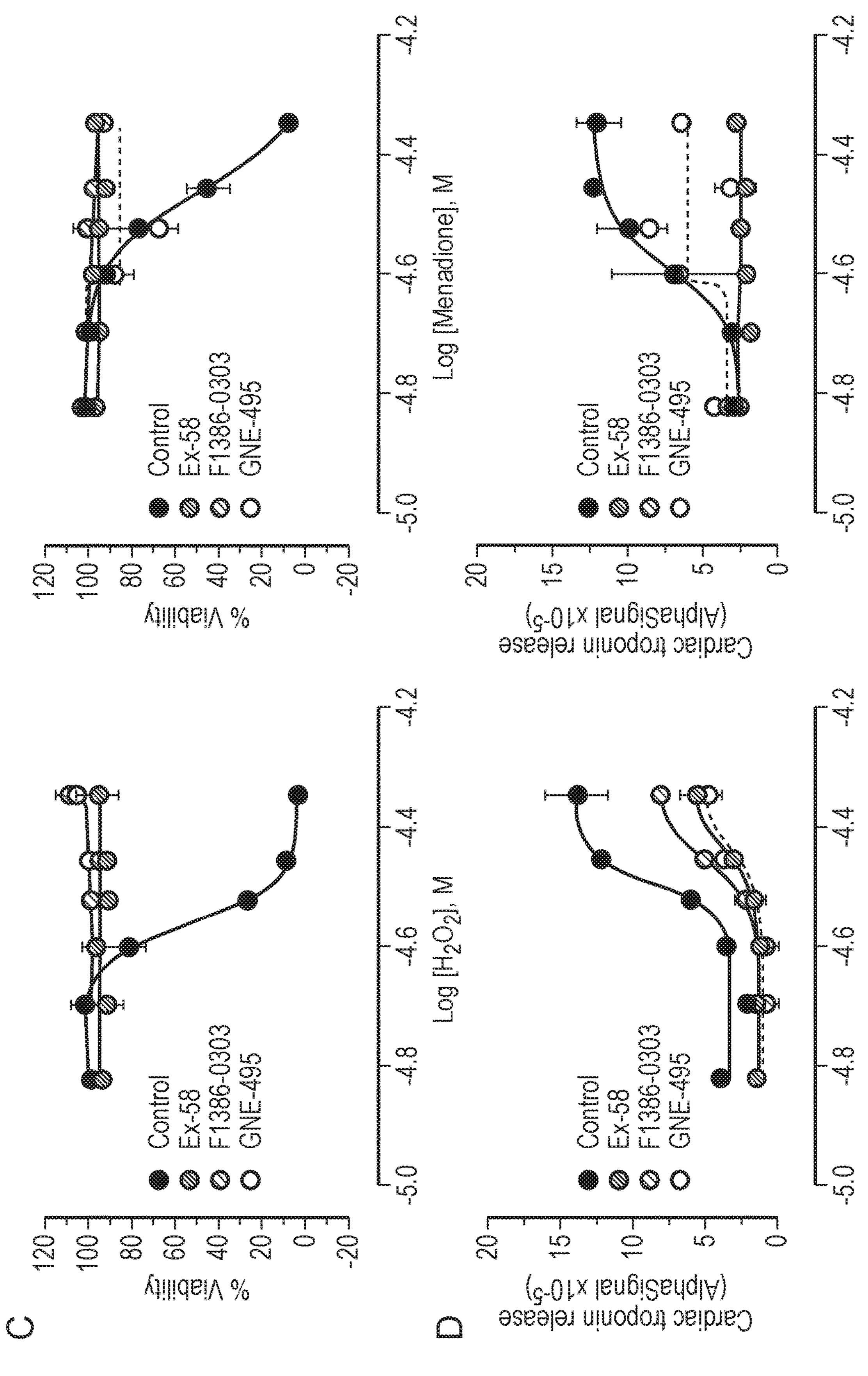

To substantiate the hypothesis that pharmacological inhibition of MAP4K4 would confer resistance to cell death in human cardiomyocytes, cytoprotection was next assessed using hiPSC-CMs. Pharmacological inhibition by F1386-0303 was protective, reducing human cardiac muscle cell death by 50% in iCell cardiomyocytes even at 1.25 μM, the lowest concentration tested (DRAQ7 uptake: FIG. 7B), equaling the benefit achieved by gene silencing. Human cardiac muscle cell protection was substantiated in a second, independent line, CorV.4U cardiomyocytes, which are more highly enriched for ventricular myocytes. At 10 μM, protection from $H_2O_2$ or menadione was virtually complete (luminescent cell viability assay, FIG. 7C; human cardiac troponin assay, FIG. 7D). Thus, F1386-0303 is a potent, selective MAP4K4 inhibitor that was first identified in this study and successfully protects human stem cell-derived cardiomyocytes from lethal oxidative stress.

Figure 6:
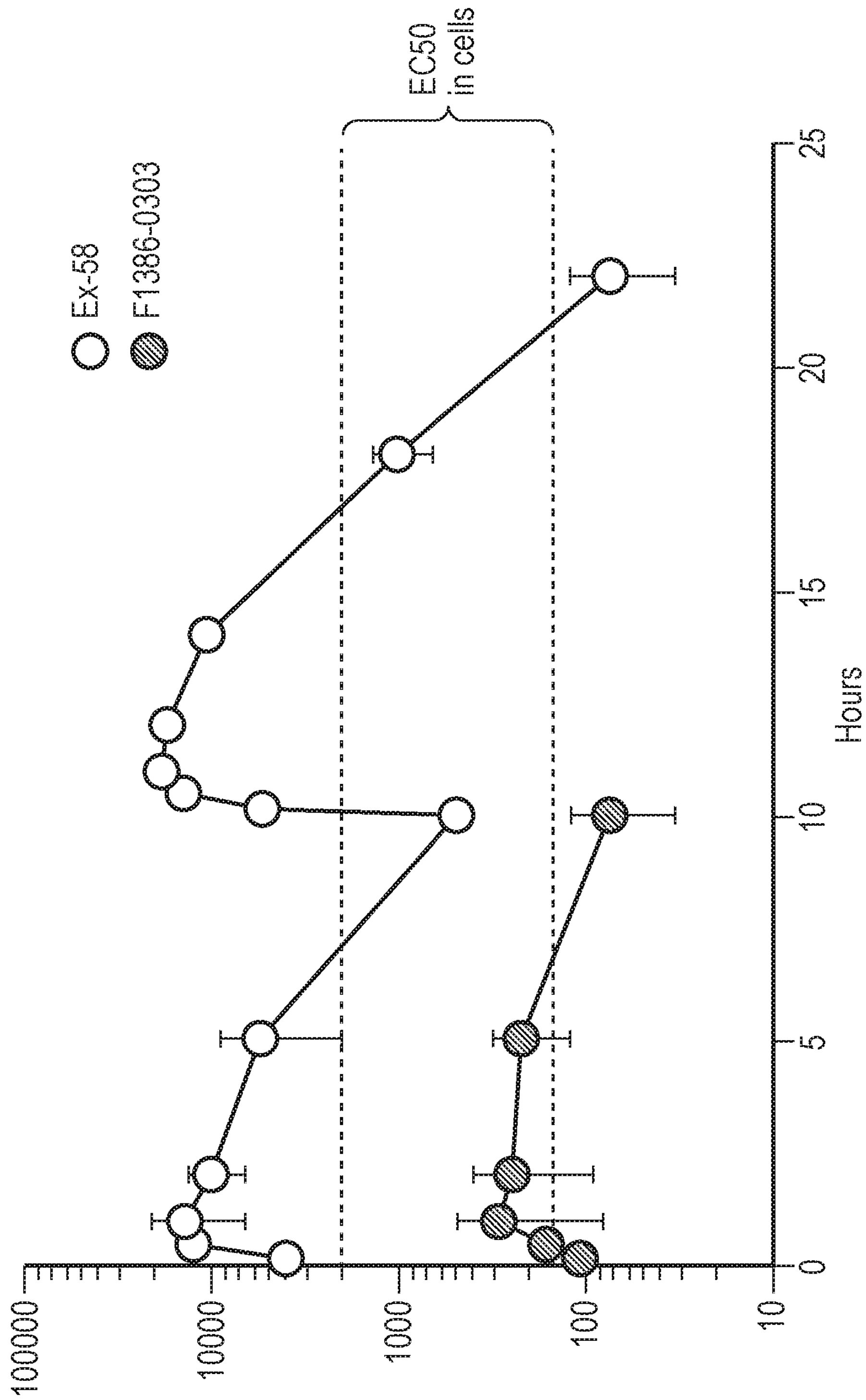
FIG. 6 provides plasma concentration overtime of a compound of the invention and a known compound.

F1386-0303 does not, however, have sufficient bioavailability in mice to be used for proof of concept studies in vivo: it is rapidly cleared and accumulates only to low levels when dosed orally in mice (FIG. 6; Table 35). Compounds of the present invention were prepared to improve on the properties of the known compound. A compound of the invention, Ex-58 showed 10-fold greater potency (IC50 3 vs 34 nM), while retaining high selectivity (Tables 34, 35). As a result of its reduced clearance, the free plasma concentration of Ex-58 was 334 and 8 nM, respectively, 1 and 10 h after a 50 mg kg-1 oral dose, more than an 80-fold improvement over the earlier compound (FIG. 6; Table 35). Ex-58 was therefore taken forward for detailed testing in human cardiomyocytes and mice. Protection of human cardiomyocytes was substantiated, using CorV.4U cells as the target, $H_2O_2$ and menadione as the death triggers, in both viability assays (FIG. 7C, D). A comparable extent of protection of human cardiomyocytes was also conferred by diverse other members of the chemical series, including DMX-51, 40, 54, 107, 123, 128 at an EC50<1 uM. In H9c2 cardiomyocytes, these seven novel MAP4K4 inhibitors all were superior to the previously reported cardioprotective drugs Cyclosporine A, Exenatide, Necrostatin, and SB203580.

TABLE 35

| | IV PK (1 mg kg$^{-1}$) | | | | Oral PK (50 mg kg$^{-1}$) | | | |
|---|---|---|---|---|---|---|---|---|
| | Cl | | | $v_d$ | | | | |
| Compound | (L hr$^{-1}$ kg$^{-1}$) | $t_{1/2}$ (h) | $C_{max}$ (nM) | (L kg$^{-1}$) | $AUC_{inf}$ | $C_{max}$ (nM) | $T_{max}$ (h) | $t_{1/2}$ (h) |
| F1386-0303 | 5.33 | 0.1 | 3262 | 1.05 | 2162 | 295 | 1.00 | 3.7 |
| Ex-58 | 2.50 | 0.6 | 1590 | 1.22 | 63733 | 13847 | 1.00 | 1.8 |

MAP4K4 Inhibition Improves Human Cardiac Muscle Cell Function

Figure 8:
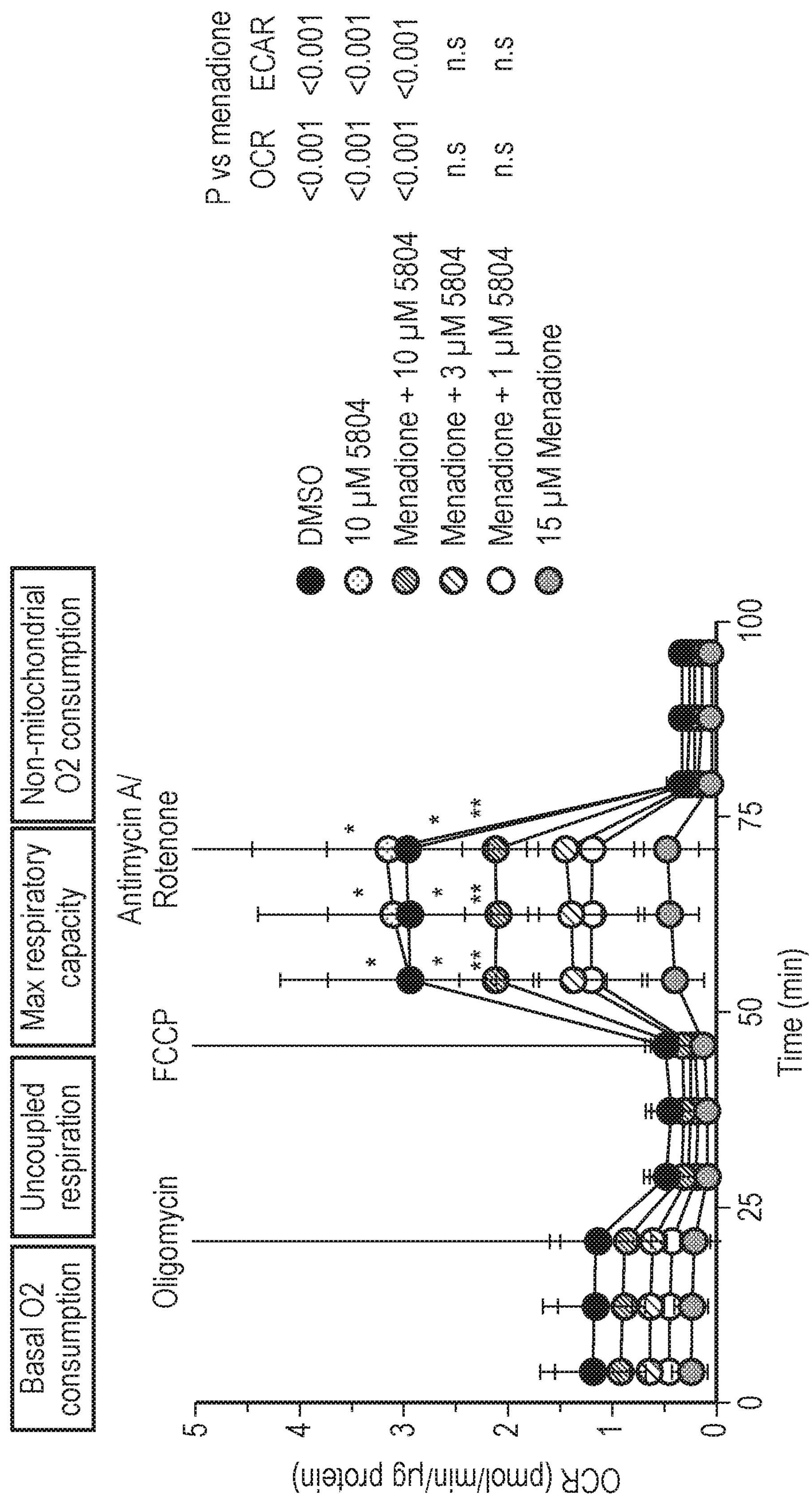
FIG. 8 provides data demonstrating that MAP4K4 inhibition improves human cardiac muscle cell function.
Figure 8:
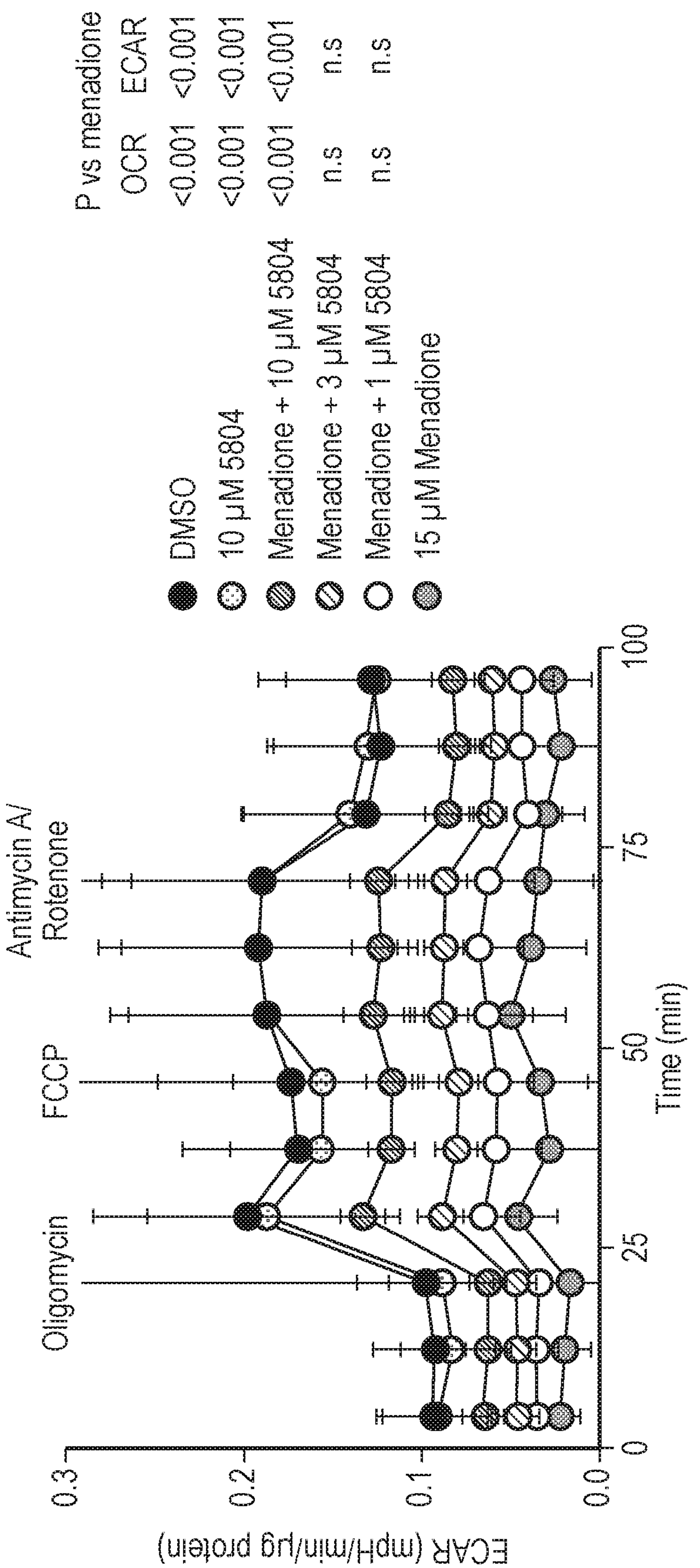
Figure 8:
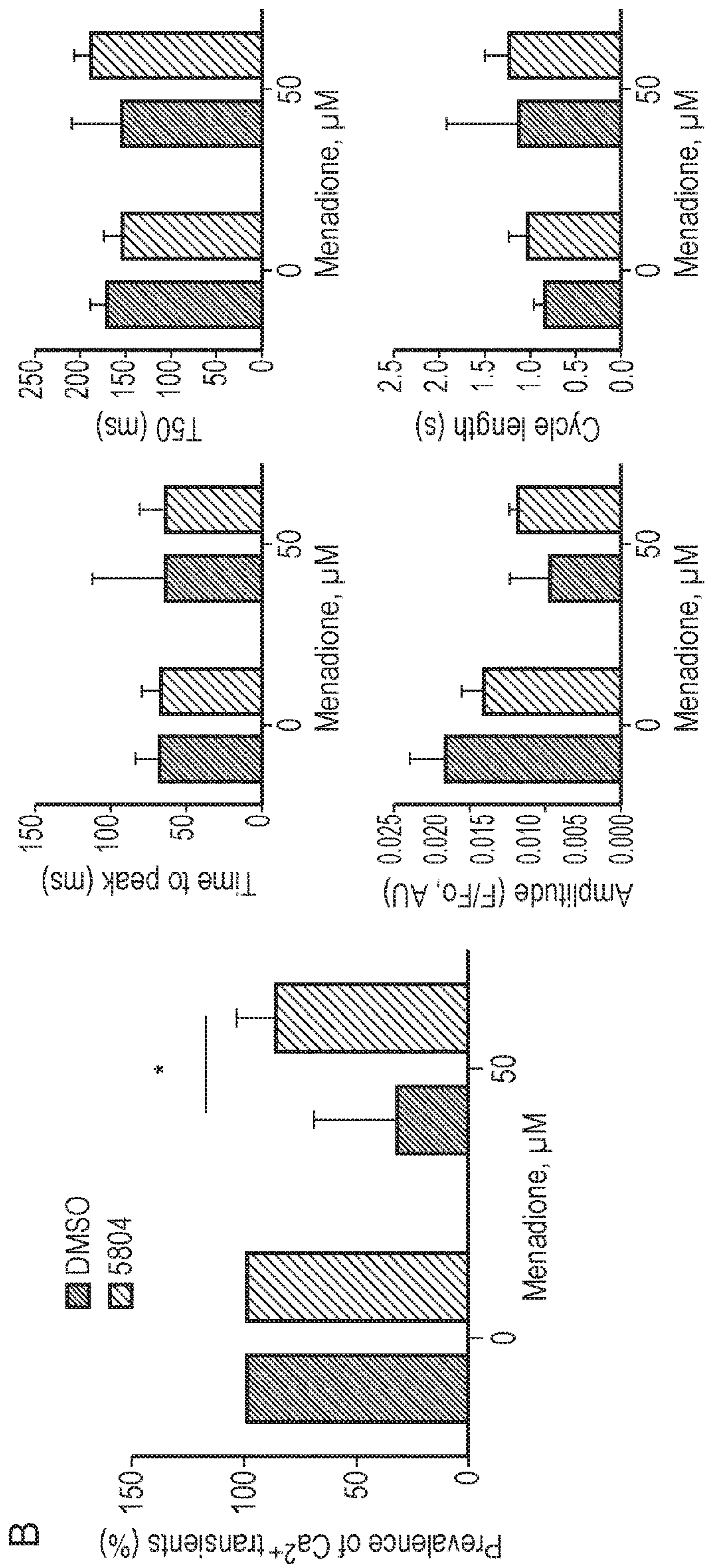

Key aspects of mitochondrial function were monitored in CorV.4U hiPSC-CMs after acute oxidative stress (15 μM menadione for 2 h), with or without Ex-58 (FIG. 8A). Maximum oxidative capacity, a measure of mitochondrial respiration, was reduced to 15% of control levels by menadione, and residual activity was improved 5-fold by 10 μM Ex-58 (FIG. 8A, left). Likewise, 10 M Ex-58 largely rescued the extracellular acidification rate, a measure of glycolytic function (FIG. 8A, right). No significant benefits were seen at lesser concentrations of the inhibitor.

Calcium cycling, a hallmark of the cardiac phenotype, likewise is susceptible to redox- and phosphorylation-dependent abnormalities. To determine whether MAP4K4 inhibition might preserve calcium homeostasis, hiPSC-CMs were assessed using the intracellular calcium indicator, Fura-2 (FIG. 8B). Under the conditions tested, the percentage of wells that exhibit calcium cycling was highly sensitive to oxidative stress, whereas beating rate and kinetics of the calcium transient in cycling cultures were not. At 50 μM menadione, spontaneous calcium oscillations persisted in only 8 of 24 cultures (33.3%), versus 21 of 24 receiving 10 μM Ex-58 (87.5%; P<0.001).

Thus, MAP4K4 inhibition preserves mitochondrial function and calcium cycling in hiPSC-CMs, in the setting of acute oxidative stress. Moreover, of relevance to potential future safety considerations, no adverse effect of Ex-58 was seen on any of the functional parameters.

MAP4K4 Inhibition Reduces Infarct Size in Mice

Figure 9:
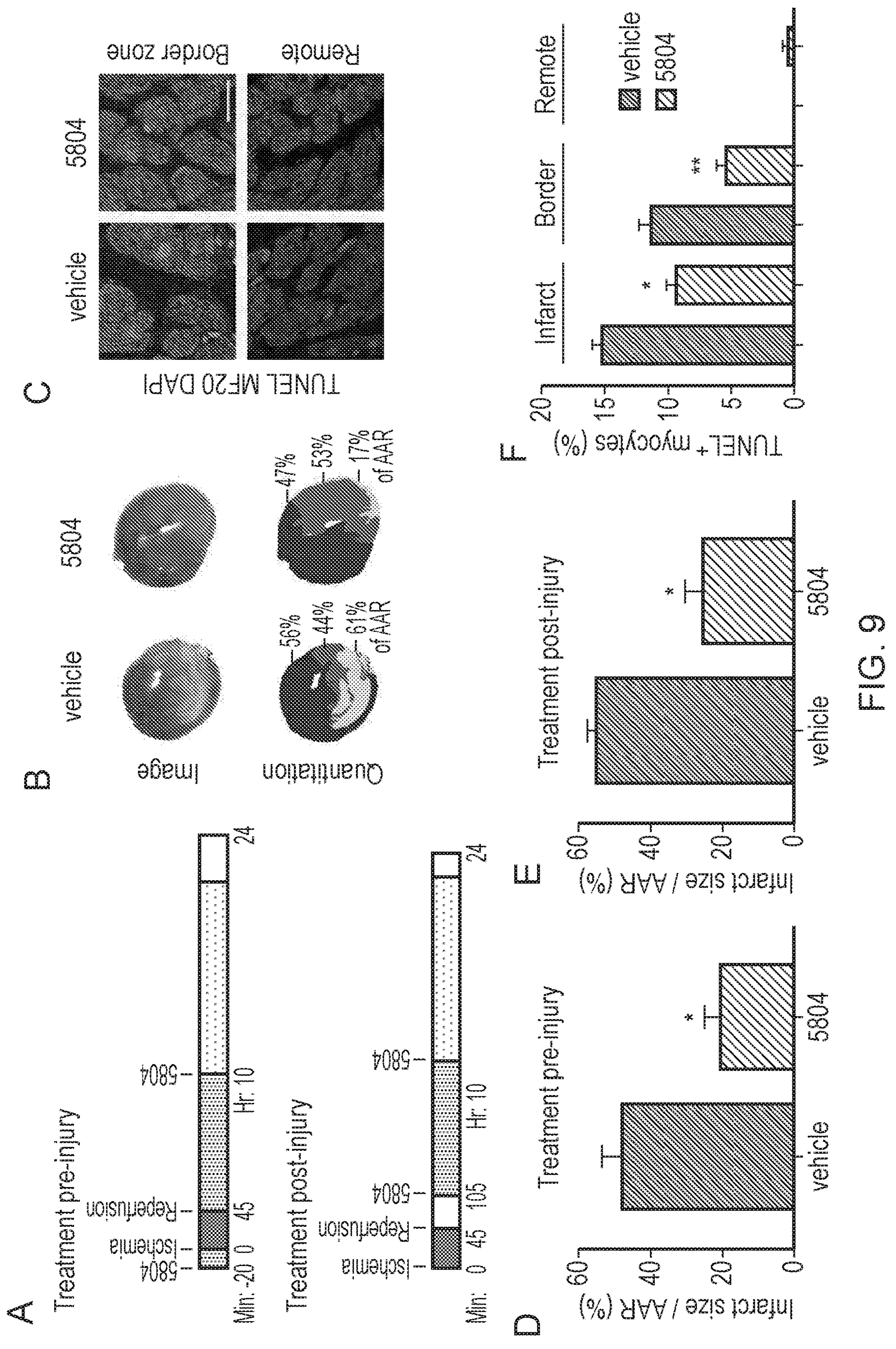
FIG. 9 provides data demonstrating that MAP4K4 inhibition reduces infarct size in mice.

To test if target validation and compound development in hiPSC-CMs might predict success in a whole-animal context, mice undergoing experimental myocardial infarction were treated with Ex-58 or the vehicle control (FIG. 9). Based on pharmacokinetic results, the mice received 50 mg $kg^{-1}$ twice by gavage, spaced 10 h apart, to achieve coverage exceeding the compound's EC50 for nearly a day (FIG. 9A). The endpoints assayed are indicated in FIG. 9B,C. Treatment was begun either 20 min prior to ischemia (FIG. 9D), or 1 h after reperfusion injury (FIG. 9E, F), the latter having greater relevance to potential clinical benefits. The suppression of cardiac muscle cell death was demonstrated in both studies, achieving respectively more than 50% and 60% reductions in infarct size as a proportion of the area at ischemic risk. In addition, TUNEL staining was performed in the post-injury study, demonstrating suppression of cardiomyocyte apoptosis within the infarct itself and the jeopardized adjacent myocardium, by 39 and 52% respectively. Reduction of infarct size in mice was also demonstrated for other novel compounds of the chemical series, Example 54. Relative to Ex-58, the latter compound exhibits superior plasma protein binding (PPB) or resistance to degradation in hepatocyte microsomes (Heps).

TABLE 36

| Parameter | Example 54 | Ex-58 |
|---|---|---|
| MAP4K4, $IC_{50}$ | 4 nM | 3 nM |
| Protection in H9c2 cardiomyocytes, $EC_{50}$ (efficacy relative to Ex-58) | 199 nM (0.3) | 350 nM (1) |
| Formulated solubility | 0.3 mg/mL | 0.1/2.8 mg/mL |
| Mouse Heps | 25 | 85 |
| Human Heps | 5 | ≤10 |
| Rat Heps | 3 | 10 |
| Pig Heps | 6 | 8 |
| Mouse/Human PPB % | 97/97 | 98/99 |
| Cyp Inhibition | >10 μM (2C9 8 μM) | >10 μM |
| In vivo efficacy (infarct size/area at risk) | 53% reduction | 65% reduction |
| Protection in human iPSC-derived ventricular cardiomyocytes, $EC_{50}$ $H_2O_2$ (efficacy relative to Ex-58) | 469 nM (0.9) | 403 nM (1) |

Prodrugs

It is envisaged that compounds of the invention may be delivered as a prodrug, wherein an active substance is generated in vivo by hydrolysis of said prodrug. It is envisaged that the prodrug may be a compound with $—CH_2OP(═O)(OH)_2$ substituted on the NH (replacing the H) of the bicyclic core of the compounds. Alternatively, the prodrug may be a compound in which a free OH is replaced by $—OP(═O)(OH)_2$.

Figure 10:
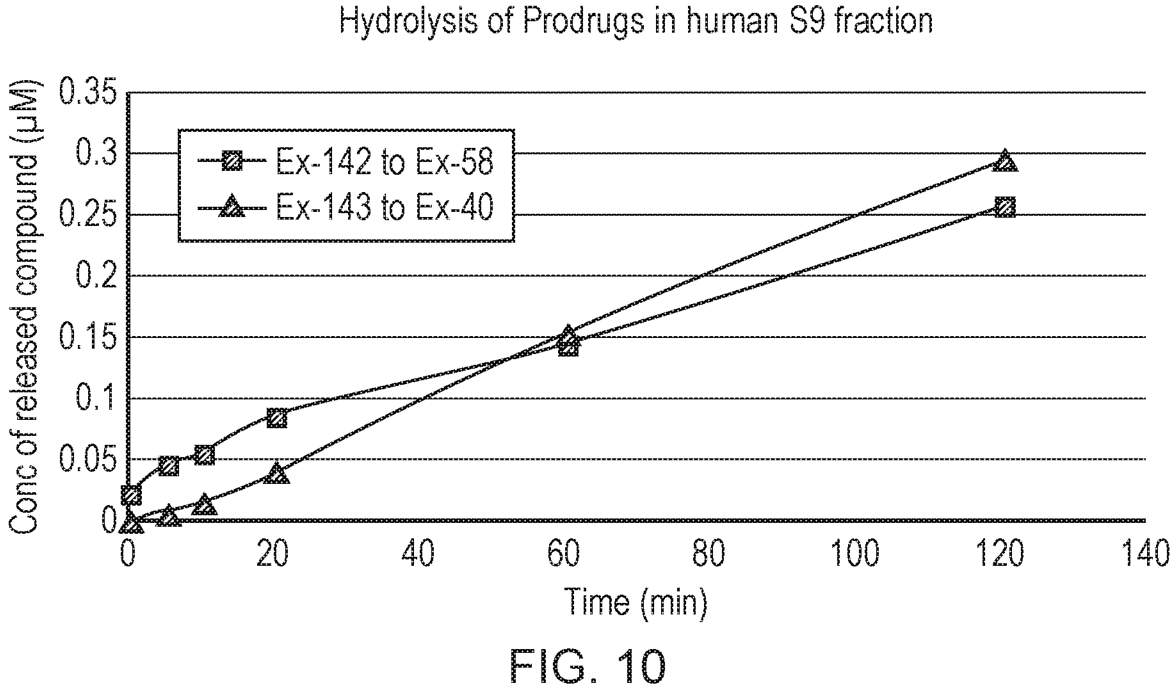
FIGS. 10 and 11 show the rate of hydrolysis of prodrugs into the corresponding compounds in human S9 liver fraction.
Figure 11:
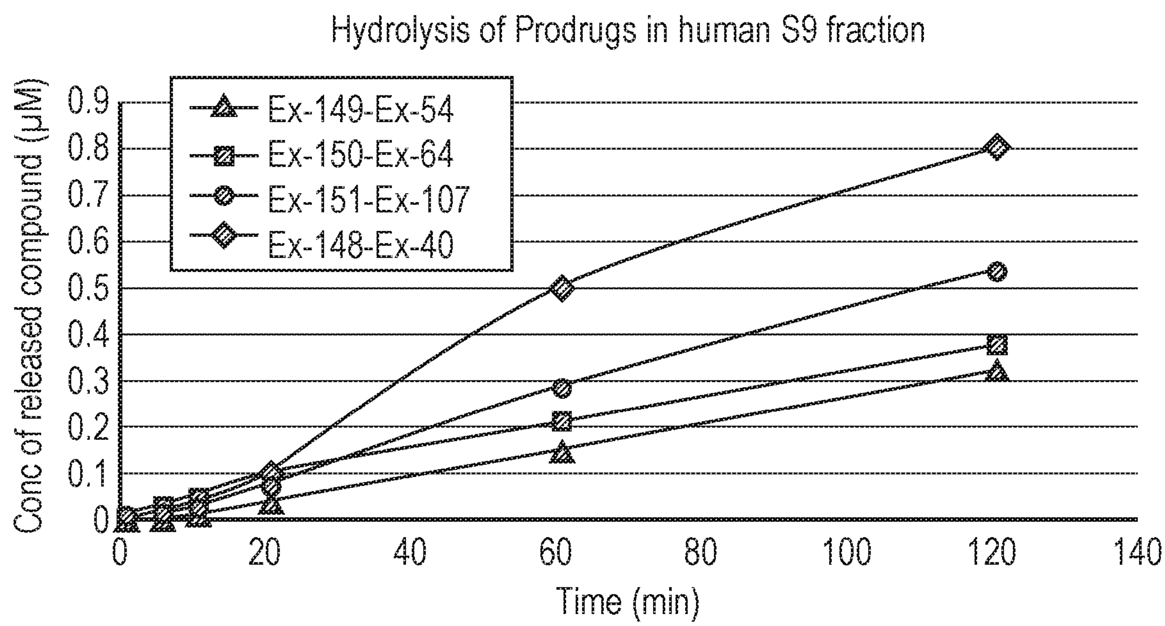

Examples of compounds that can act as prodrugs and the compounds that are generated from the said prodrugs are shown in Table 37 below Various in vitro systems have been used to study the metabolism of compounds in humans such as microsomes, hepatocytes and the liver S9 fraction. The S9 fraction consists of both microsomes and cytosol and contains most of the metabolic enzymes present in a human liver. 1 μM of the prodrugs described in Table 37 were incubated with human S9 liver fraction for 120 min and the release of the corresponding MAP4K4 inhibitor was quantified by mass spectrometry relative to a 1 μM standard of said compound. This experiment demonstrates that prodrugs of the type described herein can be hydrolysed in humans to give the corresponding MAP4K4 inhibitor. FIGS. 10 and 11 show the rate of hydrolysis of prodrugs into the corresponding compounds.

Figure 12:
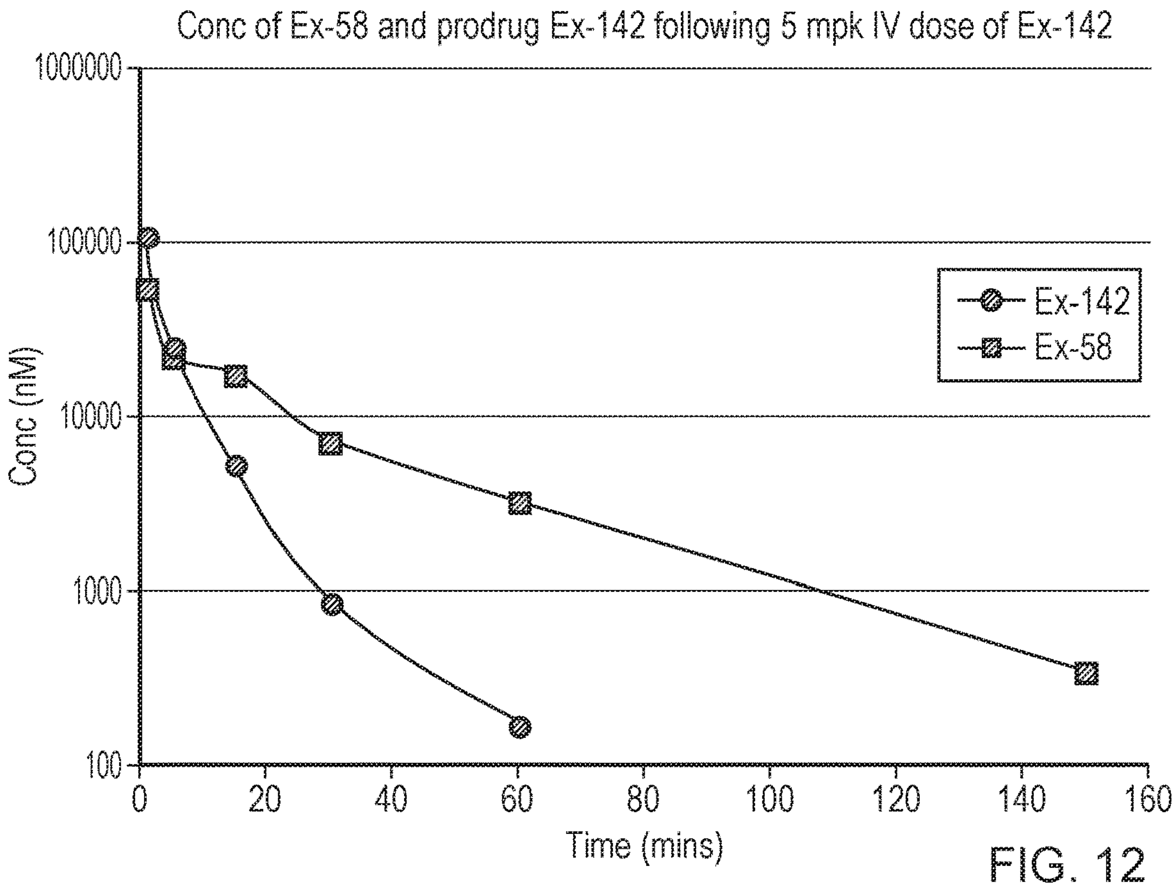
FIGS. 12 and 13 show the rate of hydrolysis of prodrugs into the corresponding compounds in rats.
Figure 13:
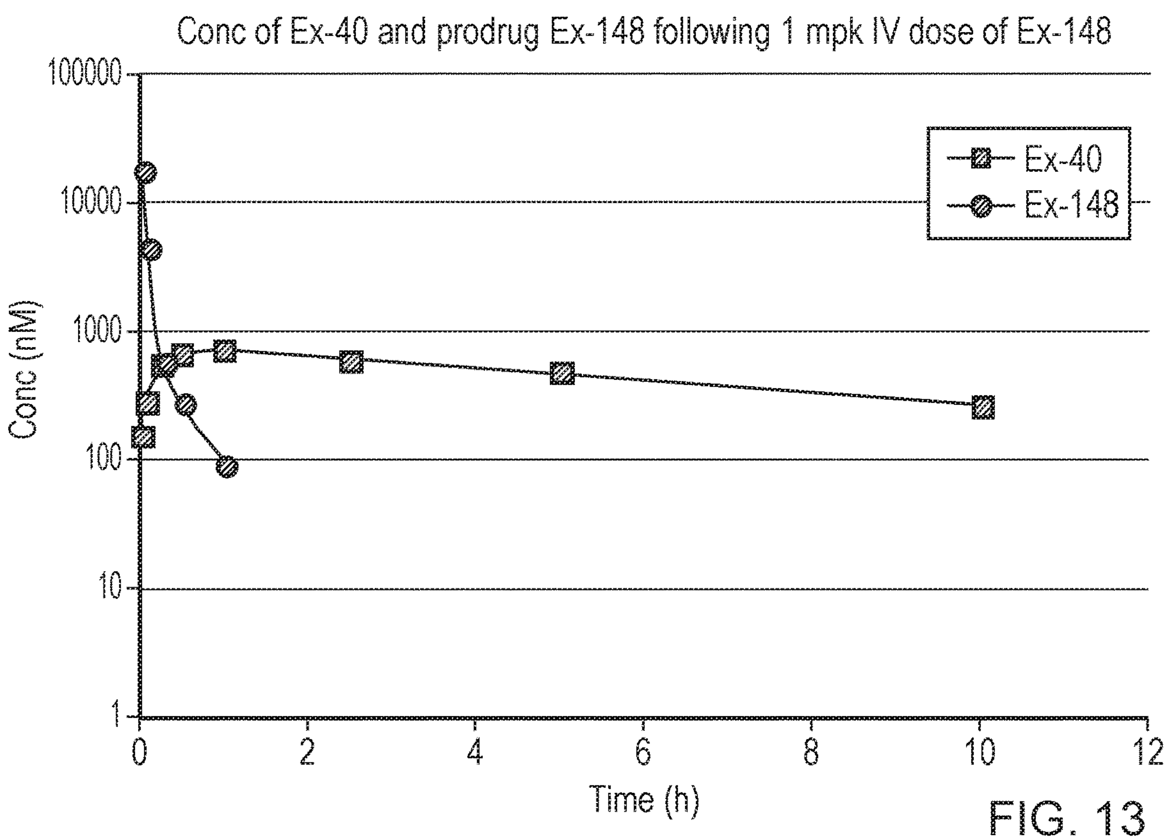

Several of the prodrugs were also tested in vivo in rats and were shown to be rapidly hydrolysed to the corresponding MAP4K4 inhibitor. In such experiments the prodrugs were dosed to female SD rats and the levels of prodrug and drug substance monitored by mass spectrometry. The data is shown in FIGS. 12 and 13.

TABLE 37
| Pro-drug | | Compound generated | |
|---|---|---|---|
| Structure | Cpd # | Structure | Cpd# |
| 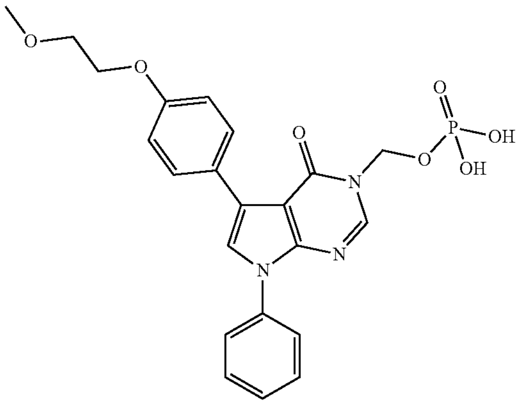 [SMILES: COCCOc1ccc(-c2cn(-c3ccccc3)c3ncn(COP(=O)(O)O)c(=O)c23)cc1] | Ex-142 | 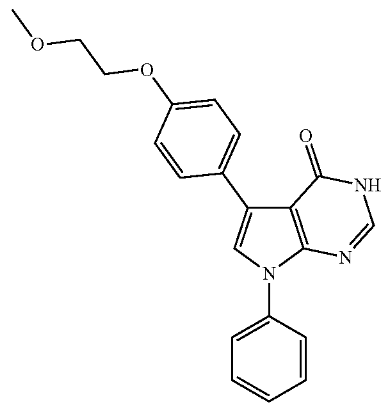 [SMILES: COCCOc1ccc(-c2cn(-c3ccccc3)c3nc[nH]c(=O)c23)cc1] | Ex-58 |
| 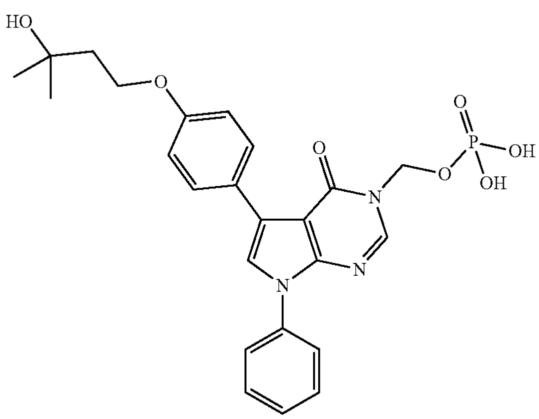 [SMILES: CC(C)(O)CCOc1ccc(-c2cn(-c3ccccc3)c3ncn(COP(=O)(O)O)c(=O)c23)cc1] | Ex-143 | 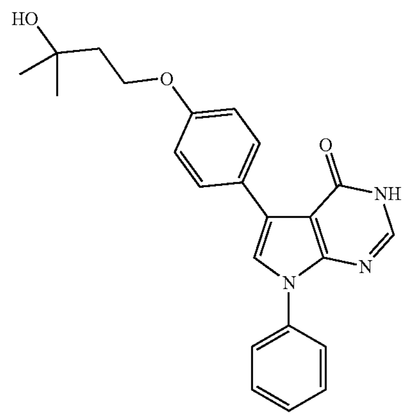 [SMILES: CC(C)(O)CCOc1ccc(-c2cn(-c3ccccc3)c3nc[nH]c(=O)c23)cc1] | Ex-40 |
| 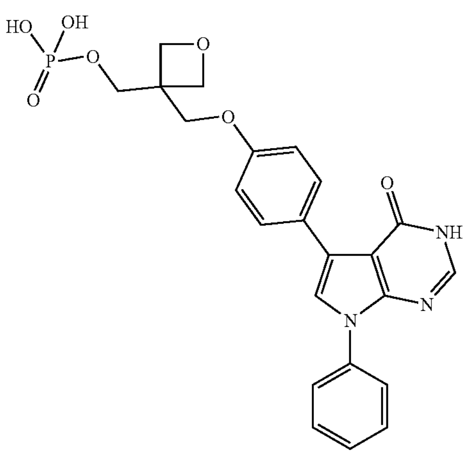 [SMILES: O=c1[nH]cnc2c1c(-c1ccc(OCC3(COP(=O)(O)O)COC3)cc1)cn2-c1ccccc1] | Ex-149 | 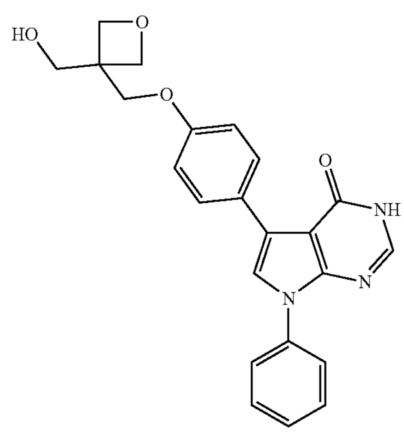 [SMILES: O=c1[nH]cnc2c1c(-c1ccc(OCC3(CO)COC3)cc1)cn2-c1ccccc1] | Ex-54 |

TABLE 37-continued

| Pro-drug | | Compound generated | |
|---|---|---|---|
| Structure | Cpd # | Structure | Cpd# |
| 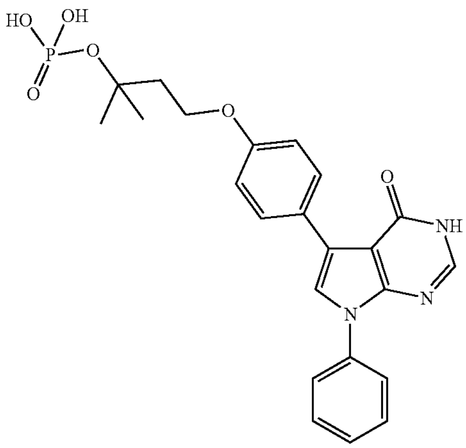 [SMILES: CC(C)(CCOc1ccc(-c2cn(-c3ccccc3)c3nc[nH]c(=O)c23)cc1)OP(=O)(O)O] | Ex-148 | 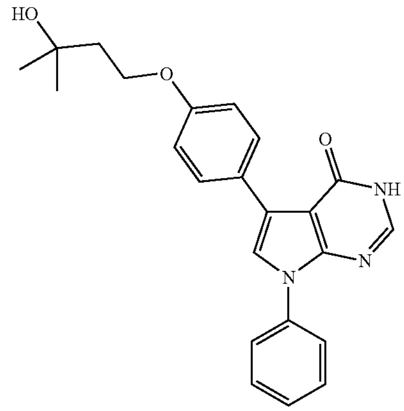 [SMILES: CC(C)(O)CCOc1ccc(-c2cn(-c3ccccc3)c3nc[nH]c(=O)c23)cc1] | Ex-40 |
| 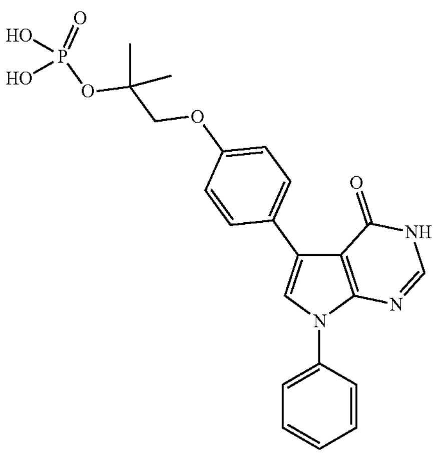 [SMILES: CC(C)(COc1ccc(-c2cn(-c3ccccc3)c3nc[nH]c(=O)c23)cc1)OP(=O)(O)O] | Ex-150 | 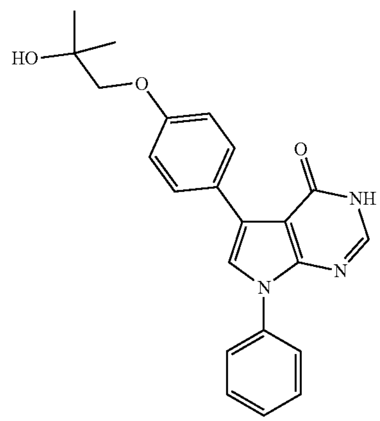 [SMILES: CC(C)(O)COc1ccc(-c2cn(-c3ccccc3)c3nc[nH]c(=O)c23)cc1] | Ex-64 |
| 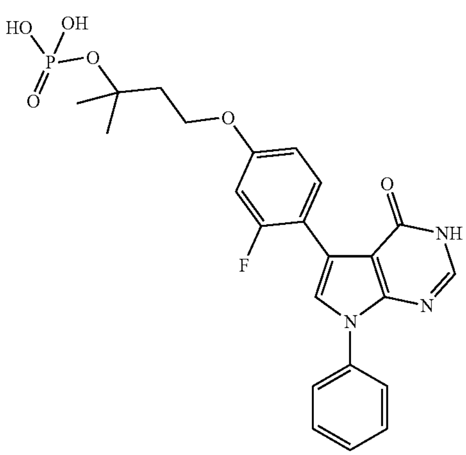 [SMILES: CC(C)(CCOc1ccc(-c2cn(-c3ccccc3)c3nc[nH]c(=O)c23)c(F)c1)OP(=O)(O)O] | Ex-151 | 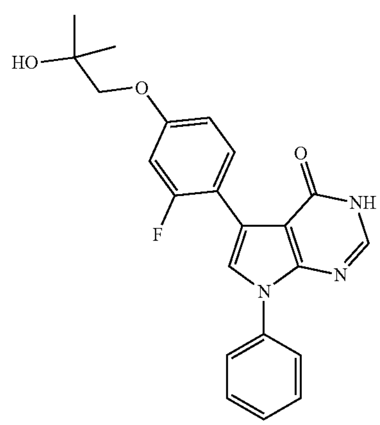 [SMILES: CC(C)(O)COc1ccc(-c2cn(-c3ccccc3)c3nc[nH]c(=O)c23)c(F)c1] | Ex-107 |

REFERENCES

Bellin, M., Marchetto, M. C., Gage, F. H., and Mummery, C. L. (2012). Induced pluripotent stem cells: the new patient? Nat Rev Mol Cell Biol 13, 713-726.

Birket, M. J., Ribeiro, M. C., Kosmidis, G., Ward, D., Leitoguinho, A. R., van de Pol, V., Dambrot, C., Devalla, H. D., Davis, R. P., Mastroberardino, P. G., et al. (2015). Contractile defect caused by mutation in MYBPC3 revealed under conditions optimized for human PSC-cardiomyocytefunction. Cell Rep 13, 733-745.

Breckwoldt, K., Letuffe-Breniere, D., Mannhardt, I., Schulze, T., Ulmer, B., Werner, T., Benzin, A., Klampe, B., Reinsch, M. C., Laufer, S., et al. (2017). Differentiation of cardiomyocytes and generation of human engineered heart tissue. Nat Protoc 12, 1177-1197.

Brown, D. I., and Griendling, K. K. (2015). Regulation of signal transduction by reactive oxygen species in the cardiovascular system. Circ Res 116, 531-549.

Burridge, P. W., Li, Y. F., Matsa, E., Wu, H., Ong, S. G., Sharma, A., Holmstrom, A., Chang, A. C., Coronado, M. J., Ebert, A. D., et al. (2016). Human induced pluripotent stem cell-derived cardiomyocytes recapitulate the predilection of breast cancer patients to doxorubicin-induced cardiotoxicity. Nat Med 22, 547-556.

Cameron, B. J., Gerry, A. B., Dukes, J., Harper, J. V., Kannan, V., Bianchi, F. C., Grand, F., Brewer, J. E., Gupta, M., Plesa, G., et al. (2013). Identification of a Titin-derived HLA-A1-presented peptide as a cross-reactive target for engineered MAGE A3-directed T cells. Sci Transl Med 5, 197ra103.

Chapman, J. O., Li, H., and Lundquist, E. A. (2008). The MIG-15 NIK kinase acts cell-autonomously in neuroblast polarization and migration in *C. elegans*. Dev Biol 324, 245-257.

Cheeseright, T. J., Mackey, M. D., and Scoffin, R. A. (2011). High content pharmacophores from molecular fields: a biologically relevant method for comparing and understanding ligands. Curr Comput Aided Drug Des 7, 190-205.

Chen, S., Li, X., Lu, D., Xu, Y., Mou, W., Wang, L., Chen, Y., Liu, Y., Li, X., Li, L. Y., et al. (2014). SOX2 regulates apoptosis through MAP4K4-survivin signaling pathway in human lung cancer cells. Carcinogenesis 35, 613-623.

Dan, I., Watanabe, N. M., and Kusumi, A. (2001). The Ste20 group kinases as regulators of MAP kinase cascades. Trends Cell Biol 11, 220-230.

Devalla, H. D., Schwach, V., Ford, J. W., Milnes, J. T., El-Haou, S., Jackson, C., Gkatzis, K., Elliott, D. A., Chuva de Sousa Lopes, S. M., Mummery, C. L., et al. (2015). Atrial-like cardiomyocytes from human pluripotent stem cells are a robust preclinical model for assessing atrial-selective pharmacology. EMBO Mol Med 7, 394-410.

Dorn, G. W., 2nd (2009). Novel pharmacotherapies to abrogate postinfarction ventricular remodeling. Nat Rev Cardiol 6, 283-291.

Fiedler, L. R., Maifoshie, E., and Schneider, M. D. (2014). Mouse models of heart failure: cell signaling and cell survival. Curr Top Dev Biol 109, 171-247.

Gao, X. M., Xu, Q., Kiriazis, H., Dart, A. M., and Du, X. J. (2005). Mouse model of post-infarct ventricular rupture: time course, strain- and gender-dependency, tensile strength, and histopathology. Cardiovasc Res 65, 469-477.

Gintant, G., Fermini, B., Stockbridge, N., and Strauss, D. (2017). The evolving roles of human iPSC-derived cardiomyocytes in drug safety and discovery. Cell Stem Cell 21, 14-17.

Gintant, G., Sager, P. T., and Stockbridge, N. (2016). Evolution of strategies to improve preclinical cardiac safety testing. Nat Rev Drug Discov 15, 457-471.

Guimaraes, C. R., Rai, B. K., Munchhof, M. J., Liu, S., Wang, J., Bhattacharya, S. K., and Buckbinder, L. (2011). Understanding the impact of the P-loop conformation on kinase selectivity. J Chem Inf Model 51, 1199-1204.

Hausenloy, D. J., and Yellon, D. M. (2015). Targeting myocardial reperfusion Injury—the search continues. N Engl J Med 373, 1073-1075.

Heusch, G. (2013). Cardioprotection: chances and challenges of its translation to the clinic. Lancet 381, 166-175.

Hinson, J. T., Chopra, A., Nafissi, N., Polacheck, W. J., Benson, C. C., Swist, S., Gorham, J., Yang, L., Schafer, S., Sheng, C. C., et al. (2015). Titin mutations in iPS cells define sarcomere insufficiency as a cause of dilated cardiomyopathy. Science 349, 982-986.

Jacquet, S., Nishino, Y., Kumphune, S., Sicard, P., Clark, J. E., Kobayashi, K. S., Flavell, R. A., Eickhoff, J., Cotten, M., and Marber, M. S. (2008). The role of RIP2 in p38 MAPK activation in the stressed heart. J Biol Chem 283, 11964-11971.

Lee, S. H., Cunha, D., Piermarocchi, C., Paternostro, G., Pinkerton, A., Ladriere, L., Marchetti, P., Eizirik, D. L., Cnop, M., and Levine, F. (2017a). High-throughput screening and bioinformatic analysis to ascertain compounds that prevent saturated fatty acid-induced beta-cell apoptosis. Biochem Pharmacol 138, 140-149.

Lee, Y. K., Lau, Y. M., Cai, Z. J., Lai, W. H., Wong, L. Y., Tse, H. F., Ng, K. M., and Siu, C. W. (2017b). Modeling treatment response for Lamin A/C related dilated cardiomyopathy in human induced pluripotent stem cells. J Am Heart Assoc 6.

Liang, P., Lan, F., Lee, A. S., Gong, T., Sanchez-Freire, V., Wang, Y., Diecke, S., Sallam, K., Knowles, J. W., Wang, P. J., et al. (2013). Drug screening using a library of human induced pluripotent stem cell-derived cardiomyocytes reveals disease-specific patterns of cardiotoxicity. Circulation 127, 1677-1691.

Lincoff, A. M., Roe, M., Aylward, P., Galla, J., Rynkiewicz, A., Guetta, V., Zelizko, M., Kleiman, N., White, H., McErlean, E., et al. (2014). Inhibition of delta-protein kinase C by delcasertib as an adjunct to primary percutaneous coronary intervention for acute anterior ST-segment elevation myocardial infarction: results of the PROTECTION AMI Randomized Controlled Trial. Eur Heart J. 35, 2516-23.

Loh S H, Francescut L, Lingor P, Bahr M, Nicotera P (2008). Identification of new kinase clusters required for neurite outgrowth and retraction by a loss-of-function RNA interference screen. Cell Death Differ 15, 283-298.

Ma, J., Guo, L., Fiene, S. J., Anson, B. D., Thomson, J. A., Kamp, T. J., Kolaja, K. L., Swanson, B. J., and January, C. T. (2011). High purity human-induced pluripotent stem cell-derived cardiomyocytes: electrophysiological properties of action potentials and ionic currents. Am J Physiol Heart Circ Physiol 301, H2006-2017.

Matsa, E., Burridge, P. W., and Wu, J. C. (2014). Human stem cells for modeling heart disease and for drug discovery. Sci Transl Med 6, 239ps236.

Michael, L. H., Entman, M. L., Hartley, C. J., Youker, K. A., Zhu, J., Hall, S. R., Hawkins, H. K., Bernes, K., and Ballantyne, C. M. (1995). Myocardial ischemia and reperfusion: a murine model. Am J Physiol 269, H2147-H2154.

Miled, C., Pontoglio, M., Garbay, S., Yaniv, M., and Weitzman, J. B. (2005). A genomic map of p53 binding sites identifies novel p53 targets involved in an apoptotic network. Cancer Res 65, 5096-5104.

Moran, A. E., Forouzanfar, M. H., Roth, G. A., Mensah, G. A., Ezzati, M., Flaxman, A., Murray, C. J., and Naghavi, M. (2014). The global burden of ischemic heart disease in 1990 and 2010: the Global Burden of Disease 2010 study. Circulation 129, 1493-1501.

Moretti, A., Bellin, M., Welling, A., Jung, C. B., Lam, J. T., Bott-Flugel, L., Dorn, T., Goedel, A., Hohnke, C., Hofmann, F., et al. (2010). Patient-specific induced pluripotent stem-cell models for long-QT syndrome. N Engl J Med 363, 1397-1409.

Ndubaku, C. O., Crawford, T. D., Chen, H., Boggs, J. W., Drobnick, J., Harris, S. F., Jesudason, R., McNamara, E., Nonomiya, J., Sambrone, A., et al. (2015). Structure-based design of GNE-495, a potent and selective MAP4K4 Inhibitor with efficacy in retinal angiogenesis. ACS Med Chem Lett 6, 913-918.

Newby, L. K., Marber, M. S., Melloni, C., Sarov-Blat, L., Aberle, L. H., Aylward, P. E., Cai, G., de Winter, R. J., Hamm, C. W., Heitner, J. F., et al. (2014). Losmapimod, a novel p38 mitogen-activated protein kinase inhibitor, in non-ST-segment elevation myocardial infarction: a randomised phase 2 trial. Lancet 384, 1187-1195.

O'Connor, M. S., Safari, A., Liu, D., Qin, J., and Songyang, Z. (2004). The human Rap1 protein complex and modulation of telomere length. J Biol Chem 279, 28585-28591.

Oh, H., Wang, S. C., Prahash, A., Sano, M., Moravec, C. S., Taffet, G. E., Michael, L. H., Youker, K. A., Entman, M. L., and Schneider, M. D. (2003). Telomere attrition and Chk2 activation in human heart failure. Proc Natl Acad Sci USA 100, 5378-5383.

Passier, R., Orlova, V., and Mummery, C. (2016). Complex tissue and disease modeling using hiPSCs. Cell Stem Cell 18, 309-321.

Piot, C., Croisille, P., Staat, P., Thibault, H., Rioufol, G., Mewton, N., Elbelghiti, R., Cung, T. T., Bonnefoy, E., Angoulvant, D., et al. (2008). Effect of cyclosporine on reperfusion injury in acute myocardial infarction. N Engl J Med 359, 473-481.

Rose, B. A., Force, T., and Wang, Y. (2010). Mitogen-activated protein kinase signaling in the heart: angels versus demons in a heart-breaking tale. Physiol Rev 90, 1507-1546.

Sakata, Y., Hoit, B. D., Liggett, S. B., Walsh, R. A., and Dorn, G. (1998). Decompensation of pressure-overload hypertrophy in G alpha q-overexpressing mice. Circulation 97, 1488-1495.

Sala, L., Yu, Z., Ward-van Oostwaard, D., van Veldhoven, J. P., Moretti, A., Laugwitz, K. L., Mummery, C. L., AP, I. J., and Bellin, M. (2016). A new hERG allosteric modulator rescues genetic and drug-induced long-QT syndrome phenotypes in cardiomyocytes from isogenic pairs of patient induced pluripotent stem cells. EMBO Mol Med 8, 1065-1081.

Sano, M., Wang, S. C., Shirai, M., Scaglia, F., Xie, M., Sakai, S., Tanaka, T., Kulkarni, P. A., Barger, P. M., Youker, K. A., et al. (2004). Activation of cardiac Cdk9 represses PGC-1 and confers a predisposition to heart failure. EMBO J 23, 3559-3569.

Schaaf, S., Shibamiya, A., Mewe, M., Eder, A., Stohr, A., Hirt, M. N., Rau, T., Zimmermann, W. H., Conradi, L., Eschenhagen, T., et al. (2011). Human engineered heart tissue as a versatile tool in basic research and preclinical toxicology. PLoS One 6, e26397.

Schroder P, Forster T, Kleine S, Becker C, Richters A, Ziegler S, Rauh D, Kumar K, Waldmann H (2015). Neuritogenic militarinone-inspired 4-hydroxypyridones target the stress pathway kinase map4k4. Angew Chem Int Ed Engl 54, 12398-12403.

Silva, J. M., Li, M. Z., Chang, K., Ge, W., Golding, M. C., Rickles, R. J., Siolas, D., Hu, G., Paddison, P. J., Schlabach, M. R., et al. (2005). Second-generation shRNA libraries covering the mouse and human genomes. Nat Genet 37, 1281-1288.

Sivasubramanian, N., Coker, M. L., Kurrelmeyer, K. M., MacLellan, W. R., DeMayo, F. J., Spinale, F. G., and Mann, D. L. (2001). Left ventricular remodeling in transgenic mice with cardiac restricted overexpression of tumor necrosis factor. Circulation 104, 826-831.

Song, W., Dyer, E., Stuckey, D. J., Copeland, O., Leung, M. C., Bayliss, C., Messer, A., Wilkinson, R., Tremoleda, J. L., Schneider, M. D., et al. (2011). Molecular mechanism of the E99K mutation in cardiac actin (ACTC gene) that causes apical hypertrophy in man and mouse. J Biol Chem 286, 27582-27593.

Stuckey, D. J., McSweeney, S. J., Thin, M. Z., Habib, J., Price, A. N., Fiedler, L. R., Gsell, W., Prasad, S. K., and Schneider, M. D. (2014). T1 mapping detects pharmacological retardation of diffuse cardiac fibrosis in mouse pressure-overload hypertrophy. Circ Cardiovasc Imaging 7, 240-249.

Su, Y. C., Treisman, J. E., and Skolnik, E. Y. (1998). The *Drosophila* Ste20-related kinase misshapen is required for embryonic dorsal closure and acts through a JNK MAPK module on an evolutionarily conserved signaling pathway. Genes Dev 12, 2371-2380.

Subramaniam, A., Jones, W. K., Gulick, J., Wert, S., Neumann, J., and Robbins, J. (1991). Tissue-specific regulation of the alpha-myosin heavy chain gene promoter in transgenic mice. J Biol Chem 266, 24613-24620.

Suematsu, N., Tsutsui, H., Wen, J., Kang, D., Ikeuchi, M., Ide, T., Hayashidani, S., Shiomi, T., Kubota, T., Hamasaki, N., et al. (2003). Oxidative stress mediates tumor necrosis factor-alpha-induced mitochondrial DNA damage and dysfunction in cardiac myocytes. Circulation 107, 1418-1423.

Taira, K., Umikawa, M., Takei, K., Myagmar, B. E., Shinzato, M., Machida, N., Uezato, H., Nonaka, S., and Kariya, K. (2004). The Traf2- and Nck-interacting kinase as a putative effector of Rap2 to regulate actin cytoskeleton. J Biol Chem 279, 49488-49496.

Vitorino, P., Yeung, S., Crow, A., Bakke, J., Smyczek, T., West, K., McNamara, E., Eastham-Anderson, J., Gould, S., Harris, S. F., et al. (2015). MAP4K4 regulates integrin-FERM binding to control endothelial cell motility. Nature 519, 425-430.

Wang M, Amano S U, Flach R J, Chawla A, Aouadi M, Czech M P (2013). Identification of MAP4K4 as a novel suppressor of skeletal muscle differentiation. Mol Cell Biol 33, 678-687.

Wei, J., Wang, W., Chopra, I., Li, H. F., Dougherty, C. J., Adi, J., Adi, N., Wang, H., and Webster, K. A. (2011). c-Jun N-terminal kinase (JNK-1) confers protection against brief but not extended ischemia during acute myocardial infarction. J Biol Chem 286, 13995-14006.

Whelan, R. S., Kaplinskiy, V., and Kitsis, R. N. (2010). Cell death in the pathogenesis of heart disease: mechanisms and significance. Annu Rev Physiol 72, 19-44.

White, B. J., Tarabishy, S., Venna, V. R., Manwani, B., Benashski, S., McCullough, L. D., and Li, J. (2012). Protection from cerebral ischemia by inhibition of TGF-beta-activated kinase. Exp Neurol 237, 238-245.

Xue, Y., Wang, X., Li, Z., Gotoh, N., Chapman, D., and Skolnik, E. Y. (2001). Mesodermal patterning defect in mice lacking the Ste20 NCK interacting kinase (NIK). Development 128, 1559-1572.

Yang, Y. M., Gupta, S. K., Kim, K. J., Powers, B. E., Cerqueira, A., Wainger, B. J., Ngo, H. D., Rosowski, K. A., Schein, P. A., Ackeifi, C. A., et al. (2013). A small molecule screen in stem-cell-derived motor neurons identifies a kinase inhibitor as a candidate therapeutic for ALS. Cell Stem Cell 12, 713-726.

Yao, Z., Zhou, G., Wang, X. S., Brown, A., Diener, K., Gan, H., and Tan, T. H. (1999). A novel human STE20-related protein kinase, HGK, that specifically activates the c-Jun N-terminal kinase signaling pathway. J Biol Chem 274, 2118-2125.

Yazawa, M., Hsueh, B., Jia, X., Pasca, A. M., Bernstein, J. A., Hallmayer, J., and Dolmetsch, R. E. (2011). Using induced pluripotent stem cells to investigate cardiac phenotypes in Timothy syndrome. Nature 471, 230-234.

Yue, J., Xie, M., Gou, X., Lee, P., Schneider, M. D., and Wu, X. (2014). Microtubules regulate focal adhesion dynamics through MAP4K4. Dev Cell 31, 572-585.

Zhang, D., Gaussin, V., Taffet, G. E., Belaguli, N. S., Yamada, M., Schwartz, R. J., Michael, L. H., Overbeek, P. A., and Schneider, M. D. (2000). TAK1 is activated in the myocardium after pressure overload and is sufficient to provoke heart failure in transgenic mice. Nat Med 6, 556-563.

Zohn, I. E., Li, Y., Skolnik, E. Y., Anderson, K. V., Han, J., and Niswander, L. (2006). p38 and a p38-interacting protein are critical for downregulation of E-cadherin during mouse gastrulation. Cell 125, 957-969.

The invention claimed is:

1. A compound of formula (I) or a pharmaceutically acceptable salt thereof:

(I)

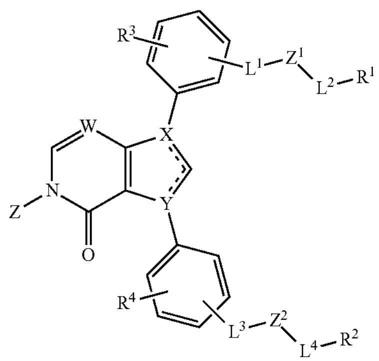

wherein

W is CH or N;

either X is N and Y is C, or Y is N and X is C;

Z is either H or $—CH_2OP(═O)(OH)_2$;

$-L^3-Z^2-L^4-R^2$ is $—O(CR^aR^b)_{1-3}-R^2$,

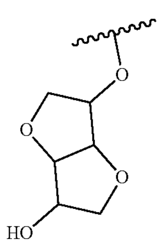

or

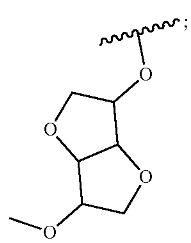

;

$R^2$ is selected from halo, $C_{1-6}$ alkyl, $C_{2-6}$ alkenyl, $C_{1-6}$ haloalkyl, $—NR^{6a}R^{6b}$, $—OR^{6a}$, $—OP(═O)(OH)_2$, $—C(O)R^{6a}$, $—NR^{5b}C(O)O—C_{1-6}$ alkyl, phenyl, a 5 or 6 membered heteroaryl ring, and a 3 to 8 membered heterocycloalkyl ring system, wherein the phenyl, heteroaryl and heterocycloalkyl rings are unsubstituted or substituted with 1 or 2 groups selected from: oxo, halo, $OR^{6a}$, $C_{1-6}$ alkyl, $C_{1-6}$ alkyl substituted with $NR^{6a}R^{6b}$, $C_{1-6}$ alkyl substituted with $OR^{6a}$, $—C(O)OR^g$, and $—NR^8C(O)R^7$;

$L^1-Z^1-L^2-R^1$ is selected from: H, Me, Cl, F, —OMe, $—CH_2OH$, —OH, $OCF_3$, $OCHF_2$, —C(O)OH, —C(O)OEt, —C(O)NHMe, $—SO_2Me$, $—SO_2NH_2$, $—C(O)NH_2$, —NHC(O)Me, $—C(O)NMe_2$, —C(O)—N-methyl piperazinyl, $—O(CH_2)_2OH$, $—CH_2$-imidazolyl, $—O(CH_2)_3NMe_2$, $—OCH_2$-pyrrolidinyl, $—OCH_2$—N-methylpyrrolidinyl, $—O(CH_2)_3$-morpholinyl, $—OCH_2CH(OH)CH_2$-morpholinyl,

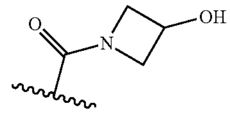

,

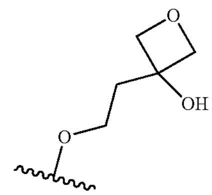

, and

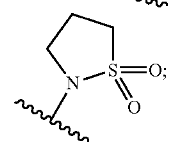

;

$R^3$ and $R^4$ are independently selected from H, halo, —CN and $C_{1-6}$ alkyl;

$R^{5b}$ is selected from: H, $C_{1-6}$ alkyl, and $C_{3-6}$ cycloalkyl;

$R^{6a}$ and $R^{6b}$ are independently selected from: H, $C_{1-6}$ alkyl, $C_{1-6}$ alkyl substituted with $—OR^e$, $C_{1-6}$ alkyl substituted with $—NR^eR^f$, and $C_{3-6}$ cycloalkyl;

$R^7$ is selected from H, $—OR^9$, $C_{1-6}$ alkyl and $C_{3-6}$ cycloalkyl;

$R^8$ is selected from H and $C_{1-6}$ alkyl;

$R^a$ and $R^b$ are each independently selected from: H, halo, $C_{1-6}$ alkyl, and $—OR^h$, or $R^a$ and $R^b$ taken together with the atom to which they are attached form a 3 to 6 membered cycloalkyl ring or a 3 to 6 membered heterocycloalkyl ring containing 1 or 2 O, N or S atoms, wherein the cycloalkyl ring is unsubstituted or substituted with 1 or 2 halo groups; and $R^e$, $R^f$, $R^9$ and $R^h$ are each independently selected from H and $C_{1-6}$ alkyl.

2. A compound of claim 1, wherein $-L^3-Z^2-L^4-R^2$ is selected from: $—OCH_2CH_2OH$, $—OCH_2CH_2OMe$, $—OCH_2C(Me)_2OH$, $—OCH_2CH_2C(Me)_2OH$, $—OCH_2CH(OH)CH_2OH$, $—OCH_2C(Me_2)OH$, $—OCH_2CH_2NH_2$, $—OCH_2CH_2NMe_2$, $—O(CH_2)_3NMe_2$, $—OCH_2CH(OH)CH_2NMe_2$, $—OCH_2CH_2NHC(O)O^tBu$, $—OCH_2CH(OH)CH_2OMe$, $—OCH_2CH(OH)CH(OH)Me$, $—OCH_2CH_2CH(OH)Me$, $—OCF_2CH_2OH$, $—OCH_2C(Me)_2OP(═O)(OH)_2$, $—OCH_2CH(Me)_2CH_2OH$, $—OCH_2CH_2C(Me)_2NH_2$, $—OCH_2C(Me)_2NH_2$, $—OCH_2CH(OH)C(Me)_2OH$, $—OCH_2C(Me)_2OMe$, $—OCH_2CH_2C(Me)_2OP(═O)(OH)_2$, $—OCH(Me)CH_2OMe$, $—OCH_2CH(Me)OMe$, $—OCH_2$-azetidinyl, $—OCH_2$—N-methylazetindinyl, —O—N-ethylpiperadinyl, $—O(CH_2)_3$-morpholinyl, $—OCH_2CH(OH)CH_2$-morpholinyl, $—OCH_2CH(OMe)CH_2$-morpholinyl, $—O(CH_2)_3$—N-methylpiperazinyl, $—OCH_2CH(OH)CH_2$—N-methylpiperazinyl, $—OCH_2CH(OH)CH_2$—N-methylpiperazinonyl, $—O(CH_2)_3$—N-methylpiperazinonyl, $—OCH_2CH(OH)CH_2$-morpholinonyl, $—OCH_2CH(OH)CH_2$-morpholinonyl, $—OCH_2CH(OH)CH_2$-thiomorpholindionyl,

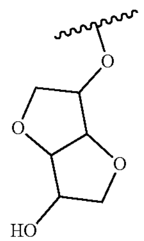
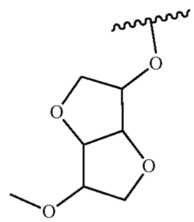
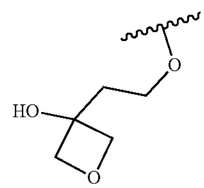
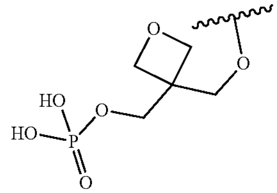
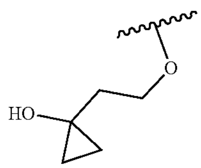
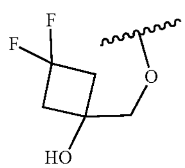
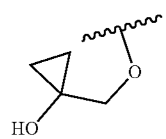
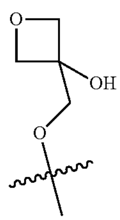
and
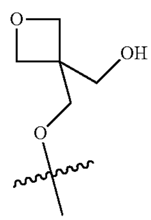
.
3. A compound selected from:
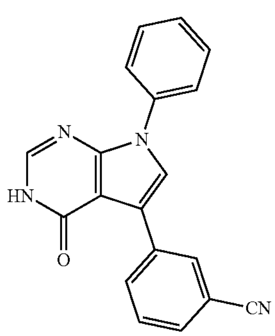
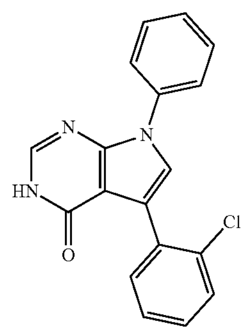
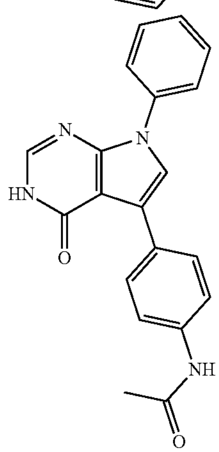
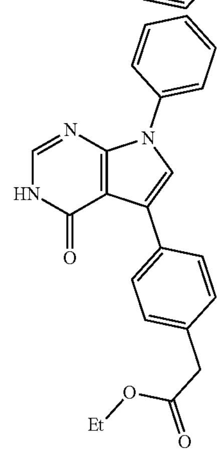
-continued
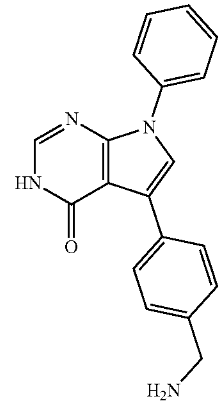
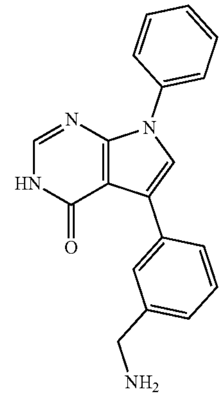
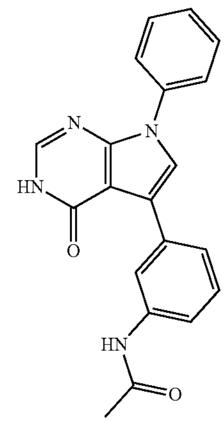
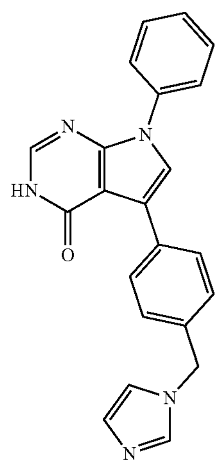
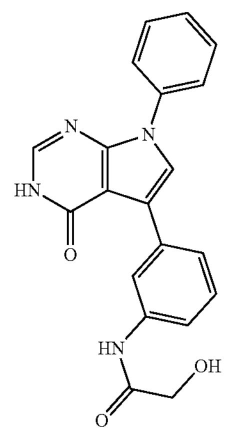
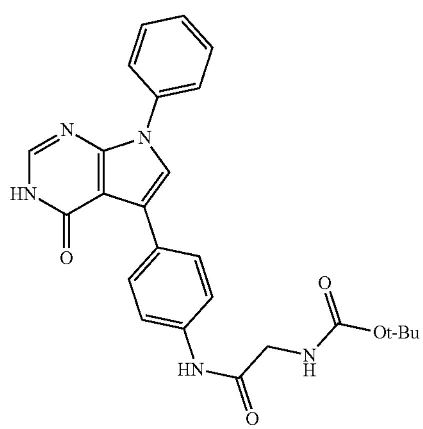

-continued
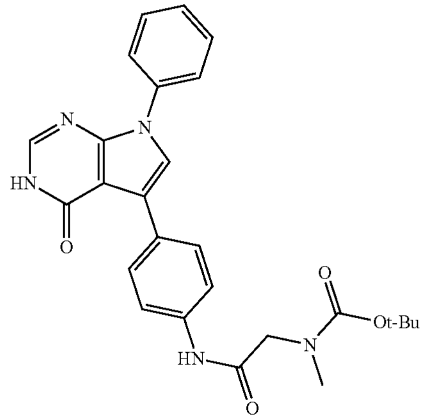
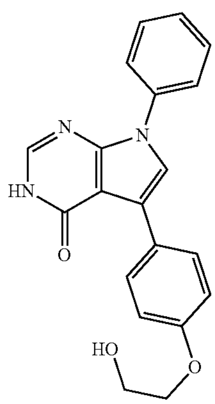
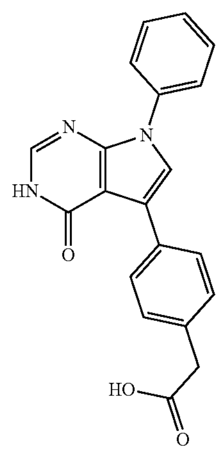
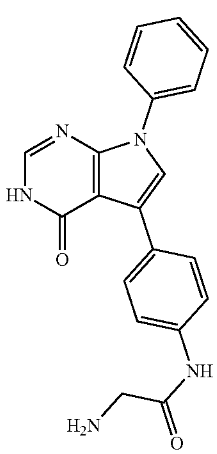
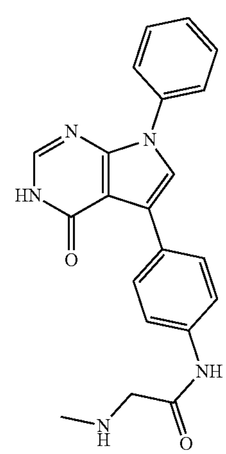
-continued
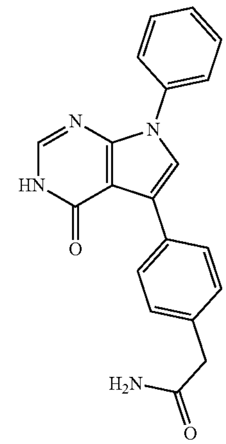
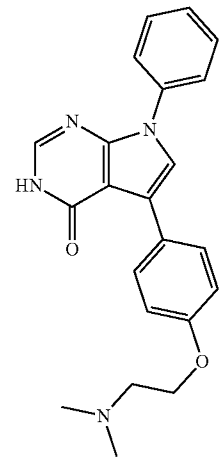
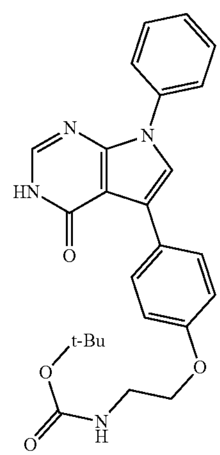
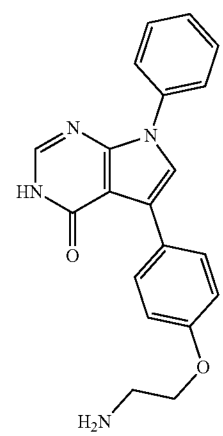
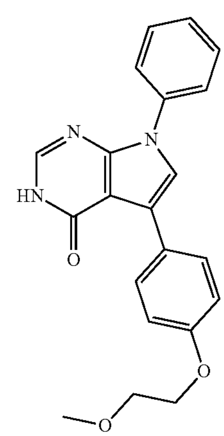
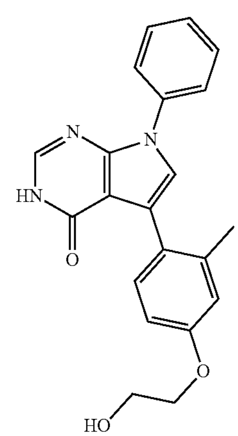

-continued
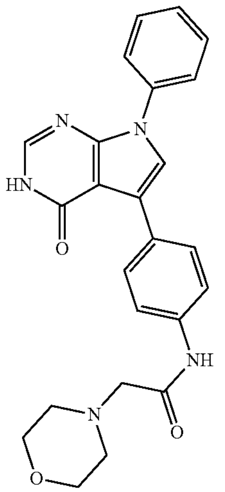
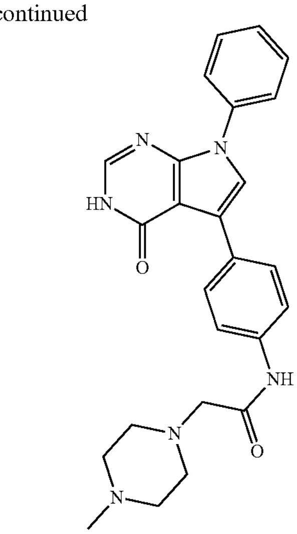
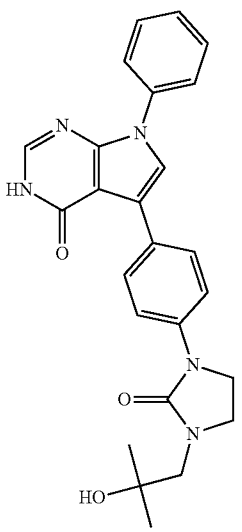
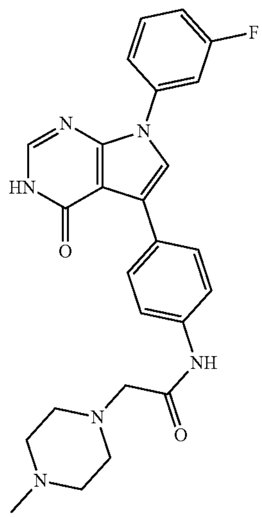
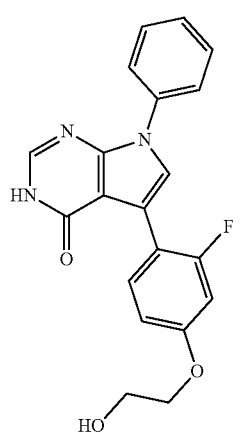
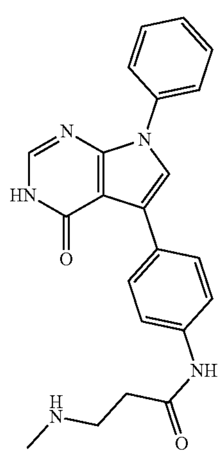
-continued
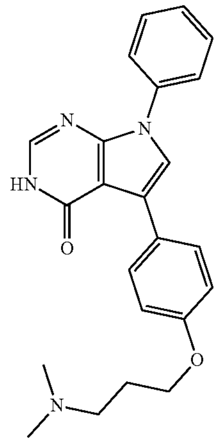
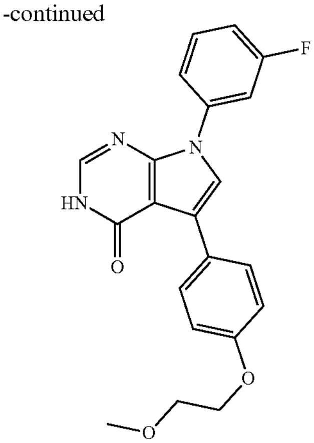
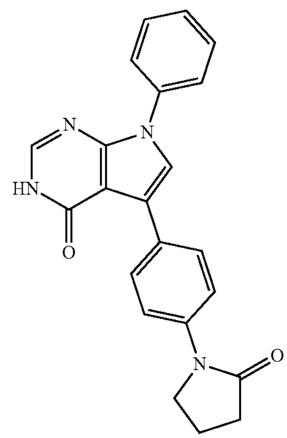
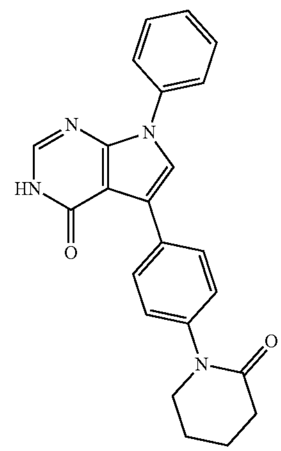
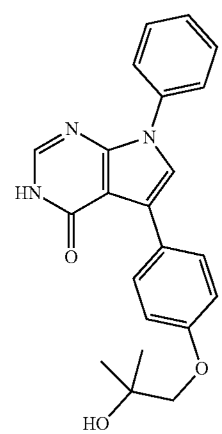
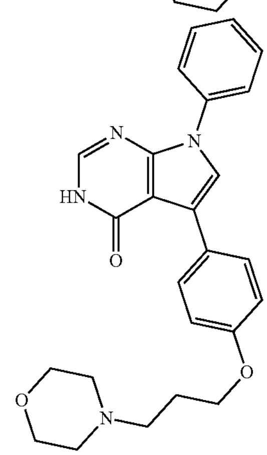
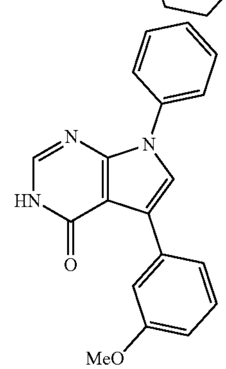

-continued
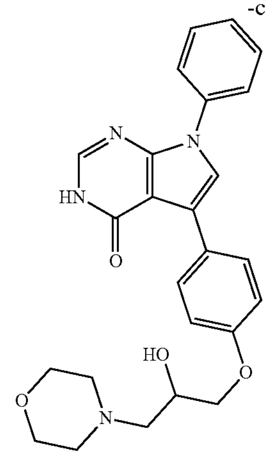
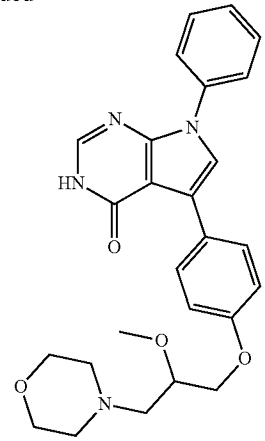
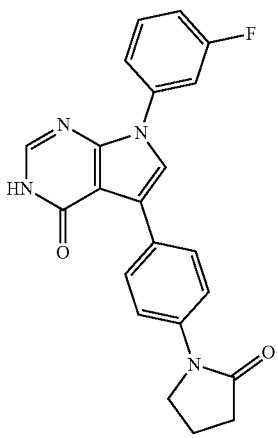
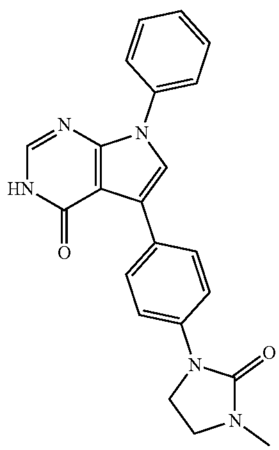
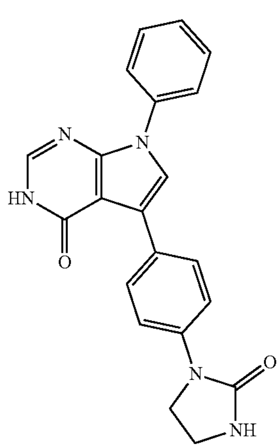
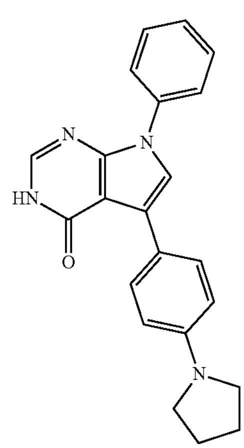
-continued
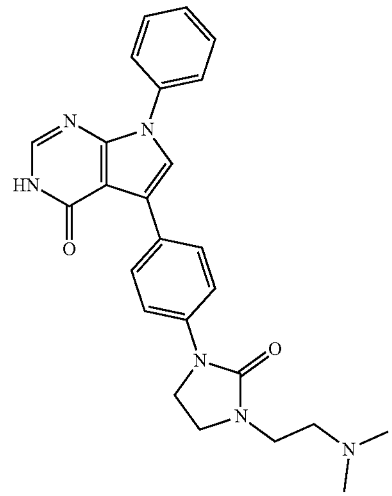
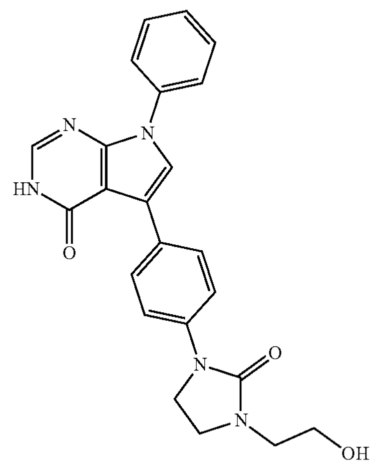
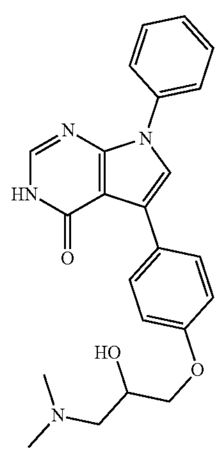
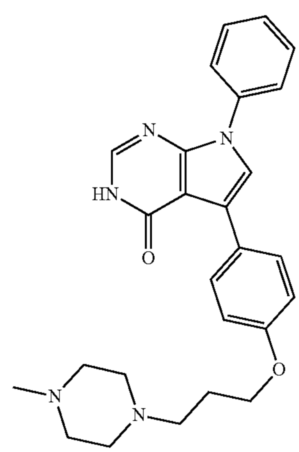

-continued
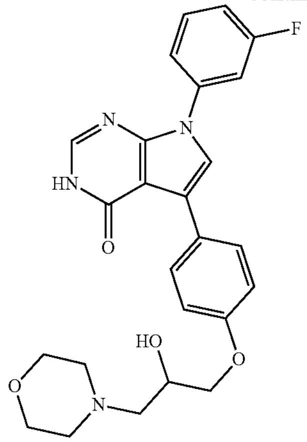
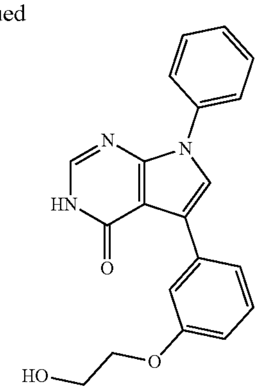
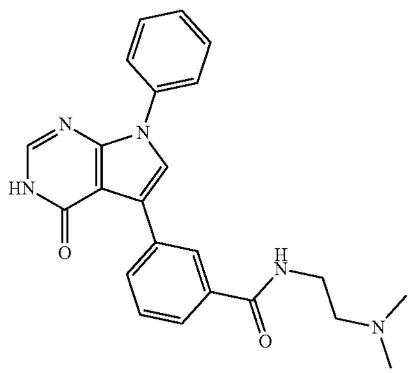
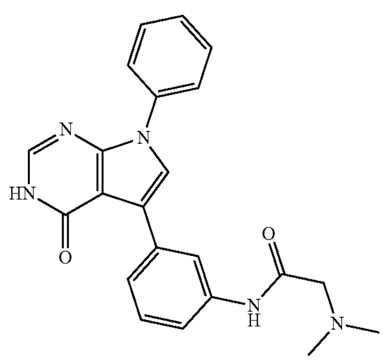
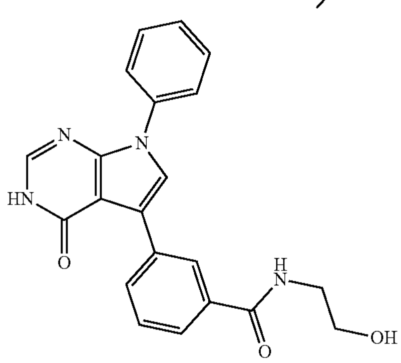
-continued
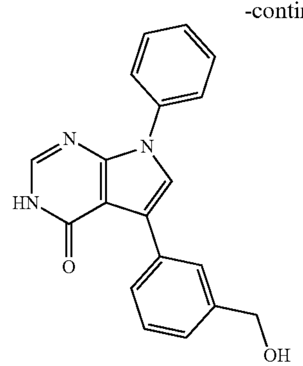
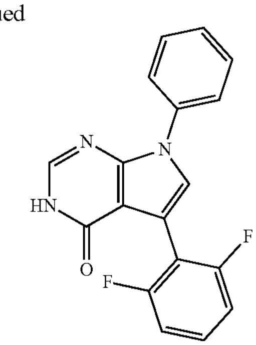
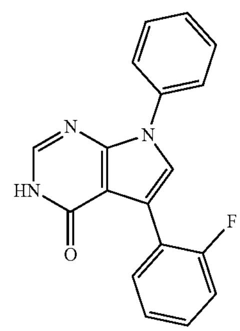
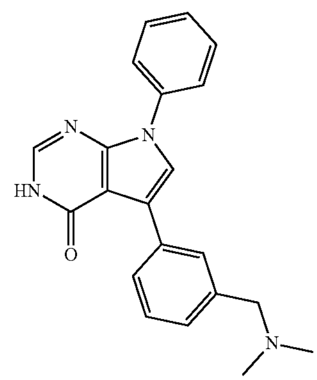
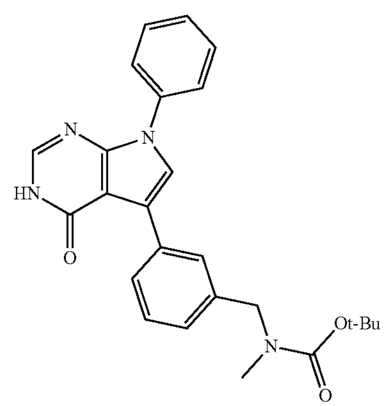
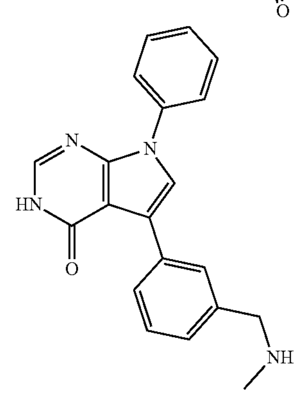

-continued
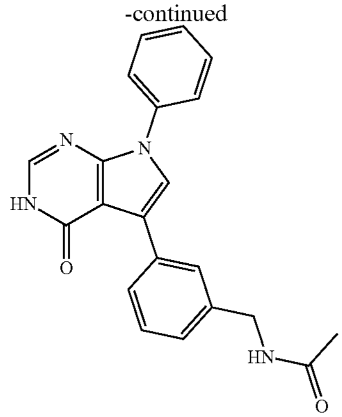
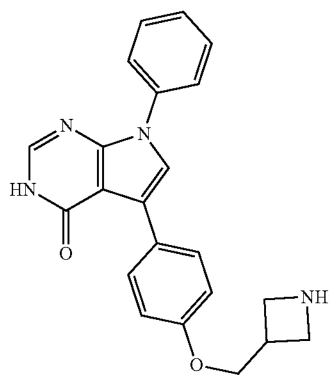
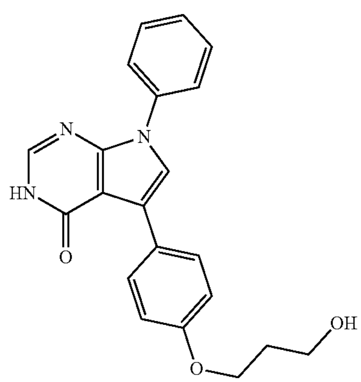
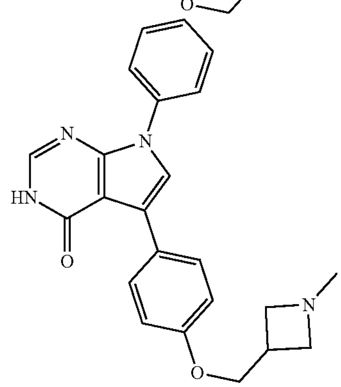
-continued
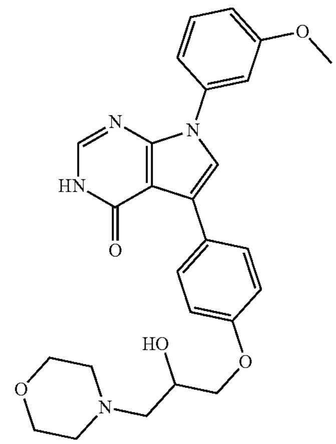
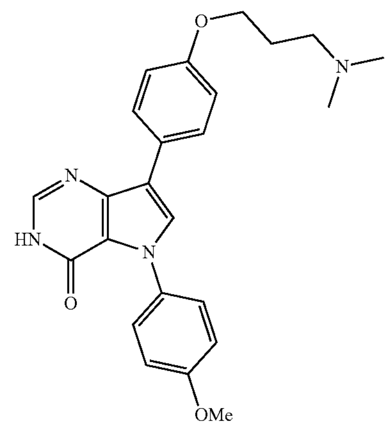 [SMILES: COc1ccc(-n2cc(-c3ccc(OCCCN(C)C)cc3)c3nc[nH]c(=O)c32)cc1]
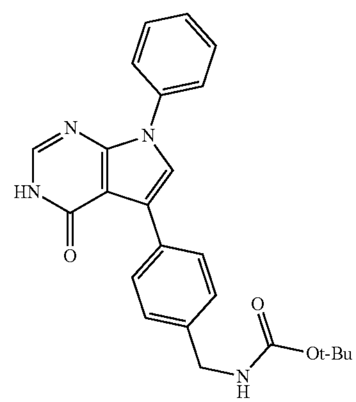
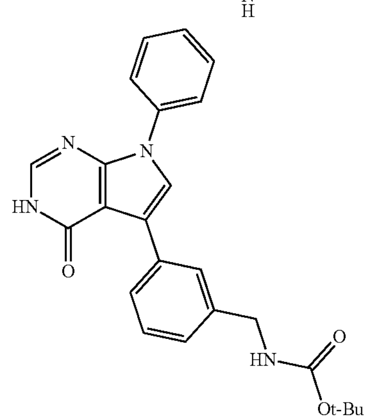

-continued
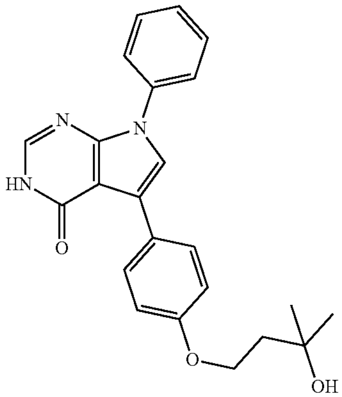
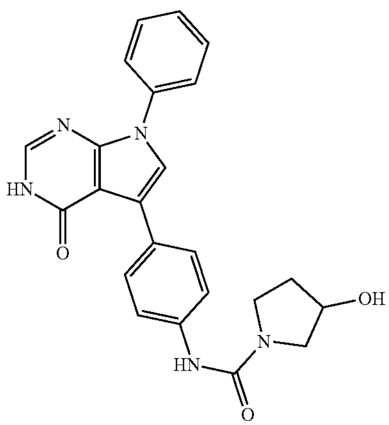
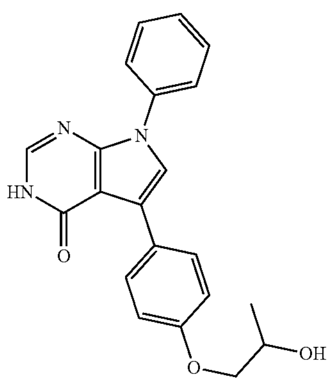
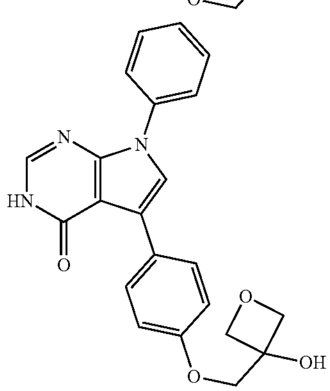
-continued
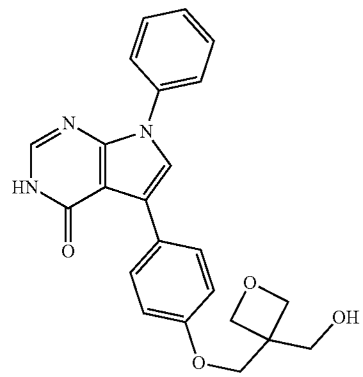
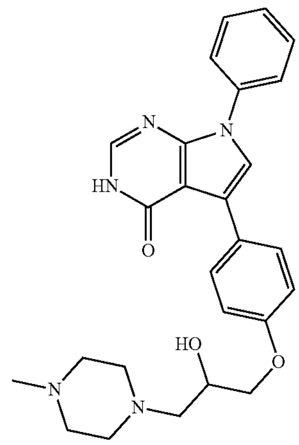
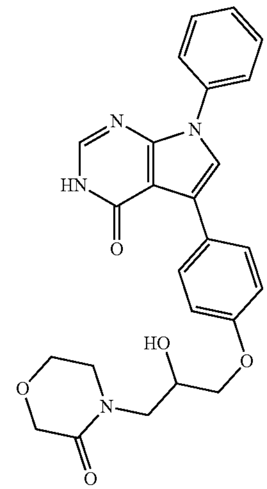
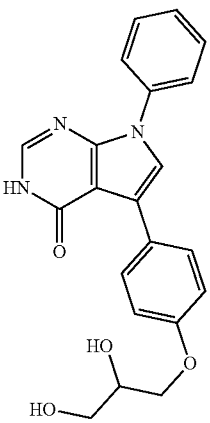
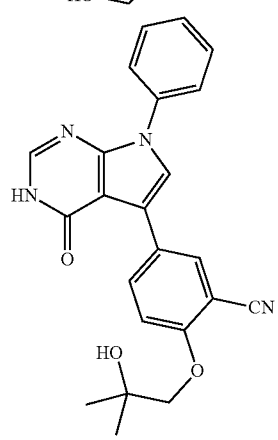

-continued
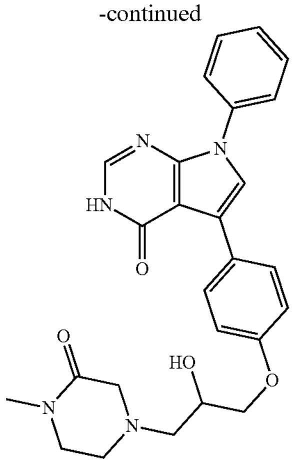
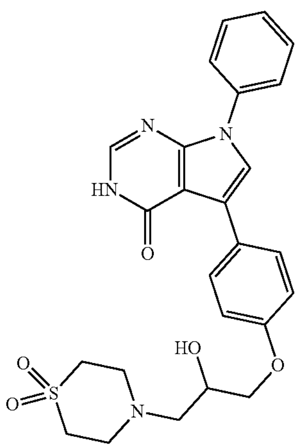
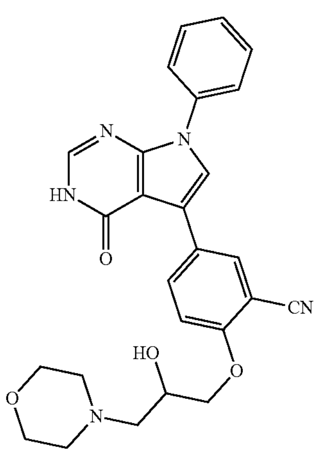
-continued
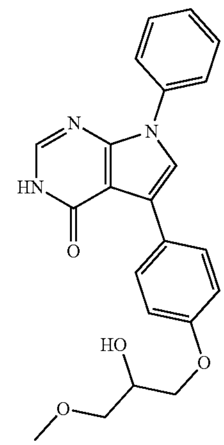
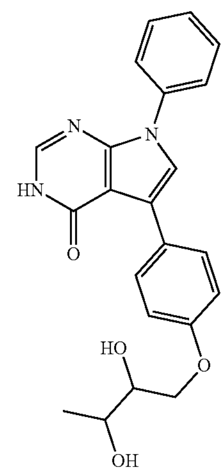
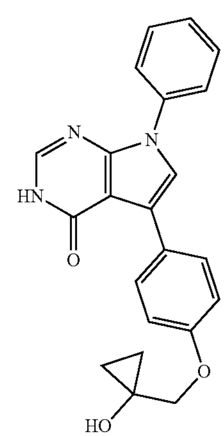

-continued
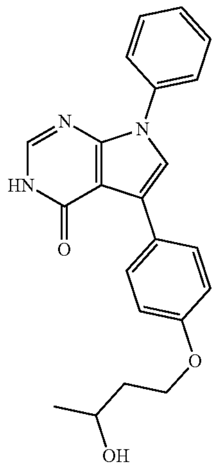
-continued
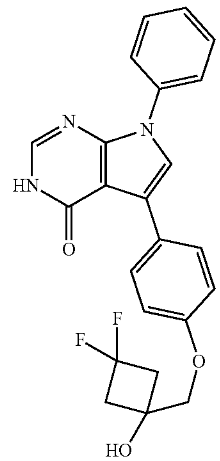
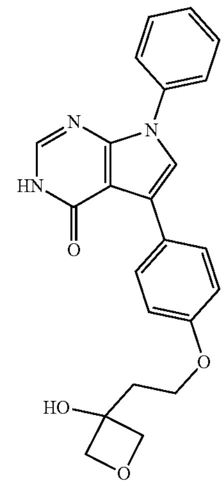
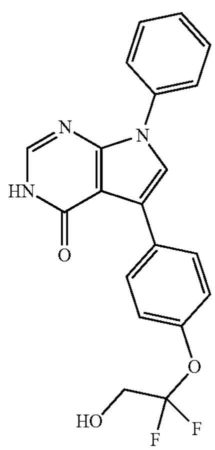
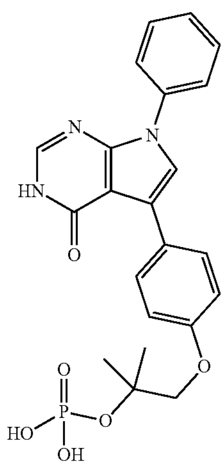
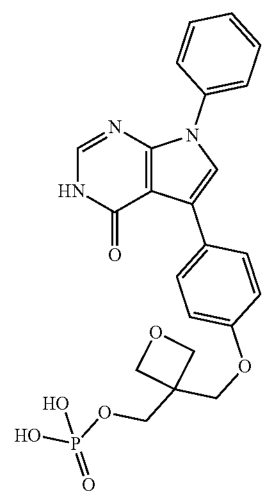 [SMILES: O=c1[nH]cnc2c1c(-c1ccc(OCC3(COP(=O)(O)O)COC3)cc1)cn2-c1ccccc1]
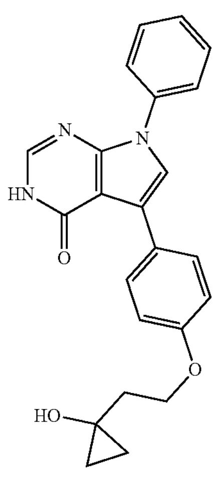
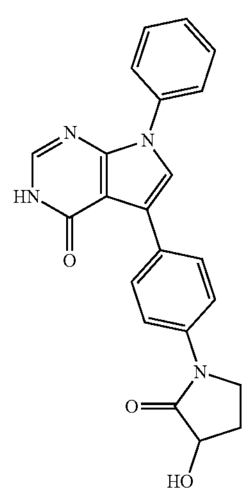
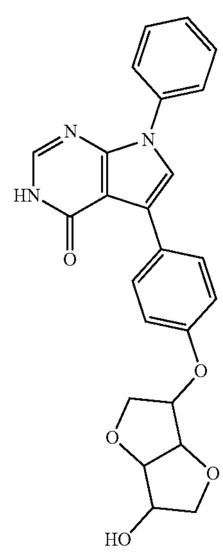

-continued
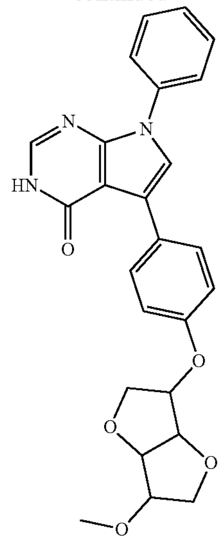
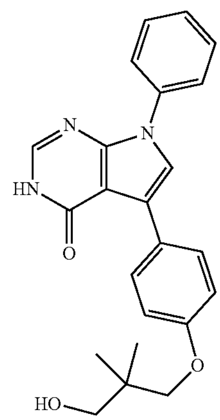 [SMILES: CC(C)(CO)COc1ccc(-c2cn(-c3ccccc3)c3nc[nH]c(=O)c23)cc1]
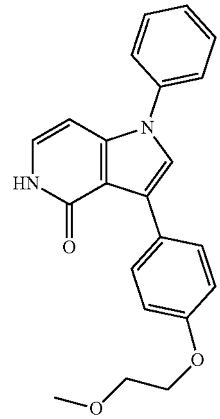 [SMILES: COCCOc1ccc(-c2cn(-c3ccccc3)c3cc[nH]c(=O)c23)cc1]
-continued
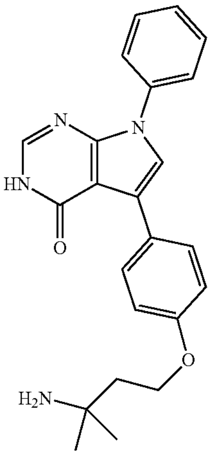
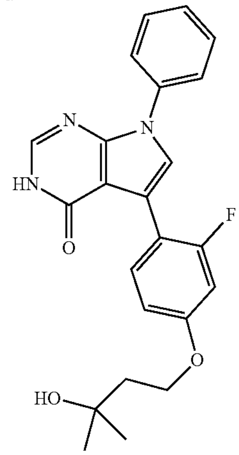
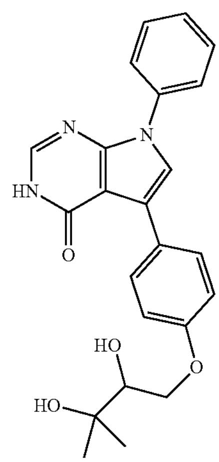
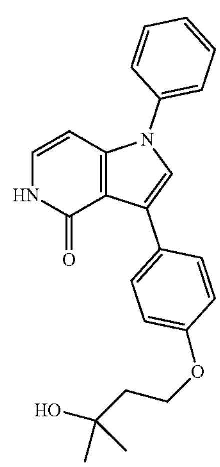
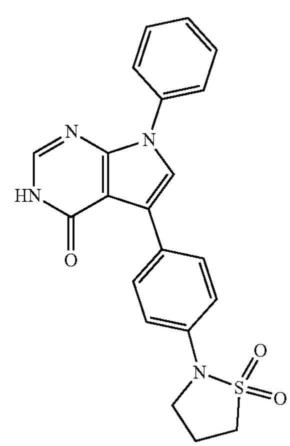

-continued
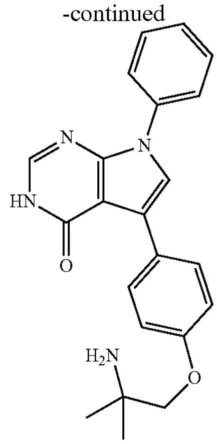
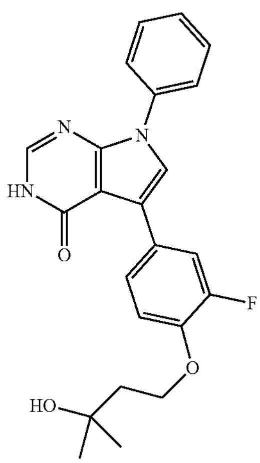
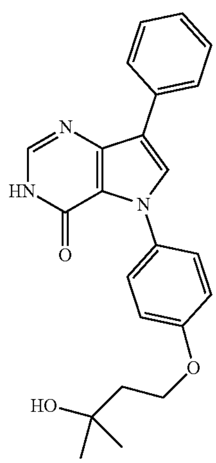
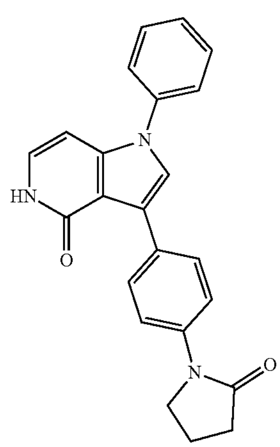
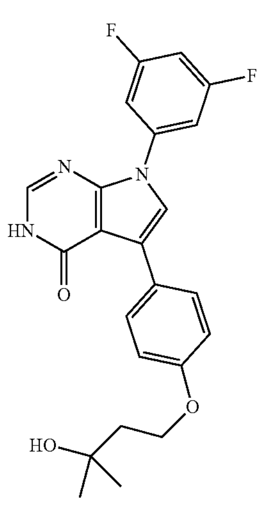
-continued
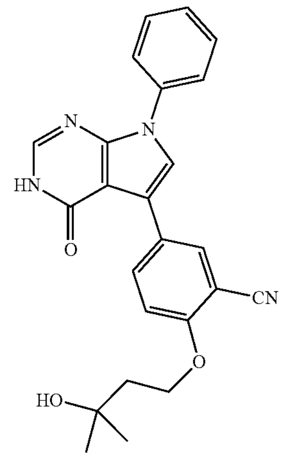
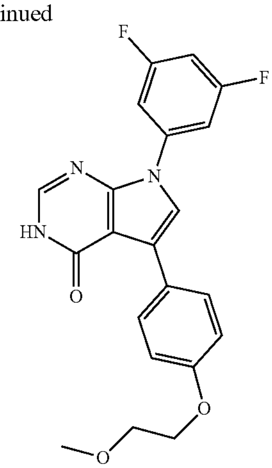
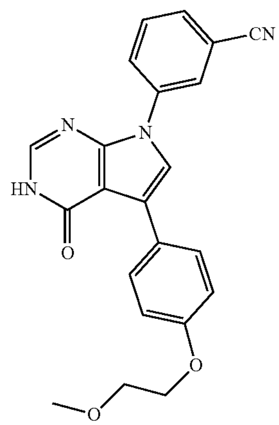
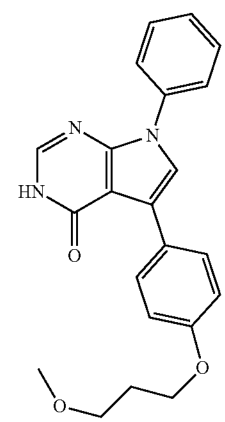
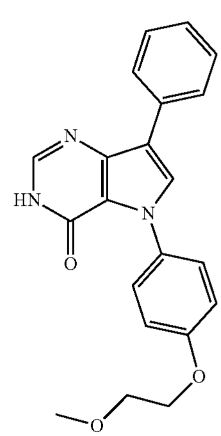
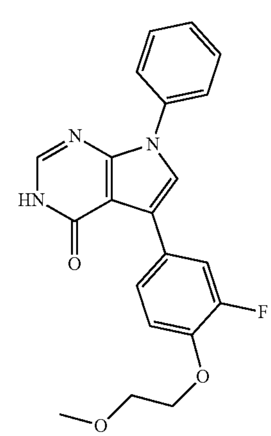

-continued
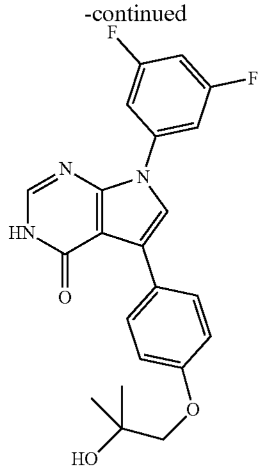
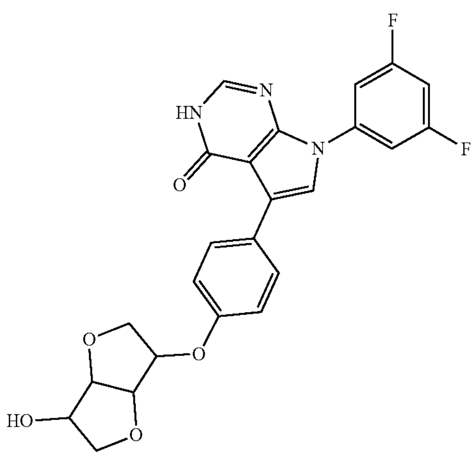
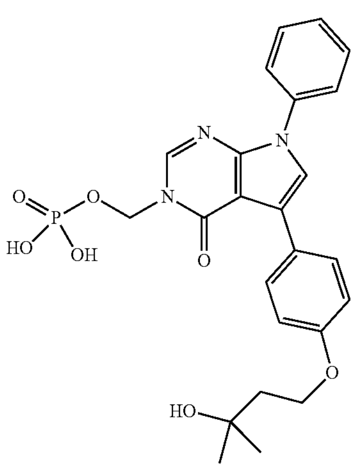
-continued
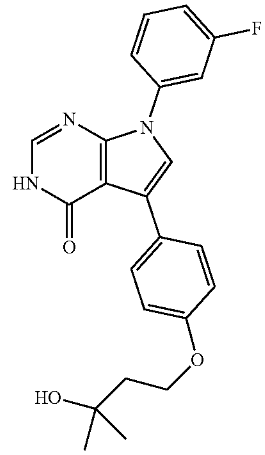
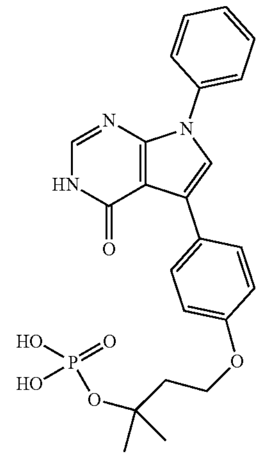
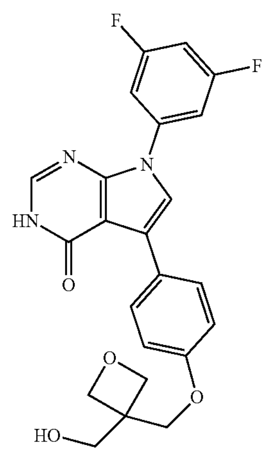
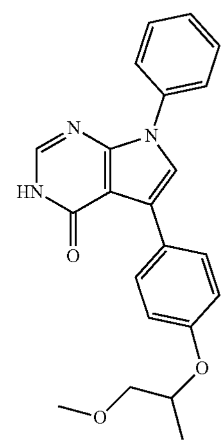
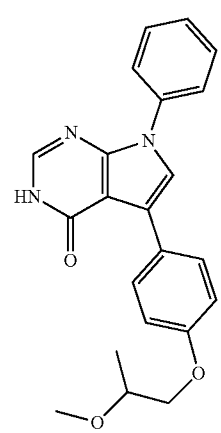

-continued

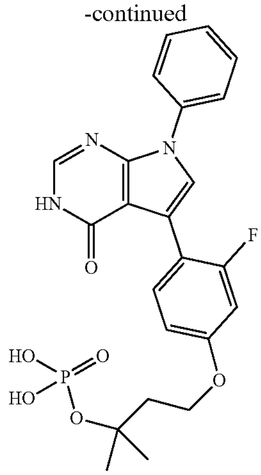

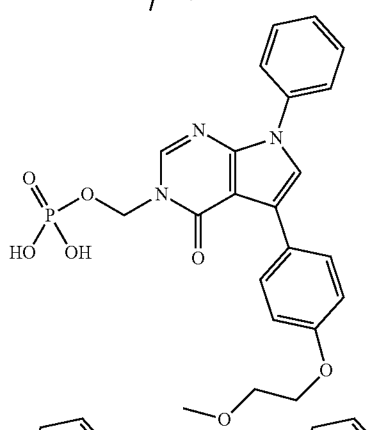

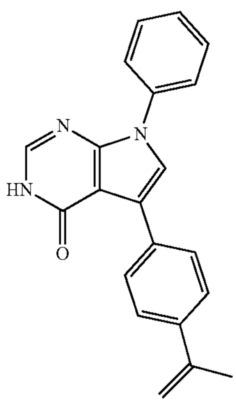

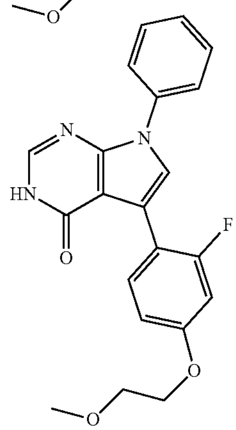

and

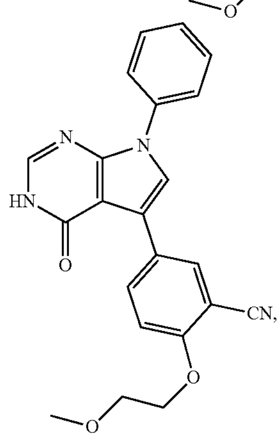

, or a pharmaceutically acceptable salt thereof.

4. A method of using stem cell-derived cardiomyocytes for the identification of therapies for myocardial infarction, wherein the method comprises contacting stem cell-derived cardiomyocytes with a compound of claim 1 in a cell culture model of cardiac muscle cell death.

5. A method of claim 4, wherein the stem cell-derived cardiomyocytes are human stem cell-derived cardiomyocytes.

6. A method of claim 4, wherein the model of cardiac muscle cell death employs a stressor selected from: $H_2O_2$, menadione, and other compounds that confer oxidative stress; hypoxia; hypoxia/reoxygenation; glucose deprivation or compounds that interfere with metabolism; cardiotoxic drugs; proteins or genes that promote cell death; interference with the expression or function of proteins or genes that antagonise cell death.

7. A method of treating a disease mediated by MAP4K4, wherein the method comprises administering to a patient in need thereof a therapeutically effective amount of a compound of claim 1 or a pharmaceutically acceptable salt thereof.

8. The method of claim 7, wherein the disease is myocardial infarction.

9. The method of claim 7, wherein the disease is infarcts.

10. The method of claim 7, wherein the disease is a condition selected from: heart muscle cell injury, heart muscle cell injury due to cardiopulmonary bypass, chronic forms of heart muscle cell injury, hypertrophic cardiomyopathies, dilated cardiomyopathies, mitochondrial cardiomyopathies, cardiomyopathies due to genetic conditions; cardiomyopathies due to high blood pressure; cardiomyopathies due to heart tissue damage from a previous heart attack; cardiomyopathies due to chronic rapid heart rate; cardiomyopathies due to heart valve problems; cardiomyopathies due to metabolic disorders; cardiomyopathies due to nutritional deficiencies of essential vitamins or minerals; cardiomyopathies due to alcohol consumption; cardiomyopathies due to use of cocaine, amphetamines or anabolic steroids; cardiomyopathies due to radiotherapy to treat cancer; cardiomyopathies due to certain infections which may injure the heart and trigger cardiomyopathy; cardiomyopathies due to hemochromatosis; cardiomyopathies due to sarcoidosis; cardiomyopathies due to amyloidosis; cardiomyopathies due to connective tissue disorders; drug- or radiation-induced cardiomyopathies; idiopathic or cryptogenic cardiomyopathies; other forms of ischemic injury selected from the group consisting of ischemia-reperfusion injury, ischemia stroke, renal artery occlusion, and global ischemia-reperfusion injury (cardiac arrest); cardiac muscle cell necrosis; and cardiac muscle cell apoptosis.

11. A method of treating myocardial infarction, wherein the method comprises administering to a patient in need thereof a therapeutically effective amount of a compound of claim 1.

12. A method of treating infarcts, wherein the method comprises administering to a patient in need thereof a therapeutically effective amount of a compound of claim 1.

13. A compound according to claim 3 which is:

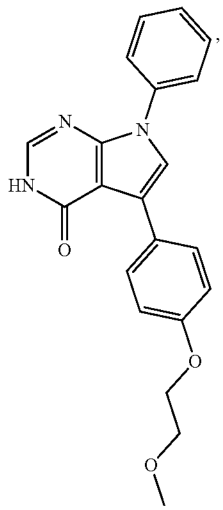 [SMILES: COCCOc1ccc(-c2cn(-c3ccccc3)c3nc[nH]c(=O)c23)cc1]

or a pharmaceutically acceptable salt thereof.

14. A compound according to claim 3 which is:

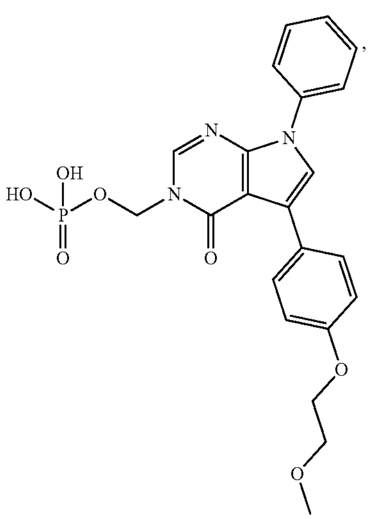 [SMILES: COCCOc1ccc(-c2cn(-c3ccccc3)c3ncn(COP(=O)(O)O)c(=O)c23)cc1]

or a pharmaceutically acceptable salt thereof.

15. A compound according to claim 3 which is:

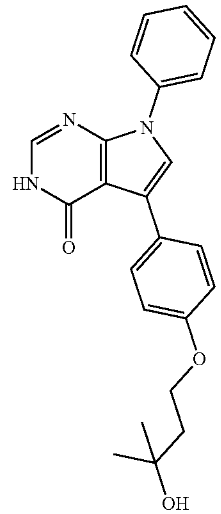

or a pharmaceutically acceptable salt thereof.

16. A compound according to claim 3 which is:

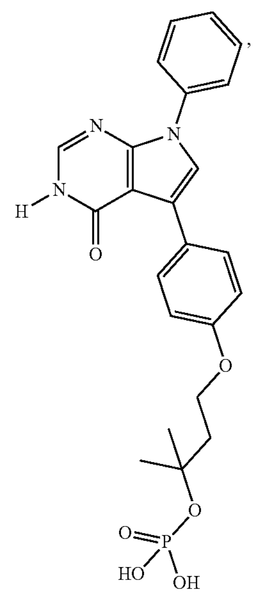 [SMILES: CC(C)(CCOc1ccc(-c2cn(-c3ccccc3)c3nc[nH]c(=O)c23)cc1)OP(=O)(O)O]

or a pharmaceutically acceptable salt thereof.

17. A compound according to claim 1, wherein $R^2$ is selected from halo, $C_{2-6}$ alkenyl, $C_{1-6}$ haloalkyl, —$NR^{6a}R^{6b}$, —$OR^{6a}$, —OP(═O)(OH)$_2$, —C(O)$R^{6a}$, —$NR^{5b}$C(O)O—$C_{1-6}$ alkyl, phenyl, a 5 or 6 membered heteroaryl ring, and a 3 to 8 membered heterocycloalkyl ring system, wherein the phenyl, heteroaryl and heterocycloalkyl rings are unsubstituted or substituted with 1 or 2 groups selected from: oxo, halo, $OR^{6a}$, $C_{1-6}$ alkyl, $C_{1-6}$ alkyl substituted with $NR^{6a}R^{6b}$, $C_{1-6}$ alkyl substituted with $OR^{6a}$, —C(O)$OR^9$, and —$NR^8$C(O)$R^7$.

* * * * *